United States Patent
Barton et al.

(10) Patent No.: US 10,681,908 B2
(45) Date of Patent: Jun. 16, 2020

(54) MOLECULES HAVING PESTICIDAL UTILITY, AND INTERMEDIATES, COMPOSITIONS, AND PROCESSES, RELATED THERETO

(71) Applicant: Dow AgroSciences LLC, Indianapolis, IN (US)

(72) Inventors: Thomas Barton, Indianapolis, IN (US); Xin Gao, Carmel, IN (US); Jim Hunter, Indianapolis, IN (US); Paul R. LePlae, Jr., Brownsburg, IN (US); William C. Lo, Fishers, IN (US); Joshodeep Boruwa, Noida (IN); Raghuram Tangirala, Bengaluru (IN); Gerald B. Watson, Zionsville, IN (US); John Herbert, Fishers, IN (US)

(73) Assignee: DOW AGROSCIENCES LLC, Indianapolis, IN (US)

( * ) Notice: Subject to any disclaimer, the term of this patent is extended or adjusted under 35 U.S.C. 154(b) by 291 days.

(21) Appl. No.: 15/408,693

(22) Filed: Jan. 18, 2017

(65) Prior Publication Data
US 2017/0208806 A1 Jul. 27, 2017

Related U.S. Application Data

(60) Provisional application No. 62/286,684, filed on Jan. 25, 2016, provisional application No. 62/286,690, filed on Jan. 25, 2016.

(51) Int. Cl.
| | | |
|---|---|---|
| A01N 41/10 | (2006.01) | |
| A01N 37/34 | (2006.01) | |
| A01N 37/20 | (2006.01) | |
| C07C 317/28 | (2006.01) | |
| C07C 321/14 | (2006.01) | |
| C07C 323/60 | (2006.01) | |
| C07C 323/25 | (2006.01) | |
| A01N 41/12 | (2006.01) | |
| A01N 41/02 | (2006.01) | |

(52) U.S. Cl.
CPC .......... *A01N 41/10* (2013.01); *A01N 37/20* (2013.01); *A01N 37/34* (2013.01); *A01N 41/02* (2013.01); *A01N 41/12* (2013.01); *C07C 317/28* (2013.01); *C07C 321/14* (2013.01); *C07C 323/25* (2013.01); *C07C 323/60* (2013.01); *C07C 2601/02* (2017.05)

(58) Field of Classification Search
None
See application file for complete search history.

(56) References Cited

U.S. PATENT DOCUMENTS

| | | | |
|---|---|---|---|
| 3,655,765 A | 4/1972 | Gelfand | |
| 4,607,053 A | 8/1986 | Karanewsky | |
| 4,833,158 A | 5/1989 | Twydell | |
| 4,873,329 A | 10/1989 | Hughes | |
| 6,013,836 A | 1/2000 | Hsu | |
| 6,013,837 A | 1/2000 | Demassey | |
| 6,028,192 A | 2/2000 | Becherer | |
| 7,375,232 B2 | 5/2008 | Clark | |
| 7,629,463 B2 | 12/2009 | Clark | |
| 7,951,828 B1 | 5/2011 | Mita | |
| 8,093,241 B2 | 1/2012 | Nakamura | |
| 8,350,044 B2 | 1/2013 | Trullinger | |
| 8,673,951 B2 | 3/2014 | Mita | |
| 9,210,927 B2 | 12/2015 | Lo | |
| 9,211,280 B2 | 12/2015 | Lo | |
| 9,211,281 B2 | 12/2015 | Lo | |
| 9,212,163 B2 | 12/2015 | Lo | |
| 9,212,164 B2 | 12/2015 | Lo | |
| 9,215,870 B2 | 12/2015 | Lo | |
| 9,226,500 B2 | 1/2016 | Lo | |

(Continued)

FOREIGN PATENT DOCUMENTS

| CN | 86104207 A | 4/1987 |
|---|---|---|
| CN | 1543460 A | 11/2004 |

(Continued)

OTHER PUBLICATIONS

Mitsos, C. "Isosteres in Medicinal Chemistry" Feb. 1, 2006, no pagination, accessed via https://www.scripps.edu/baran/images/grpmtgpdf/Mitsos_Feb_06.pdf.*
Written Opinion for PCT/US2017/013856 aka WO 2017/132015 A1.
International Search Report for PCT/US2017/013886 aka WO 2017/132019 A1.
Written Opinion for PCT/US2017/013886 aka WO 2017/132019 A1.
International Search Report for PCT/US2017/013891 aka WO 2017/132021 A1.
Written Opinion for PCT/US2017/013891 aka WO 2017/132021 A1.
International Search Report for PCT/US2017/013910 aka WO 2017/132022 A1.

(Continued)

*Primary Examiner* — Erin E Hirt

(57) ABSTRACT

This disclosure relates to the field of molecules having pesticidal utility against pests in Phyla Arthropoda, Mollusca, and Nematoda, processes to produce such molecules, intermediates used in such processes, compositions containing such molecules, and processes of using such molecules and compositions against such pests. These molecules and compositions may be used, for example, as acaricides, insecticides, miticides, molluscicides, and nematicides. This document discloses molecules having the following formula ("Formula One").

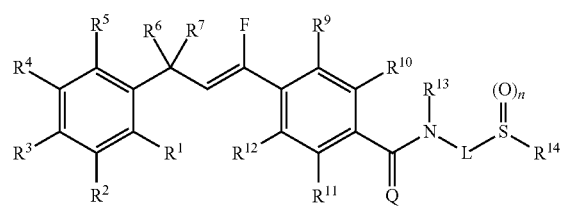

23 Claims, No Drawings

(56) References Cited

U.S. PATENT DOCUMENTS

| | | | |
|---|---|---|---|
| 9,226,501 B2 | 1/2016 | Lo | |
| 9,295,260 B2 | 3/2016 | Zhang | |
| 9,510,592 B2 | 12/2016 | Lo | |
| 9,538,756 B2 | 1/2017 | Lo | |
| 9,615,576 B2 | 4/2017 | Hunter | |
| 9,622,477 B2 | 4/2017 | Lo | |
| 9,629,363 B2 | 4/2017 | Lo | |
| 9,629,369 B2 | 4/2017 | Lo | |
| 9,630,910 B2 | 4/2017 | Lo | |
| 9,635,859 B2 | 5/2017 | Lo | |
| 9,676,704 B2 | 6/2017 | LePlae | |
| 9,701,620 B2 | 7/2017 | Lo | |
| 9,781,935 B2 | 10/2017 | Heemstra | |
| 9,839,216 B2 | 12/2017 | Pittema | |
| 9,924,716 B2 | 3/2018 | Barton | |
| 9,924,717 B2 | 3/2018 | Barton | |
| 9,930,892 B2 | 4/2018 | Barton | |
| 10,251,394 B2 | 4/2019 | Barton | |
| 2002/0068838 A1 | 6/2002 | Demassey | |
| 2003/0225302 A1 | 12/2003 | Demassey | |
| 2004/0152598 A1 | 8/2004 | Goto | |
| 2007/0027034 A1 | 2/2007 | Tank | |
| 2007/0066617 A1 | 3/2007 | Mita | |
| 2007/0207093 A1 | 9/2007 | Bryant | |
| 2008/0063678 A1 | 3/2008 | Von Deyn | |
| 2010/0093707 A1 | 4/2010 | Nakamura | |
| 2010/0254959 A1 | 10/2010 | Lahm | |
| 2010/0292253 A1 | 11/2010 | Trullinger | |
| 2011/0144334 A1 | 6/2011 | Mita | |
| 2011/0160054 A1 | 6/2011 | Breuningger | |
| 2012/0053146 A1 | 3/2012 | Parker | |
| 2012/0316124 A1 | 12/2012 | Pitterna | |
| 2012/0329649 A1 | 12/2012 | Hunter | |
| 2012/0329769 A1 | 12/2012 | Qacemi | |
| 2013/0019348 A1 | 1/2013 | Crouse | |
| 2013/0288893 A1 | 10/2013 | Buysse | |
| 2014/0343049 A1 | 11/2014 | Toueg | |
| 2015/0257387 A1 | 9/2015 | Coqueron | |
| 2016/0029635 A1 | 2/2016 | Lo | |
| 2017/0022148 A1 | 1/2017 | Lo | |
| 2017/0088507 A1 | 3/2017 | Lo | |
| 2017/0156320 A1 | 6/2017 | Lo | |
| 2017/0158597 A1 | 6/2017 | Lo | |
| 2017/0158598 A1 | 6/2017 | Lo | |
| 2017/0158624 A1 | 6/2017 | Lo | |
| 2017/0158674 A1 | 6/2017 | Hunter | |
| 2017/0158675 A1 | 6/2017 | Lo | |
| 2017/0208806 A1 | 7/2017 | Barton | |
| 2017/0210723 A1* | 7/2017 | LePlae, Jr. | ............ C07C 317/28 |
| 2017/0217876 A1 | 8/2017 | LePlae | |
| 2017/0267629 A1 | 9/2017 | Lo | |
| 2018/0009737 A1 | 1/2018 | LePlae | |
| 2018/0279612 A1 | 10/2018 | LePlae | |

FOREIGN PATENT DOCUMENTS

| | | | |
|---|---|---|---|
| CN | 101765592 A | 6/2010 | |
| CN | 102137593 A | 7/2011 | |
| CN | 102458403 A | 5/2012 | |
| EP | 2723729 A1 | 4/2014 | |
| JP | H072801 A | 1/1995 | |
| JP | 2002507978 A | 3/2002 | |
| JP | 2003176258 A | 6/2003 | |
| JP | 2005502661 A | 1/2005 | |
| JP | 2005126418 A | 5/2005 | |
| JP | 2007308471 A | 11/2007 | |
| JP | 2012526123 A | 10/2012 | |
| JP | 2014517135 A | 9/2014 | |
| WO | 8607590 A1 | 12/1986 | |
| WO | 9901422 A1 | 1/1999 | |
| WO | 2003016304 A1 | 2/2003 | |
| WO | 2009002809 A2 | 12/2008 | |
| WO | 2010023171 A2 | 3/2010 | |
| WO | 2010078300 A1 | 7/2010 | |
| WO | 2010129497 A1 | 11/2010 | |
| WO | 2012004326 A1 | 1/2012 | |
| WO | 2012148772 A1 | 11/2012 | |
| WO | 2012177813 A1 | 12/2012 | |
| WO | 2013174947 A1 | 11/2013 | |
| WO | 2014100163 A1 | 6/2014 | |
| WO | 2014100166 A1 | 6/2014 | |
| WO | 2014100170 A1 | 6/2014 | |
| WO | 2014100190 A1 | 6/2014 | |
| WO | 2014100206 A1 | 6/2014 | |
| WO | WO-2014100206 A1 * | 6/2014 | ........... C07C 237/22 |
| WO | 2014120355 A1 | 8/2014 | |
| WO | 2015097094 A1 | 7/2015 | |
| WO | 2015191430 A1 | 12/2015 | |
| WO | 2017132014 A1 | 8/2017 | |
| WO | 2017132015 A1 | 8/2017 | |
| WO | 2017132019 A1 | 8/2017 | |
| WO | 2017132021 A1 | 8/2017 | |
| WO | 2017132022 A1 | 8/2017 | |
| WO | 2017132023 A1 | 8/2017 | |
| WO | 2018183601 A1 | 10/2018 | |

OTHER PUBLICATIONS

Written Opinion for PCT/US2017/013910 aka WO 2017/132022 A1.
International Search Report for PCT/US2017/013915 aka WO 2017/132023 A1.
Written Opinion for PCT/US2017/013915 aka WO 2017/132023 A1.
International Search Report for PCT/US2018/025024 aka WO 2018/183601 A1.
Written Opinion for PCT/US2018/025024 aka WO 2018/183601 A1.
Supplementary Search Report for EP 2934142.
EP Opinion for EP 2934142.
Supplementary Search Report for EP 2934135.
EP Opinion for EP 2934135.
Supplementary Search Report for EP 2934118.
EP Opinion for EP 2934118.
EP Opinion for EP 2934117.
Supplementary Search Report for EP 3408262.
EP Opinion for EP 3408262.
EP Opinion for EP 3152189.
Supplementary Search Report for EP 3407716.
EP Opinion for EP 3407716.
Supplementary Search Report for EP 3407717.
EP Opinion for EP 3407717.
Supplementary Search Report for EP 3408263.
EP Opinion for EP 3408263.
Supplementary Search Report for EP 3407718.
EP Opinion for EP 34087718.
Supplementary Search Report for EP 3407720.
EP Opinion for EP 3407720.
Search Report Eng Trans for CN 105025715 A.
T. Konno, et al.: "A first high enantioncontrol of an asymmetric tertiary carbon center attached with a fluoroalkyl group via Rh(I)-catalyzed conjugate addition reaction", Tetrahedron Letters, Mar. 24, 2008, pp. 2106 to 2110, vol. 49, No. 13, Elsevier Science Publishers, Amsterdam, NL.
A. Unsinn, et al.: "Stereoselective synthesis of tetrasubstituted alkenes via a sequential carbocupration and a new sulfur-lithium exchange", Beilstein Journal of Organic Chemistry, Dec. 18, 2012, pp. 2202 to 2206, vol. 8, No. 248, Beilstein Institut, Frankfurt am Main, DE.
Cornell University Cooperative Extension: "Pesticide Safety Education Program (PSEP)", http://psep.cce.cornell.edu/issues/foodsafety-issues.aspx, cached Jun. 29, 2010.
S. Kagabu et al.: "Insecticidal and Neuroblocking Activites of Thiamethoxam-Type Compounds in the American Cockroach (*Periplaneta americana* L.)", Journal of Pesticide Science, 2005, pp. 111 to 115, vol. 30, No. 2, Pesticide Science Society of Japan, Tokyo, Japan.

(56) References Cited

OTHER PUBLICATIONS

Y. Shiga et al.: "Synthesis and Acaricidal Activity of N-(1,3,4-Thiadiazol-2-yl)carboxamides", Journal of Pesticide Science, 2003, pp. 58 to 60, vol. 28, No. 1, Pesticide Science Society of Japan, Tokyo, Japan.
Pubchem, Substance Record for SID 236248093, Available Date: Feb. 13, 2015 Retrieved from the Internet: https://pubchem.ncbi.nlm.nih.gov/substance/236248093.
M. D. Taylor et al. (Eds.), Pesticide Residues in Coastal Tropical Ecosystems: Distribution, Fate and Effects, Nov. 21, 2002, p. 204, CRC Press, New York, USA.
C. Mitsos, "Isosteres in medicinal chemistry" https://www.scripps.edu/baran/images/grpmtgpdf/Mitsos_Feb_06.pdf, Feb. 1, 2006, no pagination. (Year: 2006).
F. Matsumura, Toxicology of Insecticides, 2nd ed., 1985, p. 11, Plenum Press, New York, USA.
S. J. Yu, The Toxicology and Biochemistry of Insecticides, 2nd ed., 2015, p. 103, CRC Press, Boca Raton, FL.
S. Kagabu and S. Medej, "Stability Comparison of Imidacloprid and Related Compounds under Simulated Sunlight, Hydrolysis Conditions, and to Oxygen", Bioscience, Biotechnology, and Biochemistry, 1995, pp. 980 to 985, vol. 59, Japan Society for Bioscience, Biotechnology, and Agrochemistry, Taylor & Francis Group.
W. D. Kollmeyer, et al., "Discovery of the Nitromethylene Heterocycle Insecticides" in Nicotinoid Insecticides and the Nicotinic Acetylcholine Receptor, I. Yamamoto and J. E. Casida, Eds., 1999, pp. 71 to 89, Springer Japan.
P. Jeschke, "The Unique Role of Fluorine in the Design of Active Ingredients for Modern Crop Protection" pp. 586-587, 2004, pp. 570 to 589, ChemBioChem vol. 5, Wiley-VCH Verlag GmbH & Co. KGaA, Weinheim, DE.
A. Burger, "Isosterism and bioisoterism in drug design" 1991, p. 318, Progress in Drug Research, edited by J. A. Salmon.
P. Ertl, "Cheminformatics Analysis of Organic Substituents: Identification of the Most Common Substituents, Calculation of Substituents Properties, and Automatic Identification of Drug-like Bioisosteric Groups" Journal of Chemical Information and Computer Sciences, Mar. 1, 2003, pp. 374 to 380, vol. 43 No. 2, ACS Publications, Washington, DC, USA.
International Search Report for PCT/US2012/043418 aka WO 2012/177813 A1.
Written Opinion for PCT/US2012/043418 aka WO 2012/177813 A1.
Supplementary European Search Report for EP 2723729.
European Opinion for EP 2723729.
International Search Report for PCT/US2013/076079 aka WO 2014/120355 A1.
Written Opinion for PCT/US2013/076079 aka WO 2014/120355 A1.
International Search Report for PCT/US2013/076096 aka WO 2014/100163 A1.
Written Opinion for PCT/US2013/076096 aka WO 2014/100163 A1.
International Search Report for PCT/US2013/076101 aka WO 2014/100166 A1.
Written Opinion for PCT/US2013/076101 aka WO 2014/100166 A1.
International Search Report for PCT/US2013/076113 aka WO 2014/100170 A1.
Written Opinion for PCT/US2013/076113 aka WO 2014/100170 A1.
International Search Report and Written Opinion for PCT/US2013/076142 aka WO 2014/100190 A1.
Supplementary Search Report for EP 2934117.
International Search Report for PCT/US2013/076170 aka WO 2014/100206 A1.
Written Opinion for PCT/US2013/076170 aka WO 2014/100206 A1.
International Search Report for PCT/US2017/013848 aka WO 2017/132014 A1.
Written Opinion for PCT/US2017/013848 aka WO 2017/132014 A1.
International Search Report for PCT/US2015/034648 aka WO 2015/191430 A1.
Written Opinion for PCT/US2015/034648 aka WO 2015/191430 A1.
Supplementary European Search Report for EP 3152189.
International Search Report for PCT/US2017/013856 aka WO 2017/132015 A1.

* cited by examiner

MOLECULES HAVING PESTICIDAL UTILITY, AND INTERMEDIATES, COMPOSITIONS, AND PROCESSES, RELATED THERETO

CROSS REFERENCE TO RELATED APPLICATIONS

This application claims the benefit of, and priority from, U.S. Provisional Patent Application Ser. Nos. 62/286,684 and 62/286,690 both filed Jan. 25, 2016, each of which are expressly incorporated by reference herein.

FIELD OF THIS DISCLOSURE

This disclosure relates to the field of molecules having pesticidal utility against pests in Phyla Arthropoda, Mollusca, and Nematoda, processes to produce such molecules, intermediates used in such processes, pesticidal compositions containing such molecules, and processes of using such pesticidal compositions against such pests. These pesticidal compositions may be used, for example, as acaricides, insecticides, miticides, molluscicides, and nematicides.

BACKGROUND OF THIS DISCLOSURE

"Many of the most dangerous human diseases are transmitted by insect vectors" (Rivero et al.). "Historically, malaria, dengue, yellow fever, plague, filariasis, louse-borne typhus, trypanosomiasis, leishmaniasis, and other vector borne diseases were responsible for more human disease and death in the 17$^{th}$ through the early 20$^{th}$ centuries than all other causes combined" (Gubler). Vector-borne diseases are responsible for about 17% of the global parasitic and infectious diseases. Malaria alone causes over 800,000 deaths a year, 85% of which occur in children under five years of age. Each year there are about 50 to about 100 million cases of dengue fever. A further 250,000 to 500,000 cases of dengue hemorrhagic fever occur each year (Matthews). Vector control plays a critical role in the prevention and control of infectious diseases. However, insecticide resistance, including resistance to multiple insecticides, has arisen in all insect species that are major vectors of human diseases (Rivero et al.). Recently, more than 550 arthropod pest species have developed resistance to at least one pesticide (Whalon et al.).

Each year insects, plant pathogens, and weeds, destroy more than 40% of all food production. This loss occurs despite the application of pesticides and the use of a wide array of non-chemical controls, such as, crop rotations, and biological controls. If just some of this food could be saved, it could be used to feed the more than three billion people in the world who are malnourished (Pimental).

Plant parasitic nematodes are among the most widespread pests, and are frequently one of the most insidious and costly. It has been estimated that losses attributable to nematodes are from about 9% in developed countries to about 15% in undeveloped countries. However, in the United States of America a survey of 35 States on various crops indicated nematode-derived losses of up to 25% (Nicol et al.).

It is noted that gastropods (slugs and snails) are pests of less economic importance than other arthropods or nematodes, but in certain places they may reduce yields substantially, severely affecting the quality of harvested products, as well as, transmitting human, animal, and plant diseases. While only a few dozen species of gastropods are serious regional pests, a handful of species are important pests on a worldwide scale. In particular, gastropods affect a wide variety of agricultural and horticultural crops, such as, arable, pastoral, and fiber crops; vegetables; bush and tree fruits; herbs; and ornamentals (Speiser).

Termites cause damage to all types of private and public structures, as well as, to agricultural and forestry resources. In 2005, it was estimated that termites cause over US$50 billion in damage worldwide each year (Korb).

Consequently, for many reasons, including those mentioned above, there is an on-going need for the costly (estimated to be about US$256 million per pesticide in 2010), time-consuming (on average about 10 years per pesticide), and difficult, development of new pesticides (CropLife America).

DeMassey et al. discloses the following structure. For more detail, refer to U.S. 2002/0068838.

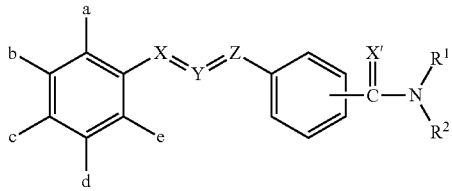

CERTAIN REFERENCES CITED IN THIS DISCLOSURE

CropLife America, The Cost of New Agrochemical Product Discovery, Development & Registration, and Research & Development predictions for the Future, 2010.

Gubler, D., Resurgent Vector-Borne Diseases as a Global Health Problem, Emerging Infectious Diseases, Vol. 4, No. 3, p. 442-450, 1998.

Korb, J., Termites, *Current Biology*, Vol. 17, No. 23, 2007.

Matthews, G., Integrated Vector Management: Controlling Vectors of Malaria and Other Insect Vector Borne Diseases, Ch. 1, p. 1-2011.

Nicol, J., Turner S.; Coyne, L.; den Nijs, L., Hocksland, L., Tahna-Maafi, Z., Current Nematode Threats to World Agriculture, *Genomic and Molecular Genetics of Plant—Nematode Interactions*, p. 21-43, 2011).

Pimental, D., Pest Control in World Agriculture, *Agricultural Sciences*—Vol. II, 2009.

Rivero, A., Vezilier, 3., Weill, M., Read, A., Gandon, S., Insect Control of Vector-Borne Diseases: When is Insect Resistance a Problem? *Public Library of Science Pathogens*, Vol. 6, No. 8, p. 1-9, 2010.

Speiser, B., Molluscicides, *Encyclopedia of Pest Management*, Ch. 219, p. 506-508, 2002.

Whalon, M., Mota-Sanchez, D., Hollingworth, R., Analysis of Global Pesticide Resistance in Arthropods, *Global Pesticide Resistance in Arthropods*, Ch. 1, p. 5-33, 2008.

DEFINITIONS USED IN THIS DISCLOSURE

The examples given in these definitions are generally non-exhaustive and must not be construed as limiting the disclosure. It is understood that a substituent should comply with chemical bonding rules and steric compatibility constraints in relation to the particular molecule to which it is attached. These definitions are only to be used for the purposes of this disclosure.

"Active ingredient" means a material having activity useful in controlling pests, and/or that is useful in helping other materials have better activity in controlling pests, examples of such materials include, but are not limited to, acaricides, algicides, avicides, bactericides, fungicides, herbicides, insecticides, molluscicides, nematicides, rodenticides, virucides, antifeedants, bird repellents, chemosterilants, herbicide safeners, insect attractants, insect repellents, mammal repellents, mating disrupters, plant activators, plant growth regulators, and synergists. Specific examples of such materials include, but are not limited to, the materials listed in active ingredient group alpha.

"Active ingredient group alpha" (hereafter "AIGA") means collectively the following materials:

(1) (3-ethoxypropyl)mercury bromide, 1,2-dibromoethane, 1,2-dichloroethane, 1,2-dichloropropane, 1,3-dichloropropene, 1-MCP, 1-methylcyclopropene, 1-naphthol, 2-(octylthio)ethanol, 2,3,3-TPA, 2,3,5-tri-iodobenzoic acid, 2,3,6-TBA, 2,4,5-T, 2,4,5-TB, 2,4,5-TP, 2,4-D, 2,4-DB, 2,4-DEB, 2,4-DEP, 2,4-DES, 2,4-DP, 2,4-MCPA, 2,4-MCPB, 2iP, 2-methoxyethylmercury chloride, 2-phenylphenol, 3,4-DA, 3,4-DB, 3,4-DP, 3,6-dichloropicolinic acid, 4-aminopyridine, 4-CPA, 4-CPB, 4-CPP, 4-hydroxyphenethyl alcohol, 8-hydroxyquinoline sulfate, 8-phenylmercurioxyquinoline, abamectin, abamectin-aminomethyl, abscisic acid, ACC, acephate, acequinocyl, acetamiprid, acethion, acetochlor, acetofenate, acetophos, acetoprole, acibenzolar, acifluorfen, aclonifen, ACN, acrep, acrinathrin, acrolein, acrylonitrile, acypetacs, afidopyropen, afoxolaner, alachlor, alanap, alanycarb, albendazole, aldicarb, aldicarb sulfone, aldimorph, aldoxycarb, aldrin, allethrin, allicin, allidochlor, allosamidin, alloxydim, allyl alcohol, allyxycarb, alorac, alpha-cypermethrin, alpha-endosulfan, alphamethrin, altretamine, aluminium phosphide, aluminum phosphide, ametoctradin, ametridione, ametryn, ametryne, amibuzin, amicarbazone, amicarthiazol, amidithion, amidoflumet, amidosulfuron, aminocarb, aminocyclopyrachlor, aminopyralid, aminotriazole, amiprofosmethyl, amiprophos, amiprophos-methyl, amisulbrom, amiton, amitraz, amitrole, ammonium sulfamate, amobam, amorphous silica gel, amorphous silicon dioxide, ampropylfos, AMS, anabasine, ancymidol, anilazine, anilofos, anisuron, anthraquinone, antu, apholate, aramite, arprocarb, arsenous oxide, asomate, aspirin, asulam, athidathion, atraton, atrazine, aureofungin, avermectin B1, AVG, aviglycine, azaconazole, azadirachtin, azafenidin, azamethiphos, azidithion, azimsulfuron, azinphosethyl, azinphos-ethyl, azinphosmethyl, azinphos-methyl, aziprotryn, aziprotryne, azithiram, azobenzene, azocyclotin, azothoate, azoxystrobin, bachmedesh, barban, barbanate, barium hexafluorosilicate, barium polysulfide, barium silicofluoride, barthrin, basic copper carbonate, basic copper chloride, basic copper sulfate, BCPC, beflubutamid, benalaxyl, benalaxyl-M, benazolin, bencarbazone, benclothiaz, bendaqingbingzhi, bendiocarb, bendioxide, benefin, benfluralin, benfuracarb, benfuresate, benmihuangcaoan, benodanil, benomyl, benoxacor, benoxafos, benquinox, bensulfuron, bensulide, bensultap, bentaluron, bentazon, bentazone, benthiavalicarb, benthiazole, benthiocarb, bentranil, benzadox, benzalkonium chloride, benzamacril, benzamizole, benzamorf, benzene hexachloride, benzfendizone, benzimine, benzipram, benzobicyclon, benzoepin, benzofenap, benzofluor, benzohydroxamic acid, benzomate, benzophosphate, benzothiadiazole, benzovindiflupyr, benzoximate, benzoylprop, benzthiazuron, benzuocaotong, benzyl benzoate, benzyladenine, berberine, beta-cyfluthrin, beta-cypermethrin, bethoxazin, BHC, bialaphos, bicyclopyrone, bifenazate, bifenox, bifenthrin, bifujunzhi, bilanafos, binapacryl, bingqingxiao, bioallethrin, bioethanomethrin, biopermethrin, bioresmethrin, biphenyl, bisazir, bismerthiazol, bismerthiazol-copper, bisphenylmercury methylenedi(x-naphthalene-y-sulphonate), bispyribac, bistrifluron, bisultap, bitertanol, bithionol, bixafen, blasticidin-S, borax, Bordeaux mixture, boric acid, boscalid, BPPS, brassinolide, brassinolide-ethyl, brevicomin, brodifacoum, brofenprox, brofenvalerate, broflanilide, brofluthrinate, bromacil, bromadiolone, bromchlophos, bromethalin, bromethrin, bromfenvinfos, bromoacetamide, bromobonil, bromobutide, bromociclen, bromocyclen, bromo-DDT, bromofenoximrn, bromofos, bromomethane, bromophos, bromophos-ethyl, bromopropylate, bromothalonil, bromoxynil, brompyrazon, bromuconazole, bronopol, BRP, BTH, bucarpolate, bufencarb, buminafos, bupirimate, buprofezin, Burgundy mixture, busulfan, busulphan, butacarb, butachlor, butafenacil, butam, butamifos, butane-fipronil, butathiofos, butenachlor, butene-fipronil, butethrin, buthidazole, buthiobate, buthiuron, butifos, butocarboxim, butonate, butopyronoxyl, butoxycarboxinm, butralin, butrizol, butroxydirm, buturon, butylamine, butylate, butylchlorophos, butylene-fipronil, cacodylic acid, cadusafos, cafenstrole, calciferol, calcium arsenate, calcium chlorate, calcium cyanamide, calcium cyanide, calcium polysulfide, calvinphos, cambendichlor, camphechlor, camphor, captafol, captan, carbam, carbamorph, carbanolate, carbaril, carbaryl, carbasulam, carbathion, carbendazim, carbendazol, carbetamide, carbofenotion, carbofuran, carbon disulfide, carbon tetrachloride, carbonyl sulfide, carbophenothion, carbophos, carbosulfan, carboxazole, carboxide, carboxin, carfentrazone, carpropamid, cartap, carvacrol, carvone, CAVP, CDAA, CDEA, CDEC, cellocidin, CEPC, ceralure, cerenox, cevadilla, Cheshunt mixture, chinalphos, chinalphos-méthyl, chinomethionat, chinomethionate, chiralaxyl, chitosan, chlobenthiazone, chlomethoxyfen, chloralose, chloramben, chloramine phosphorus, chloramphenicol, chloraniformethan, chloranil, chloranocryl, chlorantraniliprole, chlorazifop, chlorazine, chlorbenside, chlorbenzuron, chlorbicyclen, chlorbromuron, chlorbufam, chlordane, chlordecone, chlordimeform, chlorempenthrin, chloretazate, chlorethephon, chlorethoxyfos, chloreturon, chlorfenac, chlorfenapyr, chlorfenazole, chlorfenethol, chlorfenidim, chlorfenprop, chlorfenson, chlorfensulphide, chlorfenvinphos, chlorfenvinphos-methyl, chlorfluazuron, chlorflurazole, chlorflurecol, chlorfluren, chlorflurenol, chloridazon, chlorimuron, chlorinate, chlor-IPC, chlormephos, chlormequat, chlormesulone, chlormethoxynil, chlornidine, chlornitrofen, chloroacetic acid, chlorobenzilate, chlorodinitronaphthalenes, chlorofénizon, chloroform, chloromebuform, chloromethiuron, chloroneb, chlorophacinone, chlorophos, chloropicrin, chloropon, chloropropylate, chlorothalonil, chlorotoluron, chloroxifenidim, chloroxuron, chloroxynil, chlorphonium, chlorphoxim, chlorprazophos, chlorprocarb, chlorpropham, chlorpyrifos, chlorpyrifos-methyl, chlorquinox, chlorsulfuron, chlorthal, chlorthiamid, chlorthiophos, chlortoluron, chlozolinate, chltosan, cholecalciferol, choline chloride, chromafenozide, cicloheximide, cimectacarb, cimetacarb, cinerin I, cinerin II, cinerins, cinidon-ethyl, cinmethylin, cinosulfuron, cintofen, ciobutide, cisanilide, cismethrin, clacyfos, clefoxydim, clenpirin, clenpyrin, clethodim, climbazole, cliodinate, clodinafop, cloethocarb, clofencet, clofenotane, clofentezine, clofenvinfos, clofibric acid, clofop, clomazone, clomeprop, clonitralid, cloprop, cloproxydim, clopyralid, cloquintocet, cloransulam, closantel, clothianidin, clotrimazole, cloxyfonac, cloxylacon, clozylacon, CMA, CMMP, CMP, CMU, codlelure, colecalciferol, colophonate, copper 8-quinolinolate, copper acetate, copper acetoarsenite, copper arsenate, copper carbonate basic, copper hydroxide, copper naphthenate, copper oleate, copper oxychloride, copper silicate, copper sulfate, copper sulfate basic, copper zinc chromate, coumachlor, coumafene, coumafos, coumafuryl, coumaphos, coumatetralyl, coumethoxystrobin, cournithoate, coumoxystrobin, CPMC, CPMF, CPPC, credazine, cresol, cresylic acid, crimidine, crotamiton, crotoxyfos, crotoxyphos, crufomate, cryolite, cue-lure, cufraneb, cumyleron, cumyluron, cuprobam, cuprous oxide, curcumenol, CVMP, cyanamide, cyanatryn, cyanazine, cyanofenphos, cyanogen, cyanophos, cyanthoate, cyantraniliprole, cyanuric acid, cyazofamid, cybutryne, cyclafuramid, cyclanilide, cyclaniliprole, cyclethrin, cycloate, cyclohexiride, cycloprate, cyclopro-thrin, cyclopyrimorate, cyclosulfamuron, cycloxydim, cycluron, cyenopyrafen, cyflufenamid, cyflumetofen, cyfluthrin, cyhalofop, cyhalothrin, cyhexatin, cymiazole, cymoxanil, cyometrinil, cypendazole, cypermethrin, cyperquat, cyphenothrin, cyprazine, cyprazole, cyproconazole, cyprodinil, cyprofuram, cypromid, cyprosulfamide, cyromazine, cythioate, cytrex, daimuron, dalapon, daminozide, dayoutong, dazomet, DBCP, d-camphor, DCB, DCIP, DCPA, DCPTA, DCU, DDD, DDPP, DDT, DDVP, debacarb, decafentin, decamethrin, decarbofuran, deet, dehydroacetic acid, deiquat, delachlor, delnav, deltamethrin, demephion, demephion-O, demephion-S, derneton, derneton-methyl, demeton-O, demeton-O-methyl, demeton-S, demeton-S-methyl, demeton-S-methyl sulphone, demeton-S-methylsulphon, DEP, depallethrine, derris, desmedipham, desmetryn, desmetryne, d-fanshiluquebingjuzhi, diafenthiuron, dialifor, dialifos, diallate, diamidafos, dianat, diatomaceous earth, diatomite, diazinon, dibrom, dibutyl phthalate, dibutyl succinate, dicamba, dicapthon, dichlobenil, dichlofenthion, dichlofluanid, dichlone, dichloralurea, dichlorbenzuron, dichlorfenidirn, dichlorflurecol, dichlorflurenol, dichlormate, dichlormid, dichloromethane, dicloromezotiaz, dichlorophen, dichlorprop, dichlorprop-P, dichlorvos, dichlozolin, dichlozoline, diclobutrazol, diclocymet, diclofop, dicldomezine, dicloran, diclosulam, dicofol, dicophane, dicoumrarol, dicresyl, dicrotophos, dicryl, dicumarol, dicyclanil, dicyclonon, dieldrin, dienochlor, diethamquat, diethatyl, diethion, diethion, diethofencarb, dietholate, diethon, diethyl pyrocarbonate, diethyltoluamide, difenacoum, difenoconazole, difenopenten, difenoxuron, difenzoquat, difethialone, diflovidazin, diflubenzuron, diflufenican, diflufenicanil, diflufenzopyr, diflumretorim, dikegulac, dilor, dimatif, dimefluthrin, dimefox, dimefuron, dimehypo, dirmepiperate, dirmetachlone, dimetan, direthacarb, dirmethachlone, dimethachlor, dimethametryn, dimethenamid, dimethenamid-P, dimethipin, dimethirimol, dimethoate, dimethomorph, dirnethrin, dimethyl carbate, dimethyl disulfide, dimethyl phthalate, dimethylvinphos, dimetilan, dimexano, dimidazon, dimoxystrobin, dimpylate, dimuron, dinex, dingjunezuo, diniconazole, diniconazole-M, dinitramine, dinitrophenols, dinobuton, dinocap, dinocap-4, dinocap-6, dinocton, dinofenate, dinopenton, dinoprop, dinosam, dinoseb, dinosulfon, dinotefuran, dinoterb, dinoterbon, diofenolan, dioxabenzofos, dioxacarb, dioxathion, dioxation, diphacin, diphacinone, diphenadione, diphenamid, diphenamide, diphenyl sulfone, diphenylamine, diphenylsulphide, diprogulic acid, dipropalin, dipropetryn, dipterex, dipyretitrone, dipyrithione, diquat, disodium tetraborate, disosultap, disparlure, disugran, disul, disulfiram, disulfoton, ditalimfos, dithianon, dithicrofos, dithioether, dithiométon, dithiopyr, diuron, dixanthogen, d-limonene, DMDS, DMPA, DNOC, dodemorph, dodicin, dodine, dofenapyn, doguadine, dominicalure, doramectin, DPC, drazoxolon, DSMA, d-trans-allethrin, d-trans-resmethrin, dufulin, dymron, EBEP, EBP, ebufos, ecdysterone, echlomezol, EDB, EDC, EDDP, edifenphos, eglinazine, emamectin, EMPC, empenthrin, enadenine, endosulfan, endothal, endothall, endothion, endrin, enestroburin, enilconazole, enoxastrobin, ephirsulfonate, EPN, epocholeone, epofenonane, epoxiconazole, eprinomectin, epronaz, EPTC, erbon, ergocalciferol, erlujixiancaoan, esdepallethrine, esfenvalerate, ESP, esprocarb, etacelasil, etaconazole, etaphos, etem, ethaboxam, ethachlor, ethalfluralin, ethametsulfuron, ethaprochlor, ethephon, ethidimuron, ethiofencarb, ethiolate, ethion, ethiozin, ethiprole, ethirimol, ethoatemethyl, ethobenzanid, ethofumesate, ethohexadiol, ethoprop, ethoprophos, ethoxyfen, ethoxyquin, ethoxysulfuron, ethychlozate, ethyl formate, ethyl pyrophosphate, ethylan, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, ETM, etnipromid, etobenzanid, etofenprox, etoxazole, etridiazole, etrimfos, étrimphos, eugenol, EXD, famoxadone, famphur, fenac, fenamidone, fenaminosulf, fenaminstrobin, fenamiphos, fenapanil, fenarimol, fenasulam, fenazaflor, fenazaquin, fenbuconazole, fenbutatin oxide, fenchlorazole, fenchlorphos, fenclofos, fenclorim, fenethacarb, fenfluthrin, fenfuram, fenhexamid, fenidin, fenitropan, fenitrothion, fénizon, fenjuntong, fenobucarb, fenolovo, fenoprop, fenothiocarb, fenoxacrim, fenoxanil, fenoxaprop, fenoxaprop-P, fenoxasulfone, fenoxycarb, fenpiclonil, fenpirithrin, fenpropathrin, fenpropidin, fenpropimorph, fenpyrazamine, fenpyroximate, fenquinotrione, fenridazon, fenson, fensulfothion, fenteracol, fenthiaprop, fenthion, fenthion-ethyl, fentiaprop, fentin, fentrazamide, fentrifanil, fenuron, fenuron-TCA, fenvalerate, ferbam, ferimzone, ferric phosphate, ferrous sulfate, fipronil, flamprop, flamprop-M, flazasulfuron, flocoumafen, flometoquin, flonicamid, florasulam, fluacrypyrim, fluazifop, fluazifop-P, fluazinam, fluazolate, fluazuron, flubendiamide, flubenzimine, flubrocythrinate, flucarbazone, flucetosulfuron, fluchloralin, flucofuron, flucycloxuron, flucythrinate, fludioxonil, fluénéthyl, fluenetil, fluensulfone, flufenacet, flufenerim, flufenican, flufenoxuron, flufenoxystrobin, flufenprox, flufenpyr, flufenzine, flufiprole, fluhexafon, flumethrin, flumetover, flumetralin, flumetsulam, flumezin, flumiclorac, flumioxazin, flumipropyn, flunmorph, fluometuron, fluopicolide, fluopyram, fluorbenside, fluoridamid, fluoroacetamide, fluoroacetic acid, fluorochloridone, fluorodifen, fluoroglycofen, fluoroimide, fluoromide, fluoromidine, fluoronitrofen, fluoroxypyr, fluothiuron, fluotrimazole, fluoxastrobin, flupoxam, flupropacil, flupropadine, flupropanate, flupyradifurone, flupyrsulfuron, fluquinconazole, fluralaner, flurazole, flurecol, flurenol, fluridone, flurochloridone, fluromidine, fluroxypyr, flurprimidol, flursulamid, flurtamone, flusilazole, flusulfamide, flutenzine, fluthiacet, fluthiamide, flutianil, flutolanil, flutriafol, fluvalinate, fluxapyroxad, fluxofenim, folpel, folpet, fomesafen, fonofos, foramsulfuron, forchlorfenuron, formaldehyde, formetanate, formothion, formparanate, fosamine, fosetyl, fosmethilan, fospirate, fosthiazate, fosthietan, frontalin, fthalide, fuberidazole, fucaojing, fucaomi, fujunmanzhi, fulumi, fumarin, funaihecaoling, fuphenthiourea, furalane, furalaxyl, furamethrin, furametpyr, furan tebufenozide, furathiocarb, furcarbanil, furconazole, furconazole-cis, furethrin, furfural, furilazole, furmecyclox, furophanate, furyloxyfen, gamma-BHC, gamma-cyhalothrin, gamma-HCH, genit, gibberellic acid, gibberellin A3, gibberellins, gliftor, glitor, glucochloralose, glufosinate, glufosinate-P, glyodin, glyoxime, glyphosate, glyphosine, gossyplure, grandlure, griseofulvin, guanoctine, guazatine, halacrinate, halauxifen, halfenprox, halofenozide, halosafen, halosulfuron, haloxydine, haloxyfop, haloxyfop-P, haloxyfop-R, HCA, HCB, HCH, hemel, hempa, HEOD, heptachlor, heptafluthrin, heptenophos, heptopargil, herbimycin, herbimycin A, heterophos, hexachlor, hexachloran, hexachloroacetone, hexachlorobenzene, hexachlorobutadiene, hexachlorophene, hexaconazole, hexaflumuron, hexafluoramin, hexaflurate, hexalure, hexamide, hexazinone, hexylthiofos, hexythiazox, HHDN, holosulf, homobrassinolide, huancaiwo, huanchongjing, huangcaoling, huanjunzuo, hydramethylnon, hydrargaphen, hydrated lime, hydrogen cyanamide, hydrogen cyanide, hyprene, hydroxyisoxazole, hymexazol, hyquincarb, IAA, IBA, IBP, icaridin, imazalil, imazamethabenz, imazamox, imazapic, imazapyr, imazaquin, imazethapyr, imazosulfuron, imibenconazole, imicyafos, imidacloprid, imidaclothiz, iminoctadine, imiprothrin, inabenfide, indanofan, indaziflam, indoxacarb, inezin, infusorial earth, iodobonil, iodocarb, iodofenphos, iodomethane, iodosulfuron, iofensulfuron, ioxynil, ipazine, IPC, ipconazole, ipfencarbazone, ipfenfluconazole, iprobenfos, iprodione, iprovalicarb, iprymidam, ipsdienol, ipsenol, IPSP, IPX, isamidofos, isazofos, isobenzan, isocarbamid, isocarbamide, isocarbophos, isocil, isodrin, isofenphos, isofenphos-methyl, isofetamid, isolan, isomethiozin, isonoruron, isopamphos, isopolinate, isoprocarb, isoprocil, isopropalin, isopropazol, isoprothiolane, isoproturon, isopyrazam, isopyrimol, isothioate, isotianil, isouron, isovaledione, isoxaben, isoxachlortole, isoxadifen, isoxaflutole, isoxapyrifop, isoxathion, isuron, ivermectin, ixoxaben, izopamfos, izopamphos, japonilure, japothrins, jasmolin I, jasmolin II, jasmonic acid, jiahuangchongzong, jiajizengxiaolin, jiaxiangjunzhi, jiecaowan, jiecaoxi, Jinganmycin A, jodfenphos, juvenile hormone I, juvenile hormone II, juvenile hormone III, kadethrin, kappa-bifenthrin, kappa-tefluthrin, karbutilate, karetazan, kasugamycin, kejunlin, kelevan, ketospiradox, kieselguhr, kinetin, kinoprene, kiralaxyl, kresoxim-methyl, kuicaoxi, lactofen, lambda-cyhalothrin, latilure, lead arsenate, lenacil, lepimectin, leptophos, lianbenjingzhi, lime sulfur, lindane, lineatin, linuron, lirimfos, litlure, looplure, lufenuron, lüxiancaolin, lvdingjunzhi, lvfumijvzhi, lvxiancaolin, lythidathion, M-74, M-81, MAA, magnesium phosphide, malathion, maldison, maleic hydrazide, malonoben, maltodextrin, MAMA, mancopper, mancozeb, mandestrobin, mandipropamid, maneb, matrine, mazidox, MCC, MCP, MCPA, MCPA-thioethyl, MCPB, MCPP, mebenil, mecarbam, mecarbinzid, mecarphon, mecoprop, mecoprop-P, medimeform, medinoterb, medlure, mefenacet, mefenoxam, mefenpyr, mefluidide, megatomoic acid, melissyl alcohol, melitoxin, MEMC, menazon, MEP, mepanipyrim, meperfluthrin, mephenate, mephosfolan, mepiquat, mepronil, meptyldinocap, mercaptodimethur, mercaptophos, mercaptophos thiol, mercaptothion, mercuric chloride, mercuric oxide, mercurous chloride, merphos, merphos oxide, mesoprazine, mesosulfuron, mesotrione, mesulfen, mesulfenfos, mesulphen, metacresol, metaflumizone, metalaxyl, metalaxyl-M, metaldehyde, metam, metamifop, metamitron, metaphos, metaxon, metazachlor, metazosulfuron, metazoxolon, metconazole, metepa, metflurazon, methabenzthiazuron, methacrifos, methalpropalin, metham, methamidophos, methasulfocarb, methazole, methfuroxam, methibenzuron, methidathion, methiobencarb, methiocarb, methiopyrisulfuron, methiotepa, methiozolin, methiuron, methocrotophos, métholcarb, methometon, methomyl, methoprene, methoprotryn, methoprotryne, methoquin-butyl, methothrin, methoxychlor, methoxyfenozide, methoxyphenone, methyl apholate, methyl bromide, methyl eugenol, methyl iodide, methyl isothiocyanate, methyl parathion, methylacetophos, methylchloroform, methyldithiocarbamic acid, methyldymron, methylene chloride, methyl-isofenphos, methylmercaptophos, methylmercaptophos oxide, methylmercaptophos thiol, methylmercury benzoate, methylmercury dicyandiamide, methylmercury pentachlorophenoxide, methylneodecanamide, methylnitrophos, methyltriazothion, metiozolin, metiram, metiram-zinc, metobenzuron, metobromuron, metofluthrin, metolachlor, metolcarb, metometuron, metominostrobin, metosulam, metoxadiazone, metoxuron, metrafenone, metriam, metribuzin, metrifonate, metriphonate, metsulfovax, metsulfuron, mevinphos, mexacarbate, miechuwei, mieshuan, miewenjuzhi, milbemectin, milbemycin oxime, milneb, mima2nan, mipafox, MIPC, mirex, MNAF, moguchun, molinate, molosultap, momfluorothrin, monalide, monisuron, monoamitraz, monochloroacetic acid, monocrotophos, monolinuron, monomehypo, monosulfiram, monosulfuron, monosultap, monuron, monuron-TCA, morfamquat, moroxydine, morphothion, morzid, moxidectin, MPMC, MSMA, MTMC, musculare, myclobutanil, myclozolin, myricyl alcohol, N-(ethylmercury)-p-toluenesulphonanilide, NAA, NAAm, nabam, naftalofos, naled, naphthalene, naphthaleneacetamide, naphthalic anhydride, naphthalophos, naphthoxyacetic acids, naphthylacetic acids, naphthylindane-1,3-diones, naphthyloxyacetic acids, naproanilide, napropamide, napropamide-M, naptalam, natamycin, NBPOS, neburea, neburon, nendrin, neonicotine, nichlorfos, niclofen, niclosamide, nicobifen, nicosulfuron, nicotine, nicotine sulfate, nifluridide, nikkomycins, NIP, nipyraclofen, nipyralofen, nitenpyram, nithiazine, nitralin, nitrapyrin, nitrilacarb, nitrofen, nitrofluorfen, nitrostyrene, nitrothal-isopropyl, nobormide, nonanol, norbormide, norea, norflurazon, nornicotine, noruron, novaluron, noviflumuron, NPA, nuarimol, nuranone, OCH, octachlorodipropyl ether, octhilinone, o-dichlorobenzene, ofurace, omethoate, o-phenylphenol, orbencarb, orfralure, orthobencarb, ortho-dichlorobenzene, orthosulfamuron, oryctalure, orysastrobin, oryzalin, osthol, osthole, ostramone, ovatron, ovex, oxabetrinil, oxadiargyl, oxadiazon, oxadixyl, oxamate, oxamyl, oxapyrazon, oxapyrazone, oxasulfuron, oxathiapiprolin, oxaziclomefone, oxine-copper, oxine-Cu, oxolinic acid, oxpoconazole, oxycarboxin, oxydemeton-methyl, oxydeprofos, oxydisulfoton, oxyenadenine, oxyfluorfen, oxymatrine, oxytetracycline, oxythioquinox, PAC, paclobutrazol, paichongding, palletthrine, PAP, para-dichlorobenzene, parafluron, paraquat, parathion, parathion-methyl, parinol, Paris green, PCNB, PCP, PCP-Na, p-dichlorobenzene, PDJ, pebulate, pédinex, pefurazoate, pelargonic acid, penconazole, pencycuron, pendimethalin, penfenate, penflufen, penfluron, penoxalin, penoxsulam, pentachlorophenol, pentachlorophenyl laurate, pentanochlor, penthiopyrad, pentmethrin, pentoxazone, perchlordecone, perfluidone, permethrin, pethoxamid, PHC, phenamacril, phenamacril-ethyl, phénaminosulf, phenazine oxide, phénétacarbe, phenisopham, phenkapton, phenmedipham, phenmedipham-ethyl, phenobenzuron, phenothiol, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosametine, phosazetim, phosazetin, phoscyclotin, phosdiphen, phosethyl, phosfolan, phosfolan-methyl, phosglycin, phosmet, phosnichlor, phosphamide, phosphamidon, phosphine, phosphinothricin, phosphocarb, phosphorus, phostin, phoxim, phoxim-methyl, phthalide, phthalophos, phthalthrin, picarbutrazox, picaridin, picloram, picolinafen, picoxystrobin, pimaricin, pindone, pinoxaden, piperalin, piperazine, piperonyl butoxide, piperonyl cyclonene, piperophos, piproctanly, piproctanyl, piprotal, pirimetaphos, pirimicarb, piriminil, pirimioxyphos, pirimiphos-ethyl, pirimiphos-methyl, pival, pivaldione, plifenate, PMA, PMP, polybutenes, polycarbamate, polychlorcamphene, polyethoxyquinoline, polyoxin D, polyoxins, polyoxorim, polythialan, potassium arsenite, potassium azide, potassium cyanate, potassium ethylxanthate, potassium naphthenate, potassium polysulfide, potassium thiocyanate, pp'-DDT, prallethrin, precocene I, precocene II, precocene III, pretilachlor, primidophos, primisulfuron, probenazole, prochloraz, proclonol, procyazine, procymidone, prodiamine, profenofos, profluazol, profluralin, profluthrin, profoxydim, profurite-aminium, proglinazine, prohexadione, prohydrojasmon, promacyl, promecarb, prometon, prometryn, prometryne, promurit, pronamide, propachlor, propafos, propamidine, propamocarb, propanil, propaphos, propaquizafop, propargite, proparthrin, propazine, propetamphos, propham, propiconazole, propidine, propineb, propisochlor, propoxur, propoxycarbazone, propyl isome, propyrisulfuron, propyzamide, proquinazid, prosuler, prosulfalin, prosulfocarb, prosulfuron, prothidathion, prothiocarb, prothioconazole, prothiofos, prothoate, protrifenbute, proxan, prymidophos, prynachlor, psoralen, psoralene, pydanon, pyflubumide, pymetrozine, pyracarbolid, pyracdofos, pyraclonil, pyraclostrobin, pyraflufen, pyrafluprole, pyramat, pyrametostrobin, pyraoxystrobin, pyrasulfotole, pyraziflumid, pyrazolate, pyrazolynate, pyrazon, pyrazophos, pyrazosulfuron, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridaphenthione, pyridate, pyridinitril, pyrifenox, pyrifluquinazon, pyriftalid, pyrimitaphos, pyrinethanil, pyrimicarbe, pyrimidifen, pyrininobac, pyriminostrobin, pyrimiphos-ethyl, pyrimriphos-mthyl, pyrimisulfan, pyrimitate, pyrinuron, pyriofenone, pyriprole, pyripropanol, pyriproxyfen, pyrisoxazole, pyrithiobac, pyrolan, pyroquilon, pyroxasulfone, pyroxsulam, pyroxychlor, pyroxyfur, qincaosuan, qingkuling, quassia, quinacetol, quinalphos, quinalphos-methyl, quinazamid, quinclorac, quinconazole, quinmerac, quinoclamine, quinomethionate, quinonamid, quinothion, quinoxyfen, quintiofos, quintozene, quizalofop, quizalofop-P, quwenzhi, quyingding, rabenzazole, rafoxanide, R-diniconazole, rebemide, reglone, renriduron, rescalure, resmethrin, rhodethanil, rhodojaponin-III, ribavirin, rinsulfuron, rizazole, R-metalaxyl, rodethanil, ronnel, rotenone, ryania, sabadilla, saflufenacil, saijunmao, saisentong, salicylanilide, salifluofen, sanguinarine, santonin, S-bioallethrin, schradan, scilliroside, sebuthylazine, secbumeton, sedaxane, selarectin, semiamitraz, sesamex, sesamolin, sesone, sethoxydim, sevin, shuangjiaancaolin, shuangjianancaolin, S-hydroprene, siduron, sifumijvzhi, siglure, silafluofen, silatrane, silica aerogel, silica gel, silthiofam, silthiopham, silthiophan, silvex, simazine, simeconazole, simeton, simetryn, simetryne, sintofen, S-kinoprene, slaked lime, SMA, S-methoprene, S-metolachlor, sodium arsenite, sodium azide, sodium chlorate, sodium cyanide, sodium fluoride, sodium fluoroacetate, sodium hexafluorosilicate, sodium naphthenate, sodium o-phenylphenoxide, sodium orthophenylphenoxide, sodium pentachlorophenate, sodium pentachlorophenoxide, sodium polysulfide, sodium silicofluoride, sodium tetrathiocarbonate, sodium thiocyanate, solan, sophamide, spinetoram, spinosad, spirodiclofen, spiromesifen, spirotetramat, spiroxamine, stirofos, streptomycin, strychnine, sulcatol, sulcofuron, sulcotrione, sulfallate, sulfentrazone, sulfiram, sulfluramid, sulfodiazole, sulfometuron, sulfosate, sulfosulfuron, sulfotep, sulfotepp, sulfoxaflor, sulfoxide, sulfoxime, sulfur, sulfuric acid, sulfuryl fluoride, sulglycapin, sulphosate, sulprofos, sultropen, swep, tau-fluvalinate, tavron, tazimcarb, TBTO, TBZ, TCA, TCBA, TCMTB, TCNB, TDE, tebuconazole, tebufenozide, tebufenpyrad, tebufloquin, tebupirimfos, tebutam, tebuthiuron, tecloftalam, tecnazene, tecoram, tedion, teflubenzuron, tefluthrin, tefuryltrione, tembotrione, temefos, temephos, tepa, TEPP, tepraloxydim, teproloxydim, terallethrin, terbacil, terbucarb, terbuchlor, terbufos, terbumeton, terbuthylazine, terbutol, terbutryn, terbutryne, terraclor, terramicin, terramycin, tetcyclacis, tetrachloroethane, tetrachlorvinphos, tetraconazole, tetradifon, tetradisul, tetrafluron, tetramethrin, tetramethylfluthrin, tetramine, tetranactin, tetraniliprole, tetrapion, tetrasul, thallium sulfate, thallous sulfate, thenylchlor, theta-cypermethrin, thiabendazole, thiacloprid, thiadiazine, thiadifluor, thiamethoxam, thiameturon, thiapronil, thiazafluron, thiazfluron, thiazone, thiazopyr, thicrofos, thicyofen, thidiazimin, thidiazuron, thiencarbazone, thifensulfuron, thifluzamide, thimerosal, thimet, thiobencarb, thiocarboxime, thiochlorfenphim, thiochlorphenphime, thiocyanatodinitrobenzenes, thiocyclam, thiodan, thiodiazole-copper, thiodicarb, thiofanocarb, thiofanox, thiofluoximate, thiohempa, thiomersal, thiometon, thionazin, thiophanate, thiophanate-ethyl, thiophanate-methyl, thiophos, thioquinox, thiosemicarbazide, thiosultap, thiotepa, thioxamyl, thiram, thiuram, thuringiensin, tiabendazole, tiadinil, tiafenacil, tiaojiean, TIBA, tifatol, tiocarbazil, tioclorim, tioxazafen, tioxymid, tirpate, TMTD, tolclofosmethyl, tolfenpyrad, tolprocarb, tolpyralate, tolyfluanid, tolylfluanid, tolylmercury acetate, tomarin, topramezone, toxaphene, TPN, tralkoxydim, tralocythrin, tralomethrin, tralopyril, transfluthrin, transpermethrin, tretamine, triacontanol, triadimefon, triadimenol, triafamone, triallate, triallate, triamiphos, triapenthenol, triarathene, triarimol, triasulfuron, triazamate, triazbutil, triaziflam, triazophos, triazothion, triazoxide, tribasic copper chloride, tribasic copper sulfate, tribenuron, tribufos, tributyltin oxide, tricamba, trichlamide, trichlopyr, trichlorfon, trichlormetaphos-3, trichloronat, trichloronate, trichlorotrinitrobenzenes, trichlorphon, triclopyr, triclopyricarb, tricresol, tricyclazole, tricyclohexyltin hydroxide, tridemorph, tridiphane, trietazine, trifenmorph, trifenofos, trifloxystrobin, trifloxysulfuron, trifludirnmoxazin, triflumezopyrim, triflumizole, triflumuron, tarifurausulfuronn, triflusulfuron, trifop, trifopsime, triforine, trihydroxytriazine, trimedlure, trimethacarb, trimeturon, trinexapac, triphenyltin, triprene, tripropindan, triptolide, tritac, trithialan, triticonazole, tritosulfuron, trunccall, tuoyelin, uniconazole, uniconazole-P, urbacide, uredepa, valerate, validamycin, validamycin A, valifenalate, valone, varnidothion, vangard, vaniliprole, vernolate, vinclozolin, vitamin D3, warfarin, xiaochongliulin, xinjunan, xiwojunan, xiwojunzhi, XMC, xylachlor, xylenols, xylylcarb, xymiazole, yishijing, zarilamid, zeatin, zengxiaoan, zengxiaolin, zeta-cypermethrin, zinc naphthenate, zinc phosphide, zinc thiazole, zinc thiozole, zinc trichlorophenate, zinc trichlorophenoxide, zineb, ziram, zolaprofos, zoocoumarin, zoxamide, zuoanjunzhi, zuocaoan, zuojunzhi, zuomihuanglong, α-chlorohydrin, α-ecdysone, α-multistristriatin, α-naphthaleneacetic acids, and β-ecdysone;

(2) the following molecule

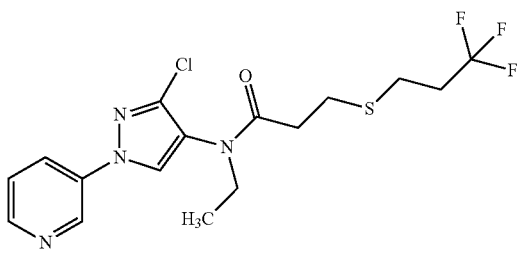 [SMILES: CCN(C(=O)CCSCCC(F)(F)F)c1cn(-c2cccnc2)nc1Cl]

N-(3-chloro-1-(pyridin-3-yl)-1H-pyrazol-4-yl)-N-ethyl-3-((3,3,3-trifluoropropyl)thio)propanamide In this document, this molecule, for ease of use, is named as "AI-1;"

(3) a molecule known as Lotilaner which has the following structure

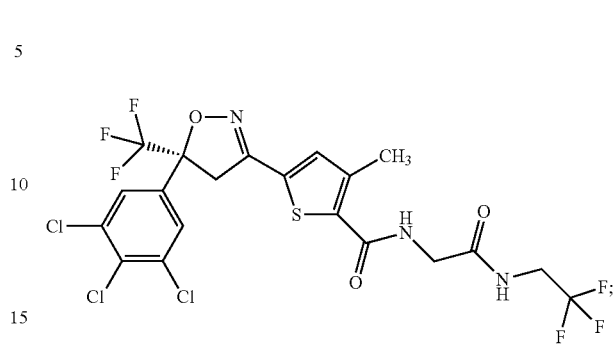

and (4) the following molecules in Table A

TABLE A

| Structure of M - active ingredients | |
|---|---|
| Name | Structure |
| M1 | 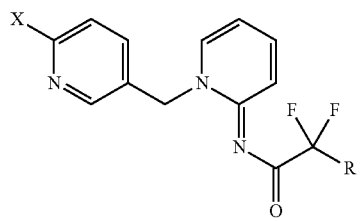 <br> R = CH, N <br> R₁ = H, Me |
| M2 | 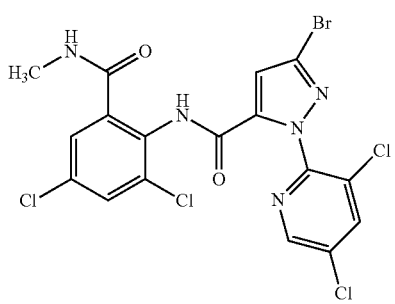 [SMILES: CNC(=O)c1cc(Cl)cc(Cl)c1NC(=O)c1cc(Br)nn1-c1ncc(Cl)cc1Cl] <br> X = F, Cl <br> R = H, F |
| M3 | |

TABLE A-continued

Structure of M - active ingredients

| Name | Structure |
|------|-----------|
| M4 | 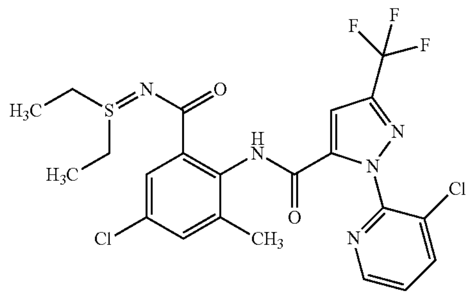 [SMILES: CCS(CC)=NC(=O)c1cc(Cl)cc(C)c1NC(=O)c1cc(C(F)(F)F)nn1-c1ncccc1Cl] |
| M5 | 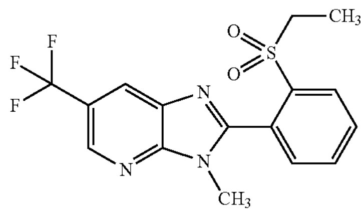 [SMILES: CCS(=O)(=O)c1ccccc1-c1nc2cc(C(F)(F)F)cnc2n1C] |
| M6 | 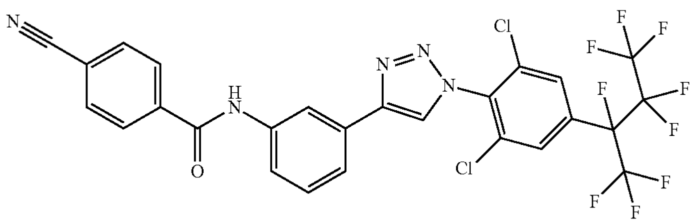 [SMILES: N#Cc1ccc(C(=O)Nc2cccc(-c3cn(-c4c(Cl)cc(C(F)(C(F)(F)F)C(F)(F)C(F)(F)F)cc4Cl)nn3)c2)cc1] |

As used in this disclosure, each of the above is an active ingredient, and two or more are active ingredients. For more information consult the "COMPENDIUM OF PESTICIDE COMMON NAMES" located at Alanwood.net and various editions, including the on-line edition, of "THE PESTICIDE MANUAL" located at bcpcdata.com.

The term "alkenyl" means an acyclic, unsaturated (at least one carbon-carbon double bond), branched or unbranched, substituent consisting of carbon and hydrogen, for example, vinyl, allyl, butenyl, pentenyl, and hexenyl.

The term "alkenyloxy" means an alkenyl further consisting of a carbon-oxygen single bond, for example, allyloxy, butenyloxy, pentenyloxy, hexenyloxy.

The term "alkoxy" means an alkyl further consisting of a carbon-oxygen single bond, for example, methoxy, ethoxy, propoxy, isopropoxy, butoxy, isobutoxy, and tert-butoxy.

The term "alkyl" means an acyclic, saturated, branched or unbranched, substituent consisting of carbon and hydrogen, for example, methyl, ethyl, propyl, isopropyl, butyl, and tert-butyl.

The term "alkynyl" means an acyclic, unsaturated (at least one carbon-carbon triple bond), branched or unbranched, substituent consisting of carbon and hydrogen, for example, ethynyl, propargyl, butynyl, and pentynyl.

The term "alkynyloxy" means an alkynyl further consisting of a carbon-oxygen single bond, for example, pentynyloxy, hexynyloxy, heptynyloxy, and octynyloxy.

The term "aryl" means a cyclic, aromatic substituent consisting of hydrogen and carbon, for example, phenyl, naphthyl, and biphenyl.

The term "biopesticide" means a microbial biological pest control agent which, in general, is applied in a similar manner to chemical pesticides. Commonly they are bacterial, but there are also examples of fungal control agents, including *Trichoderma* spp. and *Ampelomyces quisqualis*. One well-known biopesticide example is *Bacillus thuringiensis*, a bacterial disease of Lepidoptera, Coleoptera, and Diptera. Biopesticides include products based on:

(1) entomopathogenic fungi (e.g. *Metarhizium anisopliae*);

(2) entomopathogenic nematodes (e.g. *Steinernema feltiae*); and (3) entomopathogenic viruses (e.g. *Cydia pomonella* granulovirus).

Other examples of entomopathogenic organisms include, but are not limited to, baculoviruses, protozoa, and Microsporidia. For the avoidance of doubt biopesticides are considered to be active ingredients.

The term "cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, norbornenyl, bicyclo[2.2.2]octenyl, tetrahydronaphthyl, hexahydronaphthyl, and octahydronaphthyl.

The term "cycloalkenyloxy" means a cycloalkenyl further consisting of a carbon-oxygen single bond, for example, cyclobutenyloxy, cyclopentenyloxy, norbornenyloxy, and bicyclo[2.2.2]octenyloxy.

The term "cycloalkyl" means a monocyclic or polycyclic, saturated substituent consisting of carbon and hydrogen, for example, cyclopropyl, cyclobutyl, cyclopentyl, norbornyl, bicyclo[2.2.2]octyl, and decahydronaphthyl.

The term "cycloalkoxy" means a cycloalkyl further consisting of a carbon-oxygen single bond, for example, cyclopropyloxy, cyclobutyloxy, cyclopentyloxy, norbornyloxy, and bicyclo[2.2.2]octyloxy.

The term "halo" means fluoro, chloro, bromo, and iodo.

The term "haloalkoxy" means an alkoxy further consisting of, from one to the maximum possible number of identical or different, halos, for example, fluoromethoxy, trifluoromethoxy, 2,2-difluoropropoxy, chloromethoxy, trichloromethoxy, 1,1,2,2-tetrafluoroethoxy, and pentafluoroethoxy.

The term "haloalkyl" means an alkyl further consisting of, from one to the maximum possible number of, identical or different, halos, for example, fluoromethyl, trifluoromethyl, 2,2-difluoropropyl, chloromethyl, trichloromethyl, and 1,1,2,2-tetrafluoroethyl.

The term "heterocyclyl" means a cyclic substituent that may be aromatic, fully saturated, or partially or fully unsaturated, where the cyclic structure contains at least one carbon and at least one heteroatom, where said heteroatom is nitrogen, sulfur, or oxygen. Examples are:

(1) aromatic heterocyclyl substituents include, but are not limited to, benzofuranyl, benzoisothiazolyl, benzoisoxazolyl, benzoxazolyl, benzothienyl, benzothiazolyl cinnolinyl, furanyl, indazolyl, indolyl, imidazolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, and triazolyl;

(2) fully saturated heterocyclyl substituents include, but are not limited to, piperazinyl, piperidinyl, morpholinyl, pyrrolidinyl, tetrahydrofuranyl, and tetrahydropyranyl;

(3) partially or fully unsaturated heterocyclyl substituents include, but are not limited to, 1,2,3,4-tetrahydro-quinolinyl, 4,5-dihydro-oxazolyl, 4,5-dihydro-1H-pyrazolyl, 4,5-dihydro-isoxazolyl, and 2,3-dihydro-[1,3,4]-oxadiazolyl; and (4) Additional examples of heterocyclyls include the following:

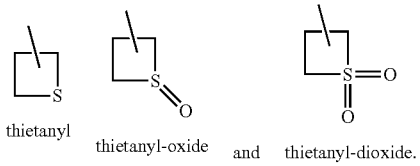

thietanyl     thietanyl-oxide     and     thietanyl-dioxide.

The term "locus" means a habitat, breeding ground, plant, seed, soil, material, or environment, in which a pest is growing, may grow, or may traverse, for example, a locus may be: where crops, trees, fruits, cereals, fodder species, vines, turf, and/or ornamental plants are growing; where domesticated animals are residing; the interior or exterior surfaces of buildings (such as places where grains are stored); the materials of construction used in buildings (such as impregnated wood); and the soil around buildings.

The phrase "MoA Material" means a material having a mode of action ("MoA") as indicated in IRAC MoA Classification v. 7.3, located at irac-online.org., which describes:

(1) Acetylcholinesterase (AChE) inhibitors;
(2) GABA-gated chloride channel antagonists;
(3) Sodium channel modulators;
(4) Nicotinic acetylcholine receptor (nAChR) agonists;
(5) Nicotinic acetylcholine receptor (nAChR) allosteric activators;
(6) Chloride channel activators;
(7) Juvenile hormone mimics;
(8) Miscellaneous nonspecific (multi-site) inhibitors;
(9) Modulators of Chordotonal Organs;
(10) Mite growth inhibitors;
(11) Microbial disruptors of insect midgut membranes;
(12) Inhibitors of mitochondrial ATP synthase;
(13) Uncouplers of oxidative phosphorylation via disruption of the proton gradient;
(14) Nicotinic acetylcholine receptor (nAChR) channel blockers;
(15) Inhibitors of chitin biosynthesis, type 0;
(16) Inhibitors of chitin biosynthesis, type 1;
(17) Moulting disruptor, Dipteran;
(18) Ecdysone receptor agonists;
(19) Octopamine receptor agonists;
(20) Mitochondrial complex III electron transport inhibitors;
(21) Mitochondrial complex I electron transport inhibitors;
(22) Voltage-dependent sodium channel blockers;
(23) Inhibitors of acetyl CoA carboxylase;
(24) Mitochondrial complex IV electron transport inhibitors;
(25) Mitochondrial complex II electron transport inhibitors; and
(28) Ryanodine receptor modulators.

The phrase "MoA material group alpha" (hereafter "MoAMGA") means collectively the following materials, abamectin, acephate, acequinocyl, acetamiprid, acrinathrin, alanycarb, aldicarb, allethrin, alpha-cypermethrin, aluminium phosphide, amitraz, azamethiphos, azinphos-ethyl, azinphos-methyl, azocyclotin, bendiocarb, benfuracarb, bensultap, beta-cyfluthrin, beta-cypermethrin, bifenthrin, bioallethrin, bioallethrin S-cyclopentenyl isomer, bioresmethrin, bistrifluron, borax, buprofezin, butocarboxim, butoxycarboxim, cadusafos, calcium phosphide, carbaryl, carbofuran, carbosulfan, cartap hydrochloride, chlorantraniliprole, chlordane, chlorethoxyfos, chlorfenapyr, chlorfenvinphos, chlorfluazuron, chlormephos, chloropicrin, chlorpyrifos, chlorpyrifos-methyl, chromafenozide, clofentezine, clothianidin, coumaphos, cyanide, cyanophos, cyantraniliprole, cycloprothrin, cyenopyrafen, cyflumetofen, cyfluthrin, cyhalothrin, cyhexatin, cypermethrin, cyphenothrin, cyromazine, d-cis-trans-allethrin, DDT, deltamethrin, demeton-S-methyl, diafenthiuron, diazinon, dichlorvos/DDVP, dicrotophos, diflovidazin, diflubenzuron, dimethoate, dimethylvinphos, dinotefuran, disulfoton, DNOC, d-trans-allethrin, emamectin benzoate, empenthrin, endosulfan, EPN, esfenvalerate, ethiofencarb, ethion, ethoprophos, etofenprox, etoxazole, famphur, fenamiphos, fenazaquin, fenbutatin oxide, fenitrothion, fenobucarb, fenoxycarb, fenpropathrin, fenpyroximate, fenthion, fenvalerate, flonicamid, fluacrypyrim, flubendiamide, flucycloxuron, flucythrinate, flufenoxuron, flumethrin, flupyradifurone, formetanate, fosthiazate, furathiocarb, gamma-cyhalothrin, halfenprox, halofenozide, heptenophos, hexaflumuron, hexythiazox, hydramethylnon, hydroprene, imicyafos, imidacloprid, imiprothrin, indoxacarb, isofenphos, isoprocarb, isoxathion, kadethrin, kinoprene, lambda-cyhalothrin, lepimectin, lufenuron, malathion, mecarbam, metaflumizone, methamidophos, methidathion, methiocarb, methomyl, methoprene, (methoxyaminothio-phosphoryl) salicylate, methoxychlor, methoxyfenozide, methyl bromide, metolcarb, mevinphos, milbemectin, monocrotophos, naled, nicotine, nitenpyram, novaluron, noviflumuron, oxamyl, oxydemeton-methyl, parathion, parathion-methyl, permethrin, phenothrin, phenthoate, phorate, phosalone, phosmet, phosphamidon, phosphine, phoxim, pirimicarb, pirimiphos-methyl, prallethrin, profenofos, propargite, propetamphos, propoxur, prothiofos, pymetrozine, pyraclofos, pyrethrin, pyridaben, pyridaphenthion, pyrimidifen, pyriproxyfen, quinalphos, resmethrin, rotenone, silafluofen, spinetoram, spinosad, spirodiclofen, spiromesifen, spirotetramat, sulfluramid, sulfotep, sulfoxaflor, sulfuryl fluoride, tartar emetic, tau-fluvalinate, tebufenozide, tebufenpyrad, tebupirimfos, teflubenzuron, tefluthrin, temephos, terbufos, tetrachlorvinphos, tetradifon, tetramethrin, tetramethrin, theta-cypermethrin, thiacloprid, thiamethoxam, thiocyclam, thiodicarb, thiofanox, thiometon, thiosultap-sodium, tolfenpyrad, tralomethrin, transfluthrin, triazamate, triazophos, trichlorfon, triflumuron, trimethacarb, vamidothion, XMC, xylylcarb, zeta-cypermethrin, and zinc phosphide. For the avoidance of doubt, each of the foregoing materials is an active ingredient.

The term "pest" means an organism that is detrimental to humans, or human concerns (such as, crops, food, livestock, etc.), where said organism is from Phyla Arthropoda, Mollusca, or Nematoda, particular examples are ants, aphids, beetles, bristletails, cockroaches, crickets, earwigs, fleas, flies, grasshoppers, leafhoppers, lice (including sea lice), locusts, mites, moths, nematodes, scales, symphylans, termites, thrips, ticks, wasps, and whiteflies, additional examples are pests in:

(1) Subphyla Chelicerata, Myriapoda, Crustacea, and Hexapoda;

(2) Classes of Arachnida, Maxillopoda, Symphyla, and Insecta;

(3) Order Anoplura. A non-exhaustive list of particular genera includes, but is not limited to, *Haematopinus* spp., *Hoplopleura* spp., *Linognathus* spp., *Pediculus* spp., and *Polyplax* spp. A non-exhaustive list of particular species includes, but is not limited to, *Haematopinus asini, Haematopinus suis, Linognathus setosus, Linognathus ovillus, Pediculus humanus capitis, Pediculus humanus humanus,* and *Pthirus pubis.*

(4) Order Coleoptera. A non-exhaustive list of particular genera includes, but is not limited to, *Acanthoscelides* spp., *Agriotes* spp., *Anthonomus* spp., *Apion* spp., *Apogonia* spp., *Aulacophora* spp., *Bruchus* spp., *Cerosterna* spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Hypera* spp., *Ips* spp., *Lyctus* spp., *Ips* spp., *Lyctus* spp., *Megascelis* spp., *Meligethes* spp., *Otiorhynchus* spp., *Otiorhynchus* spp., *Pantomorus* spp., *Phyllophaga* spp., *Phyllotreta* spp., *Rhizotrogus* spp., *Rhynchites* spp., *Rhynchophorus* spp., *Scolytus* spp., *Sphenophorus* spp., *Sitophilus* spp., and *Tribolium* spp. A non-exhaustive list of particular species includes, but is not limited to, *Acanthoscelides obtectus, Agrilus planipennis, Anoplophora glabripennis, Anthonomus grandis, Ataenius spretulus, Atomaria linearis, Bothynoderes punctiventris, Bruchus pisorum, Callosobruchus maculatus, Carpophilus hemipterus, Cassida vittata, Cerotoma trifurcata, Ceutorhynchus assimilis, Ceutorhynchus napi, Conoderus scalaris, Conoderus stigmosus, Conotrachelus nenuphar, Cotinis nitida, Crioceris asparagi, Cryptolestes ferrugineus, Cryptolestes pusillus, Cryptolestes turcicus, Cylindrocopturus adspersus, Deporaus marginatus, Dermestetes lardarius, Dermestes maculatus, Epilachna varivestis, Faustinus cubae, Hylobius pales, Hypera postica, Hypothenemus hampei, Lasioderma serricorne, Leptinotarsa decemlineata, Liogenys fuscus, Liogenys suturalis, Lissorhoptrus oryzophilus, Maecolaspis joliveti, Melanotus communis, Meligethes aeneus, Melolontha melolontha, Oberea brevis, Oberea linearis, Oryctes rhinoceros, Oryzaephilus mercator, Oryzaephilus surinamensis, Oulema melanopus, Oulema oryzae, Phylophaga cuyabana, Popillia japonica, Prostephanus truncatus, Rhyzopertha dominica, Sitona lineatus, Sitophilus granarius, Sitophilus oryzae, Sitophilus zeamais, Stegobium paniceum, Tribolium castaneum, Tribolium confusum, Trogoderma variabile,* and *Zabrus tenebrioides.*

(5) Order Dermaptera. A non-exhaustive list of particular species includes, but is not limited to, *Forficula auricularia.*

(6) Order Blattaria. A non-exhaustive list of particular species includes, but is not limited to, *Blattella germanica, Blatta orientalis, Parcoblatta pennsylvanica, Periplaneta americana, Periplaneta australasiae, Periplaneta brunnea, Periplaneta fuliginosa, Pycnoscelus surinamensis,* and *Supella longipalpa.*

(7) Order Diptera. A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Dasineura* spp., *Delia* spp., *Drosophila* spp., spp., *Fannia* spp., *Hylemyia* spp., *Liriomyza* spp., *Musca* spp., *Phorbia* spp., *Tabanus* spp., and *Tipula* spp. A non-exhaustive list of particular species includes, but is not limited to, *Agromyza frontella, Anastrepha suspensa, Anastrepha ludens, Anastrepha obliqa, Bactrocera cucurbitae, Bactrocera dorsalis, Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza brassicae, Melophagus ovinus, Musca autumnalis, Musca domestica, Oestrus ovis, Oscinella frit, Pegomya betae, Psila rosae, Rhagoletis cerasi, Rhagoletis pomonella, Rhagoletis mendax, Sitodiplosis mosellana,* and *Stomoxys calcitrans.*

(8) Order Hemiptera. A non-exhaustive list of particular genera includes, but is not limited to, *Adelges* spp., *Aulacaspis* spp., *Aphrophora* spp., *Aphis* spp., *Bemisia* spp., *Ceroplastes* spp., *Chionaspis* spp., *Chrysomphalus* spp., *Coccus* spp., *Empoasca* spp., *Lepidosaphes* spp., *Lagynotomus* spp., *Lygus* spp., *Macrosiphum* spp., *Nephotettix* spp., *Nezara* spp., *Philaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp. and *Unaspis* spp. A non-exhaustive list of particular species includes, but is not limited to, *Acrosternum hilare, Acyrthosiphon pisum, Aleyrodes proletella, Aleurodicus dispersus, Aleurothrixus floccosus, Amrrasca biguttula biguttula, Aonidiella aurantil, Aphis gossypii, Aphis glycines, Aphis pomi, Aulacorthum solani, Bemisia argentifolii, Bemisia tabaci, Blissus leucopterus, Brachycorynella asparagi, Brevennia rehi, Brevicoryne brassicae, Calocoris norvegicus, Ceroplastes rubens, Cimex hemipterus, Cimex lectularius, Dagbertus fasciatus, Dichelops furcatus, Diuraphis noxia, Diaphorina citri, Dysaphis plantaginea, Dysdercus suturellus, Edessa meditabunda, Eriosoma lanigerum, Eurygaster maura, Euschistus heros, Euschistus servus, Helopeltis antonii, Helopeltis theivora, Icerya purchasi, Idioscopus nitidulus, Laodelphax striatellus, Leptocorisa oratorius, Leptocorisa varicornis, Lygus hesperus, Maconellicoccus hirsutus, Macrosiphum euphorbae, Macrosiphumrn granarium, Macrosphumrn rosae, Macrosteles quadrilineatus, Mahanarva frimbiolata, Metopolophium dirhodum, Mictis longicornis, Myzus persicae, Nephotettix cinctipes, Neurocolpus longi-*

*rostris, Nezara viridula, Nilaparvata lugens, Parlatoria pergandii, Parlatoria ziziphi, Peregrinus maidis, Phylloxera vitifoliae, Physokermes piceae, Phytocoris californicus, Phytocoris relativus, Piezodorus guildinii, Poecilocapsus lineatus, Psallus vaccinicola, Pseudacysta perseae, Pseudococcus brevipes, Quadraspidiotus perniciosus, Rhopalosiphumrn maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis,* and *Zulia entrerriana.*

(9) Order Hymenoptera. A non-exhaustive list of particular genera includes, but is not limited to, *Acromyrmex* spp., *Atta* spp., *Camponotus* spp., *Diprion* spp., *Formica* spp., *Monomorium* spp., *Neodiprion* spp., *Pogonomyrmex* spp., *Polistes* spp., *Solenopsis* spp., *Vespula* spp., and *Xylocopa* spp. A non-exhaustive list of particular species includes, but is not limited to, *Athalia rosae, Atta texana, Iridomyrmex humilis, Monomorium minimum, Monomorium pharaonis, Solenopsis invicta, Solenopsis geminata, Solenopsis molesta, Solenopsis richteryi, Solenopsis xyloni,* and *Tapinoma sessile.*

(10) Order Isoptera. A non-exhaustive list of particular genera includes, but is not limited to, *Coptotermes* spp., *Cornitermes* spp., *Cryptotermes* spp., *Heterotermes* spp., *Kalotermes* spp., *Incisitermes* spp., *Macrotermes* spp., *Marginitermes* spp., *Microcerotermes* spp., *Procornitermes* spp., *Reticulitermes* spp., *Schedorhinotermes* spp., and *Zootermopsis* spp. A non-exhaustive list of particular species includes, but is not limited to, *Coptotermes curvignathus, Coptotermes frenchi, Coptotermes formosanus, Heterotermes aureus, Microtermes obesi, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis,* and *Reticulitermes virginicus.*

(11) Order Lepidoptera. A non-exhaustive list of particular genera includes, but is not limited to, *Adoxophyes* spp., *Agrotis* spp., *Argyrotaenia* spp., *Cacoecia* spp., *Caloptilia* spp., *Chilo* spp., *Chrysodeixis* spp., *Colias* spp., *Crambus* spp., *Diaphania* spp., *Diatraea* spp., *Earias* spp., *Ephestia* spp., *Epimecis* spp., *Feltia* spp., *Gortyna* spp., *Helicoverpa* spp., *Heliothis* spp., *Indarbela* spp., *Lithocolletis* spp., *Loxagrotis* spp., *Malacosoma* spp., *Peridroma* spp., *Phyllonorycter* spp., *Pseudaletia* spp., *Sesamia* spp., *Spodoptera* spp., *Synanthedon* spp., and *Yponomeuta* spp. A non-exhaustive list of particular species includes, but is not limited to, *Achaea janata, Adoxophyes orana, Agrotis ipsilon, Alabama argillacea, Amorbia cuneana, Amyelois transitella, Anacamptodes defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia transversa, Choristoneura rosaceana, Cnaphalocrocis medinalis, Conopomorpha cramerella, Cossus cossus, Cydia caryana, Cydia funebrana, Cydia molest, Cydia nigricana, Cydia nigricana, Cydia pomonella, Darna diducta, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Eupoecilia ambiguella, Euxoa auxiliaris, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia clerkella, Mahasena corbetti, Mamestra brassicae, Maruca testulalis, Metisa plana, Mythimna unipruncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phtlhorimaea operculella, Phyllocnistis citrella, Pieris rapae, Plathypena scabra, Plodia interpunctella, Plutella xylostella, Polychrosis viteana, Prays endocarpa, Prays oleae, Pseudaletia unipuncta, Pseudoplusia includens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda, Spodoptera eridania, Thecla basilides, Tineola bisselliella, Trichoplusia ni, Tuta absoluta, Zeuzera coffeae,* and *Zeuzera pyrina;*

(12) Order Mallophaga. A non-exhaustive list of particular genera includes, but is not limited to, *Anaticola* spp., *Bovicola* spp., *Chelopistes* spp., *Goniodes* spp., *Menacanthus* spp., and *Trichodectes* spp. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gallinae,* and *Trichodectes canis.*

(13) Order Orthoptera. A non-exhaustive list of particular genera includes, but is not limited to, *Melanoplus* spp., and *Pterophylla* spp. A non-exhaustive list of particular species includes, but is not limited to, *Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria,* and *Scudderia furcata.*

(14) Order Siphonaptera. A non-exhaustive list of particular species includes, but is not limited to, *Ceratophyllus gallinae, Ceratophyllus niger, Ctenocephalides canis, Cocephalides Canis, Ctenocephalides felis,* and *Pulex irritans.*

(15) Order Siphonostomatoida. A non-exhaustive list of particular species includes, but is not limited to, *Lepeophtheirus salmonis, Lepeophtheirus pectoralis, Caligus elongatus,* and *Caligus clemensi.*

(16) Order Thysanoptera. A non-exhaustive list of particular genera includes, but is not limited to, *Caliothrips* spp., *Frankliniella* spp., *Scirtothrips* spp., and *Thrips* spp. A non-exhaustive list of particular species includes, but is not limited to, *Frankliniella fusca, Frankliniella occidentalis, Frankliniella schultzei, Frankliniella williamsi, Heliothrips haemorrhoidalis, Rhipiphorothrips cruentatus, Scirtothrips citri, Scirtothrips dorsalis, Taeniothrips rhopalantennalis, Thrips hawaiiensis, Thrips nigropilosus, Thrips orientalis,* and *Thrips tabaci.*

(17) Order Thysanura. A non-exhaustive list of particular genera includes, but is not limited to, *Lepisma* spp. and *Thermobia* spp.

(18) Order Acarina. A non-exhaustive list of particular genera includes, but is not limited to, *Acarus* spp., *Aculops* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp. A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Notoedres cati, Oligonychus coffeae, Oligonychus ilicis, Panonychus citri, Panonychus ulmi, Phyllocoptruta oleivora, Polyphagotarsonemus latus, Rhipicephalus san-*

*guineus, Sarcoptes scabiei, Tegolophus perseaflorae, Tetranychus urticae*, and *Varroa destructor*.

(19) Order Symphyla. A non-exhaustive list of particular species includes, but is not limited to, *Scutigerella immaculata*.

(20) Phylum Nematoda. A non-exhaustive list of particular genera includes, but is not limited to, *Aphelenchoides* spp., *Belonolaimus* spp., *Criconemella* spp., *Ditylenchus* spp., *Heterodera* spp., *Hirschmanniella* spp., *Hoplolaimus* spp., *Meloidogyne* spp., *Pratylenchus* spp., and *Radopholus* spp. A non-exhaustive list of particular sp. includes, but is not limited to, *Dirofilaria immitis, Heterodera zeae, Meloidogyne incognita, Meloidogyne javanica, Onchocerca volvulus, Radopholus similis*, and *Rotylenchulus reniformis*.

The phrase "pesticidally effective amount" means the amount of a pesticide needed to achieve an observable effect on a pest, for example, the effects of necrosis, death, retardation, prevention, removal, destruction, or otherwise diminishing the occurrence and/or activity of a pest in a locus, this effect may come about when, pest populations are repulsed from a locus, pests are incapacitated in, or around, a locus, and/or pests are exterminated in, or around, a locus. Of course, a combination of these effects can occur. Generally, pest populations, activity, or both are desirably reduced more than fifty percent, preferably more than 90 percent, and most preferably more than 99 percent. In general a pesticidally effective amount, for agricultural purposes, is from about 0.0001 grams per hectare to about 5000 grams per hectare, preferably from about 0.0001 grams per hectare to about 500 grams per hectare, and it is even more preferably from about 0.0001 grams per hectare to about 50 grams per hectare.

DETAILED DESCRIPTION OF THE DISCLOSURE

This document discloses molecules of Formula One

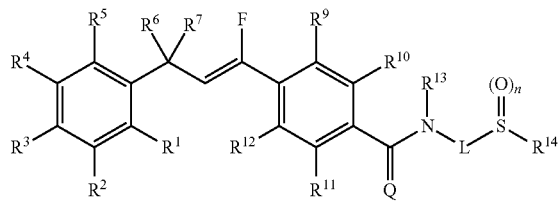

Formula One wherein:

(A) $R^1$, $R^5$, $R^6$, $R^{11}$, $R^{12}$, and $R^{13}$ are each independently selected from the group consisting of H, F, Cl, Br, I, CN, $(C_1$-$C_4)$alkyl, $(C_1$-$C_4)$haloalkyl, $(C_1$-$C_4)$alkoxy, and $(C_1$-$C_4)$haloalkoxy;

(B) $R^2$, $R^3$, and $R^4$ are each independently selected from the group consisting of H, F, Cl, Br, I, CN, $(C_1$-$C_4)$alkyl, $(C_2$-$C_4)$alkenyl, $(C_2$-$C_4)$alkynyl, $(C_1$-$C_4)$haloalkyl, $(C_1$-$C_4)$alkoxy, and $(C_1$-$C_4)$haloalkoxy;

(C) $R^7$ is $(C_1$-$C_6)$haloalkyl;

(D) $R^9$ is selected from the group consisting of (F), H, F, Cl, Br, I, CN, $(C_1$-$C_4)$alkyl, $(C_1$-$C_4)$haloalkyl, $(C_1$-$C_4)$alkoxy, and $(C_1$-$C_4)$haloalkoxy;

(E) $R^{10}$ is selected from the group consisting of (F), F, Cl, Br, I, CN, $(C_1$-$C_4)$alkyl, $(C_2$-$C_4)$alkenyl, $(C_2$-$C_4)$alkynyl, $(C_1$-$C_4)$haloalkyl, $(C_1$-$C_4)$alkoxy, and $(C_1$-$C_4)$haloalkoxy;

(F) $R^9$ and $R^{10}$ together can optionally form a 3- to 5-membered saturated or unsaturated, hydrocarbyl link, wherein said hydrocarbyl link may optionally be substituted with one or more substituents independently selected from the group consisting of F, Cl, Br, I, and CN;

(G) Q is selected from the group consisting of O or S;

(H) L is $(C_1$-$C_6)$alkyl;

(I) n is 0, 1, or 2;

(J) $R^{14}$ is selected from the group consisting of $(C_1$-$C_4)$alkyl, $(C_2$-$C_4)$alkenyl, $(C_3$-$C_4)$cycloalkyl, $(C_1$-$C_4)$haloalkyl, $(C_1$-$C_4)$alkoxy, $(C_1$-$C_4)$haloalkoxy, and phenyl, wherein each alkyl, alkenyl, cycloalkyl, haloalkyl, alkoxy, haloalkoxy, and phenyl may optionally be substituted with one or more substituents independently selected from the group consisting of F, Cl, Br, I, CN, and OH; and agriculturally acceptable acid addition salts, salt derivatives, solvates, ester derivatives, crystal polymorphs, isotopes, resolved stereoisomers, and tautomers, of the molecules of Formula One.

In another embodiment $R^1$, $R^3$, $R^4$, $R^5$, $R^6$, $R^9$, $R^{11}$, $R^{12}$, and $R^{13}$ are H. This embodiment may be used in combination with the other embodiments of $R^2$, $R^7$, $R^{10}$, Q, L, n, and $R^{14}$.

In another embodiment $R^2$ is Cl, Br, or $CH_3$. This embodiment may be used in combination with the other embodiments of $R^1$, $R^3$, $R^4$, $R^5$, $R^6$, $R^7$, $R^9$, $R^{10}$, $R^{11}$, $R^{12}$, Q, $R^{13}$, L, n, and $R^{14}$.

In another embodiment $R^3$ is F, Cl, Br, or $CH=CH_2$. This embodiment may be used in combination with the other embodiments of $R^1$, $R^2$, $R^4$, $R^5$, $R^6$, $R^7$, $R^9$, $R^{10}$, $R^{11}$, $R^{12}$, Q, $R^{13}$, L, n, and $R^{14}$.

In another embodiment $R^4$ is Cl, Br, or $CH_3$. This embodiment may be used in combination with the other embodiments of $R^1$, $R^2$, $R^3$, $R^5$, $R^6$, $R^7$, $R^9$, $R^{10}$, $R^{11}$, $R^{12}$, Q, $R^{13}$, L, n, and $R^{14}$.

In another embodiment $R^2$, $R^3$, and $R^4$ are Cl. This embodiment may be used in combination with the other embodiments of $R^1$, $R^5$, $R^6$, $R^7$, $R^9$, $R^{10}$, $R^{11}$, $R^{12}$, Q, $R^{13}$, L, n, and $R^{14}$.

In another embodiment $R^7$ is $(C_1$-$C_6)$haloalkyl. This embodiment may be used in combination with the other embodiments of $R^1$, $R^2$, $R^3$, $R^4$, $R^5$, $R^6$, $R^9$, $R^{10}$, $R^{11}$, $R^{12}$, Q, $R^{13}$, L, n, and $R^{14}$.

In another embodiment $R^7$ is $CF_3$ or $CF_2CH_3$. This embodiment may be used in combination with the other embodiments of R, $R^2$, $R^3$, $R^4$, $R^5$, $R^6$, $R^9$, $R^{10}$, $R^{11}$, $R^{12}$, Q, $R^{13}$, L, n, and $R^{14}$.

In another embodiment $R^{10}$ is Cl, Br, $CH_3$, or $CF_3$. This embodiment may be used in combination with the other embodiments of $R^1$, $R^2$, $R^3$, $R^4$, $R^5$, $R^6$, $R^7$, $R^9$, $R^{11}$, $R^{12}$, Q, $R^{13}$, L, n, and $R^{14}$.

In another embodiment Q is O. This embodiment may be used in combination with the other embodiments of $R^1$, $R^2$, $R^3$, $R^4$, $R^5$, $R^6$, $R^7$, $R^9$, $R^{10}$, $R^{11}$, $R^{12}$, $R^{13}$, L, n, and $R^{14}$.

In another embodiment L is $CH_2CH_2$ or $CH(CH_3)CH_2$, This embodiment may be used in combination with the other embodiments of $R^1$, $R^2$, $R^3$, $R^4$, $R^5$, $R^6$, $R^7$, $R^9$, $R^{10}$, $R^{11}$, $R^{12}$, Q, $R^{13}$, n, and $R^{14}$.

In another embodiment n is 0, 1, or 2. This embodiment may be used in combination with the other embodiments of $R^1$, $R^2$, $R^3$, $R^4$, $R^5$, $R^6$, $R^7$, $R^9$, $R^{10}$, $R^{11}$, $R^{12}$, Q, $R^{13}$, L, and $R^{14}$.

In another embodiment $R^{14}$ is $CH_2CH_3$ or $CH_2CF_3$. This embodiment may be used in combination with the other embodiments of $R^1$, $R^2$, $R^3$, $R^4$, $R^5$, $R^6$, $R^7$, $R^9$, $R^{10}$, $R^{11}$, $R^{12}$, Q, $R^{13}$, L, and n.

In another embodiment:
(A) $R^1$, $R^5$, $R^6$, $R^{11}$, $R^{12}$, and $R^{13}$ are H;
(B) $R^2$, $R^3$, and $R^4$ are each independently selected from the group consisting of H, F, Cl, Br, $(C_1-C_4)$alkyl, and $(C_2-C_4)$alkenyl;
(C) $R^7$ is $(C_1-C_6)$haloalkyl;
(D) $R^9$ is H;
(E) $R^{10}$ is selected from the group consisting of Cl, Br, $(C_1-C_4)$alkyl, and $(C_1-C_4)$haloalkyl;
(G) Q is O;
(H) L is $(C_1-C_6)$alkyl;
(I) n is 0, 1, or 2;
(J) $R^{14}$ is selected from the group consisting of $(C_1-C_4)$alkyl and $(C_1-C_4)$haloalkyl,
wherein each alkyl or haloalkyl may optionally be substituted with one or more substituents independently selected from the group consisting of F, Cl, Br, I, CN, and OH.

halides 1-4, wherein E is Br, Cl, or I, and $R^1$, $R^2$, $R^3$, $R^4$, $R^5$, $R^6$, and $R^7$ are as previously disclosed, by treatment with a halogenating reagent, such as N-bromosuccinimide, and triethylphosphite in a solvent that does not react with the reagents preferably dichloromethane at about 40° C. to provide benzyl halides 1-4, E is Br (Scheme 1, step c). Alternatively, benzyl alcohols 1-3 may be converted into benzyl halides 1-4, where E is Br by treatment with a sulfonyl chloride such as methanesulfonyl chloride in the presence of a base such as triethylamine and subsequent treatment of the resultant sulfonate with a transition metal bromide such as iron(III) bromide. Additionally, treatment with chlorinating reagents such as thionyl chloride in the presence of a base such as pyridine in a hydrocarbon solvent such as toluene at about 110° C. may provide benzyl halides 1-4, where E is Cl (Scheme 1, step c).

Scheme 1

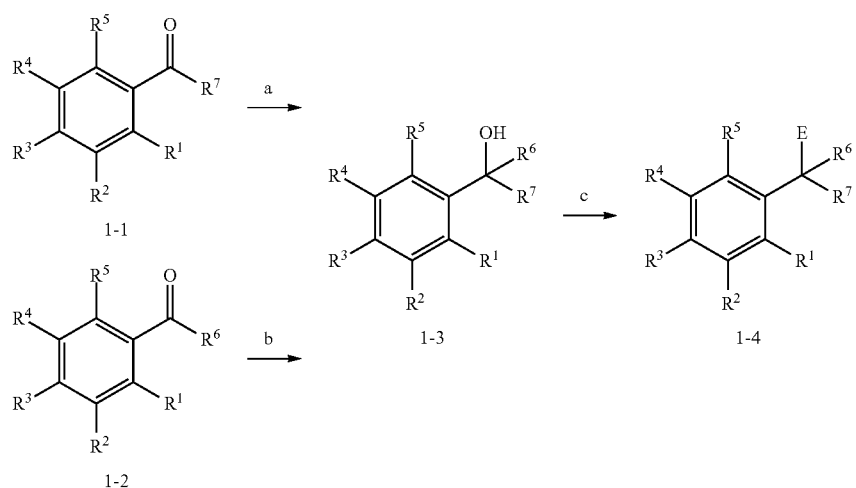

Preparation of Benzyl Halides

Benzyl alcohol 1-3, wherein $R^1$, $R^2$, $R^3$, $R^4$, $R^5$, $R^6$, and $R^7$ are as previously disclosed, may be prepared in several ways. Ketones 1-1 may be prepared by treating bromobenzenes with a lithium base such as n-butyllithium in a polar aprotic solvent preferably diethyl ether at temperatures from about −78° C. to about 0° C. followed by treatment with esters $R^7C(O)O(C_1-C_4)$alkyl, wherein $R^7$ is as previously disclosed, such as ethyl 2,2-difluoropropanoate (not shown). Treatment of ketones 1-1, wherein $R^1$, $R^2$, $R^3$, $R^4$, $R^5$, and $R^7$ are as previously disclosed, with a reducing agent such as sodium borohydride, in the presence of a base, such as aqueous sodium hydroxide, in a polar protic solvent preferably methanol at about −10° C. to about 10° C. may provide benzyl alcohols 1-3 (Scheme 1, step a). Alternatively, aldehydes 1-2, wherein $R^6$ is H and $R^1$, $R^2$, $R^3$, $R^4$, and $R^5$ are as previously disclosed, may be allowed to react with trifluorotrimethylsilane in the presence of a catalytic amount of tetrabutylammonium fluoride in a polar aprotic solvent preferably tetrahydrofuran (Scheme 1, step b) to provide benzyl alcohols 1-3, wherein $R^7$ is $CF_3$. Subsequently, benzyl alcohols 1-3 may be converted into benzyl Preparation of Fluorinated Vinylbenzoic Esters and Acids Halobenzoic acids 2-1, wherein $R^9$, $R^{10}$, $R^{11}$, and $R^{12}$ are as previously disclosed may be converted to halobenzoic acid esters 2-2, wherein $R^9$, $R^{10}$, $R^{11}$, and $R^{12}$ are as previously disclosed. Halobenzoic acids 2-1, may be treated with an acid, such as sulfuric acid, in the presence of a $(C_1-C_8)$alcohol such as ethanol, to provide halobenzoic acid ethyl esters 2-2 (Scheme 2, step a). Fluorinated vinylbenzoic acid esters 2-3 may be accessed via reaction of 2-2 with a fluorinated vinyl silane in the presence of a palladium catalyst such as tetrakis(triphenylphospine)palladium(0), a copper additive such as copper(I) iodide, and a fluoride source, such as cesium fluoride in a polar aprotic solvent preferably 1,3-dimethyl-2-imidazolidinone at temperatures ranging from about ambient temperature to about 45° C., to provide fluorinated vinyl benzoic acid esters 2-3 (Scheme 2, step b). Fluorinated vinyl benzoic acid esters 2-3 may be treated with a metal hydroxide source such as lithium hydroxide in a mixed solvent system comprising a polar aprotic solvent preferably tetrahydrofuran and polar protic solvents preferably methanol and water at about ambient temperature to provide fluorinated vinyl benzoic acids 2-4 (Scheme 2, step c).

Scheme 2

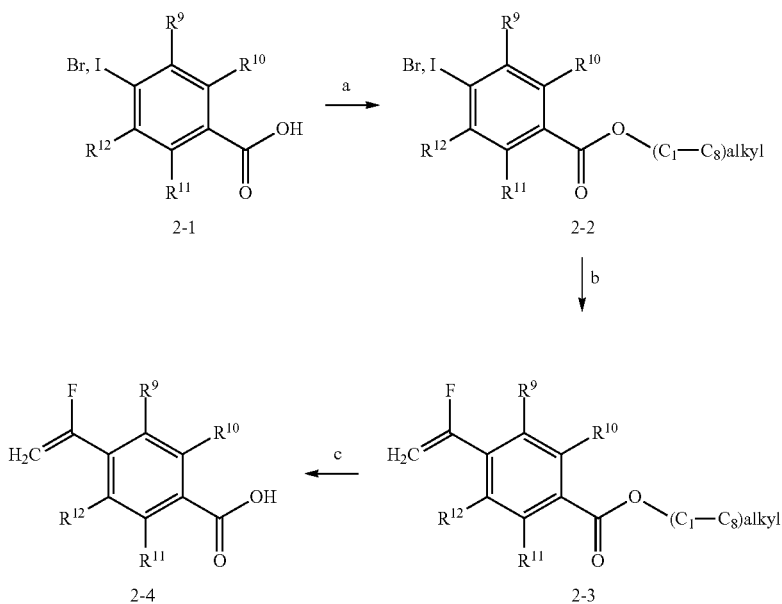

Alternatively, halobenzoic acids 2-1 may be directly treated with a vinyl borane source such as vinyltrifluoroborate or 3-hydroxy-2,3-dimethylbutan-2-yl hydrogen vinylboronate in the presence of a palladium catalyst such as 1,1'-bis(diphenylphosphino)ferrocene palladium(II) dichloride, and a base such as potassium carbonate, in a polar aprotic solvent preferably dimethylsulfoxide at temperatures ranging from about 80° C. to about 140° C., to provide vinyl benzoic acids 3-1, wherein $R^9$, $R^{10}$, $R^{11}$, and $R^{12}$ are as previously disclosed (Scheme 3, step a). Vinyl benzoic acids 3-1 may be treated with bromine source such as N-bromosuccinimide, and a fluorine source such as triethylamine trihydrofluoride, in a polar aprotic solvent preferably dichloromethane at about 0° C., to provide bromofluoroalkyl benzoic acids 3-2, wherein $R^9$, $R^{10}$, $R^{11}$, and $R^{12}$ are as previously disclosed (Scheme 3, step b). Bromofluoroalkyl benzoic acids 3-2 may be treated with a base such as potassium tert-butoxide, in a polar protic solvent preferably methanol, at temperatures ranging from about 0° C. to about ambient temperature, to provide fluorinated vinyl benzoic acids 2-4 (Scheme 3, step c).

-continued

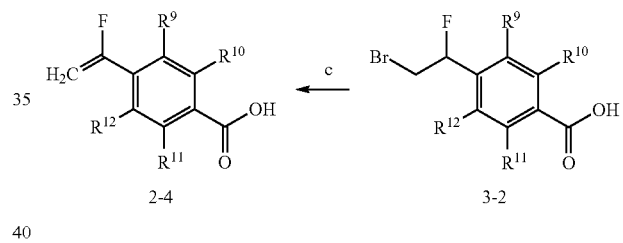

Preparation of Fluorinated Phenyl Allylbenzoic Acids

Benzyl halides 1-4 and fluorinated vinylbenzoic acids 2-4 may be treated with a copper(I) source such as copper(I) chloride or copper(I) bromide and a pyridine ligand such as 2,2-bipyridyl in a polar aprotic solvent preferably N-methyl-2-pyrrolidone, at a temperature between about 100° C. to about 180° C. to provide fluorinated phenyl allylbenzoic acids 4-1, wherein $R^1$, $R^2$, $R^3$, $R^4$, $R^5$, $R^6$, $R^7$, $R^9$, $R^{10}$, $R^{11}$, and $R^{12}$ are as previously disclosed (Scheme 4, step a).

Scheme 3

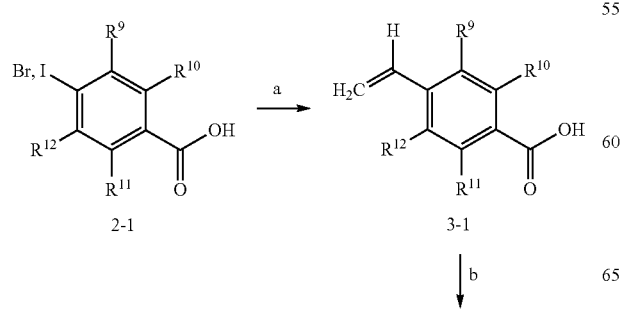

Scheme 4

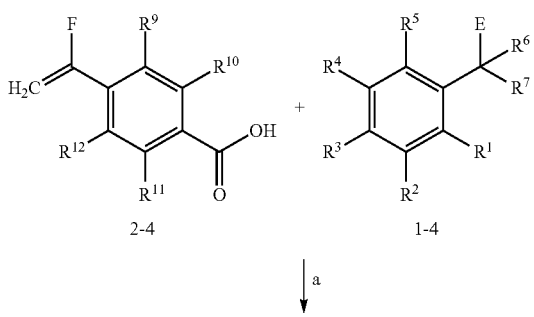

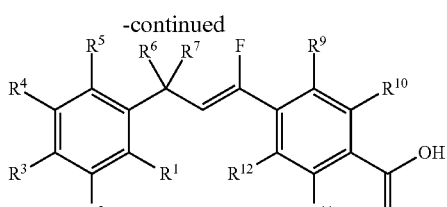

4-1

Preparation of Phenyl Allylbenzamides

Phenyl allylbenzamides 5-3, wherein $R^1$, $R^2$, $R^3$, $R^4$, $R^5$, $R^6$, $R^7$, $R^9$, $R^{10}$, $R^{11}$, $R^{12}$, $R^{13}$, L, n, and $R^{14}$ are as previously disclosed may be prepared by treatment with amines or amine salts 5-2, wherein $R^{13}$, L, n, and $R^{14}$ are as previously disclosed, and activated carboxylic acids 5-1, wherein A is an activating group, and $R^1$, $R^2$, $R^3$, $R^4$, $R^5$, $R^6$, $R^7$, $R^9$, $R^{10}$, $R^{11}$, and $R^{12}$ are as previously disclosed, with a base, such as triethylamine, diisopropylethylamine, or 4-methylmorpholine in an anhydrous aprotic solvent such as dichloromethane, tetrahydrofuran, 1,2-dichloroethane, N,N-dimethylformamide, or any combination thereof, at temperatures between about 0° C. and about 120° C. (Scheme 5, step a).

Activated carboxylic acids 5-1 may be an acid halide, such as an acid chloride, an acid bromide, or an acid fluoride; a carboxylic ester, such as a para-nitrophenyl ester, a pentafluorophenyl ester, an ethyl (hydroxyimino)cyanoacetate ester, a methyl ester, an ethyl ester, a benzyl ester, an N-hydroxysuccinimidyl ester, a hydroxybenzotriazol-1-yl ester, or a hydroxypyridyltriazol-1-yl ester; an O-acylisourea; an acid anhydride; or a thioester. Acid chlorides may be prepared from the corresponding carboxylic acids by treatment with a dehydrating chlorinating reagent, such as oxalyl chloride or thionyl chloride. Activated carboxylic acids 5-1 may be prepared from carboxylic acids in situ with a uronium salt, such as 1-[bis(dimethylamino)methylene]-1H-1,2,3-triazolo[4,5-b]pyridinium 3-oxide hexafluorophosphate (HATU), O-(benzotriazol-1-yl)-N,N,N',N'-tetramethyluronium hexafluorophosphate (HBTU), or (1-cyano-2-ethoxy-2-oxoethylidenaminooxy)dimethylamino-morpholino-carbenium hexafluorophosphate (COMU). Activated carboxylic acids 5-1 may also be prepared from carboxylic acids in situ with a phosphonium salt such as benzotriazol-1-yl-oxytripyrrolidinophosphonium hexafluorophosphate (PyBop). Activated carboxylic acids 5-1 may also be prepared from carboxylic acids in situ with a coupling reagent such as 1-(3-dimethylamino propyl)-3-ethylcarbodiimide, or dicyclohexylcarbodiimide in the presence of a triazole such as hydroxybenzotriazole.monohydrate (HOBt) or 1-hydroxy-7-azabenzotriazole (HOAt). O-Acylisoureas may be prepared with a dehydrating carbodimide such as 1-(3-dimethylamino propyl)-3-ethylcarbodiimide or dicyclohexylcarbodiimide. Activated carboxylic acids 5-1 may also be prepared from carboxylic acids in situ with a coupling reagent such as 2-chloro-1,3-dimethyl imidazolidinium hexafluorophosphate (CIP) in the presence of a triazole such as 1-hydroxy-7-azabenzotriazole (HOAt).

Phenyl allylbenzamides 5-3, wherein n is 0 (sulfide), may be oxidized to the corresponding sulfoxide, wherein n is 1, or sulfone, wherein n is 2, by treatment with one equivalent of sodium perborate in a protic solvent such as acetic acid (sulfoxide) or two equivalents of sodium perborate (sulfone). Preferably, the oxidation will be performed at temperatures between about 40° C. to about 100° C. using 1.5 equivalents of sodium perborate to provide chromatographically separable mixtures of sulfoxide and sulfone diphenyl allylbenzamides 5-3.

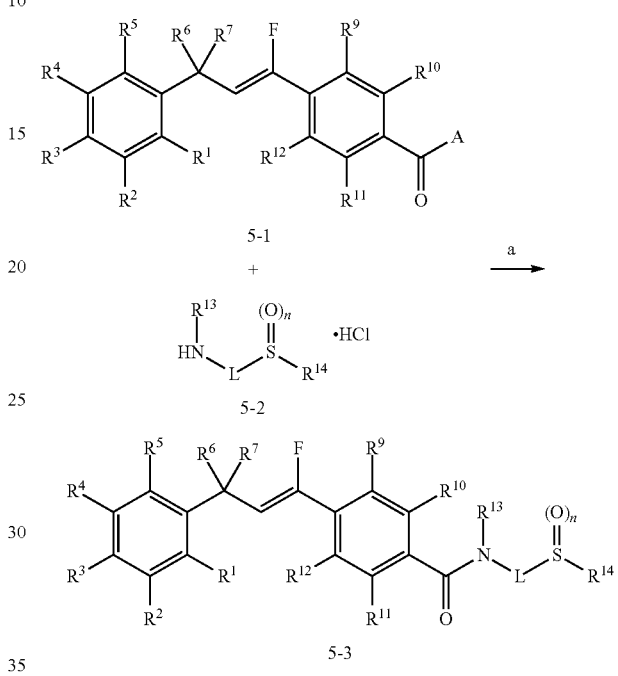

Alternatively, phenyl allylbenzamides 5-3, wherein n is 0 (sulfide), may be oxidized to the corresponding sulfoxide by treatment with hydrogen peroxide in a protic solvent such as methanol or preferably hexafluoroisopropanol. Preferably, the oxidation will be performed at temperatures between about 10° C. to about 100° C.

Amine salts 5-2 may be generated in situ from the corresponding N-tert-butoxycarbonyl amines by treatment with an acid such as hydrogen chloride. Additionally, amine salts 5-2 may be free-based in situ in the presence of a base such as sodium bicarbonate, triethylamine, or 4-methylmorpholine during reaction with activated carboxylic acids 5-1 to provide phenyl allylbenzoic amides 5-3.

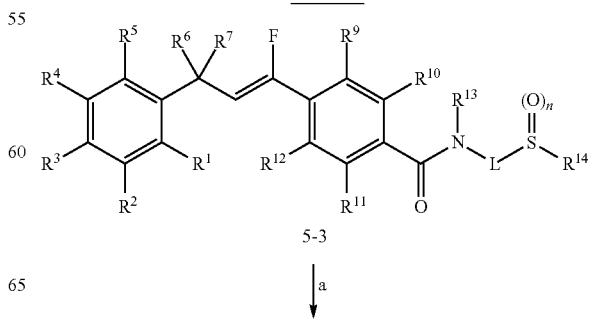

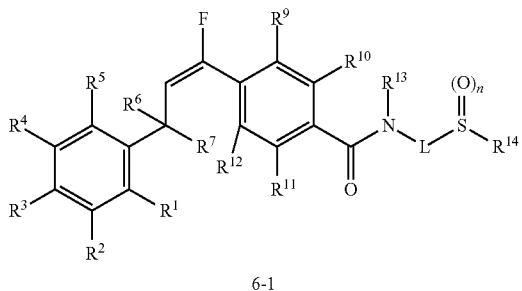

6-1

Phenyl allylbenzamides 5-3 may be exposed to ultraviolet irradiation in a deuterated or non-deuterated solvent such as acetone to provide phenyl allylbenzamides 6-1 (Scheme 6, step a).

Preparation of Amines and Amine Salts

Amines and amine salts 5-2 may be prepared as outlined in Scheme 7. N-tert-Butoxycarbonyl aminoalcohols 7-1, wherein $R^{13}$ and L are as previously disclosed, may be treated with a sulfonyl chloride such as methanesulfonyl chloride or a sulfonyl anhydride such as methanesulfonyl anhydride in the presence of a base such as triethylamine in a solvent such as dichloromethane at temperatures from about −20° C. to about 40° C. (Scheme 7, step a). The resultant N-tert-butoxycarbonyl amino sulfonates may then be treated with sodium thioacetate, prepared by treating thioacetic acid with a base such as sodium hydride, in a polar aprotic solvent such as N,N-dimethylformamide at temperatures from about 10° C. to about 40° C. to provide N-tert-butoxycarbonyl amino thioesters 7-2, wherein $R^{13}$ and L are as previously disclosed (Scheme 7, step b). Alkylation of the N-tert-butoxycarbonyl amino thioesters 7-2 may be accomplished in an oxygen free environment by first removing the acetate from the sulfur by treatment with a metal hydroxide base such as sodium hydroxide followed by treatment with halides $R^{14}$-halo, wherein $R^{14}$ is alkyl, or triflates $R^{14}$-OTf, wherein $R^{14}$ is alkyl, in a polar protic solvent such as methanol at temperatures from about −10° C. to about 40° C. to provide N-tert-butoxycarbonyl amino sulfides 7-3, wherein $R^{13}$, L, and $R^{14}$ are as previously disclosed (Scheme 7, step c). N-tert-Butoxycarbonyl amino sulfides 7-3 may then be treated with an acid such as hydrogen chloride to provide amino salts 5-2, wherein n is 0 (Scheme 7, step d). Optionally, the amine salts 5-2 may be free-based in the presence of a base such as sodium bicarbonate or triethylamine prior to use in subsequent reactions.

Scheme 7

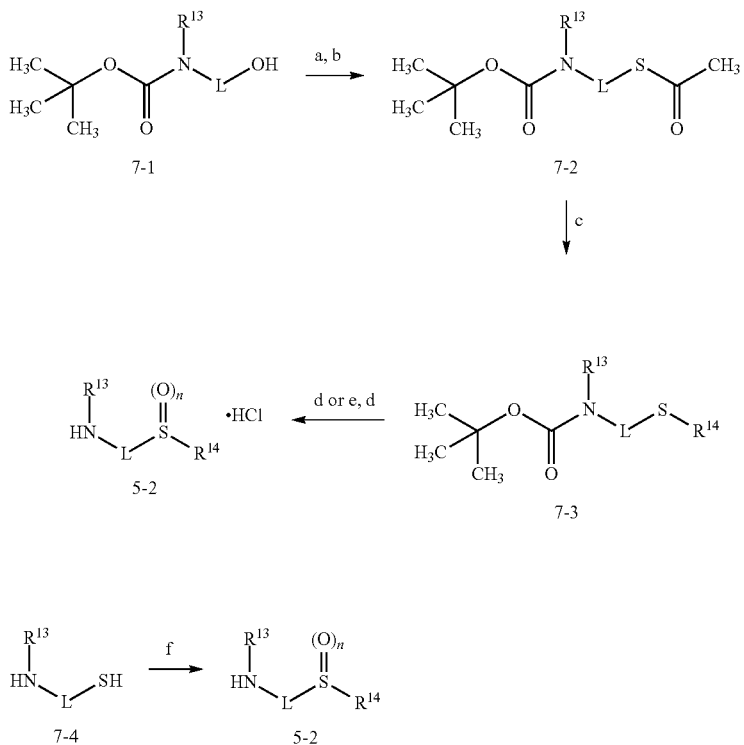

Alternatively, N-tert-butoxycarbonyl amino sulfides 7-3, may be oxidized to the corresponding sulfoxide or sulfone by treatment with one equivalent of sodium perborate in a protic solvent such as acetic acid to provide the sulfoxide; or two equivalents of sodium perborate to provide the sulfone (Scheme 7, step e). The resultant sulfones may then be treated with an acid such as hydrogen chloride to provide amine salts 5-2 (Scheme 7, step d). Optionally, the amine salts 5-2 may be free-based in the presence of a base such as sodium bicarbonate or triethylamine prior to use in subsequent reactions.

Amines 5-2 may alternatively be prepared by treating aminothiols 7-4, wherein $R^{13}$ and L are as previously disclosed with a base such as sodium hydride followed by treatment with halides $R^{14}$-halo, wherein $R^{14}$ is alkyl, or triflates $R^{14}$-OTf, wherein $R^{14}$ is alkyl, in a polar aprotic solvent such as N,N-dimethylformamide at temperatures from about 15° C. to about 50° C. (Scheme 7, step f).

Thiols 8-2, wherein $R^{14}$ is as previously disclosed, may be treated with a base such as sodium hydride followed by treatment with acids 8-1, wherein L is as previously disclosed, in a polar aprotic solvent such as N,N-dimethylformamide at temperatures from about −10° C. to about 30° C. to provide thioacids 8-3, wherein L and $R^{14}$ are as previously disclosed (Scheme 8, step a). Thioacids 8-3 may then be treated with an azide source such as diphenyl phosphorazidate in the presence of a base such as triethylamine in a solvent such as 1,2-dichloroethane at temperatures from about 60° C. to about 90° C. to effect a Curtius rearrangement. The resultant isocyanate may be treated with a benzyl alcohol such as (4-methoxyphenyl)methanol to provide benzyl carbamates 8-4, wherein $R^{13}$ is H, L, and $R^{14}$ are as previously disclosed (Scheme 8, step b). Benzyl carbamates 8-4 may be treated with an acid such as trifluoroacetic acid followed by salt metathesis with hydrochloric acid to provide amino salts 5-2, wherein $R^{13}$ is H and n is 0 (Scheme 8, step c). Optionally, the amine salts 5-2 may be free-based in the presence of a base such as sodium bicarbonate or triethylamine prior to use in subsequent reactions.

Alternatively, benzyl carbamates 8-4 may be oxidized to the corresponding sulfone by treatment with two equivalents of sodium perborate (Scheme 8, step d). The resultant sulfones may then be treated with an acid such as hydrogen chloride to provide amino salts 5-2 (Scheme 8, step c). Optionally, the amine salts 5-2 may be free-based in the presence of a base such as sodium bicarbonate or triethylamine prior to use in subsequent reactions.

EXAMPLES

These examples are for illustration purposes and are not to be construed as limiting this disclosure to only the embodiments disclosed in these examples.

Starting materials, reagents, and solvents that were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Examples using "room temperature" were conducted in climate controlled laboratories with temperatures ranging from about 20° C. to about 24° C. Molecules are given their known names, named according to naming programs within ISIS Draw, ChemDraw, or ACD Name Pro. If such programs are unable to name a molecule, such molecule is named using conventional naming rules. $^1$H NMR spectral data are in ppm (δ) and were recorded at 300, 400, 500, or 600 MHz; $^{13}$C NMR spectral data are in ppm (δ) and were recorded at 75, 100, or 150 MHz, and $^{19}$F NMR spectral data are in ppm (δ) and were recorded at 376 MHz, unless otherwise stated.

Example 1: Preparation of (Z)-2-bromo-4-(1,4,4,4-tetrafluoro-3-(3,4,5-trichlorophenyl)but-1-en-1-yl) benzoic Acid (C1)

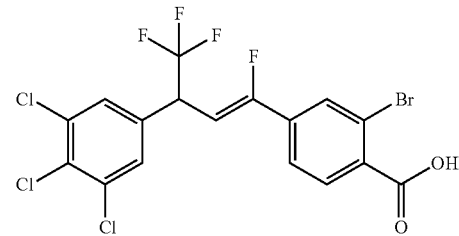

To a 25 mL round-bottomed flask were added 2,2'-bipyridine (0.255 g, 1.63 mmol), 2-bromo-4-(1-fluorovinyl) benzoic acid (C24) (1.00 g, 4.08 mmol), and 5-(1-bromo-2,2,2-trifluoroethyl)-1,2,3-trichlorobenzene (2.79 g, 8.16 mmol) in N-methylpyrrolidone (2.0 mL) to give a yellow Scheme 8

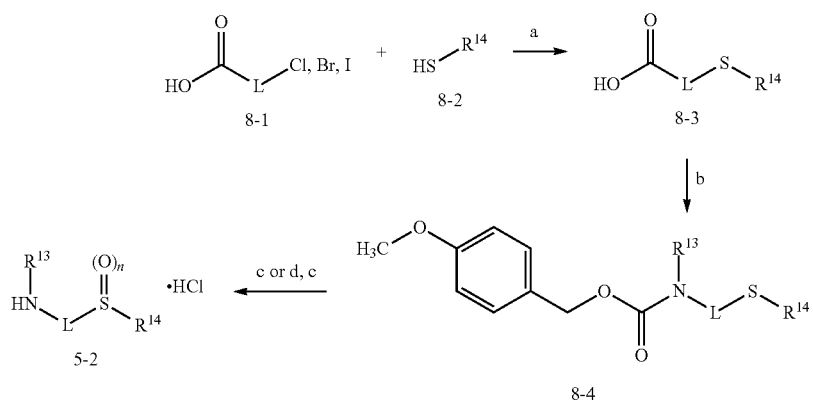

solution. Copper(I) bromide (0.117 g, 0.816 mmol) was added and the reaction mixture was purged with nitrogen for 5 minutes. The reaction was then heated to 150° C. for 3 hours. The reaction mixture was poured into ice water (100 mL). The water was filtered and the resultant black gum was dissolved in ethyl acetate (800 mL), washed with brine (2×200 mL), and water (2×200 mL), dried over magnesium sulfate, filtered, and concentrated to provide the title compound as a brown oil (1.40 g, 64%): $^1$H NMR (400 MHz, CDCl$_3$) δ 8.03 (d, J=8.2 Hz, 1H), 7.89 (d, J=1.8 Hz, 1H), 7.59 (dd, J=8.3, 1.8 Hz, 1H), 7.43 (s, 2H), 5.83 (dd, J=32.4, 9.6 Hz, 1H), 4.60 (p, J=8.8 Hz, 1H); $^{19}$F NMR (376 MHz, CDCl$_3$) δ−69.32 (d, J=2.3 Hz), −108.70−−119.01 (m); ESIMS m/z 505 ([M−H]$^−$).

The following compounds were prepared in like manner to the procedure outlined in Example 1:

(Z)-4-(1,4,4,4-Tetrafluoro-3-(3,4,5-trichlorophenyl)but-1-en-1-yl)-2-(trifluoromethyl)benzoic Acid (C2)

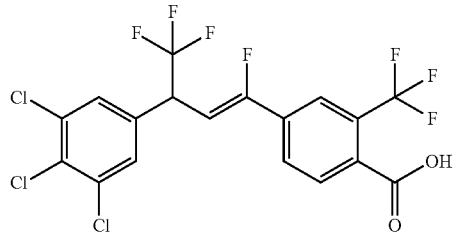

Isolated as a yellow oil (7.6 g, 68%): $^1$H NMR (400 MHz, CDCl$_3$) δ 8.04 (d, J=8.2 Hz, 1H), 7.99-7.94 (m, 1H), 7.84 (dd, J=8.2, 1.8 Hz, 1H), 7.44 (s, 2H), 5.90 (dd, J=32.4, 9.6 Hz, 1H), 4.62 (p, J=8.9 Hz, 1H); $^{19}$F NMR (376 MHz, CDCl$_3$) δ−59.60, −69.28 (d, J=2.3 Hz), −112.11; ESIMS m/z 493 ([M−H]$^−$).

(Z)-4-(1,4,4-Trifluoro-3-(3,4,5-trichlorophenyl)pent-1-en-1-yl)-2-(trifluoromethyl)benzoic Acid (C3)

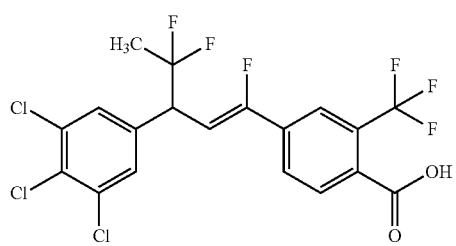 [SMILES: CC(F)(F)C(/C=C(\F)c1ccc(C(=O)O)c(C(F)(F)F)c1)c1cc(Cl)c(Cl)c(Cl)c1]

Isolated as a yellow foam (0.628 g, 60%): $^1$H NMR (400 MHz, CDCl$_3$) δ 8.00 (d, J=8.2 Hz, 1H), 7.95 (d, J=8.8 Hz, 1H), 7.81 (d, J=8.3 Hz, 1H), 7.42 (s, 2H), 5.96 (dd, J=33.6, 9.8 Hz, 1H), 4.29 (td, J=14.3, 9.8 Hz, 1H), 1.65 (t, J=18.4 Hz, 3H); $^{19}$F NMR (376 MHz, CDCl$_3$) δ −59.61, −92.97−−97.35 (m), −114.82; ESIMS m/z 491 ([M−H]$^−$).

(Z)-2-Chloro-4-(1,4,4,4-tetrafluoro-3-(3,4,5-trichlorophenyl)but-1-en-1-yl)benzoic Acid (C4)

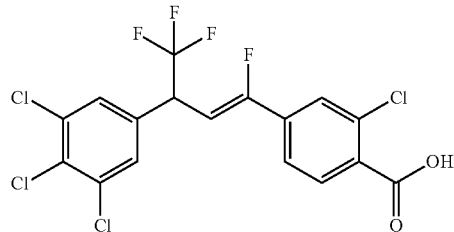

Isolated as a white solid (4.27 g, 88%): $^1$H NMR (400 MHz, CDCl$_3$) δ 8.07 (d, J=8.2 Hz, 1H), 7.68 (d, J=1.7 Hz, 1H), 7.54 (dd, J=8.3, 1.8 Hz, 1H), 7.43 (s, 2H), 5.85 (dd, J=32.4, 9.6 Hz, 1H), 4.60 (p, J=8.8 Hz, 1H); $^{19}$F NMR (376 MHz, CDCl$_3$) δ−69.33 (d, J=2.2 Hz), −112.18 (d, J=2.4 Hz); ESIMS m/z 461 ([M−H]$^−$).

(Z)-4-(3-(3,5-Dibromo-4-chlorophenyl)-1,4,4,4-tetrafluorobut-1-en-1-yl)-2-(trifluoromethyl)benzoic Acid (C5)

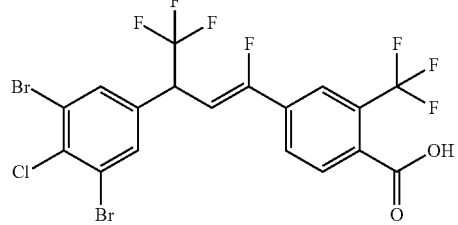

Isolated as a brown gum (2.00 g, 37%): ESIMS m/z 583 ([M−H]$^−$).

(Z)-4-(3-(3,5-Dichlorophenyl)-1,4,4,4-tetrafluorobut-1-en-1-yl)-2-(trifluoromethyl)benzoic Acid (C6)

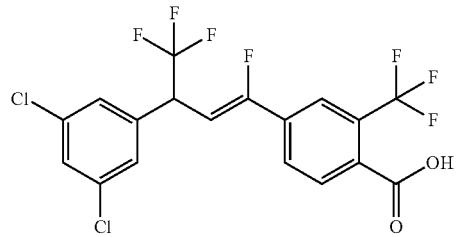 [SMILES: O=C(O)c1ccc(/C(F)=C/C(c2cc(Cl)cc(Cl)c2)C(F)(F)F)cc1C(F)(F)F]

Isolated as a brown gum (0.50 g, 43%): $^1$H NMR (400 MHz, DMSO-d$_6$) δ 13.9 (br s, 1H), 8.16 (s, 1H), 8.09 (d, J=8.0 Hz, 1H), 7.92 (d, J=8.0 Hz, 1H), 7.82 (s, 2H), 7.64 (t, J=6.0 Hz, 1H), 6.90 (dd, J=36.0, 10.4 Hz, 1H), 5.26-5.17 (m, 1H); IR (thin film) 3416, 2926, 1716, 1119 cm$^{-1}$; ESIMS m/z 449 ([M+H]$^+$).

(Z)-4-(3-(3,4-Dichlorophenyl)-1,4,4,4-tetrafluorobut-1-en-1-yl)-2-(trifluoromethyl)benzoic Acid (C7)

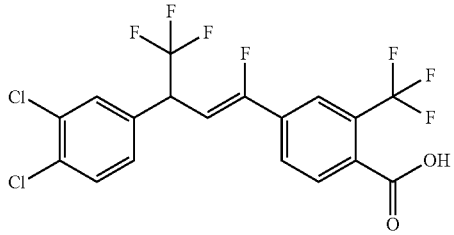

Isolated as a brown gum (2.50 g, 56%): $^1$H NMR (300 MHz, DMSO-d$_6$) δ 13.9 (br s, 1H), 8.16 (s, 1H), 8.09 (d, J=10.8 Hz, 1H), 8.08 (s, 1H), 7.92 (d, J=8.1 Hz, 1H), 7.75-7.65 (m, 2H), 6.90 (dd, J=36.0, 10.4 Hz, 1H), 5.22-5.16 (m, 1H); IR (thin film) 3440, 2927, 1716, 1175 cm$^{-1}$; ESIMS m/z 459 ([M−H]$^-$).

(Z)-4-(3-(3,5-Dibromophenyl)-1,4,4,4-tetrafluorobut-1-en-1-yl)-2-(trifluoromethyl)benzoic Acid (C8)

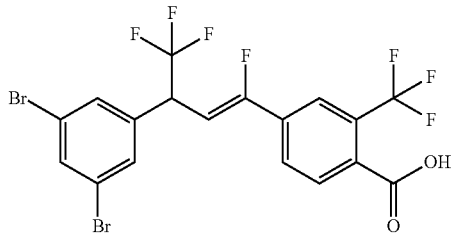

Isolated as a brown gum (2.20 g, 39%): $^1$H NMR (300 MHz, CDCl$_3$) δ 8.05-7.95 (m, 2H), 7.84 (d, J=7.2 Hz, 1H), 7.69-7.68 (m, 1H), 7.49 (s, 2H), 5.95 (dd, J=32.7, 9.6 Hz, 1H), 4.64-4.58 (p, 1H); IR (thin film) 3439, 2925, 1714, 1118, 746 cm$^{-1}$; ESIMS m/z 549 ([M−H]$^-$).

(Z)-4-(3=(3,5-Dichloro-4-fluorophenyl)-1,4,4,4-tetrafluorobut-1-en-1-yl)-2-(trifluoromethyl)benzoic Acid (C9)

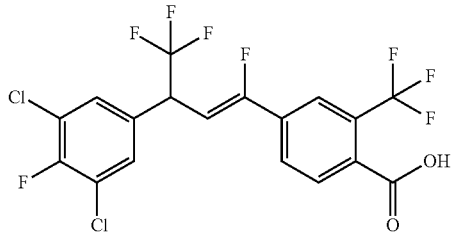 [SMILES: O=C(O)c1ccc(/C(F)=C/C(c2cc(Cl)c(F)c(Cl)c2)C(F)(F)F)cc1C(F)(F)F]

Isolated as a brown gum (1.20 g, 54%): $^1$H NMR (300 MHz, CDCl$_3$) δ 7.88 (s, 2H), 7.76-7.75 (m, 1H), 7.37 (d, J=6.0 Hz, 2H), 5.90 (dd, J=32.1, 9.0 Hz, 1H), 4.62-4.56 (p, 1H); IR (thin film) 3445, 2926, 1698, 1260, 750 cm$^{-1}$; ESIMS m/z 477 ([M−H]$^-$).

(Z)-4-(3-(4-Chloro-3,5-dimethylphenyl)-1,4,4,4-tetrafluorobut-1-en-1-yl)-2-(trifluoromethyl)benzoic Acid (C10)

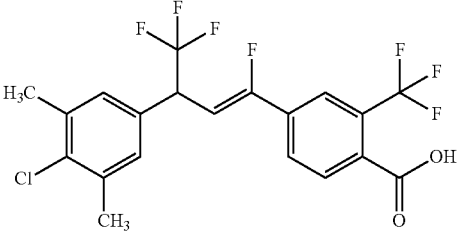 [SMILES: Cc1cc(C(/C=C(\F)c2ccc(C(=O)O)c(C(F)(F)F)c2)C(F)(F)F)cc(C)c1Cl]

Isolated as a yellow gum (2.20 g, 53%): $^1$H NMR (300 MHz, CDCl$_3$) δ 8.01 (d, J=8.1 Hz, 1H), 7.94 (s, 1H), 7.83 (d, J=8.1 Hz, 1H), 7.11 (s, 2H), 6.00 (dd, J=33.0, 9.9 Hz, 1H), 4.58-4.55 (m, 1H), 2.40 (s, 6H); IR (thin film) 3445, 1713, 852 cm$^{-1}$; ESIMS m/z 453 ([M−H]$^-$).

(Z)-4-(3-(4-Bromo-3,5-dichlorophenyl)-1,4,4,4-tetrafluorobut-1-en-1-yl)-2-(trifluoromethyl)benzoic Acid (C11)

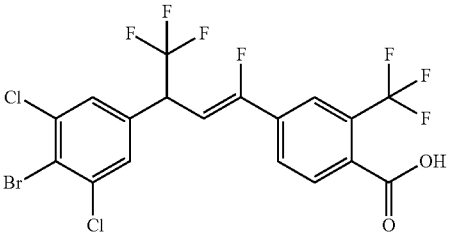

Isolated as a brown solid (1.50 g, 65%): mp 78-81° C.; $^1$H NMR (300 MHz, CDCl$_3$) δ 8.09-7.99 (m, 2H), 7.83-7.81 (m, 1H), 7.42 (s, 2H), 5.95 (dd, J=32.4 Hz, 9.6 Hz, 1H), 4.63-4.57 (m, 1H); IR (thin film) 3445, 1713, 852 cm$^{-1}$; ESIMS m/z 538 ([M+H]$^+$).

(Z)-4-(3-(3-Bromo-5-chlorophenyl)-1,4,4,4-tetrafluorobut-1-en-1-yl)-2-(trifluoromethyl)benzoic Acid (C12)

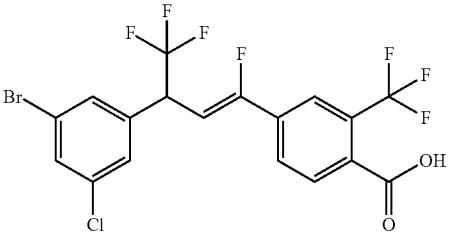

Isolated as a brown gum (2.0 g, 62%): $^1$H NMR (300 MHz, DMSO-d$_6$) δ 13.80 (br s, 1H), 8.15 (s, 1H), 8.09 (d, J=8.1 Hz, 1H), 7.93-7.78 (m, 4H), 6.91 (dd, J=35.7, 10.2 Hz, 1H), 5.27-5.14 (m, 1H); IR (thin film) 3081, 2927, 1714, 776 cm$^{-1}$; ESIMS m/z 503 ([M−H]$^-$).

(Z)-4-(3-(3,4-Dibromophenyl)-1,4,4-tetrafluorobut-1-en-1-yl)-2-(trifluoromethyl)benzoic Acid (C13)

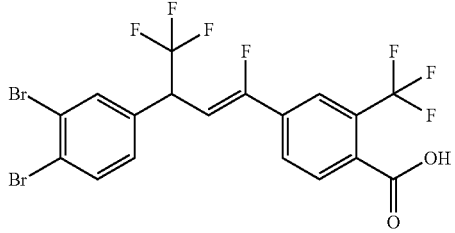

Isolated as a yellow gum (2.1 g, 78%/o): ¹H NMR (400 MHz, CDCl₃) δ 8.02 (d, J=8.4 Hz, 1H), 7.94 (s, 1H), 7.83 (d, J=8.4 Hz, 1H), 7.66 (d, J=8.4 Hz, 2H), 7.26-7.21 (m, 1H), 5.96 (dd, J=32.4, 9.2 Hz, 1H), 4.67-4.58 (p, 1H); IR (thin film) 3426, 2925, 1714, 1115 cm⁻¹; ESIMS m/z 547 ([M−H]⁻).

(Z)-2-Methyl-4-(1,4,4,4-tetrafluoro-3-(3,4,5-trichlorophenyl)but-1-en-1-yl)benzoic Acid (C14)

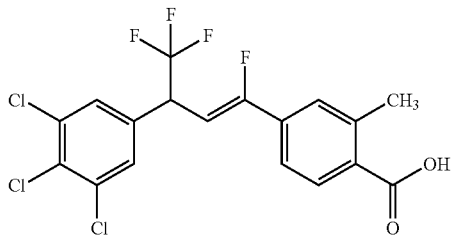

Isolated as an orange oil (0.94 g, 61%): ¹H NMR (400 MHz, CDCl₃) δ 8.09 (d, J=8.8 Hz, 1H), 7.49-7.45 (m, 2H), 7.44 (s, 2H), 5.80 (dd, J=32.7, 9.6 Hz, 1H), 4.60 (p, J=8.9 Hz, 1H), 2.69 (s, 3H); ¹⁹F NMR (376 MHz, CDCl₃) δ−69.40 (d, J=2.3 Hz), −108.40--115.65 (m); ESIMS m/z 441 ([M−H]⁻).

(Z)-2-Methyl-4-(1,4,4-trifluoro-3-(3,4,5-trichlorophenyl)pent-1-en-1-yl)benzoic Acid (C15)

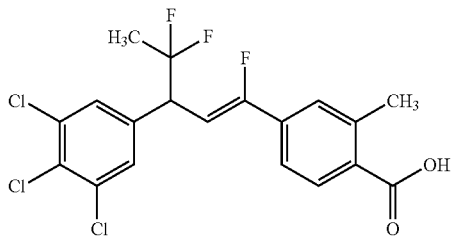 [SMILES: Cc1cc(/C(F)=C/C(c2cc(Cl)c(Cl)c(Cl)c2)C(C)(F)F)ccc1C(=O)O]

Isolated as an orange foam (0.204 g, 51%): ¹H NMR (400 MHz, CDCl₃) δ 8.07 (d, J=8.8 Hz, 1H), 7.49-7.40 (m, 4H), 5.86 (dd, J=33.9, 9.9 Hz, 1H), 4.27 (td, J=14.3, 9.7 Hz, 1H), 2.68 (s, 3H), 1.65 (t, J=18.4 Hz, 3H); ¹⁹F NMR (376 MHz, CDCl₃) δ−95.11, −95.18, −114.57; ESIMS m/z 437 ([M−H]⁻).

(Z)-4-(1,4,4-Trifluoro-3-(3,4,5-trichlorophenyl)hex-1-en-1-yl)-2-(trifluoromethyl)benzoic Acid (C16)

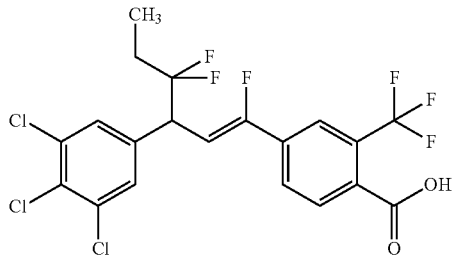 [SMILES: CCC(F)(F)C(/C=C(\F)c1ccc(C(=O)O)c(C(F)(F)F)c1)c1cc(Cl)c(Cl)c(Cl)c1]

Isolated as an orange foam (0.136 g, 63%): ¹H NMR (400 MHz, CDCl₃) δ 7.99 (dd, J=8.4, 4.0 Hz, 1H), 7.93 (s, 1H), 7.80 (d, J=7.9 Hz, 1H), 7.42 (d, J=2.6 Hz, 2H), 6.08-5.87 (m, 1H), 4.32 (td, J=14.6, 9.8 Hz, 1H), 1.87 (ddt, J=21.6, 15.4, 8.0 Hz, 2H), 1.07 (t, J=7.4 Hz, 3H); ¹³C NMR (101 MHz, CDCl₃) δ 170.72, 156.96 (d, J_{CF}=253.0 Hz), 136.85, 135.06, 134.53, 133.75, 131.90, 131.19, 130.18, 129.17, 128.60, 128.05, 127.29, 124.11, 123.36-122.67 (m), 121.39, 104.66 (d, J_{CF}=18.0 Hz), 46.46, 29.70-27.14 (m), 6.40-5.44 (m); ESIMS m/z 503 ([M−H]⁻).

(Z)-4-(3-(3,4-Dichlorophenyl)-1,4,4-trifluoropent-1-en-1-yl)-2-(trifluoromethyl)benzoic Acid (C17)

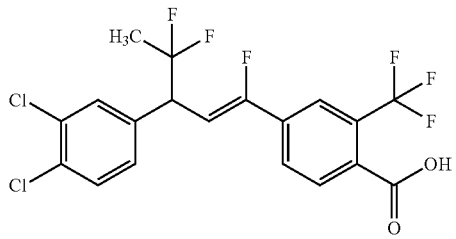 [SMILES: CC(F)(F)C(/C=C(\F)c1ccc(C(=O)O)c(C(F)(F)F)c1)c1ccc(Cl)c(Cl)c1]

Isolated as an orange glass (0.495 g, 51%): ¹H NMR (400 MHz, CDCl₃) δ 8.01 (d, J=8.2 Hz, 1H), 7.94 (d, J=1.6 Hz, 1H), 7.80 (dd, J=8.2, 1.8 Hz, 1H), 7.49 (d, J=2.1 Hz, 1H), 7.45 (d, J=8.3 Hz, 1H), 7.26 7.22 (m, 1H), 6.00 (dd, J=33.9, 9.8 Hz, 1H), 4.32 (ddd, J=15.8, 13.0, 9.8 Hz, 1H), 1.62 (t, J=18.4 Hz, 3H); ¹⁹F NMR (376 MHz, CDCl₃) δ−59.58, −89.79--99.81 (m) −115.63; IR (thin film) 3008, 1711 cm⁻¹; ESIMS m/z 455 ([M−H]⁻).

(Z)-4-(3-(3,4-Dichlorophenyl)-1,4,4-trifluoropent-1-en-1-yl)-2-(trifluoromethyl)benzoic Acid (C18)

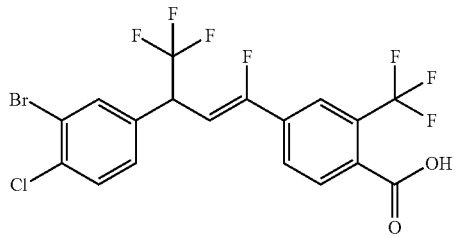

Isolated as a brown gum (2.5 g, 46%): $^1$H NMR (300 MHz, DMSO-d$_6$) δ 13.79 (br s, 1H), 8.15-8.06 (m, 3H), 7.91 (d, J=8.1 Hz, 1H), 7.71 (s, 2H), 6.90 (dd, J=36.0, 10.2 Hz, 1H), 5.21-5.15 (m, 1H); IR (thin film) 3431, 2924, 1623, 597 cm$^{-1}$; ESIMS m/z 503 ([M−H]$^-$).

(Z)-4-(3-(3-Chloro-4-fluorophenyl)-1,4,4,4-tetrafluorobut-1-en-1-yl)-2-(trifluoromethyl)benzoic Acid (C19)

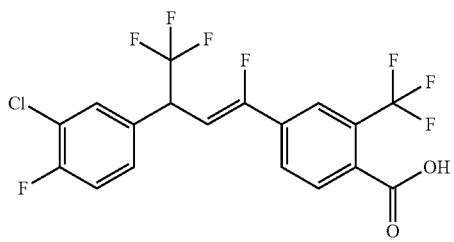

Isolated as a yellow gum (1.50 g, 57%): $^1$H NMR (300 MHz, CDCl$_3$) δ 8.01 (d, J=8.1 Hz, 2H) 7.94 (s, 2H), 7.76-7.75 (m, 1H), 7.37 (d, J=6.0 Hz, 2H), 5.90 (dd, J=32.1, 9.0 Hz, 1H); IR (thin film) 3445, 2926, 1698, 1260, 750 cm$^{-1}$; ESIMS m/z 443 ([M−H]$^-$), (Z)-4-(3-(4-Chloro-3-fluorophenyl)-1,4,4,4-tetrafluorobut-1-en-1-yl)-2-(trifluoromethyl)benzoic Acid (C20)

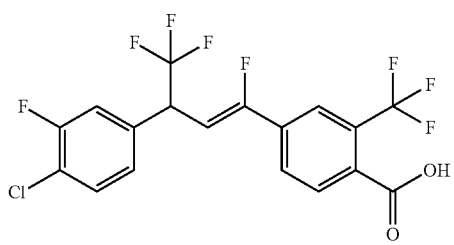

Isolated as a brown gum (0.50 g, 48%): $^1$H NMR (300 MHz, CDCl$_3$) δ 8.03 (d, J=8.1 Hz, 1H), 7.94 (s, 1H), 7.83 (d, J=7.8 Hz, 1H), 7.46-7.44 (m, 1H), 7.23-7.13 (m, 2H), 5.98 (dd, J=34.2, 9.9 Hz, 1H), 4.69-4.63 (m, 1H); IR (thin film) 3092, 1751, 750 cm$^{-1}$; ESIMS m/z 443 ([M−H]$^-$).

(Z)-4-(1,4,4,4-Tetrafluoro-3-(3,4,5-trichlorophenyl)but-1-en-1-yl)benzoic Acid (CC1)

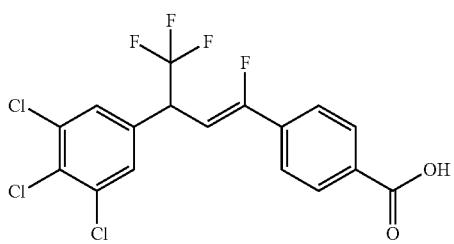 [SMILES: O=C(O)c1ccc(/C(F)=C/C(c2cc(Cl)c(Cl)c(Cl)c2)C(F)(F)F)cc1]

Isolated as a yellow gum (1.1 g, 56%): $^1$H NMR (400 MHz, CDCl$_3$) δ 8.15 (d, J=8.2 Hz, 2H), 7.67 (d, J=8.3 Hz, 2H), 7.44 (s, 2H), 5.84 (dd, J=32.6, 9.6 Hz, 1H), 4.61 (p, J=8.9 Hz, 1H); $^{19}$F NMR (376 MHz, CDCl$_3$) δ−69.38 (d, J=2.2 Hz), −109.75−−116.47 (m); ESIMS m/z 427 ([M−H]$^-$).

Example 2: Preparation of (Z)-2-iodo-4-(1,4,4,4-tetrafluoro-3-(3,4,5-trichlorophenyl)but-1-en-1-yl)benzoic Acid (C21)

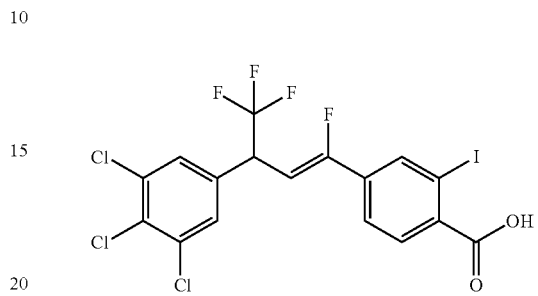

To a 25 mL vial were added (Z)-2-bromo-4-(1,4,4,4-tetrafluoro-3-(3,4,5-trichlorophenyl)but-1-en-1-yl)benzoic acid (C1) (0.500 g, 0.987 mmol), copper(I) iodide (0.0094 g, 0.049 mmol), and 1,4-dioxane (4.9 mL) to form a yellow suspension. Sodium iodide (0.296 g, 1.97 mmol) and trans-N,N'-dimethylcyclohexane-1,2-diamine (0.0140 g, 0.099 mmol) were added, and the reaction mixture was stirred at 110° C. for 3.5 hours. The reaction mixture was concentrated and purified by flash column chromatography to provide the title compound as a brown oil (0.247 g, 43%): $^1$H NMR (300 MHz, CDCl$_3$) δ 8.21 (d, J=1.7 Hz, 1H), 8.02 (d, J=8.2 Hz, 1H), 7.62 (dd, J=8.3, 1.7 Hz, 1H), 7.43 (s, 2H), 5.82 (dd, J=32.5, 9.6 Hz, 1H), 4.59 (p, J=8.9 Hz, 1H); $^{19}$F NMR (471 MHz, CDCl$_3$) δ−69.32, −112.14 (d, J=20.8 Hz); ESIMS m/z 553 ([M−H]$^-$).

Example 3: Preparation of (Z)-2-iodo-4-(1,4,4,4-tetrafluoro-3-(3,4,5-trichlorophenyl)but-1-en-1-yl)benzoic Acid (C22)

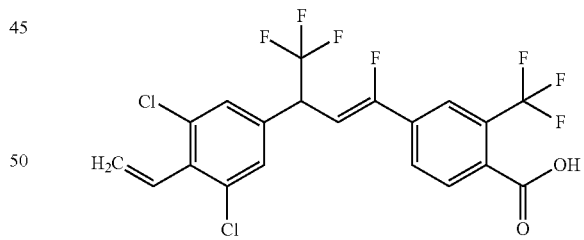

Tetrakis(triphenylphosphine)palladium(0) (0.30 g, 0.26 mmol) was added to a solution of (Z)-4-(3-(4-bromo-3,5-dichlorophenyl)-1,4,4,4-tetrafluorobut-1-en-1-yl)-2-(trifluoromethyl)benzoic acid (C11) (1.4 g, 2.6 mmol) in toluene (10 mL) at room temperature. The reaction mixture was degassed by purging with nitrogen (3×10 minutes). Tributyl vinyl stannane (0.82 g, 2.6 mmol) was added to the reaction mixture. The reaction mixture was again degassed by purging with nitrogen (3×10 minutes) and stirred at 120° C. for 3 hours. The reaction mixture was quenched with water and then extracted with ethyl acetate. The organic layer was dried over sodium sulfate, filtered, and concentrated. Purification by flash column chromatography using 30% ethyl acetate/hexanes provided the title compound as a pale yellow gum (0.80 g, 63%): $^1$H NMR (300 MHz, CDCl$_3$) δ 7.85 (s, 1H), 7.82 (d, J=8.4 Hz, 1H), 7.74 (d, J=8.4 Hz, 1H), 7.42 (s, 1H), 7.37 (s, 1H), 6.72-6.65 (dd, J=17.6 Hz, 11.6 Hz, 1H), 5.86-5.73 (m, 3H), 4.61-4.56 (m, 1H); IR (thin film) 3445, 2925, 1646, 1275, 749 cm$^{-1}$; ESIMS m/z 488 ([M+H]$^+$).

Example 4: Preparation of (Z)-4-(1,4,4,4,4,4-tetrafluoro-3-(3,4,5-trichlorophenyl)but-1-en-1-yl)-2-(trifluoromethyl)benzoyl chloride (C23)

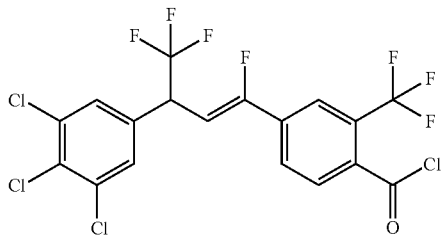 [SMILES: O=C(Cl)c1ccc(/C(F)=C/C(c2cc(Cl)c(Cl)c(Cl)c2)C(F)(F)F)cc1C(F)(F)F]

To a 25 mL vial was added (Z)-4-(1,4,4,4-tetrafluoro-3-(3,4,5-trichlorophenyl)but-1-en-1-yl)-2-(trifluoromethyl) benzoic acid (C2) (0.200 g, 0.404 mmol), oxalyl chloride (0.095 mL, 1.09 mmol), and N,N-dimethylformamide (catalytic amount) in dichloromethane (1.3 mL) to give a yellow solution. The reaction was stirred for 15 hours at room temperature. The solvent was removed under vacuum providing the title compound as a yellow gum (0.220 g, 95%): $^1$H NMR (400 MHz, CDCl$_3$) δ 7.99 (d, J=8.2 Hz, 1H), 7.92 (d, J=1.7 Hz, 1H), 7.81 (dd, J=8.2, 1.8 Hz, 1H), 7.44 (s, 2H), 5.88 (dd, J=32.5, 9.6 Hz, 1H), 4.73-4.50 (m, 1H); $^{19}$F NMR (376 MHz, CDCl$_3$) δ −59.58, −69.32, −109.75--113.19 (m); IR (thin film) 3445, 2925, 1646, 1275, 749 cm$^{-1}$; ESIMS m/z 476 ([M-Cl]$^+$).

Example 5: Preparation of 2-bromo-4-(1-fluorovinyl)benzoic Acid (C24)

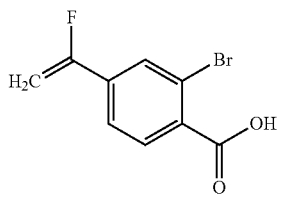

To a 250 mL round-bottomed flask were added methyl 2-bromo-4-(1-fluorovinyl)benzoate (C29) (1.8 g, 7.0 mmol), lithium hydroxide hydrate (0.88 g, 21 mmol), methanol (7.0 mL), tetrahydrofuran (21 mL), and water (7.0 mL), and the reaction mixture was stirred overnight at room temperature. The mixture was concentrated, quenched with a pH 4 buffer, and extracted with ethyl acetate to provide the title compound as a white solid (1.0 g, 56%): $^1$H NMR (400 MHz, CDCl$_3$) δ 8.01 (d, J=8.2 Hz, 1H), 7.89 (d, J=1.8 Hz, 1H), 7.57 (dd, J=8.3, 1.8 Hz, 1H), 5.21 (dd, J=48.6, 4.0 Hz, 1H), 5.06 (dd, J=17.3, 3.9 Hz, 1H); $^{19}$F NMR (471 MHz, CDCl$_3$) δ −108.71 (d, J=1.4 Hz); ESIMS m/z 244 ([M−H]$^−$).

The following compounds were prepared in like manner to the procedure outlined in Example 5:

4-(1-Fluorovinyl)-2-(trifluoromethyl)benzoic Acid (C25)

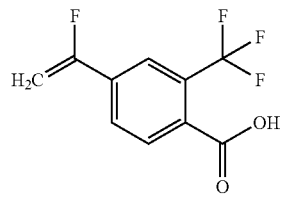

Isolated as a white solid (1.9 g, 93%): $^1$H NMR (400 MHz, methanol-d$_4$) δ 7.95 (d, J=1.5 Hz, 1H), 7.95-7.91 (m, 1H), 7.90-7.86 (m, 1H), 5.46 (dd, J=50.0, 4.1 Hz, 1H), 5.09 (dd, J=18.0, 4.1 Hz, 1H); $^{19}$F NMR (376 MHz, methanol-d$_4$) δ −61.04 (d, J=1.1 Hz), −110.93; ESIMS m/z 233 ([M−H]$^−$).

2-Chloro-4-(1-fluorovinyl)benzoic Acid (C26)

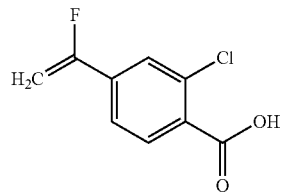

Isolated as a white solid (3.5 g, 75%): $^1$H NMR (400 MHz, acetone-d$_6$) δ 7.97 (dd, J=8.2, 0.9 Hz, 1H), 7.76 (d, J=1.7 Hz, 1H), 7.70 (dd, J=8.2, 1.7 Hz, 1H), 5.68-5.45 (m, 1H), 5.11 (dd, J=18.2, 4.1 Hz, 1H); $^{19}$F NMR (376 MHz, acetone-d$_6$) δ −108.71; ESIMS m/z 200 ([M−H]$^−$).

4-(1-Fluorovinyl)-2-methylbenzoic Acid (C27)

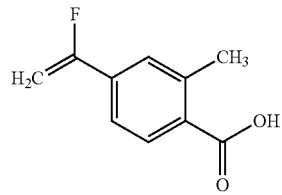

Isolated as a white solid (0.550 g, 89%): $^1$H NMR (400 MHz, methanol-d$_4$) δ 7.92 (d, J=8.1 Hz, 1H), 7.59-7.52 (m, 1H), 7.52-7.44 (m, 1H), 5.29 (dd, J=50.1, 3.7 Hz, 1H), 4.93 (dd, J=18.1, 3.7 Hz, 1H), 2.60 (s, 3H); $^{19}$F NMR (376 MHz, methanol-d$_4$) δ −110.32 (d, J=2.1 Hz); ESIMS m/z 181 ([M+H]$^+$).

Example 6: Preparation of methyl 4-(1-fluorovinyl)-2-(trifluoromethyl)benzoate (C28)

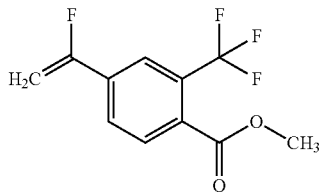

To a 100 mL round-bottomed flask was added methyl 4-bromo-2-(trifluoromethyl)benzoate (2.25 g, 8.00 mmol), (1-fluorovinyl)(methyl)diphenylsilane (3.58 g, 14.8 mmol), and 1,3-dimethylimidazolidin-2-one (40 mL). Tetrakis(triphenylphosphine)palladium(0) (0.459 g, 0.400 mmol), copper(I) iodide (0.0760 mg, 0.400 mmol), and cesium fluoride (3.62 g, 23.9 mmol) were added and the reaction was stirred at room temperature for 24 hours under a nitrogen atmosphere. Water was added to the mixture and the mixture was diluted with 3:1 hexanes/diethyl ether. The layer was separated, and the organic layer was dried over sodium sulfate, concentrated, and the residue purified by flash column chromatography provided the title compound as a colorless oil (2.00 g, 96%): $^1$H NMR (400 MHz, CDCl$_3$) δ 7.96-7.87 (m, 1H), 7.83 (dq, J=8.1, 0.7 Hz, 1H), 7.77 (dd, J=8.2, 1.7 Hz, 1H), 5.23 (dd, J=48.6, 4.0 Hz, 1H), 5.07 (dd, J=17.4, 4.0 Hz, 1H), 3.95 (s, 3H); 19F NMR (376 MHz, CDCl$_3$) δ−59.92, −108.73 (d, J=1.4 Hz); EIMS m/z 248 ([M]$^+$).

The following compounds were prepared in like manner to the procedure outlined in Example 6:

Methyl 2-bromo-4-(1-fluorovinyl)benzoate (C29)

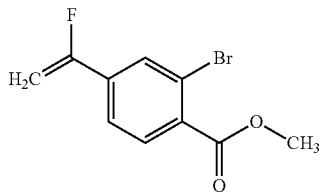

Isolated as a colorless oil (1.8 g, 93%): $^1$H NMR (400 MHz, CDCl$_3$) δ 7.84 (d, J=1.7 Hz, 1H), 7.82 (dd, J=8.2, 0.9 Hz, 1H), 7.50 (d, J=1.5 Hz, 1H), 5.16 (dd, J=48.7, 3.9 Hz, 1H), 5.01 (dd, J=17.3, 3.9 Hz, 1H), 3.94 (d, J=2.2 Hz, 3H); $^{19}$F NMR (376 MHz, CDCl$_3$) δ−108.61 (d, J=1.5 Hz); ESIMS m/z 258 ([M−H]$^−$).

Methyl 2-chloro-4-(1-fluorovinyl)benzoate (C30)

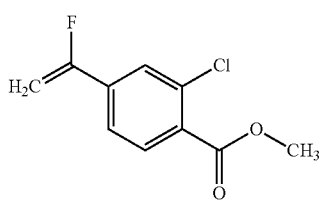

Isolated as a colorless oil (2.1 g, 99%): $^1$H NMR (400 MHz, CDCl$_3$) δ 7.86 (dd, J=8.2, 0.9 Hz, 1H), 7.64 (d, J=1.7 Hz, 1H), 7.48 (dd, J=8.3, 1.8 Hz, 1H), 5.17 (dd, J=48.7, 3.8 Hz, 1H), 5.02 (dd, J=17.3, 3.9 Hz, 1H), 3.94 (s, 3H); $^{19}$F NMR (376 MHz, CDCl$_3$) δ−108.63 (d, J=1.4 Hz); ESIMS m/z 214 ([M−H]$^−$).

Methyl 2-chloro-4-(1-fluorovinyl)benzoate (C31)

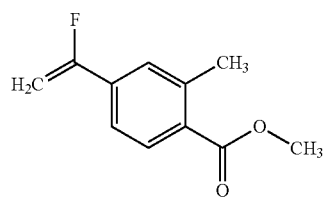

Isolated as a colorless oil (0.5 g, 85%): $^1$H NMR (400 MHz, methanol-d$_4$) δ 7.90 (d, J=8.2 Hz, 1H), 7.51 (s, 1H), 7.49 (dd, J=8.0, 1.6 Hz, 1H), 5.30 (dd, J=50.1, 3.7 Hz, 1H), 4.95 (dd, J=18.0, 3.7 Hz, 1H), 3.88 (d, J=5.9 Hz, 3H), 2.59 (s, 3H); $^{19}$F NMR (376 MHz, methanol-d$_4$) δ−110.41 (d, J=1.3 Hz); ESIMS m/z 195 ([M+H]$^+$).

Example 7: Preparation of 4-(1-fluorovinyl)-2-(trifluoromethyl)benzoic Acid (C25)

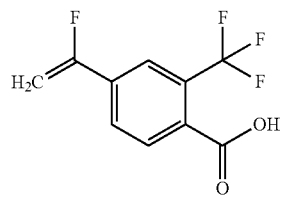

Step 1: 4-(2-bromo-1-fluoroethyl)-2-(trifluoromethyl)benzoic Acid (C32)

2-(Trifluoromethyl)-4-vinylbenzoic acid (5.3 g, 24 mmol) was dissolved in dichloromethane (123 mL) at 0° C., triethylamine trihydrofluoride was added (8.0 mL, 49 mmol) followed by N-bromosuccinimide (8.7 g, 49 mmol). The reaction mixture was stirred for 16 hours while warming to room temperature. Water was then added to the mixture, washed with dichloromethane, dried over sodium sulfate, filtered, and concentrated providing the title compound as a yellow oil which was used without further purification (5.0 g, 65%).

Step 2: 4-(1-fluorovinyl)-2-(trifluoromethyl)benzoic Acid (C25)

4-(2-Bromo-1-fluoroethyl)-2-(trifluoromethyl)benzoic acid (4.3 g, 14 mmol) was dissolved in methanol (68 mL) at 0° C. and potassium tert-butoxide (4.6 g, 41 mmol) was added as a solid while stirring. The reaction mixture was allowed to slowly warm to 23° C. and then stirred for 4 hours. Hydrochloric acid (1 N) was slowly added, and the mixture was extracted with ethyl acetate. Purification by flash column chromatography using 0-40% acetone in hexanes provided the title compound as an off-white solid (1.7 g, 53%): $^1$H NMR (400 MHz, CDCl$_3$) δ 8.02 (d, J=8.2 Hz, 1H), 8.00-7.93 (m, 1H), 7.82 (dd, J=8.2, 1.8 Hz, 1H), 5.27 (dd, J=48.5, 4.1 Hz, 1H), 5.11 (dd, J=17.3, 4.1 Hz, 1H);

The following compounds were prepared in like manner to the procedure outlined in Example 7:

4-(1-Fluorovinyl)benzoic Acid (C33)

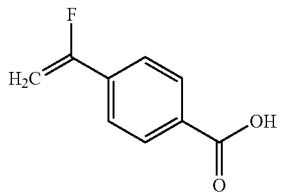

Isolated as a white solid (6.5 g, 86%): $^1$H NMR (400 MHz, CDCl$_3$) δ 8.13 (d, J=8.2 Hz, 2H), 7.69-7.62 (m, 2H), 5.21 (dd, J=49.0, 3.7 Hz, 1H), 5.02 (dd, J=17.5, 3.7 Hz, 1H); $^{19}$F NMR (376 MHz, CDCl$_3$) δ−108.35; ESIMS m/z 165 ([M−H]$^-$).

4-(1-Fluorovinyl)-2-methylbenzoic Acid (C27)

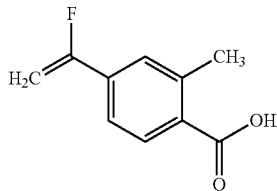

Isolated as a colorless oil (0.165 g, 89%): $^1$H NMR (400 MHz, CDCl$_3$) δ 8.12-8.03 (m, 1H), 7.46 (dd, J=5.8, 2.1 Hz, 2H), 5.17 (dd, J=49.1, 3.7 Hz, 1H), 4.98 (dd, J=17.5, 3.7 Hz, 1H), 2.68 (s, 3H); $^{19}$F NMR (376 MHz, CDCl$_3$) 5-108.50.

Example 8: Preparation of 5-(1-bromo-2,2-difluoropropyl)-1,2,3-trichlorobenzene (C34)

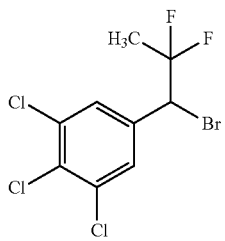

N-Bromosuccinimide (12.0 g, 67.5 mmol) was added to a solution of 2,2-difluoro-1-(3,4,5-trichlorophenyl)propan-1-ol (C43) (6.00 g, 21.8 mmol) in dichloromethane (72.6 mL). To this stirred solution was added triphenyl phosphite (17.1 mL, 65.3 mmol) slowly, dropwise, and the reaction mixture became dark brown. The reaction mixture was then heated at reflux for 3 hours. The solvent was concentrated, and the residue was triturated with diethyl ether. The solid was filtered, the filtrate was concentrated and the resultant oil was purified by flash column chromatography using hexanes as eluent to provide the title compound as a clear and colorless oil (2.20 g, 25%): $^1$H NMR (400 MHz, CDCl$_3$) δ 7.52 (s, 2H), 4.85 (dd, J=12.3, 10.4 Hz, 1H), 1.77 (t, J=18.2 Hz, 3H); $^{19}$F NMR (376 MHz, CDCl$_3$) δ−92.14−−95.01 (m); EIMS m/z 338 ([M]$^+$).

The following compounds were prepared in like manner to the procedure outlined in Example 8:

1,3-Dibromo-5-(1-bromo-2,2,2-trifluoroethyl)-2-chlorobenzene (C35)

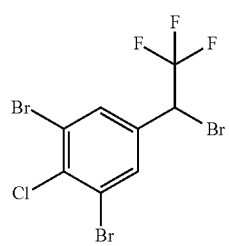

Isolated as a clear oil (28 g, 56%): $^1$H NMR (400 MHz, DMSO-d$_6$) δ 8.01-7.97 (m, 2H), 6.26-6.20 (m, 1H); IR (thin film) 1168, 736, 557 cm$^{-1}$; ESIMS m/z 428 ([M+H]$^+$).

5-(1-Bromo-2,2,2-trifluoroethyl)-2-chloro-1,3-dimethylbenzene (C36)

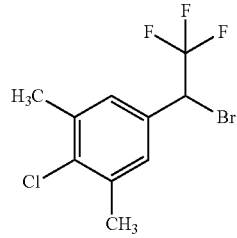

Isolated as a clear oil (6.32 g, 89%): $^1$H NMR (300 MHz, DMSO-d$_6$) δ 7.39 (s, 2H), 6.17-6.09 (m, 1H), 2.35 (s, 6H); IR (thin film) 1114, 754 cm$^{-1}$; ESIMS m/z 302 ([M+H]$^+$).

2-Bromo-5-(1-bromo-2,2,2-trifluoroethyl)-1,3-dichlorobenzene (C37)

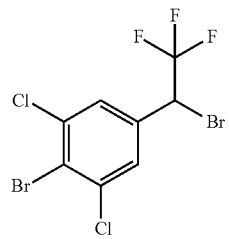

Isolated as a clear oil (19 g, 46%): $^1$H NMR (400 MHz, CDCl$_3$) δ 7.54-7.51 (m, 2H), 5.03-4.98 (m, 1H); $^{19}$F NMR (376 MHz, CDCl$_3$) δ−70.38.

4-(1-Bromo-2,2-difluoropropyl)-1,2-dichlorobenzene (C38)

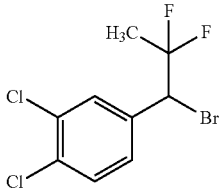

Isolated as a colorless liquid (1.40 g, 65%): $^1$H NMR (300 MHz, DMSO-$d_6$) δ 7.76-7.70 (m, 2H), 7.54 (dd, J=8.4, 1.8 Hz, 1H), 5.81-5.73 (m, 1H), 1.67 (d, J=18.9 Hz, 3H); IR (thin film) 1118, 800, 499 cm$^{-1}$; EIMS m/z 304 ([M]$^+$).

2-Bromo-4-(1-bromo-2,2,2-trifluoroethyl)-1-chlorobenzene (C39)

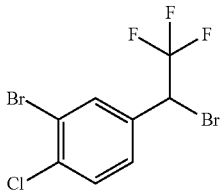

Isolated as a colorless liquid (10.5 g, 54%): $^1$H NMR (400 MHz, CDCl$_3$) δ 7.76 (d, J=1.2 Hz, 1H), 7.49-7.47 (m, 1H), 7.41-7.39 (m, 1H), 5.07-5.02 (m, 1H); IR (thin film) 3437, 2924, 1631, 1114 cm$^{-1}$; EIMS m/z 350 ([M]$^+$).

4-(1-Bromo-2,2,2-trifluoroethyl)-2-chloro-1-fluorobenzene (C40)

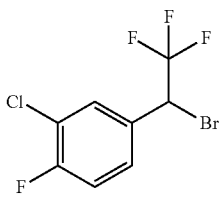 [SMILES: Fc1ccc(C(Br)C(F)(F)F)cc1Cl]

Isolated as a colorless oil (8.0 g, 73%): $^1$H NMR (300 MHz, CDCl$_3$) δ 7.59-7.57 (m, 1H), 7.42-7.33 (m, 1H), 7.20-7.14 (m, 1H), 5.10-5.03 (m, 1H); IR (thin film) 3429, 2926, 1502, 750 cm$^{-1}$; ESIMS m/z 292 ([M+H]$^+$).

4-(1-Bromo-2,2,2-trifluoroethyl)-1-chloro-2-fluorobenzene (C41)

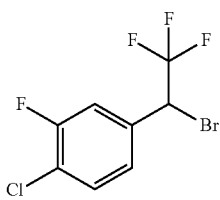 [SMILES: Fc1cc(C(Br)C(F)(F)F)ccc1Cl]

Isolated as a yellow oil (1.1 g, 45%): $^1$H NMR (400 MHz, CDCl$_3$) δ 7.44 (dd, J=8.3, 7.5 Hz, 1H), 7.34 (dd, J=9.5, 1.9 Hz, 1H), 7.26-7.22 (m, 1H), 5.08 (q, J=7.1 Hz, 1H); EIMS m/z 291 ([M]$^+$).

Example 9: Preparation of 5-(1-bromo-2,2-difluorobutyl)-1,2,3-trichlorobenzene (C42)

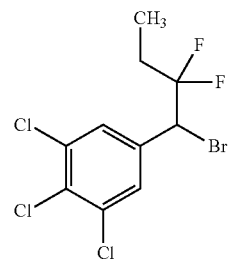 [SMILES: CCC(F)(F)C(Br)c1cc(Cl)c(Cl)c(Cl)c1]

Triethylamine (2.46 mL, 17.6 mmol) and methanesulfonyl chloride (1.10 mL, 14.1 mmol) were added to a solution of 2,2-difluoro-1-(3,4,5-trichlorophenyl)butan-1-ol (C44) (3.40 g, 11.7 mmol) in dichloromethane (58.7 mL). The reaction mixture was stirred for 1 hour, and then pentane was added. Filtration followed by concentration of the filtrate under vacuum provided a white solid. The solid was dissolved in dichloromethane (58.7 mL) to which iron(III) bromide (6.94 g, 23.5 mmol) was added. The reaction mixture was stirred overnight. The mixture was poured into water and then extracted with dichloromethane. The organics were washed with brine, dried over sodium sulfate, filtered, and concentrated. Purification by flash column chromatography using hexanes as eluent provided the title compound as a white solid (3.52 g, 72%): $^1$H NMR (400 MHz, CDCl$_3$) δ 7.51 (s, 2H), 4.85 (t, J=12.1 Hz, 1H), 2.14-1.91 (m, 2H), 1.06 (t, J=7.5 Hz, 3H); $^{13}$C NMR (101 MHz, CDCl$_3$) δ 135.55, 134.39, 132.52, 129.48, 120.25 (t, J=249.0 Hz), 49.76 (t, J=30.3 Hz), 28.03 (t, J=25.2 Hz), 6.06 (t, J=5.1 Hz); ESIMS m/z 351 ([M−H]$^-$).

Example 10: Preparation of 2,2-difluoro-1-(3,4,5-trichlorophenyl)propan-1-ol (C43)

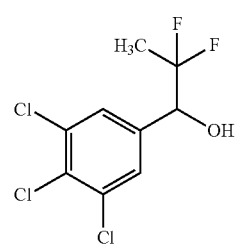

2,2-Difluoro-1-(3,4,5-trichlorophenyl)propan-1-one (C52) (1.75 g, 6.40 mmol) was dissolved in methanol (64.0 mL) at room temperature and sodium borohydride (0.290 g, 7.68 mmol) was added. The reaction was stirred at room temperature for 1 hour, until gas evolution ceased. The reaction mixture was poured into water and extracted with diethyl ether. The organic layer was washed with brine, dried over sodium sulfate, filtered, and concentrated. Purification by flash column chromatography using 0-30% acetone in hexanes as eluent provided the title compound as a clear, colorless oil (1.60 g, 91%): $^1$H NMR (400 MHz, CDCl$_3$) δ 7.50 (d, J=0.9 Hz, 2H), 4.81 (td, J=8.7, 3.8 Hz, 1H), 1.65-1.41 (m, 3H); $^{19}$F NMR (376 MHz, CDCl$_3$) δ –98.54-- 101.73 (m); IR (thin film) 3405, 1555, 1389 cm$^{-1}$.

The following compounds were prepared in like manner to the procedure outlined in Example 10:

2,2-Difluoro-1-(3,4,5-trichlorophenyl)butan-1-ol (C44)

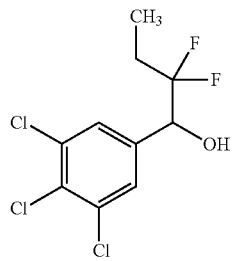 [SMILES: CCC(F)(F)C(O)c1cc(Cl)c(Cl)c(Cl)c1]

Isolated as a clear and colorless oil (3.4 g, 48%): $^1$H NMR (400 MHz, CDCl$_3$) δ 7.48 (d, J=0.9 Hz, 2H), 4.87-4.70 (m, 1H), 2.54 (dt, J=4.0, 1.0 Hz, 1H), 2.06-1.82 (m, 1H), 1.82-1.63 (m, 1H), 1.02 (t, J=7.5 Hz, 3H); $^{13}$C NMR (101 MHz, CDCl$_3$) δ 136.85, 134.20, 131.60, 127.54, 123.19 (t, J=248.0 Hz), 73.71 (t, J=30.0 Hz), 25.05 (t, J=24.6 Hz), 5.35 (t, J=5.2 Hz); EIMS m/z 287 ([M]$^+$).

1-(3,4-Dichlorophenyl)-2,2-difluoropropan-1-ol (C45)

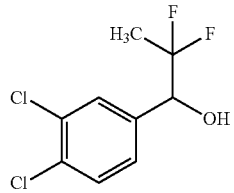

Isolated as a clear and colorless oil (2.78 g, 89%): $^1$H NMR (400 MHz, CDCl$_3$) δ 7.57 (dd, J=2.0, 0.9 Hz, 1H), 7.46 (d, J=8.3 Hz, 1H), 7.33-7.27 (m, 1H), 4.83 (td, J=8.9, 3.7 Hz, 1H), 2.55 (dt, J=3.8, 1.1 Hz, 1H), 1.50 (t, J=18.9 Hz, 3H); $^{19}$F NMR (376 MHz, CDCl$_3$) δ –99.52 (d, J=249.6 Hz), –101.09 (d, J=249.4 Hz); IR (thin film) 3417 cm$^{-1}$.

Example 11: Preparation of 1-(3-bromo-4-chlorophenyl)-2,2,2-trifluoroethanol (C46)

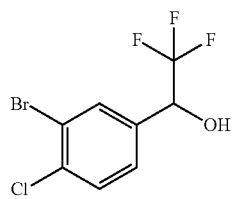

Trimethyl(trifluoromethyl)silane (10.1 mL, 68.4 mmol) and tetrabutylammonium fluoride (1.44 g, 4.56 mmol) were added to a stirred solution of 3-bromo-4-chloro-benzaldehyde (10.0 g, 45.6 mmol) in tetrahydrofuran (150 mL) at room temperature and the reaction mixture was stirred for 2 hours. The reaction mixture was diluted with dichloromethane and washed with hydrochloric acid (2 N). The separated organic layer was washed with brine, dried over sodium sulfate, filtered, and concentrated to afford the title compound as a brown liquid that was used without further purification (13.2 g, 94%):

$^1$H NMR (300 MHz, CDCl$_3$) δ 7.76 (s, 1H), 7.50-7.48 (m, 1H), 7.38-7.35 (m, 1H), 5.03-4.97 (m, 1H), 2.95 (br s, 1H); IR (thin film) 3406, 2881, 1469, 814 cm$^{-1}$; EIMS m/z 288 ([M]$^+$).

The following compounds were prepared in like manner to the procedure outlined in Example 11:

1-(3,5-Dibromo-4-chlorophenyl)-2, 2,2-trifluoroethanol (C47)

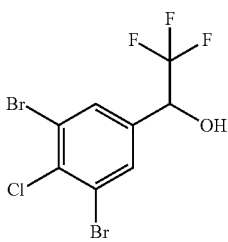

Isolated as a pale yellow liquid (7.4 g, 85%): $^1$H NMR (400 MHz, DMSO-d$_6$) δ 7.90 (s, 2H), 7.24 (d, J=5.2 Hz, 1H), 5.33 (d, J=6.4 Hz, 1H); IR (thin film) 3370, 1175, 735, 541 cm$^{-1}$; EIMS m/z 366 ([M]$^+$).

1-(4-Chloro-3,5-dimethylphenyl)-2,2,2-trifluoroethanol (C48)

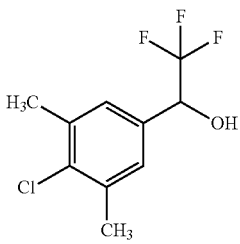

Isolated as a clear liquid (5.0 g, 70%): $^1$H NMR (400 MHz, CDCl$_3$) δ 7.18 (s, 2H), 4.95-4.92 (m, 1H), 2.40 (s, 6H); IR (thin film) 3378, 1124, 833 cm$^{-1}$; EIMS m/z 238 ([M]$^+$).

1-(4-Bromo-3,5-dichlorophenyl)-2,2,2-trifluoroethanol (C49)

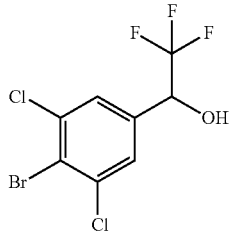

Isolated as a clear oil (33 g, 86%): $^1$H NMR (400 MHz, CDCl$_3$) δ 7.51 (s, 2H), 5.01-4.96 (m, 1H), 4.14-4.09 (m, 1H); $^{19}$F NMR (376 MHz, CDCl$_3$) δ−78.32.

1-(3-Chloro-4-fluorophenyl)-2,2,2-trifluoroethanol (C50)

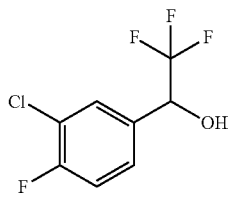 [SMILES: OC(c1ccc(F)c(Cl)c1)C(F)(F)F]

Isolated as a clear and brown gum (7.0 g, 97%): $^1$H NMR (300 MHz, CDCl$_3$) δ 7.58-7.55 (m, 1H), 7.38-7.33 (m, 1H), 7.20-7.15 (m, 1H), 5.03-4.97 (m, 1H); EIMS m/z 228 ([M]$^+$).

1-(4-Chloro-3-fluorophenyl)-2,2,2-trifluoroethanol (C51)

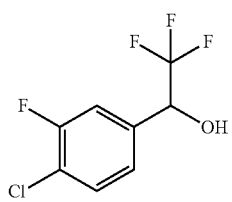 [SMILES: OC(c1ccc(Cl)c(F)c1)C(F)(F)F]

Isolated as a clear and colorless oil (1.97 g, 75%): $^1$H NMR (400 MHz, CDCl$_3$) δ 7.52-7.37 (m, 1H), 7.32 (d, J=9.6 Hz, 1H), 7.21 (d, J=8.3 Hz, 1H), 5.03 (dd, J=6.3, 3.6 Hz, 1H), 2.62 (d, J=4.0 Hz, 1H); $^{13}$C NMR (101 MHz, CDCl$_3$) δ 158.06 (J$_{CF}$=250.4 Hz), 134.40 (d, J$_{CF}$=6.6 Hz), 130.79, 123.83 (d, J$_{CF}$=3.5 Hz), 122.4 (q, J$_{CF}$=188.9 Hz), 115.8 (d, J=25.3 Hz), 71.65 (q, J$_{CF}$=31.6 Hz); EIMS m/z 228 ([M]$^+$).

Example 12: Preparation of 2,2-difluoro-1-(3,4,5-trichlorophenyl) propan-1-one (C52)

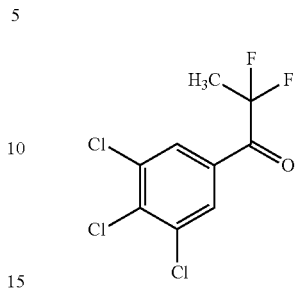

To 5-bromo-1,2,3-trichlorobenzene (2.28 g, 8.76 mmol) dissolved in diethyl ether (39.8 mL) at −78° C. under nitrogen was added n-butyllithium (3.50 mL, 8.76 mmol). The solution was stirred for 30 minutes. To this was added ethyl 2,2-difluoropropanoate (1.10 g, 7.96 mmol, as a 20% w/w solution in toluene) dropwise over 10 minutes, and the reaction mixture was stirred for an additional hour. Saturated aqueous ammonium chloride solution was added to the mixture and stirring was continued as the reaction flask warmed to room temperature. The reaction mixture was then extracted with diethyl ether, washed with water and brine, dried over sodium sulfate, filtered, and concentrated. Purification by flash column chromatography provided the title compound as a pale yellow oil (1.76 g, 73%): $^1$H NMR (400 MHz, CDCl$_3$) δ 8.11 (d, J=0.9 Hz, 2H), 1.89 (t, J=19.6 Hz, 3H); $^{19}$F NMR (376 MHz, CDCl$_3$) δ−92.66; ESIMS m/z 271 ([M−H]$^−$).

The following compounds were prepared in like manner to the procedure outlined in Example 12:

2,2-Difluoro-1-(3,4,5-trichlorophenyl)butan-1-one (C53)

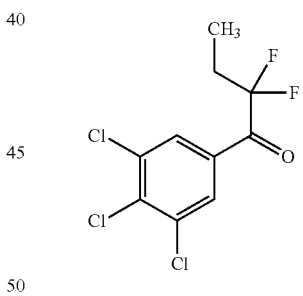

Isolated as an oil (2.3 g, 68%) and used without further purification or characterization.

1-(3,4-Dichlorophenyl)-2,2-difluoropropan-1-one (C54)

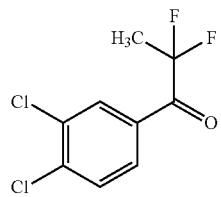

Isolated as a colorless oil (3.89 g, 71%): $^1$H NMR (400 MHz, CDCl$_3$) δ 8.21-8.18 (m, 1H), 7.99-7.93 (m, 1H), 7.59 (dd, J=8.4, 4.2 Hz, 1H), 1.89 (t, J=19.6 Hz, 3H); $^{19}$F NMR (376 MHz, CDCl$_3$) δ −92.08--93.21 (m); EIMS m/z 238/240 ([M]$^+$).

Example 13: Preparation of 4-((Z)-1,4,4,4-tetrafluoro-3-(3,4,5-trichlorophenyl)but-1-en-1-yl)-N—((R)-1-((2,2,2-trifluoroethyl)thio)propan-2-yl)-2-(trifluoromethyl)benzamide (F1)

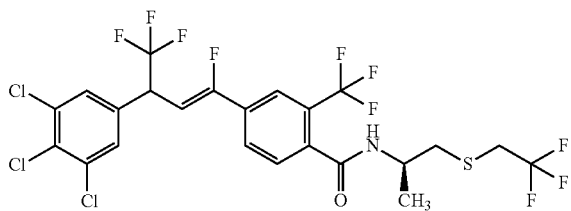

To a 25 mL vial were added (Z)-4-(1,4,4,4-tetrafluoro-3-(3,4,5-trichlorophenyl)but-1-en-1-yl)-2-(trifluoromethyl)benzoic acid (C2) (0.100 g, 0.202 mmol), (R)-1-((2,2,2-trifluoroethyl)thio)propan-2-amine hydrochloride (0.0635 g, 0.303 mmol), benzotriazol-1-yl-oxytripyrrolidinophosphonium hexafluorophosphate (0.158 g, 0.303 mmol), and dichloromethane (4.0 mL). Triethylamine (0.113 mL, 0.807 mmol) was added, and the reaction mixture was stirred at room temperature overnight. The reaction mixture was concentrated and purified by flash column chromatography to provide the title compound as a yellow oil (0.104 g, 75%).

The following compounds were prepared in like manner to the procedure outlined in Example 13:

2-Methyl-4-((Z)-1,4,4,4-tetrafluoro-3-(3,4,5-trichlorophenyl)but-1-en-1-yl)-N—((R)-1-((2,2,2-trifluoroethyl)thio)propan-2-yl)benzamide (F4)

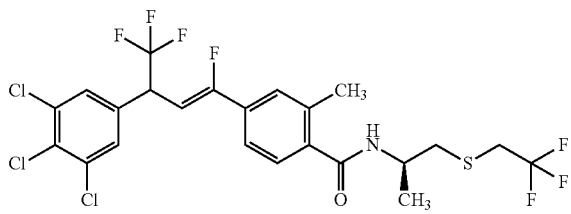 [SMILES: Cc1cc(/C(F)=C/C(c2cc(Cl)c(Cl)c(Cl)c2)C(F)(F)F)ccc1C(=O)N[C@H](C)CSCC(F)(F)F]

Isolated as a yellow oil (0.120 g, 84%). 2-Bromo-4-((Z)-1,4,4,4-tetrafluoro-3-(3,4,5-trichlorophenyl)but-1-en-1-yl)-N—((R)-1-((2,2,2-trifluoroethyl)thio)propan-2-yl)benzamide (F7)

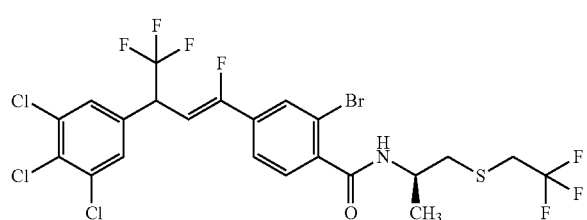

Isolated as a yellow oil (0.158 g, 57%). 2-Chloro-4-((Z)-1,4,4,4-tetrafluoro-3-(3,4,5-trichlorophenyl)but-1-en-1-yl)-N—((R)-1-((2,2,2-trifluoroethyl)thio)propan-2-yl)benzamide (F10)

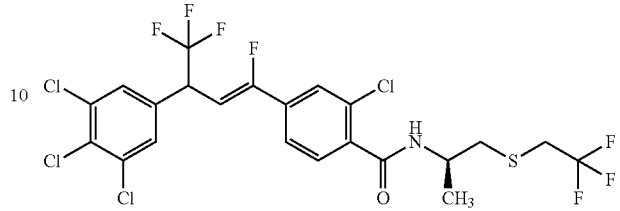

Isolated as a colorless gum (0.281 g, 80%).

2-Methyl-4-((Z)-1,4,4-trifluoro-3-(3,4,5-trichlorophenyl)pent-1-en-1-yl)-N—((R)-1-((2,2,2-trifluoroethyl)thio)propan-2-yl)benzamide (F13)

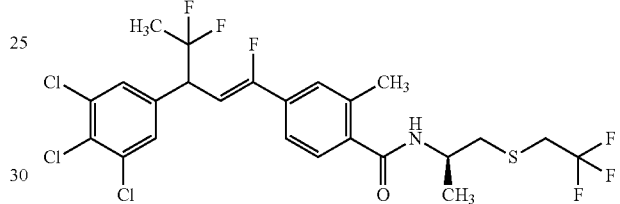

Isolated as a yellow oil (0.068 g, 74%).

2-Methyl-4-((Z)-1,4,4-trifluoro-3-(3,4,5-trichlorophenyl)pent-1-en-1-yl)-N—((R)-1-((2,2,2-trifluoroethyl)sulfonyl)propan-2-yl)benzamide (F14)

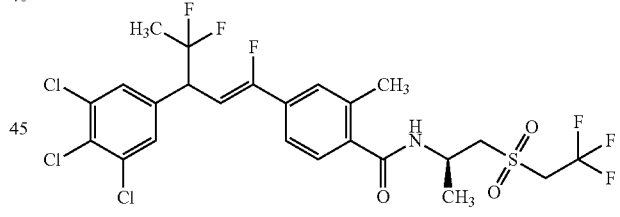

Isolated as a white gum (0.039 g, 85%).

4-((Z)-1,4,4-Trifluoro-3-(3,4,5-trichlorophenyl)pent-1-en-1-yl)-N—((R)-1-((2,2,2-trifluoroethyl)thio)propan-2-yl)-2-(trifluoromethyl)benzamide (F15)

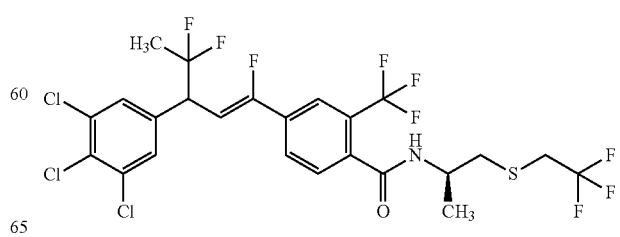

Isolated as a yellow gum (0.075 g, 68%).

4-((Z)-1,4,4-Trifluoro-3-(3,4,5-trichlorophenyl)pent-1-en-1-yl)-N—((R)-1-((2,2,2-trifluoroethyl)sulfonyl)propan-2-yl)benzamide (FC1)

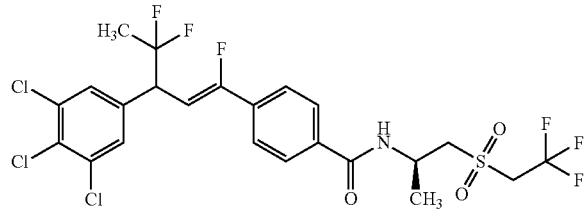 [SMILES: C[C@H](CS(=O)(=O)CC(F)(F)F)NC(=O)c1ccc(/C(F)=C/C(c2cc(Cl)c(Cl)c(Cl)c2)C(C)(F)F)cc1]

Isolated as a white foam (0.052 g, 60%).

4-((Z)-1,4,4-Trifluoro-3-(3,4,5-trichlorophenyl)pent-1-en-1-yl)-N—((R)-1-((2,2,2-trifluoroethyl)sulfonyl)propan-2-yl)-2-(trifluoromethyl)benzamide (F16)

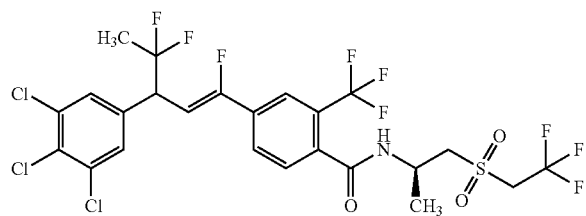 [SMILES: C[C@H](CS(=O)(=O)CC(F)(F)F)NC(=O)c1ccc(/C(F)=C/C(c2cc(Cl)c(Cl)c(Cl)c2)C(C)(F)F)cc1C(F)(F)F]

Isolated as a white gum (0.070 g, 84%).

4-((Z)-1,4,4-Trifluoro-3-(3,4,5-trichlorophenyl)pent-1-en-1-yl)-N—((R)-1-((2,2,2-trifluoroethyl)thio)propan-2-yl)benzamide (FC2)

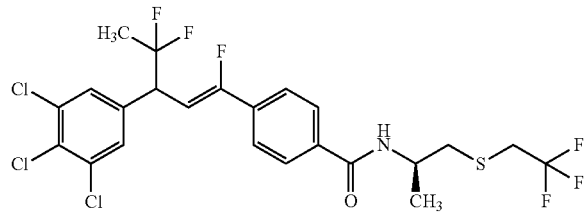 [SMILES: C[C@H](CSCC(F)(F)F)NC(=O)c1ccc(/C(F)=C/C(c2cc(Cl)c(Cl)c(Cl)c2)C(C)(F)F)cc1]

Isolated as an orange oil (0.053 g, 64%).

4-((Z)-1,4,4-Trifluoro-3-(3,4,5-trichlorophenyl)hex-1-en-1-yl)-N—((R)-1-((2,2,2-trifluoroethyl)sulfonyl)propan-2-yl)-2-(trifluoromethyl)benzamide (F38)

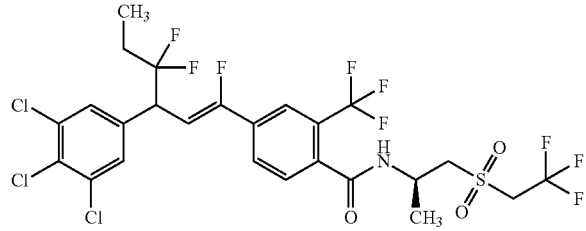 [SMILES: CCC(F)(F)C(/C=C(\F)c1ccc(C(=O)N[C@H](C)CS(=O)(=O)CC(F)(F)F)c(C(F)(F)F)c1)c1cc(Cl)c(Cl)c(Cl)c1]

Isolated as a white gum (0.052 g, 63%).

4-((Z)-1,4,4-Trifluoro-3-(3,4,5-trichlorophenyl)hex-1-en-1-yl)-N—((R)-1-((2,2,2-trifluoroethyl)thio)propan-2-yl)-2-(trifluoromethyl)benzamide (F39)

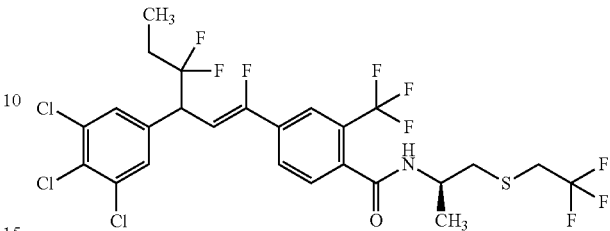

Isolated as a white glass (0.056 g, 71%).

4-((Z)-3-(3,4-Dichlorophenyl)-1,4,4-trifluoropent-1-en-1-yl)-N—((R)-1-((2,2,2-trifluoroethyl)thio)propan-2-yl)-2-(trifluoromethyl)benzamide (F57)

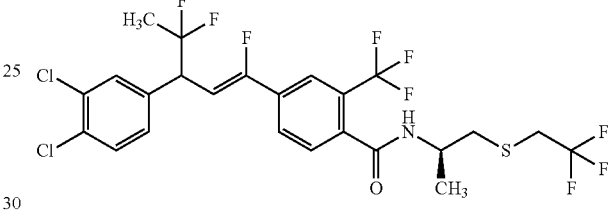

Isolated as a white gum (0.060 g, 75%).

2-Bromo-4-((Z)-3-(3,4-dichlorophenyl)-1,4,4,4-tetrafluorobut-1-en-1-yl)-N—((R)-1-((2,2,2-trifluoroethyl)thio)propan-2-yl)benzamide (F58)

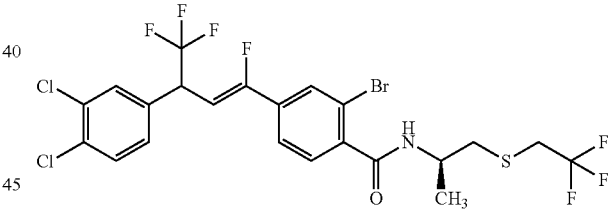

Isolated as a yellow gum (0.180 g, 59%).

Example 14: Preparation of 4-((Z)-3-(3,5-dichlorophenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F17)

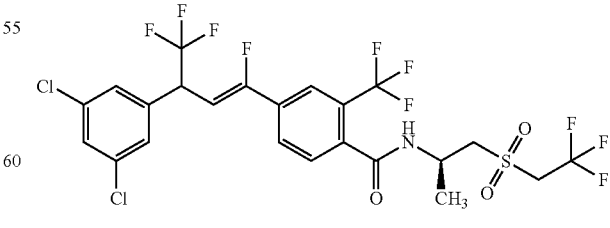

Diisopropylethylamine (0.0560 g, 0.430 mmol), 2-chloro-1,3-dimethyl imidazolidinium hexafluorophosphate (0.109 g, 0.390 mmol), and 1-hydroxy-7-azabenzotriazole (0.089 g, 0.390 mmol) were added to a solution of (Z)-4-(3-(3,5- dichlorophenyl)-1,4,4,4-tetrafluorobut-1-en-1-yl)-2-(trifluoromethyl)benzoic acid (C6) (0.180 g, 0.390 mmol), and (R)-1-((2,2,2-trifluoroethyl)sulfonyl)propan-2-amine hydrochloride (C56) (0.0881 g, 0.430 mmol) in dichloromethane (5.0 mL). The reaction mixture was stirred at room temperature for 6 hours. The reaction mixture was diluted with dichloromethane and washed with hydrochloric acid (2 N) and aqueous sodium bicarbonate. The organic layer was separated, washed with water, dried over sodium sulfate, filtered, and concentrated. Purification by flash column chromatography provided the title compound as a white solid (0.110 g, 42%).

The following compounds were prepared in like manner to the procedure outlined in Example 14:

4-((Z)-3-(3,4-Dichlorophenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F18)

Isolated as a pale yellow solid (0.120 g, 47%).

4-((Z)-3-(3,5-Dichlorophenyl)-1,4,4,4-tetrafluorobut-1-en-1-yl)-N—((R)-1-((2,2,2-trifluoroethyl)thio)propan-2-yl)-2-(trifluoromethyl)benzamide (F19)

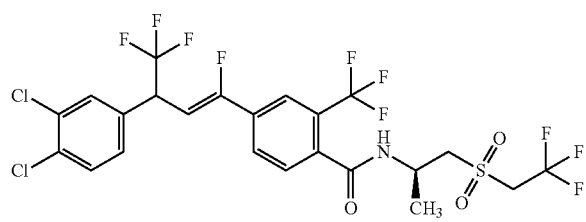 [SMILES: C[C@H](CS(=O)(=O)CC(F)(F)F)NC(=O)c1ccc(/C(F)=C/C(c2ccc(Cl)c(Cl)c2)C(F)(F)F)cc1C(F)(F)F]

Isolated as a brown gum (0.250 g, 70%).

4-((Z)-3-(3,4-Dichlorophenyl)-1,4,4,4-tetrafluorobut-1-en-1-yl)-N—((R)-1-((2,2,2-trifluoroethyl)thio)propan-2-yl)-2-(trifluoromethyl)benzamide (F20)

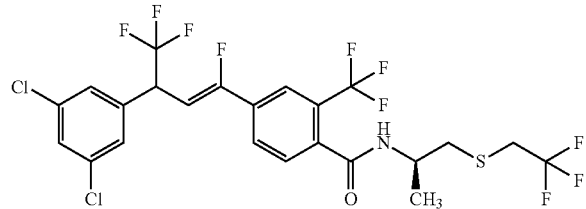

Isolated as a brown gum (0.250 g, 70%).

4-((Z)-3-(3,5-Dibromo-4-chlorophenyl)-1,4,4,4-tetrafluorobut-1-en-1-yl)-N—((R)-1-((2,2,2-trifluoroethyl)thio)propan-2-yl)-2-(trifluoromethyl)benzamide (F21)

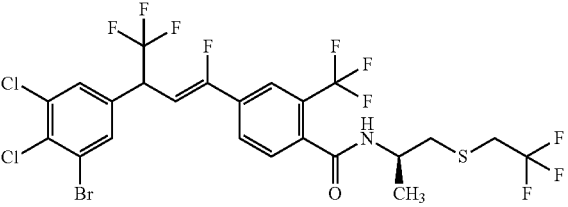

Isolated as a yellow gum (0.250 g, 57%).

4-((Z)-3-(4-Bromo-3,5-dichlorophenyl)-1,4,4,4-tetrafluorobut-1-en-1-yl)-N—((R)-1-((2,2,2-trifluoroethyl)thio)propan-2-yl)-2-(trifluoromethyl)benzamide (F24)

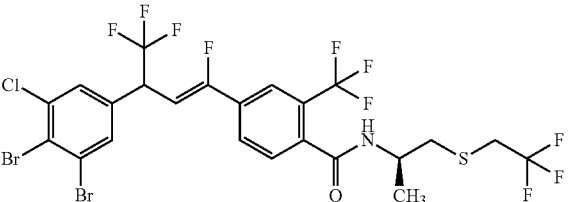

Isolated as a yellow gum (0.200 g, 49%).

4-((Z)-3-(3,5-Dichloro-4-fluorophenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F29)

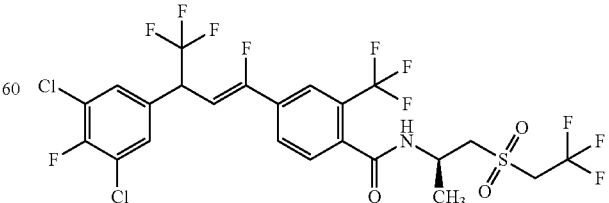

Isolated as a pale yellow solid (0.135 g, 51%).

4-((Z)-3-(3,5-Dibromophenyl)-1,4,4,4-tetrafluo-
robut-1-en-1-yl)-N—((R)-1-((2,2,2-trifluoroethyl)
thio)propan-2-yl)-2-(trifluoromethyl)benzamide
(F30)

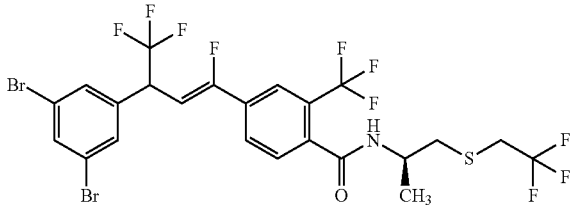

Isolated as a yellow gum (0.250 g, 57%).

4-((Z)-3-(3,5-Dichloro-4-vinylphenyl)-1,4,4,4-tetra-
fluorobut-1-en-1-yl)-N—((R)-1-((2,2,2-trifluoro-
ethyl)thio)propan-2-yl)-2-(trifluoromethyl)benz-
amide (F32)

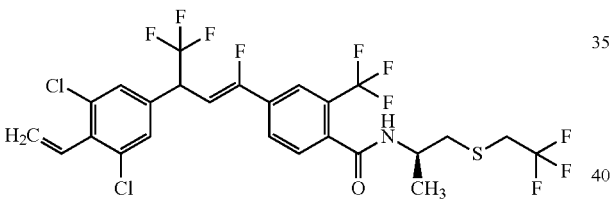

Isolated as an off-white solid (0.250 g, 47%).

4-((Z)-3-(3,5-Dichloro-4-vinylphenyl)-1,4,4,4-tetra-
fluorobut-1-en-1-yl)-N—((R)-1-((2,2,2-trifluoro-
ethyl)sulfonyl)propan-2-yl)-2-(trifluoromethyl)benz-
amide (F33)

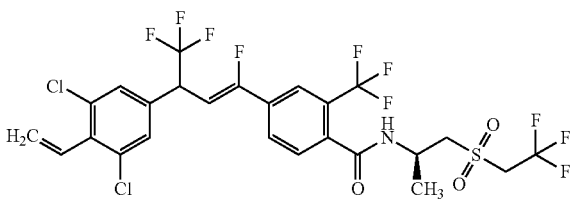 [SMILES: C=Cc1c(Cl)cc(C(/C=C(\F)c2ccc(C(=O)N[C@H](C)CS(=O)(=O)CC(F)(F)F)c(C(F)(F)F)c2)C(F)(F)F)cc1Cl]

Isolated as an off-white solid (0.120 g, 48%).

4-((Z)-3-(4-Chloro-3,5-dimethylphenyl)-1,4,4,4-
tetrafluorobut-1-en-1-yl)-N—((R)-1-((2,2,2-trifluo-
roethyl)sulfonyl)propan-2-yl)-2-(trifluoromethyl)
benzamide (F35)

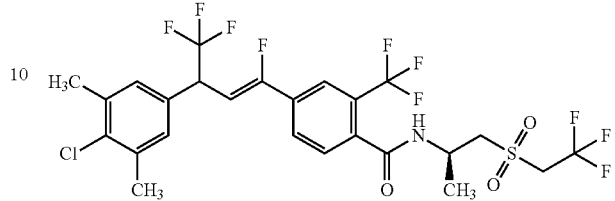

Isolated as a white solid (0.100 g, 35%).

4-((Z)-3-(3,5-Dichloro-4-fluorophenyl)-1,4,4,4-tetra-
fluorobut-1-en-1-yl)-N—((R)-1-((2,2,2-trifluoro-
ethyl)thio)propan-2-yl)-2-(trifluoromethyl)benz-
amide (F36)

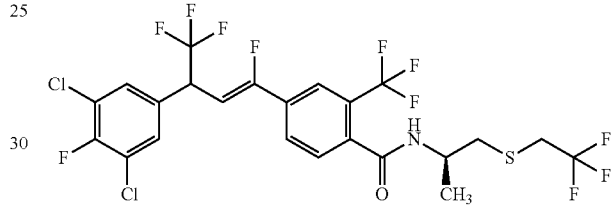

Isolated as a yellow gum (0.250 g, 59%).

4-((Z)-3-(3,5-Dibromophenyl)-1,4,4,4-tetrafluo-
robut-1-en-1-yl)-N—((R)-1-(ethylthio)propan-2-yl)-
2-(trifluoromethyl)benzamide (F40)

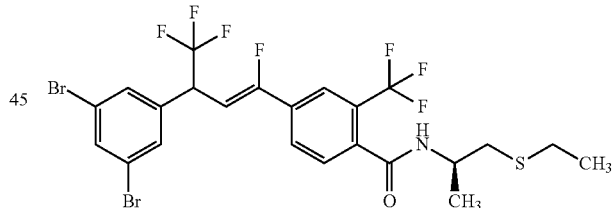

Isolated as a pale yellow gum (0.260 g, 74%).

4-((Z)-3-(3,5-Dichloro-4-fluorophenyl)-1,4,4,4-tetra-
fluorobut-1-en-1-yl)-N—((R)-1-(ethylthio)propan-2-
yl)-2-(trifluoromethyl)benzamide (F41)

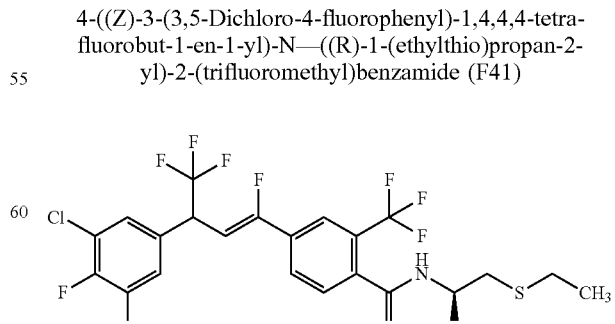

Isolated as a pale yellow gum (0.260 g, 80%).

61

4-((Z)-3-(3,5-Dichloro-4-fluorophenyl)-1,4,4,4-tetrafluorobut-1-en-1-yl)-N—((R)-1-(ethylsulfonyl)propan-2-yl)-2-(trifluoromethyl)benzamide (F43)

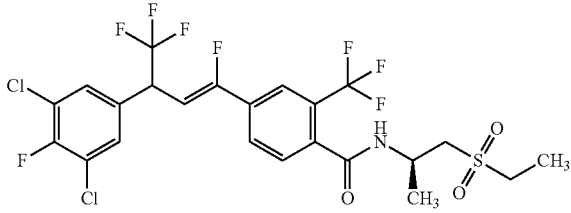 [SMILES: CCS(=O)(=O)C[C@@H](C)NC(=O)c1ccc(/C(F)=C/C(c2cc(Cl)c(F)c(Cl)c2)C(F)(F)F)cc1C(F)(F)F]

Isolated as a pale yellow solid (0.186 g, 83%).

4-((Z)-3-(3,5-Dichloro-4-vinylphenyl)-1,4,4,4-tetrafluorobut-1-en-1-yl)-N—((R)-1-(ethylthio)propan-2-yl)-2-(trifluoromethyl)benzamide (F47)

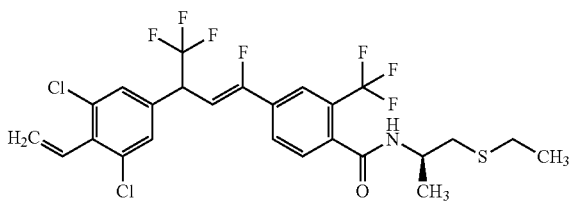 [SMILES: C=Cc1c(Cl)cc(C(/C=C(\F)c2ccc(C(=O)N[C@H](C)CSCC)c(C(F)(F)F)c2)C(F)(F)F)cc1Cl]

Isolated as a pale yellow gum (0.180 g, 37%).

4-(Z)-3-(4-Bromo-3,5-dichlorophenyl)-1,4,4,4-tetrafluorobut-1-en-1-yl)-N—((R)-1-(ethylthio)propan-2-yl)-2-(trifluoromethyl)benzamide (F48)

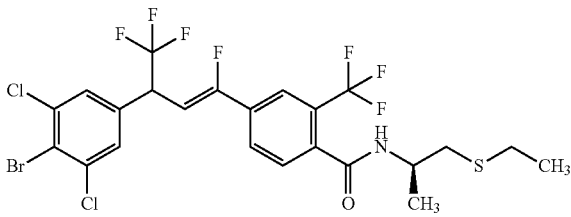

Isolated as a yellow sticky solid (0.200 g, 63%)

4-((Z)-3-(4-Chloro-3,5-dimethylphenyl)-1,4,4,4-tetrafluorobut-1-en-1-yl)-N—((R)-1-((2,2,2-trifluoroethyl)thio)propan-2-yl)-2-(trifluoromethyl)benzamide (F52)

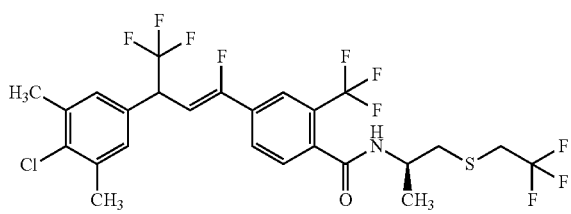 [SMILES: Cc1cc(C(/C=C(\F)c2ccc(C(=O)N[C@H](C)CSCC(F)(F)F)c(C(F)(F)F)c2)C(F)(F)F)cc(C)c1Cl]

Isolated as a yellow gum (0.150 g, 45%)

62

4-((Z)-3-(4-Chloro-3,5-dimethylphenyl)-1,4,4,4-tetrafluorobut-1-en-1-yl)-N—((R)-1-(ethylsulfonyl)propan-2-yl)-2-(trifluoromethyl)benzamide (F53)

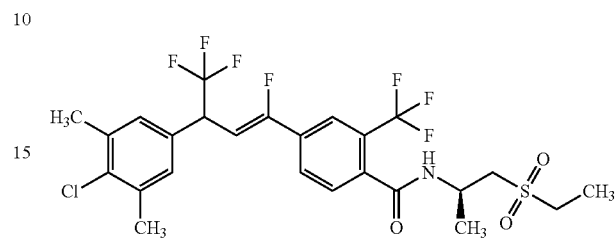

Isolated as a yellow gum (0.180 g, 86%).

4-((Z)-3-(3,4-Dibromophenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F54)

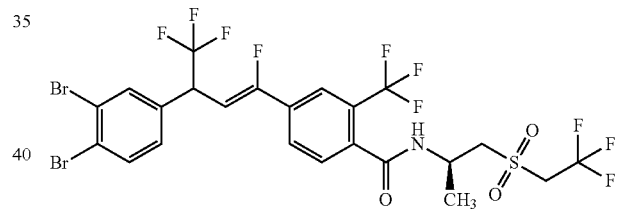

Isolated as a pale yellow solid (0.150 g, 53%).

4-((Z)-3-(3,5-Dibromo-4-chlorophenyl)-1,4,4,4-tetrafluorobut-1-en-1-yl)-N—((R)-1-(ethylsulfonyl)propan-2-yl)-2-(trifluoromethyl)benzamide (F55)

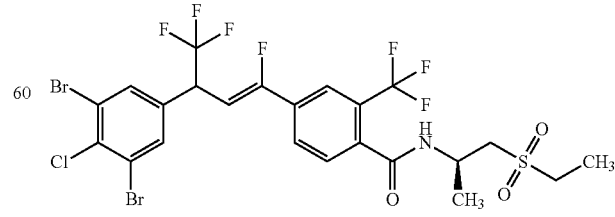

Isolated as a yellow sticky solid (0.250 g, 44%)

4-((Z)-3-(3,5-Dichlorophenyl)-1,4,4,4-tetrafluorobut-1-en-1-yl)-N—((R)-1-(ethylthio)propan-2-yl)-2-(trifluoromethyl)benzamide (F59)

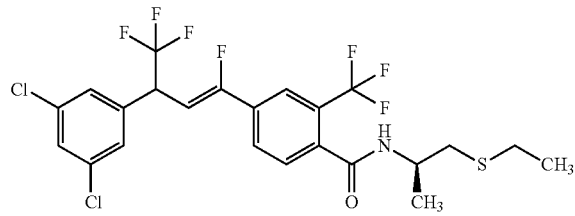 [SMILES: CCSC[C@@H](C)NC(=O)c1ccc(/C(F)=C/C(c2cc(Cl)cc(Cl)c2)C(F)(F)F)cc1C(F)(F)F]

Isolated as a yellow gum (0.180 g, 52%).)

4-((Z)-3-(3,4-Dichlorophenyl)-1,4,4,4-tetrafluorobut-1-en-1-yl)-N—((R)-1-(ethylthio)propan-2-yl)-2-(trifluoromethyl)benzamide (F60)

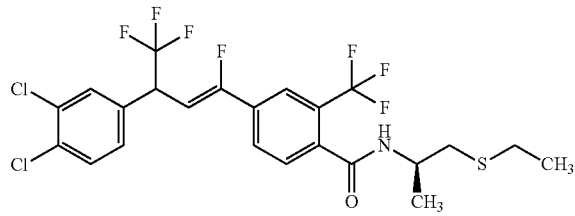 [SMILES: CCSC[C@@H](C)NC(=O)c1ccc(/C(F)=C/C(c2ccc(Cl)c(Cl)c2)C(F)(F)F)cc1C(F)(F)F]

Isolated as a yellow gum (0.180 g, 47%).

4-((Z)-3-(4-Chloro-3,5-dimethylphenyl)-1,4,4,4-tetrafluorobut-1-en-1-yl)-N—((R)-1-(ethylthio)propan-2-yl)-2-(trifluoromethyl)benzamide (F61)

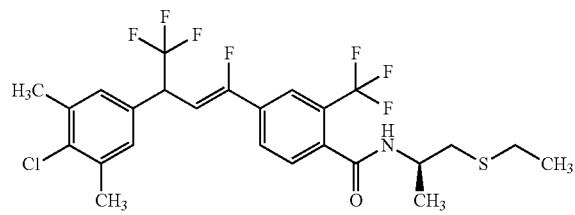 [SMILES: CCSC[C@@H](C)NC(=O)c1ccc(/C(F)=C/C(c2cc(C)c(Cl)c(C)c2)C(F)(F)F)cc1C(F)(F)F]

Isolated as a yellow gum (0.180 g, 55%)

4-((Z)-3-(3,4-Dibromophenyl)-1,4,4,4-tetrafluorobut-1-en-1-yl)-N—((R)-1-((2,2,2-trifluoroethyl)thio)propan-2-yl)-2-trifluoromethyl)benzamide (F62)

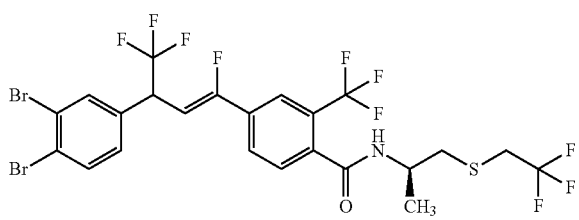 [SMILES: C[C@H](CSCC(F)(F)F)NC(=O)c1ccc(/C(F)=C/C(c2ccc(Br)c(Br)c2)C(F)(F)F)cc1C(F)(F)F]

Isolated as a yellow gum (0.300 g, 69%).

4-((Z)-3-(3-Bromo-5-chlorophenyl)-1,4,4,4-tetrafluorobut-1-en-1-yl)-N—((R)-1-((2,2,2-trifluoroethyl)thio)propan-2-yl)-2-(trifluoromethyl)benzamide (F64)

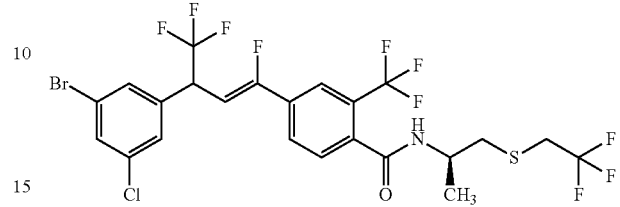

Isolated as a yellow gum (0.230 g, 59%).

Example 15: Preparation of 4-((Z)-1,4,4,4-tetrafluoro-3-(3,4,5-trichlorophenyl)but-1-en-1-yl)-N—((R)-1-((2,2,2-trifluoroethyl)sulfonyl)propan-2-yl)-2-(trifluoromethyl)benzamide (F2)

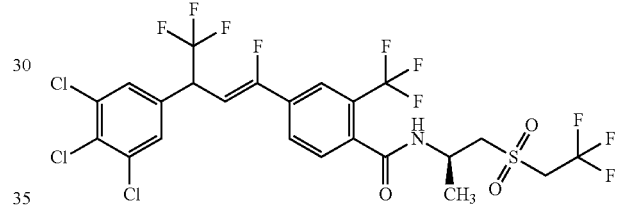

To a 100 mL round-bottomed flask was added 4-((Z)-1,4,4,4-tetrafluoro-3-(3,4,5-trichlorophenyl)but-1-en-1-yl)-N—((R)-1-((2,2,2-trifluoroethyl)thio)propan-2-yl)-2-(trifluoromethyl)benzamide (F1) (0.135 g, 0.207 mmol), sodium perborate (0.0920 g, 0.415 mmol), and acetic acid (2.1 mL). The reaction was stirred at 50° C. overnight. The reaction mixture was concentrated and purified by flash column chromatography to provide the title compound as a white solid (0.110 g, 42%).

The following compounds were prepared in like manner to the procedure outlined in Example 15:

2-Methyl-4-((Z)-1,4,4,4-tetrafluoro-3-(3,4,5-trichlorophenyl)but-1-en-1-yl)-N—((R)-1-((2,2,2-trifluoroethyl)sulfonyl)propan-2-yl)benzamide (F6)

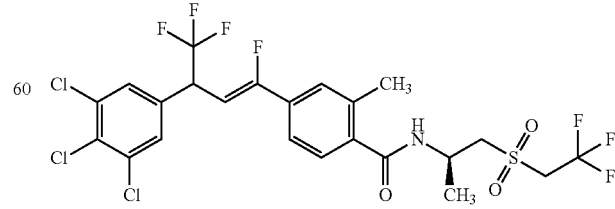

Isolated as an off-white solid (0.056 g, 98%).

2-Bromo-4-((Z)-1,4,4,4-tetrafluoro-3-(3,4,5-trichlorophenyl)but-1-en-1-yl)-N—((R)-1-((2,2,2-trifluoroethyl)sulfonyl)propan-2-yl)benzamide (F8)

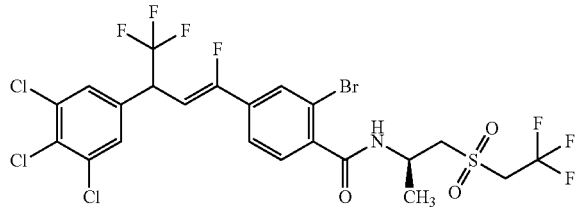

Isolated as a white solid (0.062 g, 69%).

2-Chloro-4-((Z)-1,4,4,4-tetrafluoro-3-(3,4,5-trichlorophenyl)but-1-en-1-yl)-N—((R)-1-((2,2,2-trifluoroethyl)sulfonyl)propan-2-yl)benzamide (F11)

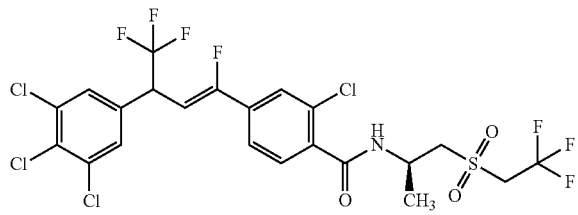

Isolated as a white solid (0.123 g, 74%).

4-((Z)-3-(3,5-Dibromo-4-chlorophenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F22)

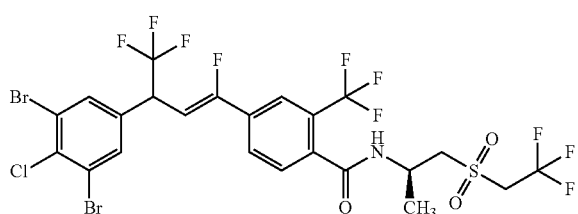

Isolated as an off-white solid (0.108 g, 48%).

4-((Z)-3-(4-Bromo-3,5-dichlorophenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F25)

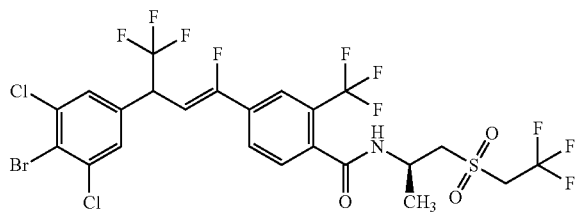

Isolated as an off-white solid (0.107 g, 42%).

4-((Z)-3-(3,5-Dibromophenyl)-1,4,4,4-tetrafluorobut-1-en-1-yl)-N—((R)-1-(ethylsulfonyl)propan-2-yl)-2-(trifluoromethyl)benzamide (F42)

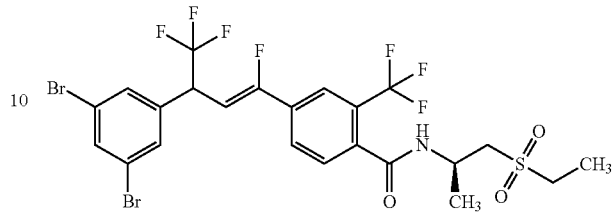

Isolated as a pale yellow gum (0.166 g, 71%).

4-((Z)-3-(3,5-Dichlorophenyl)-1,4,4,4-tetrafluorobut-1-en-1-yl)-N—((R)-1-(ethylsulfonyl)propan-2-yl)-2-(trifluoromethyl)benzamide (F45)

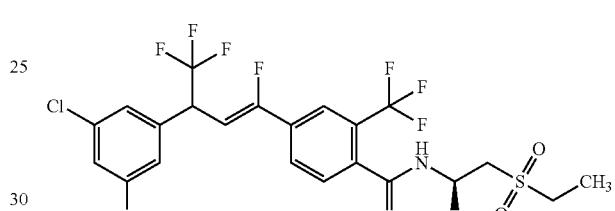

Isolated as a pale yellow solid (0.120 g, 56%).

4-((Z)-3-(3,4-Dichlorophenyl)-1,4,4,4-tetrafluorobut-1-en-1-yl)-N—((R)-1-(ethylsulfonyl)propan-2-yl)-2-(trifluoromethyl)benzamide (F46)

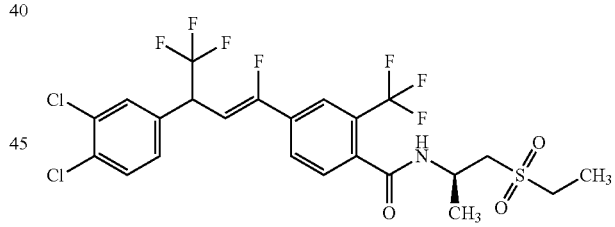

Isolated as a yellow gum (0.100 g, 55%).

4-((Z)-3-(3,5-Dibromo-4-chlorophenyl)-1,4,4,4-tetrafluorobut-1-en-1-yl)-N—((R)-1-(ethylsulfonyl)propan-2-yl)-2-(trifluoromethyl)benzamide (F56)

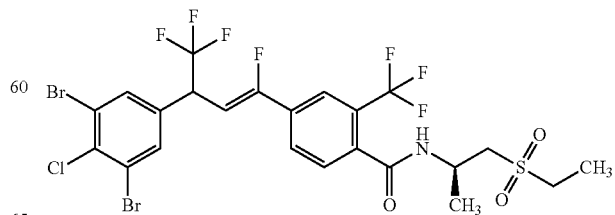

Isolated as an off white solid (0.115 g, 53%).

4-((Z)-3-(4-Bromo-3,5-chlorophenyl)-1,4,4,4-tetra-fluorobut-1-en-1-yl)-N—((R)-1-(ethylsulfonyl)pro-pan-2-yl)-2-(trifluoromethyl)benzamide (F63)

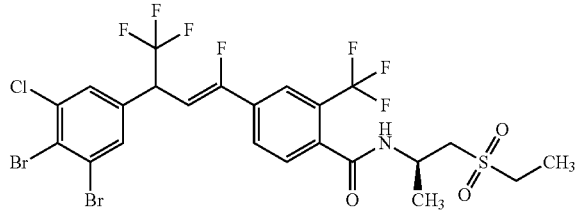

Isolated as a yellow gum (0.75 g, 41%).

4-((Z)-3-(3-Bromo-5-chlorophenyl)-1,4,4-tetrafluo-robut-1-en-1-yl)-N—((R)-1-(2,2,2-trifluoroethyl)sulfonyl)propan-2-yl)-2-(trifluoromethyl)benzamide (F65)

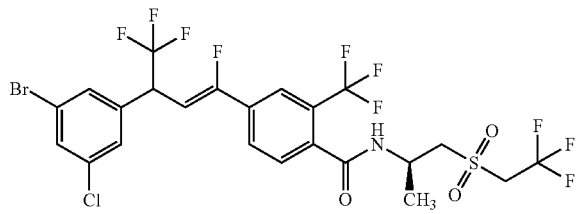 [SMILES: C[C@H](CS(=O)(=O)CC(F)(F)F)NC(=O)c1ccc(/C(F)=C/C(c2cc(Cl)cc(Br)c2)C(F)(F)F)cc1C(F)(F)F]

Isolated as a yellow solid (0.085 g, 39%)

2-Bromo-4-((Z)-3-(3,4-dichlorophenyl)-1,4,4,4-tet-rafluorobut-1-en-1-yl)-N—((R)-1-(2,2,2-trifluoro-ethyl)sulfonyl)propan-2-yl)benzamide (F67)

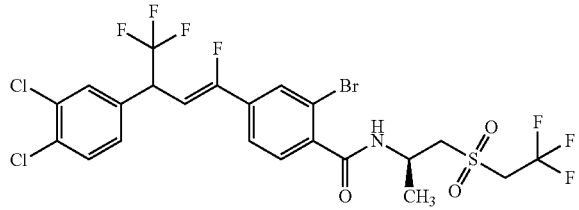 [SMILES: C[C@H](CS(=O)(=O)CC(F)(F)F)NC(=O)c1ccc(/C(F)=C/C(c2ccc(Cl)c(Cl)c2)C(F)(F)F)cc1Br]

Isolated as a white gum (0.071 g, 92%).

(R)-tert-Butyl (1-((2,2,2-trifluoroethyl)sulfonyl)pro-pan-2-yl)carbamate (C55)

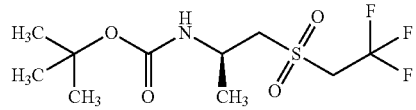

Isolated as a white solid (0.600 g, 16%): $^1$H NMR (400 MHz, DMSO-$d_6$) δ 7.03 (d, J=8.4 Hz, 1H), 4.12-3.83 (m, 2H), 3.13-2.89 (m, 2H), 1.39 (d, J=1.4 Hz, 9H), 1.18 (d, J=6.7 Hz, 3H).

Example 16: Preparation of 4-((Z)-1,4,4,4-tetra-fluoro-3-(3,4,5-trichlorophenyl)but-1-en-1-yl)-N-((2R)-1-((2,2,2-trifluoroethyl)sulfinyl)propan-2-yl)-2-(trifluoromethyl)benzamide (F3)

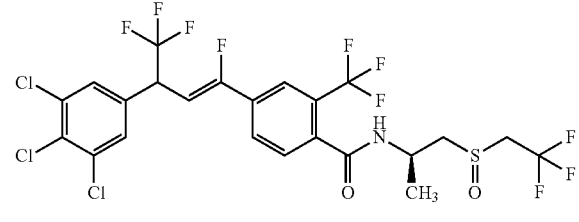

To a 25 mL vial was added 4-((Z)-1,4,4,4-tetrafluoro-3-(3,4,5-trichlorophenyl)but-1-en-1-yl)-N—((R)-1-((2,2,2-tri-fluoroethyl)thio)propan-2-yl)-2-(trifluoromethyl)benzamide (F1) (0.044 g, 0.068 mmol), hydrogen peroxide (0.0092 g, 0.081 mmol), and hexafluoropropanol (0.38 mL). The reaction was stirred for 48 hours. The reaction mixture was quenched with sodium thiosulfate, extracted with dichloromethane, dried over magnesium sulfate, filtered, and concentrated. Purification by flash column chromatography provided the title compound as an off-white solid (0.046 g, 97%).

The following compounds were prepared in like manner to the procedure outlined in Example 16:

2-Methyl-4-((Z)-1,4,4,4-tetrafluoro-3-(3,4,5-trichlo-rophenyl)but-1-en-1-yl)-N-((2R)-1-((2,2,2-trifluoro-ethyl)sulfinyl)propan-2-yl)benzamide (F5)

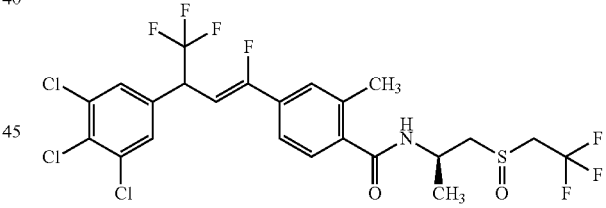

Isolated as an off-white solid (0.034 g, 61%).

2-Bromo-4-((Z)-1,4,4,4-tetrafluoro-3-(3,4,5-trichlo-rophenyl)but-1-en-1-yl)-N-((2R)-1-((2,2,2-trifluoro-ethyl)sulfinyl)propan-2-yl)benzamide (F9)

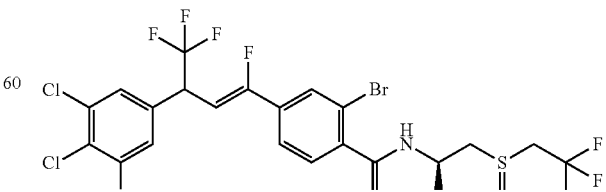

Isolated as a white solid (0.043 g, 79%).

2-Chloro-4-((Z)-1,4,4,4-tetrafluoro-3-(3,4,5-trichlorophenyl)but-1-en-1-yl)-N-((2R)-1-((2,2,2-trifluoroethyl)sulfinyl)propan-2-yl)benzamide (F12)

4-((Z)-3-(3,5-Dichlorophenyl)-1,4,4,4-tetrafluorobut-1-en-1-yl)-N-((2R)-1-((2,2,2-trifluoroethyl)sulfinyl)propan-2-yl)-2-(trifluoromethyl)benzamide (F27)

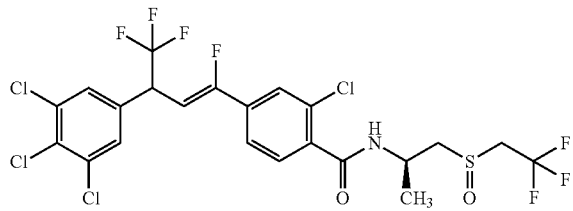

Isolated as a white solid (0.098 g, 76%).

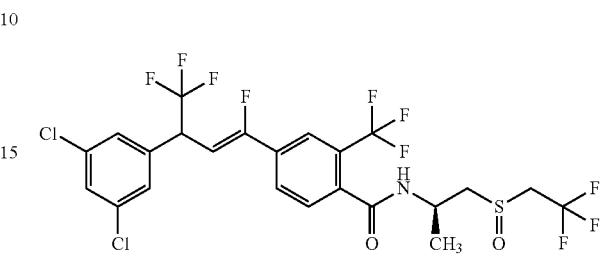

Isolated as a pale yellow solid (0.100 g, 47%).

4-((Z)-3-(3,5-Dibromo-4-chlorophenyl)-1,4,4,4-tetrafluorobut-1-en-1-yl)-N-((2R)-1-((2,2,2-trifluoroethyl)sulfinyl)propan-2-yl)-2-(trifluoromethyl)benzamide (F23)

4-((Z)-3-(3,4-Dichlorophenyl)-1,4,4,4-tetrafluorobut-1-en-1-yl)-N-((2R)-1-((2,2,2-trifluoroethyl)sulfinyl)propan-2-yl)-2-(trifluoromethyl)benzamide (F28)

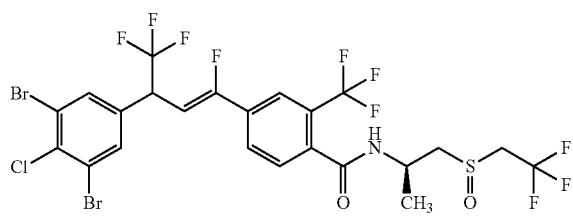 [SMILES: C[C@H](CS(=O)CC(F)(F)F)NC(=O)c1ccc(/C(F)=C/C(c2cc(Cl)c(Cl)c(Cl)c2)C(F)(F)F)cc1C(F)(F)F]

Isolated as a yellow solid (0.106 g, 51%).

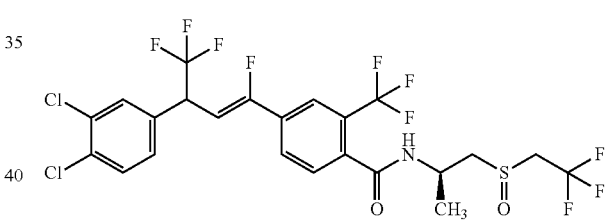

Isolated as a white solid (0.160 g, 75%).

4-((Z)-3-(4-Bromo-3,5-dichlorophenyl)-1,4,4,4-tetrafluorobut-1-en-1-yl)-N-((2R)-1-((2,2,2-trifluoroethyl)sulfinyl)propan-2-yl)-2-(trifluoromethyl)benzamide (F26)

4-((Z)-3-(3,5-Dibromophenyl)-1,4,4,4-tetrafluorobut-1-en-1-yl)-N-((2R)-1-((2,2,2-trifluoroethyl)sulfinyl)propan-2-yl)-2-(trifluoromethyl)benzamide (F31)

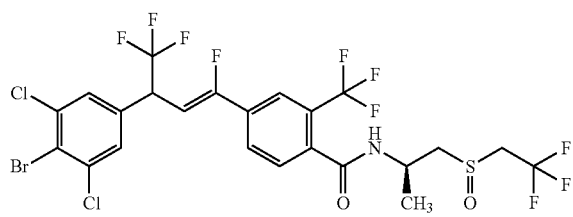

Isolated as an off-white solid (0.115 g, 56%).

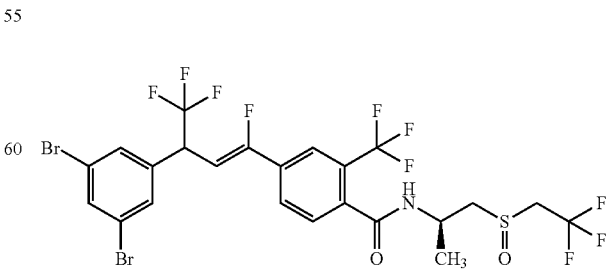

Isolated as a yellow gum (0.128 g, 71%).

4-((Z)-3-(3,5-Dichloro-4-vinylphenyl)-1,4,4,4-tetra-fluorobut-1-en-1-yl)-N-((2R)-1-((2,2,2-trifluoro-ethyl)sulfinyl)propan-2-yl)-2-(trifluoromethyl)benz-amide (F34)

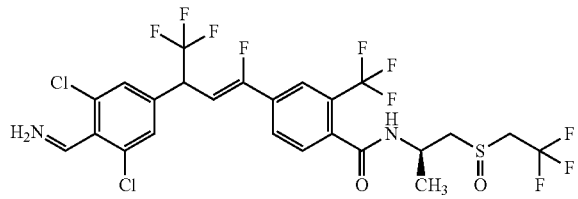 [SMILES: C[C@H](CS(=O)CC(F)(F)F)NC(=O)c1ccc(/C(F)=C/C(c2cc(Cl)c(C=N)c(Cl)c2)C(F)(F)F)cc1C(F)(F)F]

Isolated as an off-white solid (0.121 g, 69%).

4-((Z)-3-(3,5-Dichloro-4-fluorophenyl)-1,4,4,4-tetra-fluorobut-1-en-1-yl)-N-((2R)-1-((2,2,2-trifluoro-ethyl)sulfinyl)propan-2-yl)-2-(trifluoromethyl)benz-amide (F37)

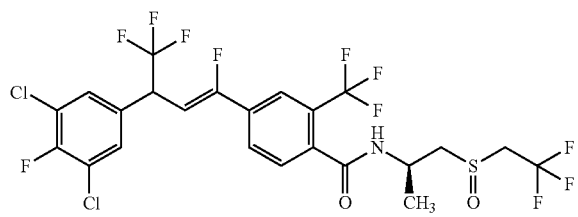 [SMILES: C[C@H](CS(=O)CC(F)(F)F)NC(=O)c1ccc(/C(F)=C/C(c2cc(Cl)c(F)c(Cl)c2)C(F)(F)F)cc1C(F)(F)F]

Isolated as a pale yellow solid (0.150 g, 71%).

4-((Z)-3-(4-Chloro-3,5-dimethylphenyl)-1,4,4,4-tetrafluorobut-1-en-1-yl)-N-((2R)-1-(ethylsulfinyl)propan-2-yl)-2-(trifluoromethyl)benzamide (F44)

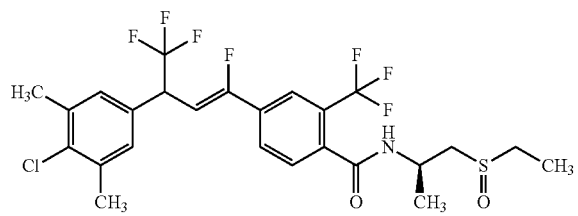 [SMILES: CCS(=O)C[C@@H](C)NC(=O)c1ccc(/C(F)=C/C(c2cc(C)c(Cl)c(C)c2)C(F)(F)F)cc1C(F)(F)F]

Isolated as an off-white solid (0.100 g, 59%).

2-Bromo-4-((Z)-3-(3,4-dichlorophenyl)-1,4,4,4-tet-rafluorobut-1-en-1-yl)-N-((2R)-1-((2,2,2-trifluoro-ethyl)sulfinyl)propan-2-yl)benzamide (F66)

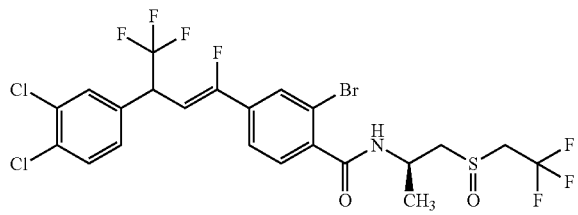 [SMILES: C[C@H](CS(=O)CC(F)(F)F)NC(=O)c1ccc(/C(F)=C/C(c2ccc(Cl)c(Cl)c2)C(F)(F)F)cc1Br]

Isolated as a white gum (0.023 g, 34%)

4-((Z)-3-(3-Bromo-5-chlorophenyl)-1,4,4,4-tetra-fluorobut-1-en-1-yl)-N-((2R)-1-((2,2,2-trifluoro-ethyl)sulfinyl)propan-2-yl)-2-(trifluoromethyl)benz-amide (F68)

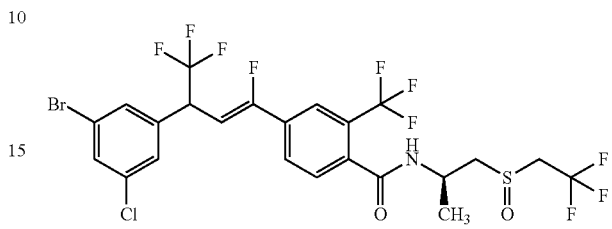

Isolated as a yellow gum (0.107 g, 48%).

Example 17: Preparation of (Z)-4-(1,4,4,4-tetra-fluoro-3-(3,4,5-trichlorophenyl)but-1-en-1-yl)-N-(2-((2,2,2-trifluoroethyl)thio)ethyl)-2-(trifluoromethyl) benzamide (F51)

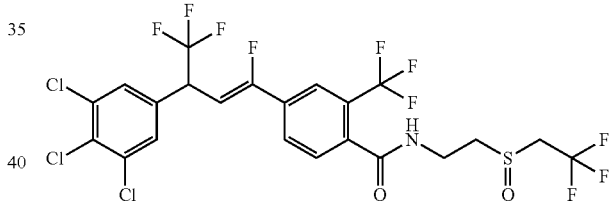

To a 25 mL vial were added (Z)-4-(1,4,4,4-tetrafluoro-3-(3,4,5-trichlorophenyl)but-1-en-1-yl)-2-(trifluoromethyl) benzoic acid (C2) (0.800 g, 1.61 mmol) and dichloromethane (4.0 mL). Oxalyl chloride (1.00 mL, 1.61 mmol) followed by N,N-dimethylformamide (0.005 mL) was then added. After two hours, the reaction was concentrated, diluted with dichloromethane, and concentrated. The material was placed in a vacuum oven (room temperature) overnight. To a separate 25 mL vial was added 2-((2,2,2-trifluoroethyl)thio)ethanamine hydrochloride (0.484 g, 2.47 mmol) in tetrahydrofuran (10 mL). Lithium carbonate (0.167 g, 2.26 mmol) and water (2 mL) were added and the vial was vortexed followed by stirring for 1 hour. The prepared acid chloride was dissolved in tetrahydrofuran (5 mL) and the amine solution was added with stirring. The reaction was concentrated, diluted with ethyl acetate, and washed with citric acid, water, and brine. The resulting organic solution was dried over magnesium sulfate, filtered, and concentrated. Purification by flash column chromatography using 50% ethyl acetate in hexanes as eluent provided the title compound as a brown oil (0.868 g, 76%).

Example 18: Preparation of (Z)-4-(1,4,4,4-tetrafluoro-3-(3,4,5-trichlorophenyl)but-1-en-1-yl)-N-(2-((2,2,2-trifluoroethyl)sulfonyl)ethyl)-2-(trifluoromethyl)benzamide (F49) and (Z)-4-(1,4,4,4-tetrafluoro-3-(3,4,5-trichlorophenyl)but-1-en-1-yl)-N-(2-((2,2,2-trifluoroethyl)sulfinyl)ethyl)-2-(trifluoromethyl)benzamide (F50)

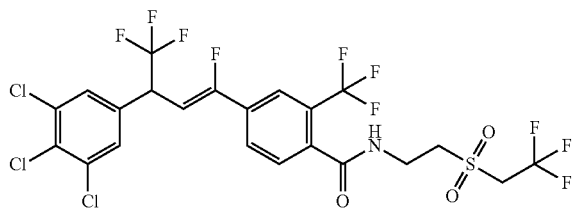

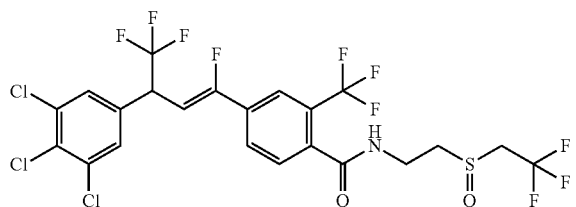 [SMILES: O=C(NCCS(=O)CC(F)(F)F)c1ccc(/C(F)=C/C(c2cc(Cl)c(Cl)c(Cl)c2)C(F)(F)F)cc1C(F)(F)F]

To a 25 mL vial was added (Z)-4-(1,4,4,4-tetrafluoro-3-(3,4,5-trichlorophenyl)but-1-en-1-yl)-N-(2-((2,2,2-trifluoroethyl)thio)ethyl)-2-(trifluoromethyl)benzamide (F51) (0.795 g, 1.25 mmol) and acetic acid (8.32 mL). Sodium perborate (0.288 g, 1.87 mmol) was added and the reaction was heated at 55° C. The reaction mixture was concentrated with heptanes at 40° C. to azeotrope the acetic acid. Purification by flash column chromatography using 0-100% ethyl acetate in hexanes as eluent provided the title compound (F49) as a colorless oil (0.113 g, 12%) and the title compound (F50) as a colorless oil (0.190 g, 21%).

Example 19: Preparation of (R)-1-((2,2,2-trifluoroethyl)sulfonyl)propan-2-amine hydrochloride (C56)

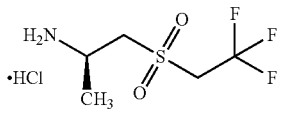

(R)-tert-Butyl (1-((2,2,2-trifluoroethyl)sulfonyl)propan-2-yl)carbamate (C57) (0.300 g, 0.983 mmol) was treated with hydrogen chloride (4 M in dioxane, 5.00 mL, 20.0 mmol) and stirred overnight. The resulting suspension was concentrated to provide the title compound as a brown solid (0.232 g, 93%): $^1$H NMR (400 MHz, DMSO-$d_6$) δ 8.44 (s, 3H), 4.93 (qd, J=10.1, 2.7 Hz, 2H), 3.86-3.69 (m, 2H), 3.66-3.55 (m, 1H), 1.41 (d, J=6.3 Hz, 3H); $^{13}$C NMR (101 MHz, DMSO-$d_6$) δ 122.13 (q, $J_{CF}$=277.1 Hz), 57.08, 54.66 (q, $J_{CF}$=29.7 Hz), 41.39, 18.51; $^{19}$F NMR (376 MHz, DMSO-$d_6$) δ−59.43.

Example 20: Preparation of (R)-tert-butyl (1-((2,2,2-trifluoroethyl)thio)propan-2-yl)carbamate (C57)

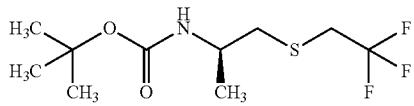 [SMILES: C[C@H](CSCC(F)(F)F)NC(=O)OC(C)(C)C]

To a 100 mL round-bottomed flask was added potassium hydroxide (0.465 g, 8.29 mmol) in degassed methanol (16.0 mL). (R)—S-(2-((tert-Butoxycarbonyl)amino)propyl) ethanethioate (C58) (1.50 g, 5.53 mmol) was added followed by 2,2,2-trifluoroethyl trifluoromethanesulfonate (2.57 g, 11.1 mmol). The reaction was stirred overnight at room temperature. The reaction mixture was concentrated. The residue was diluted with water and ethyl acetate. The layers were separated and the organic layer was washed with saturated aqueous sodium bicarbonate, dried over magnesium sulfate, filtered, and concentrated. Purification by flash column chromatography using 0-30% ethyl acetate in hexanes provided the title compound as a colorless liquid (1.07 g, 60%): 1H NMR (400 MHz, CDCl$_3$) δ 4.54 (s, 1H), 3.86 (s, 1H), 3.13 (qd, J=9.9, 2.6 Hz, 2H), 2.77 (d, J=5.9 Hz, 2H), 1.45 (s, 9H), 1.22 (dd, J=6.7, 1.4 Hz, 3H); $^{19}$F NMR (376 MHz, CDCl$_3$) δ−66.56; IR (thin film) 3340, 2978, 2934, 1687, 1505 cm$^{-1}$.

Example 21: Preparation of (R)—S-(2-((tert-butoxycarbonyl)amino)propyl) ethanethioate (C58)

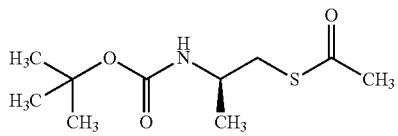

To a 100 mL round-bottomed flask was added ethanethioic S-acid (2.23 mL, 31.6 mmol) and N,N-dimethylformamide (22.6 mL) which was placed under a nitrogen atmosphere. Sodium hydride (60% in oil, 1.14 g, 28.4 mmol) was added portionwise and the orange solution was stirred for 15 minutes. (R)-2-((tert-Butoxycarbonyl)amino)propyl methanesulfonate (C59) (4.00 g, 15.8 mmol) was added and the reaction mixture was stirred. The reaction was diluted with ethyl acetate and water. The layers were separated and the aqueous layer was extracted with ethyl acetate (2×). The combined organic layers was washed with water (2×), brine, dried over magnesium sulfate, filtered, and concentrated. Purification by flash column chromatography using 0-50% ethyl acetate in hexanes provided the title compound as an off-white solid (1.29 g, 33%): $^1$H NMR (400 MHz, CDCl$_3$) δ 4.61 (s, 1H), 4.04-3.65 (m, 1H), 3.13-2.92 (m, 2H), 2.36 (s, 3H), 1.44 (s, 9H), 1.17 (d, J=6.7 Hz, 3H); $^{13}$C NMR (101 MHz, CDCl$_3$) δ 195.55, 155.15, 79.32, 46.35, 35.08, 30.57, 28.38, 20.06; IR (thin film) 3350, 2976, 2931, 1686, 1513 cm$^{-1}$.

Example 22: Preparation of (R)-2-((tert-butoxycarbonyl)amino)propyl methanesulfonate (C59)

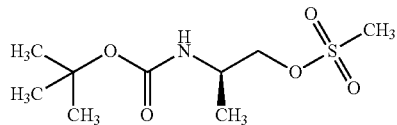

To a 250 mL round-bottomed flask was added (R)-tert-butyl (1-hydroxypropan-2-yl)carbamate (1.15 g, 6.56 mmol) and dichloromethane (26.3 mL). Triethylamine (2.74 mL, 19.7 mmol) was added, and the solution was cooled to 1° C. utilizing a water/ice bath. Methanesulfonyl chloride (0.559 mL, 7.22 mmol) was added in portions over 1 hour, and the reaction mixture was stirred overnight. The reaction mixture was diluted with water, and the layers were separated. The aqueous layer was extracted with dichloromethane. The combined extracts were dried over magnesium sulfate, filtered, and concentrated to provide the title compound as an off-white solid (1.30 g, 78%): $^1$H NMR (400 MHz, CDCl$_3$) δ 4.91-4.59 (m, 1H), 4.38-4.10 (m, 2H), 3.97 (ddd, J=13.9, 10.1, 5.5 Hz, 1H), 3.04 (s, 3H), 1.45 (s, 9H), 1.24 (d, J=6.9 Hz, 3H); $^{13}$C NMR (101 MHz, CDCl$_3$) δ 155.08, 79.79, 72.07, 45.49, 37.27, 28.31, 17.12.

The following molecules in Table 1 may be prepared according to the procedures disclosed: P1, P2, P3, P4, P5, P6, P7, P8, P9, P10, and P11

TABLE 1

Structure and Preparation Method for Prophetic Molecules

| No. | Structure |
|---|---|
| P1 | 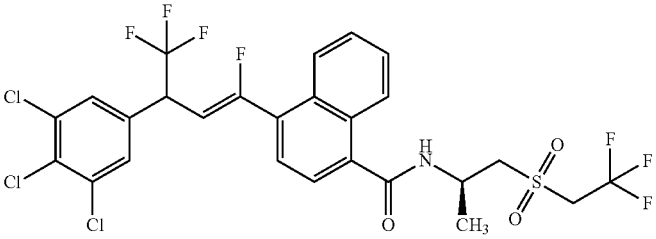 |
| P2 | 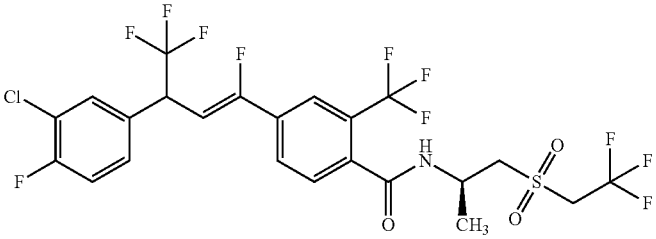 [SMILES: C[C@H](CS(=O)(=O)CC(F)(F)F)NC(=O)c1ccc(/C(F)=C/C(c2ccc(F)c(Cl)c2)C(F)(F)F)cc1C(F)(F)F] |
| P3 | 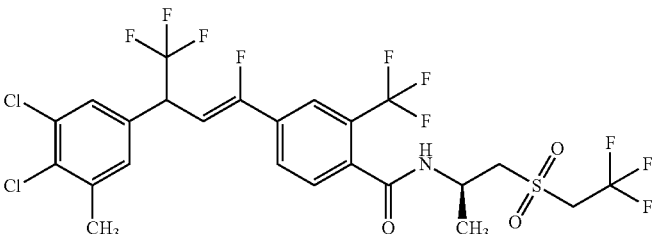 |
| P4 | 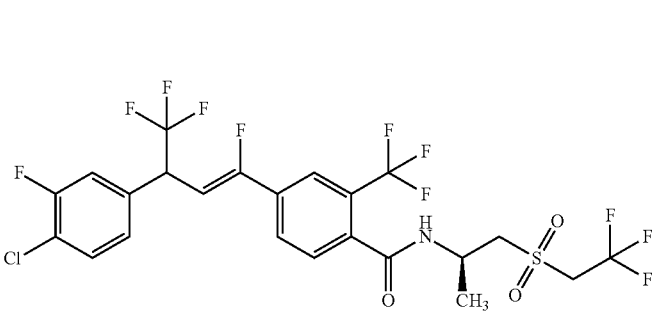 |

TABLE 1-continued

Structure and Preparation Method for Prophetic Molecules

| No. | Structure |
|---|---|
| P5 | 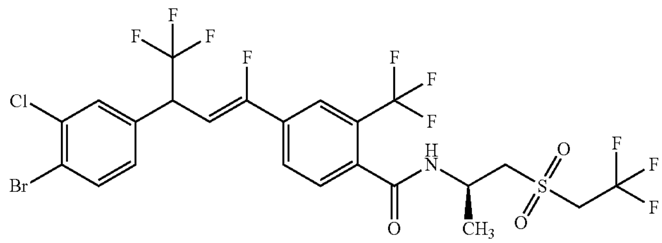 |
| P6 | 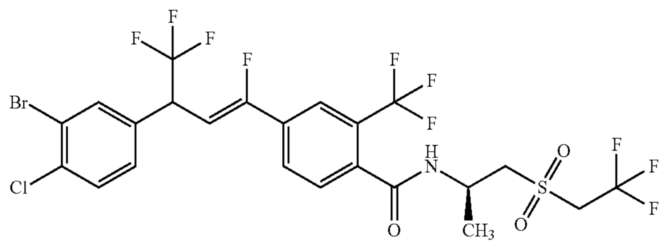 |
| P7 | 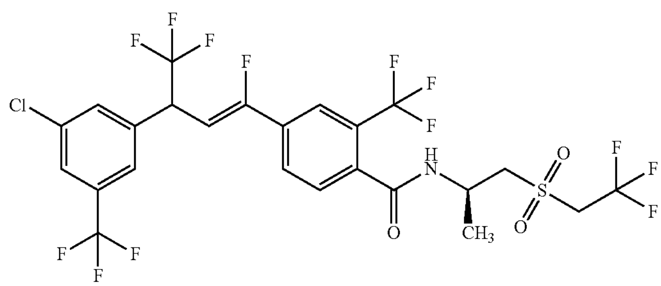 [SMILES: C[C@H](CS(=O)(=O)CC(F)(F)F)NC(=O)c1ccc(/C(F)=C/C(c2cc(Cl)cc(C(F)(F)F)c2)C(F)(F)F)cc1C(F)(F)F] |
| P8 | 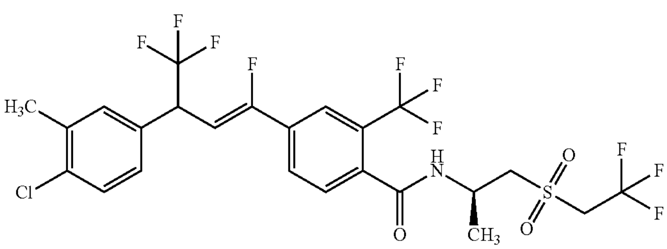 [SMILES: Cc1cc(C(/C=C(\F)c2ccc(C(=O)N[C@H](C)CS(=O)(=O)CC(F)(F)F)c(C(F)(F)F)c2)C(F)(F)F)ccc1Cl] |
| P9 | 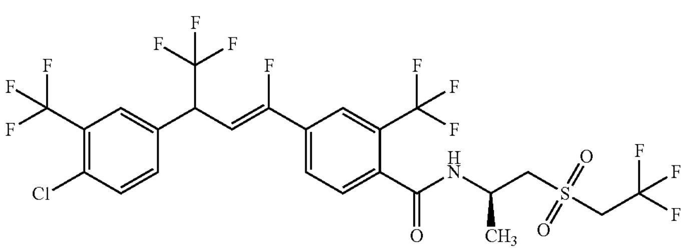 [SMILES: C[C@H](CS(=O)(=O)CC(F)(F)F)NC(=O)c1ccc(/C(F)=C/C(c2ccc(Cl)c(C(F)(F)F)c2)C(F)(F)F)cc1C(F)(F)F] |
| P10 | 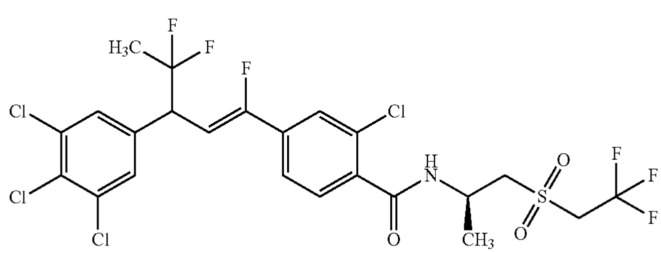 [SMILES: C[C@H](CS(=O)(=O)CC(F)(F)F)NC(=O)c1ccc(/C(F)=C/C(c2cc(Cl)c(Cl)c(Cl)c2)C(C)(F)F)cc1Cl] |

TABLE 1-continued

Structure and Preparation Method for Prophetic Molecules

| No. | Structure |
|---|---|
| P11 | (structure shown) |

The following compounds were prepared in like manner to the procedure outlined in Example 1:

(Z)-4-(1,4,4,4-Tetrafluoro-3-(3,4,5-trichlorophenyl)but-1-en-1-yl)-1-naphthoic Acid (C60)

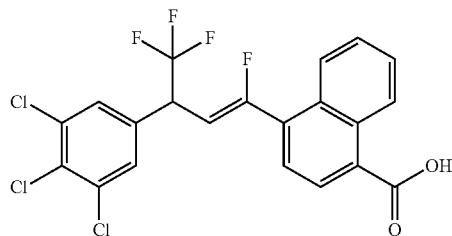 [SMILES: O=C(O)c1ccc(/C(F)=C/C(c2cc(Cl)c(Cl)c(Cl)c2)C(F)(F)F)c2ccccc12]

Isolated as a yellow solid (0.85 g, 53%): $^1$H NMR (300 MHz, CDCl$_3$) δ 8.30 (d, J=7.5 Hz, 1H), 8.07-8.05 (m, 1H), 7.70-7.61 (m, 4H), 7.49 (s, 2H), 5.69 (dd, J=9.9, 31.2 Hz, 1H), 4.75-4.69 (m, 1H); IR (thin film) 3445, 1684, 1260, 750 cm$^{-1}$; ESIMS m/z 475 ([M]$^-$).

(Z)-4-(3-(4-Bromo-3-chlorophenyl)-1,4,4,4-tetrafluorobut-1-en-1-yl)-2-(trifluoromethyl)benzoic Acid (C61)

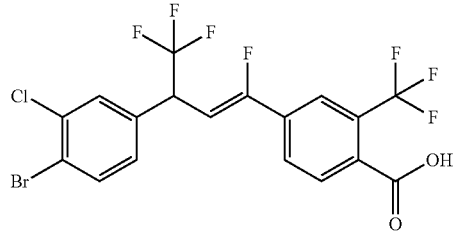

Isolated as a brown gum (2.5 g, 68%): $^1$H NMR (400 MHz, CDCl$_3$) δ 8.02 (d, J=8.4 Hz, 1H), 7.94 (s, 1H), 7.83 (d, J=7.2 Hz, 1H), 7.66 (d, J=8.4 Hz, 1H), 7.50 (s, 1H), 7.17 (dd, J=2.0, 8.4 Hz, 1H), 5.96 (dd, J=9.2, 32.0 Hz, 1H), 4.65-4.61 (m, 1H); IR (thin film) 3447, 2927, 1715, 750 cm$^{-1}$; ESIMS m/z 504 ([M–H]$^-$).

(Z)-4-(1,4,4,4-Tetrafluoro-3-(4-fluoro-3-(trifluoromethyl)phenyl)but-1-en-1-yl)-2-(trifluoromethyl)benzoic Acid (C62)

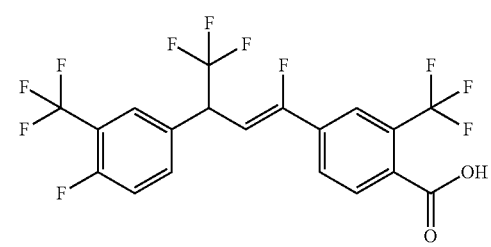 [SMILES: O=C(O)c1ccc(/C(F)=C/C(c2ccc(F)c(C(F)(F)F)c2)C(F)(F)F)cc1C(F)(F)F]

Isolated as a brown gum (1.0 g, 42%): $^1$H NMR (300 MHz, DMSO-d$_6$) δ 13.80 (br s, 1H), 8.16 (s, 1H), 8.12-8.07 (m, 3H), 7.92 (d, J=8.7 Hz, 1H), 7.66 (d, J=10.2 Hz, 1H), 6.96 (dd, J=9.9, 35.4 Hz, 1H), 5.36-5.29 (m, 1H); IR (thin film) 2926, 1715, 765 cm$^{-1}$; ESIMS m/z 477 ([M–H]$^-$).

(Z)-4-(3-(3,4-Dichloro-5-methylphenyl)-1,4,4,4-tetrafluorobut-1-en-1-yl)-2-(trifluoromethyl)benzoic Acid (C63)

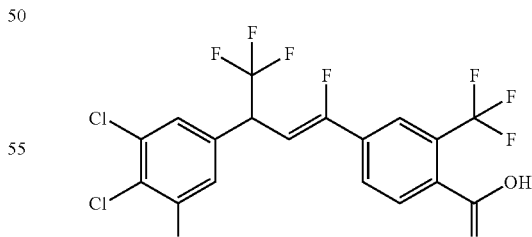

Isolated as a brown gum (1.7 g, 42%): 1H NMR (300 MHz, DMSO-d$_6$) δ 13.80 (s, 1H), 8.14 (s, 1H), 8.09 (d, J=8.1 Hz, 1H), 7.91 (d, J=8.1 Hz, 1H), 7.83 (s, 1H), 7.65 (s, 1H), 6.87 (dd, J=9.9, 36.0 Hz, 1H), 5.13-5.07 (m, 1H), 2.42 (s, 3H); IR (thin film) 3446, 2928, 1716 cm$^{-1}$; ESIMS m/z 473 ([M–H]$^{-1}$).

(Z)-4-(3-(3-Chloro-5-(trifluoromethyl)phenyl)-1,4,4,4-tetrafluorobut-1-en-1-yl)-2-(trifluoromethyl)benzoic Acid (C64)

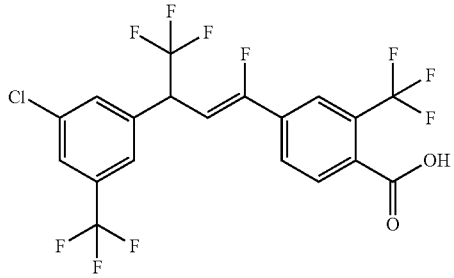 [SMILES: O=C(O)c1ccc(/C(F)=C/C(c2cc(Cl)cc(C(F)(F)F)c2)C(F)(F)F)cc1C(F)(F)F]

Isolated as a brown solid (1.0 g, 47%): $^1$H NMR (300 MHz, DMSO-$d_6$) δ 13.80 (s, 1H), 8.17-8.12 (m, 3H), 7.91-7.86 (m, 3H), 6.87 (dd, J=9.9, 36.0 Hz, 1H), 5.39-5.32 (m, 1H); ESIMS m/z 493 ([M–H]$^-$).

(Z)-4-(3-(3-Chloro-4,5-difluorophenyl)-1,4,4,4-tetrafluorobut-1-en-1-yl)-2-(trifluoromethyl)benzoic Acid (C65)

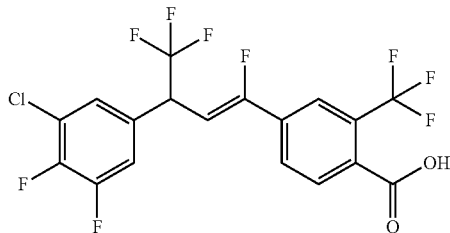 [SMILES: O=C(O)c1ccc(/C(F)=C/C(c2cc(F)c(F)c(Cl)c2)C(F)(F)F)cc1C(F)(F)F]

Isolated as a brown gum (0.55 g, 56%): $^1$H NMR (300 MHz, DMSO-$d_6$) δ 13.92 (br s, 1H), 8.14 (s, 1H), 8.08 (d, J=8.1 Hz, 1H), 7.92-7.85 (m, 3H), 6.87 (dd, J=9.9, 35.4 Hz, 1H), 5.24-5.18 (m, 1H); IR (thin film) 3085, 1715, 659 cm$^{-1}$; ESIMS m/z 461 ([M–H]$^-$).

(Z)-4-(3-(4-Chloro-3-methylphenyl)-1,4,4,4-tetrafluorobut-1-en-1-yl)-2-(trifluoromethyl)benzoic Acid (C66)

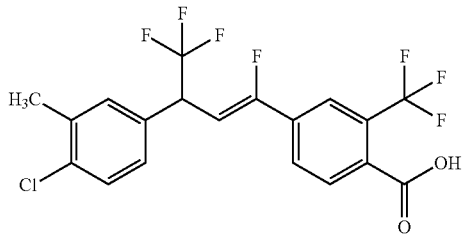 [SMILES: Cc1cc(C(/C=C(\F)c2ccc(C(=O)O)c(C(F)(F)F)c2)C(F)(F)F)ccc1Cl]

Isolated as a brown gummy oil (0.45 g, 75%): $^1$H NMR (300 MHz, DMSO-$d_6$) δ 13.60 (br s, 1H) 7.98 (s, 1H) 7.92 (d, J=8.1 Hz, 1H), 7.90 (d, J=8.1 Hz, 1H), 7.53-7.38 (m, 2H), 7.04 (dd, J=8.4, 15.6 Hz, 1H), 6.89 (d, J=15.9 Hz, 1H), 4.76-4.63 (m, 1H), 2.35 (s, 3H); IR (thin film) 3436, 1727, 1150, 765 cm$^{-1}$; ESIMS m/z 421 ([M–H]$^-$).

(Z)-4-(3-(3,5-Dichloro-4-(difluoromethyl)phenyl)-1,4,4,4-tetrafluorobut-1-en-1-yl)-2-(trifluoromethyl)benzoic Acid (C67)

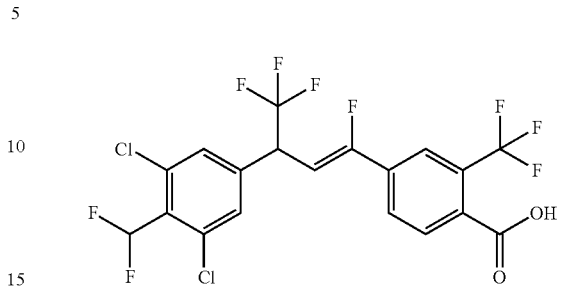

Isolated as a yellow gum (0.45 g, 25%): $^1$H NMR (400 MHz, DMSO-$d_6$) δ 13.80 (s, 1H), 8.15 (s, 1H), 8.09 (dd, J=8.0 Hz, 1H), 8.00 (s, 2H), 7.92 (d, J=8.4 Hz, 1H), 7.45 (t, J=12.9 Hz, 1H), 6.90 (dd, J=10.0, 35.6 Hz, 1H), 5.33-5.31 (m, 1H); ESIMS m/z 509 ([M–H]$^-$).

(Z)-4-(3-(3-Chloro-5-fluorophenyl)-1,4,4,4-tetrafluorobut-1-en-1-yl)-2-(trifluoromethyl)benzoic Acid (C68)

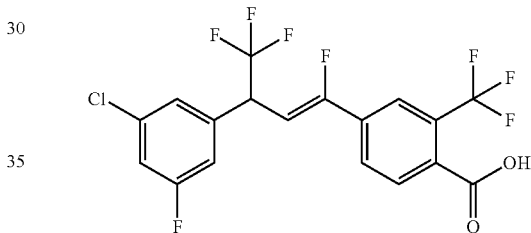

Isolated as a brown gum (0.40 g, 63%): $^1$H NMR (400 MHz, DMSO-$d_6$) δ 13.89 (br s, 1H), 8.16 (s, 1H), 8.09 (d, =8.4 Hz, 1H), 7.93-7.86 (m, 1H), 7.69 (s, 1H), 7.63 (d, J=9.6 Hz, 1H), 7.52-7.49 (m, 1H), 6.87 (dd, J=10.4, 35.6 Hz, 1H), 5.23-5.18 (m, 1H); IR (thin film) 2924, 1698, 1258 cm$^{-1}$; ESIMS m/z 443 ([M–H]$^-$).

(Z)-4-(1,4,4,4-Tetrafluoro-3-(3,4,5-trifluorophenyl)but-1-en-1-yl)-2-(trifluoromethyl)benzoic Acid (C69)

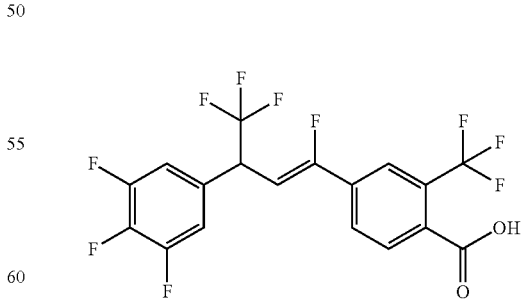

Isolated as a brown gum (0.8 g, 56%): $^1$H NMR (300 MHz, DMSO-$d_6$) δ 13.98 (br s, 1H), 8.14 (br s, 1H), 8.08-8.05 (m, 1H), 7.92-7.89 (m, 1H), 7.77-7.72 (m, 2H), 6.85 (dd, J=9.9, 35.4 Hz, 1H), 5.23-5.16 (m, 1H); IR (thin film) 3100, 1715 cm$^{-1}$; ESIMS m/z 445 ([M–H]$^-$).

(Z)-4-(3-(3-Chloro-4-ethylphenyl)-1,4,4,4-tetrafluorobut-1-en-1-yl)-2-(trifluoromethyl)benzoic Acid (C70)

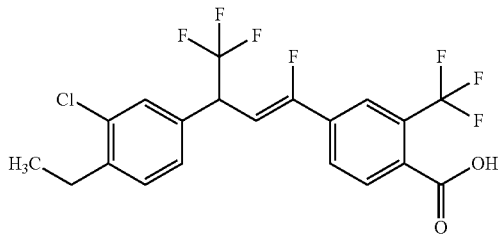

Isolated as a yellow gum (0.60 g, 53%): ${}^1$H NMR (400 MHz, DMSO-$d_6$) δ 13.75 (br s, 1H), 8.15 (s, 1H), 8.01 (d, J=8.4 Hz, 1H), 7.90 (d, J=8.4 Hz, 1H), 7.78 (d, J=8.4 Hz, 1H), 7.55 (d, J=8.4 Hz, 1H), 7.41 (d, J=8.0 Hz, 1H), 6.87 (dd, J=9.6, 35.6 Hz, 1H), 5.08-5.04 (m, 1H), 2.73-2.67 (m, 2H), 1.17 (t, J=6.0 Hz, 3H); ESIMS m/z 453 ([M–H]⁻).

(Z)-4-(3-(3-Chloro-4-methoxyphenyl)-1,4,4,4-tetrafluorobut-1-en-1-yl)-2-(trifluoromethyl)benzoic Acid (C71)

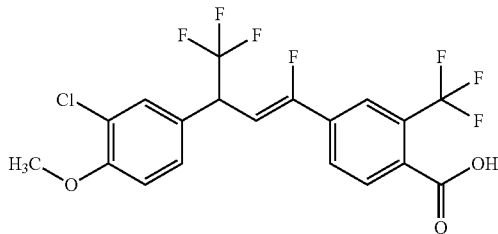 [SMILES: COc1ccc(C(/C=C(\F)c2ccc(C(=O)O)c(C(F)(F)F)c2)C(F)(F)F)cc1Cl]

Isolated as a yellow gum (0.46 g, 66%): ${}^1$H NMR (400 MHz, CDCl$_3$) δ 7.98 (d, J=8.4 Hz, 1H), 7.93 (s, 1H), 7.81 (d, J=8.0 Hz, 1H), 7.42 (s, 1H), 7.26 (s, 1H), 6.95 (d, J=8.8 Hz, 1H), 5.96 (dd, J=10.0, 32.8 Hz, 1H), 4.62-4.57 (m, 1H), 3.91 (s, 3H); ESIMS m/z 455 ([M–H]⁻).

(Z)-4-(3-(3-Bromo-4,5-dichlorophenyl)-1,4,4,4-tetrafluorobut-1-en-1-yl)-2-(trifluoromethyl)benzoic Acid (C72)

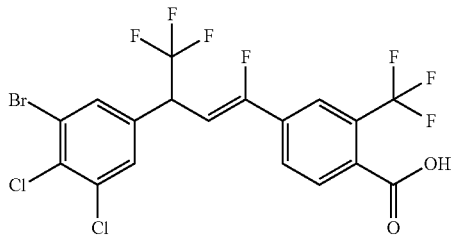

Isolated as a yellow gum (2.6 g, 27%): ${}^1$H NMR (400 MHz, CDCl$_3$) δ 11.66 (s, 1H), 8.04 (d, J=7.3 Hz, 1H), 7.97 (d, J=1.7 Hz, 1H), 7.84 (dd, J=8.2, 1.8 Hz, 1H), 7.60 (d, J=2.0 Hz, 1H), 7.49 (d, J=2.1 Hz, 1H), 5.91 (dd, J=32.4, 9.6 Hz, 1H), 4.62 (p, J=8.8 Hz, 1H); ${}^{19}$F NMR (376 MHz, CDCl$_3$) δ–57.06, –66.85, –110.35; ESIMS m/z 540 ([M–H]⁻).

(Z)-4-(3-(4-Chloro-3-fluoro-5-(trifluoromethyl)phenyl)-1,4,4,4-tetrafluorobut-1-en-1-yl)-2-(trifluoromethyl)benzoic Acid (C73)

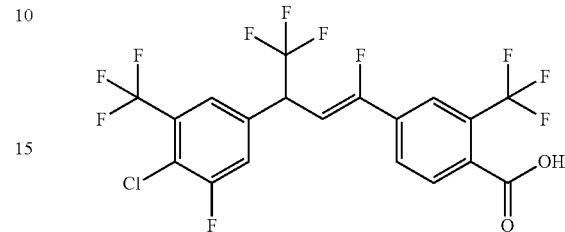

Isolated as a yellow gum (1.1 g, 54%): ${}^1$H NMR (400 MHz, CDCl$_3$) δ 8.03 (d, J=8.2 Hz, 1H), 7.98-7.93 (m, 2H), 7.84 (dd, J=8.1, 1.8 Hz, 1H), 7.54 (s, 1H), 7.44 (d, J=8.7 Hz, 1H), 5.91 (dd, J=32.4, 9.5 Hz, 1H), 4.72 (p, J=8.8 Hz, 1H); ${}^{19}$F NMR (376 MHz, CDCl$_3$) δ–59.64, –62.52, –69.35 (d, J=2.1 Hz), –109.31, –111.51 (d, J=2.3 Hz); ESIMS m/z 512 ([M–H]⁻).

(Z)-4-(3-(3-Bromo-4,5-difluorophenyl)-1,4,4,4-tetrafluorobut-1-en-1-yl)-2-(trifluoromethyl)benzoic Acid (C74)

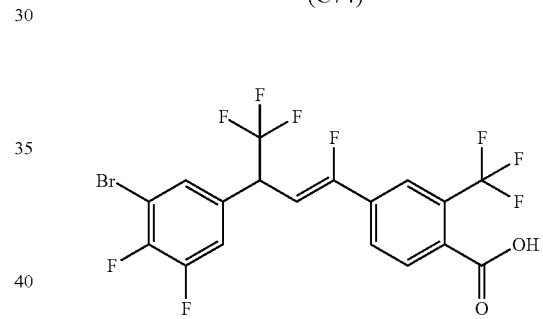

Isolated as a yellow gum (1.3 g, 54%): ${}^1$H NMR (400 MHz, CDCl$_3$) δ 9.76 (s, 1H), 8.05 (d, J=8.2 Hz, 1H), 8.01-7.91 (m, 1H), 7.84 (dd, J=8.2, 1.8 Hz, 1H), 7.39 (dt, J=4.9, 2.1 Hz, 1H), 7.22 (ddd, J=10.1, 6.6, 2.2 Hz, 1H), 5.90 (dd, J=32.5, 9.6 Hz, 1H), 4.62 (q, J=8.9 Hz, 1H); ${}^{19}$F NMR (376 MHz, CDCl$_3$) δ–59.58, –69.53 (d, J=2.3 Hz), –110.42, –129.11 (d, J=21.5 Hz), –132.15 (d, J=21.4 Hz); ESIMS m/z 505 ([M–H]⁻).

(Z)-4-(3-(3-Bromo-4-(trifluoromethyl)phenyl)-1,4,4,4-tetrafluorobut-1-en-1-yl)-2-(trifluoromethyl)benzoic Acid (C75)

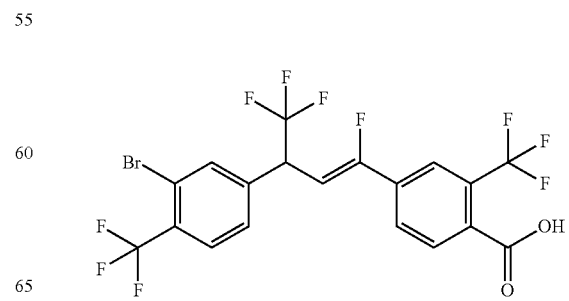

Isolated as an orange oil (0.749 g, 65%): $^1$H NMR (400 MHz, CDCl$_3$) δ 8.03 (d, J=8.2 Hz, 1H), 7.96 (d, J=1.6 Hz, 1H), 7.86-7.80 (m, 1H), 7.77 (d, J=1.7 Hz, 1H), 7.73 (d, J=8.2 Hz, 1H), 7.51-7.44 (m, 1H), 5.94 (dd, J=32.5, 9.6 Hz, 1H), 4.72 (p, J=8.9 Hz, 1H); 19F NMR (376 MHz, CDCl$_3$) δ−59.59, −62.85, −69.07 (d, J=2.3 Hz), −112.26; IR (thin film) 3084, 1709 cm$^{-1}$; ESIMS m/z 539 ([M−H]$^-$).

(Z)-4-(3-(3-Chloro-4-(trifluoromethyl)phenyl)-1,4,4,4-tetrafluorobut-1-en-1-yl)-2-(trifluoromethyl)benzoic Acid (C76)

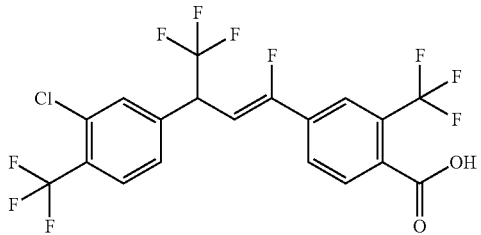 [SMILES: O=C(O)c1ccc(/C(F)=C/C(c2ccc(C(F)(F)F)c(Cl)c2)C(F)(F)F)cc1C(F)(F)F]

Isolated as an orange oil (1.22 g, 58%): $^1$H NMR (300 MHz, CDCl$_3$) δ 8.04 (d, J=8.2 Hz, 1H), 7.96 (d, J=1.7 Hz, 1H), 7.84 (dd, J=8.3, 1.8 Hz, 1H), 7.74 (d, J=8.2 Hz, 1H), 7.57 (d, J=1.6 Hz, 1H), 7.43 (d, J=8.2 Hz, 1H), 5.94 (dd, J=32.5, 9.6 Hz, 1H), 4.73 (p, J=8.9 Hz, 1H); IR (thin film) 3022, 1710 cm$^{-1}$; ESIMS m/z 493 ([M−H]$^-$).

(Z)-4-(3-(3-Chloro-5-(2,2,2-trifluoroethyl)phenyl)-1,4,4,4-tetrafluorobut-1-en-1-yl)-2-(trifluoromethyl)benzoic Acid (C77)

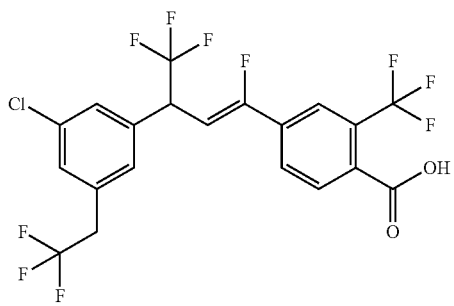

Isolated as an orange oil (0.513 g, 59%): $^1$H NMR (400 MHz, CDCl$_3$) δ 8.03 (d, J=8.2 Hz, 1H), 7.96 (s, 1H), 7.83 (dd, J=8.2, 1.3 Hz, 1H), 7.40 (s, 1H), 7.33 (s, 1H), 7.22 (s, 1H), 5.93 (dd, J=32.6, 9.7 Hz, 1H), 4.67 (p, J=8.9 Hz, 1H), 3.39 (q, J=10.5 Hz, 2H); $^{19}$F NMR (376 MHz, CDCl$_3$) δ−59.60, −65.69, −69.25 (d, J=2.3 Hz), −112.97; IR (thin film) 3018, 1710 cm$^{-1}$; ESIMS m/z 507 ([M−H]$^-$).

(Z)-4-(1,4,4-Trifluoro-3-(3,4,5-trichlorophenyl)but-1-en-1-yl)-2-(trifluoromethyl)benzoic Acid (C78)

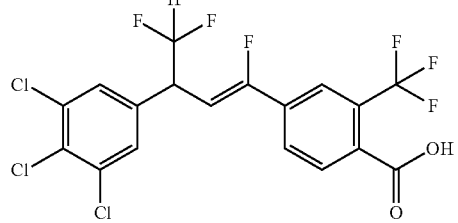

Isolated as a brown foam (1.8 g, 49%): $^1$H NMR (300 MHz, CDCl$_3$) δ 8.04 (d, J=8.1 Hz, 1H), 7.97 (s, 1H), 7.84 (d, J=8.2 Hz, 1H), 7.42 (s, 2H), 6.25-5.80 (m, 2H), 4.55-4.23 (m, 1H); IR (thin film) 2979, 1706, 1615, 1573, 1404 cm$^{-1}$; ESIMS m/z 475 ([M−H]$^-$).

(Z)-4-(3-(3-Chloro-4-(trifluoromethoxy)phenyl)-1,4,4,4-tetrafluorobut-1-en-1-yl)-2-(trifluoromethyl)benzoic Acid (C79)

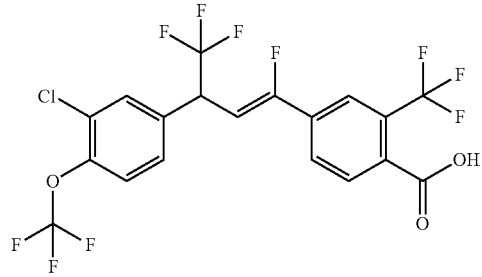 [SMILES: O=C(O)c1ccc(/C(F)=C/C(c2ccc(OC(F)(F)F)c(Cl)c2)C(F)(F)F)cc1C(F)(F)F]

Isolated as an orange oil (0.428 g, 56%): 1H NMR (400 MHz, CDCl$_3$) δ 8.04 (d, J=8.2 Hz, 1H), 7.99-7.94 (m, 1H), 7.84 (dd, J=8.2, 1.8 Hz, 1H), 7.54 (s, 1H), 7.36 (q, J=1.0 Hz, 2H), 5.93 (dd, J=32.5, 9.7 Hz, 1H), 4.68 (p, J=8.9 Hz, 1H); $^{19}$F NMR (376 MHz, CDCl$_3$) δ−57.82, −59.60, −69.36 (d, J=2.2 Hz), −112.78 (d, J=2.7 Hz); IR (thin film) 3010, 1711, 1497, 1412 cm$^{-1}$; ESIMS m/z 509 ([M−H]$^-$).

(Z)-4-(3-(3-Chloro-5-(trifluoromethoxy)phenyl)-1,4,4,4-tetrafluorobut-1-en-1-yl)-2-(trifluoromethyl)benzoic Acid (C80)

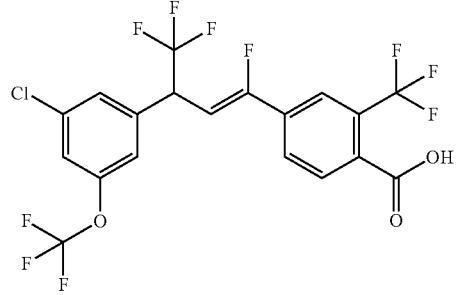

Isolated as an orange oil (0.744 g, 68%): $^1$H NMR (400 MHz, CDCl$_3$) δ 8.04 (d, J=8.2 Hz, 1H), 8.01-7.94 (m, 1H), 7.84 (dd, J=8.2, 1.7 Hz, 1H), 7.36 (d, J=1.6 Hz, 1H), 7.27 (dt, J=2.3, 1.1 Hz, 1H), 7.17 (s, 1H), 5.91 (dd, J=32.4, 9.6 Hz, 1H), 4.68 (p, J=8.8 Hz, 1H); $^{19}$F NMR (376 MHz, CDCl$_3$) δ −57.93, −59.60, −69.24 (d, J=2.5 Hz), −112.31 (d, J=2.6 Hz); IR (thin film) 3005, 1712, 1605, 1507, 1408 cm$^{-1}$; ESIMS m/z 509 ([M−H]$^-$).

(Z)-4-(3-(3-Chloro-5-(1,1-difluoroethyl)phenyl)-1,4,4,4-tetrafluorobut-1-en-1-yl)-2-(trifluoromethyl)benzoic Acid (C81)

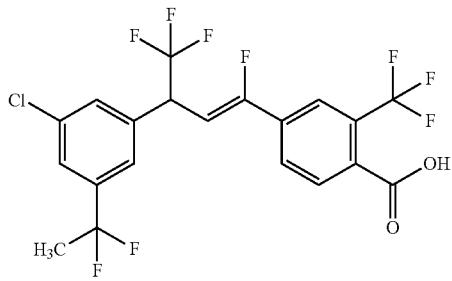 [SMILES: CC(F)(F)c1cc(Cl)cc(C(/C=C(\F)c2ccc(C(=O)O)c(C(F)(F)F)c2)C(F)(F)F)c1]

Isolated as a brown foam (0.190 g, 62.1%): $^1$H NMR (400 MHz, CDCl$_3$) δ 7.99 (d, J=8.1 Hz, 1H), 7.78 (s, 1H), 7.66 (d, J=8.2 Hz, 1H), 7.52 (s, 1H), 7.46 (s, 1H), 7.40 (s, 1H), 6.67 (d, J=15.9 Hz, 1H), 6.56 (dd, J=15.9, 7.7 Hz, 1H), 4.23 (p, J=8.7 Hz, 1H), 1.93 (t, J=18.2 Hz, 3H); $^{19}$F NMR (376 MHz, CDCl$_3$) δ −59.56, −69.23, −88.19, −112.74; IR (thin film) 3006, 1706 cm$^{-1}$; ESIMS m/z 471 ([M−H]$^-$).

(Z)-4-(3-(4-Chloro-3-(trifluoromethoxy)phenyl)-1,4,4,4-tetrafluorobut-1-en-1-yl)-2-(trifluoromethyl)benzoic Acid (C82)

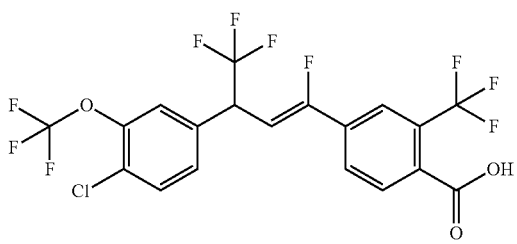 [SMILES: O=C(O)c1ccc(/C(F)=C/C(c2ccc(Cl)c(OC(F)(F)F)c2)C(F)(F)F)cc1C(F)(F)F]

Isolated as an orange oil (0.712 g, 65%): $^1$H NMR (400 MHz, CDCl$_3$) δ 8.03 (d, J=8.1 Hz, 1H), 7.95 (d, J=1.6 Hz, 1H), 7.83 (dd, J=8.2, 1.8 Hz, 1H), 7.53 (d, J=8.3 Hz, 1H), 7.37 (s, 1H), 7.32 (dd, J=8.5, 2.1 Hz, 1H), 5.92 (dd, J=32.5, 9.6 Hz, 1H), 4.69 (p, J=8.9 Hz, 1H); $^{19}$F NMR (376 MHz, CDCl$_3$) δ −57.85, −59.63, −69.49 (d, J=2.2 Hz), −112.48 (t, J=2.7 Hz; IR (thin film) 3089, 1713, 1490 cm$^{-1}$; ESIMS m/z 509 ([M−H]$^-$).

(Z)-4-(3-(3-Chloro-5-(1,1-difluoropropyl)phenyl)-1,4,4,4-tetrafluorobut-1-en-1-yl)-2-(trifluoromethyl)benzoic Acid (C83)

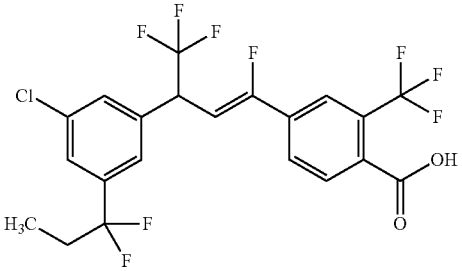 [SMILES: CCC(F)(F)c1cc(Cl)cc(C(/C=C(\F)c2ccc(C(=O)O)c(C(F)(F)F)c2)C(F)(F)F)c1]

Isolated as a red foam (0.365 g, 56%): $^1$H NMR (400 MHz, CDCl$_3$) δ 8.03 (t, J=7.3 Hz, 1H), 7.96 (s, 1H), 7.87-7.79 (m, 1H), 7.47 (s, 1H), 7.38 (s, 1H), 7.26 (s, 1H), 5.94 (dd, J=32.5, 9.7 Hz, 1H), 4.70 (p, J=8.9 Hz, 1H), 2.14 (td, J=16.3, 7.6 Hz, 2H), 1.01 (t, J=7.5 Hz, 3H); $^{19}$F NMR (376 MHz, CDCl$_3$) δ −59.60 (d, J=6.4 Hz), −69.27 (d, J=2.3 Hz), −98.03 (d, J=2.7 Hz), −112.71; ESIMS m/z 503 ([M−H]$^-$).

(Z)-4-(3-(3,4-Dichloro-2-methylphenyl)-1,4,4,4-tetrafluorobut-1-en-1-yl)-2-(trifluoromethyl)benzoic Acid (C84)

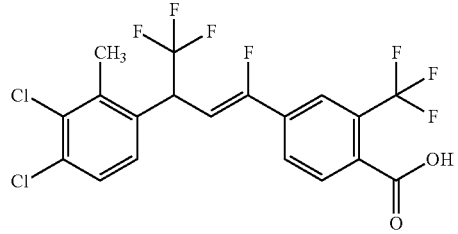 [SMILES: Cc1c(C(/C=C(\F)c2ccc(C(=O)O)c(C(F)(F)F)c2)C(F)(F)F)ccc(Cl)c1Cl]

Isolated as an orange foam (0.412 g, 58%); $^1$H NMR (400 MHz, CDCl$_3$) δ 8.02 (d, J=8.2 Hz, 1H), 7.97-7.93 (m, 1H), 7.88 (d, J=8.3 Hz, 1H), 7.83-7.78 (m, 1H), 7.38 (d, J=8.5 Hz, 1H), 7.29 (d, J=8.6 Hz, 1H), 5.94 (dd, J=33.0, 9.3 Hz, 1H), 5.03 (p, J=8.9 Hz, 1H), 2.59 (s, 3H; $^{19}$F NMR (376 MHz, CDCl$_3$) δ −59.63 (d, J=18.7 Hz), −69.01 (d, J=2.2 Hz), −112.72; ESIMS m/z 473 ([M−H]$^-$).

(Z)-4-(3-(3-Chloro-5-(1,1-difluorobutyl)phenyl)-1,4,4,4-tetrafluorobut-1-en-1-yl)-2-(trifluoromethyl)benzoic Acid (C85)

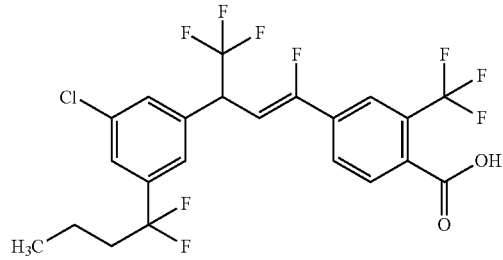 [SMILES: CCCC(F)(F)c1cc(Cl)cc(C(/C=C(\F)c2ccc(C(=O)O)c(C(F)(F)F)c2)C(F)(F)F)c1]

Isolated as a red foam (0.361 g, 57%); $^1$H NMR (400 MHz, CDCl$_3$) δ 8.03 (d, J=8.1 Hz, 1H), 7.96 (s, 1H), 7.86-7.82 (m, 1H), 7.46 (s, 1H), 7.38 (s, 1H), 7.26 (s, 1H), 5.94 (dd, J=32.5, 9.7 Hz, 1H), 4.70 (p, J=8.8 Hz, 1H), 2.17-1.99 (m, 2H), 1.47 (dq, J=15.1, 7.5 Hz, 2H), 0.95 (t, J=7.4 Hz, 3H); $^{19}$F NMR (376 MHz, CDCl$_3$) δ−59.62 (d, J=6.3 Hz), −69.26 (d, J=2.3 Hz), −95.97 (d, J=2.8 Hz), −112.70; ESIMS m/z 517 ([M−H]$^-$).

The following compounds were prepared in like manner to the procedure outlined in Example 3:

(Z)-4-(3-(3,4-Dichloro-5-vinylphenyl)-1,4,4,4-tetrafluorobut-1-en-1-yl)-2-(trifluoromethyl)benzoic Acid (C86)

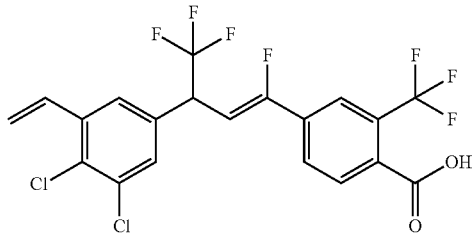 [SMILES: C=Cc1cc(C(/C=C(\F)c2ccc(C(=O)O)c(C(F)(F)F)c2)C(F)(F)F)cc(Cl)c1Cl]

Isolated as a yellow wax (0.19 g, 65%): $^1$H NMR (400 MHz, CDCl$_3$) δ 9.76 (s, 1H), 8.02 (d, J=8.2 Hz, 1H), 7.95 (s, 1H), 7.82 (d, J=8.2 Hz, 1H), 7.52-7.39 (m, 2H), 7.09 (dd, J=17.5, 11.0 Hz, 1H), 6.04-5.85 (m, 1H), 5.76 (dd, J=17.5, 13.8 Hz, 1H), 5.55-5.45 (m, 1H), 4.65 (p, J=8.9 Hz, 1H); $^{19}$F NMR (376 MHz, CDCl$_3$) δ−59.56, −67.15, −113.15; ESIMS m/z 487 ([M−H]$^-$).

(Z)-4-(3-(3,4-Dichloro-5-(prop-1-en-2-yl)phenyl)-1,4,4,4-tetrafluorobut-1-en-1-yl)-2-(trifluoromethyl)benzoic Acid (C87)

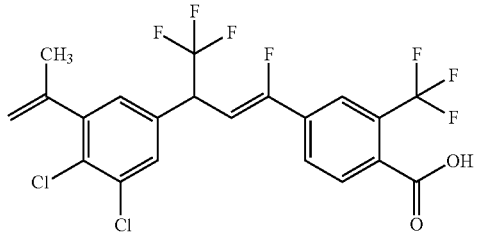 [SMILES: C=C(C)c1cc(C(/C=C(\F)c2ccc(C(=O)O)c(C(F)(F)F)c2)C(F)(F)F)cc(Cl)c1Cl]

Isolated as a brown gum (0.041 g, 90%): $^1$H NMR (400 MHz, CDCl$_3$) δ 7.98 (s, 1H), 7.93 (s, 1H), 7.81 (d, J=8.2 Hz, 1H), 7.70 (ddt, J=12.3, 7.0, 1.4 Hz, 1H), 7.44 (d, J=2.2 Hz, 1H), 7.14 (d, J=2.2 Hz, 1H), 5.90 (dd, J=32.6, 9.8 Hz, 1H), 5.28 (q, J=1.5 Hz, 1H), 4.99 (t, J=1.2 Hz, 1H), 4.62 (p, J=8.9 Hz, 1H), 2.10 (t, J=1.2 Hz, 3H); $^{19}$F NMR (376 MHz, CDCl$_3$) δ−59.57, −68.49, −112.88; ESIMS m/z 501 ([M−H]$^-$).

(Z)-4-(1,4,4,4-Tetrafluoro-3-(3,4,5-trichlorophenyl)but-1-en-1-yl)-2-vinylbenzoic Acid (C88)

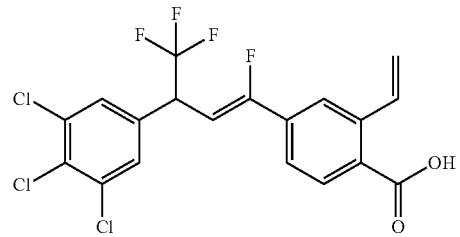 [SMILES: C=Cc1cc(/C(F)=C/C(c2cc(Cl)c(Cl)c(Cl)c2)C(F)(F)F)ccc1C(=O)O]

Isolated as a yellow gum (0.3 g, 86%): $^1$H NMR (400 MHz, CDCl$_3$) δ 8.06 (d, J=8.4 Hz, 1H), 7.81-7.64 (m, 2H), 7.61-7.49 (m, 2H), 7.44 (s, 2H), 5.95-5.67 (m, 2H), 5.47 (dd, J=15.5, 11.0 Hz, 1H), 4.63 (dp, J=13.9, 8.9 Hz, 1H); $^{19}$F NMR (376 MHz, CDCl$_3$) δ−69.35, −112.10; ESIMS m/z 451 ([M−H]$^-$).

(Z)-4-(3-(3-Chloro-5-vinylphenyl)-1,4,4,4-tetrafluorobut-1-en-1-yl)-2-(trifluoromethyl)benzoic Acid (C89)

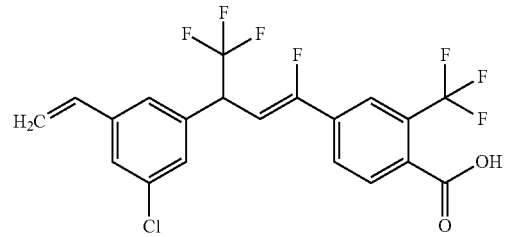 [SMILES: C=Cc1cc(Cl)cc(C(/C=C(\F)c2ccc(C(=O)O)c(C(F)(F)F)c2)C(F)(F)F)c1]

Isolated as a yellow gum (0.065 g, 58%): $^1$H NMR (400 MHz, CDCl$_3$) δ 7.95-7.92 (m, 2H), 7.81 (dd, J=8.2, 1.8 Hz, 1H), 7.57 (dd, J=7.5, 1.7 Hz, 1H), 7.41 (t, J=1.8 Hz, 1H), 7.30 (s, 1H), 7.30 (s, 1H), 6.67 (dd, J=17.6, 10.9 Hz, 1H), 5.94 (s, 1H), 5.80 (d, J=17.5 Hz, 1H), 5.37 (d, J=10.9 Hz, 1H), 4.77-4.55 (m, 1H); $^{19}$F NMR (376 MHz, CDCl$_3$) δ −59.66, −69.30, −112.51; ESIMS m/z 452 ([M−H]$^-$).

The following compound was prepared in like manner to the procedure outlined in Example 7:

(4-(1-Fluorovinyl)-1-naphthoic Acid (C90)

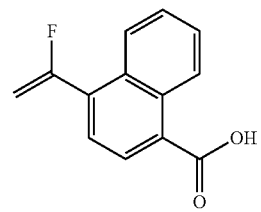 [SMILES: C=C(F)c1ccc(C(=O)O)c2ccccc12]

Isolated as an off-white solid (0.70 g, 52%): mp 154-156° C.; $^1$H NMR (400 MHz, DMSO-d$_6$) δ 13.40 (br s, 1H), 8.88-8.84 (m, 1H), 8.17-8.10 (m, 2H), 7.75-7.66 (m, 3H), 5.39 (dd, J=3.6, 17.2 Hz, 1H), 5.23 (dd, J=36.0, 50.4 Hz, 1H); ESIMS m/z 215 ([M−H]$^-$).

The following compounds were prepared in like manner to the procedure outlined in Example 8:

1-Bromo-4-(1-bromo-2,2,2-trifluoroethyl)-2-chlorobenzene (C91)

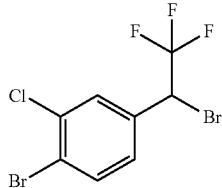 [SMILES: FC(F)(F)C(Br)c1ccc(Br)c(Cl)c1]

Isolated as a light yellow oil (7.0 g, 51%): ¹H NMR (400 MHz, CDCl₃) δ 7.65-7.62 (m, 1H), 7.61-7.59 (m, 1H), 7.29-7.25 (m, 1H), 5.08-5.02 (m, 1H); EIMS m/z 352 ([M]⁺).

5-(1-Bromo-2,2,2-trifluoroethyl)-1-chloro-2,3-difluorobenzene (C92)

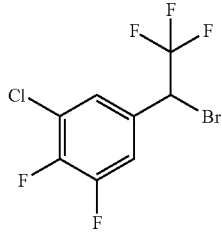 [SMILES: Fc1cc(C(Br)C(F)(F)F)cc(Cl)c1F]

Isolated as a colorless oil (2.5 g, 31%): ¹H NMR (400 MHz, CDCl₃) δ 7.35-7.28 (m, 2H), 5.05-4.99 (m, 1H); IR (thin film) 2965, 1508, 758 cm⁻¹; EIMS m/z 308 ([M]⁺).

4-(1-Bromo-2,2,2-trifluoroethyl)-1-chloro-2-methylbenzene (C93)

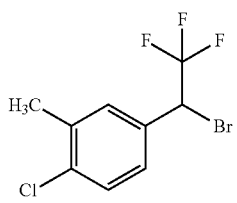

Isolated as a colorless oil (5.0 g, 44%): ¹H NMR (300 MHz, DMSO-d₆) δ 7.55-7.50 (m, 2H), 7.44 (d, J=8.4 Hz, 1H), 6.24-6.16 (m, 1H), 2.36 (s, 3H); IR (thin film) 1112, 749, 564 cm⁻¹; EIMS m/z 286 ([M]⁺).

5-(1-Bromo-2,2,2-trifluoroethyl)-1,3-dichloro-2-(difluoromethyl)benzene (C94)

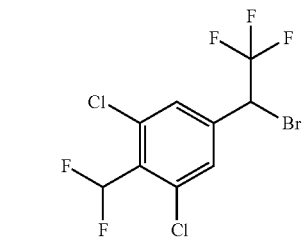 [SMILES: FC(F)c1c(Cl)cc(C(Br)C(F)(F)F)cc1Cl]

Isolated as a brown solid (2.2 g, 60%): ¹H NMR (400 MHz, DMSO-d₆) δ 7.71 (s, 2H), 7.46 (t, J=51.6 Hz, 1H), 6.32-6.26 (m, 1H); EIMS m/z 336 ([M]⁺).

1-(1-Bromo-2,2,2-trifluoroethyl)-3-chloro-5-fluorobenzene (C95)

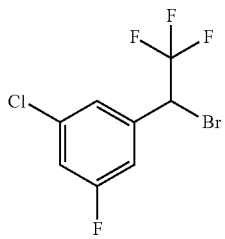 [SMILES: Fc1cc(Cl)cc(C(Br)C(F)(F)F)c1]

Isolated as a colorless oil (1.3 g, 32%): ¹H NMR (400 MHz, CDCl₃) δ 7.29 (s, 1H), 7.17-7.13 (m, 2H), 5.07-5.01 (m, 1H); IR (thin film) 3419, 1265, 746 cm⁻¹; EIMS m/z 290 ([M]⁺).

4-(1-Bromo-2, 2,2-trifluoroethyl)-2-chloro-1-ethylbenzene (C96)

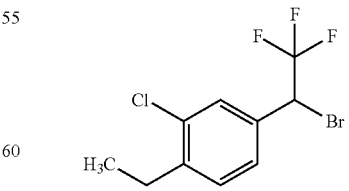

Isolated as a yellow oil (3.5 g, 57%): ¹H NMR (400 MHz, DMSO-d₆) δ 7.59 (s, 1H), 7.53-7.45 (m, 2H), 6.25-6.17 (m, 1H), 2.75-2.69 (m, 2H), 1.19 (t, J=7.6 Hz, 3H); IR (thin film) 3444, 2926, 1627, 750 cm⁻¹; EIMS m/z 300 ([M]⁺).

4-(1-Bromo-2,2,2-trifluoroethyl)-2-chloro-1-methoxybenzene (C97)

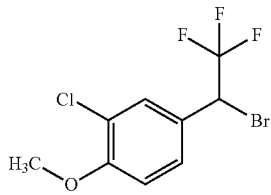

Isolated as a pale yellow oil (2.5 g, 33%): $^1$H NMR (300 MHz, DMSO-$d_6$) δ 7.61 (s, 1H), 7.55 (d, J=8.7 Hz, 1H), 7.26 (d, J=8.7 Hz, 1H), 6.22-6.14 (m, 1H), 3.89 (s, 3H); EIMS m/z 302 ([M]$^+$).

5-(1-Bromo-2,2,2-trifluoroethyl)-2-chloro-1-fluoro-3-(trifluoromethyl)benzene (C98)

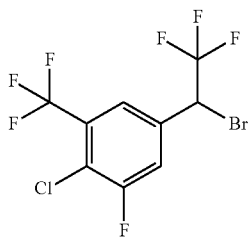

Isolated as a yellow gum (2.5 g, 49%): $^1$H NMR (400 MHz, CDCl$_3$) δ 7.62 (t, J=1.6 Hz, 1H), 7.57 (dd, =8.7, 2.1 Hz, 1H), 5.12 (q, J=7.0 Hz, 1H); $^{19}$F NMR (376 MHz, CDCl$_3$) δ −62.69, −70.52, −108.76; ESIMS m/z 359 ([M−H]$^-$).

1-Bromo-5-(1-bromo-2,2,2-trifluoroethyl)-2,3-dichlorobenzene (C99)

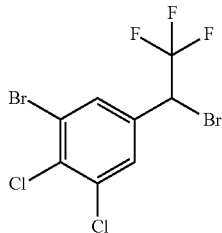

Isolated as a yellow oil (4.5 g, 46%): $^1$H NMR (400 MHz, CDCl$_3$) δ 7.58 (d, J=2.1 Hz, 1H), 7.46 (d, J=2.1 Hz, 1H), 4.35 (q, J=6.9 Hz 1H); $^{19}$F NMR (376 MHz, CDCl$_3$) δ −70.40; ESIMS m/z 386 ([M−H]$^-$).

1-Bromo-5-(1-bromo-2,2,2-trifluoroethyl)-2,3-difluorobenzene (C100)

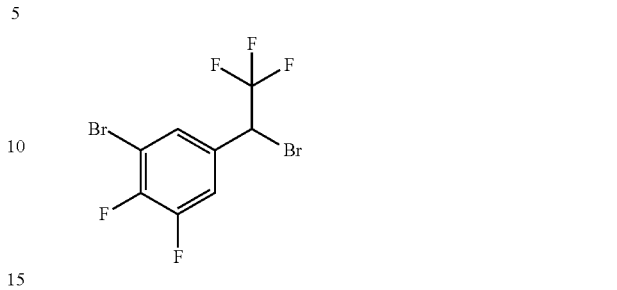

Isolated as a pale yellow oil (1.8 g, 64%): $^1$H NMR (400 MHz, CDCl$_3$) δ 7.52-7.44 (m, 1H), 7.36 (td, J=7.4, 7.0, 3.4 Hz, 1H), 5.03 (q, J=7.0 Hz, 1H); $^{19}$F NMR (376 MHz, CDCl$_3$) δ−70.63, −126.49 (d, J=21.3 Hz), −131.58 (dd, J=21.3, 0.9 Hz); ESIMS m/z 336 ([M−H]$^-$).

2-Bromo-4-(1-bromo-2,2,2-trifluoroethyl)-1-(trifluoromethyl)benzene (C101)

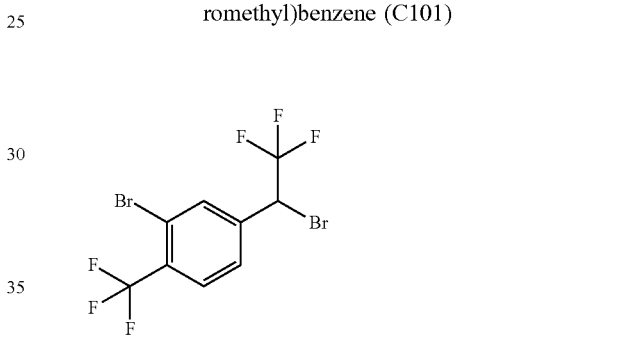

Isolated as a pale yellow oil (3.88 g, 61%); $^1$H NMR (400 MHz, CDCl$_3$) δ 7.93-7.80 (m, 1H), 7.73 (d, J=8.2 Hz, 1H), 7.57 (d, J=8.3 Hz, 1H), 5.10 (q, J=7.1 Hz, 1H); 19F NMR (376 MHz, CDCl$_3$) δ−63.02, −70.25; IR (thin film) 1609 cm$^{-1}$; ESIMS m/z 386 ([M+H]$^+$).

4-(1-Bromo-2,2,2-trifluoroethyl)-2-chloro-1-(trifluoromethyl)benzene (C102)

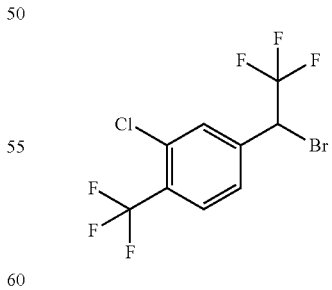

Isolated as a colorless oil (3.33 g, 46%); $^1$H NMR (300 MHz, CDCl$_3$) δ 7.73 (d, J=8.2 Hz, 1H), 7.68 (s, 1H), 7.52 (d, J=8.2 Hz, 1H), 5.11 (q, J=7.1 Hz, 1H); $^{13}$C NMR (75 MHz, CDCl$_3$) δ 137.94, 133.06 (q, J=1.9 Hz), 132.10, 129.93 (q, J=32.0 Hz), 128.10 (q, J=5.3 Hz), 127.47, 124.46, 120.81, 44.84 (q, J=34.8 Hz); ESIMS m/z 342 ([M+H]$^+$).

1-(1-Bromo-2,2,2-trifluoroethyl)-3-chloro-5-(2,2,2-trifluoroethyl)benzene (C103)

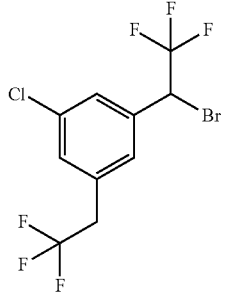 [SMILES: FC(F)(F)Cc1cc(Cl)cc(C(Br)C(F)(F)F)c1]

Isolated as a clear oil (0.930 g, 73%): $^1$H NMR (400 MHz, CDCl$_3$) δ 7.51 (s, 1H), 7.35 (s, 1H), 7.32 (s, 1H), 5.07 (q, J=7.2 Hz, 1H), 3.38 (q, J=10.5 Hz, 2H); $^{19}$F NMR (376 MHz, CDCl$_3$) δ −65.71, −70.43; IR (thin film) 1113 cm$^{-1}$; EIMS m/z 356 ([M]$^+$).

5-(1-Bromo-2,2-difluoroethyl)-1,2,3-trichlorobenzene (C104)

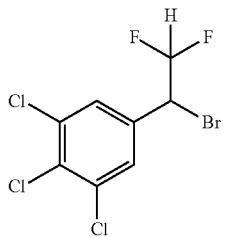 [SMILES: FC(F)C(Br)c1cc(Cl)c(Cl)c(Cl)c1]

Isolated as a clear oil (8.3 g, 67%): $^1$H NMR (500 MHz, CDCl$_3$) δ 7.49 (s, 2H), 6.00 (td, J=55.4, 3.8 Hz, 1H), 4.85 (ddd, J=13.7, 10.4, 3.8 Hz, 1H); $^{19}$F NMR (471 MHz, CDCl$_3$) δ−116.16 (ddd, J=278.0, 55.2, 10.4 Hz), −119.84 (ddd, J=278.1, 55.6, 13.4 Hz); IR (thin film) 1552, 1431 cm$^{-1}$; ESIMS m/z 324 ([M+H]$^+$).

4-(1-Bromo-2,2,2-trifluoroethyl)-2-chloro-1-(trifluoromethoxy)benzene (C105)

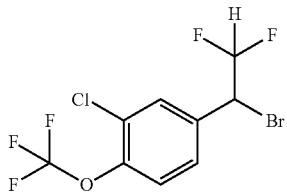 [SMILES: FC(F)C(Br)c1ccc(OC(F)(F)F)c(Cl)c1]

Isolated as a colorless oil (2.83 g, 62%): $^1$H NMR (400 MHz, CDCl$_3$) δ 7.65 (d, J=2.2 Hz, 1H), 7.45 (dd, J=8.6, 2.3 Hz, 1H), 7.36 (dd, J=8.6, 1.5 Hz, 1H), 5.09 (q, J=7.1 Hz, 1H); $^{19}$F NMR (376 MHz, CDCl$_3$) δ−57.75, −70.52; IR (thin film) 1497 cm$^{-1}$; EIMS m/z 356 ([M]$^+$).

1-(1-Bromo-2,2,2-trifluoroethyl)-3-chloro-5-(trifluoromethoxy)benzene (C106)

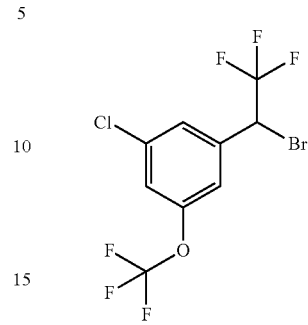

Isolated as a colorless oil (2.27 g, 60%): $^1$H NMR (400 MHz, CDCl$_3$) δ 7.45 (d, J=1.7 Hz, 1H), 7.30 (s, 1H), 7.28 (s, 1H), 5.07 (q, J=7.1 Hz, 1H); $^{19}$F NMR (376 MHz, CDCl$_3$) δ−58.02, −70.44; IR (thin film) 1588, 1450 cm$^{-1}$; EIMS m/z 358 ([M]$^+$).

1-(1-Bromo-2,2,2-trifluoroethyl)-3-chloro-5-(1,1-difluoroethyl)benzene (C107)

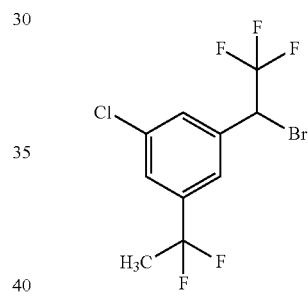

Isolated as a clear oil (0.665 g, 68%): $^1$H NMR (400 MHz, CDCl$_3$) δ 7.59 (s, 1H), 7.53 (s, 1H), 7.50 (s, 1H), 5.10 (q, J=7.2 Hz, 1H), 1.92 (t, J=18.2 Hz, 3H); $^{19}$F NMR (376 MHz, CDCl$_3$) δ−70.39, −88.36 (d, J=1.6 Hz); IR (thin film) 1588 cm$^{-1}$; ESIMS m/z 336 ([M+H]$^+$).

4-(1-Bromo-2,2,2-trifluoroethyl)-1-chloro-2-(trifluoromethoxy)benzene (C108)

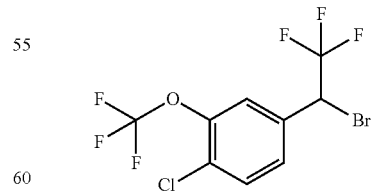

Isolated as a clear oil (2.50 g, 56%): 1H NMR (400 MHz, CDCl$_3$) δ 7.52 (d, J=8.4 Hz, 1H), 7.48 (s, 1H), 7.41 (dd, J=8.4, 2.1 Hz, 1H), 5.10 (q, J=7.1 Hz, 1H); $^{19}$F NMR (376 MHz, CDCl$_3$) δ−57.94, −70.63; IR (thin film) 1492, 1423 cm$^{-1}$; EIMS m/z 356 ([M]$^+$).

1-(1-Bromo-2,2,2-trifluoroethyl)-3-chloro-5-(1,1-difluoropropyl)benzene (C109)

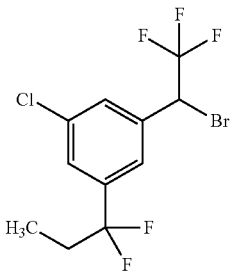 [SMILES: CCC(F)(F)c1cc(Cl)cc(C(Br)C(F)(F)F)c1]

Isolated as a clear oil (0.670 g, 64%): $^1$H NMR (400 MHz, CDCl$_3$) δ 7.58 (s, 1H), 7.50 (s, 1H), 7.46 (s, 1H), 5.10 (q, J=7.1 Hz, 1H), 2.13 (ddt, J=23.7, 16.1, 7.5 Hz, 2H), 1.00 (t, J=7.5 Hz, 3H); 19F NMR (376 MHz, CDCl$_3$) δ−70.43, −98.11; IR (thin film) 1111 cm$^{-1}$; ESIMS m/z 352 ([M+H]$^+$).

1-(1-Bromo-2,2,2-trifluoroethyl)-3,4-dichloro-2-methylbenzene (C110)

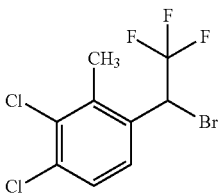

Isolated as a pale yellow oil (0.721 g, 79%): $^1$H NMR (400 MHz, CDCl$_3$) δ 7.58 (d, J=8.6 Hz, 1H), 7.40 (d, J=8.6 Hz, 1H), 5.46 (q, J=7.2 Hz, 1H), 2.51 (s, 3H); $^{19}$F NMR (376 MHz, CDCl$_3$) δ−69.49; IR (thin film) 1159, 1105 cm$^{-1}$.

1-(1-Bromo-2,2,2-trifluoroethyl)-3-chloro-5-(1,1-difluorobutyl)benzene (C111)

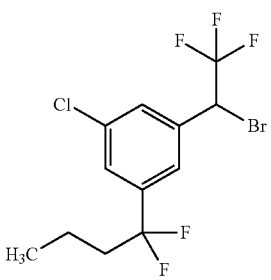 [SMILES: CCCC(F)(F)c1cc(Cl)cc(C(Br)C(F)(F)F)c1]

Isolated as a clear oil (0.670 g, 72%): $^1$H NMR (400 MHz, CDCl$_3$) δ 7.58 (s, 1H), 7.49 (s, 1H), 7.46 (s, 1H), 5.10 (q, J=7.2 Hz, 1H), 2.15-2.01 (m, 2H), 1.52-1.41 (m, 2H), 0.95 (t, J=7.4 Hz, 3H); $^{19}$F NMR (376 MHz, CDCl$_3$) δ−70.42, −96.06. IR (thin film) 1254, 1164, 1111 cm$^{-1}$.

5-(1-Bromo-2,2,2-trifluoroethyl)-1,2-dichloro-3-methyl benzene (C171)

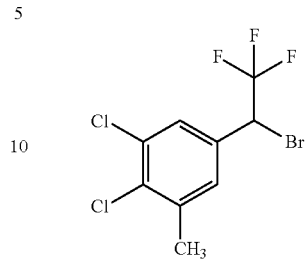

Isolated as a clear oil (6.7 g, 67%): $^1$H NMR (300 MHz, CDCl$_3$) δ 7.46 (s, 1H), 7.28 (s, 1H), 5.02 (q, J=7.2 Hz, 1H), 2.45 (s, 3H); IR (thin film) 1260, 1113, 750 cm$^{-1}$; EIMS m/z 322 ([M]$^+$).

The following compound was prepared in like manner to the procedure outlined in Example 10:

2,2-Difluoro-1-(3,4,5-trichlorophenyl)ethan-1-ol (C112)

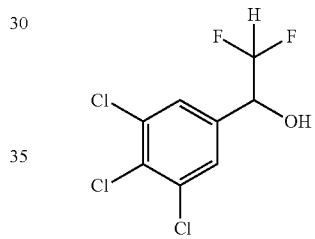

Isolated as a pale yellow solid (9.4 g, 98%): $^1$H NMR (500 MHz, CDCl$_3$) δ 7.48 (s, 2H), 5.72 (td, J=55.7, 4.7 Hz, 1H), 4.80 (tt, J=9.3, 4.2 Hz, 1H), 2.65 (s, 1H); $^{19}$F NMR (471 MHz, CDCl$_3$) δ−127.41 (m); IR (thin film) 3381 cm$^{-1}$; ESIMS m/z 260 ([M+H]$^+$).

1-(4-Chloro-3-fluoro-5-(trifluoromethyl)phenyl)-2,2,2-trifluoroethan-1-ol (C113)

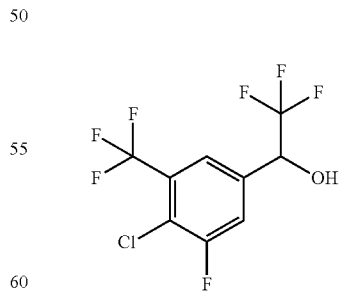

Isolated as a yellow gum (5.0 g, 73%): $^1$H NMR (400 MHz, CDCl$_3$) δ 7.63 (s, 1H), 7.54 (dd, J=8.9, 1.7 Hz, 1H), 5.16-5.02 (m, 1H), 2.95-2.74 (m, 1H); $^{19}$F NMR (376 MHz, CDCl$_3$) δ−62.56, −78.52, −110.00; ESIMS m/z 296 ([M−H]$^-$).

1-(3-Bromo-4,5-dichlorophenyl)-2,2,2-trifluoroethan-1-ol (C114)

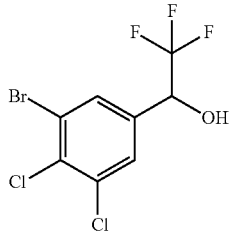 [SMILES: OC(c1cc(Cl)c(Cl)c(Cl)c1)C(F)F]

Isolated as a yellow oil (5.5 g, 86%): $^1$H NMR (400 MHz, CDCl$_3$) δ 7.68 (s, 1H), 7.57 (s, 1H), 5.00 (q, J=11.5 Hz, 1H), 4.75 (s, 1H); $^{19}$F NMR (376 MHz, CDCl$_3$) δ−78.32; ESIMS m/z 323 ([M−H]$^-$).

1-(3-Bromo-4,5-difluorophenyl)-2,2,2-trifluoroethan-1-ol (C115)

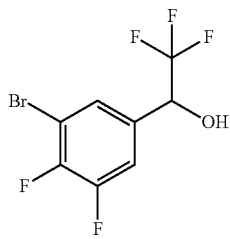

Isolated as a yellow oil (5.5 g, 90%): $^1$H NMR (400 MHz, CDCl$_3$) δ 7.44 (dd, J=17.9, 5.5 Hz, 2H), 5.02 (q, J=6.5 Hz, 1H), 1.55 (br, 1H); $^{19}$F NMR (376 MHz, CDCl$_3$) δ−78.63, −128.47 (d, J=21.3 Hz), −135.58 (dd, J=21.3, 0.9 Hz); ESIMS m/z 291 ([M−H]$^-$).

1-(3-Chloro-5-fluorophenyl)-2,2,2-trifluoroethan-1-ol (C116)

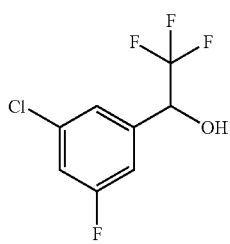 [SMILES: OC(c1cc(F)cc(Cl)c1)C(F)(F)F]

Isolated as an off-white solid (3.0 g, 83%): $^1$H NMR (300 MHz, CDCl$_3$) δ 7.28-7.26 (m, 1H), 7.15-7.12 (m, 2H), 5.04-4.97 (m, 1H), 3.64-3.58 (m, 1H); IR (thin film) 3421, 1266, 742 cm$^{-1}$; EIMS m/z 228 ([M]$^+$).

1-(3,4-Dichloro-5-methylphenyl)-2,2,2-trifluoroethan-1-ol (C172)

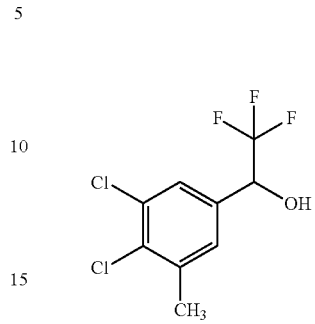

Isolated as a pale yellow oil (4.6 g, 79%): $^1$H NMR (300 MHz, CDCl$_3$) δ 7.44 (s, 1H), 7.26 (s, 1H), 4.97 (q, J=6.6 Hz, 1H), 2.44 (s, 3H); IR (thin film) 3428, 1275, 1262, 750 cm$^{-1}$; EIMS m/z 258 ([M]$^+$).

The following compounds were prepared in like manner to the procedure outlined in Example 11:

1-(4-Bromo-3-chlorophenyl)-2,2,2-trifluoroethan-1-ol (C117)

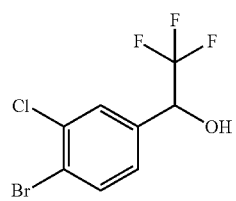

Isolated as a brown gum (12 g, 77%): 1H NMR (400 MHz, CDCl$_3$) δ 7.65-7.60 (m, 1H), 7.59 (s, 1H), 7.23-7.19 (m, 1H), 5.09-5.01 (m, 1H), 2.86 (br s, 1H); EIMS m/z 290 ([M]$^+$).

1-(4-Chloro-3-methylphenyl)-2,2,2-trifluoroethan-1-ol (C118)

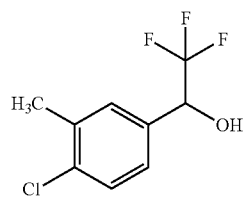

Isolated as a brown oil (7.2 g, 95%): $^1$H NMR (300 MHz, DMSO-d$_6$) δ 7.46 (m, 2H), 7.34 (d, J=8.4 Hz, 1H), 5.19-5.10 (m, 1H), 3.62-3.58 (m, 1H), 2.34 (s, 3H); IR (thin film) 3400, 1128, 720 cm$^{-1}$; EIMS m/z 242 ([M]$^+$).

1-(3-Chloro-4,5-difluorophenyl)-2,2,2-trifluoroethan-1-ol (C119)

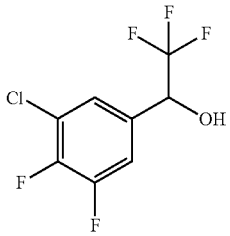 [SMILES: OC(c1cc(F)c(F)c(Cl)c1)C(F)(F)F]

Isolated as a colorless oil (4.6 g, 33%): $^1$H NMR (300 MHz, CDCl$_3$) δ 7.34-7.30 (m, 2H), 5.01-4.95 (m, 1H), 3.21 (br s, 1H); IR (thin film) 3302, 1709, 750 cm$^{-1}$; EIMS m/z 246 ([M]$^+$).

1-(3,5-Dichloro-4-(difluoromethyl)phenyl)-2,2,2-trifluoroethan-1-ol (C120)

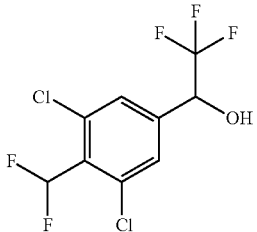 [SMILES: OC(c1cc(Cl)c(C(F)F)c(Cl)c1)C(F)(F)F]

Isolated as a pale yellow gum (2.6 g, 62%): $^1$H NMR (400 MHz, DMSO-d$_6$) δ 7.73 (s, 2H), 7.45 (t, J=52.0 Hz, 1H), 7.30 (d, J=6.4 Hz, 1H), 5.39 (m, 1H); IR (thin film) 3418, 1562, 1135 cm$^{-1}$; EIMS m/z 294 ([M]$^+$).

1-(3-Chloro-4-ethylphenyl)-2,2,2-trifluoroethan-1-ol (C121)

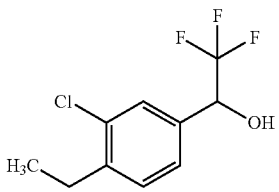

Isolated as a yellow gum (5.0 g, 36%): $^1$H NMR (400 MHz, CDCl$_3$) δ 7.42 (s, 1H), 7.38-7.31 (m, 2H), 5.02-4.95 (m, 1H), 2.81-2.74 (m, 2H), 2.61 (br s, 1H), 1.24 (t, J=8.0 Hz, 3H); IR (thin film) 3420, 2973, 1565, 1131 cm$^{-1}$; EIMS m/z 238 ([M]$^+$).

1-(3-Chloro-4-methoxyphenyl)-2,2,2-trifluoroethan-1-ol (C122)

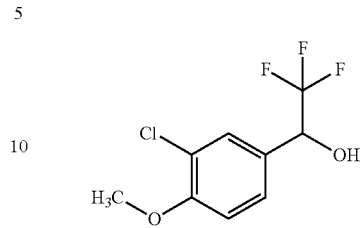

Isolated as a brown viscous oil (4.0 g, 79%): $^1$H NMR (400 MHz, DMSO-d$_6$) δ 7.51 (s, 1H), 7.43 (d, J=8.1 Hz, 1H), 7.19 (d, J=8.4 Hz, 1H), 6.85 (d, J=5.2 Hz, 1H), 5.16-5.12 (m, 1H), 3.86 (s, 3H); IR (thin film) 3445, 2952, 1606, 1262 cm$^{-1}$; EIMS m/z 240 ([M]$^+$).

1-(3-Bromo-4-(trifluoromethyl)phenyl)-2,2,2-trifluoroethan-1-ol (C123)

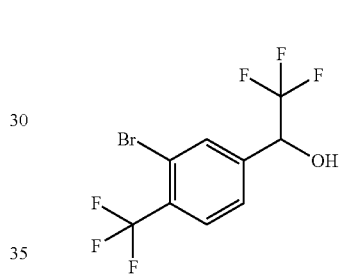

Isolated as a pale yellow oil (3.88 g, 61%): $^1$H NMR (400 MHz, CDCl$_3$) δ 7.87 (d, J=1.6 Hz, 1H), 7.74 (d, J=8.2 Hz, 1H), 7.59-7.50 (m, 1H), 5.09 (qd, J=6.4, 3.8 Hz, 1H), 2.88 (d, J=4.3 Hz, 1H); $^{19}$F NMR (376 MHz, CDCl$_3$) δ−62.86, −78.24; IR (thin film) 3392 cm$^{-1}$; ESIMS m/z 322 ([M−H]$^-$).

1-(3-Chloro-4-(trifluoromethyl)phenyl)-2,2,2-trifluoroethan-1-ol (C124)

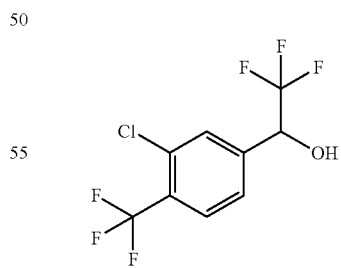

Isolated as a colorless oil (5.90 g, 88%): $^1$H NMR (300 MHz, CDCl$_3$) δ 7.74 (d, J=8.2 Hz, 1H), 7.68 (s, 1H), 7.50 (ddt, J=8.1, 2.0, 0.9 Hz, 1H), 5.25-4.95 (m, 1H), 3.14 (s, 1H); $^{13}$C NMR (75 MHz, CDCl$_3$) δ 139.39, 132.66, 130.35, 129.23 (q, J=31.8 Hz), 127.67 (q, J=5.3 Hz), 125.76, 124.39, 120.78, 71.40 (q, J=32.4 Hz); ESIMS m/z 278 ([M+H]$^+$).

1-(3-Chloro-5-(2,2,2-trifluoroethyl)phenyl)-2,2,2-trifluoroethan-1-ol (C125)

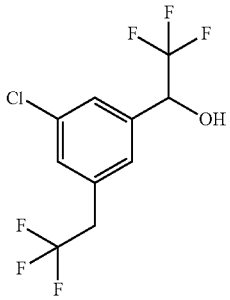 [SMILES: OC(c1cc(Cl)cc(CC(F)(F)F)c1)C(F)(F)F]

Isolated as a pale yellow oil (1.05 g, 61%): $^1$H NMR (400 MHz, CDCl$_3$) δ 7.49 (s, 1H), 7.35 (s, 1H), 7.31 (s, 1H), 5.07-5.00 (m, 1H), 3.38 (q, J=10.5 Hz, 2H), 2.64 (d, J=4.4 Hz, 1H); $^{19}$F NMR (376 MHz, CDCl$_3$) δ−65.75, −78.39; IR (thin film) 3562 cm$^{-1}$; EIMS m/z 292.

1-(3-Chloro-4-(trifluoromethoxy)phenyl)-2,2,2-trifluoroethan-1-ol (C126)

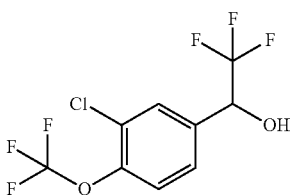 [SMILES: OC(c1ccc(OC(F)(F)F)c(Cl)c1)C(F)(F)F]

Isolated as a clear oil (3.4 g, 86%): $^1$H NMR (300 MHz, CDCl$_3$) δ 7.64 (dq, J=1.9, 0.6 Hz, 1H), 7.47-7.33 (m, 2H), 5.04 (qd, J=6.5, 4.4 Hz, 1H), 2.98 (d, J=4.1 Hz, 1H); IR (thin film) 3392, 1496 cm$^{-1}$; EIMS m/z 294 ([M]$^+$).

1-(3-Chloro-5-(trifluoromethoxy)phenyl)-2,2,2-trifluoroethan-1-ol (C127)

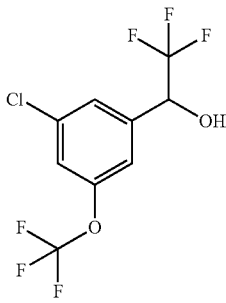 [SMILES: OC(c1cc(Cl)cc(OC(F)(F)F)c1)C(F)(F)F]

Isolated as a clear oil (3.15 g, 80%): $^1$H NMR (400 MHz, CDCl$_3$) δ 7.45 (s, 1H), 7.30-7.26 (m, 2H), 5.04 (q, J=6.4 Hz, 1H); $^{19}$F NMR (376 MHz, CDCl$_3$) δ−58.01, −78.40; IR (thin film) 3305, 1587, 1442 cm$^{-1}$; EIMS m/z 294 ([M]$^+$).

1-(3-Chloro-5-(1,1-difluoroethyl)phenyl)-2,2,2-trifluoroethan-1-ol (C128)

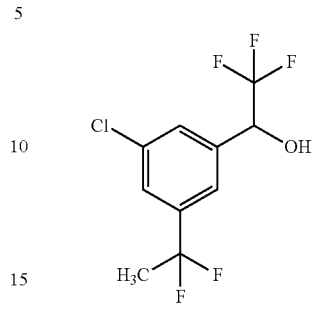

Isolated as a clear oil (0.800 g, 90%): $^1$H NMR (400 MHz, CDCl$_3$) δ 7.56 (s, 1H), 7.54 (s, 1H), 7.51 (s, 1H), 5.14-5.01 (m, 1H), 2.77 (s, 1H), 1.92 (t, J=18.2 Hz, 3H); $^{19}$F NMR (376 MHz, CDCl$_3$) δ−78.37, −88.20 (d, J=9.9 Hz); IR (thin film) 3422 cm$^{-1}$; EIMS m/z 274 ([M]$^+$).

1-(4-Chloro-3-(trifluoromethoxy)phenyl)-2,2,2-trifluoroethan-1-ol (C129)

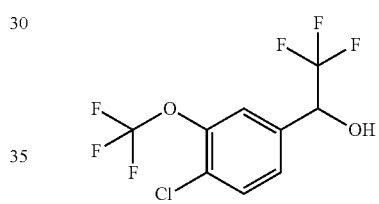

Isolated as a clear oil (3.72 g, 95%): $^1$H NMR (400 MHz, CDCl$_3$) δ 7.53 (d, J=8.3 Hz, 1H), 7.49 (s, 1H), 7.38 (d, J=8.4 Hz, 1H), 5.06 (dd, J=6.6, 3.4 Hz, 1H), 3.80-3.70 (m, 1H), 2.92 (s, 1H); $^{19}$F NMR (376 MHz, CDCl$_3$) δ−57.90, −78.59; IR (thin film) 3396, 1489 cm$^{-1}$; EIMS m/z 294 ([M]$^+$).

1-(3-Chloro-5-(1,1-difluoropropyl)phenyl)-2,2,2-trifluoroethan-1-ol (C130)

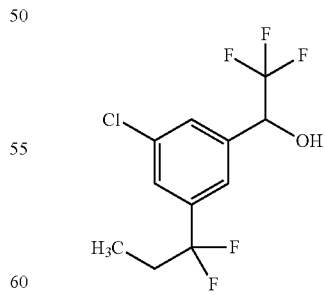

Isolated as a clear yellow oil (0.850 g, 92%): $^1$H NMR (400 MHz, CDCl$_3$) δ 7.56 (s, 1H), 7.50 (s, 1H), 7.46 (s, 1H), 5.07 (d, J=4.4 Hz, 1H), 2.77 (s, 1H), 2.27-2.04 (m, 2H), 0.99 (t, J=7.5 Hz, 3H); $^{19}$F NMR (376 MHz, CDCl$_3$) δ−78.40, −97.91 (d, J=3.7 Hz); IR (thin film) 3407 cm$^{-1}$.

1-(3,4-Dichloro-2-methylphenyl)-2,2,2-trifluoroethan-1-ol (C131)

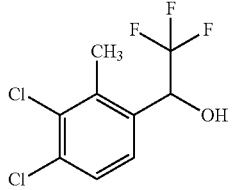

Isolated as a white solid (0.734 g, 30%): ¹H NMR (400 MHz, CDCl₃) δ 7.51 (d, J=8.5 Hz, 1H), 7.41 (d, J=8.6 Hz, 1H), 5.41-5.31 (m, 1H), 2.78 (d, J=4.6 Hz, 1H), 2.46 (s, 3H); ¹⁹F NMR (376 MHz, CDCl₃) δ −77.78; IR (thin film) 3370 cm⁻¹. ESIMS m/z 257 ([M−H]⁻).

1-(3-Chloro-5-(1,1-difluorobutyl)phenyl)-2,2,2-trifluoroethanol (C132)

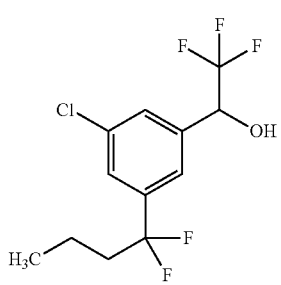 [SMILES: CCCC(F)(F)c1cc(Cl)cc(C(O)C(F)(F)F)c1]

Isolated as a clear yellow oil (0.870 g, 97%): ¹H NMR (400 MHz, CDCl₃) δ 7.56 (s, 1H), 7.50 (s, 1H), 7.46 (s, 1H), 5.06 (dt, J=10.8, 5.4 Hz, 1H), 2.77 (s, 1H), 2.15-2.00 (m, 2H), 1.53-1.38 (m, 2H), 0.94 (t, J=7.4 Hz, 3H); ¹⁹F NMR (376 MHz, CDCl₃) δ −78.39, −95.86 (d, J=8.2 Hz); IR (thin film) 3407 cm⁻¹; EIMS m/z 302.1 ([M]⁺).

The following compound was prepared in like manner to the procedure outlined in Example 12:

2,2-Difluoro-1-(3,4,5-trichlorophenyl)ethan-1-one (C133)

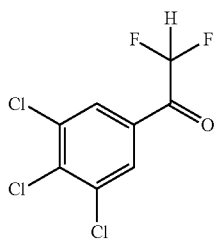

Isolated as an off-white solid (9.25 g, 88%): mp 45-48° C.; ¹H NMR (500 MHz, CDCl₃) δ 7.71 (s, 2H), 6.21 (t, J=53.5 Hz, 1H); ¹⁹F NMR (471 MHz, CDCl₃) δ−126.71 (d, J=53.4 Hz); IR (thin film) 1743, 1559 cm⁻¹; ESIMS m/z 260 ([M+H]⁺).

The following compounds were prepared in like manner to the procedure outlined in Example 13:

4-((Z)-3-(3-Chloro-4-ethylphenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F141)

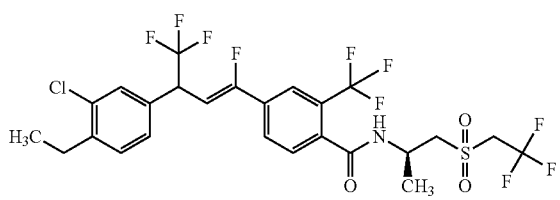 [SMILES: CCc1ccc(C(/C=C(\F)c2ccc(C(=O)N[C@H](C)CS(=O)(=O)CC(F)(F)F)c(C(F)(F)F)c2)C(F)(F)F)cc1Cl]

Isolated as a pale yellow solid (0.110 g, 43%).

4-((Z)-3-(3-Chloro-4-methoxyphenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F142)

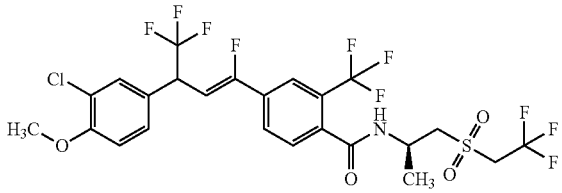 [SMILES: COc1ccc(C(/C=C(\F)c2ccc(C(=O)N[C@H](C)CS(=O)(=O)CC(F)(F)F)c(C(F)(F)F)c2)C(F)(F)F)cc1Cl]

Isolated as a pale yellow solid (0.140 g, 55%).

4-((Z)-3-(4-Chloro-3-fluoro-5-(trifluoromethyl)phenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F71)

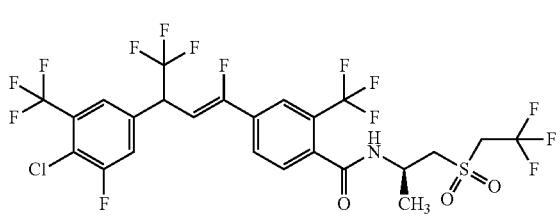 [SMILES: C[C@H](CS(=O)(=O)CC(F)(F)F)NC(=O)c1ccc(/C(F)=C/C(c2cc(F)c(Cl)c(C(F)(F)F)c2)C(F)(F)F)cc1C(F)(F)F]

Isolated as a white wax (0.106 g, 91%).

4-((Z)-3-(3,4-Dichloro-5-vinylphenyl)-1,4,4,4-tetra-
fluorobut-1-en-1-yl)-N—((R)-1-((2,2,2-trifluoro-
ethyl)sulfonyl)propan-2-yl)-2-(trifluoromethyl)benz-
amide (F73)

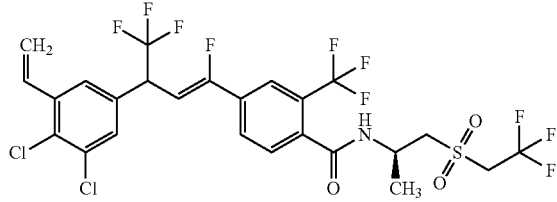 [SMILES: C=Cc1cc(C(/C=C(\F)c2ccc(C(=O)N[C@H](C)CS(=O)(=O)CC(F)(F)F)c(C(F)(F)F)c2)C(F)(F)F)cc(Cl)c1Cl]

Isolated as a white wax (0.024 g, 41%).

4-((Z)-3-(3-Bromo-4,5-dichlorophenyl)-1,4,4,4-tet-
rafluorobut-1-en-1-yl)-N—((R)-1-((2,2,2-trifluoro-
ethyl)sulfonyl)propan-2-yl)-2-(trifluoromethyl)benz-
amide (F80)

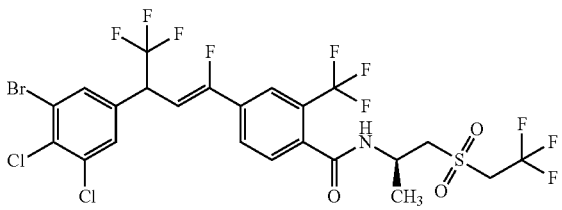 [SMILES: C[C@H](CS(=O)(=O)CC(F)(F)F)NC(=O)c1ccc(/C(F)=C/C(c2cc(Cl)c(Cl)c(Br)c2)C(F)(F)F)cc1C(F)(F)F]

Isolated as a yellow wax (0.108 g, 16%).

4-((Z)-3-(3-Bromo-4,5-difluorophenyl)-1,4,4,4-tetra-
fluorobut-1-en-1-yl)-N—((R)-1-((2,2,2-trifluoro-
ethyl)sulfonyl)propan-2-yl)-2-(trifluoromethyl)benz-
amide (F94)

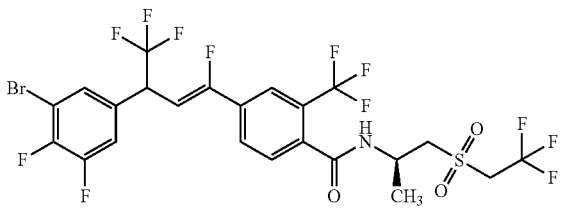 [SMILES: C[C@H](CS(=O)(=O)CC(F)(F)F)NC(=O)c1ccc(/C(F)=C/C(c2cc(F)c(F)c(Br)c2)C(F)(F)F)cc1C(F)(F)F]

Isolated as a yellow wax (0.015 g, 21%).

4-((Z)-3-(3-Chloro-5-vinylphenyl)-1,4,4,4-tetrafluo-
robut-1-en-1-yl)-N—((R)-1-((2,2,2-trifluoroethyl)
sulfonyl)propan-2-yl)-2-(trifluoromethyl)benzamide
(F112)

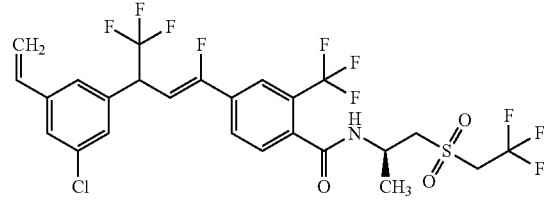 [SMILES: C=Cc1cc(Cl)cc(C(/C=C(\F)c2ccc(C(=O)N[C@H](C)CS(=O)(=O)CC(F)(F)F)c(C(F)(F)F)c2)C(F)(F)F)c1]

Isolated as a white wax (0.027 g, 36%).

4-((Z)-3-(3,4-Dichloro-5-(prop-1-en-2-yl)phenyl)-1,
4,4,4-tetrafluorobut-1-en-1-yl)-N—((R)-1-((2,2,2-
trifluoroethyl)sulfonyl)propan-2-yl)-2-(trifluorom-
ethyl)benzamide (F114)

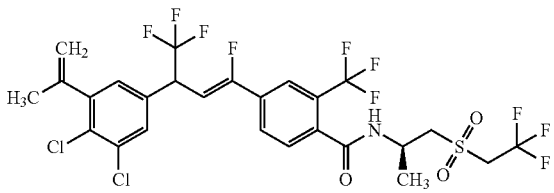 [SMILES: C=C(C)c1cc(C(/C=C(\F)c2ccc(C(=O)N[C@H](C)CS(=O)(=O)CC(F)(F)F)c(C(F)(F)F)c2)C(F)(F)F)cc(Cl)c1Cl]

Isolated as a yellow wax (0.036 g, 53%).

4-((Z)-1,4,4,4-Tetrafluoro-3-(3,4,5-trichlorophenyl-
but-1-en-1-yl)-N—((R)-1-((2,2,2-trifluoroethyl)sul-
fonyl)propan-2-yl)-2-vinylbenzamide (F116)

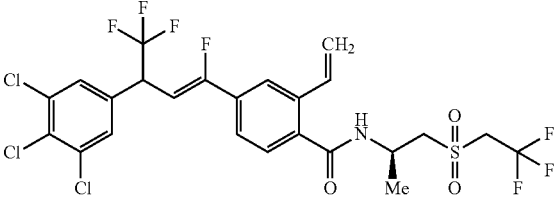

Isolated as a yellow gum (0.016 g, 12%).

4-((Z)-3-(4-Chloro-3-fluoro-5-(trifluoromethyl)phe-
nyl)-1,4,4,4-tetrafluorobut-1-en-1-yl)-N—((R)-1-((2,
2,2-trifluoroethyl)thio)propan-2-yl)-2-(trifluorom-
ethyl)benzamide (F117)

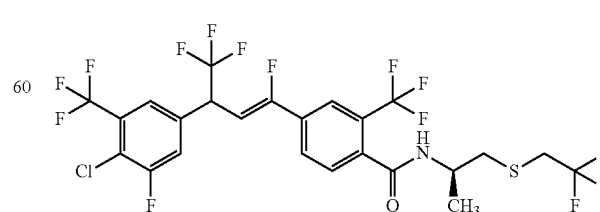

Isolated as a yellow gum (0.177 g, 86%).

109

4-((Z)-3-(3-Chloro-4-(trifluoroethyl)phenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F91)

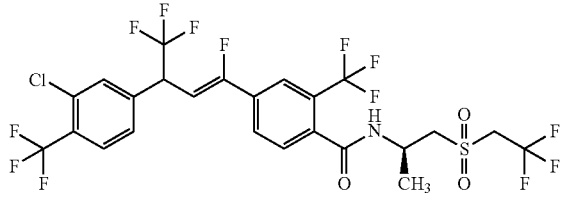 [SMILES: C[C@H](CS(=O)(=O)CC(F)(F)F)NC(=O)c1ccc(/C(F)=C/C(c2ccc(C(F)(F)F)c(Cl)c2)C(F)(F)F)cc1C(F)(F)F]

Isolated as a white foam (0.109 g, 56%).

4-((Z)-3-(3-Chloro-4-(trifluoroethyl)phenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F93)

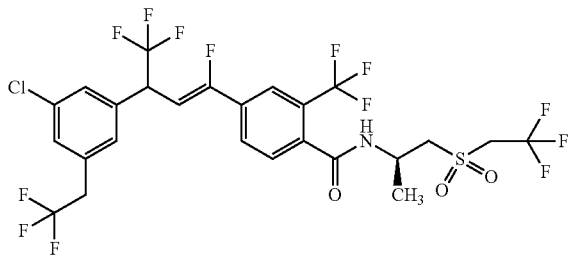 [SMILES: C[C@H](CS(=O)(=O)CC(F)(F)F)NC(=O)c1ccc(/C(F)=C/C(c2cc(Cl)cc(CC(F)(F)F)c2)C(F)(F)F)cc1C(F)(F)F]

Isolated as an off-white foam (0.100 g, 73%).

4-((Z)-3-(3-Bromo-4-(trifluoromethyl)phenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F95)

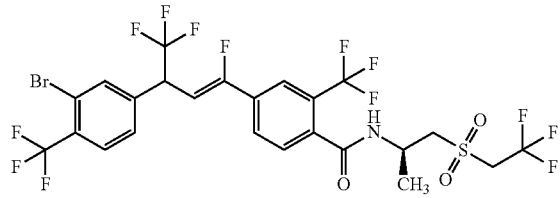 [SMILES: C[C@H](CS(=O)(=O)CC(F)(F)F)NC(=O)c1ccc(/C(F)=C/C(c2ccc(C(F)(F)F)c(Br)c2)C(F)(F)F)cc1C(F)(F)F]

Isolated as an orange foam (0.140 g, 69%).

110

4-((Z)-1,4,4-Trifluoro-3-(3,4,5-trichlorophenyl)but-1-en-1-yl)-N—((R)-1-((2,2,2-trifluoroethyl)sulfonyl)propan-2-yl)-2-(trifluoromethyl)benzamide (F98)

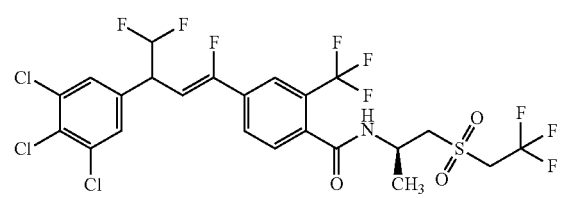 [SMILES: C[C@H](CS(=O)(=O)CC(F)(F)F)NC(=O)c1ccc(/C(F)=C/C(c2cc(Cl)c(Cl)c(Cl)c2)C(F)F)cc1C(F)(F)F]

Isolated as an off-white solid (0.145 g, 51%).

4-((Z)-3-(3-Chloro-4-(trifluoromethoxy)phenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F109)

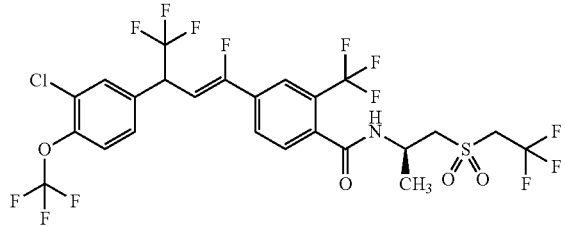

Isolated as a pale yellow glass (0.070 g, 77%).

4-((Z)-3-(3-Chloro-5-(trifluoromethoxy)phenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F110)

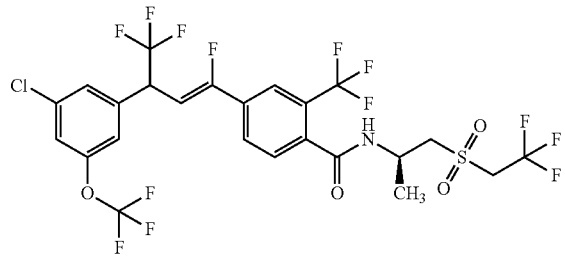 [SMILES: C[C@H](CS(=O)(=O)CC(F)(F)F)NC(=O)c1ccc(/C(F)=C/C(c2cc(Cl)cc(OC(F)(F)F)c2)C(F)(F)F)cc1C(F)(F)F]

Isolated as a pale yellow glass (0.083 g, 68%).

111

4-((Z)-3-(3-Chloro-5-(1,1-difluoroethyl)phenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F120)

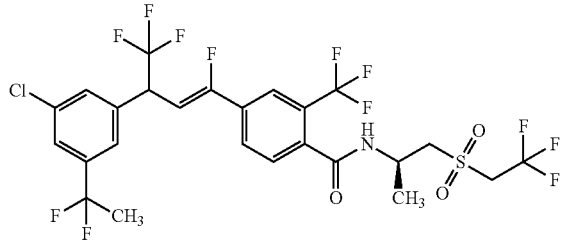 [SMILES: C[C@H](CS(=O)(=O)CC(F)(F)F)NC(=O)c1ccc(/C(F)=C/C(c2cc(Cl)cc(C(C)(F)F)c2)C(F)(F)F)cc1C(F)(F)F]

Isolated as a yellow foamy glass (0.077 g, 66%).

4-((Z)-3-(4-Chloro-3-(trifluoromethoxy)phenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F127)

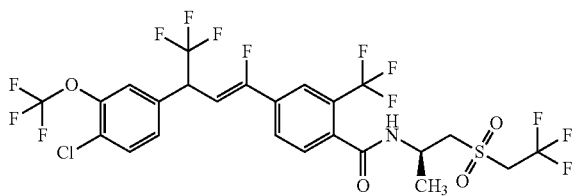 [SMILES: C[C@H](CS(=O)(=O)CC(F)(F)F)NC(=O)c1ccc(/C(F)=C/C(c2ccc(Cl)c(OC(F)(F)F)c2)C(F)(F)F)cc1C(F)(F)F]

Isolated as a pale yellow glass (0.095 g, 68%).

4-((Z)-3-(3-Chloro-5-(1,1-difluoropropyl)phenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F131)

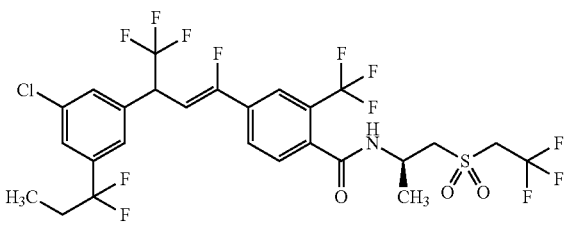 [SMILES: CCC(F)(F)c1cc(Cl)cc(C(/C=C(\F)c2ccc(C(=O)N[C@H](C)CS(=O)(=O)CC(F)(F)F)c(C(F)(F)F)c2)C(F)(F)F)c1]

Isolated as an off-white foam (0.090 g, 55%).

112

4-((Z)-3-(3,4-Dichloro-2-methylphenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F132)

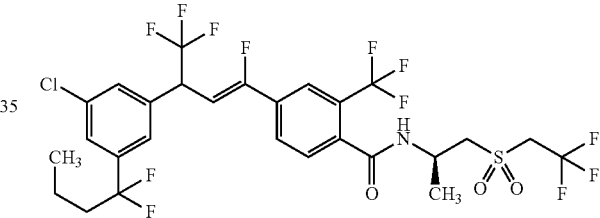

Isolated as a white foamy solid (0.080 g, 57%).

4-((Z)-3-(3-Chloro-5-(1,1-difluorobutyl)phenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F143)

Isolated as an off-white foam (0.086 g, 53%).

The following compounds were prepared in like manner to the procedure outlined in Example 14:

4-((Z)-3-(3,5-Dibromophenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F69)

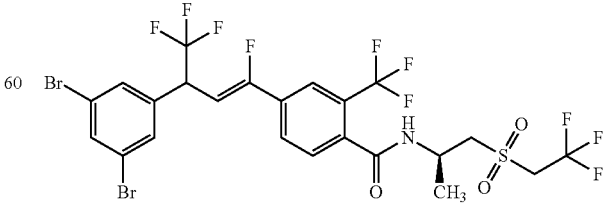

Isolated as a yellow solid (0.150 g, 62%).

113

4-((Z)-1,4,4,4-Tetrafluoro-3-(4-fluoro-3-(trifluoromethyl)phenyl)but-1-en-1-yl)-N—((R)-1-((2,2,2-trifluoroethyl)sulfonyl)propan-2-yl)-2-(trifluoromethyl)benzamide (F77)

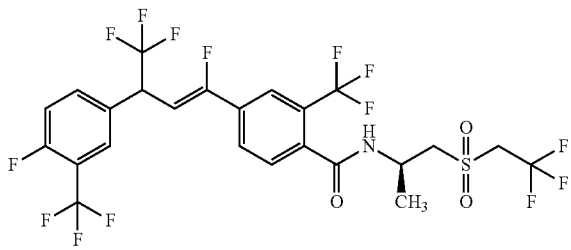 [SMILES: C[C@H](CS(=O)(=O)CC(F)(F)F)NC(=O)c1ccc(/C(F)=C/C(c2ccc(F)c(C(F)(F)F)c2)C(F)(F)F)cc1C(F)(F)F]

Isolated as a pale yellow solid (0.100 g, 48%).

4-((Z)-3-(3,4-Dichloro-5-methylphenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F78)

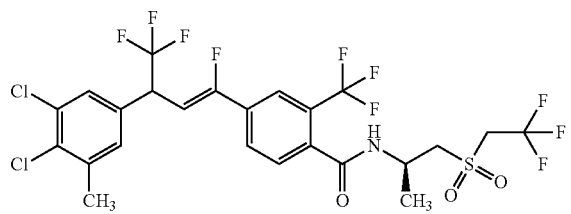 [SMILES: Cc1cc(C(/C=C(\F)c2ccc(C(=O)N[C@H](C)CS(=O)(=O)CC(F)(F)F)c(C(F)(F)F)c2)C(F)(F)F)cc(Cl)c1Cl]

Isolated as a pale yellow solid (0.170 g, 57%).

4-((Z)-3-(3-Bromo-4-chlorophenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F79)

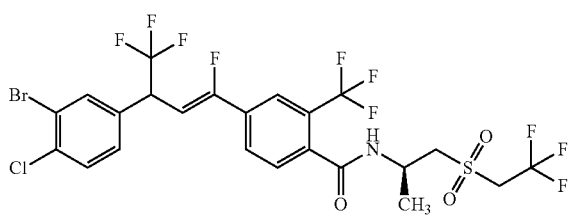

Isolated as a yellow gum (0.095 g, 29%).

114

4-((Z)-3-(3-Chloro-5-(trifluoromethyl)phenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F81)

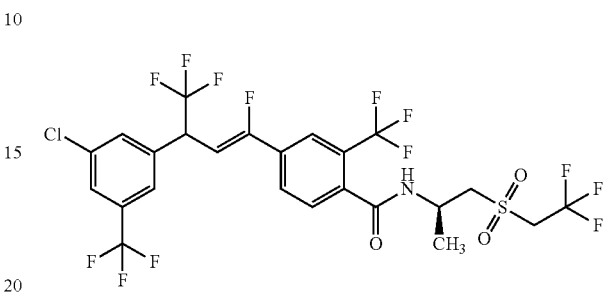

Isolated as an off-white solid (0.060 g, 24%).

4-((Z)-1,4,4,4-Tetrafluoro-3-(4-fluoro-3-(trifluoromethyl)phenyl)but-1-en-1-yl)-N—((R)-1-((2,2,2-trifluoroethyl)thio)propan-2-yl)-2-(trifluoromethyl)benzamide (F102)

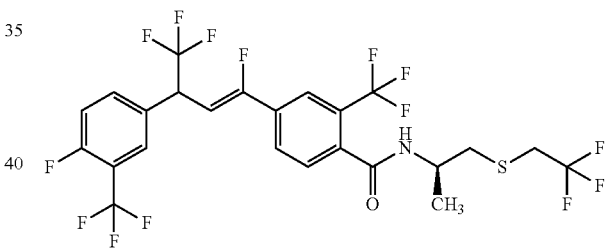

Isolated as a yellow gum (0.090 g, 34%).

4-((Z)-3-(3-Chloro-4,5-difluorophenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F103)

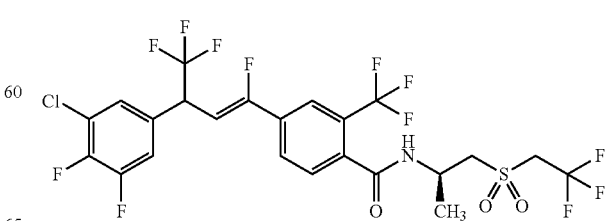

Isolated as a pale yellow gum (0.135 g, 46%).

| 115 | 116 |
|---|---|
| 4-((Z)-3-(3-Dichloro-4-difluoromethyl)phenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F104) | 4-((Z)-1,4,4,4-Tetrafluoro-3-(3,4,5-trichlorophenyl)but-1-en-1-yl)-N—((R)-1-((2,2,2-trifluoroethyl)sulfonyl)propan-2-yl)-1-naphthamide (PF1) |

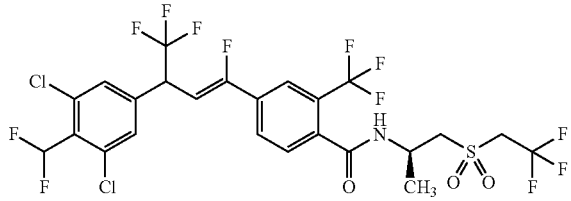 [SMILES: C[C@H](CS(=O)(=O)CC(F)(F)F)NC(=O)c1ccc(/C(F)=C/C(c2cc(Cl)c(C(F)F)c(Cl)c2)C(F)(F)F)cc1C(F)(F)F]

Isolated as a pale yellow solid (0.106 g, 40%).

Isolated as a brown solid (0.120 g, 51%).

4-((Z)-3-(3-Chloro-5-fluorophenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F126)

4-((Z)-3-(3-Chloro-4-fluorophenyl)-1,4,4,4-tetrafluorobut-1-en-1-yl)-N—((R)-1-((2,2,2-trifluoroethyl)sulfonyl)propan-2-yl)-2-(trifluoromethyl)benzamide (PF2)

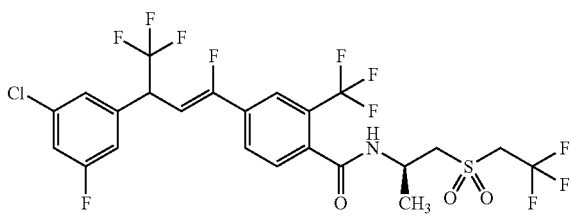

Isolated as a pale yellow gum (0.095 g, 46%).

Isolated as a yellow solid (0.130 g, 46%).

4-((Z)-1,4,4,4-Tetrafluoro-3-(3,4,5-trifluorophenyl)but-1-en-1-yl)-N—((R)-1-((2,2,2-trifluoroethyl)sulfonyl)propan-2-yl)-2-(trifluoromethyl)benzamide (F133)

4-((Z)-3-(4-Chloro-3-fluorophenyl)-1,4,4,4-tetrafluorobut-1-en-1-yl)-N—((R)-1-((2,2,2-trifluoroethyl)sulfonyl)propan-2-yl)-2-(trifluoromethyl)benzamide (PF4)

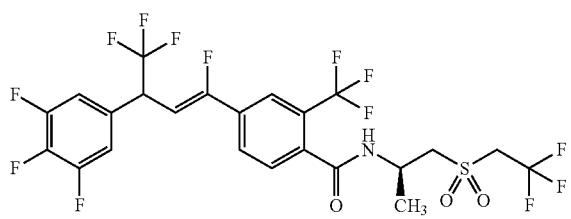 [SMILES: C[C@H](CS(=O)(=O)CC(F)(F)F)NC(=O)c1ccc(/C(F)=C/C(c2cc(F)c(F)c(F)c2)C(F)(F)F)cc1C(F)(F)F] 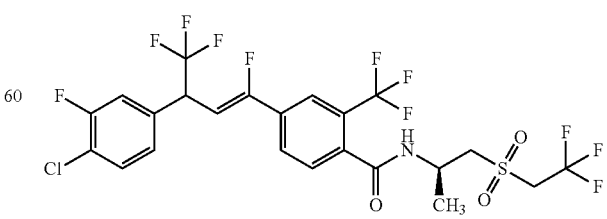

Isolated as a pale yellow gum (0.100 g, 33%).

Isolated as a white solid (0.070 g, 26%).

117

4-((Z)-3-(4-Bromo-3-chlorophenyl)-1,4,4,4-tetra-
fluorobut-1-en-1-yl)-N—((R)-1-((2,2,2-trifluoro-
ethyl)sulfonyl)propan-2-yl)-2-(trifluoromethyl)benz-
amide (PF5)

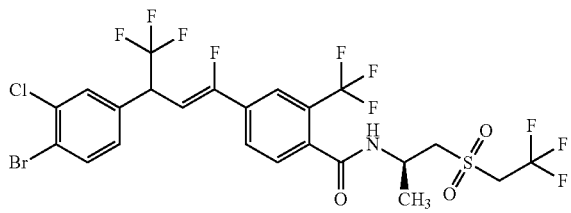

Isolated as an off-white solid (0.131 g, 48%).

4-((Z)-3-(4-Chloro-3-methylphenyl)-1,4,4,4-tetra-
fluorobut-1-en-1-yl)-N—((R)-1-((2,2,2-trifluoro-
ethyl)sulfonyl)propan-2-yl)-2-(trifluoromethyl)benz-
amide (PF8)

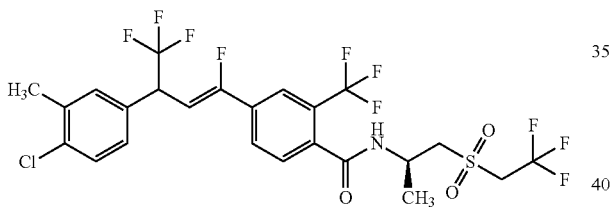

Isolated as a pale yellow solid (0.037 g, 14%).

The following compound was prepared in like manner to the procedure outlined in Example 15:

4-((Z)-3-(3,5-Dichloro-4-vinylphenyl)-1,4,4,4-tetra-
fluorobut-1-en-1-yl)-N—((R)-1-(ethylsulfonyl)pro-
pan-2-yl)-2-(trifluoromethyl)benzamide (F119)

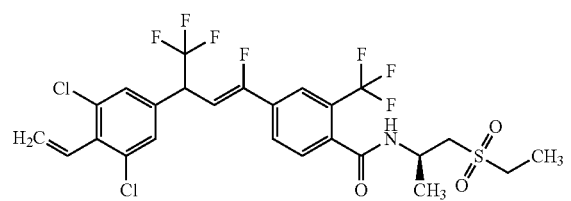 [SMILES: C=Cc1c(Cl)cc(C(/C=C(\F)c2ccc(C(=O)N[C@H](C)CS(=O)(=O)CC)c(C(F)(F)F)c2)C(F)(F)F)cc1Cl]

Isolated as an off-white solid (0.075 g, 59%).

The following compound was prepared in like manner to the procedure outlined in Example 16:

The following compounds were prepared in like manner to the procedure outlined in Example 17:

118

N—((R)-1-(((Cyanomethyl)thio)propan-2-yl)-4-((Z)-
1,4,4,4-tetrafluoro-3-(3,4,5-trichlorophenyl)but-1-
en-1-yl)-2-(trifluoromethyl)benzamide (F83)

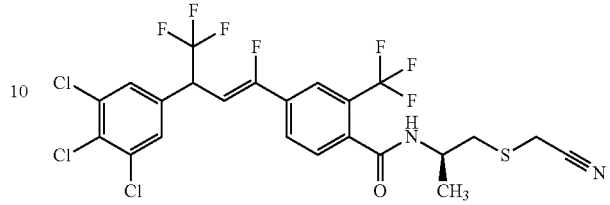

Isolated as an orange glass (0.540 g, 57%).

N—((R)-1-((2-Cyanoethyl)thio)propan-2-yl)-4-((Z)-
1,4,4,4-tetrafluoro-3-(3,4,5-trichlorophenyl)but-1-
en-1-yl)-2-(trifluoromethyl)benzamide (F128)

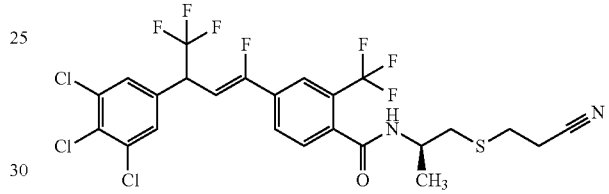

Isolated as a beige foam (0.386 g, 59%).

N—((R)-1-((2,2-Difluoroethyl)thio)propan-2-yl)-4-
((Z)-1,4,4,4-tetrafluoro-3-(3,4,5-trichlorophenyl)but-
1-en-1-yl)-2-(trifluoromethyl)benzamide (F82)

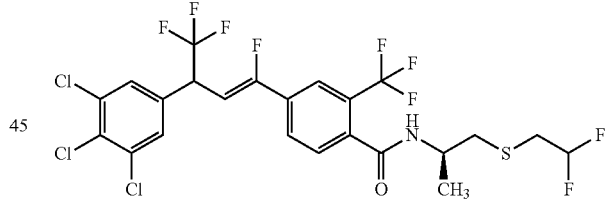

Isolated as a yellow glass (0.306 g, 51%).

N—((R)-1-(Methylthio)propan-2-yl)-4-((Z)-1,4,4,4-
tetrafluoro-3-(3,4,5-trichlorophenyl)but-1-en-1-yl)-
2-(trifluoromethyl)benzamide (F75)

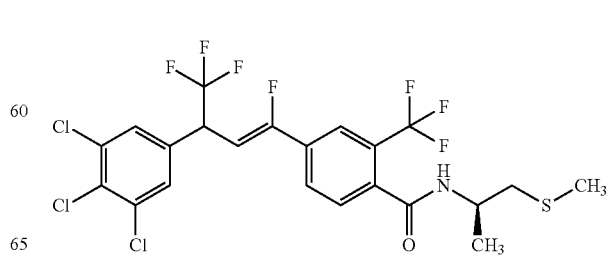

4-((Z)-1,4,4,4-Tetrafluoro-3-(3,4,5-trichlorophenyl)
but-1-en-1-yl)-2-(trifluoromethyl)-N—((R)-1-((3,3,
3-trifluoropropyl)thio)propan-2-yl)benzamide
(F137)

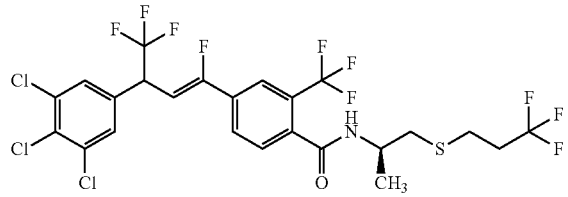 [SMILES: C[C@H](CSCCC(F)(F)F)NC(=O)c1ccc(/C(F)=C/C(c2cc(Cl)c(Cl)c(Cl)c2)C(F)(F)F)cc1C(F)(F)F]

Isolated as a yellow foam (0.479 g, 78%).

The following compounds were prepared in like manner to the procedure outlined in Example 18:

N-((2R)-1-((2,2-Difluoroethyl)sulfinyl)propan-2-yl)-
4-((Z)-1,4,4,4-tetrafluoro-3-(3,4,5-trichlorophenyl)
but-1-en-1-yl)-2-(trifluoromethyl)benzamide (F86)
and N—((R)-1-((2,2-difluoroethyl)sulfonyl)propan-
2-yl)-4-((Z)-1,4,4,4-tetrafluoro-3-(3,4,5-trichloro-
phenyl)but-1-en-1-yl)-2-(trifluoromethyl)benzamide
(F129)

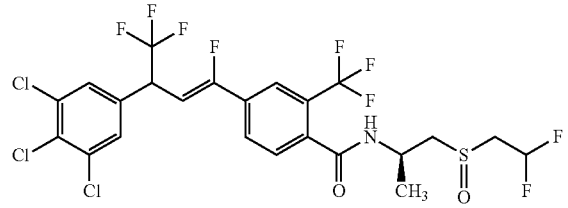 [SMILES: C[C@H](CS(=O)CC(F)F)NC(=O)c1ccc(/C(F)=C/C(c2cc(Cl)c(Cl)c(Cl)c2)C(F)(F)F)cc1C(F)(F)F]

Isolated as a yellow foam (0.096 g, 33%).

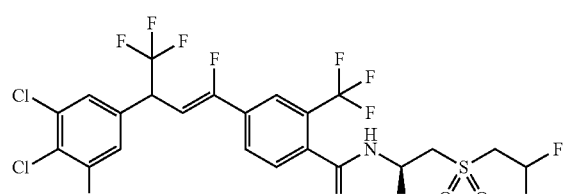

Isolated as a yellow foam (0.074 g, 27%).

N—((R)-1-((2-Fluoroethyl)sulfonyl)propan-2-yl)-4-
((Z)-1,4,4,4-tetrafluoro-3-(3,4,5-trichlorophenyl)but-
1-en-1-yl)-2-(trifluoromethyl)benzamide (F85)

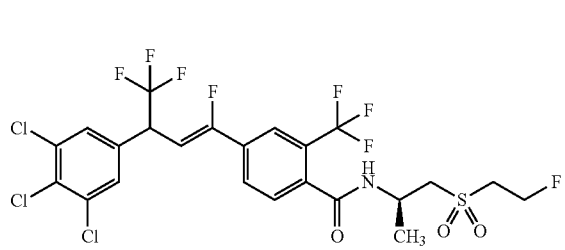 [SMILES: C[C@H](CS(=O)(=O)CCF)NC(=O)c1ccc(/C(F)=C/C(c2cc(Cl)c(Cl)c(Cl)c2)C(F)(F)F)cc1C(F)(F)F]

Isolated as a white foam (0.027 g, 21%).

N-((2R)-1-(Methylsulfinyl)propan-2-yl)-4-((Z)-1,4,
4,4-tetrafluoro-3-(3,4,5-trichlorophenyl)but-1-en-1-
yl)-2-(trifluoromethyl)benzamide (F88) and
N—((R)-1-(methylsulfonyl)propan-2-yl)-4-((Z)-1,4,
4,4-tetrafluoro-3-(3,4,5-trichlorophenyl)but-1-en-1-
yl)-2-(trifluoromethyl)benzamide (F87)

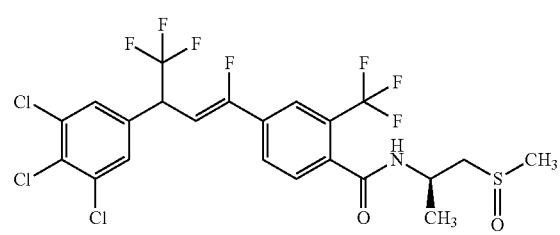 [SMILES: C[C@H](CS(C)=O)NC(=O)c1ccc(/C(F)=C/C(c2cc(Cl)c(Cl)c(Cl)c2)C(F)(F)F)cc1C(F)(F)F]

Isolated as a pale yellow foam (0.066 g, 25%).

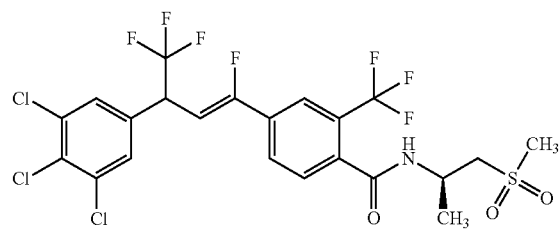 [SMILES: C[C@H](CS(C)(=O)=O)NC(=O)c1ccc(/C(F)=C/C(c2cc(Cl)c(Cl)c(Cl)c2)C(F)(F)F)cc1C(F)(F)F]

Isolated as a colorless glass (0.087 g, 35%).

N-((2R)-1-((2-Cyanoethyl)sulfinyl)propan-2-yl)-4-
((Z)-1,4,4,4-tetrafluoro-3-(3,4,5-trichlorophenyl)but-
1-en-1-yl)-2-(trifluoromethyl)benzamide (F122) and
N—((R)-1-((2-cyanoethyl)sulfonyl)propan-2-yl)-4-
((Z)-1,4,4,4-tetrafluoro-3-(3,4,5-trichlorophenyl)but-
1-en-1-yl)-2-(trifluoromethyl)benzamide (F123)

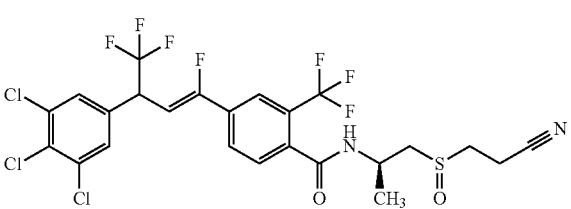 [SMILES: C[C@H](CS(=O)CCC#N)NC(=O)c1ccc(/C(F)=C/C(c2cc(Cl)c(Cl)c(Cl)c2)C(F)(F)F)cc1C(F)(F)F]

Isolated as a yellow foam (0.090 g, 35%).

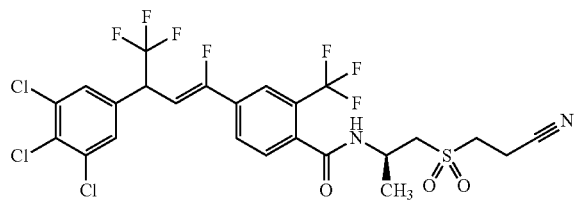 [SMILES: C[C@H](CS(=O)(=O)CCC#N)NC(=O)c1ccc(/C(F)=C/C(c2cc(Cl)c(Cl)c(Cl)c2)C(F)(F)F)cc1C(F)(F)F]

Isolated as a white amorphous solid (0.085 g, 32%).

4-((Z)-1,4,4,4-Tetrafluoro-3-(3,4,5-trichlorophenyl)
but-1-en-1-yl)-2-(trifluoromethyl)-N-((2R)-1-((3,3,3-
trifluoropropyl)sulfinyl)propan-2-yl)benzamide
(F121) and 4-((Z)-1,4,4,4-tetrafluoro-3-(3,4,5-
trichlorophenyl)but-1-en-1-yl)-2-(trifluoromethyl)-
N—((R)-1-((3,3,3-trifluoropropyl)sulfonyl)propan-
2-yl)benzamide (F130)

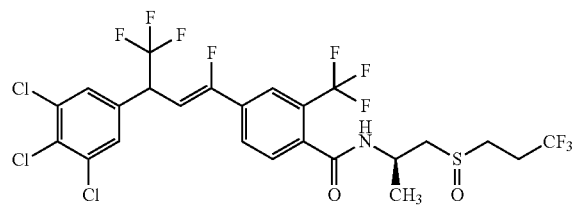 [SMILES: C[C@H](CS(=O)CCC(F)(F)F)NC(=O)c1ccc(/C(F)=C/C(c2cc(Cl)c(Cl)c(Cl)c2)C(F)(F)F)cc1C(F)(F)F]

Isolated as a yellow foam (0.085 g, 32%).

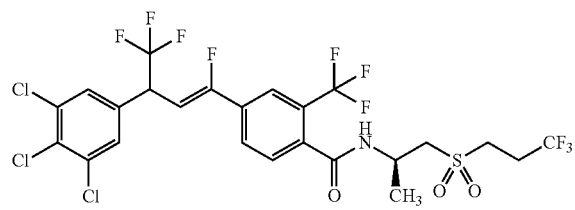 [SMILES: C[C@H](CS(=O)(=O)CCC(F)(F)F)NC(=O)c1ccc(/C(F)=C/C(c2cc(Cl)c(Cl)c(Cl)c2)C(F)(F)F)cc1C(F)(F)F]

Isolated as a white amorphous solid (0.099 g, 35%).

(Z)—N-(2-(Methylsulfinyl)propyl)-4-(1,4,4,4-tetra-
fluoro-3-(3,4,5-trichlorophenyl)but-1-en-1-yl)-2-
(trifluoromethyl)benzamide (F90) and (Z)—N-(2-
(methylsulfonyl)propyl)-4-(1,4,4,4-tetrafluoro-3-(3,
4,5-trichlorophenyl)but-1-en-1-yl)-2-
(trifluoromethyl)benzamide (F124)

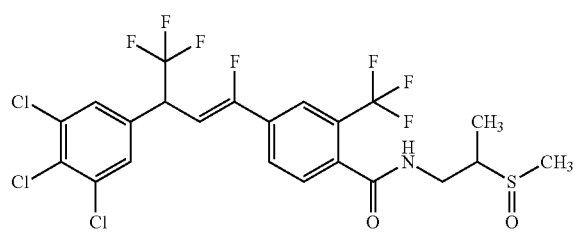 [SMILES: CC(CNC(=O)c1ccc(/C(F)=C/C(c2cc(Cl)c(Cl)c(Cl)c2)C(F)(F)F)cc1C(F)(F)F)S(C)=O]

Isolated as a white foam (0.068 g, 41%).

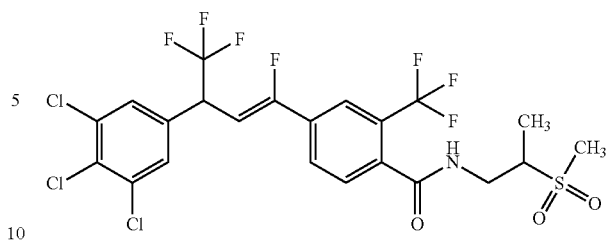

Isolated as a white foam (0.079 g, 47%).

N-((2R)-1-((2,2-Difluoropropyl)sulfinyl)propan-2-
yl)-4-((Z)-1,4,4,4-tetrafluoro-3-(3,4,5-trichlorophe-
nyl)but-1-en-1-yl)-2-(trifluoromethyl)benzamide
(F96) and N—((R)-1-((2,2-difluoropropyl)sulfonyl)
propan-2-yl)-4-((Z)-1,4,4,4-tetrafluoro-3-(3,4,5-
trichlorophenyl)but-1-en-1-yl)-2-(trifluoromethyl)
benzamide (F97)

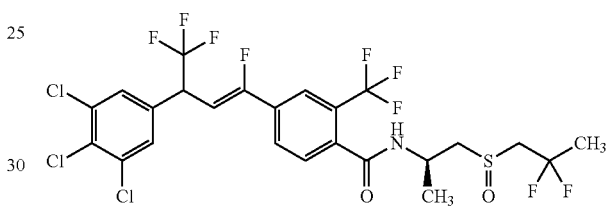

Isolated as a colorless glass (0.102 g, 53%) using 1.4 equivalents of sodium perborate.

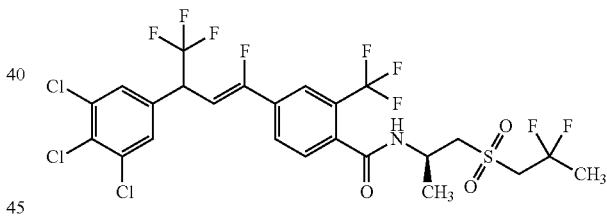

Isolated as a white foam (0.079 g, 40%) using 1.4 equivalents of sodium perborate.

(Z)—N-(2-((2-Fluoroethyl)sulfinyl)ethyl)-4-(1,4,4,4-
tetrafluoro-3-(3,4,5-trichlorophenyl)but-1-en-1-yl)-
2-(trifluoromethyl)benzamide (F138)

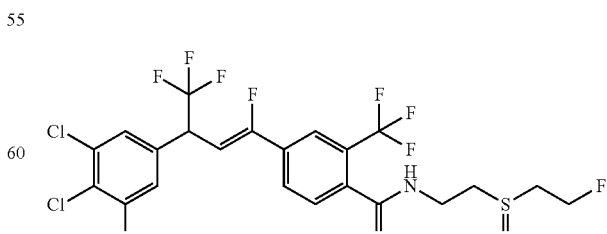

Isolated as a white foam (0.100 g, 82%) using one equivalent of sodium perborate.

N-((2R)-1-((2-Fluoroethyl)sulfinyl)propan-2-yl)-4-((Z)-1,4,4,4-tetrafluoro-3-(3,4,5-trichlorophenyl)but-1-en-1-yl)-2-(trifluoromethyl)benzamide (F99)

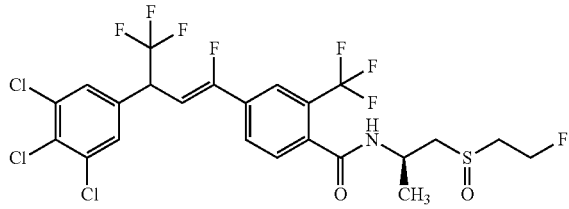

Isolated as a colorless glass (0.102 g, 53%) using one equivalent of sodium perborate.

The following compounds were prepared in like manner to the procedure outlined in Example 19:

(R)-1-((Cyclopropylmethyl)thio)propan-2-amine hydrochloride (C134)

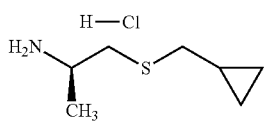

Isolated as a white amorphous solid (0.339 g, 89%): $^1$H NMR (500 MHz, DMSO-$d_6$) δ 8.18 (s, 3H), 3.28 (dt, J=7.6, 6.1 Hz, 1H), 2.85 (dd, J=13.7, 5.8 Hz, 1H), 2.67 (dd, J=13.7, 7.8 Hz, 1H), 2.55-2.45 (m, 2H), 1.26 (d, J=6.5 Hz, 3H), 1.04-0.90 (m, 1H), 0.57-0.47 (m, 2H), 0.29-0.15 (m, 2H); IR (thin film) 3384, 2912, 1623, 1513 cm$^{-1}$; HRMS-ESI (m/z) [M+H]$^+$ calcd for $C_7H_{15}NS$, 146.0998; found, 146.1000.

(2R)-1-(((2,2-Difluorocyclopropyl)methyl)thio)propan-2-amine hydrochloride (C135)

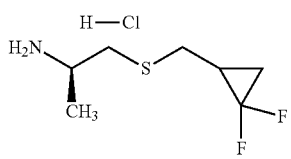

Isolated as a yellow/orange amorphous solid (0.592 g, 81%): $^1$H NMR (500 MHz, DMSO-$d_6$) δ 8.28 (s, 3H), 3.34-3.23 (m, 1H), 2.95-2.86 (m, 1H), 2.77-2.61 (m, 3H), 2.00 (dtq, J=13.7, 11.4, 7.5 Hz, 1H), 1.69-1.58 (m, 1H), 1.37-1.21 (m, 4H); IR (thin film) 3392, 2923, 1610, 1510 cm$^{-1}$; HRMS-ESI (m/z) [M+H]$^+$ calcd for $C_7H_{13}F_2NS$, 182.0810; found, 182.0808.

(R)-1-((2,2-Difluoroethyl)thio)propan-2-amine hydrochloride (C136)

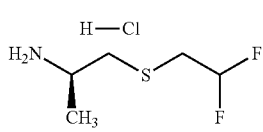

Isolated as a yellow/white amorphous solid (0.228 g, 89%): $^1$H NMR (400 MHz, DMSO-$d_6$) δ 8.28 (s, 3H), 6.20 (tt, J=56.3, 4.2 Hz, 1H), 3.38-3.24 (m, 1H), 3.07 (td, J=16.8, 4.2 Hz, 2H), 2.92 (dd, J=13.8, 5.8 Hz, 1H), 2.75 (dd, J=13.8, 7.5 Hz, 1H), 1.27 (d, J=6.5 Hz, 3H); IR (thin film) 2896, 1585, 1502 cm$^{-1}$.

(R)-1-((2-Fluoroethyl)thio)propan-2-amine hydrochloride (C137)

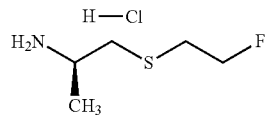

Isolated as a yellow oil (0.475 g, 99%): 1H NMR (400 MHz, DMSO-$d_6$) δ 8.15 (s, 3H), 4.64 (t, J=6.1 Hz, 1H), 4.52 (t, J=6.1 Hz, 1H), 3.30 (dq, J=12.4, 6.2 Hz, 1H), 2.92 (t, J=6.1 Hz, 1H), 2.90-2.80 (m, 2H), 2.71 (dd, J=13.8, 7.4 Hz, 1H), 1.26 (d, J=6.6 Hz, 3H); IR (thin film) 3386, 2938, 1617, 1509 cm$^{-1}$.

2-((2-Fluoroethyl)thio)ethan-1-amine hydrochloride (C138)

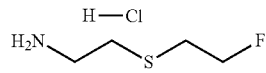

Isolated as a colorless oil (0.357 g, 95%): $^1$H NMR (500 MHz, DMSO-$d_6$) δ 8.13 (s, 3H), 4.62 (t, J=6.0 Hz, 1H), 4.52 (t, J=6.1 Hz, 1H), 2.97 (t, J=7.3 Hz, 2H), 2.90 (t, J=6.1 Hz, 1H), 2.86 (t, J=6.0 Hz, 1H), 2.80 (t, J=7.2 Hz, 2H); $^{19}$F NMR (471 MHz, DMSO-$d_6$) δ−212.81 (tt, J=46.9, 22.8 Hz); IR (thin film) 3385, 2959, 2898 cm$^{-1}$; HRMS-ESI (m/z) [M+H]$^+$ calcd for $C_4H_{10}FNS$, 124.0591; found, 124.0594.

2-((2,2-Difluoropropyl)thio)ethan-1-amine hydrochloride (C139)

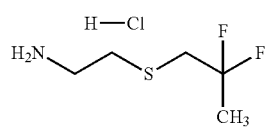

Isolated as a beige amorphous solid (0.323 g, 94%): $^1$H NMR (500 MHz, DMSO-$d_6$) δ 8.30 (s, 3H), 3.31 (q, J=6.7 Hz, 1H), 3.14 (td, J=15.1, 1.8 Hz, 2H), 2.94 (dd, J=13.7, 5.8 Hz, 1H), 2.75 (dd, J=13.6, 7.6 Hz, 1H), 1.70 (t, J=18.8 Hz, 3H), 1.27 (d, J=6.5 Hz, 3H); $^{19}$F NMR (471 MHz, DMSO-$d_6$) δ−87.66--87.95 (m); IR (thin film) 3390, 2924 cm$^{-1}$; HRMS-ESI (m/z) [M+H]$^+$ calcd for $C_6H_{13}F_2NS$, 170.0810; found, 170.0812.

(R)-1-((2-Methoxyethyl)thio)propan-2-amine hydrochloride (C140)

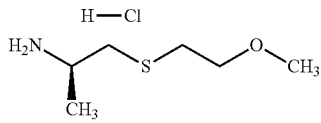

Isolated as a golden oil (0.276 g, 92%): $^1$H NMR (500 MHz, DMSO-$d_6$) δ 8.18 (s, 3H), 3.49 (t, J=6.4 Hz, 2H), 3.26 (s, 3H), 2.82 (dd, J=13.8, 5.9 Hz, 1H), 2.74-2.61 (m, 3H), 1.26 (d, J=6.5 Hz, 3H); IR (thin film) 3385, 2926, 1628, 1517 cm$^{-1}$; HRMS-ESI (m/z) [M+H]$^+$ calcd for $C_6H_{15}NOS$, 150.0947; found, 150.0947.

(R)-2-((2-Aminopropyl)thio)acetonitrile hydrochloride (C141)

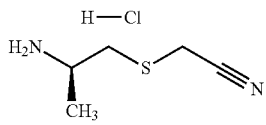

Isolated as a salmon amorphous solid (0.315 g, 78%): $^1$H NMR (400 MHz, DMSO-$d_6$) δ 8.27 (s, 3H), 3.90-3.79 (m, 2H), 3.47-3.35 (m, 1H), 3.00 (dd, J=13.9, 5.9 Hz, 1H), 2.83 (dd, J=13.9, 7.6 Hz, 1H), 1.29 (d, J=6.5 Hz, 3H); IR (thin film) 2841, 2241 cm$^{-1}$; HRMS-ESI (m/z) [M+H]$^+$ calcd for $C_5H_{10}N_2S$, 131.0637; found, 131.0636.

(R)-3-((2-Aminopropyl)thio)propanenitrile hydrochloride (C142)

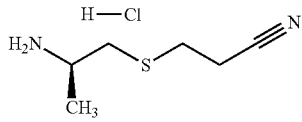

Isolated as an orange oil (0.350 g, 90%): $^1$H NMR (400 MHz, CDCl$_3$) δ 7.88-7.83 (m, 1H), 7.78 (dd, J=8.1, 1.8 Hz, 1H), 7.61 (d, J=8.1 Hz, 1H), 7.43 (s, 2H), 5.90-5.74 (m, 2H), 4.60 (p, J=8.8 Hz, 1H), 4.46-4.32 (m, 1H), 2.89-2.68 (m, 4H), 2.49-2.34 (m, 2H), 1.35 (d, J=6.7 Hz, 3H); HRMS-ESI (m/z) [M+H]$^+$ calcd for $C_6H_{12}N_2S$, 145.0794; found, 145.0793.

(R)-1-((3,3,3-Trifluoropropyl)thio)propan-2-amine hydrochloride (C143)

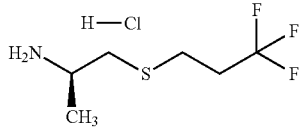

Isolated as an orange oil (0.345 g, 89%): $^1$H NMR (400 MHz, DMSO-$d_6$) δ 8.15 (s, 3H), 3.30-3.19 (m, 1H), 2.84 (dd, J=13.9, 6.0 Hz, 1H), 2.78-2.52 (m, 5H), 1.26 (d, J=6.5 Hz, 3H); IR (thin film) 2899 cm$^{-1}$; HRMS-ESI (m/z) [M+H]$^+$ calcd for $C_6H_{12}F_3NS$, 188.0715; found, 188.0715.

The following compound was prepared in like manner to the procedure outlined in Example 20:

tert-Butyl (R)-(1-((2,2-difluoropropyl)thio)propan-2-yl)carbamate (C144)

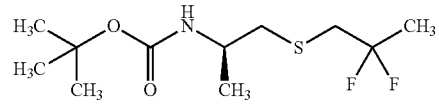 [SMILES: C[C@H](CSCC(C)(F)F)NC(=O)OC(C)(C)C]

Isolated as a pale yellow oil (0.562 g, 19%): $^1$H NMR (300 MHz, CDCl$_3$ δ 4.62 (s, 1H), 3.99-3.74 (m, 1H), 2.91 (t, J=14.1 Hz, 2H), 2.82-2.66 (m, 2H), 1.71 (t, J=18.3 Hz, 3H), 1.45 (s, 9H), 1.21 (d, J=6.7 Hz, 3H); $^{19}$F NMR (471 MHz, CDCl$_3$) δ−87.83−−89.54 (m); $^{13}$C NMR (126 MHz, CDCl$_3$) δ 155.14, 123.89 (t, J=239.8 Hz), 79.45, 45.97, 40.09, 39.01 (t, J=29.1 Hz), 28.39, 22.33 (t, J=27.1 Hz), 19.95; HRMS-ESI (m/z) [M+H]$^+$ calcd for $C_{11}H_{21}F_2NO_2S$, 292.1153; found, 292.1152.

Example 23: Preparation of 4-vinyl-1-naphthoic Acid (C145)

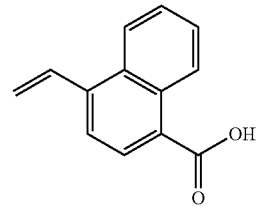

To a stirred solution of 4-bromo-1-naphthoic acid (2.50 g, 9.98 mmol) in dimethyl sulfoxide (32.3 mL) was added potassium vinyltrifluoroborate (1.33 g, 9.96 mmol), potassium carbonate (3.85 g, 27.9 mmol) and [1,1'-bis(diphenylphosphino)ferrocene]-dichloropalladium(II) (0.364 g, 0.498 mmol). The reaction mixture was heated in an 80° C. bath for 18 hours. The reaction mixture was cooled to ambient temperature and diluted with 1 N aqueous hydrochloric acid solution (150 mL) and water (150 mL). The mixture was extracted with ethyl acetate. The organic layer was washed with brine, dried over sodium sulfate and concentrated under reduced pressure to afford the crude compound. The crude compound was purified by column chromatography (SiO$_2$, eluting with 0-100% ethyl acetate in hexanes) to afford the title compound as a bright yellow solid (1.36 g, 62%): mp 147-155° C.; $^1$H NMR (300 MHz, acetone-$d_6$) δ 11.42 (s, 1H), 9.16-9.03 (m, 1H), 8.31-8.25 (m, 2H), 7.77 (dd, J=7.7, 0.7 Hz, 1H), 7.70-7.57 (m, 3H), 5.95 (dd, J=17.2, 1.5 Hz, 1H), 5.62 (dd, J=11.1, 1.5 Hz, 1H); ESIMS m/z 197 ([M−H]$^−$).

Example 24: Preparation
1-bromo-3-chloro-5-(2,2,2-trifluoroethyl)benzene
(C146)

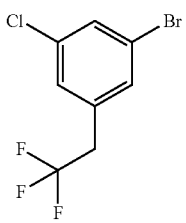 [SMILES: FC(F)(F)Cc1cc(Cl)cc(Br)c1]

(3-Bromo-5-chlorophenyl)boronic acid (4 g, 17.00 mmol) was added to a flask with 2,2,2-trifluoroethan-1-amine hydrochloride (9.22 g, 68.0 mmol), sodium nitrite (5.87 g, 85 mmol), and ammonium chloride (3.64 g, 68.0 mmol). The reaction was heated to 100° C. overnight. At this point, the solvent was removed, and the residue was dissolved in dimethyl sulfoxide (20 mL). Potassium fluoride (1.976 g, 34.0 mmol) was added, and the mixture was heated to 100° C. for 2 hours. After cooling, the mixture was diluted with water and extracted with dichloromethane. After extraction and solvent removal, the residue was purified by silica gel chromatography eluting with hexanes. The title compound was recovered as a clear, colorless oil that crystallized upon standing (3.00 g, 64.5%): $^1$H NMR (300 MHz, CDCl$_3$) δ 7.52 (t, J=1.8 Hz, 1H), 7.35 (s, 1H), 7.24 (s, 1H), 3.32 (q, 1=10.5 Hz, 2H). $^{19}$F NMR (471 MHz, CDCl$_3$) δ−65.64. ESIMS m/z 274 ([M+H]$^+$).

Example 25: Preparation
3-chloro-5-(2,2,2-trifluoroethyl)benzaldehyde
(C147)

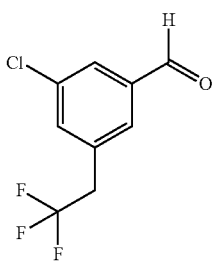 [SMILES: O=Cc1cc(Cl)cc(CC(F)(F)F)c1]

1-Bromo-3-chloro-5-(2,2,2-trifluoroethyl)benzene (C146) (2 g, 7.31 mmol) was dissolved in tetrahydrofuran at 0° C., and isopropylmagnesium chloride-lithium chloride complex (1.3 M solution in tetrahydrofuran; 6.75 mL, 8.78 mmol) was added dropwise. The reaction mixture was stirred for 4 hours with warming to room temperature, and N,N-dimethylformamide (0.680 mL, 8.78 mmol) was added dropwise. The reaction mixture was stirred for 30 minutes, then 1 N aqueous hydrochloric acid was added, and the mixture was extracted with diethyl ether. The combined organic layers were washed with brine, dried over sodium sulfate and concentrated to a yellow oil. Purification by silica gel chromatography eluting 0-20% acetone in hexanes gave the title compound as a pale yellow oil (1.33 g, 82%): $^1$H NMR (400 MHz, CDCl$_3$) δ 9.98 (s, 1H), 7.90-7.78 (m, 1H), 7.71 (s, 1H), 7.56 (s, 1H), 3.45 (q, J=10.5 Hz, 2H); $^{19}$F NMR (376 MHz, CDCl$_3$) δ−65.67; IR (thin film) 1704 cm$^{-1}$; EIMS m/z 221 ([M]$^+$).

The following compounds were prepared in like manner to the procedure outlined in Example 25:

3-Chloro-5-(1,1-difluoroethyl)benzaldehyde (C154)

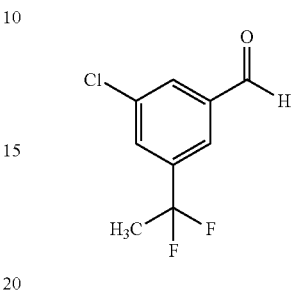

Isolated as a yellow oil (0.665 g, 62%): $^1$H NMR (400 MHz, CDCl$_3$) δ 10.01 (s, 1H), 7.96-7.85 (m, 2H), 7.75 (s, 1H), 1.96 (t, J=18.2 Hz, 3H); $^{19}$F NMR (376 MHz, CDCl$_3$) δ−88.26; IR (thin film) 1705 cm$^{-1}$; ESIMS m/z 205 ([M+H]$^+$).

3-Chloro-5-(1,1-difluoropropyl)benzaldehyde (C155)

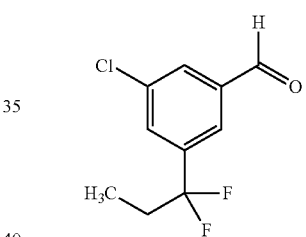

Isolated as a clear yellow oil (0.700 g, 86%): $^1$H NMR (400 MHz, CDCl$_3$) δ 10.01 (s, 1H), 7.92 (d, J=1.7 Hz, 1H), 7.86 (s, 1H), 7.71 (t, J=1.8 Hz, 1H), 2.27-2.06 (m, 2H), 1.02 (t, J=7.5 Hz, 3H); $^{19}$F NMR (376 MHz, CDCl$_3$) δ−97.93; IR (thin film) 1705 cm$^{-1}$; EIMS m/z 218 ([M]$^+$).

3-Chloro-5-(1,1-difluorobutyl)benzaldehyde (C156)

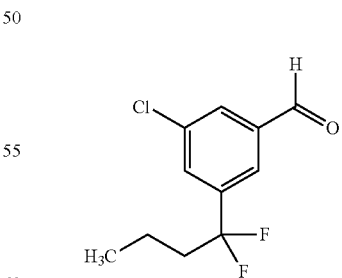

Isolated as a clear yellow oil (0.690 g, 89%): $^1$H NMR (400 MHz, CDCl$_3$) δ 10.01 (s, 1H), 7.91 (d, J=1.5 Hz, 1H), 7.86 (s, 1H), 7.71 (d, J=1.6 Hz, 1H), 2.20-2.03 (m, 2H), 1.53-1.41 (m, 2H), 0.96 (t, J=7.4 Hz, 3H); $^{19}$F NMR (376 MHz, CDCl$_3$) δ−95.90; IR (thin film) 1704 cm$^{-1}$; EIMS m/z 232 ([M]$^+$).

Example 26: Preparation of 1-(3-bromo-5-chlorophenyl)ethan-1-one (C148)

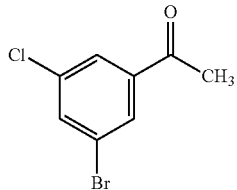

1,3-Dibromo-5-chlorobenzene (5.0 g, 18.5 mmol) was dissolved in diethyl ether (61.6 mL) and cooled to −78° C. Because the compound came out of solution, the mixture was removed from the cooling bath. As soon as stirring was again visible from temperature warming, n-butyllithium (8.14 mL, 20.34 mmol) was added dropwise, and the solution was re-immersed in the cold bath. The solution took on a bright yellow color, and the mixture was stirred for 30 minutes. At this point a slight yellow precipitate was visible. N-Methoxy-N-methylacetamide (2.359 mL, 22.19 mmol) was added dropwise, and the reaction mixture was stirred for 10 minutes, then warmed slowly to room temperature. The reaction mixture was quenched with 1 N hydrochloric acid and was extracted with diethyl ether. The combined organic extracts were washed with brine, dried over sodium sulfate and concentrated. The resulting oil was purified on silica running a 0-15% gradient of acetone in hexanes. The title compound was isolated as a white solid (3.7 g, 86%): mp 33-36° C.; $^1$H NMR (300 MHz, CDCl$_3$) δ 7.97-7.95 (m, 1H), 7.85 (dd, J=1.5 Hz, 1H), 7.71 (t, J=1.8 Hz, 1H), 2.59 (s, 3H); IR (thin film) 1687 cm$^{-1}$; ESIMS m/z 233 ([M+H]$^+$).

The following compounds were prepared in like manner to the procedure outlined in Example 26:

1-(3-Bromo-5-chlorophenyl)propan-1-one (C149)

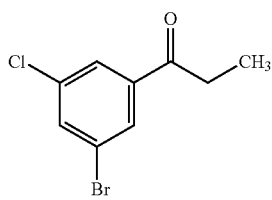

Isolated as a white solid (1.71 g, 62%): $^1$H NMR (400 MHz, CDCl$_3$) δ 7.96 (t, J=1.6 Hz, 1H), 7.90-7.81 (m, 1H), 7.69 (t, J=1.8 Hz, 1H), 2.96 (q, J=7.2 Hz, 2H), 1.22 (t, J=7.2 Hz, 3H); $^{13}$C NMR (101 MHz, CDCl$_3$) δ 198.01, 139.51, 135.78, 135.33, 129.38, 126.91, 123.25, 32.06, 7.98; ESIMS m/z 248 ([M+H]$^+$).

1-(3-Bromo-5-chlorophenyl)butan-1-one (C150)

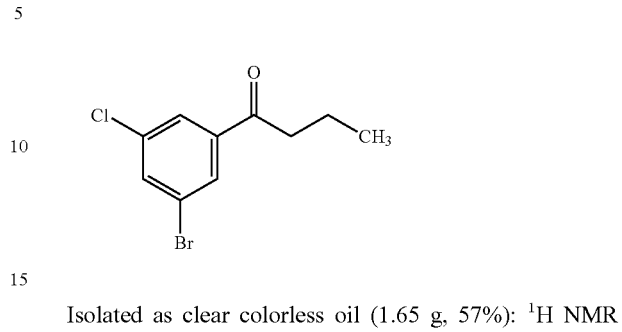

Isolated as clear colorless oil (1.65 g, 57%): $^1$H NMR (400 MHz, CDCl$_3$) δ 7.95 (t, J=1.6 Hz, 1H), 7.84 (t, J=1.7 Hz, 1H), 7.69 (t, J=1.8 Hz, 1H), 2.90 (t, J=7.2 Hz, 2H), 1.76 (h, J=7.4 Hz, 2H), 1.00 (t, J=7.4 Hz, 3H); $^{13}$C NMR (101 MHz, CDCl$_3$) δ 197.53, 139.67, 135.75, 135.28, 129.40, 126.93, 123.22, 40.61, 17.47, 13.72; IR (thin film) 1693, 1559, 1203 cm$^{-1}$; ESIMS m/z 262 ([M+H]$^+$).

Example 27: Preparation of 1-bromo-3-chloro-5-(1,1-difluoroethyl)benzene (C151)

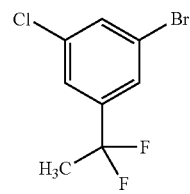

1-(3-Bromo-5-chlorophenyl)ethan-1-one (C148) (1.6 g, 6.85 mmol) was dissolved in dichloromethane (34.3 mL) to which were added sequentially Deoxo-Fluor® (bis(2-methoxyethyl)aminosulfur trifluoride; 4.42 mL, 10.28 mmol) and one drop of methanol. The reaction mixture was stirred at room temperature overnight. An additional 1.5 equivalents of Deoxo-Fluor® were added, and the reaction mixture was heated to 40° C. for 24 hours. The reaction mixture was concentrated under light vacuum (300 mbar) to remove the dichloromethane and was heated to 70° C. for 3 hours. The reaction was quenched by slow addition of saturated aqueous sodium bicarbonate solution with stirring. The layers were separated and the aqueous layer was extracted with dichloromethane. The combined organic extracts were washed with brine, dried over sodium sulfate, and concentrated. Purification by silica gel chromatography eluting with hexanes provided the title compound as a clear, colorless oil (1.34 g, 77%): $^1$H NMR (400 MHz, CDCl$_3$) δ 7.57 (d, J=1.7 Hz, 1H), 7.53 (s, 1H), 7.43 (s, 1H), 1.89 (t, J=18.2 Hz, 3H); $^{19}$F NMR (376 MHz, CDCl$_3$) δ−88.39; ESIMS m/z 255 ([M+H]$^+$).

The following compounds were prepared in like manner to the procedure outlined in Example 27:

1-Bromo-3-chloro-5-(1,1-difluoropropyl)benzene
(C152)

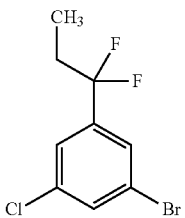

Isolated as a clear yellow oil (1.00 g, 83%): $^1$H NMR (400 MHz, CDCl$_3$) δ 7.57 (t, J=1.8 Hz, 1H), 7.50 (s, 1H), 7.39 (s, 1H), 2.11 (ddt, J=23.7, 16.2, 7.5 Hz, 2H), 0.99 (t, J=7.5 Hz, 3H); $^{19}$F NMR (376 MHz, CDCl$_3$) δ −97.97; IR (thin film) 1566 cm$^{-1}$; ESIMS m/z 268 ([M+H]$^+$).

1-Bromo-3-chloro-5-(1,1-difluorobutyl)benzene
(C153)

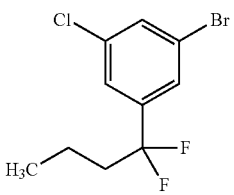

Isolated as a clear yellow oil (0.940 g, 96%): $^1$H NMR (400 MHz, CDCl$_3$) δ 7.57 (t, J=1.8 Hz, 1H), 7.49 (s, 1H), 7.39 (s, 1H), 2.14-1.98 (m, 2H), 1.51-1.39 (m, 2H), 0.95 (t, J=7.4 Hz, 3H); $^{19}$F NMR (376 MHz, CDCl$_3$) δ −95.94; IR (thin film) 1565 cm$^{-1}$; ESIMS m/z 282 ([M+H]$^+$).

Example 29: Preparation of (Z)-4-(1,4,4,4-tetrafluoro-3-(3,4,5-trichlorophenyl)but-1-en-1-yl)-2-(trifluoromethyl)-N-(2-((trifluoromethyl)thio)ethyl)benzamide (F92)

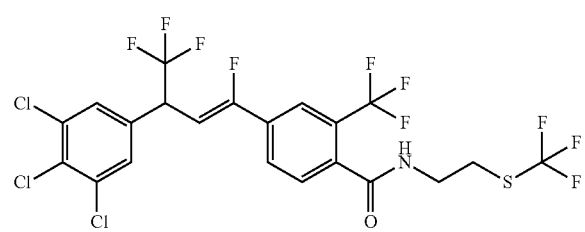 [SMILES: O=C(NCCSC(F)(F)F)c1ccc(/C(F)=C/C(c2cc(Cl)c(Cl)c(Cl)c2)C(F)(F)F)cc1C(F)(F)F]

(Z)-4-(1,4,4,4-Tetrafluoro-3-(3,4,5-trichlorophenyl) but-1-en-1-yl)-2-(trifluoromethyl)benzoyl chloride (C23) (1.0 mL, 0.45 M, 0.45 mmol) in dichloromethane was added to a colorless solution of 2-((trifluoromethyl)thio)ethan-1-amine (100 mg, 0.689 mmol) and 4-methylmorpholine (0.148 mL, 1.350 mmol) in N,N-dimethylformamide (2 mL). The reaction mixture was agitated for two hours. The reaction mixture was diluted with ethyl acetate and 5% aqueous citric acid, and the layers were separated. The organic solution was washed with water, dried with magnesium sulfate, filtered, and concentrated. The resulting residue was purified by chromatography on SiO$_2$ with a linear gradient of 0-50% ethyl acetate in hexanes providing the title compound as a yellow oil (0.204 g, 69%).

The following compounds were prepared in like manner to the procedure outlined in Example 29:

(Z)—N-(2-(Methylthio)propyl)-4-(1,4,4,4-tetrafluoro-3-(3,4,5-trichlorophenyl)but-1-en-1-yl)-2-(trifluoromethyl)benzamide (F89)

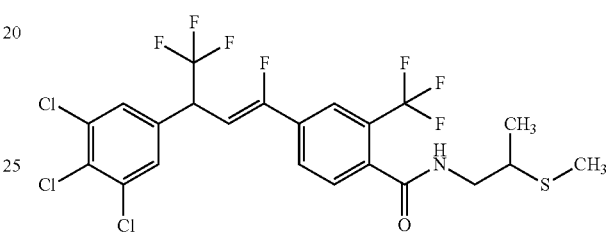

Isolated as a yellow glass (0.20 g, 34%).

N—((R)-1-((2-Fluoroethyl)thio)propan-2-yl)-4-((Z)-1,4,4,4-tetrafluoro-3-(3,4,5-trichlorophenyl)but-1-en-1-yl)-2-(trifluoromethyl)benzamide (F84)

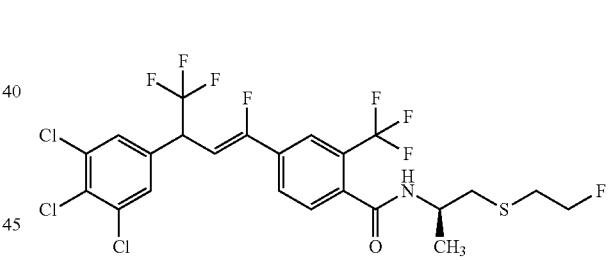

Isolated as a pale yellow glass (0.273 g, 35%).

(Z)—N-(2-((2-Fluoroethyl)thio)ethyl)-4-(1,4,4,4-tetrafluoro-3-(3,4,5-trichlorophenyl)but-1-en-1-yl)-2-(trifluoromethyl)benzamide (F125)

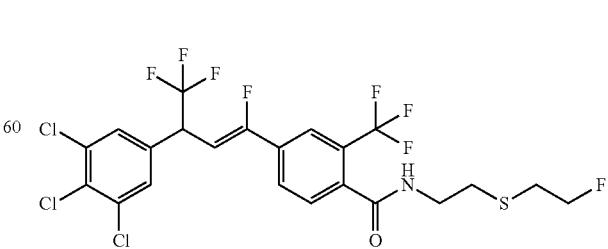

Isolated as a colorless oil (0.249 g, 34%).

N—((R)-1-((2,2-Difluoropropyl)thio)propan-2-yl)-4-((Z)-1,4,4,4-tetrafluoro-3-(3,4,5-trichlorophenyl)but-1-en-1-yl)-2-(trifluoromethyl)benzamide (F113)

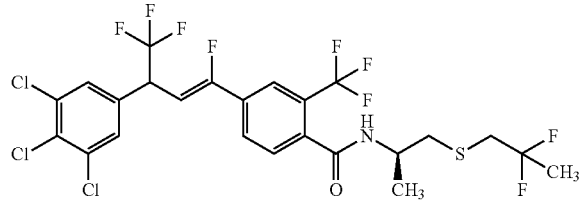 [SMILES: C[C@H](CSCC(C)(F)F)NC(=O)c1ccc(/C(F)=C/C(c2cc(Cl)c(Cl)c(Cl)c2)C(F)(F)F)cc1C(F)(F)F]

Isolated as a yellow foam (0.300 g, 45%).

(Z)—N-(2-Methyl-1-(methylsulfonyl)propan-2-yl)-4-(1,4,4,4-tetrafluoro-3-(3,4,5-trichlorophenyl)but-1-en-1-yl)-2-(trifluoromethyl)benzamide (F100)

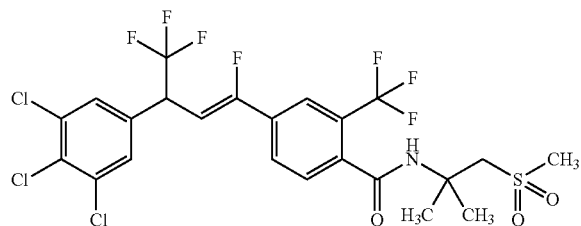 [SMILES: CC(C)(CS(C)(=O)=O)NC(=O)c1ccc(/C(F)=C/C(c2cc(Cl)c(Cl)c(Cl)c2)C(F)(F)F)cc1C(F)(F)F]

Isolated as a yellow foam (0.089 g, 23%) using diisopropylethyl amine in place of N-methyl morpholine.

Example 30: Preparation of (Z)—N-(3-(methylthio)butan-2-yl)-4-(1,4,4,4-tetrafluoro-3-(3,4,5-trichlorophenyl)but-1-en-1-yl)-2-(trifluoromethyl)benzamide (F101)

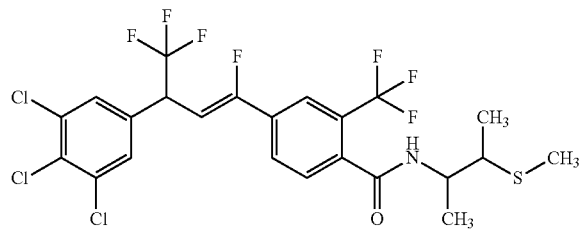 [SMILES: CSC(C)C(C)NC(=O)c1ccc(/C(F)=C/C(c2cc(Cl)c(Cl)c(Cl)c2)C(F)(F)F)cc1C(F)(F)F]

2-(3H-[1,2,3]Triazolo[4,5-b]pyridin-3-yl)-1,1,3,3-tetramethylisouronium hexafluorophosphate(V) (460 mg, 1.211 mmol) was added to an orange solution of (Z)-4-(1,4,4,4-tetrafluoro-3-(3,4,5-trichlorophenyl)but-1-en-1-yl)-2-(trifluoromethyl)benzoic acid (C2) (400 mg, 0.807 mmol), N-ethyl-N-isopropylpropan-2-amine (324 μL, 1.856 mmol), and 3-(methylthio)butan-2-amine (115 mg, 0.969 mmol) in N,N-dimethylformamide (2.7 mL). The reaction mixture was stirred overnight at room temperature. The reaction mixture was diluted with water and ethyl acetate. The organic solution was washed with 5% citric acid, water, and brine, dried with sodium sulfate, filtered, and concentrated. The resulting residue was purified by flash silica chromatography. The title compound was isolated as a yellow glass (0.37 g, 69%).

Example 31: Preparation of tert-butyl (R)-(1-((2-fluoroethyl)thio)propan-2-yl)carbamate (C157)

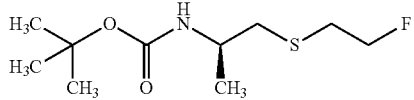

Aqueous sodium hydroxide (2.0 M, 8.5 mL, 17 mmol) was added to a solution of (R)—S-(2-((tert-butoxycarbonyl)amino)propyl) ethanethioate (C58) (2.0 g, 8.5 mmol) in isopropanol at 0° C. After stirring 2 hours, 1-fluoro-2-iodoethane (1.76 g, 10.1 mmol) was added and the reaction mixture was left to stir overnight. The reaction mixture was partioned between ethyl acetate and water. The organics were separated, washed with saturated sodium bicarbonate and brine, dried with magnesium sulfate, and concentrated. The resulting residue was purified by flash silica chromatography. The title compound was isolated as a pale yellow liquid (1.55 g 72%): $^1$H NMR (500 MHz, DMSO-$d_6$) δ 6.80 (d, J=8.2 Hz, 1H), 4.53 (dt, J=47.3, 6.4 Hz, 2H), 3.54 (h, J=6.9 Hz, 1H), 2.81 (dt, J=21.2, 6.4 Hz, 2H), 2.63-2.51 (m, 2H), 1.38 (s, 9H), 1.07 (d, J=6.7 Hz, 3H); $^{19}$F NMR (471 MHz, DMSO-$d_6$) δ −211.55 (tt, J=46.9, 21.3 Hz); $^{13}$C NMR (126 MHz, DMSO-$d_6$) δ 155.41, 83.20 (d, J=167.3 Hz), 78.02, 46.51, 38.34, 31.84 (d, J=20.5 Hz), 28.72, 20.19; IR (thin film) 3340, 2975, 2931, 1687, 1504 cm$^{-1}$.

The following compounds were prepared in like manner to the procedure outlined in Example 31:

tert-Butyl (R)-(1-((2,2-difluoroethyl)thio)propan-2-yl)carbamate (C158)

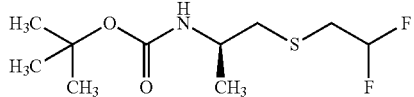

Isolated as a pale yellow oil (0.323 g, 39%): $^1$H NMR (400 MHz, CDCl$_3$) δ 5.89 (tt, J=56.5, 4.5 Hz, 1H), 4.54 (s, 1H), 3.84 (s, 1H), 2.89 (tdd, J=15.4, 4.5, 1.4 Hz, 2H), 2.79-2.62 (m, 2H), 1.45 (s, 10H), 1.21 (d, J=6.7 Hz, 3H); IR (thin film) 1688 cm$^{-1}$; HRMS-ESI (m/z) [M+Na]$^+$ calcd for $C_{10}H_{19}F_2NO_2S$, 278.0997; found, 278.1009.

tert-Butyl (R)-(1-((3,3,3-trifluoropropyl)thio)propan-2-yl)carbamate (C159)

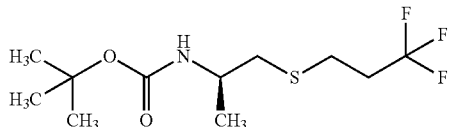

Isolated as an off-white/yellow amorphous solid (1.03 g, 31%): $^1$H NMR (400 MHz, CDCl$_3$) δ 4.59 (s, 1H), 3.86 (dd, J=13.6, 7.3 Hz, 1H), 2.77-2.66 (m, 3H), 2.66-2.57 (m, 1H), 2.46-2.31 (m, 2H), 1.45 (s, 9H), 1.21 (d, J=6.7 Hz, 3H); IR (thin film) 1692 cm$^{-1}$; HRMS-ESI (m/z) [M+Na]$^+$ calcd for $C_{11}H_{20}F_3NO_2S$, 310.1059; found, 310.1060.

tert-Butyl (R)-(1-((cyanomethyl)thio)propan-2-yl)carbamate (C160)

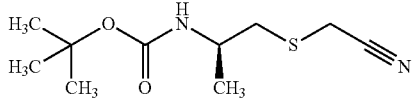

Isolated as a white solid (2.1 g, 55%): mp 61-62° C.; $^1$H NMR (500 MHz, CDCl$_3$) δ 4.52 (s, 1H), 3.90 (dt, J=13.7, 7.4 Hz, 1H), 3.47 (d, J=17.2 Hz, 1H), 3.32 (d, J=17.1 Hz, 1H), 2.82 (ddd, J=52.8, 13.7, 6.0 Hz, 2H), 1.45 (s, 9H), 1.26 (d, J=6.7 Hz, 3H); IR (thin film) 2244, 1683 cm$^{-1}$; HRMS-ESI (m/z) [M+H]$^+$ calcd for C$_{10}$H$_{18}$N$_2$O$_2$S, 253.0981; found, 253.0979.

tert-Butyl (R)-(1-((2-cyanoethyl)thio)propan-2-yl)carbamate (C161)

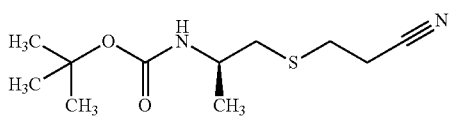 [SMILES: C[C@H](CSCCC#N)NC(=O)OC(C)(C)C]

Isolated as an off-white/beige amorphous solid (2.5 g, 59%): mp 63-65° C.; $^1$H NMR (500 MHz, CDCl$_3$) δ 4.58 (d, J=9.2 Hz, 1H), 3.91-3.70 (m, 1H), 2.89-2.58 (m, 7H), 1.45 (s, 9H), 1.22 (d, J=6.7 Hz, 3H); IR (thin film) 1688 cm$^{-1}$; HRMS-ESI (m/z) [M+Na]$^+$ calcd for C$_{11}$H$_{20}$N$_2$O$_2$S, 267.1138; found, 267.1142.

tert-Butyl (R)-(1-(methylthio)propan-2-yl)carbamate (C162)

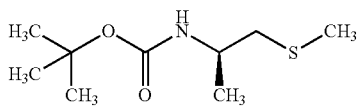

Isolated as an orange oil (2.8 g, 79%): $^1$H NMR (400 MHz, CDCl$_3$) δ 4.61 (s, 1H), 3.84 (d, J=12.5 Hz, 1H), 2.65 (dd, J=13.4, 5.2 Hz, 1H), 2.55 (dd, J=13.4, 6.6 Hz, 1H), 2.14 (s, 3H), 1.45 (s, 9H), 1.22 (d, J=6.6 Hz, 3H); IR (thin film) 1686 cm$^{-1}$; HRMS-ESI (m/z) [M+Na]$^+$ calcd for C$_9$H$_{19}$NO$_2$S, 228.1029; found, 228.1039.

tert-Butyl (R)-(1-((2-methoxyethyl)thio)propan-2-yl)carbamate (C163)

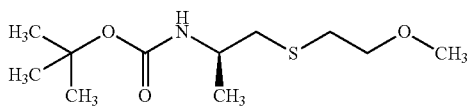 [SMILES: COCCSC[C@@H](C)NC(=O)OC(C)(C)C]

Isolated as a pale yellow oil (0.558 g, 58%) using 2-methoxyethyl 4-methylbenzenesulfonate: $^1$H NMR (500 MHz, CDCl$_3$) δ 4.76 (s, 1H), 3.84 (s, 1H), 3.56 (t, J=6.4 Hz, 2H), 3.38 (s, 3H), 2.80-2.69 (m, 3H), 2.64 (dd, J=14.0, 5.9 Hz, 1H), 1.45 (s, 9H), 1.21 (d, J=6.7 Hz, 3H); IR (thin film) 3333, 2975, 2928, 1691 cm$^{-1}$; HRMS-ESI (m/z) [M+Na]$^+$ calcd for C$_{11}$H$_{23}$NO$_3$S, 272.1291 found, 272.1296.

tert-Butyl (R)-(1-((cyclopropylmethyl)thio)propan-2-yl)carbamate (C164)

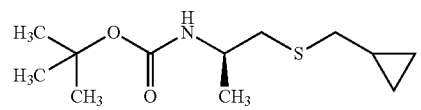

Isolated as a yellow oil (0.600 g, 60%) using (bromomethyl)cyclopropane: 1H NMR (500 MHz, CDCl$_3$) δ 4.65 (s, 1H), 3.85 (s, 1H), 2.73 (dd, J=13.3, 5.1 Hz, 1H), 2.64 (dd, J=13.8, 6.5 Hz, 1H), 2.53-2.45 (m, 2H), 1.44 (s, 9H), 1.21 (d, J=6.7 Hz, 3H), 1.04-0.93 (m, 1H), 0.56 (dtd, J=8.2, 2.8, 1.6 Hz, 2H), 0.30-0.15 (m, 2H); IR (thin film) 3341, 3079, 2975, 2930, 1688, 1501 cm$^{-1}$; HRMS-ESI (m/z) [M+Na]$^+$ calcd for C$_{12}$H$_{23}$NO$_2$S, 268.1342; found, 268.1340.

tert-Butyl ((2R)-1-(((2,2-difluorocyclopropyl)methyl)thio)propan-2-yl)carbamate (C165)

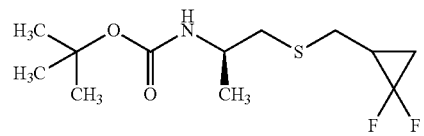

Isolated as an orange oil (1.0 g, 82%) using 2-(bromomethyl)-1,1-difluorocyclopropane: $^1$H NMR (500 MHz, CDCl$_3$) δ 4.59 (s, 1H), 3.85 (s, 1H), 2.79-2.49 (m, 4H), 1.84-1.73 (m, 1H), 1.55-1.47 (m, 1H), 1.44 (s, 9H), 1.21 (d, J=6.7 Hz, 3H), 1.09 (dddd, J=15.3, 13.1, 7.7, 3.8 Hz, 1H); IR (thin film) 3339, 2976, 2931, 1688, 1502 cm$^{-1}$; HRMS-ESI (m/z) [M+Na]$^+$ calcd for C$_{12}$H$_{21}$F$_2$NO$_2$S, 304.1153; found, 304.1150.

Example 32: Preparation of tert-butyl (2-((2-fluoroethyl)thio)ethyl)carbamate (C166)

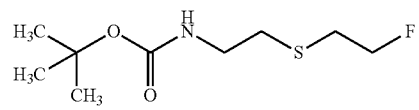

Sodium hydride (60% dispersion in paraffin, 1.0 g, 25 mmol) was added to tert-butyl (2-mercaptoethyl)carbamate (4.0 g, 22.6 mmol) in N,N-dimethylformamide (59.8 mL) at 0° C. After stirring 20 minutes, 1-fluoro-2-iodoethane (2.6 g, 15.0 mmol) was added and the reaction mixture was left to stir overnight. The reaction mixture was diluted with water and extracted with diethyl ether (2×). The organic layer was washed with water and brine, dried with magnesium sulfate, filtered, and concentrated. The resulting liquid was purified by flash silica chromatography. The title compound was isolated as a colorless liquid (1.5 g, 43%): $^1$H NMR (500 MHz, DMSO-d$_6$) δ 6.98-6.86 (m, 1H), 4.53 (dt, J=47.3, 6.3

Hz, 2H), 3.08 (dt, J=7.6, 6.1 Hz, 2H), 2.81 (dt, J=21.7, 6.3 Hz, 2H), 2.57 (dd, J=7.9, 6.4 Hz, 2H), 1.38 (s, 9H); $^{13}$C NMR (126 MHz, DMSO-d$_6$) δ 155.96, 83.26 (d, J=167.6 Hz), 78.17, 40.40, 31.66, 31.27 (d, J=20.7 Hz), 28.69; $^{19}$F NMR (471 MHz, DMSO-d$_6$) δ −211.77 (tt, J=47.3, 21.7 Hz); IR (thin film) 1689 cm$^{-1}$; HRMS-ESI (m/z) [M+Na]$^+$ calcd for C$_9$H$_{18}$FNO$_2$S, 246.0934; found, 246.0937.

Example 33: Preparation of 4-((Z)-3-(3,4-dichloro-5-formylphenyl)-1,4,4,4-tetrafluorobut-1-en-1-yl)-N—((R)-1-((2,2,2-trifluoroethyl)sulfonyl)propan-2-yl)-2-(trifluoromethyl)benzamide (C167)

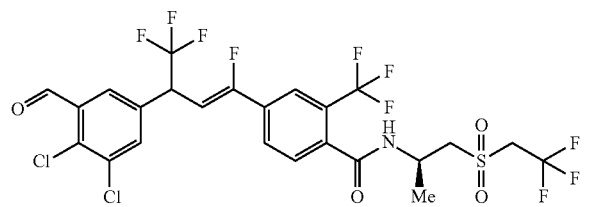 [SMILES: C[C@H](CS(=O)(=O)CC(F)(F)F)NC(=O)c1ccc(/C(F)=C/C(c2cc(Cl)c(Cl)c(C=O)c2)C(F)(F)F)cc1C(F)(F)F]

Osmium tetroxide (2.5% in tert-butanol, 60 mg, 0.006 mmol) was added to a solution of 4-((Z)-3-(3,4-dichloro-5-vinylphenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F73) (0.08 g, 0.12 mmol) in tetrahydrofuran-water (2:1, 1.0 mL) at room temperature. The reaction mixture was stirred for 5 minutes. Sodium periodate (0.076 g, 0.356 mmol) was added to the reaction mixture. The reaction mixture was stirred at 20° C. for 12 hours. The reaction mixture was quenched with sodium bisulfate (100 mg) and then extracted with ethyl acetate (10 mL). The organic layer was dried over sodium sulfate, filtered, and concentrated. Purification by flash column chromatography using 40% ethyl acetate in hexanes provided the title compound as a pale yellow gum (0.055 g, 65%): $^1$H NMR (400 MHz, CDCl$_3$) δ 10.47 (d, J=1.2 Hz, 1H), 7.92-7.80 (m, 2H), 7.75 (dd, J=8.8, 1.6 Hz, 2H), 7.61 (d, J=8.0 Hz, 1H), 6.39 (dd, J=8.1, 3.0 Hz, 1H), 6.04-5.79 (m, 1H), 4.79-4.62 (m, 2H), 4.17-4.03 (m, 1H), 3.96 (dt, J=15.5, 9.3 Hz, 1H), 3.54 (dd, J=14.5, 6.6 Hz, 1H), 3.40 (dd, J=14.5, 5.0 Hz, 1H), 1.52 (d, J=6.9 Hz, 3H); $^{19}$F NMR (376 MHz, CDCl$_3$) δ−59.11 (d, J=2.4 Hz), −61.14, −67.67, −107.51; ESIMS m/z 674 ([M−H]$^-$).

Example 34: Preparation of 4-((Z)-3-(3,4-dichloro-5-(difluoromethyl)phenyl)-1,4,4,4-tetrafluorobut-1-en-1-yl)-N—((R)-1-((2,2,2-trifluoroethyl)sulfonyl)propan-2-yl)-2-(trifluoromethyl)benzamide (F70)

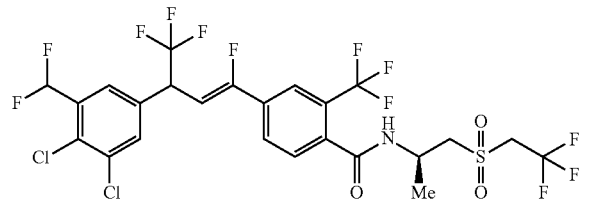 [SMILES: C[C@H](CS(=O)(=O)CC(F)(F)F)NC(=O)c1ccc(/C(F)=C/C(c2cc(Cl)c(Cl)c(C(F)F)c2)C(F)(F)F)cc1C(F)(F)F]

Bis(2-methoxyethyl)aminosulfur trifluoride (114 mg, 0.517 mmol) was added to a solution of 4-((Z)-3-(3,4-dichloro-5-formylphenyl)-1,4,4,4-tetrafluorobut-1-en-1-yl)-N—((R)-1-((2, 2,2-trifluoroethyl)sulfonyl)propan-2-yl)-2-(trifluoromethyl)benzamide (C167) (0.07 g, 0.103 mmol) in dichloromethane (0.5 mL) at room temperature. One drop of methanol was added and the reaction mixture was stirred at 20° C. for 12 hours. The reaction mixture was quenched with water (5 mL) and then extracted with ethyl acetate (15 mL). The organic layer was dried over sodium sulfate, filtered, and concentrated. Purification by flash column chromatography using 35% ethyl acetate in hexanes provided the title compound as a white wax (0.030 g, 38%).

Example 35: Separation of 4-((R,Z)-1,4,4,4-tetrafluoro-3-(3,4,5-trichlorophenyl)but-1-en-1-yl)-N—((R)-1-((2,2,2-trifluoroethyl)sulfonyl)propan-2-yl)-2-(trifluoromethyl)benzamide (F72) and 4-((S,Z)-1,4,4,4-tetrafluoro-3-(3,4,5-trichlorophenyl)but-1-en-1-yl)-N—((R)-1-((2,2,2-trifluoroethyl)sulfonyl)propan-2-yl)-2-(trifluoromethyl)benzamide (F136)

The title molecules were prepared as as a mixture as described in Example 15. The diastereomeric pairs were separated by supercritical fluid (SCF) chromatography using Chiralpak AD-H (250×21 mm), 5µ column using methanol as the mobile phase (isocratic 70:30, CO$_2$ and methanol respectively) with a flow rate of 60 g/min at ambient temperature. Diastereomer F72 was collected at a retention time of 1.78 minutes and possessed an optical rotation of $[α]_D^{25}$=+41.8 (c, 0.29% in MeOH). Diastereomer F136 was collected at 2.60 minutes and possessed an optical rotation of $[α]_D^{25}$=−73.3 (c, 0.28% in MeOH).

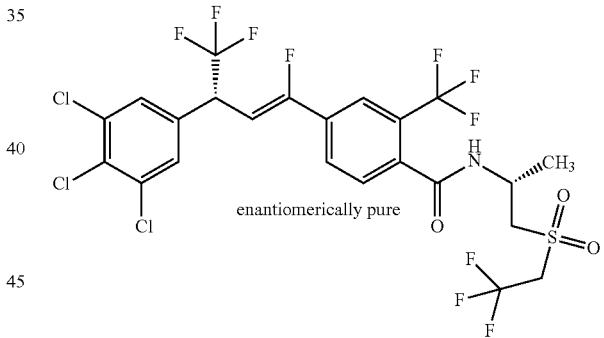

F72 was isolated as an off-white solid.

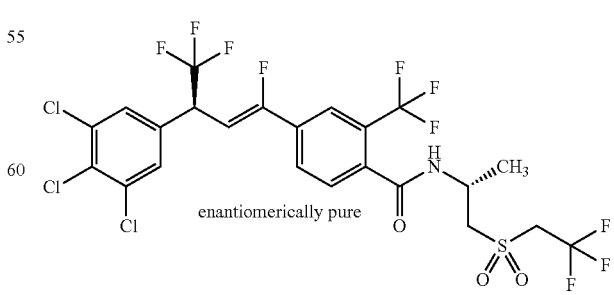

F136 was isolated as an off-white solid.

Example 36: Preparation of 3-chloro-4,5-difluorobenzaldehyde (C168)

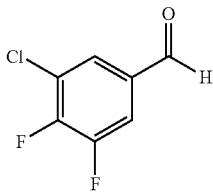 [SMILES: O=Cc1cc(F)c(F)c(Cl)c1]

To a stirred solution of methyl (3-chloro-4,5-difluorophenyl)methanol (4.00 g, 22.4 mmol) in methylene chloride (150 mL) was added manganese dioxide (15.0 g, 179 mmol). After stirring for 12 hours at room temperature, the reaction mixture was filtered through Celite®. The filtrate was concentrated under reduced pressure to afford the title compound as a colorless oil (3.5 g, 86%): $^1$H NMR (300 MHz, CDCl$_3$) δ 9.89 (s, 1H), 7.77-7.74 (m, 1H), 7.66-7.61 (m, 1H); IR (thin film) 3302, 1709, 750 cm$^{-1}$; EIMS m/z 176 ([M]$^+$).

Example 37: Preparation of 3,5-dichloro-4-(difluoromethyl)benzaldehyde (C169)

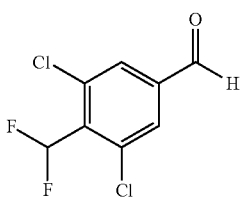 [SMILES: O=Cc1cc(Cl)c(C(F)F)c(Cl)c1]

To a stirred solution of methyl 3,5-dichloro-4-(difluoromethyl)benzoate (C170) (5.00 g, 19.6 mmol) in methylene chloride (20 mL) cooled in a −78° C. bath was added dropwise diisobutylaluminum hydride (1 M in THF; 39.2 mL, 39.2 mmol). After 2 hours, the reaction mixture was treated with cold water and extracted with methylene chloride. The organic layer was washed with brine, dried over sodium sulfate and concentrated under reduced pressure to afford crude compound. Purification by column chromatography (SiO$_2$, 100-200 mesh, eluting with 5% ethyl acetate in petroleum ether) afforded the title compound as a pale brown solid (3.0 g, 66%): $^1$H NMR (400 MHz, DMSO-d$_6$) δ 10.00 (s, 1H), 8.05 (s, 2H), 7.52 (t, J=52.0 Hz, 1H); IR (thin film) 1709, 1362, 1057 cm$^{-1}$; EIMS m/z 224 ([M]$^+$).

Example 38: Preparation of methyl 3,5-dichloro-4-(difluoromethyl)benzoate (C170)

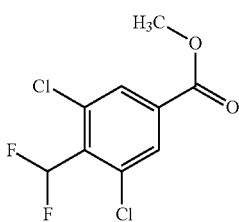

Bis(2-methoxyethyl)aminosulfur trifluoride (1.93 g, 8.80 mmol) was added to a solution methyl 3,5-dichloro-4-formylbenzoate (1.00 g, 4.29 mmol) in dichloromethane (10 mL) at room temperature. One drop of methanol was added and the reaction mixture was stirred at 20° C. for 12 hours. The reaction mixture was quenched with water (100 mL) and then extracted with ethyl acetate (300 mL). The organic layer was dried over sodium sulfate, filtered, and concentrated. Purification by flash column chromatography provided the title compound as a pale yellow solid (0.70 g, 63%): $^1$H NMR (300 MHz, DMSO-d$_6$) δ 8.02 (s, 2H), 7.50 (t, J=52.2 Hz, 1H), 3.99 (s, 3H); EIMS m/z 254 ([M]$^+$).

Example 39: Preparation of 1-(3,4-dichloro-5-methylphenyl)-2,2,2-trifluoroethan-1-one (C173)

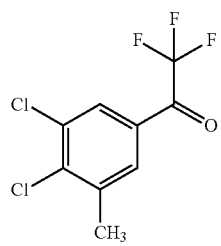

To 5-bromo-1,2-dichloro-3-methylbenzene (6.9 g, 29 mmol) in tetrahydrofuran (65 mL) cooled in an ice bath under nitrogen was added isopropylmagnesium chloride lithium chloride complex in tetrahydrofuran (26.8 mL, 34.8 mmol). After 1 hour methyl 2,2,2-trifluoroacetate (3.79 mL, 37.7 mmol) was added. After 30 minutes, the ice bath was removed, and the solution was stirred for 1 hour. The reaction mixture was quenched with aqueous hydrochloric acid (2 N). The mixture was concentrated and extracted with dichloromethane. The organic layer was washed with brine, dried over sodium sulfate, filtered, and concentrated. Purification by column chromatography (SiO$_2$, petroleum ether) provided the title compound as a white solid (5.9 g, 80%): $^1$H NMR (400 MHz, CDCl$_3$) δ 8.00 (s, 1H), δ 7.83 (s, 1H), 2.51 (s, 3H); EIMS m/z 256 ([M]$^+$).

Biological Assays

The following bioassays against Beet Armyworm (*Spodoptera exigua*), Cabbage Looper (*Trichoplusia ni*), Corn Earworm (*Helicoverpa zea*), Green Peach Aphid (*Myzus persicae*), and Yellow Fever Mosquito (*Aedes aegypti*), are included herein due to the damage they inflict. Furthermore, the Beet Armyworm, Corn Earworm, and Cabbage Looper are three good indicator species for a broad range of chewing pests. Additionally, the Green Peach Aphid is a good indicator species for a broad range of sap-feeding pests. The results with these four indicator species along with the Yellow Fever Mosquito show the broad usefulness of the molecules of Formula One in controlling pests in Phyla Arthropoda, Mollusca, and Nematoda (For further information see Methods for the Design and Optimization of New Active Ingredients, *Modern Methods in Crop Protection Research*, Edited by Jeschke, P., Kramer, W., Schirmer, U., and Matthias W., p. 1-20, 2012).

Example A: Bioassays on Beet Armyworm (*Spodoptera Exigua*, LAPHEG) ("BAW"), Corn Earworm (*Helicoverpa zea*, HELIZE) ("CEW"), and Cabbage Looper (*Trichoplusia ni*, TRIPNI) ("CL")

Beet army worm is a serious pest of economic concern for alfalfa, asparagus, beets, citrus, corn, cotton, onions, peas, peppers, potatoes, soybeans, sugar beets, sunflowers, tobacco, tomatoes, among other crops. It is native to Southeast Asia but is now found in Africa, Australia, Japan, North America, and Southern Europe. The larvae may feed in large swarms causing devastating crop losses. It is known to be resistant to several pesticides.

Cabbage Looper is a serious pest found throughout the world. It attacks alfalfa, beans, beets, broccoli, Brussel sprouts, cabbage, cantaloupe, cauliflower, celery, collards, cotton, cucumbers, eggplant, kale, lettuce, melons, mustard, parsley, peas, peppers, potatoes, soybeans, spinach, squash, tomatoes, turnips, and watermelons, among other crops. This species is very destructive to plants due to its voracious appetite. The larvae consume three times their weight in food daily. The feeding sites are marked by large accumulations of sticky, wet, fecal material. It is known to be resistant to several pesticides.

Corn earworm is considered by some to be the most costly crop pest in North America. It often attacks valuable crops, and the harvested portion of the crop. This pest damages alfalfa, artichoke, asparagus, cabbage, cantaloupe, collard, corn, cotton, cowpea, cucumber, eggplant, lettuce, lima bean, melon, okra, pea, pepper, potato, pumpkin, snap bean, soybean, spinach, squash, sugarcane, sweet potato, tomato, and watermelon, among other crops. Furthermore, this pest is also known to be resistant to certain insecticides.

Consequently, because of the above factors control of these pests is important. Furthermore, molecules that control these pests (BAW, CEW, and CL), which are known as chewing pests, are useful in controlling other pests that chew on plants.

Certain molecules disclosed in this document were tested against BAW, CEW, and CL using procedures described in the following examples. In the reporting of the results, the "BAW, CEW, & CL Rating Table" was used (See Table Section).

Bioassays on BAW

Bioassays on BAW were conducted using a 128-well diet tray assay. One to five second instar BAW larvae were placed in each well (3 mL) of the diet tray that had been previously filled with 1 mL of artificial diet to which 50 µg/cm² of the test molecule (dissolved in 50 µL of 90:10 acetone-water mixture) had been applied (to each of eight wells) and then allowed to dry. Trays were covered with a clear self-adhesive cover and held at 25° C., 14:10 light-dark for five to seven days. Percent mortality was recorded for the larvae in each well; activity in the eight wells was then averaged. The results are indicated in the table entitled "Table ABC: Biological Results" (See Table Section).

Bioassays on CL

Bioassays on CL were conducted using a 128-well diet tray assay. One to five second instar CL larvae were placed in each well (3 mL) of the diet tray that had been previously filled with 1 mL of artificial diet to which 50 µg/cm² of the test molecule (dissolved in 50 µL of 90:10 acetone-water mixture) had been applied (to each of eight wells) and then allowed to dry. Trays were covered with a clear self-adhesive cover and held at 25° C., 14:10 light-dark for five to seven days. Percent mortality was recorded for the larvae in each well; activity in the eight wells was then averaged. The results are indicated in the table entitled "Table ABC: Biological Results" (See Table Section).

Example B: Bioassays on Green Peach Aphid (*Myzus Persicae*, MYZUPE) ("GPA")

GPA is the most significant aphid pest of peach trees, causing decreased growth, shriveling of the leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, papaya, peppers, sweet potatoes, tomatoes, watercress, and zucchini, among other crops. GPA also attacks many ornamental crops such as carnation, chrysanthemum, flowering white cabbage, poinsettia, and roses. GPA has developed resistance to many pesticides. Consequently, because of the above factors control of this pest is important. Furthermore, molecules that control this pest (GPA), which is known as a sap-feeding pest, are useful in controlling other pests that feed on the sap from plants.

Certain molecules disclosed in this document were tested against GPA using procedures described in the following example. In the reporting of the results, the "GPA & YFM Rating Table" was used (See Table Section).

Cabbage seedlings grown in 3-inch pots, with 2-3 small (3-5 cm) true leaves, were used as test substrate. The seedlings were infested with 20-50 GPA (wingless adult and nymph stages) one day prior to chemical application. Four pots with individual seedlings were used for each treatment. Test molecules (2 mg) were dissolved in 2 mL of acetone/methanol (1:1) solvent, forming stock solutions of 1000 ppm test molecule. The stock solutions were diluted 5× with 0.025% Tween 20 in water to obtain the solution at 200 ppm test molecule. A hand-held aspirator-type sprayer was used for spraying a solution to both sides of cabbage leaves until runoff. Reference plants (solvent check) were sprayed with the diluent only containing 20% by volume of acetone/methanol (1:1) solvent. Treated plants were held in a holding room for three days at approximately 25° C. and ambient relative humidity (RH) prior to grading. Evaluation was conducted by counting the number of live aphids per plant under a microscope. Percent Control was measured by using Abbott's correction formula (W. S. Abbott, "A Method of Computing the Effectiveness of an Insecticide" J. Econ. Entomol. 18 (1925), pp. 265-267) as follows.

Corrected % Control=100*(X−Y)/X where

X=No. of live aphids on solvent check plants and
Y=No. of live aphids on treated plants
The results are indicated in the table entitled "Table ABC: Biological Results" (See Table Section).

Example C: Bioassays on Yellow Fever Mosqurro (*Aedes aegypti*, AEDSAE) ("YFM")

YFM prefers to feed on humans during the daytime and is most frequently found in or near human habitations. YFM is a vector for transmitting several diseases. It is a mosquito that can spread the dengue fever and yellow fever viruses. Yellow fever is the second most dangerous mosquito-borne disease after malaria. Yellow fever is an acute viral hemorrhagic disease and up to 50% of severely affected persons without treatment will die from yellow fever. There are an estimated 200,000 cases of yellow fever, causing 30,000 deaths, worldwide each year. Dengue fever is a nasty, viral disease; it is sometimes called "breakbone fever" or "breakheart fever" because of the intense pain it can produce. Dengue fever kills about 20,000 people annually. Consequently, because of the above factors control of this pest is important. Furthermore, molecules that control this pest (YFM), which is known as a sucking pest, are useful in controlling other pests that cause human and animal suffering.

Certain molecules disclosed in this document were tested against YFM using procedures described in the following paragraph. In the reporting of the results, the "GPA & YFM Rating Table" was used (See Table Section).

Master plates containing 400 µg of a molecule dissolved in 100 µL of dimethyl sulfoxide (DMSO) (equivalent to a 4000 ppm solution) are used. A master plate of assembled molecules contains 15 µL per well. To this plate, 135 µL of a 90:10 water:acetone mixture is added to each well. A robot (Biomek® NXP Laboratory Automation Workstation) is programmed to dispense 15 µL aspirations from the master plate into an empty 96-well shallow plate ("daughter" plate). There are 6 reps ("daughter" plates) created per master. The created daughter plates are then immediately infested with YFM larvae.

The day before plates are to be treated, mosquito eggs are placed in Millipore water containing liver powder to begin hatching (4 g. into 400 mL). After the daughter plates are created using the robot, they are infested with 220 µL of the liver powder/larval mosquito mixture (about 1 day-old larvae). After plates are infested with mosquito larvae, a non-evaporative lid is used to cover the plate to reduce drying. Plates are held at room temperature for 3 days prior to grading. After 3 days, each well is observed and scored based on mortality. The results are indicated in the table entitled "Table ABC: Biological Results" (See Table Section).

Agriculturally Acceptable Acid Addition Salts, Salt Derivatives, Solvates, Ester Derivatives, Polymorphs, Isotopes, and Radionuclides Molecules of Formula One may be formulated into agriculturally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxyl-methanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, and magnesium.

Molecules of Formula One may be formulated into salt derivatives. By way of a non-limiting example, a salt derivative may be prepared by contacting a free base with a sufficient amount of the desired acid to produce a salt. A free base may be regenerated by treating the salt with a suitable dilute aqueous base solution such as dilute aqueous sodium hydroxide, potassium carbonate, ammonia, and sodium bicarbonate. As an example, in many cases, a pesticide, such as 2,4-D, is made more water-soluble by converting it to its dimethylamine salt.

Molecules of Formula One may be formulated into stable complexes with a solvent, such that the complex remains intact after the non-complexed solvent is removed. These complexes are often referred to as "solvates." However, it is particularly desirable to form stable hydrates with water as the solvent.

Molecules of Formula One may be made into ester derivatives. These ester derivatives can then be applied in the same manner as the molecules disclosed in this document is applied.

Molecules of Formula One may be made as various crystal polymorphs. Polymorphism is important in the development of agrochemicals since different crystal polymorphs or structures of the same molecule can have vastly different physical properties and biological performances.

Molecules of Formula One may be made with different isotopes. Of particular importance are molecules having $^2H$ (also known as deuterium) or $^3H$ (also known as tritium) in place of 1H. Molecules of Formula One may be made with different radionuclides. Of particular importance are molecules having $^{14}C$. Molecules of Formula One having deuterium, tritium, or $^{14}C$ may be used in biological studies allowing tracing in chemical and physiological processes and half-life studies, as well as, MoA studies.

Stereoisomers

Molecules of Formula One may exist as one or more stereoisomers. Thus, certain molecules may be produced as racemic mixtures. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures. Certain molecules disclosed in this document can exist as two or more isomers. The various isomers include geometric isomers, diastereomers, and enantiomers. Thus, the molecules disclosed in this document include geometric isomers, racemic mixtures, individual stereoisomers, and optically active mixtures. It will be appreciated by those skilled in the art that one isomer may be more active than the others. The structures disclosed in the present disclosure are drawn in only one geometric form for clarity, but are intended to represent all geometric forms of the molecule.

Combinations

In another embodiment of this invention, molecules of Formula One may be used in combination (such as, in a compositional mixture, or a simultaneous or sequential application) with one or more active ingredients.

In another embodiment of this invention, molecules of Formula One may be used in combination (such as, in a compositional mixture, or a simultaneous or sequential application) with one or more active ingredients each having a MoA that is the same as, similar to, but more likely—different from, the MoA of the molecules of Formula One.

In another embodiment, molecules of Formula One may be used in combination (such as, in a compositional mixture, or a simultaneous or sequential application) with one or more molecules having acaricidal, algicidal, avicidal, bactericidal, fungicidal, herbicidal, insecticidal, molluscicidal, nematicidal, rodenticidal, and/or virucidal properties.

In another embodiment, the molecules of Formula One may be used in combination (such as, in a compositional mixture, or a simultaneous or sequential application) with one or more molecules that are antifeedants, bird repellents, chemosterilants, herbicide safeners, insect attractants, insect repellents, mammal repellents, mating disrupters, plant activators, plant growth regulators, and/or synergists.

In another embodiment, molecules of Formula One may also be used in combination (such as in a compositional mixture, or a simultaneous or sequential application) with one or more biopesticides.

In another embodiment, in a pesticidal composition combinations of a molecule of Formula One and an active ingredient may be used in a wide variety of weight ratios. For example, in a two component mixture, the weight ratio of a molecule of Formula One to an active ingredient, may be from about 100:1 to about 1:100; in another example the weight ratio may be about 50:1 to about 1:50; in another example the weight ratio may be about 20:1 to about 1:20; in another example the weight ratio may be about 10:1 to about 1:10; in another example the weight ratio may be about 5:1 to 1:5; in another example the weight ratio may be about 3:1 to about 1:3; in another example the weight ratio may be about 2:1 to about 1:2; and in a final example the weight ratio may be about 1:1 (See Table B). However, in general, weight ratios less than about 10:1 to about 1:10 are preferred. It is also preferred sometimes to use a three or four component mixture comprising a molecule of Formula One and one or more active ingredients.

TABLE B

Weight Ratios
Molecule of the Formula One:active ingredient

100:1 to 1:100
50:1 to 1:50
20:1 to 1:20
10:1 to 1:10
5:1 to 1:5
3:1 to 1:3
2:1 to 1:2
1:1

Weight ratios of a molecule of Formula One to an active ingredient may also be depicted as X:Y; wherein X is the parts by weight of a molecule of Formula One and Y is the parts by weight of active ingredient. The numerical range of the parts by weight for X is $0 < X \leq 100$ and the parts by weight for Y is $0 < Y \leq 100$ and is shown graphically in TABLE C. By way of non-limiting example, the weight ratio of a molecule of Formula One to an active ingredient may be 20:1.

TABLE C

| active ingredient (Y) Parts by weight | | | | | | | | | |
|---|---|---|---|---|---|---|---|---|---|
| 100 | X, Y | | X, Y | | | X, Y | | | |
| 50 | X, Y | X, Y | X, Y | | | X, Y | X, Y | | |
| 20 | X, Y | | X, Y | X, Y | | X, Y | | X, Y | |
| 15 | X, Y | X, Y | | | | | X, Y | X, Y | X, Y |
| 10 | X, Y | | X, Y | | | | | | |
| 5 | X, Y | X, Y | X, Y | | | X, Y | | | |
| 3 | X, Y | X, Y | | X, Y | X, Y | | X, Y | X, Y | X, Y |
| 2 | X, Y | | X, Y | X, Y | | X, Y | | X, Y | |
| 1 | X, Y | X, Y | X, Y | X, Y | X, Y | X, Y | X, Y | X, Y | X, Y |
| | 1 | 2 | 3 | 5 | 10 | 15 | 20 | 50 | 100 |
| | molecule of Formula One (X) Parts by weight | | | | | | | | |

Ranges of weight ratios of a molecule of Formula One to an active ingredient may be depicted as $X_1:Y_1$ to $X_2:Y_2$, wherein X and Y are defined as above.

In one embodiment, the range of weight ratios may be $X_1:Y_1$ to $X_2:Y_2$, wherein $X_1 > Y_1$ and $X_2 < Y_2$. By way of non-limiting example, the range of a weight ratio of a molecule of Formula One to an active ingredient may be between 3:1 and 1:3, inclusive of the endpoints.

In another embodiment, the range of weight ratios may be $X_1:Y_1$ to $X_2:Y_2$, wherein $X_1 > Y_1$ and $X_2 > Y_2$. By way of non-limiting example, the range of weight ratio of a molecule of Formula One to an active ingredient may be between 15:1 and 3:1, inclusive of the endpoints.

In another embodiment, the range of weight ratios may be $X_1:Y_1$ to $X_2:Y_2$, wherein $X_1 < Y_1$ and $X_2 < Y_2$. By way of non-limiting example, the range of weight ratios of a molecule of Formula One to an active ingredient may be between about 1:3 and about 1:20, inclusive of the endpoints.

Formulations

A pesticide is rarely suitable for application in its pure form. It is usually necessary to add other substances so that the pesticide may be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra-low volume solutions.

Pesticides are applied most often as aqueous suspensions or emulsions prepared from concentrated formulations of such pesticides.

Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually selected from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and molecule and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. Dusts may be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. Baits may be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides may be microencapsulated by suspending the pesticide particles or droplets in plastic polymers of various types. By altering the chemistry of the polymer or by changing factors in the processing, microcapsules may be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one molecule which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers.

Other Formulation Components

Generally, when the molecules disclosed in Formula One are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, oil-in-water emulsions, suspoemulsions, and ultra-low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of $C_9$ and $C_{10}$ aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

Applications

Molecules of Formula One may be applied to any locus. Particular crop loci to apply such molecules include loci where alfalfa, almonds, apples, barley, beans, canola, corn, cotton, crucifers, lettuce, oats, oranges, pears, peppers, potatoes, rice, sorghum, soybeans, strawberries, sugarcane, sugar beets, sunflowers, tobacco, tomatoes, wheat, and other valuable crops are growing or the seeds thereof are going to be planted.

Molecules of Formula One may also be applied where plants, such as crops, are growing and where there are low levels (even no actual presence) of pests that can commercially damage such plants. Applying such molecules in such locus is to benefit the plants being grown in such locus. Such benefits, may include, but are not limited to: helping the plant grow a better root system; helping the plant better withstand stressful growing conditions; improving the health of a plant; improving the yield of a plant (e.g. increased biomass and/or increased content of valuable ingredients); improving the vigor of a plant (e.g. improved plant growth and/or greener leaves); improving the quality of a plant (e.g. improved content or composition of certain ingredients); and improving the tolerance to abiotic and/or biotic stress of the plant.

Molecules of Formula One may be applied with ammonium sulfate when growing various plants as this may provide additional benefits.

Molecules of Formula One may be applied on, in, or around plants genetically modified to express specialized traits, such as *Bacillus thuringiensis* or other insecticidal toxins, or those expressing herbicide resistance, or those with "stacked" foreign genes expressing insecticidal toxins, herbicide resistance, nutrition-enhancement, or any other beneficial traits.

Molecule of Formula One may be applied to the foliar and/or fruiting portions of plants to control pests. Such molecules will either come in direct contact with the pest, or the pest will consume such molecules when eating the plant or while extracting sap from the plant.

Molecule of Formula One may also be applied to the soil, and when applied in this manner, root and stem feeding pests may be controlled. The roots may absorb such molecules thereby taking it up into the foliar portions of the plant to control above ground chewing and sap feeding pests.

Systemic movement of pesticides in plants may be utilized to control pests on one portion of the plant by applying (for example by spraying a locus) a molecule of Formula One to a different portion of the plant. For example, control of foliar-feeding insects may be achieved by drip irrigation or furrow application, by treating the soil with for example pre- or post-planting soil drench, or by treating the seeds of a plant before planting.

Molecules of Formula One may be used with baits. Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait.

Molecules of Formula One may be encapsulated inside, or placed on the surface of a capsule. The size of the capsules can range from nanometer size (about 100-900 nanometers in diameter) to micrometer size (about 10-900 microns in diameter).

Molecules of Formula One may be applied to eggs of pests. Because of the unique ability of the eggs of some pests to resist certain pesticides, repeated applications of such molecules may be desirable to control newly emerged larvae.

Molecules of Formula One may be applied as seed treatments. Seed treatment may be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement, drought resistance, or any other beneficial traits. Furthermore, such seed treatments with molecules of Formula One may further enhance the ability of a plant to better withstand stressful growing conditions. This results in a healthier, more vigorous plant, which can lead to higher yields at harvest time. Generally, about 1 gram of such molecules to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits.

Molecules of Formula One may be applied with one or more active ingredients in a soil amendment.

Molecules of Formula One may be used for controlling endoparasites and ectoparasites in the veterinary medicine sector or in the field of non-human-animal keeping. Such molecules may be applied by oral administration in the form of, for example, tablets, capsules, drinks, granules, by dermal application in the form of, for example, dipping, spraying, pouring on, spotting on, and dusting, and by parenteral administration in the form of, for example, an injection.

Molecules of Formula One may also be employed advantageously in livestock keeping, for example, cattle, sheep, pigs, chickens, salmon, and geese. They may also be employed advantageously in pets such as, horses, dogs, and cats. Particular pests to control would be fleas and ticks that are bothersome to such animals. Suitable formulations are administered orally to the animals with the drinking water or feed. The dosages and formulations that are suitable depend on the species.

Molecules of Formula One may also be used for controlling parasitic worms, especially of the intestine, in the animals listed above.

Molecules of Formula One may also be employed in therapeutic methods for human health care. Such methods include, but are limited to, oral administration in the form of, for example, tablets, capsules, drinks, granules, and by dermal application.

Molecules of Formula One may also be applied to invasive pests. Pests around the world have been migrating to new environments (for such pest) and thereafter becoming a new invasive species in such new environment. Such molecules may also be used on such new invasive species to control them in such new environments.

Consequently, in light of the above and the Tables in the Table Section, the following items are provided.

1. A molecule having the following formula

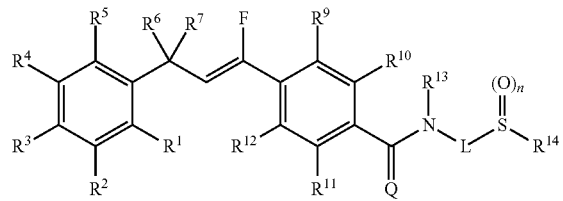

Formula One wherein:
(A) $R^1$, $R^5$, $R^6$, $R^{11}$, $R^{12}$, and $R^{13}$ are each independently selected from the group consisting of H, F, Cl, Br, I, CN, $(C_1-C_4)$alkyl, $(C_1-C_4)$haloalkyl, $(C_1-C_4)$alkoxy, and $(C_1-C_4)$haloalkoxy
preferably, $R^1$, $R^5$, $R^6$, $R^{11}$, $R^{12}$, and $R^{13}$ are H;
(B) $R^2$, $R^3$, and $R^4$ are each independently selected from the group consisting of H, F, Cl, Br, I, CN, $(C_1-C_4)$alkyl, $(C_2-C_4)$alkenyl, $(C_2-C_4)$alkynyl, $(C_1-C_4)$haloalkyl, $(C_1-C_4)$alkoxy, and $(C_1-C_4)$haloalkoxy
preferably, $R^2$, is Cl, Br, or $CH_3$, $R^3$ is F, Cl, Br or $CH=CH_2$, and $R^4$ is Cl, Br, or $CH_3$,
more preferably, $R^2$, $R^3$, and $R^4$ is Cl;
(C) $R^7$ is $(C_1-C_6)$haloalkyl
preferably $R^7$ is $CF_3$ or $CF_2CH_3$;
(D) $R^9$ is selected from the group consisting of (F), H, F, Cl, Br, I, CN, $(C_1-C_4)$alkyl, $(C_1-C_4)$haloalkyl, $(C_1-C_4)$alkoxy, and $(C_1-C_4)$haloalkoxy
preferably $R^9$ is H;
(E) $R^{10}$ is selected from the group consisting of (F), F, Cl, Br, I, CN, $(C_1-C_4)$alkyl, $(C_2-C_4)$alkenyl, $(C_2-C_4)$alkynyl, $(C_1-C_4)$haloalkyl, $(C_1-C_4)$alkoxy, and $(C_1-C_4)$haloalkoxy
preferably $R^{10}$ is Cl, Br, $CH_3$, or $CF_3$;
(F) $R^9$ and $R^{10}$ together can optionally form a 3- to 5-membered saturated or unsaturated, hydrocarbyl link, wherein said hydrocarbyl link may optionally be substituted with one or more substituents independently selected from the group consisting of F, Cl, Br, I, and CN;

(G) Q is selected from the group consisting of O or S preferably Q is O;
(H) L is $(C_1-C_6)$alkyl
preferably L is $CH_2CH_2$ or $CH(CH_3)CH_2$;
(I) n is 0, 1, or 2;
(J) $R^{14}$ is selected from the group consisting of $(C_1-C_4)$alkyl, $(C_2-C_4)$alkenyl, $(C_3-C_4)$cycloalkyl, $(C_1-C_4)$haloalkyl, $(C_1-C_4)$alkoxy, $(C_1-C_4)$haloalkoxy, and phenyl, wherein each alkyl, alkenyl, cycloalkyl, haloalkyl, alkoxy, haloalkoxy, and phenyl may optionally be substituted with one or more substituents independently selected from the group consisting of F, Cl, Br, I, CN, and OH preferably $R^{14}$ is $CH_2CH_3$ or $CH_2CF_3$; and
agriculturally acceptable acid addition salts, salt derivatives, solvates, ester derivatives, crystal polymorphs, isotopes, resolved stereoisomers, and tautomers, of the molecules of Formula One.

2. A molecule according to 1 wherein
(A) $R^1$, $R^5$, $R^6$, $R^{11}$, $R^{12}$, and $R^{13}$ are H;
(B) $R^2$, $R^3$, and $R^4$ are each independently selected from the group consisting of H, F, Cl, Br, $(C_1-C_4)$alkyl, and $(C_2-C_4)$alkenyl;
(C) $R^7$ is $(C_1-C_6)$haloalkyl;
(D) $R^9$ is H;
(E) $R^{10}$ is selected from the group consisting of Cl, Br, $(C_1-C_4)$alkyl, and $(C_1-C_4)$haloalkyl;
(G) Q is O;
(H) L is $(C_1-C_6)$alkyl;
(I) n is 0, 1, or 2;
(3) $R^{14}$ is selected from the group consisting of $(C_1-C_4)$alkyl and $(C_1-C_4)$haloalkyl,
wherein each alkyl or haloalkyl may optionally be substituted with one or more substituents independently selected from the group consisting of F, Cl, Br, I, CN, and OH.

3. A molecule according to 1 wherein said molecule is selected from the group consisting of one of the molecules in Table 2.

4. A molecule according to 1 wherein said molecule is selected from the group consisting of one of the molecules in Table 1.

5. A pesticidal composition comprising a molecule according to any one of 1, 2, 3, or 4, further comprising one or more active ingredients.

6. A pesticidal composition according to 5 wherein said active ingredient is from AIGA.

7. A pesticidal composition according to 5 wherein said active ingredient is selected from the group consisting of AI-1, 1,3-dichloropropene, chlorpyrifos, chlorpyrifos-methyl, hexaflumuron, methoxyfenozide, noviflumuron, spinetoram, spinosad, sulfoxaflor, and sulfuryl fluoride.

8. A pesticidal composition comprising a molecule according to any one of 1, 2, 3, or 4, further comprising a MoA Material.

9. A pesticidal composition according to 7 wherein said MoA Material is from MoAMGA.

10. A pesticidal composition according to any one of 5, 6, 7, 8, or 9, wherein the weight ratio of the molecule according to Formula One to said active ingredient is selected from Table B.

11. A process to control a pest said process comprising applying to a locus, a pesticidally effective amount of a molecule according to any one of the 1, 2, 3, or 4.

12. A process to control a pest said process comprising applying to a locus, a pesticidally effective amount of a pesticidal composition according to any one of the 5, 6, 7, 8, 9, or 10.

13. A molecule according to any one of 1, 2, 3, or 4, or a pesticidal composition according to any of 5, 6, 7, 8, 9, or 10, wherein said molecule is in the form of agriculturally acceptable acid addition salt.

14. A molecule according to any one of 1, 2, 3, or 4, or a pesticidal composition according to any of 5, 6, 7, 8, 9, or 10, wherein said molecule is in the form of a salt derivative.

15. A molecule according to any one of 1, 2, 3, or 4, or a pesticidal composition according to any of 5, 6, 7, 8, 9, or 10, wherein said molecule is in the form of solvate.

16. A molecule according to any one of 1, 2, 3, or 4, or a pesticidal composition according to any of 5, 6, 7, 8, 9, or 10, wherein said molecule is in the form of an ester derivative.

17. A molecule according to any one of 1, 2, 3, or 4, or a pesticidal composition according to any of 5, 6, 7, 8, 9, or 10, wherein said molecule is in the form of a crystal polymorph.

18. A molecule according to any one of 1, 2, 3, or 4, or a pesticidal composition according to any of 5, 6, 7, 8, 9, or 10, wherein said molecule has deuterium, tritium, and or $^{14}C$.

19. A molecule according to any one of 1, 2, 3, or 4, or a pesticidal composition according to any of 5, 6, 7, 8, 9, or 10, wherein said molecule is in the form of one or more stereoisomers 20. A molecule according to any one of 1, 2, 3, or 4, or a pesticidal composition according to any of 5, 6, 7, 8, 9, or 10, wherein said molecule is in the form of a resolved stereoisomer.

21. A pesticidal composition according to any of 5, 6, 7, 8, 9, or 10, wherein said pesticidal composition further comprises another active ingredient.

22. A pesticidal composition according to any of 5, 6, 7, 8, 9, or 10, wherein said pesticidal composition further comprises two more active ingredients.

23. A pesticidal composition according to any of 5, 6, 7, 8, 9, or 10, wherein said active ingredient has a MOA different from the MoA of said molecule of Formula One.

24. A pesticidal composition according to any of 5, 6, 7, 8, 9, or 10, wherein said pesticidal composition comprises an active ingredient having acaricidal, algicidal, avicidal, bactericidal, fungicidal, herbicidal, insecticidal, molluscicidal, nematicidal, rodenticidal, and/or virucidal properties.

25. A pesticidal composition according to any of 5, 6, 7, 8, 9, or 10, wherein said pesticidal composition comprises an active ingredient that is an antifeedant, bird repellent, chemosterilant, herbicide safener, insect attractant, insect repellent, mammal repellent, mating disrupter, plant activator, plant growth regulator, and/or synergist.

26. A pesticidal composition according to any of 5, 6, 7, 8, 9, or 10, wherein said pesticidal composition comprises an active ingredient that is a biopesticide.

27. A pesticidal composition according to any of 5, 6, 7, 8, 9, or 10, wherein said weight ratio of a molecule of Formula One to an active ingredient is 100:1 to 1:100.

28. A pesticidal composition according to any of 5, 6, 7, 8, 9, or 10, wherein said weight ratio of a molecule of Formula One to an active ingredient is 50:1 to 1:50.

29. A pesticidal composition according to any of 5, 6, 7, 8, 9, or 10, wherein said weight ratio of a molecule of Formula One to an active ingredient is 20:1 to 1:20

30. A pesticidal composition according to any of 5, 6, 7, 8, 9, or 10, wherein said weight ratio of a molecule of Formula One to an active ingredient is 10:1 to 1:10.

31. A pesticidal composition according to any of 5, 6, 7, 8, 9, or 10, wherein said weight ratio of a molecule of Formula One to an active ingredient is 5:1 to 1:5.

32. A pesticidal composition according to any of 5, 6, 7, 8, 9, or 10, wherein said weight ratio of a molecule of Formula One to an active ingredient is 3:1 to 1:3.

33. A pesticidal composition according to any of 5, 6, 7, 8, 9, or 10, wherein said weight ratio of a molecule of Formula One to an active ingredient is 2:1 to 1:2.

34. A pesticidal composition according to any of 5, 6, 7, 8, 9, or 10, wherein said weight ratio of a molecule of Formula One to an active ingredient is 1:1.

35. A pesticidal composition according to any of 5, 6, 7, 8, 9, or 10, wherein said weight ratio of a molecule of Formula One to an active ingredient is depicted as X:Y; wherein X is the parts by weight of a molecule of Formula One and Y is the parts by weight of active ingredient; further wherein the numerical range of the parts by weight for X is $0<X\leq100$ and the parts by weight for Y is $0<Y\leq100$; and further wherein X and Y are selected from Table C.

36. A pesticidal composition according to 35 wherein a range of weight ratios of a molecule of Formula One to an active ingredient is depicted as $X_1:Y_1$ to $X_2:Y_2$; further wherein $X_1>Y_1$ and $X_2<Y_2$.

37. A pesticidal composition according to 35 wherein a range of weight ratios of a molecule of Formula One to an active ingredient is depicted as $X_1:Y_1$ to $X_2: Y_2$; further wherein $X_1>Y_1$ and $X_2>Y_2$.

38. A pesticidal composition according to 35 wherein a range of weight ratios of a molecule of Formula One to an active ingredient is depicted as $X_1:Y_1$ to $X_2: Y_2$; further wherein $X_1<Y_1$ and $X_2<Y_2$.

39. A pesticidal composition according to 35 wherein said composition is synergistic.

40. A process according to 12 wherein said pest is from Phylum Arthropoda.

41. A process according to 12 wherein said pest is from Phylum Mollusca.

42. A process according to 12 wherein said pest is from Phylum Nematoda.

43. A process according to 12 wherein said pests are ants, aphids, beetles, bristletails, cockroaches, crickets, earwigs, fleas, flies, grasshoppers, leafhoppers, lice (including sea lice), locusts, mites, moths, nematodes, scales, symphylans, termites, *thrips*, ticks, wasps, and/or whiteflies.

44. A process according to 12 wherein said locus is where alfalfa, almonds, apples, barley, beans, canola, corn, cotton, crucifers, lettuce, oats, oranges, pears, peppers, potatoes, rice, sorghum, soybeans, strawberries, sugarcane, sugar beets, sunflowers, tobacco, tomatoes, wheat, and other valuable crops are growing or the seeds thereof are planted.

45. A pesticidal composition according to any of 5, 6, 7, 8, 9, or 10, wherein said pesticidal composition further comprises ammonium sulfate.

46. A process according to 12 wherein said locus is where plants genetically modified to express specialized traits are planted.

47. A process according to 12 wherein said applying is done to the foliar and/or fruiting portions of plants.

48. A process according to 12 wherein said applying is done to the soil.

49. A process according to 12 wherein said applying is done by drip irrigation, furrow application, or pre- or post-planting soil drench.

50. A process according to 12 wherein said applying is done to the foliar and/or fruiting portions of plants, or by treating the seeds of a plant before planting.

51. A pesticidal composition comprising a molecule according to any one of 1, 2, 3, or 4, and a seed.

52. A process comprising applying a molecule according to any one of 1, 2, 3, or 4, or a pesticidal composition according to any of 5, 6, 7, 8, 9, or 10, to a seed.

53. A process comprising applying a molecule according to 1, 2, 3, or 4, to a locus that includes a non-human animal to control endoparasites and/or ectoparasites.

54. A process to produce a pesticidal composition, said process comprising mixing a molecule according to any one of claims 1, 2, 3, or 4, with one or more active ingredients.

The headings in this document are for convenience only and must not be used to interpret any portion hereof.

Table Section

TABLE 2

Structure and Preparation Method for F Series Molecules

| No. | Structure | Prep.* |
|---|---|---|
| F1 | 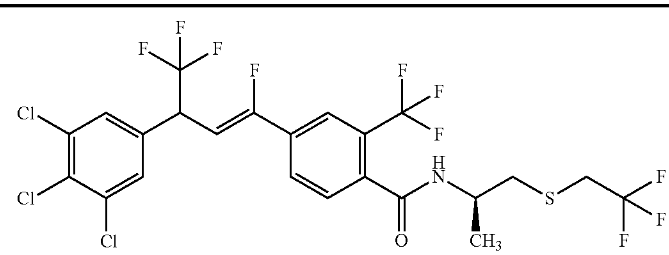 | 13 |
| F2 | 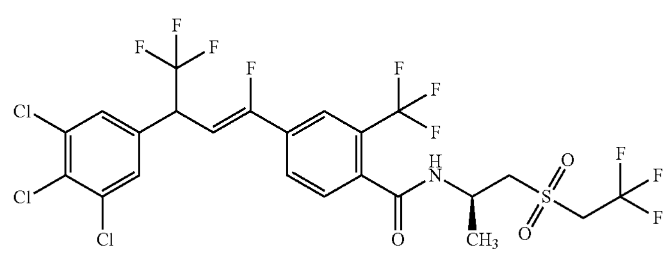 [SMILES: C[C@H](CS(=O)(=O)CC(F)(F)F)NC(=O)c1ccc(/C(F)=C/C(c2cc(Cl)c(Cl)c(Cl)c2)C(F)(F)F)cc1C(F)(F)F] | 15 |

TABLE 2-continued

Structure and Preparation Method for F Series Molecules

| No. | Structure | Prep.* |
|---|---|---|
| F3 | 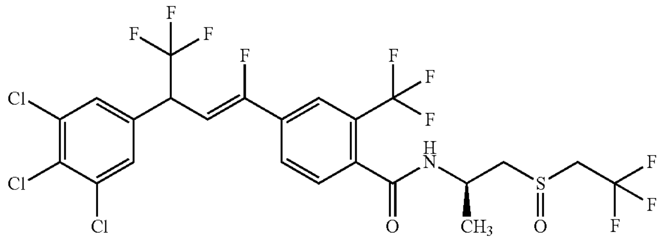 [SMILES: C[C@H](CS(=O)CC(F)(F)F)NC(=O)c1ccc(/C(F)=C/C(c2cc(Cl)c(Cl)c(Cl)c2)C(F)(F)F)cc1C(F)(F)F] | 16 |
| F4 | 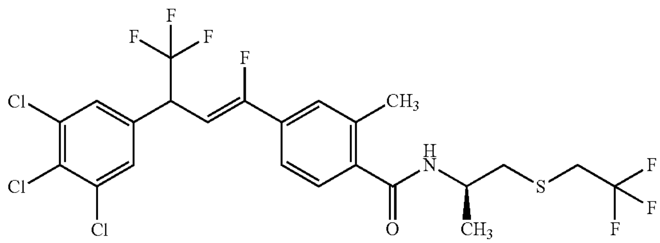 [SMILES: Cc1cc(/C(F)=C/C(c2cc(Cl)c(Cl)c(Cl)c2)C(F)(F)F)ccc1C(=O)N[C@H](C)CSCC(F)(F)F] | 13 |
| F5 | 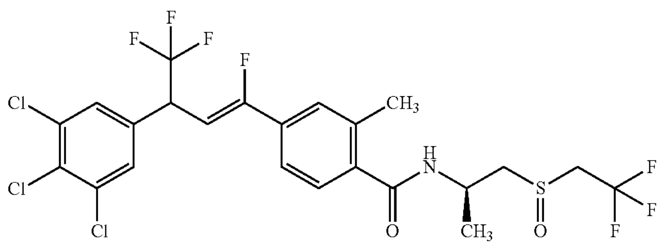 | 16 |
| F6 | 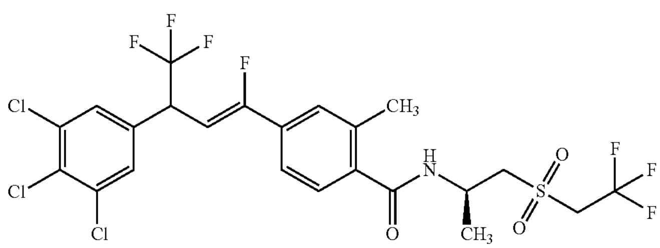 [SMILES: Cc1cc(/C(F)=C/C(c2cc(Cl)c(Cl)c(Cl)c2)C(F)(F)F)ccc1C(=O)N[C@H](C)CS(=O)(=O)CC(F)(F)F] | 15 |
| F7 | 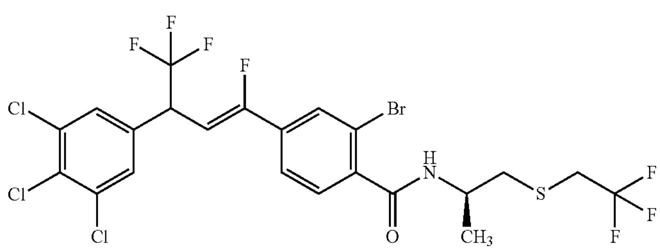 | 13 |
| F8 | 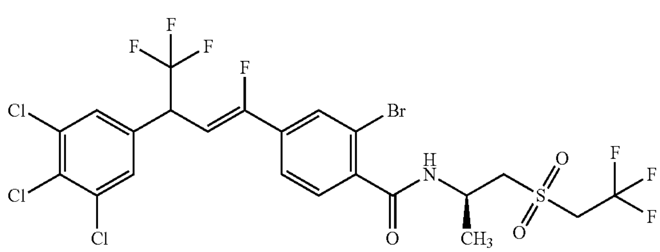 [SMILES: C[C@H](CS(=O)(=O)CC(F)(F)F)NC(=O)c1ccc(/C(F)=C/C(c2cc(Cl)c(Cl)c(Cl)c2)C(F)(F)F)cc1Br] | 15 |

TABLE 2-continued

Structure and Preparation Method for F Series Molecules

| No. | Structure | Prep.* |
|---|---|---|
| F9 | 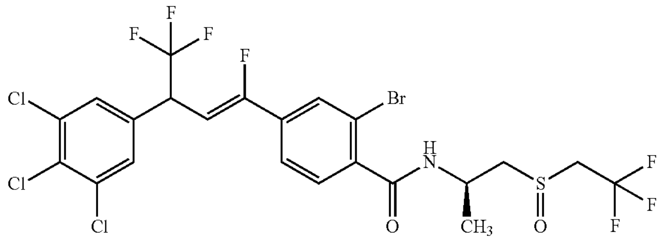 | 16 |
| F10 | 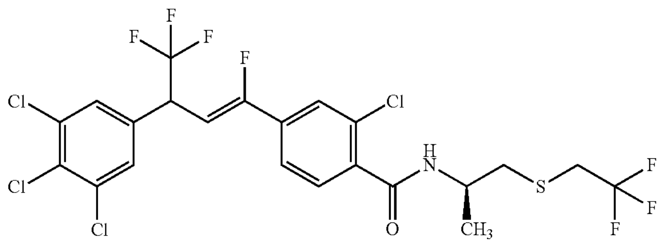 [SMILES: C[C@H](CSCC(F)(F)F)NC(=O)c1ccc(/C(F)=C/C(c2cc(Cl)c(Cl)c(Cl)c2)C(F)(F)F)cc1Cl] | 13 |
| F11 | 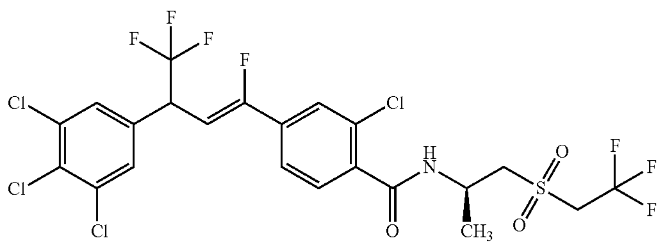 | 15 |
| F12 | 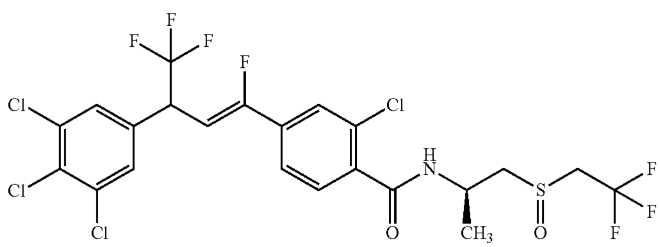 [SMILES: C[C@H](CS(=O)CC(F)(F)F)NC(=O)c1ccc(/C(F)=C/C(c2cc(Cl)c(Cl)c(Cl)c2)C(F)(F)F)cc1Cl] | 16 |
| F13 | 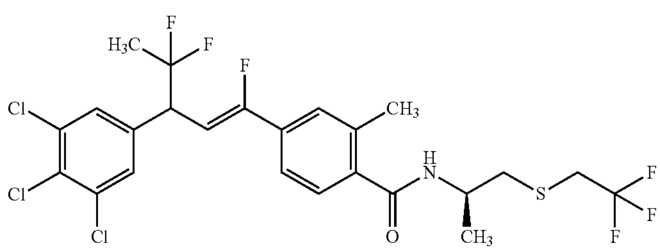 [SMILES: Cc1cc(/C(F)=C/C(c2cc(Cl)c(Cl)c(Cl)c2)C(C)(F)F)ccc1C(=O)N[C@H](C)CSCC(F)(F)F] | 13 |
| F14 | 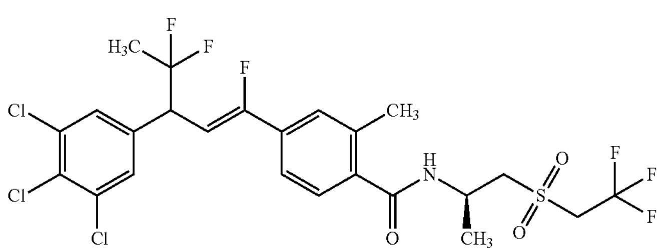 [SMILES: Cc1cc(/C(F)=C/C(c2cc(Cl)c(Cl)c(Cl)c2)C(C)(F)F)ccc1C(=O)N[C@H](C)CS(=O)(=O)CC(F)(F)F] | 13 |

TABLE 2-continued

Structure and Preparation Method for F Series Molecules

| No. | Structure | Prep.* |
|---|---|---|
| F15 | 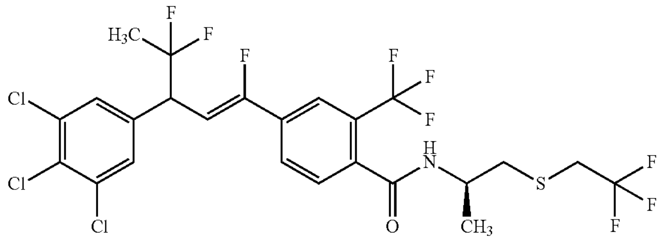 [SMILES: C[C@H](CSCC(F)(F)F)NC(=O)c1ccc(/C(F)=C/C(c2cc(Cl)c(Cl)c(Cl)c2)C(C)(F)F)cc1C(F)(F)F] | 13 |
| F16 | 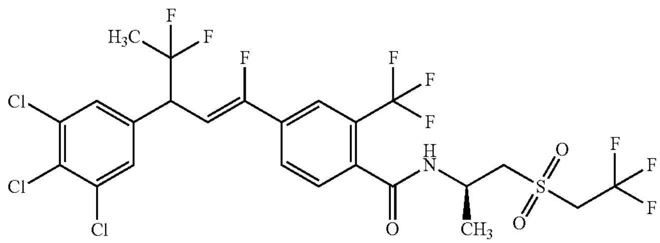 [SMILES: C[C@H](CS(=O)(=O)CC(F)(F)F)NC(=O)c1ccc(/C(F)=C/C(c2cc(Cl)c(Cl)c(Cl)c2)C(C)(F)F)cc1C(F)(F)F] | 13 |
| F17 | 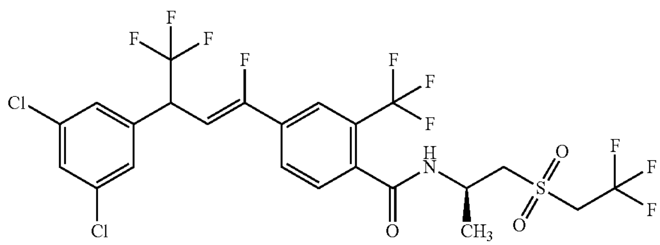 [SMILES: C[C@H](CS(=O)(=O)CC(F)(F)F)NC(=O)c1ccc(/C(F)=C/C(c2cc(Cl)cc(Cl)c2)C(F)(F)F)cc1C(F)(F)F] | 14 |
| F18 | 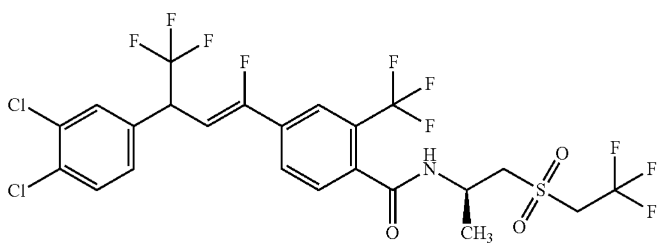 [SMILES: C[C@H](CS(=O)(=O)CC(F)(F)F)NC(=O)c1ccc(/C(F)=C/C(c2ccc(Cl)c(Cl)c2)C(F)(F)F)cc1C(F)(F)F] | 14 |
| F19 | 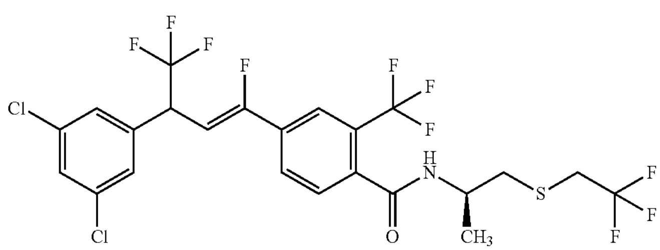 | 14 |
| F20 | 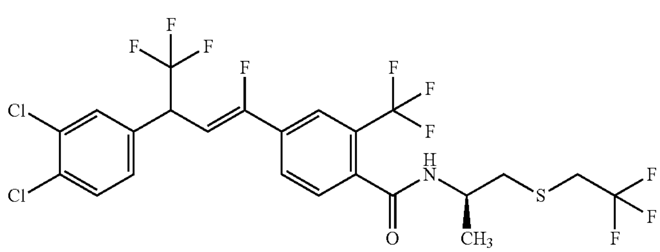 [SMILES: C[C@H](CSCC(F)(F)F)NC(=O)c1ccc(/C(F)=C/C(c2ccc(Cl)c(Cl)c2)C(F)(F)F)cc1C(F)(F)F] | 14 |

TABLE 2-continued

Structure and Preparation Method for F Series Molecules

| No. | Structure | Prep.* |
|---|---|---|
| F21 | 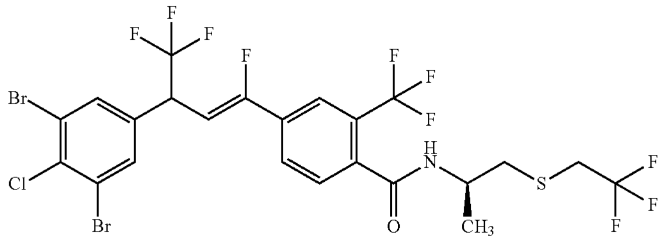 | 14 |
| F22 | 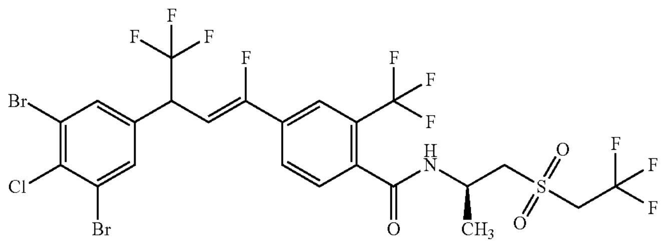 | 15 |
| F23 | 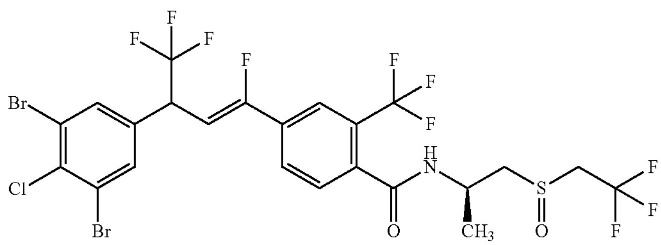 | 16 |
| F24 | 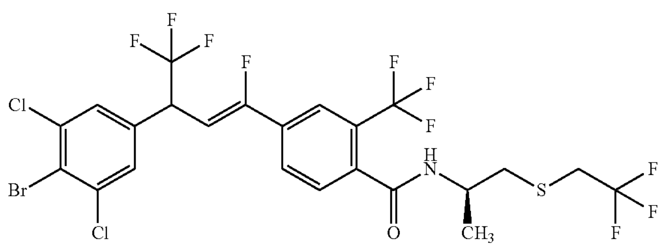 | 14 |
| F25 | 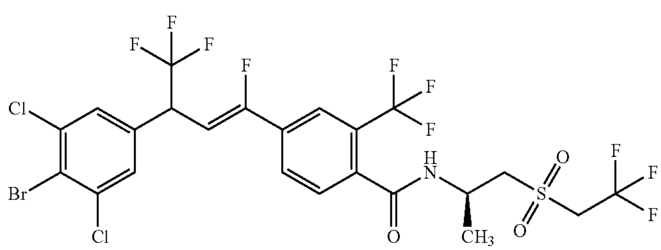 | 15 |
| F26 | 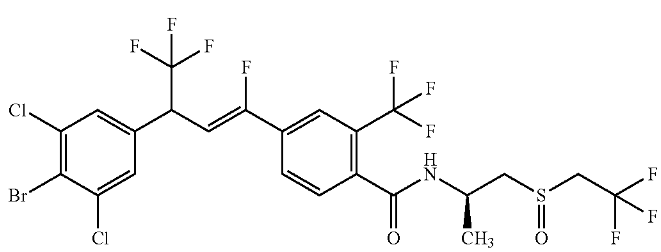 | 16 |

TABLE 2-continued

Structure and Preparation Method for F Series Molecules

| No. | Structure | Prep.* |
|---|---|---|
| F27 | 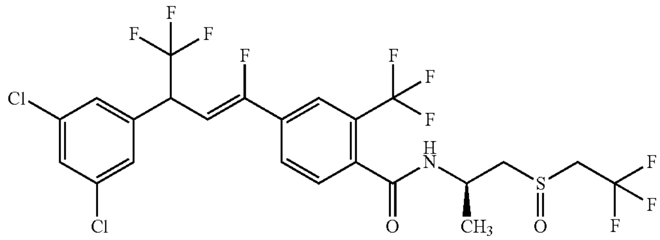 [SMILES: C[C@H](CS(=O)CC(F)(F)F)NC(=O)c1ccc(/C(F)=C/C(c2cc(Cl)cc(Cl)c2)C(F)(F)F)cc1C(F)(F)F] | 16 |
| F28 | 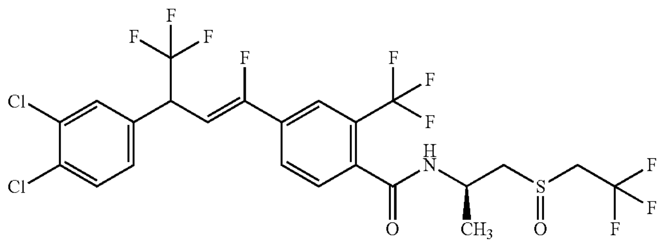 [SMILES: C[C@H](CS(=O)CC(F)(F)F)NC(=O)c1ccc(/C(F)=C/C(c2ccc(Cl)c(Cl)c2)C(F)(F)F)cc1C(F)(F)F] | 16 |
| F29 | 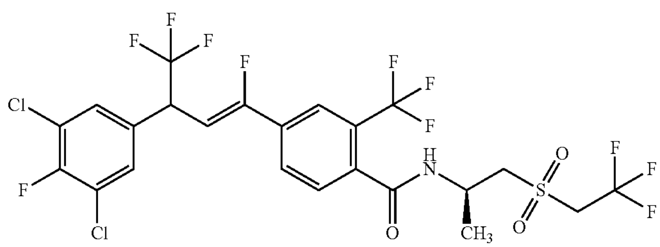 [SMILES: C[C@H](CS(=O)(=O)CC(F)(F)F)NC(=O)c1ccc(/C(F)=C/C(c2cc(Cl)c(F)c(Cl)c2)C(F)(F)F)cc1C(F)(F)F] | 14 |
| F30 | 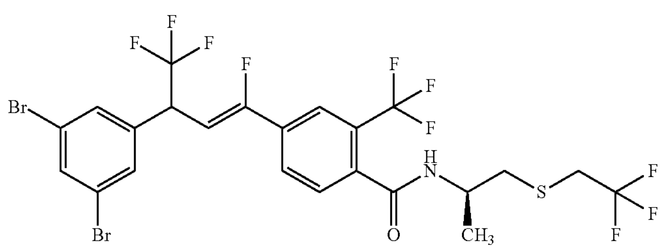 | 14 |
| F31 | 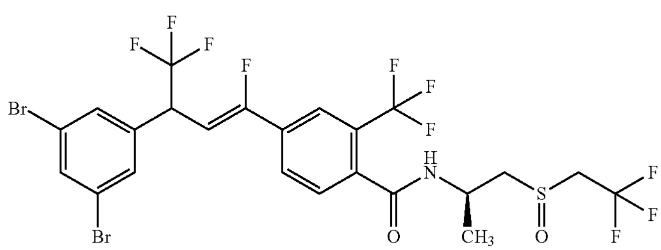 | 16 |
| F32 | 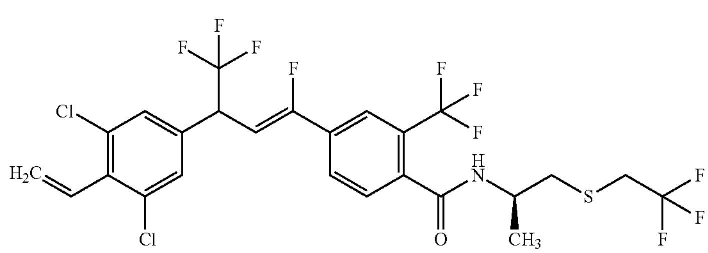 [SMILES: C=Cc1c(Cl)cc(C(/C=C(\F)c2ccc(C(=O)N[C@H](C)CSCC(F)(F)F)c(C(F)(F)F)c2)C(F)(F)F)cc1Cl] | 14 |

TABLE 2-continued

Structure and Preparation Method for F Series Molecules

| No. | Structure | Prep.* |
|---|---|---|
| F33 | 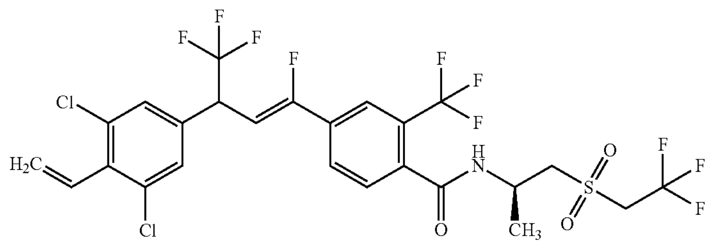 [SMILES: C=Cc1c(Cl)cc(C(/C=C(\F)c2ccc(C(=O)N[C@H](C)CS(=O)(=O)CC(F)(F)F)c(C(F)(F)F)c2)C(F)(F)F)cc1Cl] | 14 |
| F34 | 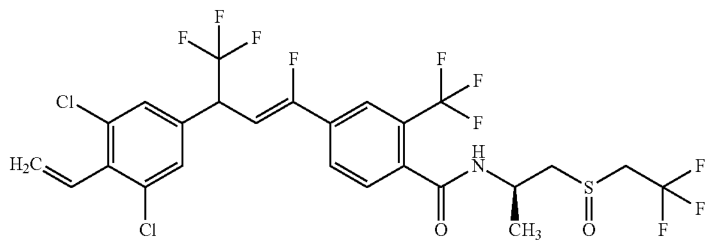 [SMILES: C=Cc1c(Cl)cc(C(/C=C(\F)c2ccc(C(=O)N[C@H](C)CS(=O)CC(F)(F)F)c(C(F)(F)F)c2)C(F)(F)F)cc1Cl] | 16 |
| F35 | 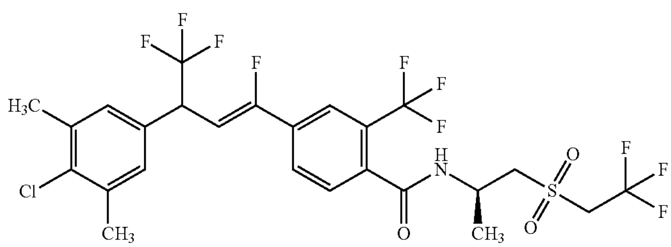 [SMILES: Cc1cc(C(/C=C(\F)c2ccc(C(=O)N[C@H](C)CS(=O)(=O)CC(F)(F)F)c(C(F)(F)F)c2)C(F)(F)F)cc(C)c1Cl] | 14 |
| F36 | 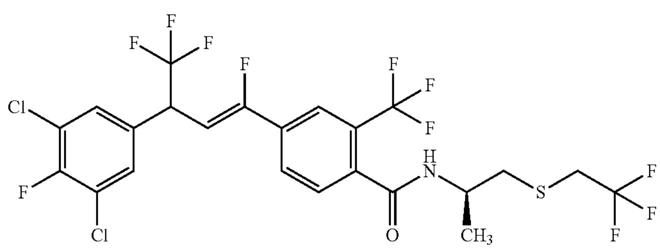 | 14 |
| F37 | 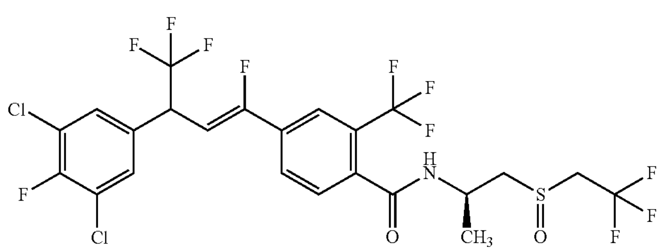 | 16 |
| F38 | 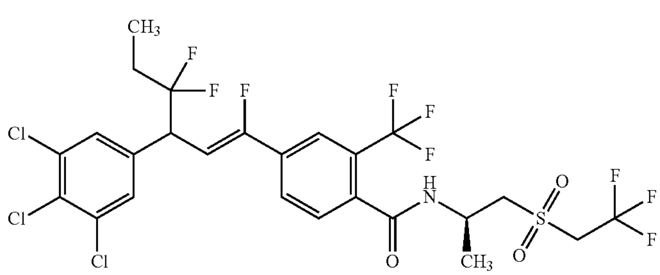 [SMILES: CCC(F)(F)C(/C=C(\F)c1ccc(C(=O)N[C@H](C)CS(=O)(=O)CC(F)(F)F)c(C(F)(F)F)c1)c1cc(Cl)c(Cl)c(Cl)c1] | 13 |

TABLE 2-continued

Structure and Preparation Method for F Series Molecules

| No. | Structure | Prep.* |
|---|---|---|
| F39 | 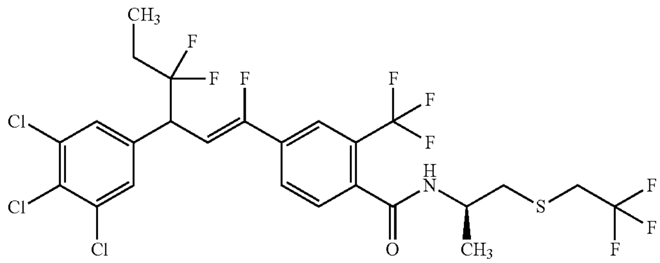 [SMILES: CCC(F)(F)C(/C=C(\F)c1ccc(C(=O)N[C@H](C)CSCC(F)(F)F)c(C(F)(F)F)c1)c1cc(Cl)c(Cl)c(Cl)c1] | 13 |
| F40 | 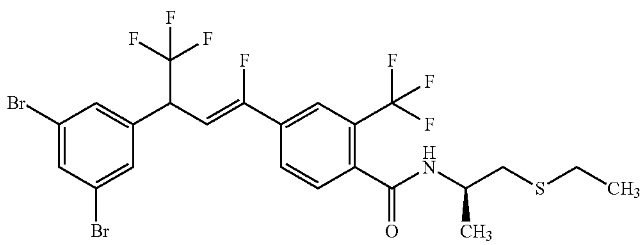 | 14 |
| F41 | 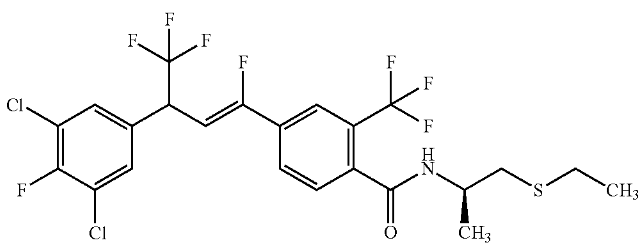 [SMILES: CCSC[C@@H](C)NC(=O)c1ccc(/C(F)=C/C(c2cc(Cl)c(F)c(Cl)c2)C(F)(F)F)cc1C(F)(F)F] | 14 |
| F42 | 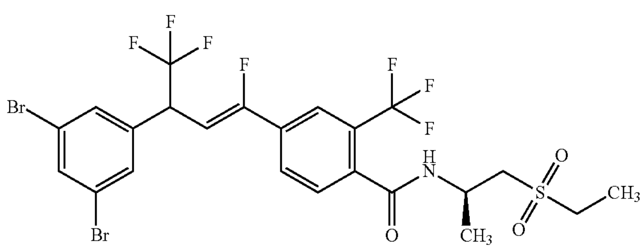 | 15 |
| F43 | 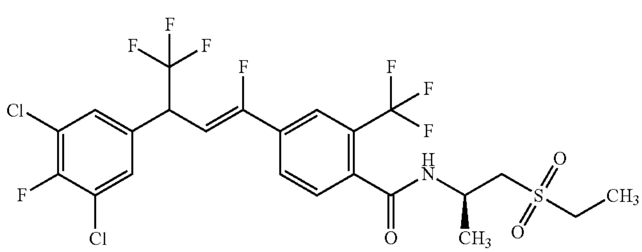 [SMILES: CCS(=O)(=O)C[C@@H](C)NC(=O)c1ccc(/C(F)=C/C(c2cc(Cl)c(F)c(Cl)c2)C(F)(F)F)cc1C(F)(F)F] | 14 |
| F44 | 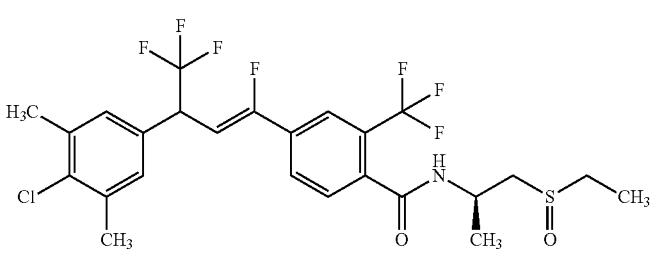 [SMILES: CCS(=O)C[C@@H](C)NC(=O)c1ccc(/C(F)=C/C(c2cc(C)c(Cl)c(C)c2)C(F)(F)F)cc1C(F)(F)F] | 16 |

TABLE 2-continued
Structure and Preparation Method for F Series Molecules
| No. | Structure | Prep.* |
|-----|-----------|--------|
| F45 | 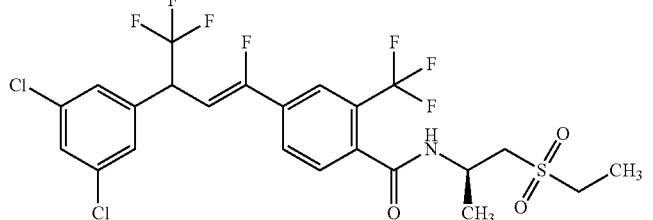 | 15 |
| F46 | 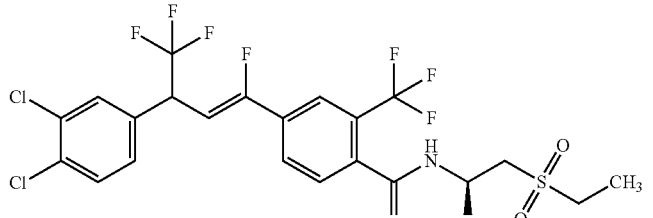 | 15 |
| F47 | 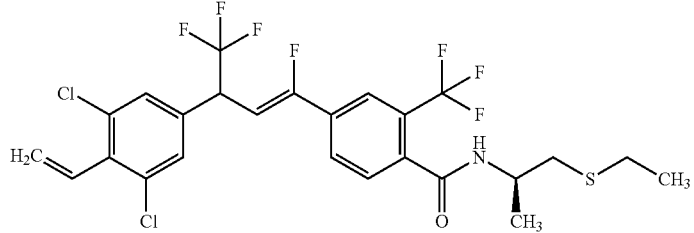 [SMILES: C=Cc1c(Cl)cc(C(/C=C(\F)c2ccc(C(=O)N[C@H](C)CSCC)c(C(F)(F)F)c2)C(F)(F)F)cc1Cl] | 14 |
| F48 | 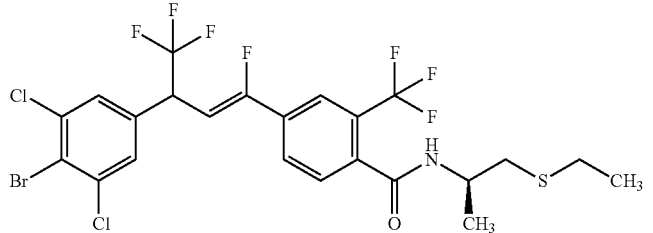 | 14 |
| F49 | 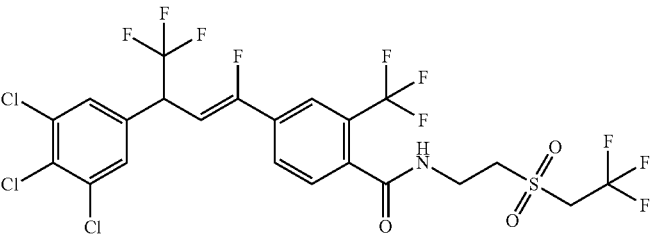 [SMILES: O=C(NCCS(=O)(=O)CC(F)(F)F)c1ccc(/C(F)=C/C(c2cc(Cl)c(Cl)c(Cl)c2)C(F)(F)F)cc1C(F)(F)F] | 18 |
| F50 | 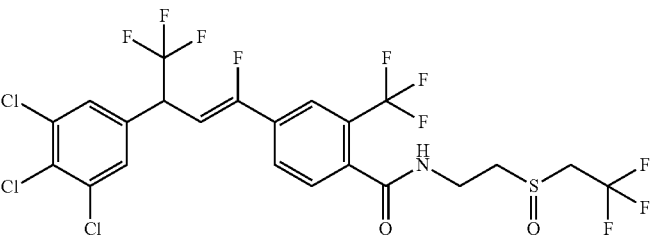 [SMILES: O=C(NCCS(=O)CC(F)(F)F)c1ccc(/C(F)=C/C(c2cc(Cl)c(Cl)c(Cl)c2)C(F)(F)F)cc1C(F)(F)F] | 18 |

TABLE 2-continued

Structure and Preparation Method for F Series Molecules

| No. | Structure | Prep.* |
|-----|-----------|--------|
| F51 | 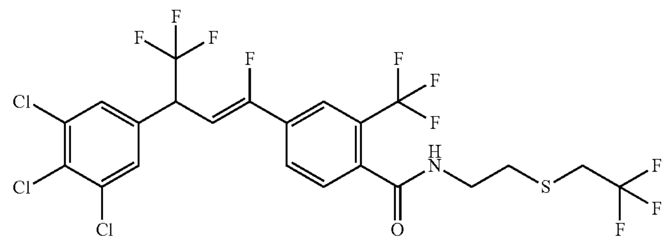 [SMILES: O=C(NCCSCC(F)(F)F)c1ccc(/C(F)=C/C(c2cc(Cl)c(Cl)c(Cl)c2)C(F)(F)F)cc1C(F)(F)F] | 17 |
| F52 | 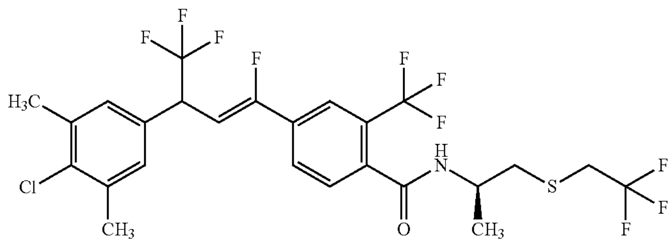 [SMILES: Cc1cc(C(/C=C(\F)c2ccc(C(=O)N[C@H](C)CSCC(F)(F)F)c(C(F)(F)F)c2)C(F)(F)F)cc(C)c1Cl] | 14 |
| F53 | 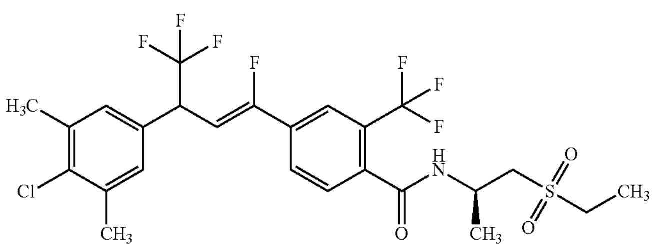 [SMILES: CCS(=O)(=O)C[C@@H](C)NC(=O)c1ccc(/C(F)=C/C(c2cc(C)c(Cl)c(C)c2)C(F)(F)F)cc1C(F)(F)F] | 14 |
| F54 | 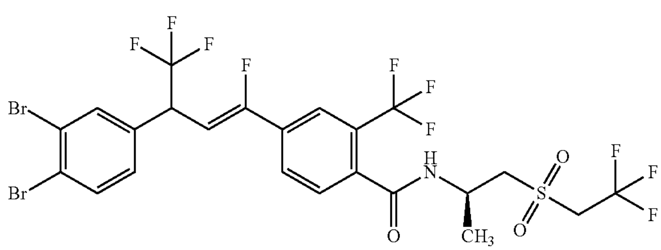 | 14 |
| F55 | 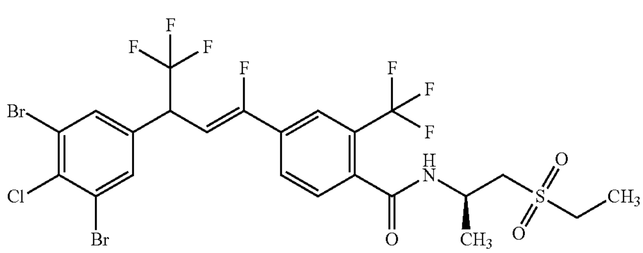 | 14 |
| F56 | 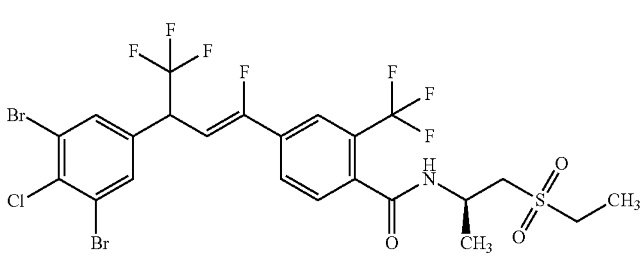 | 15 |

TABLE 2-continued

Structure and Preparation Method for F Series Molecules

| No. | Structure | Prep.* |
|---|---|---|
| F57 | 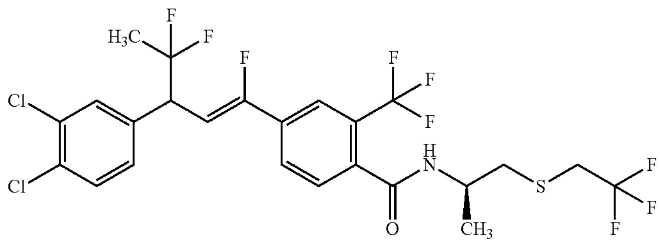 [SMILES: C[C@H](CSCC(F)(F)F)NC(=O)c1ccc(/C(F)=C/C(c2ccc(Cl)c(Cl)c2)C(C)(F)F)cc1C(F)(F)F] | 13 |
| F58 | 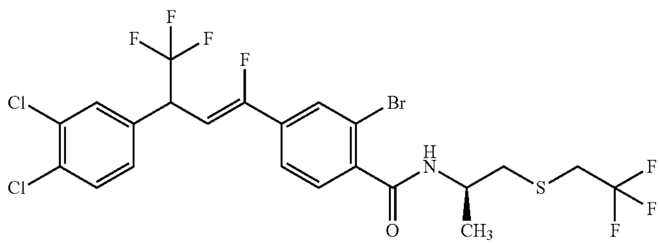 [SMILES: C[C@H](CSCC(F)(F)F)NC(=O)c1ccc(/C(F)=C/C(c2ccc(Cl)c(Cl)c2)C(F)(F)F)cc1Br] | 13 |
| F59 | 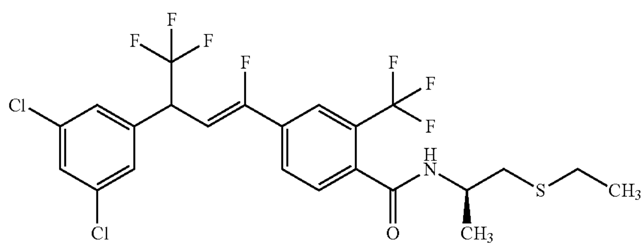 [SMILES: CCSC[C@@H](C)NC(=O)c1ccc(/C(F)=C/C(c2cc(Cl)cc(Cl)c2)C(F)(F)F)cc1C(F)(F)F] | 14 |
| F60 | 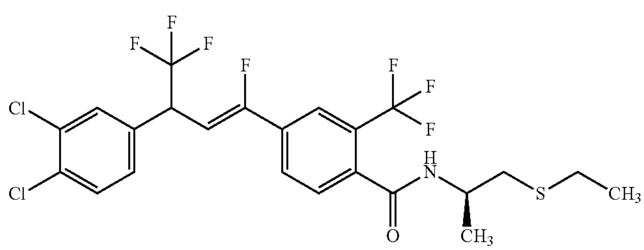 [SMILES: CCSC[C@@H](C)NC(=O)c1ccc(/C(F)=C/C(c2ccc(Cl)c(Cl)c2)C(F)(F)F)cc1C(F)(F)F] | 14 |
| F61 | 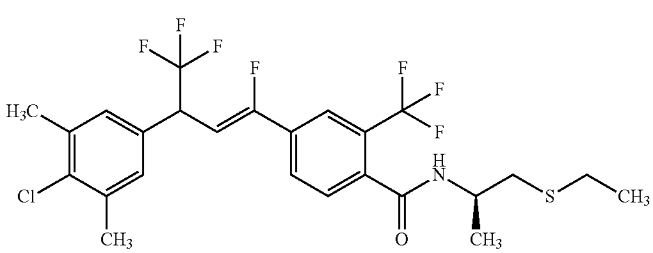 [SMILES: CCSC[C@@H](C)NC(=O)c1ccc(/C(F)=C/C(c2cc(C)c(Cl)c(C)c2)C(F)(F)F)cc1C(F)(F)F] | 14 |
| F62 | 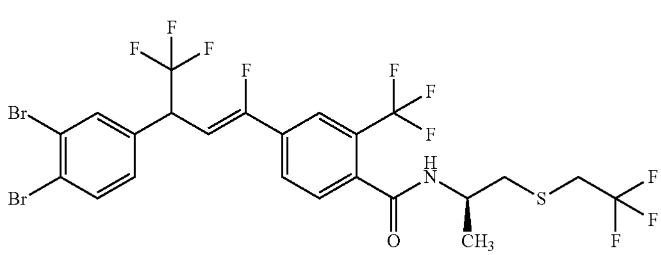 [SMILES: C[C@H](CSCC(F)(F)F)NC(=O)c1ccc(/C(F)=C/C(c2ccc(Br)c(Br)c2)C(F)(F)F)cc1C(F)(F)F] | 14 |

TABLE 2-continued

Structure and Preparation Method for F Series Molecules

| No. | Structure | Prep.* |
|---|---|---|
| F63 | 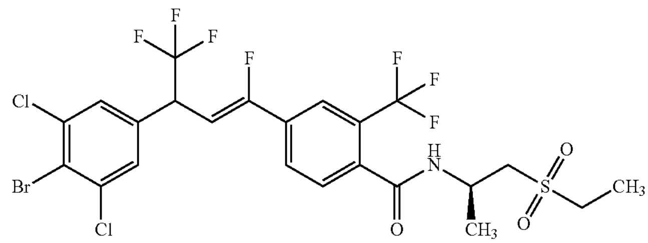 [SMILES: CCS(=O)(=O)C[C@@H](C)NC(=O)c1ccc(/C(F)=C/C(c2cc(Cl)c(Br)c(Cl)c2)C(F)(F)F)cc1C(F)(F)F] | 15 |
| F64 | 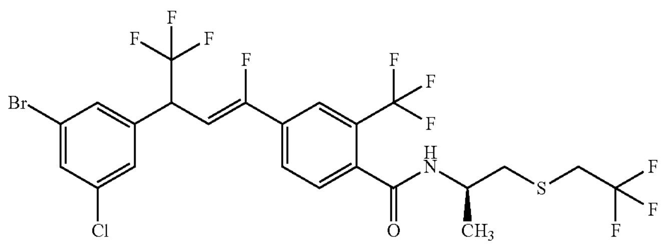 [SMILES: C[C@H](CSCC(F)(F)F)NC(=O)c1ccc(/C(F)=C/C(c2cc(Cl)cc(Br)c2)C(F)(F)F)cc1C(F)(F)F] | 14 |
| F65 | 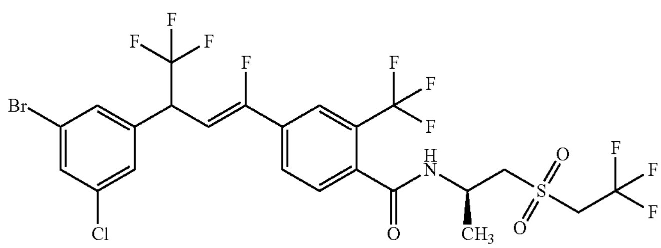 | 15 |
| F66 | 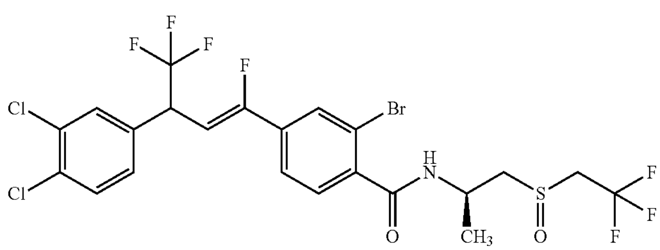 [SMILES: C[C@H](CS(=O)CC(F)(F)F)NC(=O)c1ccc(/C(F)=C/C(c2ccc(Cl)c(Cl)c2)C(F)(F)F)cc1Br] | 16 |
| F67 | 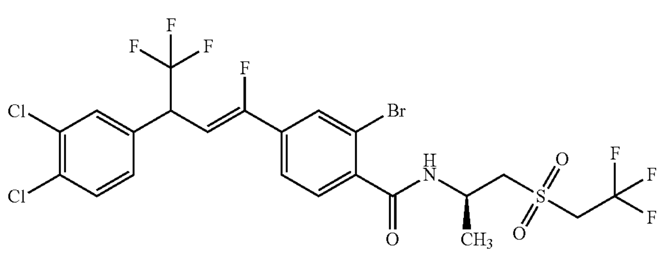 [SMILES: C[C@H](CS(=O)(=O)CC(F)(F)F)NC(=O)c1ccc(/C(F)=C/C(c2ccc(Cl)c(Cl)c2)C(F)(F)F)cc1Br] | 15 |
| F68 | 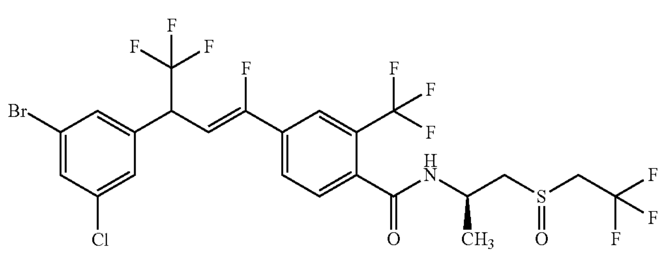 [SMILES: C[C@H](CS(=O)CC(F)(F)F)NC(=O)c1ccc(/C(F)=C/C(c2cc(Cl)cc(Br)c2)C(F)(F)F)cc1C(F)(F)F] | 16 |

TABLE 2-continued

Structure and Preparation Method for F Series Molecules

| No. | Structure | Prep.* |
|---|---|---|
| F69 | 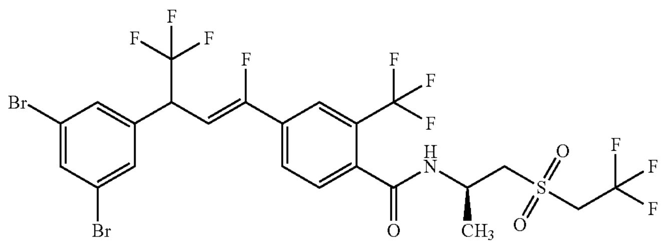 | 14 |
| F70 | 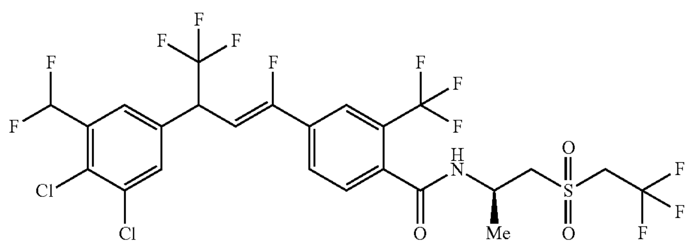 [SMILES: C[C@H](CS(=O)(=O)CC(F)(F)F)NC(=O)c1ccc(/C(F)=C/C(c2cc(Cl)c(Cl)c(C(F)F)c2)C(F)(F)F)cc1C(F)(F)F] | 34 |
| F71 | 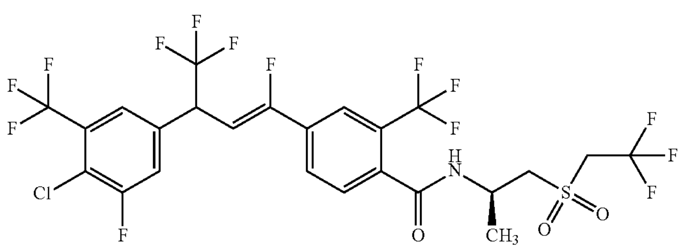 | 13 |
| F72 | enantiomerically pure | 35 |
| F73 | 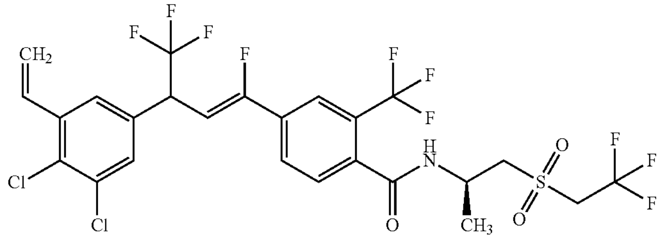 [SMILES: C=Cc1cc(C(/C=C(\F)c2ccc(C(=O)N[C@H](C)CS(=O)(=O)CC(F)(F)F)c(C(F)(F)F)c2)C(F)(F)F)cc(Cl)c1Cl] | 13 |

TABLE 2-continued

Structure and Preparation Method for F Series Molecules

| No. | Structure | Prep.* |
|---|---|---|
| F75 | 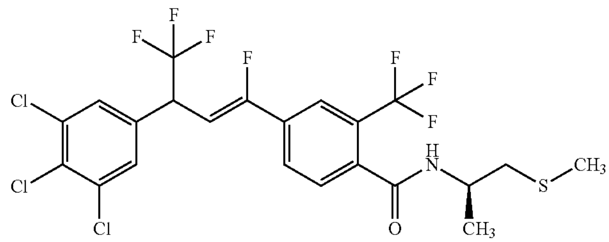 [SMILES: CSC[C@@H](C)NC(=O)c1ccc(/C(F)=C/C(c2cc(Cl)c(Cl)c(Cl)c2)C(F)(F)F)cc1C(F)(F)F] | 17 |
| F77 | 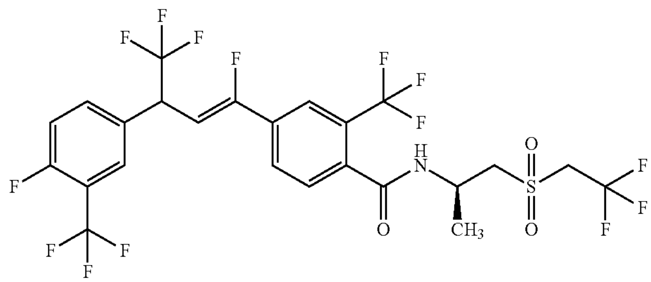 [SMILES: C[C@H](CS(=O)(=O)CC(F)(F)F)NC(=O)c1ccc(/C(F)=C/C(c2ccc(F)c(C(F)(F)F)c2)C(F)(F)F)cc1C(F)(F)F] | 14 |
| F78 | 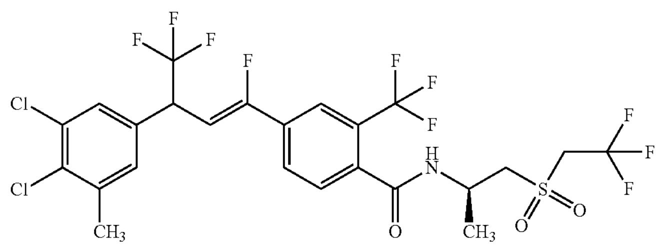 [SMILES: Cc1cc(C(/C=C(\F)c2ccc(C(=O)N[C@H](C)CS(=O)(=O)CC(F)(F)F)c(C(F)(F)F)c2)C(F)(F)F)cc(Cl)c1Cl] | 14 |
| F79 | 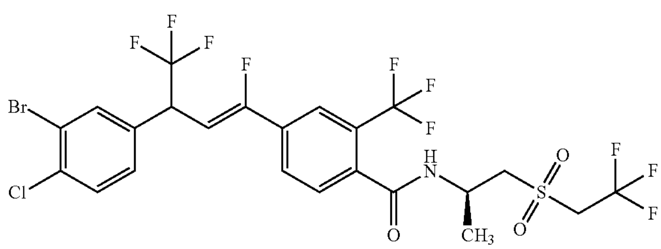 | 14 |
| F80 | 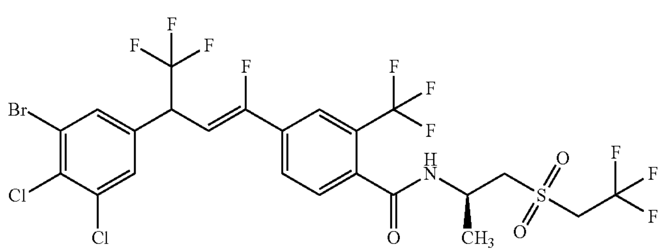 | 13 |
| F81 | 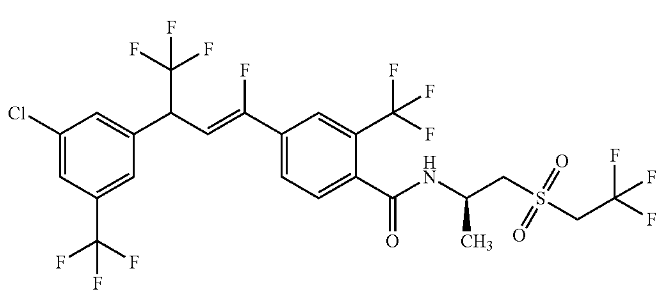 [SMILES: C[C@H](CS(=O)(=O)CC(F)(F)F)NC(=O)c1ccc(/C(F)=C/C(c2cc(Cl)cc(C(F)(F)F)c2)C(F)(F)F)cc1C(F)(F)F] | 14 |

TABLE 2-continued

Structure and Preparation Method for F Series Molecules

| No. | Structure | Prep.* |
|---|---|---|
| F82 | 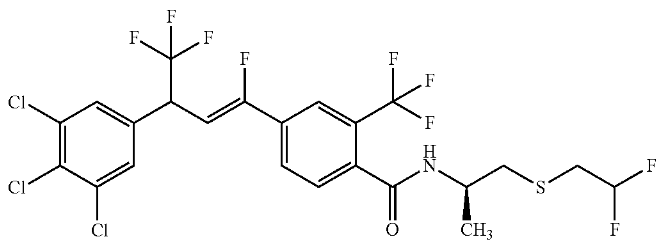 [SMILES: C[C@H](CSCC(F)F)NC(=O)c1ccc(/C(F)=C/C(c2cc(Cl)c(Cl)c(Cl)c2)C(F)(F)F)cc1C(F)(F)F] | 17 |
| F83 | 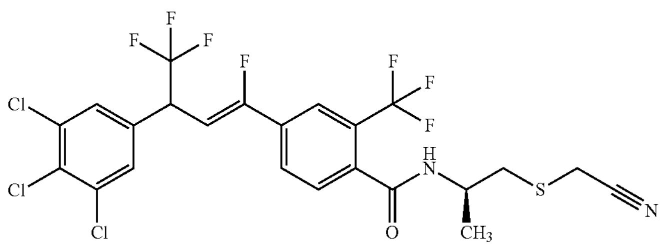 | 17 |
| F84 | 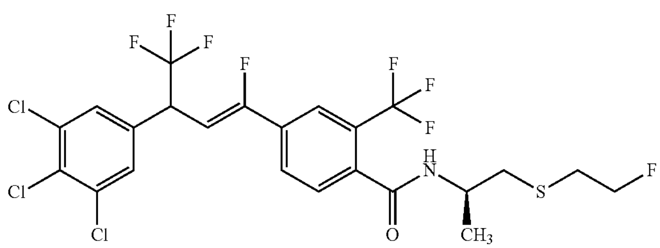 [SMILES: C[C@H](CSCCF)NC(=O)c1ccc(/C(F)=C/C(c2cc(Cl)c(Cl)c(Cl)c2)C(F)(F)F)cc1C(F)(F)F] | 29 |
| F85 | 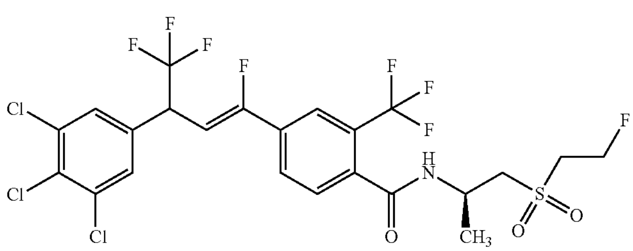 [SMILES: C[C@H](CS(=O)(=O)CCF)NC(=O)c1ccc(/C(F)=C/C(c2cc(Cl)c(Cl)c(Cl)c2)C(F)(F)F)cc1C(F)(F)F] | 18 |
| F86 | 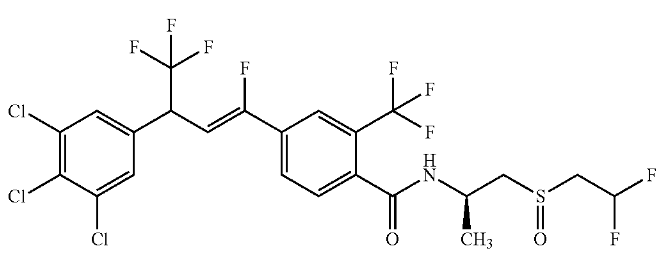 [SMILES: C[C@H](CS(=O)CC(F)F)NC(=O)c1ccc(/C(F)=C/C(c2cc(Cl)c(Cl)c(Cl)c2)C(F)(F)F)cc1C(F)(F)F] | 18 |
| F87 | 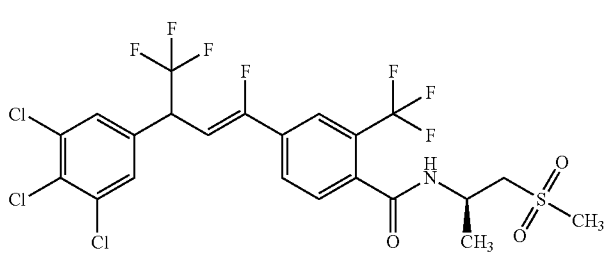 [SMILES: C[C@H](CS(C)(=O)=O)NC(=O)c1ccc(/C(F)=C/C(c2cc(Cl)c(Cl)c(Cl)c2)C(F)(F)F)cc1C(F)(F)F] | 18 |

TABLE 2-continued

Structure and Preparation Method for F Series Molecules

| No. | Structure | Prep.* |
|---|---|---|
| F88 | 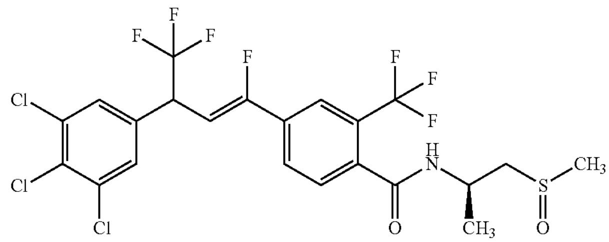 [SMILES: C[C@H](CS(C)=O)NC(=O)c1ccc(/C(F)=C/C(c2cc(Cl)c(Cl)c(Cl)c2)C(F)(F)F)cc1C(F)(F)F] | 18 |
| F89 | 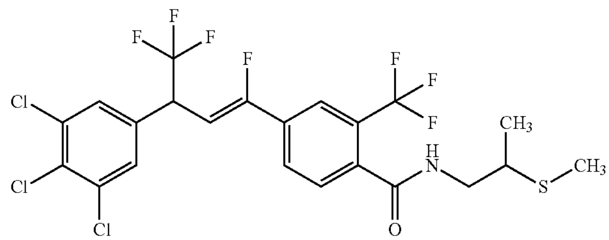 [SMILES: CSC(C)CNC(=O)c1ccc(/C(F)=C/C(c2cc(Cl)c(Cl)c(Cl)c2)C(F)(F)F)cc1C(F)(F)F] | 29 |
| F90 | 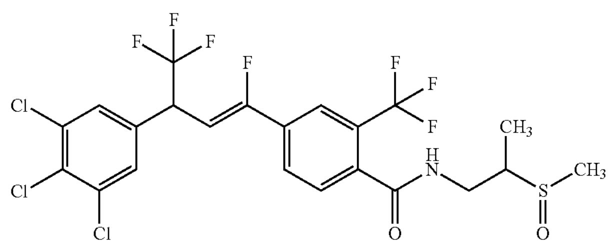 [SMILES: CC(CNC(=O)c1ccc(/C(F)=C/C(c2cc(Cl)c(Cl)c(Cl)c2)C(F)(F)F)cc1C(F)(F)F)S(C)=O] | 18 |
| F91 | 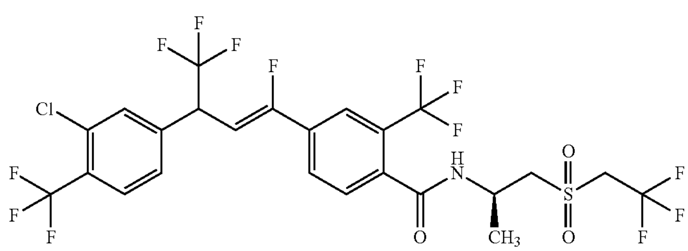 [SMILES: C[C@H](CS(=O)(=O)CC(F)(F)F)NC(=O)c1ccc(/C(F)=C/C(c2ccc(C(F)(F)F)c(Cl)c2)C(F)(F)F)cc1C(F)(F)F] | 13 |
| F92 | 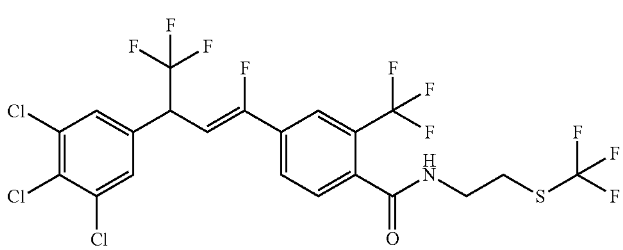 [SMILES: O=C(NCCSC(F)(F)F)c1ccc(/C(F)=C/C(c2cc(Cl)c(Cl)c(Cl)c2)C(F)(F)F)cc1C(F)(F)F] | 29 |
| F93 | 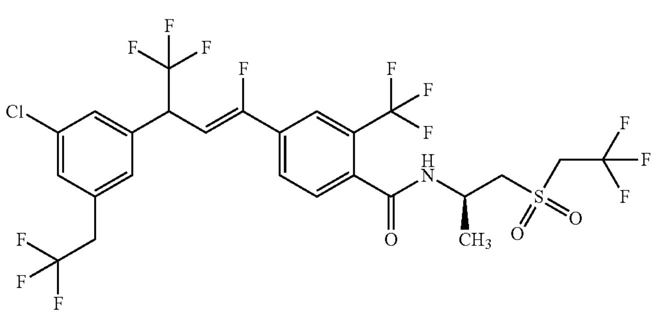 [SMILES: C[C@H](CS(=O)(=O)CC(F)(F)F)NC(=O)c1ccc(/C(F)=C/C(c2cc(Cl)cc(CC(F)(F)F)c2)C(F)(F)F)cc1C(F)(F)F] | 13 |

TABLE 2-continued

Structure and Preparation Method for F Series Molecules

| No. | Structure | Prep.* |
|---|---|---|
| F94 | 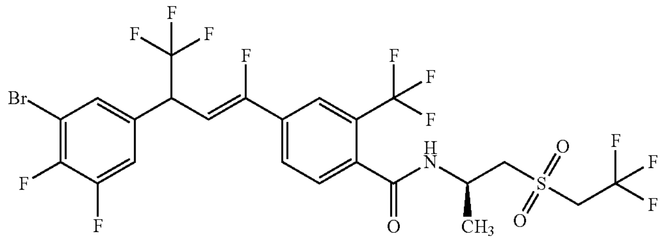 | 13 |
| F95 | 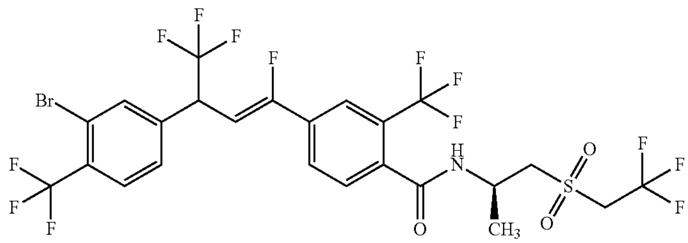 [SMILES: C[C@H](CS(=O)(=O)CC(F)(F)F)NC(=O)c1ccc(/C(F)=C/C(c2ccc(C(F)(F)F)c(Br)c2)C(F)(F)F)cc1C(F)(F)F] | 13 |
| F96 | 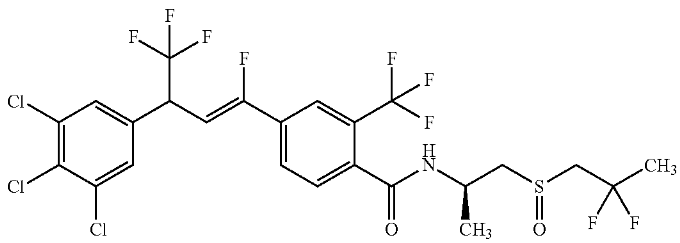 [SMILES: C[C@H](CS(=O)CC(C)(F)F)NC(=O)c1ccc(/C(F)=C/C(c2cc(Cl)c(Cl)c(Cl)c2)C(F)(F)F)cc1C(F)(F)F] | 18 |
| F97 | 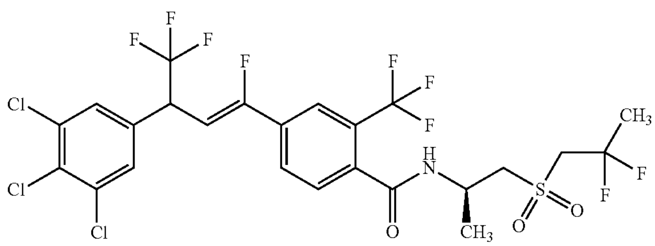 [SMILES: C[C@H](CS(=O)(=O)CC(C)(F)F)NC(=O)c1ccc(/C(F)=C/C(c2cc(Cl)c(Cl)c(Cl)c2)C(F)(F)F)cc1C(F)(F)F] | 18 |
| F98 | 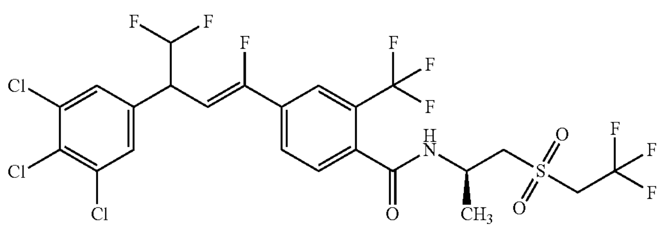 [SMILES: C[C@H](CS(=O)(=O)CC(F)(F)F)NC(=O)c1ccc(/C(F)=C/C(c2cc(Cl)c(Cl)c(Cl)c2)C(F)F)cc1C(F)(F)F] | 13 |
| F99 | 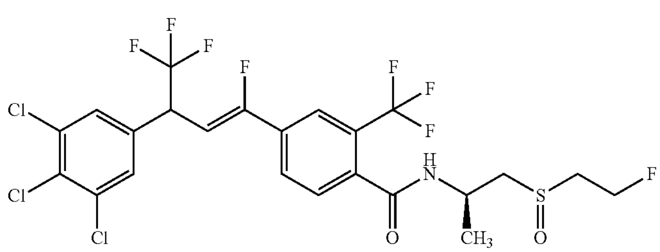 [SMILES: C[C@H](CS(=O)CCF)NC(=O)c1ccc(/C(F)=C/C(c2cc(Cl)c(Cl)c(Cl)c2)C(F)(F)F)cc1C(F)(F)F] | 18 |

TABLE 2-continued

Structure and Preparation Method for F Series Molecules

| No. | Structure | Prep.* |
|---|---|---|
| F100 | 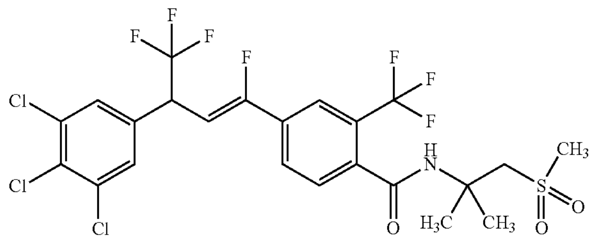 [SMILES: CC(C)(CS(C)(=O)=O)NC(=O)c1ccc(/C(F)=C/C(c2cc(Cl)c(Cl)c(Cl)c2)C(F)(F)F)cc1C(F)(F)F] | 29 |
| F101 | 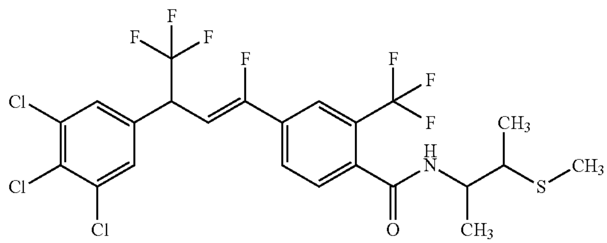 [SMILES: CSC(C)C(C)NC(=O)c1ccc(/C(F)=C/C(c2cc(Cl)c(Cl)c(Cl)c2)C(F)(F)F)cc1C(F)(F)F] | 30 |
| F102 | 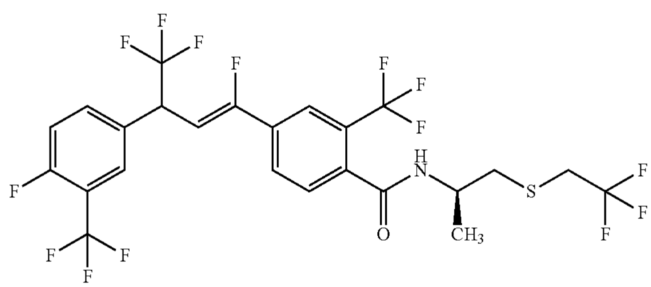 [SMILES: C[C@H](CSCC(F)(F)F)NC(=O)c1ccc(/C(F)=C/C(c2ccc(F)c(C(F)(F)F)c2)C(F)(F)F)cc1C(F)(F)F] | 14 |
| F103 | 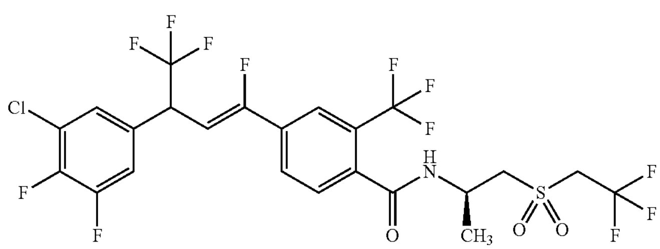 [SMILES: C[C@H](CS(=O)(=O)CC(F)(F)F)NC(=O)c1ccc(/C(F)=C/C(c2cc(F)c(F)c(Cl)c2)C(F)(F)F)cc1C(F)(F)F] | 14 |
| F104 | 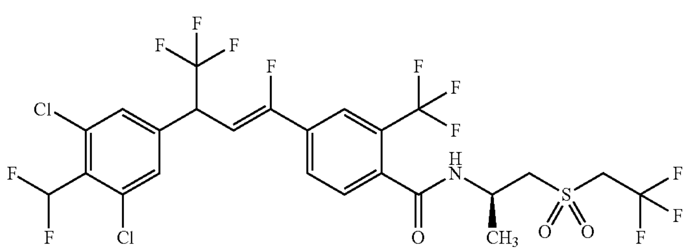 [SMILES: C[C@H](CS(=O)(=O)CC(F)(F)F)NC(=O)c1ccc(/C(F)=C/C(c2cc(Cl)c(C(F)F)c(Cl)c2)C(F)(F)F)cc1C(F)(F)F] | 14 |
| F109 | 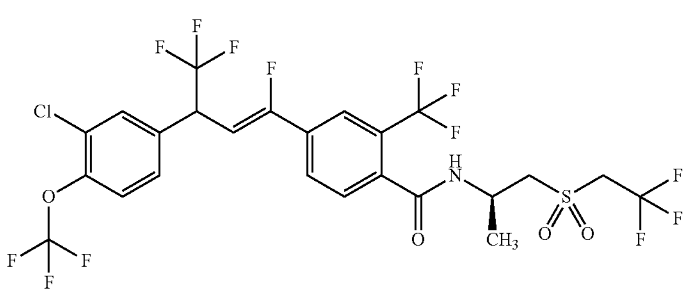 [SMILES: C[C@H](CS(=O)(=O)CC(F)(F)F)NC(=O)c1ccc(/C(F)=C/C(c2ccc(OC(F)(F)F)c(Cl)c2)C(F)(F)F)cc1C(F)(F)F] | 13 |

TABLE 2-continued

Structure and Preparation Method for F Series Molecules

| No. | Structure | Prep.* |
|---|---|---|
| F110 | 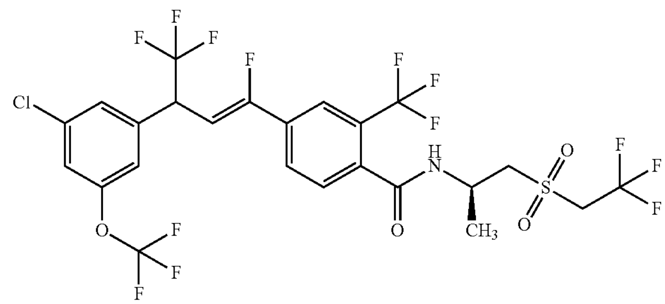 [SMILES: C[C@H](CS(=O)(=O)CC(F)(F)F)NC(=O)c1ccc(/C(F)=C/C(c2cc(Cl)cc(OC(F)(F)F)c2)C(F)(F)F)cc1C(F)(F)F] | 13 |
| F112 | 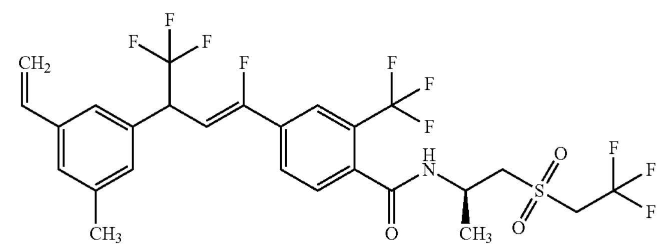 | 13 |
| F113 | 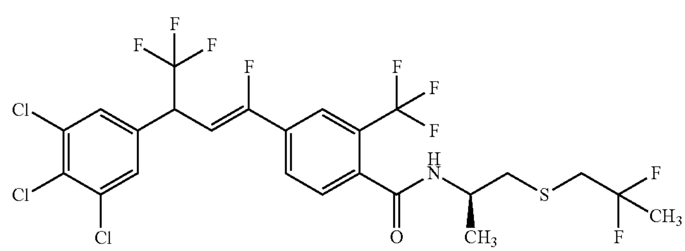 [SMILES: C[C@H](CSCC(C)(F)F)NC(=O)c1ccc(/C(F)=C/C(c2cc(Cl)c(Cl)c(Cl)c2)C(F)(F)F)cc1C(F)(F)F] | 29 |
| F114 | 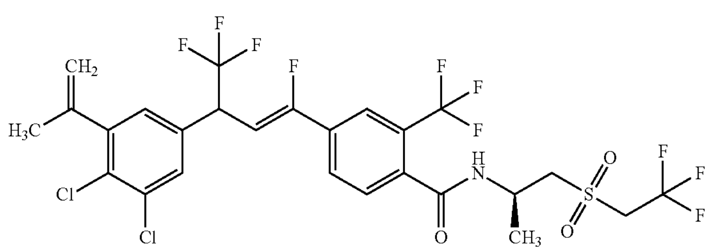 [SMILES: C=C(C)c1cc(C(/C=C(\F)c2ccc(C(=O)N[C@H](C)CS(=O)(=O)CC(F)(F)F)c(C(F)(F)F)c2)C(F)(F)F)cc(Cl)c1Cl] | 13 |
| F116 | 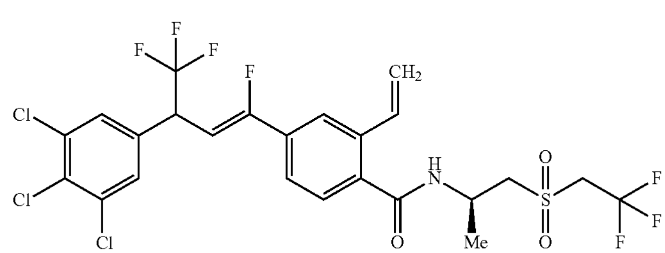 [SMILES: C=Cc1cc(/C(F)=C/C(c2cc(Cl)c(Cl)c(Cl)c2)C(F)(F)F)ccc1C(=O)N[C@H](C)CS(=O)(=O)CC(F)(F)F] | 13 |
| F117 | 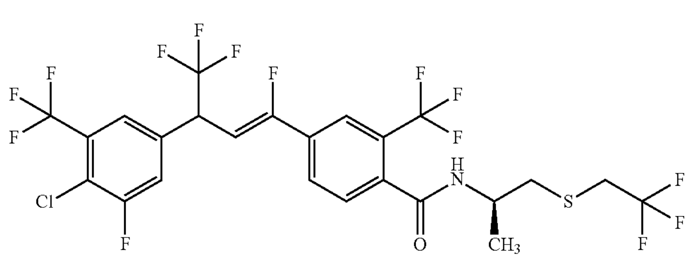 [SMILES: C[C@H](CSCC(F)(F)F)NC(=O)c1ccc(/C(F)=C/C(c2cc(F)c(Cl)c(C(F)(F)F)c2)C(F)(F)F)cc1C(F)(F)F] | 13 |

TABLE 2-continued

Structure and Preparation Method for F Series Molecules

| No. | Structure | Prep.* |
|---|---|---|
| F119 | 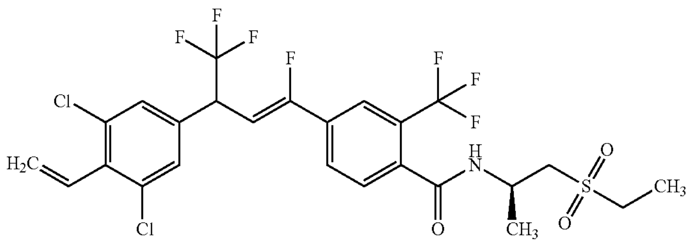 [SMILES: C=Cc1c(Cl)cc(C(/C=C(\F)c2ccc(C(=O)N[C@H](C)CS(=O)(=O)CC)c(C(F)(F)F)c2)C(F)(F)F)cc1Cl] | 15 |
| F120 | 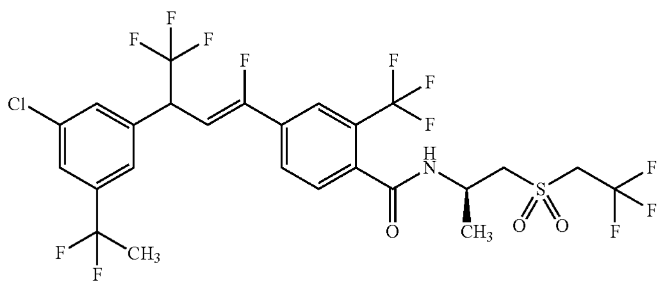 [SMILES: C[C@H](CS(=O)(=O)CC(F)(F)F)NC(=O)c1ccc(/C(F)=C/C(c2cc(Cl)cc(C(C)(F)F)c2)C(F)(F)F)cc1C(F)(F)F] | 13 |
| F121 | 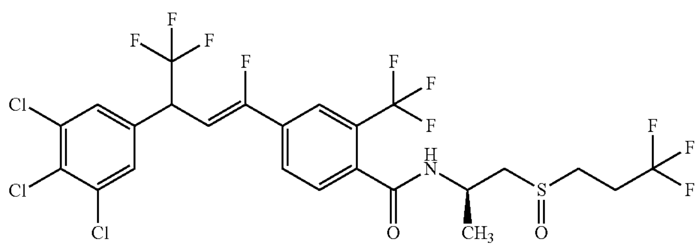 [SMILES: C[C@H](CS(=O)CCC(F)(F)F)NC(=O)c1ccc(/C(F)=C/C(c2cc(Cl)c(Cl)c(Cl)c2)C(F)(F)F)cc1C(F)(F)F] | 18 |
| F122 | 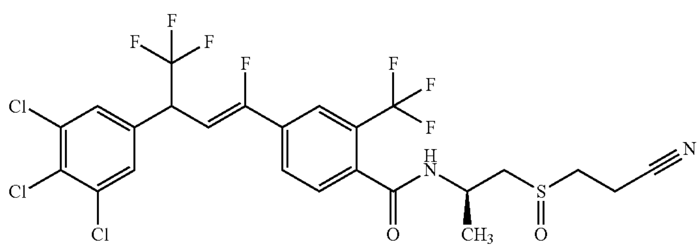 [SMILES: C[C@H](CS(=O)CCC#N)NC(=O)c1ccc(/C(F)=C/C(c2cc(Cl)c(Cl)c(Cl)c2)C(F)(F)F)cc1C(F)(F)F] | 18 |
| F123 | 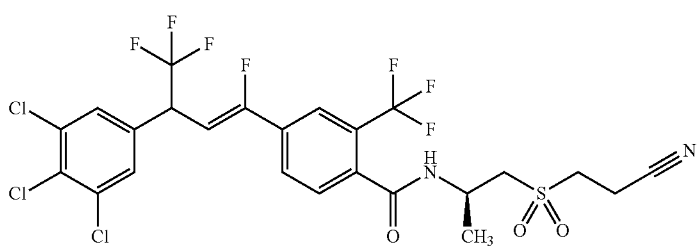 [SMILES: C[C@H](CS(=O)(=O)CCC#N)NC(=O)c1ccc(/C(F)=C/C(c2cc(Cl)c(Cl)c(Cl)c2)C(F)(F)F)cc1C(F)(F)F] | 18 |
| F124 | 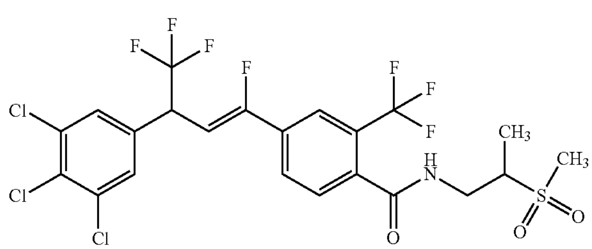 [SMILES: CC(CNC(=O)c1ccc(/C(F)=C/C(c2cc(Cl)c(Cl)c(Cl)c2)C(F)(F)F)cc1C(F)(F)F)S(C)(=O)=O] | 18 |

TABLE 2-continued

Structure and Preparation Method for F Series Molecules

| No. | Structure | Prep.* |
|---|---|---|
| F125 | 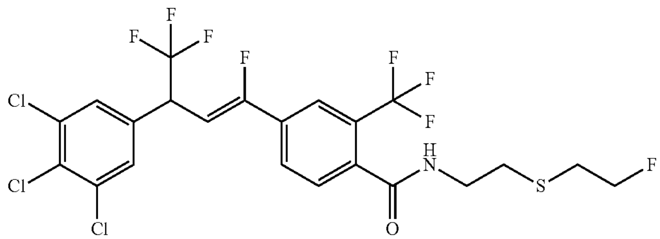 [SMILES: O=C(NCCSCCF)c1ccc(/C(F)=C/C(c2cc(Cl)c(Cl)c(Cl)c2)C(F)(F)F)cc1C(F)(F)F] | 29 |
| F126 | 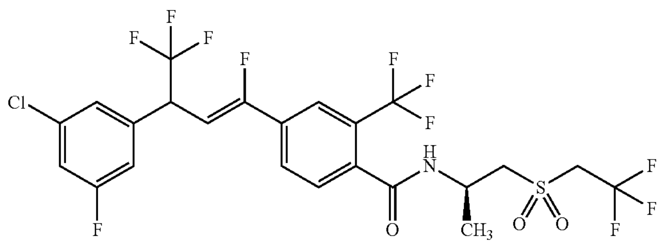 [SMILES: C[C@H](CS(=O)(=O)CC(F)(F)F)NC(=O)c1ccc(/C(F)=C/C(c2cc(F)cc(Cl)c2)C(F)(F)F)cc1C(F)(F)F] | 14 |
| F127 | 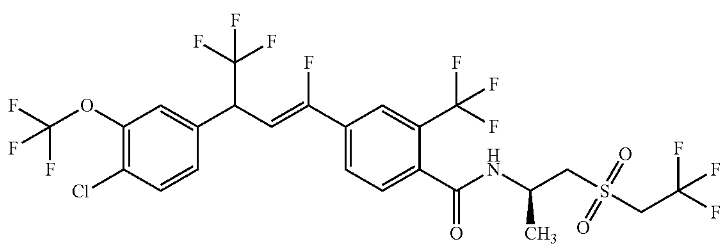 [SMILES: C[C@H](CS(=O)(=O)CC(F)(F)F)NC(=O)c1ccc(/C(F)=C/C(c2ccc(Cl)c(OC(F)(F)F)c2)C(F)(F)F)cc1C(F)(F)F] | 13 |
| F128 | 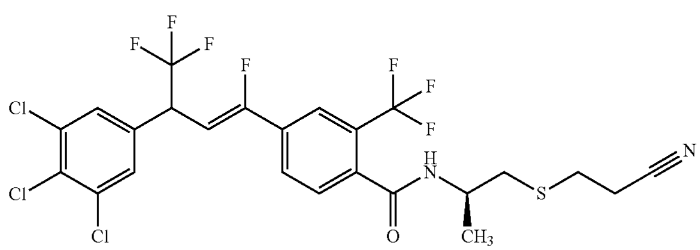 [SMILES: C[C@H](CSCCC#N)NC(=O)c1ccc(/C(F)=C/C(c2cc(Cl)c(Cl)c(Cl)c2)C(F)(F)F)cc1C(F)(F)F] | 17 |
| F129 | 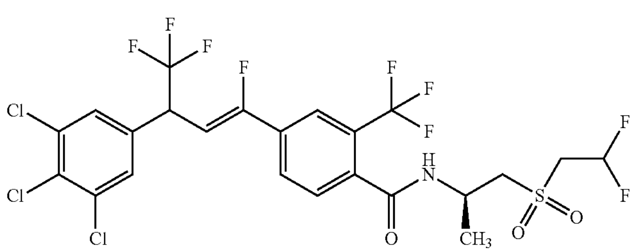 | 18 |
| F130 | 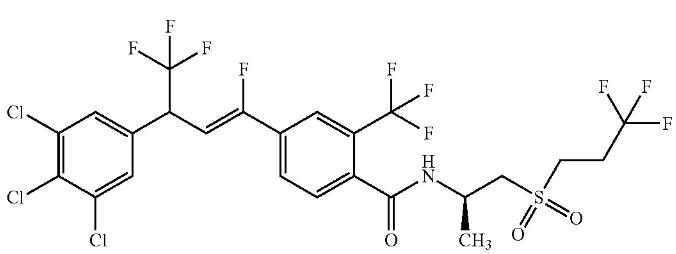 [SMILES: C[C@H](CS(=O)(=O)CCC(F)(F)F)NC(=O)c1ccc(/C(F)=C/C(c2cc(Cl)c(Cl)c(Cl)c2)C(F)(F)F)cc1C(F)(F)F] | 18 |

TABLE 2-continued

Structure and Preparation Method for F Series Molecules

| No. | Structure | Prep.* |
|---|---|---|
| F131 | 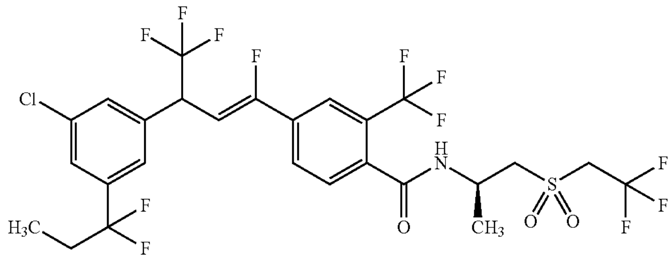 [SMILES: CCC(F)(F)c1cc(Cl)cc(C(/C=C(\F)c2ccc(C(=O)N[C@H](C)CS(=O)(=O)CC(F)(F)F)c(C(F)(F)F)c2)C(F)(F)F)c1] | 13 |
| F132 | 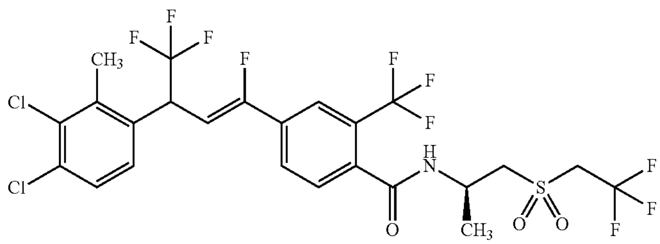 [SMILES: Cc1c(C(/C=C(\F)c2ccc(C(=O)N[C@H](C)CS(=O)(=O)CC(F)(F)F)c(C(F)(F)F)c2)C(F)(F)F)ccc(Cl)c1Cl] | 13 |
| F133 | 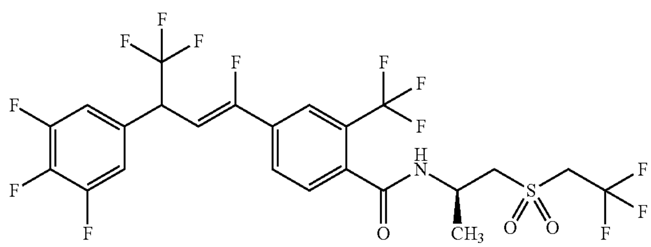 [SMILES: C[C@H](CS(=O)(=O)CC(F)(F)F)NC(=O)c1ccc(/C(F)=C/C(c2cc(F)c(F)c(F)c2)C(F)(F)F)cc1C(F)(F)F] | 14 |
| F136 | enantiomerically pure | 35 |
| F137 | 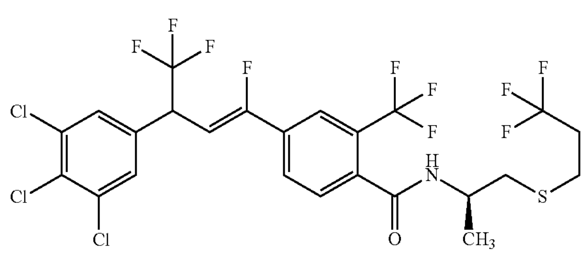 [SMILES: C[C@H](CSCCC(F)(F)F)NC(=O)c1ccc(/C(F)=C/C(c2cc(Cl)c(Cl)c(Cl)c2)C(F)(F)F)cc1C(F)(F)F] | 17 |

TABLE 2-continued
Structure and Preparation Method for F Series Molecules
| No. | Structure | Prep.* |
|---|---|---|
| F138 | 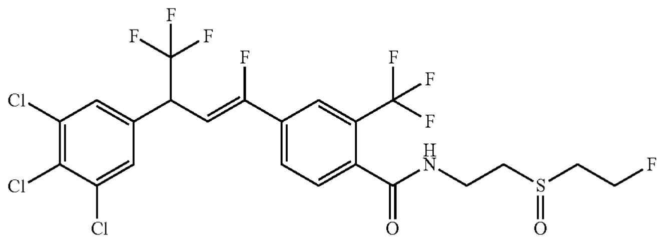 [SMILES: O=C(NCCS(=O)CCF)c1ccc(/C(F)=C/C(c2cc(Cl)c(Cl)c(Cl)c2)C(F)(F)F)cc1C(F)(F)F] | 18 |
| F141 | 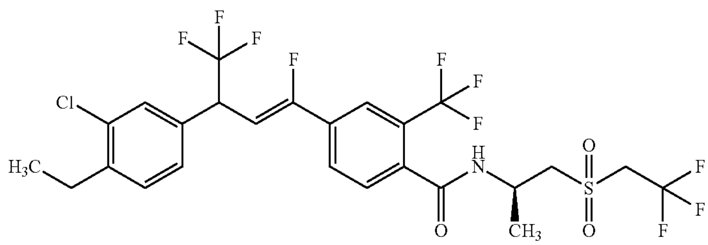 [SMILES: CCc1ccc(C(/C=C(\F)c2ccc(C(=O)N[C@H](C)CS(=O)(=O)CC(F)(F)F)c(C(F)(F)F)c2)C(F)(F)F)cc1Cl] | 13 |
| F142 | 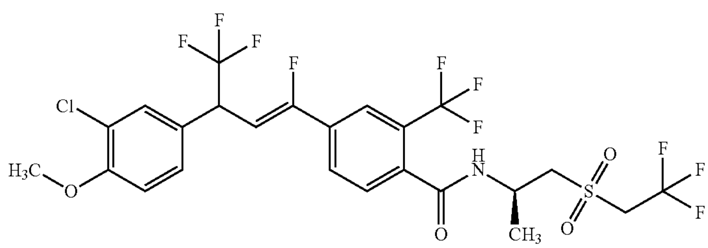 [SMILES: COc1ccc(C(/C=C(\F)c2ccc(C(=O)N[C@H](C)CS(=O)(=O)CC(F)(F)F)c(C(F)(F)F)c2)C(F)(F)F)cc1Cl] | 13 |
| F143 | 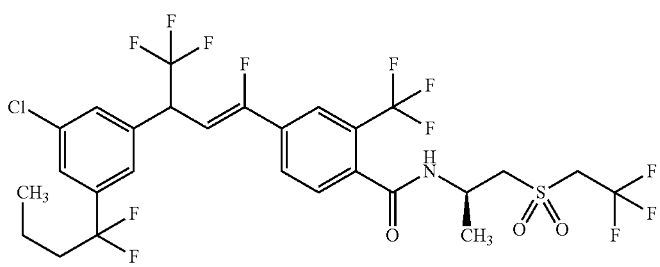 [SMILES: CCCC(F)(F)c1cc(Cl)cc(C(/C=C(\F)c2ccc(C(=O)N[C@H](C)CS(=O)(=O)CC(F)(F)F)c(C(F)(F)F)c2)C(F)(F)F)c1] | 13 |
*prepared according to example number
TABLE 3
Structure and Preparation Method for C Series Molecules
| No. | Structure | Prep.* |
|---|---|---|
| C1 | 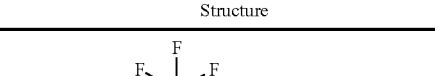 | 1 |

TABLE 3-continued

Structure and Preparation Method for C Series Molecules

| No. | Structure | Prep.* |
|---|---|---|
| C2 | 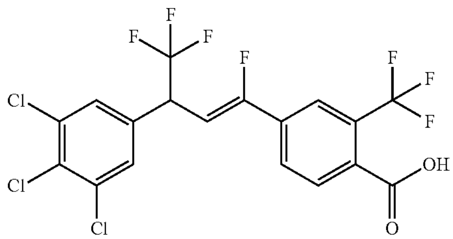 | 1 |
| C3 | 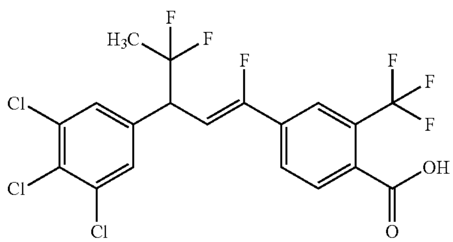 [SMILES: CC(F)(F)C(/C=C(\F)c1ccc(C(=O)O)c(C(F)(F)F)c1)c1cc(Cl)c(Cl)c(Cl)c1] | 1 |
| C4 | 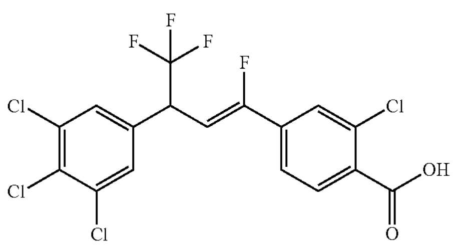 | 1 |
| C5 | 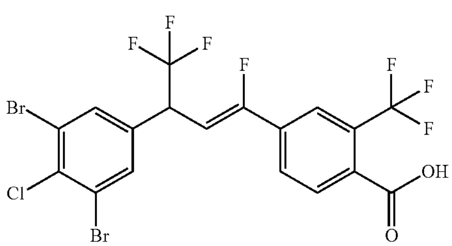 | 1 |
| C6 | 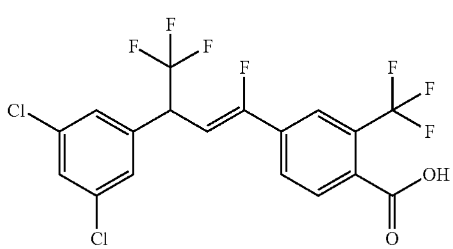 | 1 |
| C7 | 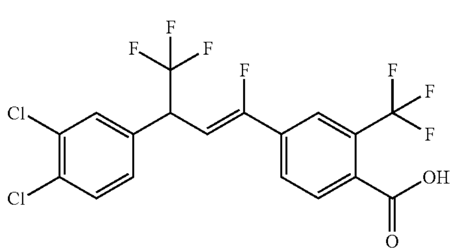 | 1 |

TABLE 3-continued

Structure and Preparation Method for C Series Molecules

| No. | Structure | Prep.* |
|---|---|---|
| C8 | 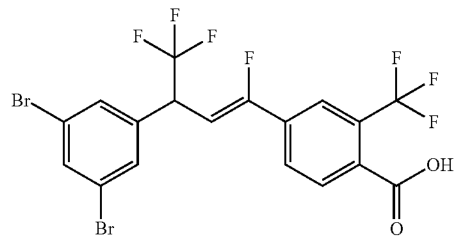 [SMILES: O=C(O)c1ccc(/C(F)=C/C(c2cc(Cl)cc(Cl)c2)C(F)(F)F)cc1C(F)(F)F] | 1 |
| C9 | 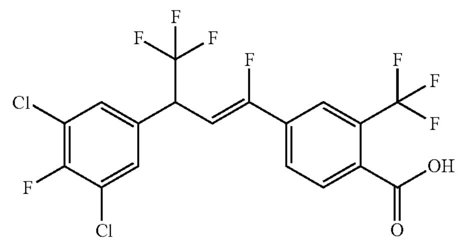 [SMILES: O=C(O)c1ccc(/C(F)=C/C(c2cc(Cl)c(F)c(Cl)c2)C(F)(F)F)cc1C(F)(F)F] | 1 |
| C10 | 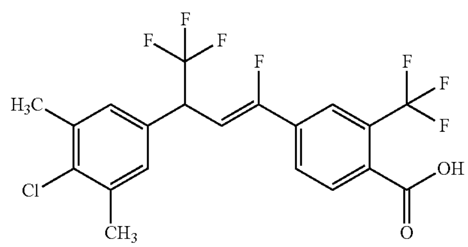 [SMILES: Cc1cc(C(/C=C(\F)c2ccc(C(=O)O)c(C(F)(F)F)c2)C(F)(F)F)cc(C)c1Cl] | 1 |
| C11 | 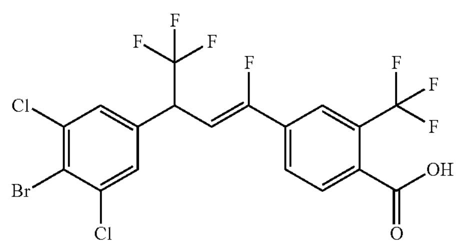 | 1 |
| C12 | 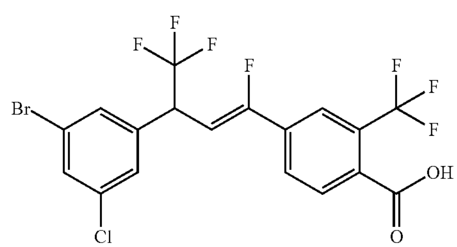 | 1 |
| C13 | 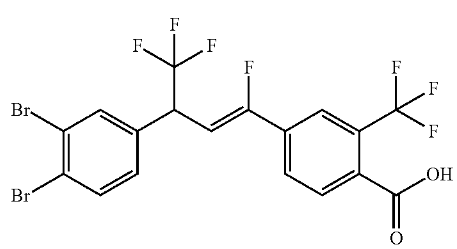 | 1 |

TABLE 3-continued
Structure and Preparation Method for C Series Molecules
| No. | Structure | Prep.* |
|---|---|---|
| C14 | 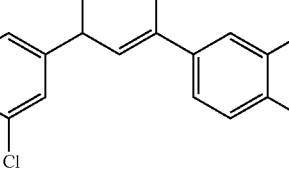 | 1 |
| C15 | 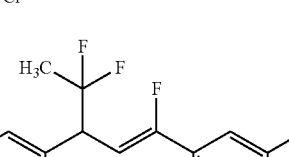 | 1 |
| C16 | 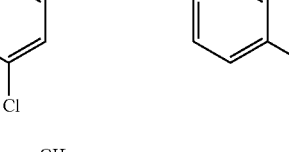 | 1 |
| C17 | 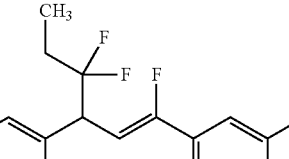 | 1 |
| C18 | 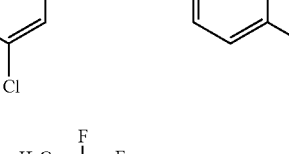 | 1 |
| C19 | 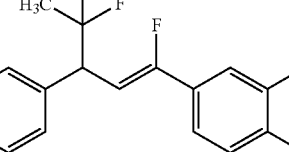 | 1 |

TABLE 3-continued

Structure and Preparation Method for C Series Molecules

| No. | Structure | Prep.* |
|---|---|---|
| C20 | 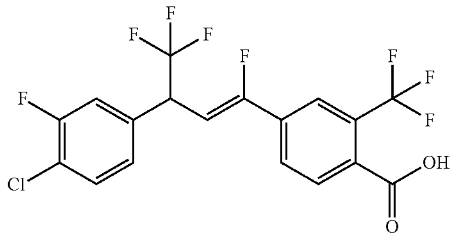 [SMILES: O=C(O)c1ccc(/C(F)=C/C(c2ccc(Cl)c(F)c2)C(F)(F)F)cc1C(F)(F)F] | 1 |
| C21 | 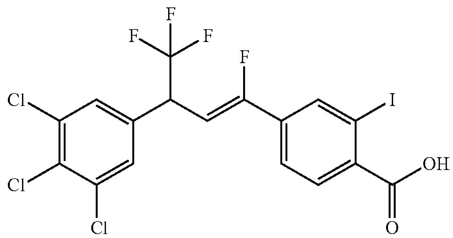 [SMILES: O=C(O)c1ccc(/C(F)=C/C(c2cc(Cl)c(Cl)c(Cl)c2)C(F)(F)F)cc1I] | 2 |
| C22 | 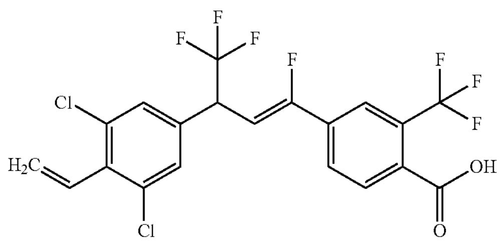 [SMILES: C=Cc1c(Cl)cc(C(/C=C(\F)c2ccc(C(=O)O)c(C(F)(F)F)c2)C(F)(F)F)cc1Cl] | 3 |
| C23 | 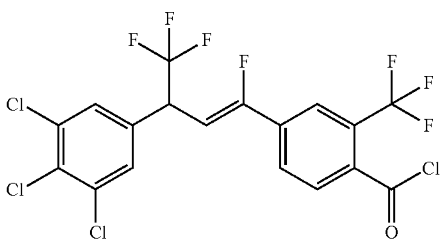 [SMILES: O=C(Cl)c1ccc(/C(F)=C/C(c2cc(Cl)c(Cl)c(Cl)c2)C(F)(F)F)cc1C(F)(F)F] | 4 |
| C24 | 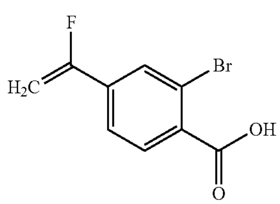 | 5 |
| C25 | 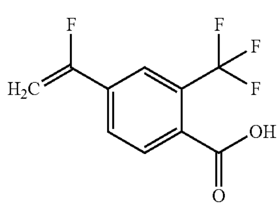 [SMILES: C=C(F)c1ccc(C(=O)O)c(C(F)(F)F)c1] | 5, 7 |

TABLE 3-continued

Structure and Preparation Method for C Series Molecules

| No. | Structure | Prep.* |
|---|---|---|
| C26 | 4-(1-fluorovinyl)-2-chlorobenzoic acid | 5 |
| C27 | 4-(1-fluorovinyl)-2-methylbenzoic acid | 5, 7 |
| C28 | methyl 4-(1-fluorovinyl)-2-(trifluoromethyl)benzoate | 6 |
| C29 | methyl 4-(1-fluorovinyl)-2-bromobenzoate | 6 |
| C30 | methyl 4-(1-fluorovinyl)-2-chlorobenzoate | 6 |
| C31 | methyl 4-(1-fluorovinyl)-2-methylbenzoate | 6 |
| C32 | 4-(2-bromo-1-fluoroethyl)-2-(trifluoromethyl)benzoic acid | 7 |

TABLE 3-continued

Structure and Preparation Method for C Series Molecules

| No. | Structure | Prep.* |
|-----|-----------|--------|
| C33 | 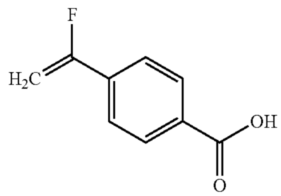 | 7 |
| C34 | 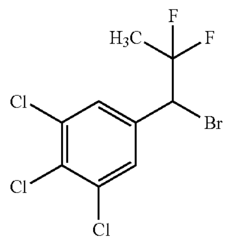 | 8 |
| C35 | 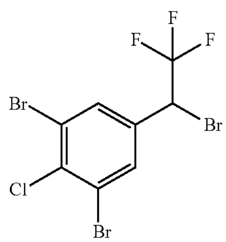 | 8 |
| C36 | 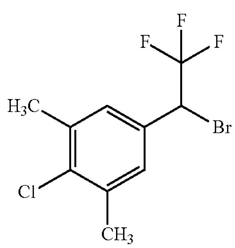 | 8 |
| C37 | 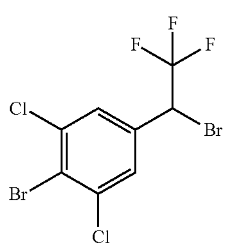 | 8 |
| C38 | 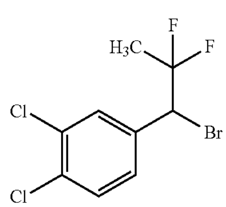 | 8 |

TABLE 3-continued

Structure and Preparation Method for C Series Molecules

| No. | Structure | Prep.* |
|---|---|---|
| C39 | 1-(3-bromo-4-chlorophenyl)-2,2,2-trifluoro-1-bromoethane | 8 |
| C40 | 1-(3-chloro-4-fluorophenyl)-2,2,2-trifluoro-1-bromoethane | 8 |
| C41 | 1-(4-chloro-3-fluorophenyl)-2,2,2-trifluoro-1-bromoethane | 8 |
| C42 | 1-(3,4,5-trichlorophenyl)-2,2-difluoro-1-bromobutane | 9 |
| C43 | 1-(3,4,5-trichlorophenyl)-2,2-difluoropropan-1-ol | 10 |
| C44 | 1-(3,4,5-trichlorophenyl)-2,2-difluorobutan-1-ol | 10 |

TABLE 3-continued

Structure and Preparation Method for C Series Molecules

| No. | Structure | Prep.* |
|---|---|---|
| C45 | 3,4-dichlorophenyl-C(OH)H-C(CH₃)F₂ | 10 |
| C46 | 3-bromo-4-chlorophenyl-C(OH)H-CF₃ | 11 |
| C47 | 3,5-dibromo-4-chlorophenyl-C(OH)H-CF₃ | 11 |
| C48 | 4-chloro-3,5-dimethylphenyl-C(OH)H-CF₃ | 11 |
| C49 | 4-bromo-3,5-dichlorophenyl-C(OH)H-CF₃ | 11 |
| C50 | 3-chloro-4-fluorophenyl-C(OH)H-CF₃ | 11 |
| C51 | 4-chloro-3-fluorophenyl-C(OH)H-CF₃ | 11 |

TABLE 3-continued

Structure and Preparation Method for C Series Molecules

| No. | Structure | Prep.* |
|---|---|---|
| C52 | 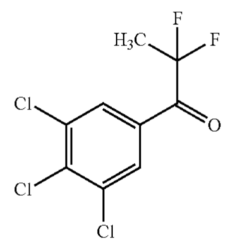 | 12 |
| C53 | 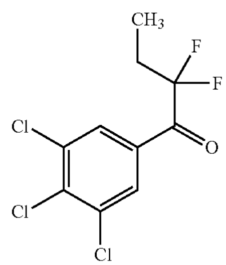 [SMILES: CCC(F)(F)C(=O)c1cc(Cl)c(Cl)c(Cl)c1] | 12 |
| C54 | 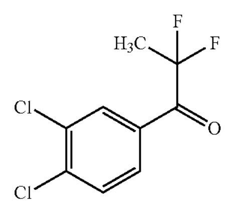 | 12 |
| C55 | 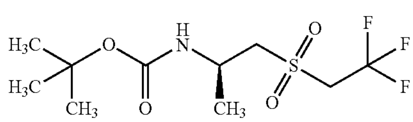 [SMILES: C[C@H](CS(=O)(=O)CC(F)(F)F)NC(=O)OC(C)(C)C] | 15 |
| C56 | 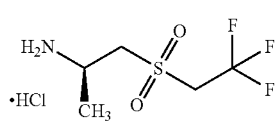 | 19 |
| C57 | 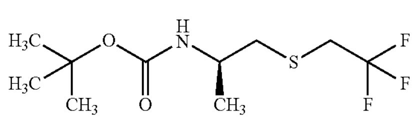 [SMILES: C[C@H](CSCC(F)(F)F)NC(=O)OC(C)(C)C] | 20 |
| C58 | 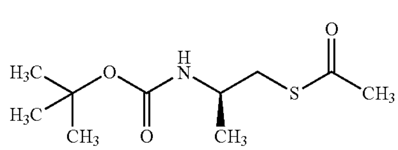 | 21 |
| C59 | 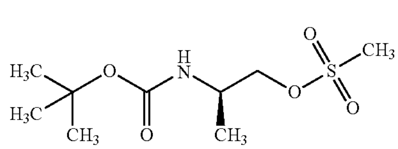 [SMILES: C[C@H](COS(C)(=O)=O)NC(=O)OC(C)(C)C] | 22 |

TABLE 3-continued

Structure and Preparation Method for C Series Molecules

| No. | Structure | Prep.* |
|---|---|---|
| C60 | 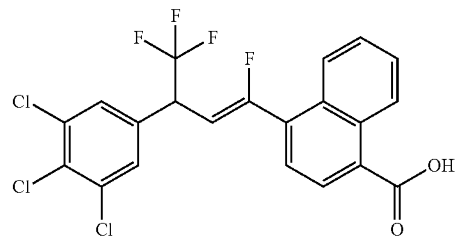 [SMILES: O=C(O)c1ccc(/C(F)=C/C(c2cc(Cl)c(Cl)c(Cl)c2)C(F)(F)F)c2ccccc12] | 1 |
| C61 | 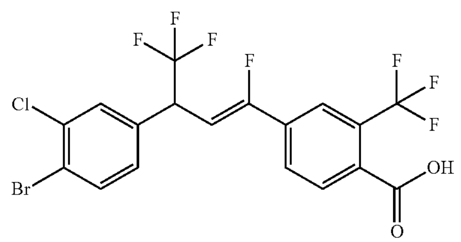 | 1 |
| C62 | 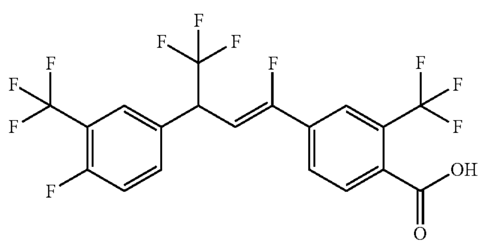 [SMILES: O=C(O)c1ccc(/C(F)=C/C(c2ccc(F)c(C(F)(F)F)c2)C(F)(F)F)cc1C(F)(F)F] | 1 |
| C63 | 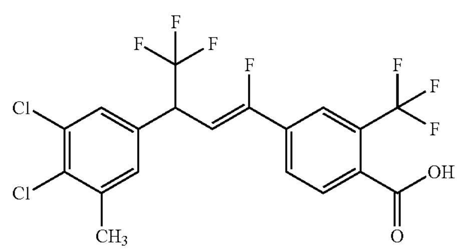 [SMILES: Cc1cc(C(/C=C(\F)c2ccc(C(=O)O)c(C(F)(F)F)c2)C(F)(F)F)cc(Cl)c1Cl] | 1 |
| C64 | 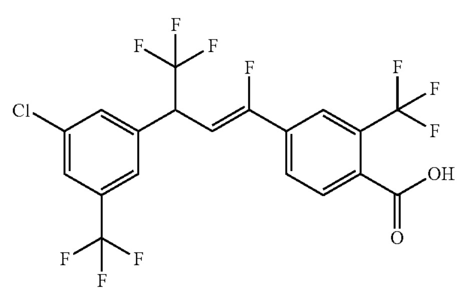 [SMILES: O=C(O)c1ccc(/C(F)=C/C(c2cc(Cl)cc(C(F)(F)F)c2)C(F)(F)F)cc1C(F)(F)F] | 1 |
| C65 | 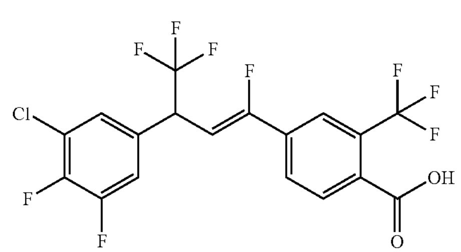 [SMILES: O=C(O)c1ccc(/C(F)=C/C(c2cc(F)c(F)c(Cl)c2)C(F)(F)F)cc1C(F)(F)F] | 1 |

TABLE 3-continued

Structure and Preparation Method for C Series Molecules

| No. | Structure | Prep.* |
|---|---|---|
| C66 | 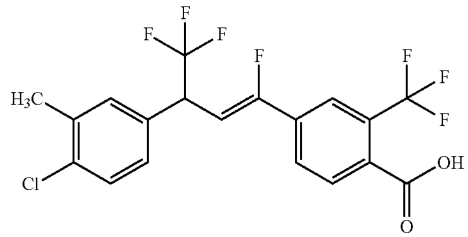 [SMILES: Cc1cc(C(/C=C(\F)c2ccc(C(=O)O)c(C(F)(F)F)c2)C(F)(F)F)ccc1Cl] | 1 |
| C67 | 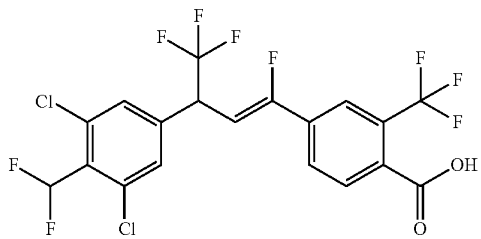 [SMILES: O=C(O)c1ccc(/C(F)=C/C(c2cc(Cl)c(C(F)F)c(Cl)c2)C(F)(F)F)cc1C(F)(F)F] | 1 |
| C68 | 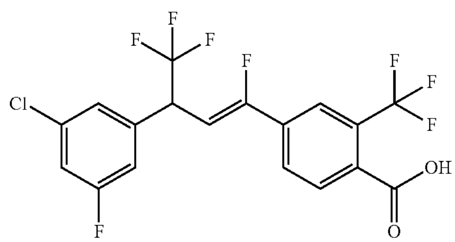 [SMILES: O=C(O)c1ccc(/C(F)=C/C(c2cc(F)cc(Cl)c2)C(F)(F)F)cc1C(F)(F)F] | 1 |
| C69 | 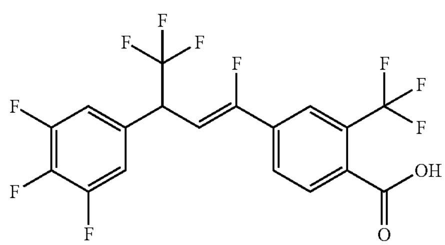 [SMILES: O=C(O)c1ccc(/C(F)=C/C(c2cc(F)c(F)c(F)c2)C(F)(F)F)cc1C(F)(F)F] | 1 |
| C70 | 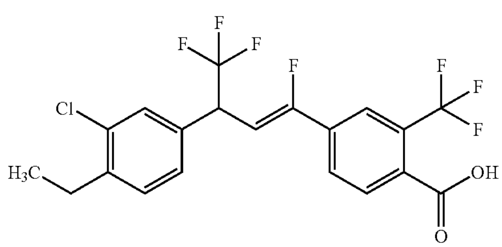 [SMILES: CCc1ccc(C(/C=C(\F)c2ccc(C(=O)O)c(C(F)(F)F)c2)C(F)(F)F)cc1Cl] | 1 |
| C71 | 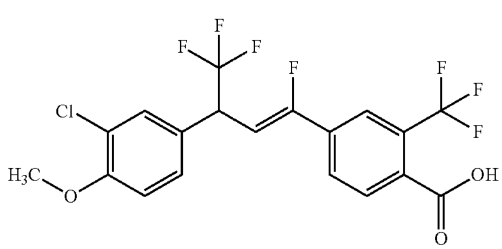 [SMILES: COc1ccc(C(/C=C(\F)c2ccc(C(=O)O)c(C(F)(F)F)c2)C(F)(F)F)cc1Cl] | 1 |

TABLE 3-continued

Structure and Preparation Method for C Series Molecules

| No. | Structure | Prep.* |
|---|---|---|
| C72 | 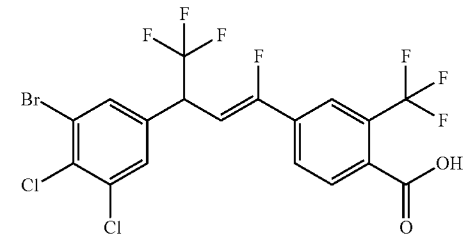 | 1 |
| C73 | 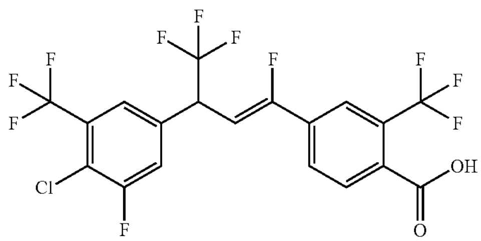 [SMILES: O=C(O)c1ccc(/C(F)=C/C(c2cc(F)c(Cl)c(C(F)(F)F)c2)C(F)(F)F)cc1C(F)(F)F] | 1 |
| C74 | 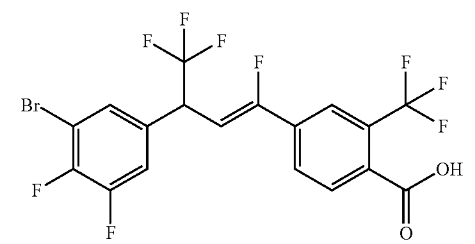 | 1 |
| C75 | 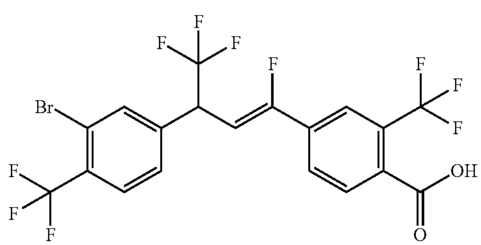 | 1 |
| C76 | 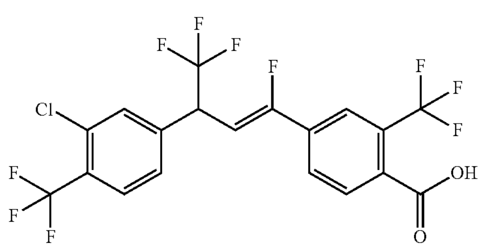 | 1 |
| C77 | 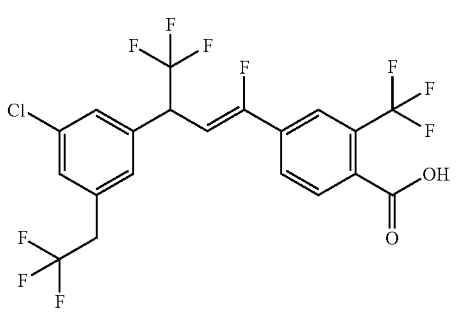 [SMILES: O=C(O)c1ccc(/C(F)=C/C(c2cc(Cl)cc(CC(F)(F)F)c2)C(F)(F)F)cc1C(F)(F)F] | 1 |

TABLE 3-continued

Structure and Preparation Method for C Series Molecules

| No. | Structure | Prep.* |
|-----|-----------|--------|
| C78 | 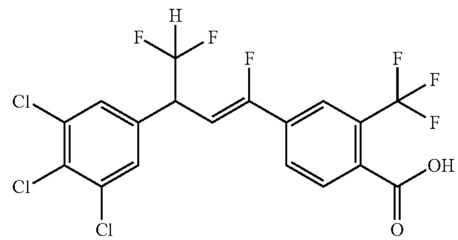 [SMILES: O=C(O)c1ccc(/C(F)=C/C(c2cc(Cl)c(Cl)c(Cl)c2)C(F)F)cc1C(F)(F)F] | 1 |
| C79 | 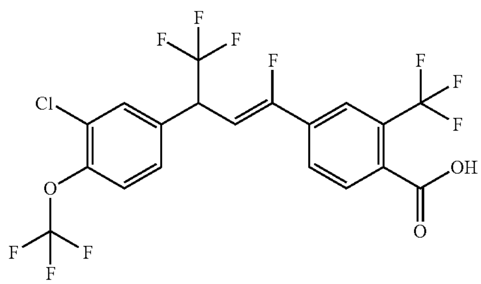 [SMILES: O=C(O)c1ccc(/C(F)=C/C(c2ccc(OC(F)(F)F)c(Cl)c2)C(F)(F)F)cc1C(F)(F)F] | 1 |
| C80 | 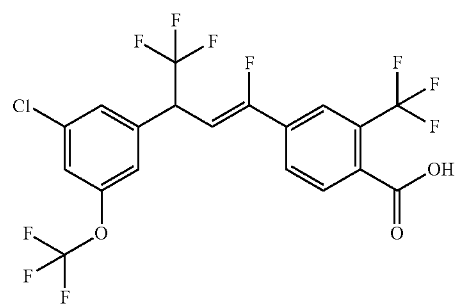 | 1 |
| C81 | 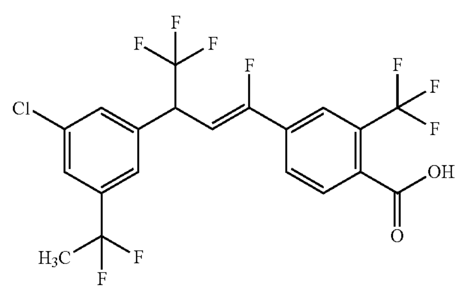 [SMILES: CC(F)(F)c1cc(Cl)cc(C(/C=C(\F)c2ccc(C(=O)O)c(C(F)(F)F)c2)C(F)(F)F)c1] | 1 |
| C82 | 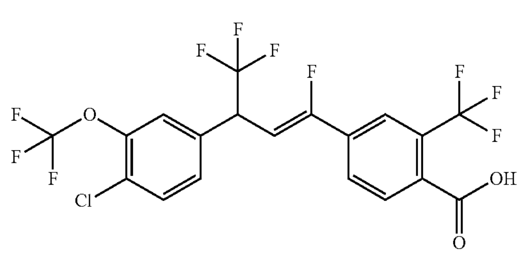 [SMILES: O=C(O)c1ccc(/C(F)=C/C(c2ccc(Cl)c(OC(F)(F)F)c2)C(F)(F)F)cc1C(F)(F)F] | 1 |

TABLE 3-continued
Structure and Preparation Method for C Series Molecules
| No. | Structure | Prep.* |
|---|---|---|
| C83 | 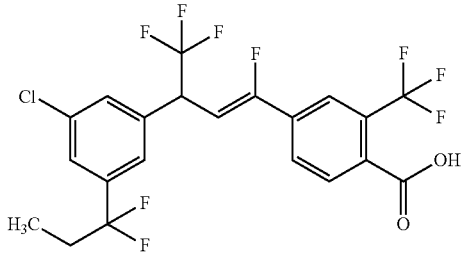 [SMILES: CCC(F)(F)c1cc(Cl)cc(C(/C=C(\F)c2ccc(C(=O)O)c(C(F)(F)F)c2)C(F)(F)F)c1] | 1 |
| C84 | 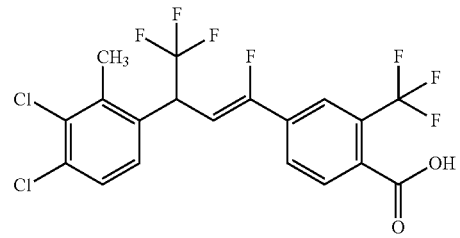 [SMILES: Cc1c(C(/C=C(\F)c2ccc(C(=O)O)c(C(F)(F)F)c2)C(F)(F)F)ccc(Cl)c1Cl] | 1 |
| C85 | 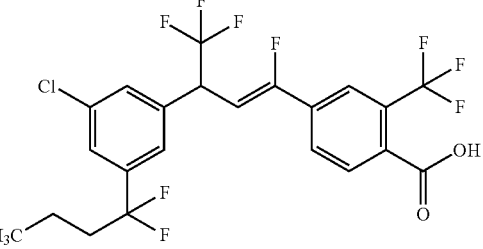 | 1 |
| C86 | 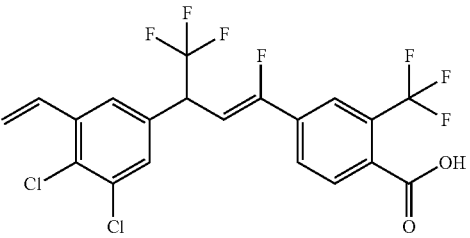 [SMILES: C=Cc1cc(C(/C=C(\F)c2ccc(C(=O)O)c(C(F)(F)F)c2)C(F)(F)F)cc(Cl)c1Cl] | 3 |
| C87 | 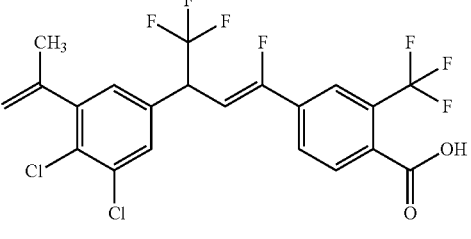 | 3 |
| C88 | 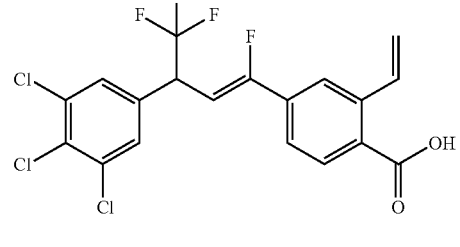 | 3 |

TABLE 3-continued

Structure and Preparation Method for C Series Molecules

| No. | Structure | Prep.* |
|---|---|---|
| C89 | 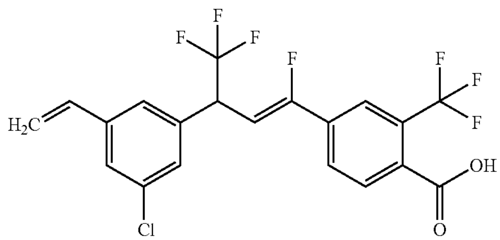 [SMILES: C=Cc1cc(Cl)cc(C(/C=C(\F)c2ccc(C(=O)O)c(C(F)(F)F)c2)C(F)(F)F)c1] | 3 |
| C90 | 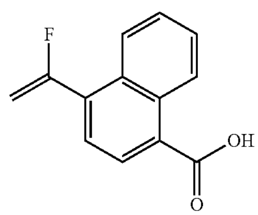 [SMILES: C=C(F)c1ccc(C(=O)O)c2ccccc12] | 7 |
| C91 | 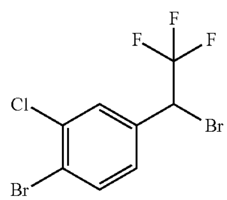 | 8 |
| C92 | 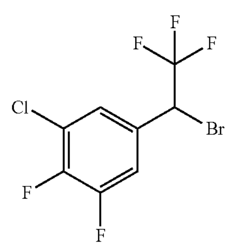 [SMILES: Fc1cc(C(Br)C(F)(F)F)cc(Cl)c1F] | 8 |
| C93 | 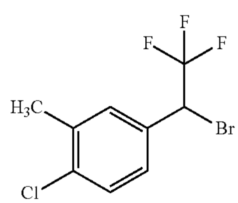 | 8 |
| C94 | 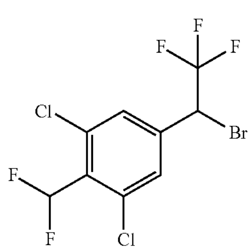 [SMILES: FC(F)c1c(Cl)cc(C(Br)C(F)(F)F)cc1Cl] | 8 |

TABLE 3-continued
Structure and Preparation Method for C Series Molecules
| No. | Structure | Prep.* |
|---|---|---|
| C95 | 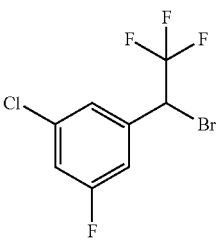 | 8 |
| C96 | 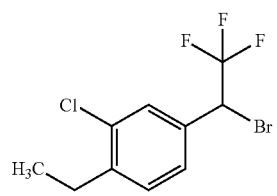 | 8 |
| C97 | 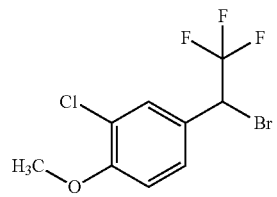 | 8 |
| C98 | 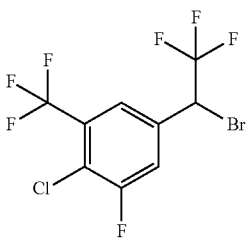 [SMILES: Fc1cc(C(Br)C(F)(F)F)cc(C(F)(F)F)c1Cl] | 8 |
| C99 | 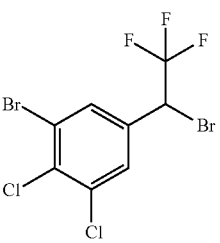 | 8 |
| C100 | 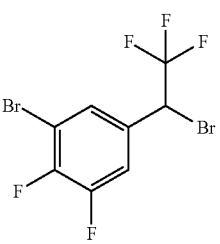 | 8 |

TABLE 3-continued

Structure and Preparation Method for C Series Molecules

| No. | Structure | Prep.* |
|---|---|---|
| C101 | 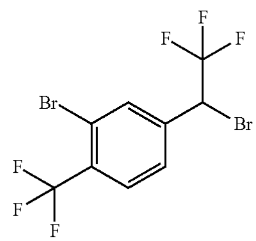 [SMILES: FC(F)(F)c1ccc(C(Br)C(F)(F)F)cc1Br] | 8 |
| C102 | 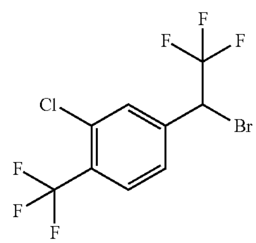 [SMILES: FC(F)(F)c1ccc(C(Br)C(F)(F)F)cc1Cl] | 8 |
| C103 | 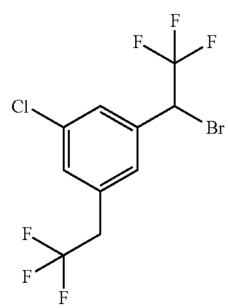 [SMILES: FC(F)(F)Cc1cc(Cl)cc(C(Br)C(F)(F)F)c1] | 8 |
| C104 | 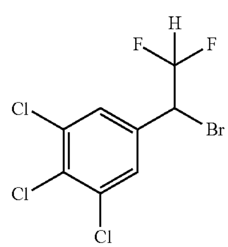 [SMILES: FC(F)C(Br)c1cc(Cl)c(Cl)c(Cl)c1] | 8 |
| C105 | 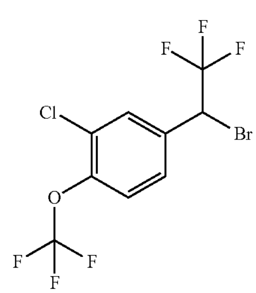 [SMILES: FC(F)(F)Oc1ccc(C(Br)C(F)(F)F)cc1Cl] | 8 |

TABLE 3-continued
Structure and Preparation Method for C Series Molecules
| No. | Structure | Prep.* |
|---|---|---|
| C106 | 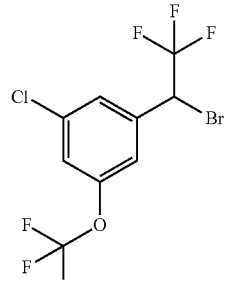 | 8 |
| C107 | 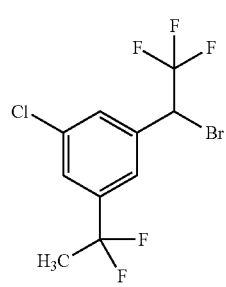 [SMILES: CC(F)(F)c1cc(Cl)cc(C(Br)C(F)(F)F)c1] | 8 |
| C108 | 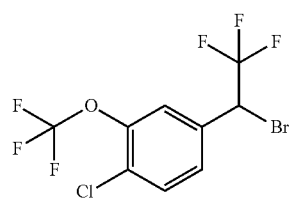 | 8 |
| C109 | 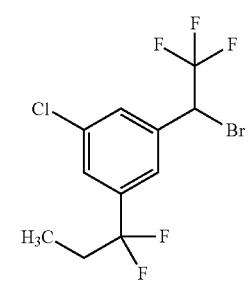 | 8 |
| C110 | 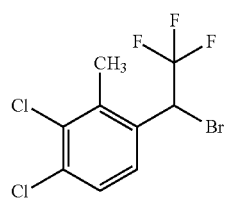 | 8 |
| C111 | 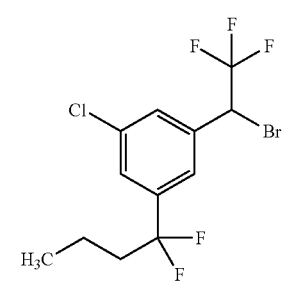 [SMILES: CCCC(F)(F)c1cc(Cl)cc(C(Br)C(F)(F)F)c1] | 8 |

TABLE 3-continued

Structure and Preparation Method for C Series Molecules

| No. | Structure | Prep.* |
|---|---|---|
| C112 | 3,4,5-trichlorophenyl-CHF$_2$-CH(OH) | 10 |
| C113 | 4-chloro-3-fluoro-5-(trifluoromethyl)phenyl-CF$_3$-CH(OH) | 10 |
| C114 | 3-bromo-4,5-dichlorophenyl-CF$_3$-CH(OH) | 10 |
| C115 | 3-bromo-4,5-difluorophenyl-CF$_3$-CH(OH) | 10 |
| C116 | 3,5-dichloro... | 10 |
| C117 | 4-bromo-3-chlorophenyl-CF$_3$-CH(OH) | 11 |

TABLE 3-continued

Structure and Preparation Method for C Series Molecules

| No. | Structure | Prep.* |
|---|---|---|
| C118 | 1-(4-chloro-3-methylphenyl)-2,2,2-trifluoroethan-1-ol | 11 |
| C119 | 1-(3-chloro-4,5-difluorophenyl)-2,2,2-trifluoroethan-1-ol | 11 |
| C120 | 1-(3,5-dichloro-4-(difluoromethyl)phenyl)-2,2,2-trifluoroethan-1-ol | 11 |
| C121 | 1-(3-chloro-4-ethylphenyl)-2,2,2-trifluoroethan-1-ol | 11 |
| C122 | 1-(3-chloro-4-methoxyphenyl)-2,2,2-trifluoroethan-1-ol | 11 |
| C123 | 1-(3-bromo-4-(trifluoromethyl)phenyl)-2,2,2-trifluoroethan-1-ol | 11 |

TABLE 3-continued

Structure and Preparation Method for C Series Molecules

| No. | Structure | Prep.* |
|---|---|---|
| C124 | 3-chloro-4-(trifluoromethyl)phenyl-CH(OH)-CF3 | 11 |
| C125 | 3-chloro-5-(2,2,2-trifluoroethyl)phenyl-CH(OH)-CF3 | 11 |
| C126 | 3-chloro-4-(trifluoromethoxy)phenyl-CH(OH)-CF3 | 11 |
| C127 | 3-chloro-5-(trifluoromethoxy)phenyl-CH(OH)-CF3 | 11 |
| C128 | 3-chloro-5-(1,1-difluoroethyl)phenyl-CH(OH)-CF3 | 11 |

TABLE 3-continued

Structure and Preparation Method for C Series Molecules

| No. | Structure | Prep.* |
|---|---|---|
| C129 | 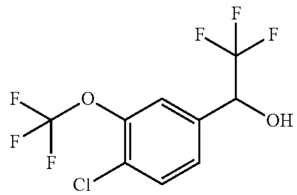 [SMILES: OC(c1ccc(Cl)c(OC(F)(F)F)c1)C(F)(F)F] | 11 |
| C130 | 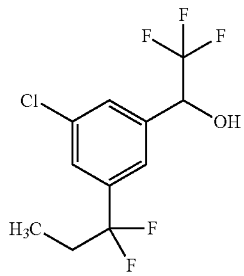 [SMILES: CCC(F)(F)c1cc(Cl)cc(C(O)C(F)(F)F)c1] | 11 |
| C131 | 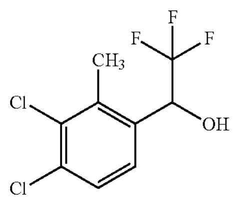 | 11 |
| C132 | 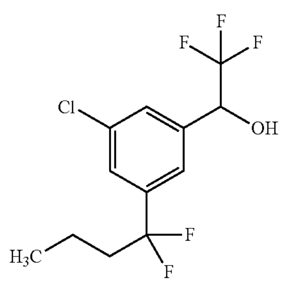 [SMILES: CCCC(F)(F)c1cc(Cl)cc(C(O)C(F)(F)F)c1] | 11 |
| C133 | 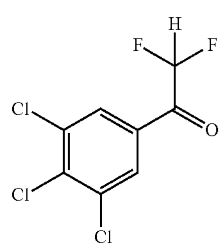 [SMILES: O=C(c1cc(Cl)c(Cl)c(Cl)c1)C(F)F] | 12 |
| C134 | 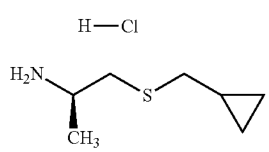 | 19 |
| C135 | 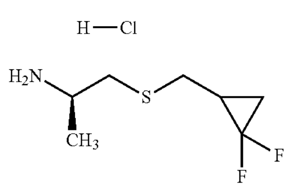 | 19 |

TABLE 3-continued

Structure and Preparation Method for C Series Molecules

| No. | Structure | Prep.* |
|---|---|---|
| C136 | H₂N–CH(CH₃)–CH₂–S–CH₂–CHF₂ · HCl | 19 |
| C137 | H₂N–CH(CH₃)–CH₂–S–CH₂–CH₂F · HCl | 19 |
| C138 | H₂N–CH₂–CH₂–S–CH₂–CH₂F · HCl | 19 |
| C139 | H₂N–CH₂–CH₂–S–CH₂–CF₂–CH₃ · HCl | 19 |
| C140 | H₂N–CH(CH₃)–CH₂–S–CH₂–CH₂–O–CH₃ · HCl | 19 |
| C141 | H₂N–CH(CH₃)–CH₂–S–CH₂–CN · HCl | 19 |
| C142 | H₂N–CH(CH₃)–CH₂–S–CH₂–CH₂–CN · HCl | 19 |
| C143 | H₂N–CH(CH₃)–CH₂–S–CH₂–CH₂–CF₃ · HCl | 19 |
| C144 | (CH₃)₃C–O–C(O)–NH–CH(CH₃)–CH₂–S–CH₂–C(CH₃)(F)(F) [Boc-protected amine with thioether to CF₂CH₃ group] | 20 |
| C145 | 4-vinyl-1-naphthoic acid | 23 |

TABLE 3-continued

Structure and Preparation Method for C Series Molecules

| No. | Structure | Prep.* |
|---|---|---|
| C146 | 3-bromo-5-chloro-1-(2,2,2-trifluoroethyl)benzene | 24 |
| C147 | 3-chloro-5-(2,2,2-trifluoroethyl)benzaldehyde | 25 |
| C148 | 1-(3-bromo-5-chlorophenyl)ethan-1-one | 26 |
| C149 | 1-(3-bromo-5-chlorophenyl)propan-1-one | 26 |
| C150 | 1-(3-bromo-5-chlorophenyl)butan-1-one | 26 |
| C151 | 1-bromo-3-chloro-5-(1,1-difluoroethyl)benzene | 27 |
| C152 | 1-bromo-3-chloro-5-(1,1-difluoropropyl)benzene | 27 |

TABLE 3-continued

Structure and Preparation Method for C Series Molecules

| No. | Structure | Prep.* |
|---|---|---|
| C153 | 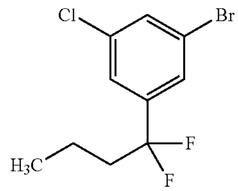 | 27 |
| C154 | 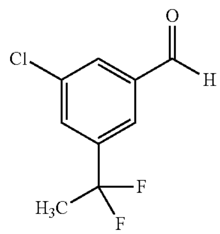 | 25 |
| C155 | 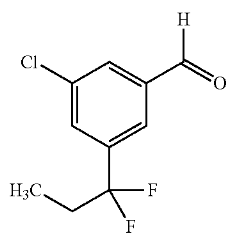 | 25 |
| C156 | 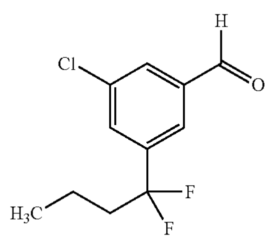 | 25 |
| C157 | 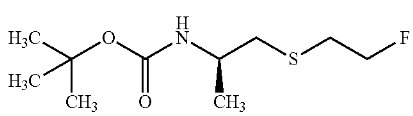 | 31 |
| C158 | 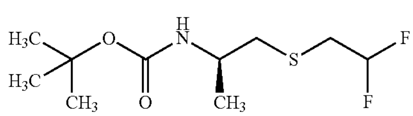 | 31 |
| C159 | 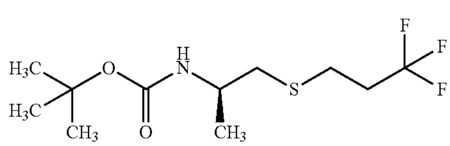 [SMILES: C[C@H](CSCCC(F)(F)F)NC(=O)OC(C)(C)C] | 31 |
| C160 | 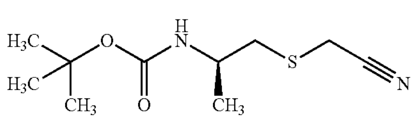 | 31 |
| C161 | 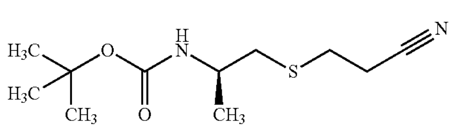 | 31 |

TABLE 3-continued

Structure and Preparation Method for C Series Molecules

| No. | Structure | Prep.* |
|---|---|---|
| C162 | 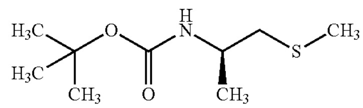 | 31 |
| C163 | 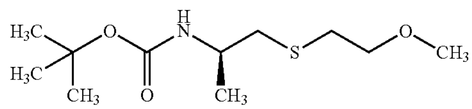 [SMILES: COCCSC[C@@H](C)NC(=O)OC(C)(C)C] | 31 |
| C164 | 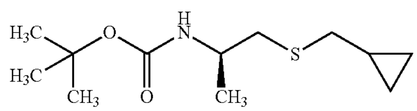 [SMILES: C[C@H](CSCC1CC1)NC(=O)OC(C)(C)C] | 31 |
| C165 | 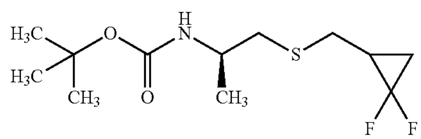 [SMILES: C[C@H](CSCC1CC1(F)F)NC(=O)OC(C)(C)C] | 31 |
| C166 | 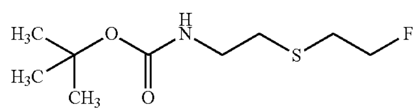 | 32 |
| C167 | 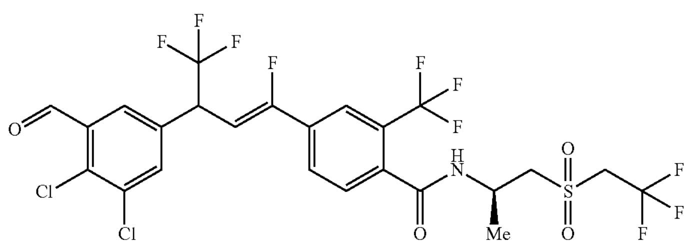 [SMILES: C[C@H](CS(=O)(=O)CC(F)(F)F)NC(=O)c1ccc(/C(F)=C/C(c2cc(Cl)c(Cl)c(C=O)c2)C(F)(F)F)cc1C(F)(F)F] | 33 |
| C168 | 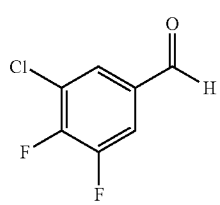 [SMILES: O=Cc1cc(F)c(F)c(Cl)c1] | 36 |
| C169 | 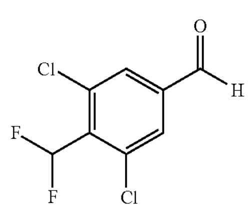 [SMILES: O=Cc1cc(Cl)c(C(F)F)c(Cl)c1] | 37 |
| C170 | 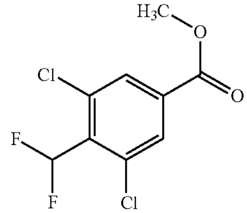 | 38 |

TABLE 3-continued

Structure and Preparation Method for C Series Molecules

| No. | Structure | Prep.* |
|---|---|---|
| C171 | 3,4-dichloro-5-methylphenyl-CH(Br)-CF3 | 8 |
| C172 | 3,4-dichloro-5-methylphenyl-CH(OH)-CF3 | 10 |
| C173 | 3,4-dichloro-5-methylphenyl-C(=O)-CF3 | 39 |

*prepared according to example number

TABLE 4

Analytical Data for Molecules in Table 2

| No. | Mp (° C.) | Mass (m/z) | $^1$H NMR | $^{13}$C NMR; $^{19}$F NMR; IR |
|---|---|---|---|---|
| F1 | | 650 ([M − H]$^-$) | $^1$H NMR (400 MHz, CDCl$_3$) δ 7.85 (d, J = 1.6 Hz, 1H), 7.77 (dd, J = 8.1, 1.7 Hz, 1H), 7.63-7.57 (m, 1H), 7.44 (s, 2H), 5.94-5.73 (m, 2H), 4.61 (p, J = 8.8 Hz, 1H), 4.49-4.31 (m, 1H), 3.29-3.06 (m, 2H), 3.00-2.78 (m, 2H), 1.34 (d, J = 6.7 Hz, 3H) | $^{19}$F NMR (376 MHz, CDCl$_3$) δ −59.01, −66.50, −69.34, −108.70--115.58 (m) |
| F2 | | 682 ([M − H]$^-$) | $^1$H NMR (400 MHz, CDCl$_3$) δ 7.83 (d, J = 1.7 Hz, 1H), 7.75 (dd, J = 8.1, 1.7 Hz, 1H), 7.61 (d, J = 8.1 Hz, 1H), 7.44 (s, 2H), 6.27 (d, J = 8.1 Hz, 1H), 5.83 (dd, J = 32.6, 9.6 Hz, 1H), 4.69 (dtd, J = 8.1, 6.7, 4.9 Hz, | $^{19}$F NMR (376 MHz, CDCl$_3$) δ −59.10, −61.14, −66.70--73.28 (m), −112.04 (t, J = 9.4 Hz) |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| | | | 1H), 4.59 (q, J = 8.9 Hz, 1H), 4.18-3.87 (m, 2H), 3.53 (dd, J = 14.5, 6.6 Hz, 1H), 3.40 (dd, J = 14.5, 5.0 Hz, 1H), 1.52 (d, J = 6.9 Hz, 3H) | |
| F3 | | 666 ([M − H]$^-$) | $^1$H NMR (400 MHz, CDCl$_3$) δ 7.83 (d, J = 1.6 Hz, 1H), 7.74 (ddd, J = 8.1, 4.6, 1.7 Hz, 1H), 7.58 (dd, J = 11.4, 8.0 Hz, 1H), 7.44 (s, 2H), 6.95-6.33 (m, 1H), 5.82 (ddd, J = 32.5, 9.6, 4.8 Hz, 1H), 4.78-4.51 (m, 2H), 3.77-3.41 (m, 2H), 3.30-3.12 (m, 2H), 1.53 (dd, J = 34.9, 6.9 Hz, 3H) | $^{19}$F NMR (376 MHz, CDCl$_3$) δ −59.02 (d, J = 4.7 Hz), −60.69 (d, J = 65.3 Hz), −67.74--70.14 (m), −110.42--113.48 (m) |
| F4 | | 596 ([M − H]$^-$) | $^1$H NMR (400 MHz, CDCl$_3$) δ 7.43 (s, 2H), 7.41 (d, J = 1.6 Hz, 1H), 7.39 (d, J = 1.1 Hz, 2H), 5.80 (d, J = 8.2 Hz, 1H), 5.71 (dd, J = 32.9, 9.6 Hz, 1H), 4.58 (p, J = 8.9 Hz, 1H), 4.39 (dtd, J = 8.4, 6.7, 5.7 Hz, 1H), 3.33-3.03 (m, 2H), 2.95 (dd, J = 13.3, 5.6 Hz, 1H), 2.85 (dd, J = 13.2, 6.5 Hz, 1H), 2.48 (d, J = 0.6 Hz, 3H), 1.35 (d, J = 6.7 Hz, 3H) | $^{19}$F NMR (376 MHz, CDCl$_3$) δ −66.41, −69.45 (d, J = 2.3 Hz), −111.59 |
| F5 | | 614 ([M + H]$^+$) | $^1$H NMR (400 MHz, CDCl$_3$) δ 7.46-7.35 (m, 5H), 6.80 (d, J = 8.0 Hz, 1H), 5.71 (ddd, J = 32.9, 9.5, 5.3 Hz, 1H), 4.78-4.49 (m, 2H), 3.86-3.45 (m, 2H), 3.35-3.04 (m, 2H), 2.46 (d, J = 3.4 Hz, 3H), 1.54 (dd, J = 35.1, 6.8 Hz, 3H) | $^{19}$F NMR (376 MHz, CDCl$_3$) δ −60.61 (d, J = 90.0 Hz), −69.45 (dd, J = 5.4, 2.2 Hz), −105.94--114.23 (m) |
| F6 | | 626 ([M − H]$^-$) | $^1$H NMR (400 MHz, CDCl$_3$) δ 7.54-7.32 (m, 5H), 6.18 (d, J = 8.1 Hz, 1H), 5.72 (dd, J = 32.9, 9.6 Hz, 1H), 4.70 (p, J = 6.7 Hz, 1H), 4.58 (p, J = 8.9 Hz, 1H), 4.22-3.88 (m, 2H), 3.60-3.32 (m, 2H), 2.47 (s, 3H), | $^{19}$F NMR (376 MHz, CDCl$_3$) δ −61.10, −69.45 (d, J = 2.3 Hz), −108.33--114.90 (m) |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| F7 | | 662 ([M + H]$^+$) | 1.55 (d, J = 6.9 Hz, 3H) $^1$H NMR (400 MHz, CDCl$_3$) δ 7.77 (d, J = 1.6 Hz, 1H), 7.66-7.49 (m, 2H), 7.42 (s, 2H), 6.07 (d, J = 8.2 Hz, 1H), 5.76 (dd, J = 32.5, 9.6 Hz, 1H), 4.58 (p, J = 8.9 Hz, 1H), 4.41 (dq, J = 8.2, 6.3 Hz, 1H), 3.29-3.07 (m, 2H), 2.92 (d, J = 5.9 Hz, 2H), 1.37 (d, J = 6.7 Hz, 3H) | $^{19}$F NMR (376 MHz, CDCl$_3$) δ −66.44, −69.37 (d, J = 2.3 Hz), −111.87 (d, J = 13.2 Hz) |
| F8 | | 694 ([M − H]$^-$) | $^1$H NMR (400 MHz, CDCl$_3$) δ 7.74 (d, J = 1.4 Hz, 1H), 7.60-7.48 (m, 2H), 7.43 (s, 2H), 6.48 (d, J = 8.0 Hz, 1H), 5.77 (dd, J = 32.6, 9.6 Hz, 1H), 4.81-4.66 (m, 1H), 4.24-388 (m, 2H), 3.57 (dd, J = 14.5, 6.2 Hz, 1H), 3.40 (dd, J = 14.5, 5.2 Hz, 1H), 1.56 (d, J = 6.9 Hz, 3H) | $^{19}$F NMR (376 MHz, CDCl$_3$) δ −61.03, −69.36 (d, J = 2.3 Hz), −109.75−−113.19 (m) |
| F9 | | 676 ([M − H]$^-$) | $^1$H NMR (400 MHz, Acetone-d$_6$) δ 7.98 (t, J = 1.8 Hz, 1H), 7.90 (s, 2H), 7.76 (dd, J = 8.1, 1.7 Hz, 1H), 7.54 (dd, J = 8.0, 5.5 Hz, 1H), 6.56 (dd, J = 34.3, 9.9 Hz, 1H), 5.23-4.96 (m, 1H), 4.70-4.51 (m, 1H), 4.11-3.72 (m, 2H), 3.39-3.21 (m, 2H), 1.47 (dd, J = 10.1, 6.8 Hz, 3H) | $^{19}$F NMR (376 MHz, Acetone-d$_6$) δ 115.94 (d, J = 76.1 Hz), 107.17 (d, J = 2.6 Hz), 63.16 |
| F10 | | 616 ([M − H]$^-$) | $^1$H NMR (400 MHz, CDCl$_3$) δ 7.77-7.64 (m, 1H), 7.57 (d, J = 1.7 Hz, 1H), 7.49 (dd, J = 8.1, 1.7 Hz, 1H), 7.43 (s, 2H), 6.37 (d, J = 8.1 Hz, 1H), 5.78 (dd, J = 32.6, 9.6 Hz, 1H), 4.59 (p, J = 8.9 Hz, 1H), 4.40 (dq, J = 8.1, 6.3 Hz, 1H), 3.33-3.01 (m, 2H), 2.91 (d, J = 6.0 Hz, 2H), 1.37 (d, J = 6.7 Hz, 3H) | $^{19}$F NMR (376 MHz, CDCl$_3$) δ −66.47, −69.38, −111.97 |
| F11 | | 647 ([M − H]$^-$) | $^1$H NMR (400 MHz, Acetone-d$_6$) δ 7.90 (s, 2H), 7.83 (d, J = 1.7 Hz, | $^{19}$F NMR (376 MHz, Acetone-d$_6$) δ |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| | | | 1H), 7.73 (dd, J = 8.1, 1.7 Hz, 1H), 7.61 (d, J = 8.1 Hz, 1H), 6.56 (dd, J = 34.3, 9.9 Hz, 1H), 5.09 (p, J = 9.2 Hz, 1H), 4.84-4.62 (m, 1H), 4.53 (q, J = 9.9 Hz, 2H), 3.72 (dd, J = 14.4, 6.8 Hz, 1H), 3.55 (dd, J = 14.4, 5.7 Hz, 1H), 1.50 (d, J = 6.8 Hz, 3H) | −61.38, −70.31, −112.29--116.17 (m) |
| F12 | | 634 ([M + H]$^+$) | $^1$H NMR (400 MHz, Acetone-d$_6$) δ 7.90 (s, 2H), 7.82 (dd, J = 3.1, 1.7 Hz, 1H), 7.77-7.67 (m, 1H), 7.58 (dd, J = 8.1, 4.4 Hz, 1H), 6.56 (dd, J = 34.3, 9.9 Hz, 1H), 5.08 (p, J = 9.2 Hz, 1H), 4.63 (dqd, J = 8.0, 6.7, 3.6 Hz, 1H), 4.16-3.67 (m, 2H), 3.43-3.19 (m, 2H), 1.47 (dd, J = 9.0, 6.8 Hz, 3H) | $^{19}$F NMR (376 MHz, Acetone-d$_6$) δ −61.55 (d, J = 73.3 Hz), −70.29 (d, J = 2.6 Hz), −114.30 |
| F13 | | 594 ([M + H]$^+$) | $^1$H NMR (400 MHz, CDCl$_3$) δ 7.43-7.37 (m, 5H), 5.86-5.67 (m, 2H), 4.39 (dq, J = 8.4, 6.5 Hz, 1H), 4.26 (td, J = 14.4, 9.9 Hz, 1H), 3.28-3.09 (m, 2H), 2.95 (dd, J = 13.2, 5.6 Hz, 1H), 2.86 (dd, J = 13.3, 6.5 Hz, 1H), 2.47 (s, 3H), 1.65 (t, J = 18.4 Hz, 3H), 1.35 (d, J = 6.7 Hz, 3H) | $^{19}$F NMR (376 MHz, CDCl$_3$) δ −66.41, −95.19, −114.17 |
| F14 | | 626 ([M + H]$^+$) | $^1$H NMR (400 MHz, CDCl$_3$) δ 7.44-7.36 (m, 5H), 6.21 (d, J = 8.1 Hz, 1H), 5.77 (dd, J = 34.0, 9.9 Hz, 1H), 4.70 (dt, J = 13.3, 6.6 Hz, 1H), 4.26 (td, J = 14.3, 9.8 Hz, 1H), 4.17-3.94 (m, 3H), 3.59-3.38 (m, 2H), 2.47 (s, 3H), 1.64 (t, J = 18.4 Hz, 3H) | $^{19}$F NMR (376 MHz, CDCl$_3$) δ −61.10, −95.18, −114.25 |
| F15 | | 646 ([M − H]$^−$) | $^1$H NMR (400 MHz, CDCl$_3$) δ 7.83 (d, J = 1.7 Hz, 1H), 7.75 (dd, J = 8.1, 1.7 Hz, 1H), 7.58 (d, J = 8.1 Hz, 1H), 7.42 (s, 2H), 5.96-5.82 (m, 2H), 4.39 (dq, J = 8.3, | $^{19}$F NMR (376 MHz, CDCl$_3$) δ −58.96, −66.49, −92.97--97.94 (m), 114.62, −114.62 |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| | | | 6.3 Hz, 1H), 4.28 (td, J = 14.3, 9.8 Hz, 1H), 3.29-3.06 (m, 2H), 2.98-2.81 (m, 2H), 1.64 (t, J = 18.5 Hz, 3H), 1.34 (d, J = 6.7 Hz, 3H) | |
| F16 | | 681 ([M + H]$^+$) | $^1$H NMR (400 MHz, CDCl$_3$) δ 7.82 (d, J = 1.6 Hz, 1H), 7.74 (dd, J = 8.1, 1.7 Hz, 1H), 7.60 (d, J = 8.1 Hz, 1H), 7.42 (s, 2H), 6.24 (d, J = 8.1 Hz, 1H), 5.89 (dd, J = 33.8, 9.8 Hz, 1H), 4.78-4.61 (m, 1H), 4.27 (td, J = 14.3, 9.8 Hz, 1H), 4.09 (dq, J = 15.5, 9.1 Hz, 1H), 3.97 (dq, J = 15.5, 9.3 Hz, 1H), 3.53 (dd, J = 14.5, 6.5 Hz, 1H), 3.40 (dd, J = 14.5, 5.0 Hz, 1H), 1.64 (t, J = 18.6 Hz, 3H), 1.53 (d, J = 6.9 Hz, 3H) | $^{19}$F NMR (376 MHz, CDCl$_3$) δ −59.03, −61.13, −93.19--96.78 (m), −114.69 |
| F17 | | 648 ([M + H]$^+$) | $^1$H NMR (400 MHz, DMSO-d$_6$) δ 8.83 (d, J = 8.4 Hz, 1H), 8.14 (s, 1H), 8.08-8.07 (m, 1H), 7.81 (s, 2H), 7.69-7.64 (m, 1H), 7.63 (d, J = 8.4 Hz, 1H), 6.85 (dd, J = 36.0, 10.0 Hz, 1H), 5.23-5.18 (m, 1H), 4.78-4.70 (m, 2H), 4.56-4.53 (m, 1H), 3.59-3.49 (m, 2H), 1.13-1.09 (m, 3H) | IR (thin film) 3274, 2929, 1655, 1127 cm$^{-1}$ |
| F18 | | 666 ([M + H$_2$O]$^+$) | $^1$H NMR (400 MHz, DMSO-d$_6$) δ 8.83 (d, J = 8.4 Hz, 1H), 8.13 (s, 1H), 8.08 (d, J = 8.4 Hz, 1H), 7.79 (s, 1H), 7.74 (d, J = 8.4 Hz, 1H), 7.68-7.61 (m, 2H), 6.82 (dd, J = 36.0, 10.0 Hz, 1H), 5.20-5.16 (m, 1H), 4.78-4.70 (m, 2H), 4.57-4.50 (m, 1H), 3.59-3.49 (m, 2H), 1.13-1.09 (m, 3H) | IR (thin film) 3432, 2924, 1657, 1127 cm$^{-1}$ |
| F19 | | 616 ([M + H]$^+$) | $^1$H NMR (400 MHz, DMSO-d$_6$) δ 8.60 (d, J = 7.6 Hz, 1H), 8.12 (s, 1H), 8.06 (d, J = 8.8 Hz, | IR (thin film) 3432, 2927, 1645, |

TABLE 4-continued

Analytical Data for Molecules in Table 2

| No. | Mp (° C.) | Mass (m/z) | ¹H NMR | ¹³C NMR; ¹⁹F NMR; IR |
|---|---|---|---|---|
| | | | 1H), 7.81 (s, 2H), 7.68 (t, J = 2.0 Hz, 1H), 7.60 (d, J = 8.4 Hz, 1H), 6.84 (dd, J = 36.4, 10.4 Hz, 1H), 5.23-5.18 (m, 1H), 4.11-4.08 (m, 1H), 3.57-3.49 (m, 2H), 2.82-2.79 (m, 2H), 1.23-1.19 (m, 3H) | 1121 cm⁻¹ |
| F20 | | 616 ([M + H]⁺) | ¹H NMR (400 MHz, DMSO-d₆) δ 8.60 (d, J = 7.6 Hz, 1H), 8.12 (s, 1H), 8.06 (d, J = 8.8 Hz, 1H), 7.99 (s, 1H), 7.74 (d, J = 8.4 Hz, 1H), 7.65 (d, J = 10.4 Hz, 1H), 7.59 (d, J = 7.6 Hz, 1H), 6.82 (dd, J = 35.6, 10.4 Hz, 1H), 5.20-5.15 (m, 1H), 4.11-4.08 (m, 1H), 3.57-3.54 (m, 2H), 2.82-2.80 (m, 2H), 1.23-1.18 (m, 3H) | IR (thin film) 3432, 2928, 1645, 1260 cm⁻¹ |
| F21 | | 738 ([M + H]⁺) | ¹H NMR (300 MHz, DMSO-d₆) δ 8.61 (d, J = 8.1 Hz, 1H), 8.17 (s, 2H), 8.12 (s, 1H), 8.06 (d, J = 8.4 Hz, 1H), 7.61 (d, J = 8.1 Hz, 1H), 6.87 (dd, J = 36.0, 10.2 Hz, 1H), 5.26-5.19 (m, 1H), 4.12-4.07 (m, 1H), 3.59-3.48 (q, 2H), 2.82-2.79 (m, 2H), 1.23 (d, J = 7.2 Hz, 3H) | IR (thin film) 3422, 2925, 1646, 1260, 749 cm⁻¹ |
| F22 | 140-142 | 770 ([M + H]⁺) | ¹H NMR (300 MHz, DMSO-d₆) δ 8.84 (d, J = 8.1 Hz, 1H), 8.17 (s, 2H), 8.13 (s, 1H), 8.08 (d, J = 8.1 Hz, 1H), 7.64 (d, J = 8.1 Hz, 1H), 6.87 (dd, J = 36.0, 10.2 Hz, 1H), 5.26-5.19 (m, 1H), 4.79-4.69 (m, 2H), 4.56-4.52 (m, 1H), 3.56-3.42 (m, 2H), 1.23 (d, J = 7.2 Hz, 3H) | IR (thin film) 3422, 2925, 1646, 1260, 749 cm⁻¹ |
| F23 | 134-136 | 754 ([M + H]⁺) | ¹H NMR (400 MHz, DMSO-d₆) δ 8.87-8.76 (m, 1H), 8.17-8.04 (m, 4H), 7.64 (dd, J = 16.0, 8.4 Hz, 1H), 6.85 (dd, J = 36.0, | |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| | | | 10.4 Hz, 1H), 5.25-5.20 (m, 1H), 4.40-4.38 (m, 1H), 4.11-3.99 (m, 2H), 3.31-3.08 (m, 2H), 1.31 (d, J = 6.4 Hz, 3H) | |
| F24 | | 694 ([M + H]$^+$) | $^1$H NMR (300 MHz, DMSO-d$_6$) δ 8.61 (d, J = 8.1 Hz, 1H), 8.12-8.00 (m, 4H), 7.61 (d, J = 8.1 Hz, 1H), 6.86 (dd, J = 35.4, 9.9 Hz, 1H), 5.26-5.19 (m, 1H), 4.12-4.07 (m, 1H), 3.58-3.48 (m, 2H), 2.82-2.77 (m, 2H), 1.23 (d, J = 7.8 Hz, 3H) | IR (thin film) 3436, 2926, 1645, 1121, 750 cm$^{-1}$ |
| F25 | 135-137 | 726 ([M + H]$^+$) | $^1$H NMR (400 MHz, DMSO-d$_6$) δ 8.83 (d, J = 8.4 Hz, 1H), 8.16-8.00 (m, 4H), 7.64 (d, J = 8.0 Hz, 1H), 6.84 (dd, J = 36.0, 10.4 Hz, 1H), 5.25-5.20 (m, 1H), 4.78-4.70 (m, 2H), 4.58-4.51 (m, 1H), 3.59-3.31 (m, 2H), 1.31 (d, J = 7.2 Hz, 3H) | |
| F26 | 112-114 | 711 ([M + H]$^+$) | $^1$H NMR (300 MHz, DMSO-d$_6$) δ 8.87-8.76 (m, 1H), 8.13 (s, 1H), 8.07-8.00 (m, 3H), 7.65-7.58 (m, 1H), 6.86 (dd, J = 35.7, 9.9 Hz, 1H), 5.26-5.19 (m, 1H), 4.42-4.35 (m, 1H), 4.11-3.99 (m, 2H), 3.22-3.04 (m, 2H), 1.30 (d, J = 6.6 Hz, 3H) | |
| F27 | | 633 ([M + H]$^+$) | $^1$H NMR (400 MHz, DMSO-d$_6$) δ 8.87-8.76 (m, 1H), 8.14 (s, 1H), 8.07 (d, J = 8.0 Hz, 1H), 7.81 (s, 2H), 7.68-7.64 (m, 1H), 7.62-7.58 (m, 1H), 6.82 (dd, J = 35.6, 10.0 Hz, 1H), 5.23-5.18 (m, 1H), 4.92-4.82 (m, 1H), 4.14-3.95 (m, 2H), 3.22-3.02 (m, 2H), 1.31-1.28 (m, 3H) | IR (thin film) 3428, 2925, 1651, 1117 cm$^{-1}$ |
| F28 | | 632 ([M + H]$^+$) | $^1$H NMR (400 MHz, DMSO-d$_6$) δ 8.86-8.76 (m, 1H), 8.13 (s, 1H), | IR (thin film) 3276, 2925, |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| | | | 8.06 (d, J = 8.4 Hz, 1H), 7.99 (s, 1H), 7.74 (d, J = 8.4 Hz, 1H), 7.67-7.58 (m, 2H), 6.83 (dd, J = 36.6, 10.4 Hz, 1H), 5.20-5.15 (m, 1H), 4.39-4.38 (m, 1H), 4.11-3.98 (m, 2H), 3.19-3.05 (m, 2H), 1.23-1.18 (m, 3H) | 1651, 816 cm$^{-1}$ |
| F29 | 138-141 | 666 ([M + H]$^+$) | $^1$H NMR (400 MHz, DMSO-d$_6$) δ 8.83 (d, J = 8.0 Hz, 1H), 8.12 (s, 1H), 8.07 (d, J = 8.0 Hz, 1H), 8.00 (s, 2H), 7.64 (d, J = 8.4 Hz, 1H), 6.83 (dd, J = 35.6, 10.4 Hz, 1H), 5.24-5.23 (m, 1H), 4.78-4.70 (m, 2H), 4.56-4.53 (m, 1H), 3.59-3.46 (m, 2H), 1.31 (d, J = 6.4 Hz, 3H) | |
| F30 | | 702 ([M − H]$^−$) | $^1$H NMR (400 MHz, DMSO-d$_6$) δ 8.61 (d, J = 8.0 Hz, 1H), 8.12 (s, 1H), 8.06 (d, J = 8.0 Hz, 1H), 7.96 (s, 2H), 7.91-7.90 (m, 1H) 7.60 (d, J = 7.6 Hz, 1H), 6.85 (dd, J = 36.0, 10.0 Hz, 1H), 5.21-5.20 (m, 1H), 4.11-4.08 (m, 1H), 3.57-3.50 (m, 2H), 2.85-2.77 (m, 2H), 1.20 (d, J = 6.4 Hz, 3H) | IR (thin film) 3430, 2927, 1645, 1260, 748 cm$^{-1}$ |
| F31 | | 720 ([M + H]$^+$) | $^1$H NMR (300 MHz, DMSO-d$_6$) δ 8.87 (dd, J = 8.4, 7.8 Hz, 1H), 8.13 (s, 1H), 8.07 (d, J = 8.1 Hz, 1H), 7.96 (s, 2H), 7.90 (s, 1H), 7.64-7.58 (m, 1H), 6.87 (dd, J = 36.0, 9.9 Hz, 1H), 5.22-5.20 (m, 1H), 4.42-4.37 (m, 1H), 4.11-3.99 (m, 2H), 3.19-3.08 (m, 2H), 1.31 (d, J = 3.0 Hz, 3H) | IR (thin film) 3277, 2926, 1651, 1135, 646 cm$^{-1}$ |
| F32 | 70-72 | 642 ([M + H]$^+$) | $^1$H NMR (400 MHz, CDCl$_3$) δ 7.85 (s, 1H), 7.79 (d, J = 8.4 Hz, 1H), 7.62 (d, J = 7.6 Hz, 1H), 7.42 (s, 1H), 7.37 (s, 1H), 6.72-6.62 (dd, J = 17.6, | |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| | | | 11.6 Hz, 1H), 5.86-5.76 (m, 3H), 4.62-4.57 (m, 1H), 4.22-4.38 (m, 1H), 3.19-3.14 (m, 2H), 2.91-2.88 (m, 2H), 1.35 (d, J = 6.8 Hz, 3H) | |
| F33 | 125-128 | 674 ([M + H]$^+$) | $^1$H NMR (400 MHz, CDCl$_3$) δ 7.86 (s, 1H), 7.79 (d, J = 8.4 Hz, 1H), 7.66 (d, J = 8.0 Hz, 1H), 7.41 (s, 1H), 7.37 (s, 1H), 6.71-6.63 (dd, J = 17.6, 11.6 Hz, 1H), 6.12 (d, J = 8.0 Hz, 1H), 5.87-5.74 (m, 2H), 4.73-4.69 (m, 1H), 4.61-4.57 (m, 1H), 4.12-3.93 (m, 2H), 3.56-3.49 (m, 1H), 3.44-3.39 (m, 1H), 1.56 (d, J = 6.8 Hz, 3H) | |
| F34 | 88-90 | 658 ([M + H]$^+$) | $^1$H NMR (300 MHz, CDCl$_3$) δ 7.85 (s, 1H), 7.80 (d, J = 7.8 Hz, 1H), 7.60 (d, J = 8.1 Hz, 1H), 7.42 (s, 1H), 7.36 (s, 1H), 6.79-6.76 (m, 1H), 6.14-6.12 (m, 1H), 5.89-5.74 (m, 2H), 4.66-4.56 (m, 2H), 3.57-3.51 (m, 2H), 3.27-3.13 (m, 2H), 1.52 (d, J = 6.9 Hz, 3H) | |
| F35 | | 642 ([M + H]$^+$) | $^1$H NMR (300 MHz, DMSO-d$_6$) δ 8.83 (d, J = 8.1 Hz, 1H), 8.09 (s, 1H), 8.07 (d, J = 8.4 Hz, 1H), 7.63 (d, J = 8.1 Hz, 1H), 7.44 (s, 2H), 6.78 (dd, J = 35.7, 9.9 Hz, 1H), 4.95-4.89 (m, 1H), 4.79-4.69 (m, 2H), 4.56-4.51 (m, 1H), 3.60-3.53 (m, 2H), 2.35 (s, 6H), 1.31 (d, J = 7.2 Hz, 3H) | IR (thin film) 3278, 2929, 1654, 854 cm$^{-1}$ |
| F36 | | 635 ([M + H]$^+$) | $^1$H NMR (300 MHz, DMSO-d$_6$) δ 8.61 (d, J = 8.1 Hz, 1H), 8.11 (s, 1H), 8.05 (d, J = 8.4 Hz, 2H), 8.00 (d, J = 6.3 Hz, 1H), 7.61 (d, J = 8.1 Hz, 1H), 6.85 (dd, | IR (thin film) 3433, 2926, 1651, 1261, 750 cm$^{-1}$ |

TABLE 4-continued

Analytical Data for Molecules in Table 2

| No. | Mp (° C.) | Mass (m/z) | ¹H NMR | ¹³C NMR; ¹⁹F NMR; IR |
|---|---|---|---|---|
| | | | J = 36.0, 10.2 Hz, 1H), 5.24-5.23 (m, 1H), 4.12-4.07 (m, 1H), 3.58-3.48 (m, 2H), 2.82-2.80 (m, 2H), 1.28 (d, J = 7.5 Hz, 3H) | |
| F37 | | 650 ([M + H]⁺) | ¹H NMR (300 MHz, DMSO-d₆) δ 8.87 (dd, J = 8.1, 8.1 Hz, 1H), 8.13 (s, 1H), 8.07 (d, J = 7.8 Hz, 1H), 8.01 (d, J = 6.6 Hz, 2H), 7.61-7.58 (m, 1H), 6.85 (dd, J = 36.0, 10.2 Hz, 1H), 5.25-5.24 (m, 1H), 4.40-4.38 (m, 1H), 4.10-3.99 (m, 2H), 3.16-3.08 (m, 2H), 1.31 (d, J = 3.3 Hz, 3H) | IR (thin film) 3271, 2926, 1652, 1140 cm⁻¹ |
| F38 | | 694 ([M + H]⁺) | ¹H NMR (400 MHz, CDCl₃) δ 7.78 (d, J = 1.8 Hz, 1H), 7.70 (dt, J = 9.4, 2.5 Hz, 1H), 7.55 (dd, J = 8.1, 4.4 Hz, 1H), 7.42 (d, J = 4.6 Hz, 2H), 6.44 (dd, J = 8.3, 3.6 Hz, 1H), 5.89 (ddd, J = 33.9, 9.7, 2.0 Hz, 1H), 4.68 (tdd, J = 8.7, 6.9, 3.4 Hz, 1H), 4.30 (td, J = 14.6, 9.8 Hz, 1H), 4.10 (dq, J = 15.5, 9.1 Hz, 1H), 3.97 (dq, J = 15.5, 9.3 Hz, 1H), 3.54 (ddd, J = 14.5, 6.7, 1.7 Hz, 1H), 3.38 (ddd, J = 14.4, 5.0, 1.7 Hz, 1H), 2.01-1.79 (m, 2H), 1.50 (dd, J = 6.9, 1.8 Hz, 3H), 1.07 (t, J = 7.4 Hz, 3H) | ¹⁹F NMR (471 MHz, CDCl₆) δ 58.99, −61.11, −102.40−−107.19 (m), −114.95 |
| F39 | | 663 ([M + H]⁺) | ¹H NMR (400 MHz, CDCl₃) δ 7.81 (d, J = 1.9 Hz, 1H), 7.72 (ddd, J = 5.9, 4.3, 1.6 Hz, 1H), 7.54 (dd, J = 8.2, 4.6 Hz, 1H), 7.42 (d, J = 4.3 Hz, 2H), 5.99-5.80 (m, 2H), 4.44-4.23 (m, 2H), 3.23-3.09 (m, 2H), 2.97-2.81 (m, 2H), 1.97-1.78 (m, 2H), 1.32 (dd, J = 6.7, 1.4 Hz, 3H), 1.07 (t, J = 7.5 Hz, 3H) | ¹⁹F NMR (471 MHz, CDCl₃) δ −58.94, −66.49, −102.19−−107.72 (m), −114.99 |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| F40 | | 650 ([M + H]$^+$) | $^1$H NMR (400 MHz, DMSO-d$_6$) δ 8.55 (d, J = 8.4 Hz, 1H), 8.11 (s, 1H), 8.05 (d, J = 8.4 Hz, 1H), 7.96 (s, 2H), 7.91-7.90 (m, 1H), 7.61 (d, J = 8.0 Hz, 1H), 6.84 (dd, J = 35.6, 10.4 Hz, 1H), 5.21-5.20 (m, 1H), 4.06-4.02 (m, 1H), 2.71-2.66 (m, 1H), 2.58-2.49 (m, 3H), 1.27-1.18 (m, 6H) | IR (thin film) 3434, 2997, 1659 cm$^{-1}$ |
| F41 | | 578 ([M − H]$^-$) | $^1$H NMR (400 MHz, DMSO-d$_6$) δ 8.55 (d, J = 8.4 Hz, 1H), 8.11 (s, 1H), 8.04 (d, J = 8.0 Hz, 1H), 8.00-7.99 (m, 2H), 7.61 (d, J = 8.4 Hz, 1H), 6.83 (dd, J = 36.0, 10.4 Hz, 1H), 5.24-5.23 (m, 1H), 4.08-4.00 (m, 1H), 2.71-2.66 (m, 1H), 2.58-2.49 (m, 3H), 1.26-1.17 (m, 6H) | IR (thin film) 3432, 1654, 1033, 749 cm$^{-1}$ |
| F42 | | 680 ([M − H]$^-$) | $^1$H NMR (400 MHz, DMSO-d$_6$) δ 8.73 (d, J = 7.6 Hz, 1H), 8.12 (s, 1H), 8.06 (d, J = 8.4 Hz, 1H), 7.95 (s, 2H), 7.90-7.89 (m, 1H), 7.65 (d, J = 7.6 Hz, 1H), 6.83 (dd, J = 15.6, 10.4 Hz, 1H), 5.20-5.19 (m, 1H), 4.50-4.43 (m, 1H), 3.34-3.33 (m, 1H), 3.29-3.26 (m, 1H), 3.17-3.12 (m, 2H), 1.29-1.22 (m, 6H) | IR (thin film) 3435, 2997, 1660, 1031 cm$^{-1}$ |
| F43 | | 610 ([M − H]$^-$) | $^1$H NMR (400 MHz, DMSO-d$_6$) δ 8.73 (d, J = 8.4 Hz, 1H), 8.11 (s, 1H), 8.06 (d, J = 8.4 Hz, 1H), 7.99 (d, J = 6.4 Hz, 2H), 7.66 (dd, J = 7.6 Hz, 1H), 6.82 (dd, J = 35.6, 10.4 Hz, 1H), 5.23-5.22 (m, 1H), 4.48-4.44 (m, 1H), 3.38-3.33 (m, 1H), 3.28-3.23 (m, 1H), 3.17-3.12 (m, 2H), 1.29-1.22 (m, 6H) | IR (thin film) 3422, 2926, 1650, 749 cm$^{-1}$ |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| F44 | | 624 ([M − H]$^-$) | $^1$H NMR (400 MHz, DMSO-d$_6$) δ 8.86 (dd, J = 32.8, 8.0 Hz, 1H), 8.10 (s, 1H), 8.06 (d, J = 8.4 Hz, 1H), 7.63-7.57 (m, 1H), 7.45 (s, 2H), 6.76 (dd, J = 36.4, 10.4 Hz, 1H), 4.90-4.84 (m, 1H), 4.41-4.36 (m, 1H), 4.14-3.99 (m, 2H), 3.22-3.04 (m, 2H), 2.49 (s, 6H), 1.33-1.24 (m, 6H) | IR (thin film) 3432, 2926, 1651 cm$^{-1}$ |
| F45 | | 592 ([M − H]$^-$) | $^1$H NMR (300 MHz, DMSO-d$_6$) δ 8.75 (d, J = 8.1 Hz, 1H), 8.13 (s, 1H), 8.07 (d, J = 7.5 Hz, 1H), 7.81 (s, 2H), 7.69-7.63 (m, 2H), 6.86 (dd, J = 36.0, 10.2 Hz, 1H), 5.24-5.13 (m, 1H), 4.49-4.43 (m, 1H), 3.41-3.34 (m, 2H), 3.24-3.13 (m, 2H), 1.29-1.21 (m, 6H) | IR (thin film) 3442, 2922, 1650, 749 cm$^{-1}$ |
| F46 | | 608 ([M − H]$^-$) | $^1$H NMR (300 MHz, DMSO-d$_6$) δ 8.75 (d, J = 8.1 Hz, 1H), 8.12 (s, 1H), 8.06 (d, J = 7.5 Hz, 1H), 7.99 (s, 1H), 7.75 (d, J = 8.4 Hz, 1H), 7.68-7.63 (m, 2H), 6.85 (dd, J = 35.7, 9.9 Hz, 1H), 5.19-5.14 (m, 1H), 4.49-4.43 (m, 1H), 3.34-3.27 (m, 2H), 3.18-3.14 (m, 2H), 1.29-1.21 (m, 6H) | IR (thin film) 3433, 2922, 1645 cm$^{-1}$ |
| F47 | | 587 ([M − H]$^-$) | $^1$H NMR (400 MHz, CDCl$_3$) δ 7.85 (s, 1H), 7.78 (d, J = 8.0 Hz, 1H), 7.64 (d, J = 8.4 Hz, 1H), 7.42 (s, 1H), 7.37 (s, 1H), 6.72-6.65 (dd, J = 17.6, 11.6 Hz, 1H), 5.91-5.84 (m, 2H), 5.79-5.73 (m, 1H), 4.61-4.57 (m, 1H), 4.40-4.37 (m, 1H), 2.82-2.62 (m, 2H), 2.62 (q, J = 8.0 Hz, 2H), 1.29-1.25 (m, 6H) | IR (thin film) 3421, 2925, 1643, 1260, 1119, 764 cm$^{-1}$ |
| F48 | | 638 ([M − H]$^-$) | $^1$H NMR (300 MHz, DMSO-d$_6$) δ 8.55 (d, J = 7.8 Hz, 1H), 8.11 (s, 1H), 8.05-8.00 (m, | IR (thin film) 3426, 1651 cm$^{-1}$ |

TABLE 4-continued

Analytical Data for Molecules in Table 2

| No. | Mp (° C.) | Mass (m/z) | ¹H NMR | ¹³C NMR; ¹⁹F NMR; IR |
|---|---|---|---|---|
| | | | 3H), 7.61 (d, J = 7.8 Hz, 1H), 6.87 (dd, J = 36.0, 10.2 Hz, 1H), 5.25-5.22 (m, 1H), 4.06-4.02 (m, 1H), 2.59-2.49 (m, 4H), 1.22 (m, 6H) | |
| F49 | | 668 ([M − H]⁻) | ¹H NMR (500 MHz, DMSO-$d_6$) δ 8.96 (t, J = 5.7 Hz, 1H), 8.13-8.11 (m, 1H), 8.09-8.03 (m, 3H), 7.65 (d, J = 8.1 Hz, 1H), 6.80 (dd, J = 35.7, 10.1 Hz, 1H), 5.25 (p, J = 9.4 Hz, 1H), 4.20-3.97 (m, 2H), 3.77-3.57 (m, 2H), 3.26-3.11 (m, 2H) | ¹⁹F NMR (471 MHz, DMSO-$d_6$) δ −57.98, −59.75 (t, J = 11.1 Hz), −68.58 (d, J = 9.0 Hz), −113.70 (d, J = 35.8 Hz) |
| F50 | | 652 ([M − H]⁻) | ¹H NMR (500 MHz, DMSO-$d_6$) δ 8.97 (t, J = 5.7 Hz, 1H), 8.13 (d, J = 1.8 Hz, 1H), 8.07 (dd, J = 8.2, 1.8 Hz, 1H), 8.05 (s, 2H), 7.65 (d, J = 8.1 Hz, 1H), 6.80 (dd, J = 35.7, 10.1 Hz, 1H), 5.25 (p, J = 9.4 Hz, 1H), 4.24-3.95 (m, 2H), 3.78-3.54 (m, 2H), 3.27-3.11 (m, 2H) | ¹⁹F NMR (471 MHz, DMSO-$d_6$) δ −57.99, −59.76 (t, J = 11.0 Hz), −68.59 (d, J = 9.1 Hz), −113.71 (d, J = 35.8 Hz) |
| F51 | | 636 ([M − H]⁻) | ¹H NMR (500 MHz, CDCl₃) δ 7.86 (d, J = 1.7 Hz, 1H), 7.78 (dd, J = 8.1, 1.7 Hz, 1H), 7.60 (d, J = 8.0 Hz, 1H), 7.44 (s, 2H), 6.16 (t, J = 6.0 Hz, 1H), 5.82 (dd, J = 32.5, 9.6 Hz, 1H), 4.61 (p, J = 8.9 Hz, 1H), 3.68 (q, J = 6.3 Hz, 2H), 3.14 (q, J = 9.8 Hz, 2H), 2.93 (t, J = 6.4 Hz, 2H) | ¹⁹F NMR (471 MHz, CDCl₃) δ −59.13, −66.46 (t, J = 9.8 Hz), −69.33 (dd, J = 8.5, 2.1 Hz), −111.95 (d, J = 32.6 Hz) |
| F52 | | 610 ([M + H]⁺) | ¹H NMR (300 MHz, DMSO-$d_6$) δ 8.60 (d, J = 7.8 Hz, 1H), 8.08 (s, 1H), 8.05 (d, J = 9.6 Hz, 1H), 7.59 (d, J = 8.1 Hz, 1H), 7.45 (s, 2H), 6.78 (dd, J = 36.0, 10.2 Hz, 1H), 4.95-4.89 (m, 1H), 4.14-4.04 (m, 1H), 3.58-3.47 (m, 2H), 2.86-2.80 (m, 2H), 2.35 (s, 6H), 1.23-1.07 (m, 3H) | IR (thin film) 3429, 2926, 1645 cm⁻¹ |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| F53 | | 588 ([M + H]$^+$) | $^1$H NMR (300 MHz, DMSO-d$_6$) δ 8.75 (d, J = 8.1 Hz, 1H), 8.09 (s, 1H), 8.06 (d, J = 8.4 Hz, 1H), 7.65 (d, J = 7.8 Hz, 1H), 7.45 (s, 2H), 6.78 (dd, J = 36.0, 9.9 Hz, 1H), 4.95-4.89 (m, 1H), 4.49-4.46 (m, 1H), 3.38-3.36 (m, 1H), 3.31-3.24 (m, 1H), 3.18-3.13 (m, 2H), 2.35 (s, 6H), 1.29-1.26 (m, 6H) | IR (thin film) 3286, 2928, 1651, 1130 cm$^{-1}$ |
| F54 | | 734 ([M − H]$^−$) | $^1$H NMR (300 MHz, DMSO-d$_6$) δ 8.83 (d, J = 8.1 Hz, 1H), 8.13 (s, 1H), 8.09 (d, J = 9.9 Hz, 2H), 7.86 (d, J = 8.4 Hz, 1H), 7.63 (d, J = 7.8 Hz, 2H), 6.85 (dd, J = 36.0, 9.9 Hz, 1H), 5.19-5.18 (m, 1H), 4.79-4.69 (m, 2H), 4.56-4.52 (m, 1H), 3.60-3.47 (m, 2H), 1.31 (d, J = 6.6 Hz, 3H) | IR (thin film) 3274, 2931, 1655, 1127 cm$^{-1}$ |
| F55 | | 684 ([M + H]$^+$) | $^1$H NMR (400 MHz, DMSO-d$_6$) δ 8.55 (d, J = 7.6 Hz, 1H), 8.19-8.17 (m, 2H), 8.11 (s, 1H), 8.05 (d, J = 8.4 Hz, 1H), 7.61 (d, J = 8.0 Hz, 1H), 6.84 (dd, J = 35.6, 10.4 Hz, 1H), 5.24-5.19 (m, 1H), 4.06-4.02 (m, 1H), 2.59-2.49 (m, 4H), 1.26-1.18 (m, 6H) | IR (thin film) 3417, 1651 cm$^{-1}$ |
| F56 | | 716 ([M + H]$^+$) | $^1$H NMR (300 MHz, DMSO-d$_6$) δ 8.75 (d, J = 6.9 Hz, 1H), 8.17-8.04 (m, 4H), 7.66 (d, J = 8.10 Hz, 1H), 6.87 (dd, J = 35.4, 10.5 Hz, 1H), 5.22-5.19 (m, 1H), 4.46-4.35 (m, 1H), 3.31-3.14 (m, 4H), 1.27-1.24 (m, 6H) | IR (thin film) 3422, 1650, 1260, 749 cm$^{-1}$ |
| F57 | | 613 ([M + H]$^+$) | $^1$H NMR (400 MHz, CDCl$_3$) δ 7.75 (d, J = 7.9 Hz, 1H), 7.58 (d, J = 8.1 Hz, 1H), 7.48 (d, J = 2.1 Hz, 1H), 7.45 (d, J = 8.3 Hz, 1H), 7.23 (dd, | $^{19}$F NMR (376 MHz, CDCl$_3$) δ −58.93, −66.49, −92.40--97.99 (m), −115.38 |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| | | | J = 8.3, 2.1 Hz, 1H), 5.92 (dd, J = 34.0, 9.8 Hz, 1H), 5.79 (d, J = 8.2 Hz, 1H), 4.46-4.23 (m, 2H), 3.29-3.04 (m, 2H), 2.98-2.79 (m, 2H), 1.62 (t, J = 18.4 Hz, 3H), 1.35 (dd, J = 6.7, 1.8 Hz, 3H) | |
| F58 | | | $^1$H NMR (400 MHz, CDCl$_3$) δ 7.75 (d, J = 1.4 Hz, 1H), 7.68-7.35 (m, 4H), 7.28-7.20 (m, 1H), 6.12 (d, J = 8.2 Hz, 1H), 5.78 (dd, J = 32.8, 9.6 Hz, 1H), 4.61 (p, J = 9.1 Hz, 1H), 4.40 (dq, J = 8.0, 6.2 Hz, 1H), 3.29-3.08 (m, 2H), 2.92 (d, J = 6.0 Hz, 2H), 1.37 (d, J = 6.7 Hz, 3H) | $^{19}$F NMR (376 MHz, CDCl$_3$) δ −66.44, −69.48, −108.63--115.35 (m) |
| F59 | | 560 ([M − H]$^-$) | $^1$H NMR (400 MHz, DMSO-d$_6$) δ 8.55 (d, J = 8.4 Hz, 1H), 8.12 (s, 1H), 8.05 (d, J = 8.0 Hz, 1H), 7.81 (s, 2H), 7.68 (t, J = 3.6 Hz, 1H), 7.61 (d, J = 7.6 Hz, 1H), 6.84 (dd, J = 35.6, 10.0 Hz, 1H), 5.23-5.08 (m, 1H), 4.11-4.08 (m, 1H), 2.68-2.65 (m, 1H), 2.45-2.39 (m, 3H), 1.23-1.09 (m, 6H) | IR (thin film) 3416, 1648, 1122 cm$^{-1}$ |
| F60 | | 560 ([M − H]$^-$) | $^1$H NMR (400 MHz, DMSO-d$_6$) δ 8.55 (d, J = 8.0 Hz, 1H), 8.04-8.00 (m, 2H), 7.74 (d, J = 8.4 Hz, 1H), 7.68-7.65 (m, 1H), 7.60 (d, J = 7.6 Hz, 1H), 6.82 (dd, J = 36.0, 10.0 Hz, 1H), 5.20-5.18 (m, 1H), 4.08-4.01 (m, 1H), 2.71-2.58 (m, 1H), 2.56-2.49 (m, 3H), 1.63-1.14 (m, 6H) | IR (thin film) 3435, 2925, 1643, 750 cm$^{-1}$ |
| F61 | | 556 ([M + H]$^+$) | $^1$H NMR (300 MHz, DMSO-d$_6$) δ 8.55 (d, J = 8.1 Hz, 1H), 8.07 (s, 1H), 8.04 (d, J = 8.4 Hz, 1H), 7.06 (d, J = 8.4 Hz, 1H), 7.45 (s, 2H), 6.74 (dd, J = 36.3, | IR (thin film) 3415, 2929, 1645, 749 cm$^{-1}$ |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| | | | 10.2 Hz, 1H), 4.95-4.89 (m, 1H), 4.06-4.02 (m, 1H), 2.72-2.65 (m, 2H), 2.59-2.54 (m, 2H), 2.35 (s, 6H), 1.23-1.17 (m, 6H) | |
| F62 | | 702 ([M − H]$^-$) | $^1$H NMR (300 MHz, DMSO-d$_6$) δ 8.61 (d, J = 8.1 Hz, 1H), 8.12 (d, J = 6.6 Hz, 2H), 8.05 (d, J = 7.8 Hz, 1H), 7.86 (d, J = 8.4 Hz, 1H), 7.62-7.57 (m, 2H), 6.84 (dd, J = 36.0, 9.9 Hz, 1H), 5.19-5.18 (m, 1H), 4.14-4.07 (m, 1H), 3.58-3.48 (m, 2H), 2.86-2.72 (m, 2H), 1.21 (d, J = 7.2 Hz, 3H) | IR (thin film) 3438, 2926, 1646, 1261, 750 cm$^{-1}$ |
| F63 | | 670 ([M − H]$^-$) | $^1$H NMR (400 MHz, DMSO-d$_6$) δ 8.75 (d, J = 7.6 Hz, 1H), 8.12 (s, 1H), 8.06 (d, J = 9.2 Hz, 1H), 8.00 (s, 2H), 7.66 (d, J = 8.0 Hz, 1H), 6.84 (dd, J = 36.0, 10.0 Hz, 1H), 5.25-5.20 (m, 1H), 4.46-4.40 (m, 1H), 3.38-3.34 (m, 2H), 3.17-3.12 (m, 2H), 1.29-1.22 (m, 6H) | IR (thin film) 3426, 1651 cm$^{-1}$ |
| F64 | | 660 ([M + H]$^+$) | $^1$H NMR (300 MHz, DMSO-d$_6$) δ 8.61 (d, J = 8.1 Hz, 1H), 8.12 (s, 1H), 8.06 (d, J = 8.1 Hz, 1H), 7.93 (s, 1H), 7.84 (s, 1H), 7.79 (s, 1H), 7.60 (d, J = 8.1 Hz, 1H), 6.86 (dd, J = 35.4, 10.2 Hz, 1H), 5.23-5.16 (m, 1H), 4.12-4.07 (m, 1H), 3.59-3.48 (m, 2H), 2.82-2.79 (m, 2H), 1.23 (d, J = 7.2 Hz, 3H) | IR (thin film) 3266, 2928, 1644, 1121 cm$^{-1}$ |
| F65 | 142-146 | 692 ([M + H]$^+$) | $^1$H NMR (300 MHz, DMSO-d$_6$) δ 8.84 (d, J = 8.1 Hz, 1H), 8.13 (s, 1H), 8.08 (d, J = 8.1 Hz, 1H), 7.93 (s, 1H), 7.84 (s, 1H), 7.79 (s, 1H), 7.64 (d, J = 8.1 Hz, 1H), 6.87 (dd, J = 36.0, 10.2 Hz, 1H), 5.23-5.17 (m, 1H), | |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| | | | 4.79-4.69 (m, 2H), 4.56-4.52 (m, 1H), 3.58-3.31 (m, 2H), 1.31 (d, J = 6.6 Hz, 3H) | |
| F66 | | 644 ([M + H]$^+$) | $^1$H NMR (400 MHz, CDCl$_3$) δ 7.82-7.66 (m, 1H), 7.56-7.43 (m, 4H), 7.24 (dd, J = 8.3, 2.3 Hz, 1H), 6.90 (d, J = 7.9 Hz, 1H), 5.79 (dtd, J = 32.8, 9.5, 5.9 Hz, 1H), 4.76-4.50 (m, 2H), 3.74 (dq, J = 14.2, 10.0 Hz, 1H), 3.63-3.45 (m, 1H), 3.23 (pd, J = 13.4, 6.4 Hz, 2H), 1.53 (d, J = 6.8 Hz, 3H) | $^{19}$F NMR (376 MHz, CDCl$_3$) δ −60.60 (d, J = 77.7 Hz), −69.49 (dd, J = 6.4, 2.3 Hz), −112.69 (d, J = 37.8 Hz) |
| F67 | | | $^1$H NMR (400 MHz, CDCl$_3$) δ 7.73 (d, J = 1.5 Hz, 1H), 7.54-7.43 (m, 4H), 7.24 (dd, J = 8.4, 2.3 Hz, 1H), 6.47 (d, J = 8.0 Hz, 1H), 5.79 (dd, J = 32.8, 9.8 Hz, 1H), 4.80-4.46 (m, 2H), 4.24-3.84 (m, 2H), 3.57 (dd, J = 14.6, 6.2 Hz, 1H), 3.40 (dd, J = 14.6, 5.3 Hz, 1H), 1.55 (d, J = 6.9 Hz, 3H) | $^{19}$F NMR (376 MHz, CDCl$_3$) δ −61.05, −69.50, −110.35--115.88 (m); IR (thin film) 3323, 1649, 1116, 728 cm$^{-1}$ |
| F68 | | 676 ([M + H]$^+$) | $^1$H NMR (400 MHz, DMSO-d$_6$) δ 8.87 (dd, J = 33.2, 7.6 Hz, 1H), 8.13 (s, 1H), 8.07 (d, J = 8.4 Hz, 1H), 7.93 (s, 1H), 7.84 (s, 1H), 7.80-7.79 (m, 1H), 7.64-7.58 (m, 1H), 6.85 (dd, J = 36.4, 10.4 Hz, 1H), 5.22-5.17 (m, 1H), 4.42-4.38 (m, 1H), 4.13-3.95 (m, 2H), 3.23-3.05 (m, 2H), 1.31 (d, J = 6.9 Hz, 3H) | IR (thin film) 3395, 2927, 1651, 1139 cm$^{-1}$ |
| F69 | 114-116 | 736 ([M + H]$^+$) | $^1$H NMR (400 MHz, DMSO-d$_6$) δ 8.83 (d, J = 8.4 Hz, 1H), 8.13 (s, 1H), 8.08 (d, J = 7.6 Hz, 1H), 7.96 (s, 2H), 7.91-7.90 (m, 1H), 7.63 (d, J = 8.0 Hz, 1H), 6.85 (dd, J = 10.0, 36.0 Hz, 1H), 5.21 (t, J = 9.6 Hz, 1H), 4.78-4.70 (m, 2H), | |

TABLE 4-continued

Analytical Data for Molecules in Table 2

| No. | Mp (° C.) | Mass (m/z) | ¹H NMR | ¹³C NMR; ¹⁹F NMR; IR |
|---|---|---|---|---|
| | | | 4.58-4.51 (m, 1H), 3.59-3.48 (m, 2H), 1.31 (d, J = 2.4 Hz, 3H) | |
| F70 | | 696 ([M − H]⁻) | ¹H NMR (400 MHz, CDCl₃) δ 7.84 (d, J = 6.8 Hz, 1H), 7.78 (d, J = 8.1 Hz, 1H), 7.63 (d, J = 11.6 Hz, 3H), 6.95 (t, J = 54.6 Hz, 1H), 6.40 (d, J = 8.1 Hz, 1H), 5.88 (dd, J = 32.6, 9.5 Hz, 1H), 4.70 (p, J = 8.6 Hz, 2H), 4.12 (ddd, J = 14.2, 8.2, 5.2 Hz, 1H), 3.97 (dt, J = 15.5, 9.2 Hz, 1H), 3.54 (dd, J = 14.5, 6.7 Hz, 1H), 3.41 (dd, J = 14.6, 4.9 Hz, 1H), 1.53 (d, J = 6.9 Hz, 3H) | ¹⁹F NMR (376 MHz, CDCl₃) δ −59.12 −61.15, −69.43 (d, J = 18.3 Hz), −108.40−−113.63 (m), −115.94 (d, J = 114.6 Hz) |
| F71 | | 697 ([M − H]⁻) | ¹H NMR (400 MHz, CDCl₃) δ 7.80 (d, J = 1.6 Hz, 1H), 7.73 (dd, J = 8.1, 1.7 Hz, 1H), 7.59 (d, J = 8.1 Hz, 1H), 7.54 (s, 1H), 7.44 (dd, J = 8.9, 2.0 Hz, 1H), 6.42 (d, J = 8.1 Hz, 1H), 5.86 (dd, J = 32.5, 9.5 Hz, 1H), 4.84-4.47 (m, 2H), 4.19-3.84 (m, 2H), 3.53 (dd, J = 14.5, 6.8 Hz, 1H), 3.39 (dd, J = 14.5, 4.9 Hz, 1H), 1.50 (d, J = 6.9 Hz, 3H) | ¹⁹F NMR (376 MHz, CDCl₃) δ −59.20, −61.17, −62.56, −69.48, −109.49, −111.60 |
| F72 | | 682 ([M + H]⁺) | ¹H NMR (300 MHz, DMSO-d₆) δ 8.84 (d, J = 9.0 Hz, 1H), 8.13 (s, 1H), 8.05 (s, 1H), 8.04 (s, 2H), 7.64 (d, J = 8.1 Hz, 1H), 6.85 (dd, J = 9.9, 35.4 Hz, 1H), 5.27-5.21 (m, 1H), 4.79-4.69 (m, 2H), 4.57-4.51 (m, 1H), 3.61-3.31 (m, 2H), 1.31 (d, J = 6.6 Hz, 3H) | |
| F73 | | 673 ([M − H]⁻) | ¹H NMR (400 MHz, CDCl₃) δ 7.85 (d, J = 1.7 Hz, 1H), 7.77 (dd, J = 8.0, 1.7 Hz, 1H), 7.63 (d, J = 8.1 Hz, 1H), 7.47-7.42 (m, 2H), 7.09 (dd, J = 17.5, 11.0 Hz, 1H), 6.22 (d, J = 8.1 Hz, 1H), 5.86 (dd, J = 32.7, 9.7 Hz, | ¹⁹F NMR (376 MHz, CDCl₃) δ −59.05, −61.13, −67.37−−70.21 (m), −110.35−−113.11 (m) |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| | | | 1H), 5.80 (s, 1H), 5.47 (dd, J = 18.2, 11.0 Hz, 1H), 4.81-4.53 (m, 2H), 4.20-3.89 (m, 2H), 3.54 (dd, J = 14.5, 6.5 Hz, 1H), 3.41 (dd, J = 14.5, 5.0 Hz, 1H), 1.54 (d, J = 6.9 Hz, 3H) | |
| F75 | | HRMS-ESI (m/z) [M + H]$^+$ calcd for C$_{22}$H$_{17}$Cl$_3$F$_7$NOS, 584.0030; found, 584.0028 | $^1$H NMR (400 MHz, CDCl$_3$) δ 7.85 (s, 1H), 7.77 (dd, J = 8.2, 1.7 Hz, 1H), 7.62 (d, J = 8.1 Hz, 1H), 7.43 (s, 2H), 5.94-5.66 (m, 2H), 4.60 (p, J = 8.8 Hz, 1H), 4.47-4.31 (m, 1H), 2.81-2.64 (m, 2H), 2.17 (s, 3H), 1.35 (d, J = 6.7 Hz, 3H) | IR (thin film) 3253, 3064, 2974, 1646, 1552 cm$^{-1}$ |
| F77 | | 666 ([M + H]$^+$) | $^1$H NMR (400 MHz, DMSO-d$_6$) δ 8.82 (d, J = 8.0 Hz, 1H), 8.13 (s, 2H), 8.08 (d, J = 8.0 Hz, 1H), 7.89 (s, 1H), 7.65-7.57 (m, 2H), 6.88 (dd, J = 10.0, 35.6 Hz, 1H), 5.33-5.29 (m, 1H), 4.77-4.70 (m, 2H), 4.55-4.52 (m, 1H), 3.59-3.55 (m, 2H), 1.31 (d, J = 6.9 Hz, 3H) | IR(thin film) 3691, 1657, 1170 cm$^{-1}$ |
| F78 | | 662 ([M + H]$^+$) | $^1$H NMR (300 MHz, DMSO-d$_6$) δ 8.83 (d, J = 8.1 Hz, 1H), 8.11 (s, 1H), 8.08 (d, J = 8.1 Hz, 1H), 7.83 (s, 1H), 7.64 (s, 1H), 7.61 (s, 1H), 6.82 (dd, J = 9.9, 36.0 Hz, 1H), 5.12-5.06 (m, 1H), 4.79-4.69 (m, 2H), 4.56-4.53 (m, 1H), 3.60-3.53 (m, 2H), 2.42 (s, 3H), 1.31 (d, J = 6.9 Hz, 3H) | IR(thin film) 3285, 2949, 1656 cm$^{-1}$ |
| F79 | | 692 ([M + H]$^+$) | $^1$H NMR (400 MHz, DMSO-d$_6$) δ 8.83 (d, J = 8.0 Hz, 1H), 8.13-8.06 (m, 3H), 7.73-7.68 (m, 2H), 7.63 (d, J = 7.6 Hz, 1H), 6.83 (dd, J = 10.0, 36.0 Hz, 1H), 5.20-5.15 (m, 1H), 4.78-4.70 (m, 2H), | IR (thin film) 3274, 1654, 1127 cm$^{-1}$ |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| | | | 4.56-4.52 (m, 1H), 3.59-3.46 (m, 2H), 1.31 (d, J = 6.4 Hz, 3H) | |
| F80 | | 726 ([M − H]$^-$) | $^1$H NMR (400 MHz, CDCl$_3$) δ 7.83 (d, J = 1.6 Hz, 1H), 7.80 (s, 1H), 7.69-7.55 (m, 2H), 7.48 (d, J = 2.1 Hz, 1H), 6.42 (d, J = 8.1 Hz, 1H), 5.96-5.74 (m, 1H), 4.79-4.52 (m, 2H), 4.07-3.84 (m, 2H), 3.54 (dd, J = 14.5, 6.8 Hz, 1H), 3.49-3.33 (m, 1H), 1.51 (d, J = 6.9 Hz, 3H) | $^{19}$F NMR (376 MHz, CDCl$_3$) δ −59.11, −61.12, −69.33 (d, J = 1.9 Hz), −112.01 (d, J = 21.1 Hz) |
| F81 | 133-136 | 682 ([M + H]$^+$) | $^1$H NMR (300 MHz, DMSO-d$_6$) δ 8.80 (d, J = 8.1 Hz, 1H), 8.17 (d, J = 9.3 Hz, 1H), 8.09-8.07 (m, 3H), 7.94 (s, 1H), 7.64 (d, J = 8.1 Hz, 1H), 6.94 (dd, J = 10.2 Hz, 35.1 Hz, 1H), 5.39-5.33 (m, 1H), 4.79 (q, J = 10.5 Hz, 2H), 4.57-4.52 (m, 1H), 3.58-3.31 (m, 2H) 1.31 (d, J = 6.9 Hz, 3H) | |
| F82 | | HRMS-ESI (m/z) [M + H]$^+$ calcd for C$_{23}$H$_{17}$Cl$_3$F$_9$NOS, 633.9999; found, 633.9996 | $^1$H NMR (400 MHz, CDCl$_3$) δ 7.85 (s, 1H), 7.80-7.74 (m, 1H), 7.62 (d, J = 8.1 Hz, 1H), 7.43 (s, 2H), 6.10-5.73 (m, 3H), 4.60 (p, J = 8.8 Hz, 1H), 4.39 (dt, J = 13.5, 6.5 Hz, 1H), 3.00-2.79 (m, 4H), 1.34 (d, J = 6.7 Hz, 3H) | IR (thin film) 3262, 2977, 1643 cm$^{-1}$ |
| F83 | | HRMS-ESI (m/z) [M + H]$^+$ calcd for C$_{23}$H$_{16}$Cl$_3$F$_7$N$_2$OS, 608.9983; found, 608.9987 | $^1$H NMR (400 MHz, CDCl$_3$) δ 7.87-7.82 (m, 1H), 7.76 (dd, J = 8.0, 1.8 Hz, 1H), 7.61 (d, J = 8.1 Hz, 1H), 7.44 (s, 2H), 5.92-5.74 (m, 2H), 4.61 (p, J = 8.8 Hz, 1H), 4.43 (dtd, J = 8.5, 6.9, 5.6 Hz, 1H), 3.58-3.29 (m, 2H), 3.04-2.84 (m, 2H), 1.38 (d, J = 6.7 Hz, 3H) | IR (thin film) 3275, 3077, 2976, 2246, 1647, 1553 cm$^{-1}$ |
| F84 | | HRMS-ESI (m/z) [M + H]$^+$ calcd for C$_{23}$H$_{18}$Cl$_3$F$_8$NOS, 616.0093; found, 616.0102 | $^1$H NMR (500 MHz, DMSO-d$_6$) δ 8.57 (d, J = 8.2 Hz, 1H), 8.12 (s, 1H), 8.05 (s, 3H), 7.61 (d, J = 8.1 Hz, | $^{19}$F NMR (471 MHz, DMSO-d$_6$) δ −57.94, −68.58 (d, J = 9.2 Hz), |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| | | | 1H), 6.79 (dd, J = 35.8, 10.1 Hz, 1H), 5.24 (p, J = 9.4 Hz, 1H), 4.57 (dtd, J = 47.3, 6.3, 2.0 Hz, 2H), 4.06 (dt, J = 14.4, 7.0 Hz, 1H), 2.87 (dtd, J = 21.9, 6.3, 2.0 Hz, 2H), 2.69 (qd, J = 13.4, 7.0 Hz, 2H), 1.19 (d, J = 6.7 Hz, 3H) | −113.62 (d, J = 35.7 Hz), −211.62--−212.00 (m); IR (thin film) 1645, 1552 cm$^{-1}$ |
| F85 | | HRMS-ESI (m/z) [M + H]$^+$ calcd for C$_{23}$H$_{18}$Cl$_3$F$_8$NO$_3$S, 647.9991; found, 647.9996 | $^1$H NMR (400 MHz, CDCl$_3$) δ 7.87-7.83 (m, 1H), 7.77 (dd, J = 8.1, 1.7 Hz, 1H), 7.66 (d, J = 8.1 Hz, 1H), 7.43 (s, 2H), 6.30 (d, J = 8.3 Hz, 1H), 5.82 (dd, J = 32.6, 9.6 Hz, 1H), 4.98 (ddd, J = 5.4, 3.8, 1.7 Hz, 1H), 4.86 (ddd, J = 5.4, 3.9, 1.6 Hz, 1H), 4.75 (ddd, J = 13.3, 9.4, 5.9 Hz, 1H), 4.60 (p, J = 8.9 Hz, 1H), 3.58 (dddd, J = 23.8, 15.6, 6.5, 4.2 Hz, 1H), 3.46-3.30 (m, 3H), 1.53 (d, J = 6.9 Hz, 3H) | $^{19}$F NMR (376 MHz, CDCl$_3$) δ 17.23, −59.10, −69.33 (d, J = 2.2 Hz), −111.89 (d, J = 2.5 Hz) |
| F86 | | 650 ([M + H]$^+$) | $^1$H HMR (500 MHz, DMSO-d$_6$) δ 8.90-8.68 (m, 1H), 8.15-8.01 (m, 4H), 7.63 (dd, J = 23.2, 8.0 Hz, 1H), 6.79 (dd, J = 35.7, 10.1 Hz, 1H), 6.60-6.28 (m, 1H), 5.25 (p, J = 9.4 Hz, 1H), 4.39 (dq, J = 13.5, 6.8 Hz, 1H), 3.69-3.40 (m, 2H), 3.16-2.99 (m, 2H), 1.32-1.26 (m, 3H) | IR (thin film) 3245, 3060, 1659, 1552 cm$^{-1}$ |
| F87 | | HRMS-ESI (m/z) [M + H]$^+$ calcd for C$_{22}$H$_{17}$Cl$_3$F$_7$NO$_3$S, 615.9929; found, 615.9928 | $^1$H NMR (500 MHz, DMSO-d$_6$) δ 8.75 (d, J = 8.2 Hz, 1H), 8.14-8.11 (m, 1H), 8.08-8.03 (m, 3H), 7.66 (d, J = 8.1 Hz, 1H), 6.79 (dd, J = 35.7, 10.1 Hz, 1H), 5.25 (p, J = 9.1 Hz, 1H), 4.48 (hept, J = 6.8 Hz, 1H), 3.41-3.30 (m, 2H), 3.05 (s, 3H), 1.27 (d, J = 6.7 Hz, 3H) | IR (thin film) 3256, 3066, 1665, 1553 cm$^{-1}$ |
| F88 | | HRMS-ESI (m/z) [M + H]$^+$ calcd for C$_{22}$H$_{17}$Cl$_3$F$_7$NO$_2$S, | $^1$H NMR (500 MHz, DMSO-d$_6$) δ 8.84-8.66 (m, 1H), | IR (thin film) 3252, |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| | | 599.9980; found, 599.9990 | 8.16-7.97 (m, 4H), 7.68-7.58 (m, 1H), 6.79 (dd, J = 35.7, 10.1 Hz, 1H), 5.25 (p, J = 9.4 Hz, 1H), 4.39-4.26 (m, 1H), 3.01-2.82 (m, 2H), 2.64-2.56 (m, 3H), 1.31-1.23 (m, 3H) | 3063, 1661, 1552 cm$^{-1}$ |
| F89 | | HRMS-ESI (m/z) [M + H]$^+$ calcd for C$_{22}$H$_{17}$Cl$_3$F$_7$NOS, 584.0030; found, 584.0029 | $^1$H NMR (500 MHz, DMSO-d$_6$) δ 8.74 (t, J = 5.9 Hz, 1H), 8.12 (d, J = 1.6 Hz, 1H), 8.07-8.02 (m, 3H), 7.64 (d, J = 8.1 Hz, 1H), 6.79 (dd, J = 35.7, 10.1 Hz, 1H), 5.25 (p, J = 9.4 Hz, 1H), 3.47 (dt, J = 13.3, 5.8 Hz, 1H), 3.20 (ddd, J = 13.6, 8.0, 5.9 Hz, 1H), 2.93-2.81 (m, 1H), 2.09 (s, 3H), 1.23 (d, J = 6.8 Hz, 3H) | IR (thin film) 1653, 1553, 1524 cm$^{-1}$ |
| F90 | | HRMS-ESI (m/z) [M + H]$^+$ calcd for C$_{22}$H$_{17}$Cl$_3$F$_7$NO$_2$S, 599.9980; found, 599.9990 | $^1$H NMR (500 MHz, DMSO-d$_6$) δ 8.95-8.76 (m, 1H), 8.13 (d, J = 1.7 Hz, 1H), 8.09-8.03 (m, 3H), 7.68-7.62 (m, 1H), 6.80 (dd, J = 35.7, 10.1 Hz, 1H), 5.25 (p, J = 9.4 Hz, 1H), 3.73-3.34 (m, 2H), 3.02-2.85 (m, 1H), 2.57-2.52 (m, 3H), 1.22-1.15 (m, 3H) | IR (thin film) 3252, 3063, 1661, 1552 cm$^{-1}$ |
| F91 | | 682 ([M + H]$^+$) | $^1$H NMR (400 MHz, CDCl$_3$) δ 7.86 (d, J = 1.4 Hz, 1H), 7.81-7.76 (m, 1H), 7.73 (d, J = 8.2 Hz, 1H), 7.65 (d, J = 8.1 Hz, 1H), 7.56 (d, J = 1.7 Hz, 1H), 7.42 (d, J = 8.1 Hz, 1H), 6.14 (d, J = 8.1 Hz, 1H), 5.87 (dd, J = 32.5, 9.6 Hz, 1H), 4.82-4.62 (m, 2H), 4.26-3.86 (m, 2H), 3.54 (dd, J = 14.5, 6.5 Hz, 1H), 3.42 (dd, J = 14.5, 5.0 Hz, 1H), 1.55 (d, J = 6.9 Hz, 3H) | $^{19}$F NMR (376 MHz, CDCl$_3$) δ −59.06, −61.13, −62.80, −69.11 (d, J = 2.3 Hz), −112.06; IR (thin film) 3285, 1650 cm$^{-1}$ |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| F92 | | HRMS-ESI (m/z) [M + H]$^+$ calcd for C$_{21}$H$_{12}$Cl$_3$F$_{10}$NOS, 623.9591; found, 623.9589 | $^1$H NMR (500 MHz, DMSO-d$_6$) δ 8.90 (t, J = 5.7 Hz, 1H), 8.14-8.11 (m, 1H), 8.05 (s, 3H), 7.65 (d, J = 8.0 Hz, 1H), 6.80 (dd, J = 35.8, 10.1 Hz, 1H), 5.25 (p, J = 9.4 Hz, 1H), 3.53 (q, J = 6.5 Hz, 2H), 3.18 (t, J = 6.8 Hz, 2H) | IR (thin film) 1661, 1553 cm$^{-1}$ |
| F93 | | 696 ([M + H]$^+$) | $^1$H NMR (400 MHz, CDCl$_3$) δ 7.86 (s, 1H), 7.78 (d, J = 8.1 Hz, 1H), 7.64 (d, J = 8.1 Hz, 1H), 7.39 (s, 1H), 7.32 (s, 1H), 7.22 (s, 1H), 6.25 (d, J = 8.1 Hz, 1H), 5.86 (dd, J = 32.7, 9.7 Hz, 1H), 4.78-4.58 (m, 2H), 4.18-4.04 (m, 1H), 4.04-3.88 (m, 1H), 3.58-3.34 (m, 4H), 1.54 (d, J = 6.9 Hz, 3H) | $^{19}$F NMR (376 MHz, CDCl$_3$) δ −59.07, −61.14, −65.70, −69.31 (d, J = 2.2 Hz), −112.79; IR (thin film) 3265, 1652 cm$^{-1}$ |
| F94 | | 692 ([M − H]$^-$) | $^1$H NMR (400 MHz, CDCl$_3$) δ 7.86 (s, 1H), 7.78 (d, J = 8.1 Hz, 1H), 7.65 (d, J = 8.0 Hz, 1H), 7.40-7.35 (m, 1H), 7.24-7.18 (m, 1H), 6.16 (d, J = 8.2 Hz, 1H), 5.82 (dd, J = 32.5, 9.6 Hz, 1H), 4.72 (dt, J = 13.3, 6.7 Hz, 1H), 4.64-4.50 (m, 3H), 3.54 (dd, J = 14.5, 6.4 Hz, 1H), 3.42 (dd, J = 14.5, 5.1 Hz, 1H), 1.55 (d, J = 7.0 Hz, 3H) | $^{19}$F NMR (376 MHz, CDCl$_3$) δ −59.08 (d, J = 19.3 Hz), −61.14 (d, J = 3.1 Hz), −69.55 (d, J = 2.4 Hz), −129.12 (d, J = 21.5 Hz), −132.14 (d, J = 21.5 Hz) |
| F95 | | 726 ([M + H]$^+$) | $^1$H NMR (400 MHz, CDCl$_3$) δ 7.86 (s, 1H), 7.79 (d, J = 7.8 Hz, 1H), 7.76 (s, 1H), 7.73 (d, J = 8.2 Hz, 1H), 7.65 (d, J = 8.0 Hz, 1H), 7.47 (d, J = 8.2 Hz, 1H), 6.12 (d, J = 8.2 Hz, 1H), 5.87 (dd, J = 32.6, 9.6 Hz, 1H), 4.85-4.58 (m, 2H), 4.21-3.85 (m, 2H), 3.54 (dd, J = 14.5, 6.4 Hz, 1H), 3.42 (dd, J = 14.6, 5.1 Hz, 1H), 1.56 (s, 3H) | $^{19}$F NMR (376 MHz, CDCl$_3$) δ −59.05, −61.13, −62.84, −69.09 (d, J = 2.3 Hz), −112.03; IR (thin film) 3266, 1652 cm$^{-1}$ |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| F96 | | HRMS-ESI (m/z) [M + H]$^+$ calcd for C$_{24}$H$_{19}$Cl$_3$F$_9$NO$_2$S, 664.0112; found, 664.0105 | $^1$H NMR (500 MHz, DMSO-d$_6$, mixture of diastereomers) δ 8.87-8.69 (m, 1H), 8.19-8.11 (m, 1H), 8.09-8.02 (m, 3H), 7.67-7.58 (m, 1H), 6.79 (dd, J = 35.7, 10.1 Hz, 1H), 5.25 (p, J = 9.4 Hz, 1H), 4.44-4.30 (m, 1H), 3.69-3.41 (m, 2H), 3.15-3.00 (m, 2H), 1.84-1.69 (m, 3H), 1.35-1.24 (m, 3H) | $^{19}$F NMR (471 MHz, DMSO-d$_6$, mixture of diastereomers) δ −57.94 (d, J = 5.7 Hz, really two singlets), −68.58 (d, J = 9.0 Hz), −80.77--81.91 (m), −84.39--85.73 (m), −113.62 (d, J = 35.6 Hz) |
| F97 | | HRMS-ESI (m/z) [M + H]$^+$ calcd for C$_{24}$H$_{19}$Cl$_3$F$_9$NO$_3$S, 680.0054; found, 680.0056 | $^1$H NMR (500 MHz, DMSO-d$_6$) δ 8.80 (d, J = 8.2 Hz, 1H), 8.13 (d, J = 2.0 Hz, 1H), 8.07 (dd, J = 8.1, 1.7 Hz, 1H), 8.05 (d, J = 1.0 Hz, 2H), 7.64 (d, J = 8.1 Hz, 1H), 6.79 (dd, J = 35.7, 10.1 Hz, 1H), 5.25 (p, J = 9.4 Hz, 1H), 4.54 (hept, J = 6.9 Hz, 1H), 4.16 (td, J = 14.4, 4.4 Hz, 2H), 3.49 (dd, J = 14.1, 7.2 Hz, 1H), 3.41 (dd, J = 14.1, 5.8 Hz, 1H), 1.81 (t, J = 19.6 Hz, 3H), 1.29 (d, J = 6.7 Hz, 3H) | $^{19}$F NMR (471 MHz, DMSO-d$_6$) δ −57.97, −68.58 (d, J = 8.9 Hz), −81.85--84.63 (m), −113.60 (d, J = 35.6 Hz) |
| F98 | | 666 ([M + H]$^+$) | $^1$H NMR (500 MHz, CDCl$_3$) δ 7.86 (s, 1H), 7.78 (d, J = 8.0 Hz, 1H), 7.63 (d, J = 8.1 Hz, 1H), 7.40 (s, 2H), 6.16 (d, J = 7.9 Hz, 1H), 6.00 (td, J = 55.8, 2.7 Hz, 1H), 5.82 (dd, J = 33.9, 9.4 Hz, 1H), 4.77-4.64 (m, 1H), 4.43-4.27 (m, 1H), 4.09 (dq, J = 18.1, 9.1 Hz, 1H), 4.03-3.91 (m, 1H), 3.54 (dd, J = 14.5, 6.4 Hz, 1H), 3.42 (dd, J = 14.5, 5.0 Hz, 1H), 1.55 (d, J = 7.0 Hz, 3H) | $^{19}$F NMR (471 MHz, CDCl$_3$) δ −59.03, −61.13, −112.97, −118.69--122.74 (m) |
| F99 | | HRMS-ESI (m/z) [M + H]$^+$ calcd for C$_{23}$H$_{18}$Cl$_3$F$_8$NO$_2$S, 632.00342; found, 632.0039 | $^1$H NMR (500 MHz, DMSO-d$_6$, mixture of diastereomers) δ 8.84-8.67 (m, 1H), 8.20-8.11 (m, 1H), 8.09-8.01 (m, 3H), 7.64 (dd, J = 25.6, 8.1 Hz, 1H), | $^{19}$F NMR (471 MHz, DMSO-d$_6$, mixture of diastereomers) δ −57.93, −57.96, −68.57 (d, J = 9.1 Hz), |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| | | | 6.79 (dd, J = 35.7, 10.0 Hz, 1H), 5.25 (p, J = 9.4 Hz, 1H), 5.00-4.70 (m, 2H), 4.50-4.30 (m, 1H), 3.31-3.20 (m, 1H), 3.18-2.92 (m, 3H), 1.36-1.24 (m, 3H) | −113.60 (d, J = 35.6 Hz), −218.82 (tdd, J = 47.2, 34.4, 21.3 Hz), −219.20 (tdd, J = 46.9, 34.1, 21.7 Hz); IR (thin film) 3245, 3061, 1652, 1552 cm$^{-1}$ |
| F100 | | HRMS-ESI (m/z) [M + H]$^+$ calcd for C$_{23}$H$_{19}$Cl$_3$F$_7$NO$_3$S, 630.0086; found, 630.0094 | $^1$H NMR (500 MHz, DMSO-d$_6$) δ 8.53 (s, 1H), 8.09 (d, J = 1.7 Hz, 1H), 8.07-8.01 (m, 3H), 7.67 (d, J = 8.1 Hz, 1H), 6.77 (dd, J = 35.7, 10.1 Hz, 1H), 5.24 (p, J = 9.4 Hz, 1H), 3.81 (s, 2H), 3.02 (s, 3H), 1.91 (s, 3H), 1.51 (s, 6H) | $^{19}$F NMR (471 MHz, DMSO-d$_6$) δ −57.81, −68.60 (d, J = 9.2 Hz), −113.52 (d, J = 35.7 Hz) |
| F101 | | HRMS-ESI (m/z) [M + H]$^+$ calcd for C$_{23}$H$_{19}$Cl$_3$F$_7$NOS, 598.0187; found, 598.0194 | $^1$H NMR (500 MHz, CDCl$_3$, diastereomers) δ 7.86 (s, 1H), 7.80-7.75 (m, 1H), 7.63-7.57 (m, 1H), 7.43 (s, 2H), 6.22-5.90 (m, 1H), 5.81 (dd, J = 32.6, 9.6 Hz, 1H), 4.60 (p, J = 8.9 Hz, 1H), 4.43-4.31 (m, 1H), 2.96-2.88 (m, 1H), 2.19-2.10 (m, 3H), 1.40-1.22 (m, 6H) | $^{19}$F NMR (471 MHz, CDCl$_3$, diastereomers) δ −59.03, −59.05, −69.34 (d, J = 8.6 Hz), −111.85 (d, J = 32.1 Hz) |
| F102 | | 634 ([M + H]$^+$) | $^1$H NMR (300 MHz, DMSO-d$_6$) δ 8.61 (d, J = 8.1 Hz, 1H), 8.12 (s, 2H), 8.06 (d, J = 8.1 Hz, 2H), 7.67-7.60 (m, 2H), 6.90 (dd, J = 9.9, 36.0 Hz, 1H), 5.35-5.28 (m, 1H), 4.12-4.01 (m, 1H), 3.59-3.49 (m, 2H), 2.82-2.75 (m, 2H), 1.23 (d, J = 7.5 Hz, 3H) | IR (thin film) 3444, 2987, 1645, 764 cm$^{-1}$ |
| F103 | | 650 ([M + H]$^+$) | $^1$H HMR (300 MHz, DMSO-d$_6$) δ 8.84 (d, J = 7.8 Hz, 1H), 8.12 (s, 1H), 8.07 (d, J = 8.1 Hz, 1H), 7.89-7.84 (m, 2H), 7.64 (d, J = 8.1 Hz, 1H), 6.83 (dd, J = 9.9, 35.7 Hz, 1H), 5.23-5.17 (m, 1H), 4.79-4.69 (m, 2H), | IR (thin film) 3438, 1652 cm$^{-1}$ |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| | | | 4.56-4.52 (m, 1H), 3.54-3.45 (m, 2H), 1.31 (d, J = 6.6 Hz, 3H) | |
| F104 | | 698 ([M + H]$^+$) | $^1$H NMR (400 MHz, DMSO-d$_6$) δ 8.82 (d, J = 8.0 Hz, 1H), 8.13 (br s, 1H), 8.07 (d, J = 8.0 Hz, 1H), 8.00 (s, 2H), 7.63 (d, J = 8.0 Hz, 1H), 6.79 (dd, J = 10.4, 36.0 Hz, 1H), 5.30 (t, J = 8.0 Hz, 1H), 4.77-4.70 (m, 2H), 3.59-3.46 (m, 2H), 2.80 (s, 2H), 1.30 (d, J = 8.0 Hz, 3H) | IR(thin film) 1731, 1267, 1049 cm$^{-1}$ |
| F109 | | 698 ([M + H]$^+$) | $^1$H NMR (400 MHz, CDCl$_3$) δ 7.86 (s, 1H), 7.79 (d, J = 7.6 Hz, 1H), 7.65 (d, J = 8.1 Hz, 1H), 7.53 (s, 1H), 7.35 (s, 2H), 6.13 (d, J = 8.2 Hz, 1H), 5.86 (dd, J = 32.6, 9.6 Hz, 1H), 4.79-4.60 (m, 2H), 4.17-4.03 (m, 1H), 4.03-3.91 (m, 1H), 3.54 (dd, J = 14.6, 6.4 Hz, 1H), 3.42 (dd, J = 14.6, 5.0 Hz, 1H), 1.55 (d, J = 7.2 Hz, 3H) | $^{19}$F NMR (376 MHz, CDCl$_3$) δ −57.82, −59.04, −61.14, −69.40 (d, J = 2.2 Hz), −112.56 (d, J = 2.7 Hz); IR (thin film) 3256, 2970, 1738, 1714, 1655, 1547 cm$^{-1}$ |
| F110 | | 698 ([M + H]$^+$) | $^1$H NMR (400 MHz, CDCl$_3$) δ 7.84 (d, J = 1.6 Hz, 1H), 7.76 (dd, J = 8.1, 1.7 Hz, 1H), 7.63 (d, J = 8.0 Hz, 1H), 7.35 (d, J = 1.6 Hz, 1H), 7.27 (s, 1H), 7.17 (s, 1H), 6.65 (d, J = 8.1 Hz, 1H), 5.84 (dd, J = 32.6, 9.6 Hz, 1H), 4.77-4.59 (m, 2H), 4.13 (dq, J = 15.4, 9.1 Hz, 1H), 3.98 (dq, J = 15.6, 9.3 Hz, 1H), 3.56 (dd, J = 14.6, 6.7 Hz, 1H), 3.40 (dd, J = 14.6, 4.9 Hz, 1H), 1.53 (d, J = 6.9 Hz, 3H) | $^{19}$F NMR (376 MHz, CDCl$_3$) δ −57.95, −59.15, −61.14, −69.31 (d, J = 2.2 Hz), −112.17; IR (thin film) 3267, 2979, 2878, 1652, 1535 cm$^{-1}$ |
| F112 | | 638 ([M − H]$^-$) | $^1$H NMR (300 MHz, CDCl$_3$) δ 7.85 (d, J = 1.6 Hz, 1H), 7.77 (d, J = 8.1 Hz, 1H), 7.63 (d, J = 8.1 Hz, 1H), 7.41 (t, J = 1.7 Hz, 1H), 7.28 (s, 2H), 6.67 (dd, J = 17.6, | IR (thin film) 3210, 2916, 1681, 1363 cm$^{-1}$ |

TABLE 4-continued

Analytical Data for Molecules in Table 2

| No. | Mp (° C.) | Mass (m/z) | ¹H NMR | ¹³C NMR; ¹⁹F NMR; IR |
|---|---|---|---|---|
| | | | 10.9 Hz, 1H), 6.30 (d, J = 8.1 Hz, 1H), 5.99-5.74 (m, 2H), 5.37 (d, J = 10.9 Hz, 1H), 4.77-4.55 (m, 2H), 3.96 (dt, J = 15.5, 9.3 Hz, 1H), 3.54 (dd, J = 14.5, 6.5 Hz, 1H), 3.41 (dd, J = 14.5, 5.1 Hz, 1H), 2.63 (s, 1H), 1.54 (d, J = 6.9 Hz, 3H) | |
| F113 | | HRMS-ESI (m/z) [M + H]⁺ calcd for $C_{24}H_{19}Cl_3F_9NOS$, 648.0155; found, 648.0159 | ¹H NMR (500 MHz, DMSO-d₆) δ 8.59 (d, J = 8.2 Hz, 1H), 8.13 (s, 1H), 8.08-8.01 (m, 3H), 7.61 (d, J = 8.1 Hz, 1H), 6.79 (dd, J = 35.8, 10.1 Hz, 1H), 5.25 (p, J = 9.4 Hz, 1H), 4.14-4.05 (m, 1H), 3.15-3.06 (m, 2H), 2.82-2.69 (m, 2H), 1.71 (t, J = 18.7 Hz, 3H), 1.20 (d, J = 6.7 Hz, 3H) | ¹⁹F NMR (471 MHz, DMSO-d₆) δ −57.96, −68.59 (d, J = 9.1 Hz), −86.61--88.33 (m), −113.64 (d, J = 35.5 Hz); IR (thin film) 1651, 1552 cm⁻¹ |
| F114 | | 688 ([M − H]⁻) | ¹H NMR (500 MHz, CDCl₃) δ 7.84 (t, J = 2.4 Hz, 1H), 7.76 (dt, J = 8.3, 2.6 Hz, 1H), 7.62 (d, J = 8.1 Hz, 1H), 7.45-7.39 (m, 1H), 7.14 (t, J = 2.1 Hz, 1H), 6.32 (d, J = 8.1 Hz, 1H), 5.84 (ddd, J = 32.8, 11.9, 9.7 Hz, 1H), 5.37-5.22 (m, 1H), 4.99 (t, J = 1.3 Hz, 1H), 4.73-4.67 (m, 1H), 4.61 (p, J = 9.0 Hz, 1H), 4.19-4.04 (m, 1H), 4.04-3.90 (m, 1H), 3.54 (dd, J = 14.5, 6.6 Hz, 1H), 3.41 (dd, J = 14.5, 5.0 Hz, 1H), 2.10 (t, J = 1.2 Hz, 3H), 1.53 (d, J = 6.9 Hz, 3H) | ¹⁹F NMR (471 MHz, CDCl₃) δ −59.07, −60.23--62.29 (m), −67.61--71.87 (m), −107.95--115.02 (m) |
| F116 | | 640 ([M − H]⁻) | ¹H NMR (400 MHz, CDCl₃) δ 7.69 (d, J = 1.6 Hz, 1H), 7.53 (d, J = 8.2 Hz, 1H), 7.47 (dd, J = 8.2, 1.6 Hz, 1H), 7.44 (s, 2H), 7.12-6.96 (m, 1H), 6.26 (d, J = 8.0 Hz, 1H), 5.91-5.63 (m, 2H), 5.56-5.36 (m, 1H), 4.71 (ddd, J = 13.2, | ¹⁹F NMR (376 MHz, CDCl₃) δ −61.08, −69.38, −111.47 |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| | | | 9.3, 6.0 Hz, 1H), 4.60 (p, J = 8.9 Hz, 1H), 4.21-4.05 (m, 1H), 3.98 (dq, J = 15.6, 9.3 Hz, 1H), 3.53 (dd, J = 14.5, 6.4 Hz, 1H), 3.43 (dd, J = 14.5, 5.0 Hz, 1H), 1.54 (d, J = 6.9 Hz, 3H) | |
| F117 | | 667 ([M − H]$^-$) | $^1$H NMR (400 MHz, CDCl$_3$) δ 7.84 (d, J = 1.7 Hz, 1H), 7.77 (dd, J = 8.2, 1.8 Hz, 1H), 7.60 (d, J = 8.1 Hz, 1H), 7.54 (d, J = 2.1 Hz, 1H), 7.44 (dd, J = 8.9, 2.0 Hz, 1H), 5.98-5.73 (m, 2H), 4.71 (p, J = 8.8 Hz, 1H), 4.38 (dh, J = 8.0, 6.5 Hz, 1H), 3.29-3.01 (m, 2H), 2.97-2.79 (m, 2H), 1.34 (d, J = 6.7 Hz, 3H) | $^{19}$F NMR (376 MHz, CDCl$_3$) δ −59.06, −62.55, −66.52, −69.45, −109.45, −111.40 |
| F119 | 100-104 | 620 ([M + H]$^+$) | $^1$H NMR (400 MHz, CDCl$_3$) δ 7.85 (s, 1H), 7.79 (d, J = 8.4 Hz, 1H), 7.65 (d, J = 7.6 Hz, 1H), 7.41 (s, 1H), 7.37 (s, 1H), 6.72-6.65 (m, 1H), 6.36-6.34 (m, 1H), 5.88-5.74 (m, 2H), 4.69-4.57 (m, 2H), 3.41 (dd, J = 5.6, 14.4 Hz, 1H), 3.23 (dd, J = 4.8, 14.4 Hz, 1H), 3.14 (q, J = 7.2 Hz, 2H), 1.58 (d, J = 6.8 Hz, 3H), 1.45 (t, J = 7.2 Hz, 3H) | |
| F120 | | 678 ([M + H]$^+$) | $^1$H NMR (400 MHz, CDCl$_3$) δ 7.85 (s, 1H), 7.78 (d, J = 8.1 Hz, 1H), 7.63 (d, J = 8.1 Hz, 1H), 7.50 (s, 1H), 7.46 (s, 1H), 7.42 (s, 1H), 6.20 (d, J = 8.1 Hz, 1H), 5.87 (dd, J = 32.6, 9.7 Hz, 1H), 4.79-4.60 (m, 2H), 4.16-4.03 (m, 1H), 4.03-3.89 (m, 1H), 3.54 (dd, J = 14.5, 6.5 Hz, 1H), 3.41 (dd, J = 14.5, 5.0 Hz, 1H), 1.93 (t, J = 18.2 Hz, 3H), 1.54 (d, J = 6.9 Hz, 3H) | $^{19}$F NMR (376 MHz, CDCl$_3$) δ −59.05, −61.14, −69.27 (d, J = 1.6 Hz), −88.19 (d, J = 6.8 Hz), −112.56; IR (thin film) 3278, 1651 cm$^{-1}$ |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| F121 | | HRMS-ESI (m/z) [M + H]$^+$ calcd for C$_{24}$H$_{18}$Cl$_3$F$_{10}$NO$_2$S, 682.0010; found, 682.0028 | $^1$H NMR (500 MHz, DMSO-d$_6$) δ 8.96-8.60 (m, 1H), 8.22-7.95 (m, 4H), 7.68-7.58 (m, 1H), 6.79 (dd, J = 35.7, 10.0 Hz, 1H), 5.25 (p, J = 9.4 Hz, 1H), 4.37 (hept, J = 7.2 Hz, 1H), 3.18-2.86 (m, 4H), 2.80-2.60 (m, 2H), 1.34-1.24 (m, 3H) | IR (thin film) 3246, 3061, 1659, 1552 cm$^{-1}$ |
| F122 | | HRMS-ESI (m/z) [M + H]$^+$ calcd for C$_{24}$H$_{18}$Cl$_3$F$_7$N$_2$O$_2$S, 639.0089; found, 639.0082 | $^1$H NMR (500 MHz, DMSO-d$_6$) δ 8.86-8.70 (m, 1H), 8.17-8.02 (m, 4H), 7.69-7.59 (m, 1H), 6.79 (dd, J = 35.7, 10.0 Hz, 1H), 5.25 (p, J = 9.3 Hz, 1H), 4.43-4.32 (m, 1H), 3.26-3.13 (m, 1H), 3.10-2.87 (m, 5H), 1.36-1.19 (m, 3H) | IR (thin film) 3246, 3060, 2249, 1658, 1552 cm$^{-1}$ |
| F123 | | HRMS-ESI (m/z) [M + H]$^+$ calcd for C$_{24}$H$_{18}$Cl$_3$F$_7$N$_2$O$_3$S, 655.0038; found, 655.0043 | $^1$H NMR (500 MHz, DMSO-d$_6$) δ 8.79 (d, J = 8.1 Hz, 1H), 8.17-8.00 (m, 4H), 7.65 (d, J = 8.0 Hz, 1H), 6.79 (dd, J = 35.7, 10.1 Hz, 1H), 5.25 (p, J = 9.4 Hz, 1H), 4.50 (hept, J = 6.9 Hz, 1H), 3.58 (td, J = 7.1, 2.2 Hz, 2H), 3.49-3.39 (m, 2H), 3.02 (t, J = 7.1 Hz, 2H), 1.28 (d, J = 6.6 Hz, 3H) | IR (thin film) 3246, 3059, 2252, 1659, 1552 cm$^{-1}$ |
| F124 | | HRMS-ESI (m/z) [M + H]$^+$ calcd for C$_{22}$H$_{17}$Cl$_3$F$_7$NO$_2$S, 599.9980; found, 599.9990 | $^1$H NMR (500 MHz, DMSO-d$_6$) δ 8.85 (t, J = 5.8 Hz, 1H), 8.14 (d, J = 1.7 Hz, 1H), 8.11-8.02 (m, 3H), 7.69 (d, J = 8.1 Hz, 1H), 6.81 (dd, J = 35.7, 10.1 Hz, 1H), 5.25 (p, J = 9.4 Hz, 1H), 3.78 (dt, J = 13.2, 5.4 Hz, 1H), 3.46-3.34 (m, 2H), 3.04 (s, 3H), 1.32 (d, J = 6.7 Hz, 3H) | IR (thin film) 3252, 3063, 1661, 1552 cm$^{-1}$ |
| F125 | | HRMS-ESI (m/z) [M + H]$^+$ calcd for C$_{22}$H$_{16}$Cl$_3$F$_8$NOS, 601.9936; found, 601.9946 | $^1$H NMR (500 MHz, DMSO-d$_6$) δ 8.74 (t, J = 5.7 Hz, 1H), 8.12 (d, J = 1.7 Hz, 1H), 8.09-8.01 (m, 3H), 7.63 (d, J = 8.1 Hz, 1H), 6.79 (dd, J = 35.7, 10.1 Hz, 1H), 5.25 (p, J = 9.4 Hz, | $^{19}$F NMR (471 MHz, DMSO-d$_6$) δ −57.97, −68.59 (d, J = 9.0 Hz), −113.69 (d, J = 35.7 Hz), −212.01 (tt, J = 47.1, 22.0 Hz); IR (thin |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| | | | 1H), 4.62 (t, J = 6.2 Hz, 1H), 4.53 (t, J = 6.2 Hz, 1H), 3.42 (dt, J = 7.6, 6.1 Hz, 2H), 2.90 (t, J = 6.2 Hz, 1H), 2.86 (t, J = 6.2 Hz, 1H), 2.73 (t, J = 7.1 Hz, 2H) | film) 3274, 3077, 1651, 1552 cm$^{-1}$ |
| F126 | | 632 ([M + H]$^+$) | $^1$H NMR (300 MHz, DMSO-d$_6$) δ 8.86 (d, J = 8.1 Hz, 1H), 8.14 (s, 1H), 8.08 (d, J = 7.5 Hz, 1H), 7.69-7.61 (m, 3H), 7.54-7.50 (m, 1H), 6.86 (dd, J = 10.2, 36.0 Hz, 1H), 5.24-5.18 (m, 1H), 4.80-4.70 (m, 2H), 4.57-4.52 (m, 1H), 3.62-3.45 (m, 2H), 1.31 (d, J = 6.9 Hz, 3H) | IR (thin film) 3421, 1651 cm$^{-1}$ |
| F127 | | 698 ([M + H]$^+$) | $^1$H NMR (400 MHz, CDCl$_3$) δ 7.85 (d, J = 1.7 Hz, 1H), 7.78 (dd, J = 8.0, 1.7 Hz, 1H), 7.64 (d, J = 8.0 Hz, 1H), 7.52 (d, J = 8.3 Hz, 1H), 7.36 (s, 1H), 7.31 (dd, J = 8.4, 2.1 Hz, 1H), 6.14 (d, J = 8.2 Hz, 1H), 5.85 (dd, J = 32.6, 9.5 Hz, 1H), 4.76-4.60 (m, 2H), 4.19-4.04 (m, 1H), 4.04-3.89 (m, 1H), 3.53 (dd, J = 14.5, 6.5 Hz, 1H), 3.42 (dd, J = 14.5, 5.0 Hz, 1H), 1.29 (d, J = 7.0 Hz, 3H) | $^{19}$F NMR (376 MHz, CDCl$_3$) δ −57.87, −59.08, −61.15, −69.55 (d, J = 2.4 Hz), −112.29; IR (thin film) 3282, 1714, 1652, 1540, 1491 cm$^{-1}$ |
| F128 | | HRMS-ESI (m/z) [M + H]$^+$ calcd for C$_{24}$H$_{18}$Cl$_3$F$_7$N$_2$OS, 623.0140; found, 623.0151 | $^1$H NMR (400 MHz, CDCl$_3$) δ 7.90-7.82 (m, 1H), 7.78 (dd, J = 8.3, 1.7 Hz, 1H), 7.62 (d, J = 8.1 Hz, 1H), 7.43 (s, 2H), 5.89-5.74 (m, 2H), 4.60 (p, J = 8.7 Hz, 1H), 4.41-4.28 (m, 1H), 2.95-2.83 (m, 3H), 2.81-2.68 (m, 3H), 1.35 (d, J = 6.7 Hz, 3H) | IR (thin film) 3260, 2974, 2108, 1644, 1552 cm$^{-1}$ |
| F129 | | 666 ([M + H]$^+$) | $^1$H NMR (400 MHz, CDCl$_3$) δ 7.89-7.82 (m, 1H), 7.78 (dd, J = 8.2, 1.7 Hz, 1H), 7.65 (d, J = 8.1 Hz, 1H), 7.43 (s, 2H), 6.42-6.08 (m, 2H), 5.82 (dd, J = 32.5, | $^{19}$F NMR (376 MHz, CDCl$_3$) δ −59.04, −69.32 (d, J = 2.3 Hz), −111.92 (d, J = 2.7 Hz), −115.78 (d, J = 3.4 Hz) |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| | | | 9.6 Hz, 1H), 4.79-4.67 (m, 1H), 4.60 (p, J = 8.9 Hz, 1H), 3.85-3.57 (m, 2H), 3.47 (dd, J = 14.5, 6.6 Hz, 1H), 3.36 (dd, J = 14.5, 4.8 Hz, 1H), 1.54 (d, J = 7.0 Hz, 3H) | |
| F130 | | HRMS-ESI (m/z) [M + H]$^+$ calcd for C$_{24}$H$_{18}$Cl$_3$F$_{10}$NO$_3$S, 697.9960; found, 697.9971 | $^1$H NMR (500 MHz, DMSO-d$_6$) δ 8.79 (d, J = 8.2 Hz, 1H), 8.13 (s, 1H), 8.09-8.02 (m, 3H), 7.64 (d, J = 8.1 Hz, 1H), 6.79 (dd, J = 35.7, 10.1 Hz, 1H), 5.25 (p, J = 9.3 Hz, 1H), 4.51 (hept, J = 6.8 Hz, 1H), 3.54-3.43 (m, 4H), 2.86-2.71 (m, 2H), 1.29 (d, J = 6.7 Hz, 3H) | IR (thin film) 3245, 3062, 1660, 1553 cm$^{-1}$ |
| F131 | | 692 ([M + H]$^+$) | $^1$H NMR (400 MHz, CDCl$_3$) δ 7.84 (s, 1H), 7.76 (dd, J = 8.1, 1.3 Hz, 1H), 7.61 (d, J = 8.1 Hz, 1H), 7.46 (s, 2H), 7.38 (s, 1H), 6.25 (d, J = 8.0 Hz, 1H), 5.87 (dd, J = 32.6, 9.7 Hz, 1H), 4.76-4.61 (m, 2H), 4.17-4.03 (m, 1H), 4.03-3.89 (m, 1H), 3.54 (dd, J = 14.5, 6.5 Hz, 1H), 3.41 (dd, J = 14.5, 5.0 Hz, 1H), 2.21-2.05 (m, 2H), 1.53 (d, J = 6.9 Hz, 3H), 1.00 (t, J = 7.5 Hz, 3H) | $^{19}$F NMR (376 MHz, CDCl$_3$) δ −59.07, −61.14, −69.33 (t, J = 1.8 Hz), −98.00, −112.60; IR (thin film) 3269, 2987, 1651, 1538 cm$^{-1}$ |
| F132 | | 662 ([M + H]$^+$) | $^1$H NMR (400 MHz, CDCl$_3$) δ 7.84 (s, 1H), 7.76 (d, J = 6.8 Hz, 1H), 7.63 (d, J = 8.0 Hz, 1H), 7.37 (d, J = 8.5 Hz, 1H), 7.29-7.26 (m, 1H), 6.11 (d, J = 7.8 Hz, 1H), 5.87 (dd, J = 33.1, 9.3 Hz, 1H), 5.01 (p, J = 9.0 Hz, 1H), 4.71 (dt, J = 13.3, 6.6 Hz, 1H), 4.17-4.02 (m, 1H), 4.02-3.90 (m, 1H), 3.53 (dd, J = 14.4, 6.4 Hz, 1H), 3.42 (dd, J = 14.5, 5.0 Hz, 1H), 2.59 (s, 3H), 1.55 (d, J = 5.7 Hz, 3H) | $^{19}$F NMR (376 MHz, CDCl$_3$) δ −59.04, −61.13, −69.06, −112.52; IR (thin film) 3265, 1650, 1536 cm$^{-1}$ |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| F133 | | 633.85 ([M + H]$^+$) | $^1$H NMR (300 MHz, DMSO-d$_6$) δ 8.84 (d, J = 8.1 Hz, 1H), 8.12-8.04 (m, 2H), 7.77-7.72 (m, 2H), 7.64 (d, J = 8.1 Hz, 1H), 6.80 (dd, J = 10.2, 35.7 Hz, 1H), 5.22-5.15 (m, 1H), 4.79-4.69 (m, 2H), 4.56-4.52 (m, 1H), 3.60-3.45 (m, 2H), 1.31 (d, J = 6.9 Hz, 3H) | IR (thin film) 3431, 1657 cm$^{-1}$ |
| F136 | | 682 ([M + H]$^+$) | $^1$H NMR (300 MHz, DMSO-d$_6$) δ 8.84 (d, J = 9.0 Hz, 1H), 8.13 (s, 1H), 8.05 (s, 1H), 8.04 (s, 2H), 7.64 (d, J = 8.1 Hz, 1H), 6.85 (dd, J = 9.9, 35.4 Hz, 1H), 5.27-5.21 (m, 1H), 4.79-4.69 (m, 2H), 4.57-4.51 (m, 1H), 3.61-3.31 (m, 2H), 1.31 (d, J = 6.6 Hz, 3H) | |
| F137 | | HRMS-ESI (m/z) [M + H]$^+$ calcd for C$_{24}$H$_{18}$Cl$_3$F$_{10}$NOS, 666.0061; found, 666.0059 | $^1$H NMR (400 MHz, CDCl$_3$) δ 7.88-7.83 (m, 1H), 7.78 (dd, J = 8.1, 1.8 Hz, 1H), 7.61 (d, J = 8.1 Hz, 1H), 7.43 (s, 2H), 5.90-5.74 (m, 2H), 4.60 (p, J = 8.8 Hz, 1H), 4.46-4.32 (m, 1H), 2.89-2.68 (m, 4H), 2.49-2.34 (m, 2H), 1.35 (d, J = 6.7 Hz, 3H) | IR (thin film) 3260, 1642, 1553 cm$^{-1}$ |
| F138 | | HRMS-ESI (m/z) [M + H]$^+$ calcd for C$_{22}$H$_{16}$Cl$_3$F$_8$NO$_2$S, 617.9885; found, 617.9886 | $^1$H NMR (500 MHz, DMSO-d$_6$) δ 8.92 (t, J = 5.6 Hz, 1H), 8.13 (d, J = 1.7 Hz, 1H), 8.11-8.04 (m, 3H), 7.66 (d, J = 8.1 Hz, 1H), 6.80 (dd, J = 35.7, 10.1 Hz, 1H), 5.25 (p, J = 9.4 Hz, 1H), 4.97-4.70 (m, 2H), 3.73-3.56 (m, 2H), 3.33 (s, 1H), 3.18-3.05 (m, 2H), 2.97 (dt, J = 12.7, 6.0 Hz, 1H) | $^{19}$F NMR (471 MHz, DMSO-d$_6$) δ −57.98, −68.59 (d, J = 9.1 Hz), −113.70 (d, J = 35.7 Hz), −219.11 (tdd, J = 46.9, 34.4, 21.6 Hz); IR (thin film) 3426, 3248, 3061, 1664, 1553 cm$^{-1}$ |
| F141 | | 642 ([M + H]$^+$) | $^1$H NMR (300 MHz, DMSO-d$_6$) δ 8.83 (d, J = 8.4 Hz, 1H), 8.13 (s, 1H), 8.08 (d, J = 8.1 Hz, 1H), 7.73 (s, 1H), 7.63 (d, J = 8.1 Hz, 1H), | IR (thin film) 3271, 2930, 1655, 1127 cm$^{-1}$ |

TABLE 4-continued

Analytical Data for Molecules in Table 2

| No. | Mp (° C.) | Mass (m/z) | $^1$H NMR | $^{13}$C NMR; $^{19}$F NMR; IR |
|---|---|---|---|---|
| | | | 7.56 (d, J = 7.8 Hz, 1H), 7.42 (d, J = 8.1 Hz, 1H), 6.84 (dd, J = 9.9, 36.0 Hz, 1H), 5.08-5.02 (m, 1H), 4.79-4.69 (m, 2H), 4.56-4.52 (m, 1H), 3.60-3.47 (m, 2H), 2.74-2.66 (m, 2H), 1.31 (d, J = 6.6 Hz, 3H), 1.17 (t, J = 7.8 Hz, 3H) | |
| F142 | | 642 ([M − H]$^−$) | $^1$H NMR (300 MHz, DMSO-d$_6$) δ 8.83 (d, J = 8.1 Hz, 1H), 8.12 (s, 1H), 8.08 (d, J = 8.1 Hz, 1H), 7.75 (s, 1H), 7.63 (s, 1H), 7.59-7.56 (m, 1H), 7.21 (d, J = 8.7 Hz, 1H), 6.83 (dd, J = 10.2, 35.7 Hz, 1H), 5.04-4.98 (m, 1H), 4.79-4.69 (m, 2H), 4.59-4.52 (m, 1H), 3.86 (s, 3H), 3.60-3.47 (m, 2H), 1.31 (d, J = 6.6 Hz, 3H) | IR (thin film) 3421, 2927, 1650, 1022 cm$^{−1}$ |
| F143 | 125-128 | 704 ([M − H]$^−$) | $^1$H NMR (400 MHz, CDCl$_3$) δ 7.85 (s, 1H), 7.79-7.74 (m, 1H), 7.63 (d, J = 8.1 Hz, 1H), 7.46 (s, 2H), 7.38 (s, 1H), 6.21 (d, J = 8.1 Hz, 1H), 5.87 (dd, J = 32.6, 9.7 Hz, 1H), 4.78-4.61 (m, 2H), 4.19-4.03 (m, 1H), 4.03-3.90 (m, 1H), 3.54 (dd, J = 14.5, 6.5 Hz, 1H), 3.41 (dd, J = 14.5, 5.0 Hz, 1H), 2.15-2.01 (m, 2H), 1.54 (d, J = 6.9 Hz, 3H), 1.52-1.41 (m, 2H), 0.95 (t, J = 7.4 Hz, 3H) | $^{19}$F NMR (376 MHz, CDCl$_3$) δ −59.06, −61.13, −69.31, −95.94, −112.56 |

TABLE 5

Structure and Preparation Method for FC Series Compounds

| No. | Structure | Prep.* |
|---|---|---|
| FC1 | [Structure: 3,4,5-trichlorophenyl group connected to CH(C(CH3)F2) group, linked via C=CF to phenyl-C(O)NH-CH(CH3)-CH2-S(O)2-CH2-CF3] | 13 |
| FC2 | [Structure: 3,4,5-trichlorophenyl group connected to CH(C(CH3)F2) group, linked via C=CF to phenyl-C(O)NH-CH(CH3)-CH2-S-CH2-CF3] | 13 |

*prepared according to example number

TABLE 6

Structure and Preparation Method for CC Series Molecules

| No. | Structure | Prep.* |
|---|---|---|
| CC1 | [Structure: 3,4,5-trichlorophenyl group connected to CH(CF3) group, linked via C=CF to phenyl-COOH] | 1 |

*prepared according to example number

TABLE 7

Analytical Data for Compounds in Table 5

| No. | Mp (° C.) | Mass (m/z) | ¹H NMR | ¹³C NMR; ¹⁹F NMR; IR |
|---|---|---|---|---|
| FC1 | | 617 ([M + H]⁺) | ¹H NMR (300 MHz, CDCl₃) δ 7.81 (d, J = 8.2 Hz, 2H), 7.64 (d, J = 8.5 Hz, 2H), 7.43 (s, 2H), 6.57 (d, J = 7.9 Hz, 1H), 5.79 (dd, J = 32.7, 9.6 Hz, 1H), 4.73 (dt, J = 13.0, 6.3 Hz, 1H), 4.60 (p, J = 9.0 Hz, 1H), 4.00 (p, J = 9.2 Hz, 2H), 3.57 (dd, J = 14.5, 5.8 Hz, 1H), 3.43 (dd, J = 14.5, 5.2 Hz, 1H), 1.59 (d, J = 7.0 Hz, 3H) | ¹⁹F NMR (376 MHz, CDCl₃) δ −61.04, −69.40, −111.75 |

TABLE 7-continued
Analytical Data for Compounds in Table 5
| No. | Mp (° C.) | Mass (m/z) | $^1$H NMR | $^{13}$C NMR; $^{19}$F NMR; IR |
|---|---|---|---|---|
| FC2 | | 584 ([M + H]$^+$) | $^1$H NMR (400 MHz, CDCl$_3$) δ 7.80 (d, J = 8.2 Hz, 2H), 7.66-7.59 (m, 2H), 7.43 (s, 2H), 6.22 (d, J = 7.9 Hz, 1H), 5.78 (dd, J = 32.8, 9.6 Hz, 1H), 4.60 (p, J = 8.9 Hz, 1H), 4.49-4.34 (m, 1H), 3.26-3.05 (m, 2H), 2.99-2.86 (m, 2H), 1.40-1.34 (m, 3H) | $^{19}$F NMR (376 MHz, CDCl$_3$) δ −66.49, −69.41, −111.71 |
TABLE 8
Structure and Preparation Method for PF Series Compounds
| No. | Structure | Prep.* |
|---|---|---|
| PF1 | 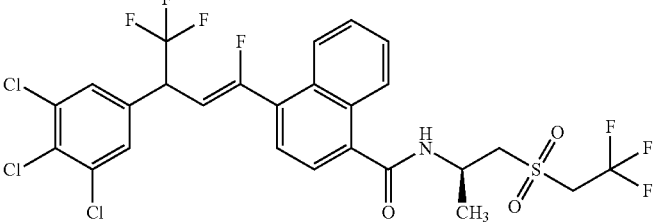 | 13 |
| PF2 | 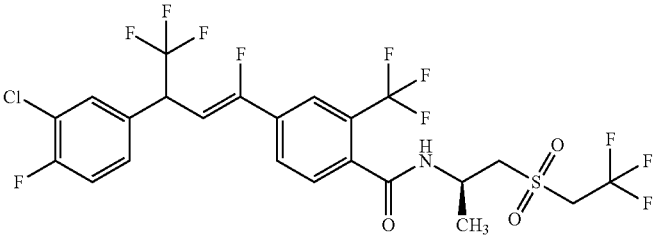 | 13 |
| PF4 | 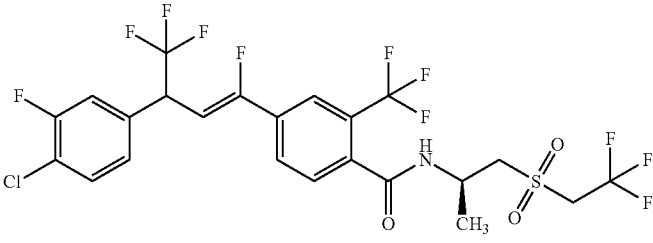 | 13 |
| PF5 | 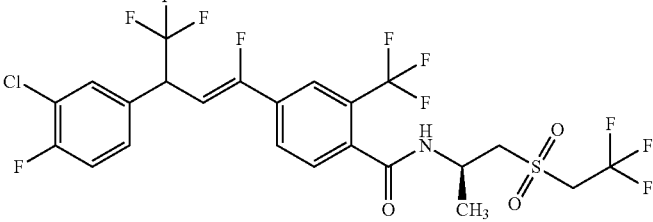 | 13 |

TABLE 8-continued

Structure and Preparation Method for PF Series Compounds

| No. | Structure | Prep.* |
|---|---|---|
| PF8 | (structure) | 13 |

*prepared according to example number

TABLE 9

Analytical Data for Compounds in Table 8

| No. | Mp (° C.) | Mass (m/z) | $^1$H NMR | $^{13}$C NMR; $^{19}$F NMR; IR |
|---|---|---|---|---|
| PF1 | | 664 ([M + H]$^+$) | $^1$H NMR (300 MHz, DMSO-d$_6$) δ 8.87 (d, J = 8.1 Hz, 1H), 8.26 (d, J = 7.5 Hz, 1H), 8.07 (s, 2H), 7.98-7.96 (m, 1H), 7.75-7.69 (m, 2H), 7.67 (s, 1H), 7.63 (d, J = 7.5 Hz, 1H), 6.29 (dd, J = 9.9, 34.2 Hz, 1H), 5.35-5.29 (m, 1H), 4.82-4.69 (m, 3H), 3.71-3.66 (m, 1H), 3.57-3.50 (m, 1H), 1.39 (d, J = 6.6 Hz, 3H) | IR (thin film) 3429, 1651, 1023, 706 cm$^{-1}$ |
| PF2 | | 630 ([M − H]$^-$) | $^1$H NMR (400 MHz, DMSO-d$_6$) δ 8.83 (d, J = 8.4 Hz, 1H), 8.13 (s, 1H), 8.07 (d, J = 7.6 Hz, 1H), 7.96 (d, J = 6.8 Hz, 1H), 7.69-7.68 (m, 1H), 7.63 (d, J = 7.6 Hz, 1H), 7.53-7.48 (m, 1H) 6.83 (dd, J = 9.6, 35.6 Hz, 1H), 5.18-5.13 (m, 1H), 4.78-4.70 (m, 2H), 4.55-4.52 (m, 1H), 3.59-3.31 (m, 2H), 1.30 (d, J = 4.0 Hz, 3H) | IR (thin film) 3279, 2969, 1655, 1127 cm$^{-1}$ |
| PF4 | | 632 ([M + H]$^+$) | $^1$H NMR (400 MHz, DMSO-d$_6$) δ 8.80 (d, J = 8.0 Hz, 1H), 8.09 (s, 1H), 8.04 (d, J = 8.4 Hz, 1H), 7.77 (d, J = 10.8 Hz, 1H), 7.67 (t, J = 8.0 Hz, 1H), 7.60 (d, J = 8.0 Hz, 1H), 7.51 (d, J = 8.8 Hz, 1H), 6.77 (dd, J = 9.6, 35.6 Hz, 1H), 5.16-5.11 (m, 1H), 4.74-4.66 (m, 2H), 4.52-4.49 (m, 1H), 3.56-3.42 (m, 2H), 1.36 (d, J = 6.4 Hz, 3H) | IR (thin film) 3428, 2969, 1650 cm$^{-1}$ |

TABLE 9-continued

Analytical Data for Compounds in Table 8

| No. | Mp (° C.) | Mass (m/z) | $^1$H NMR | $^{13}$C NMR; $^{19}$F NMR; IR |
|---|---|---|---|---|
| PF5 | 133-135 | 692 ([M − H]$^−$) | $^1$H NMR (300 MHz, DMSO-d$_6$) δ 8.84 (d, J = 8.1 Hz, 1H), 8.13 (s, 1H), 8.08 (d, J = 7.8 Hz, 1H), 7.97 (s, 1H), 7.87 (d, J = 8.4 Hz, 1H), 7.63 (d, J = 8.1 Hz, 1H), 7.59 (d, J = 8.4 Hz, 1H), 6.85 (dd, J = 9.9 Hz, 36.0 Hz, 1H), 5.20-5.13 (m, 1H), 4.79 (q, J = 10.2 Hz, 2H), 4.56-4.51 (m, 1H), 3.55-3.49 (m, 2H), 1.31 (d, J = 6.6 Hz, 3H) | |
| PF8 | 69-70 | 626 ([M − H]$^−$) | $^1$H NMR (400 MHz, DMSO-d$_6$) δ 8.80 (d, J = 8.4 Hz, 1H), 8.11 (s, 1H), 8.07 (d, J = 8.4 Hz, 1H), 7.62-7.60 (m, 2H), 7.47 (s, 2H), 6.78 (dd, J = 10.4 Hz, 36.4 Hz, 1H), 5.02-4.98 (m, 1H), 4.77 (q, J = 10.4 Hz, 2H), 4.56-4.52 (m, 1H), 3.59-3.31 (m, 2H), 2.35 (s, 3H), 1.30 (d, J = 6.8 Hz, 3H) | |

BAW, CEW, & CL Rating Table

| % Control (or Mortality) | Rating |
|---|---|
| 50-100 | A |
| More than 0-Less than 50 | B |
| Not Tested | C |
| No activity noticed in this bioassay | D |

GPA & YFM Rating Table

| % Control (or Mortality) | Rating |
|---|---|
| 80-100 | A |
| More than 0-Less than 80 | B |
| Not Tested | C |
| No activity noticed in this bioassay | D |

TABLE ABC

Biological Results

| | Pests | | | |
|---|---|---|---|---|
| No. | BAW | CL | GPA | YFM |
| F1 | A | A | B | C |
| F2 | A | A | B | C |
| F3 | A | A | B | C |
| F4 | A | A | C | C |
| F5 | A | A | C | C |
| F6 | A | A | C | C |
| F7 | A | A | C | C |
| F8 | A | A | C | C |
| F9 | A | A | C | C |
| F10 | A | A | C | C |
| F11 | A | A | C | C |
| F12 | A | A | C | C |
| F13 | A | A | C | C |
| F14 | A | A | C | C |
| F15 | A | A | C | C |
| F16 | A | A | C | C |
| F17 | A | A | C | A |
| F18 | A | A | C | A |
| F19 | A | A | C | A |
| F20 | A | A | C | D |
| F21 | A | A | A | A |
| F22 | A | A | B | A |
| F23 | A | A | C | A |
| F24 | A | A | C | C |
| F25 | A | A | C | A |
| F26 | A | A | C | A |
| F27 | A | A | C | A |
| F28 | A | A | C | B |
| F29 | A | A | C | A |
| F30 | A | A | C | A |
| F31 | A | A | C | B |
| F32 | A | A | C | A |
| F33 | A | A | C | A |
| F34 | A | A | C | A |

TABLE ABC-continued

Biological Results

| No. | BAW | CL | GPA | YFM |
|---|---|---|---|---|
| F35 | A | A | C | A |
| F36 | A | A | C | A |
| F37 | A | A | C | A |
| F38 | A | A | C | C |
| F39 | A | A | C | C |
| F40 | A | A | C | C |
| F41 | A | A | C | C |
| F42 | A | A | B | A |
| F43 | A | A | A | A |
| F44 | A | A | C | A |
| F45 | A | A | C | A |
| F46 | A | A | B | B |
| F47 | A | A | C | C |
| F48 | A | A | C | C |
| F49 | A | A | C | A |
| F50 | A | A | C | C |
| F51 | A | A | C | C |
| F52 | A | A | C | D |
| F53 | A | A | C | D |
| F54 | A | A | C | A |
| F55 | A | A | C | A |
| F56 | A | A | C | A |
| F57 | A | A | C | C |
| F58 | A | A | C | C |
| F59 | C | C | C | C |
| F60 | C | C | C | C |
| F61 | C | C | C | C |
| F62 | A | A | C | C |
| F63 | A | A | C | C |
| F64 | A | A | C | C |
| F65 | A | A | C | B |
| F66 | A | A | C | C |
| F67 | A | A | C | C |
| F68 | A | A | B | A |
| F69 | A | A | B | A |
| F70 | A | A | C | C |
| F71 | A | A | C | C |
| F72 | A | A | C | C |
| F73 | A | A | C | C |
| F75 | A | A | C | C |
| F76 | A | A | B | D |
| F77 | A | A | C | C |
| F78 | A | A | C | B |
| F79 | A | A | C | C |
| F80 | A | A | C | C |
| F81 | A | A | C | C |
| F82 | A | A | C | C |
| F83 | A | A | C | C |
| F84 | A | A | C | C |
| F85 | A | A | C | C |
| F86 | A | A | C | C |
| F87 | A | A | C | C |
| F88 | A | A | A | C |
| F89 | A | A | C | C |
| F90 | A | A | C | C |
| F91 | A | A | C | D |
| F92 | A | A | C | B |
| F93 | A | A | C | C |
| F94 | A | A | C | C |
| F95 | A | A | C | A |
| F96 | A | A | C | C |
| F97 | A | A | C | C |
| F98 | A | A | C | A |
| F99 | A | A | C | A |
| F100 | A | A | C | C |
| F101 | A | A | C | C |
| F102 | A | A | C | A |
| F103 | A | A | C | A |
| F104 | A | A | D | A |
| F109 | A | A | C | C |
| F110 | A | A | C | C |
| F112 | A | A | C | C |
| F113 | A | A | C | C |
| F114 | A | A | C | C |
| F116 | A | A | C | C |
| F117 | A | A | C | C |
| F119 | A | A | C | A |
| F120 | A | A | C | C |
| F121 | A | A | C | A |
| F122 | A | A | B | A |
| F123 | A | A | D | A |
| F124 | A | A | C | C |
| F125 | A | A | C | D |
| F126 | A | A | C | C |
| F127 | A | A | C | C |
| F128 | A | A | C | C |
| F129 | A | A | C | C |
| F130 | A | A | C | B |
| F131 | A | A | C | A |
| F132 | A | A | C | C |
| F133 | A | A | C | C |
| F136 | A | A | C | C |
| F137 | A | A | C | C |
| F138 | A | A | C | C |
| F141 | A | A | C | D |
| F142 | A | A | C | B |
| F143 | A | A | C | D |
| PF1 | A | A | C | A |
| PF2 | A | A | B | B |
| PF4 | A | A | C | C |
| PF5 | A | A | C | B |
| PF8 | A | A | C | C |

Comparative Data

Bioassays on BAW and CL were conducted according to the procedures outlined in Example A: Bioassays on Beet Armyworm ("BAW") and Cabbage Looper ("CL") using the indicated concentrations. The results are indicated in Table CD1 and Table CD2.

TABLE CD1

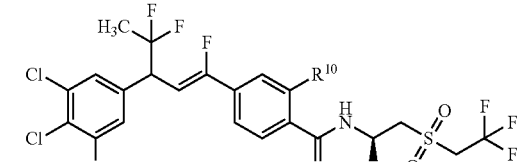

| No. | $R^{10}$ | 5 µg/cm² | | 0.5 µg/cm² | | 0.05 µg/cm² | |
|---|---|---|---|---|---|---|---|
| | | BAW | CL | BAW | CL | BAW | CL |
| FC1 | H | 100* | 100 | 20 | 81 | 0 | 0 |
| F14 | $CH_3$ | 100 | 100 | 100 | 100 | 69 | 100 |
| F16 | $CF_3$ | 100 | 100 | 100 | 100 | 100 | 100 |

*Percent control (or mortality)

TABLE CD2

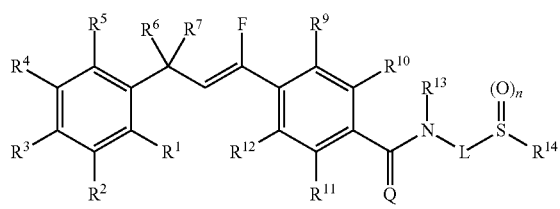

| No. | $R^{10}$ | 5 µg/cm² | | 0.5 µg/cm² | | 0.05 µg/cm² | |
|---|---|---|---|---|---|---|---|
| | | BAW | CL | BAW | CL | BAW | CL |
| FC2 | H | 100* | 100 | 20 | 0 | 0 | 0 |
| F10 | Cl | 100 | 100 | 100 | 100 | 0 | 6 |
| F7 | Br | 100 | 100 | 100 | 56 | 0 | 0 |
| F4 | $CH_3$ | 100 | 100 | 100 | 60 | 67 | 7 |
| F1 | $CF_3$ | — | — | 100 | 100 | 100 | 31 |

*Percent control (or mortality)

The invention claimed is:

1. A molecule having the following formula

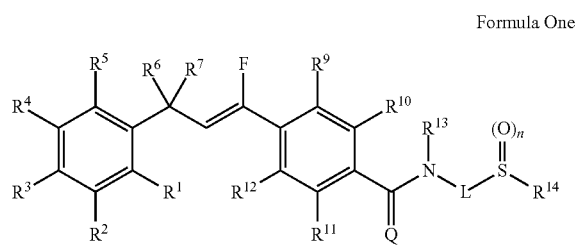

Formula One wherein:
(A) $R^1$, $R^5$, $R^6$, $R^{11}$, $R^{12}$, and $R^{13}$ are each independently selected from the group consisting of H, F, Cl, Br, I, CN, $(C_1$-$C_4)$alkyl, $(C_1$-$C_4)$haloalkyl, $(C_1$-$C_4)$alkoxy, and $(C_1$-$C_4)$haloalkoxy;
(B) $R^2$, $R^3$, and $R^4$ are each independently selected from the group consisting of H, F, Cl, Br, I, CN, $(C_1$-$C_4)$alkyl, $(C_2$-$C_4)$alkenyl, $(C_2$-$C_4)$alkynyl, $(C_1$-$C_4)$haloalkyl, $(C_1$-$C_4)$alkoxy, and $(C_1$-$C_4)$haloalkoxy;
(C) $R^7$ is $(C_1$-$C_6)$haloalkyl;
(D) $R^9$ is selected from the group consisting of H, F, Cl, Br, I, CN, $(C_1$-$C_4)$alkyl, $(C_1$-$C_4)$haloalkyl, $(C_1$-$C_4)$alkoxy, and $(C_1$-$C_4)$haloalkoxy;
(E) $R^{10}$ is selected from the group consisting of F, Cl, Br, I, CN, $(C_1$-$C_4)$alkyl, $(C_2$-$C_4)$alkenyl, $(C_2$-$C_4)$alkynyl, $(C_1$-$C_4)$haloalkyl, $(C_1$-$C_4)$alkoxy, and $(C_1$-$C_4)$haloalkoxy; or
(F) $R^9$ and $R^{10}$ together can optionally form a 3- to 5-membered saturated or unsaturated, hydrocarbyl link, wherein said hydrocarbyl link may optionally be substituted with one or more substituents independently selected from the group consisting of F, Cl, Br, I, and CN;
(G) Q is selected from the group consisting of O or S;
(H) L is $(C_1$-$C_6)$alkyl;
(I) n is 0, 1, or 2;
(J) $R^{14}$ is selected from the group consisting of $(C_1$-$C_4)$alkyl, $(C_2$-$C_4)$alkenyl, $(C_3$-$C_4)$cycloalkyl, $(C_1$-$C_4)$haloalkyl, $(C_1$-$C_4)$alkoxy, $(C_1$-$C_4)$haloalkoxy, and phenyl, wherein each alkyl, alkenyl, cycloalkyl, haloalkyl, alkoxy, haloalkoxy, and phenyl may optionally be substituted with one or more substituents independently selected from the group consisting of F, Cl, Br, I, CN, and OH; and agriculturally acceptable acid addition salts, salts, solvates, esters, crystal polymorphs, isotopes, and resolved stereoisomers, of the molecules of Formula One.

2. A molecule having the following formula

Formula One wherein:
(A) $R^1$, $R^5$, $R^6$, $R^{11}$, $R^{12}$, and $R^{13}$ are each independently selected from the group consisting of H, F, Cl, Br, I, CN, $(C_1$-$C_4)$alkyl, $(C_1$-$C_4)$haloalkyl, $(C_1$-$C_4)$alkoxy, and $(C_1$-$C_4)$haloalkoxy;
(B) $R^2$, $R^3$, and $R^4$ are each independently selected from the group consisting of H, F, Cl, Br, I, CN, $(C_1$-$C_4)$alkyl, $(C_2$-$C_4)$alkenyl, $(C_2$-$C_4)$alkynyl, $(C_1$-$C_4)$haloalkyl, $(C_1$-$C_4)$alkoxy, and $(C_1$-$C_4)$haloalkoxy;
(C) $R^7$ is $(C_1$-$C_6)$haloalkyl;
(D) $R^9$ is selected from the group consisting of H, F, Cl, Br, I, CN, $(C_1$-$C_4)$alkyl, $(C_1$-$C_4)$haloalkyl, $(C_1$-$C_4)$alkoxy, and $(C_1$-$C_4)$haloalkoxy;
(E) $R^{10}$ is selected from the group consisting of, F, Cl, Br, I, CN, $(C_1$-$C_4)$alkyl, $(C_2$-$C_4)$alkenyl, $(C_2$-$C_4)$alkynyl, $(C_1$-$C_4)$haloalkyl, $(C_1$-$C_4)$alkoxy, and $(C_1$-$C_4)$haloalkoxy; or
(F) $R^9$ and $R^{10}$ together can optionally form a 3- to 5-membered saturated or unsaturated, hydrocarbyl link, wherein said hydrocarbyl link may optionally be substituted with one or more substituents independently selected from the group consisting of F, Cl, Br, I, and CN;
(G) Q is selected from the group consisting of O or S;
(H) L is $(C_1$-$C_6)$alkyl;
(I) n is 0, 1, or 2; and
(J) $R^{14}$ is selected from the group consisting of $(C_1$-$C_4)$alkyl, $(C_2$-$C_4)$alkenyl, $(C_3$-$C_4)$cycloalkyl, $(C_1$-$C_4)$haloalkyl, $(C_1$-$C_4)$alkoxy, $(C_1$-$C_4)$haloalkoxy, and phenyl, wherein each alkyl, alkenyl, cycloalkyl, haloalkyl, alkoxy, haloalkoxy, and phenyl may optionally be substituted with one or more substituents independently selected from the group consisting of F, Cl, Br, I, CN, and OH.

3. A molecule according to claim 2 wherein $R^1$, $R^3$, $R^4$, $R^5$, $R^6$, $R^9$, $R^{11}$, $R^{12}$, and $R^{13}$ are H.

4. A molecule according to claim 2 wherein $R^2$ is Cl, Br, or $CH_3$.

5. A molecule according to claim 2 wherein $R^3$ is F, Cl, Br, or CH=$CH_2$.

6. A molecule according to claim 2 wherein $R^4$ is Cl, Br, or $CH_3$.

7. A molecule according to claim 2 wherein $R^2$, $R^3$, and $R^4$ are Cl.

8. A molecule according to claim 2 wherein $R^7$ is $CF_3$ or $CF_2CH_3$.

9. A molecule according to claim 2 wherein $R^{10}$ is Cl, Br, $CH_3$, or $CF_3$.

10. A molecule according to claim 2 wherein Q is O.

11. A molecule according to claim 2 wherein L is $CH_2CH_2$ or $CH(CH_3)CH_2$.

12. A molecule according to claim 2 wherein $R^{14}$ is $CH_2CH_3$ or $CH_2CF_3$.

13. A molecule according to claim 2 wherein
(A) $R^1$, $R^5$, $R^6$, $R^{11}$, $R^{12}$, and $R^{13}$ are H;
(B) $R^2$, $R^3$, and $R^4$ are each independently selected from the group consisting of H, F, Cl, Br, $(C_1-C_4)$alkyl, and $(C_2-C_4)$alkenyl;
(C) $R^2$ is $(C_1-C_6)$haloalkyl;
(D) $R^9$ is H;
(E) $R^{10}$ is selected from the group consisting of Cl, Br, $(C_1-C_4)$alkyl, and $(C_1-C_4)$haloalkyl;
(G) Q is O;
(H) L is $(C_1-C_6)$alkyl;
(I) n is 0, 1, or 2;
(J) $R^{14}$ is selected from the group consisting of $(C_1-C_4)$alkyl and $(C_1-C_4)$haloalkyl, wherein each alkyl or haloalkyl may optionally be substituted with one or more substituents independently selected from the group consisting of F, Cl, Br, I, CN, and OH.

14. A pesticidal composition comprising a molecule according to claim 2 further comprising one or more active ingredients.

15. A pesticidal composition according to claim 14 wherein said active ingredient is selected from the group consisting of N-(3-chloro-1-(pyridin-3-yl)-1H-pyrazol-4-yl)-N-ethyl-3-((3,3,3-trifluoropropyl)thio)propanamide[AI-1], 1,3-dichloropropene, chlorpyrifos, chlorpyrifos-methyl, hexaflumuron, methoxyfenozide, noviflumuron, spinetoram, spinosad, sulfoxaflor, and sulfuryl fluoride.

16. A pesticidal composition comprising a molecule according to claim 2 and a seed.

17. A process to control a pest said process comprising applying to a locus, a pesticidally effective amount of a pesticidal composition wherein said pesticidal composition comprises a molecule according to claim 2.

18. A molecule according to claim 2 wherein said molecule is selected from one of the following molecules

| No. | Structure |
|---|---|
| F1 | 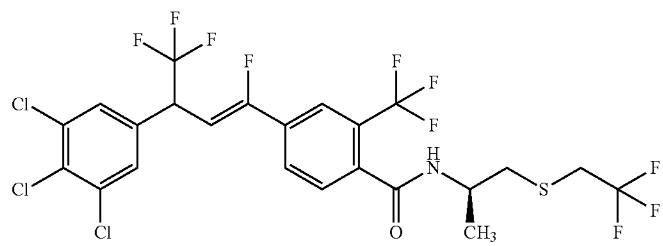 [SMILES: C[C@H](CSCC(F)(F)F)NC(=O)c1ccc(/C(F)=C/C(c2cc(Cl)c(Cl)c(Cl)c2)C(F)(F)F)cc1C(F)(F)F] |
| F2 | 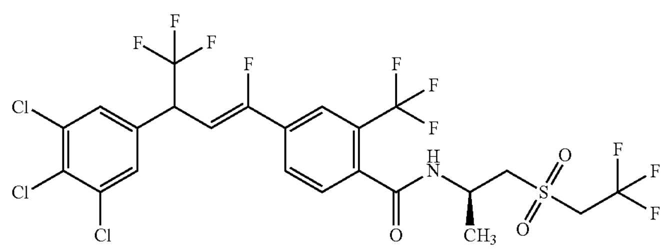 |
| F3 | 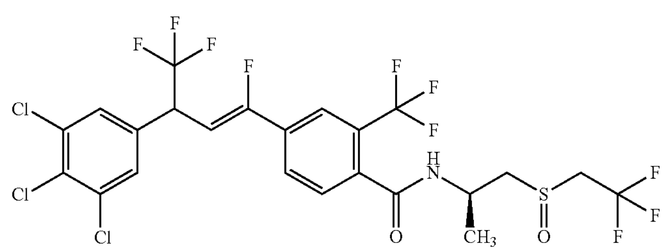 [SMILES: C[C@H](CS(=O)CC(F)(F)F)NC(=O)c1ccc(/C(F)=C/C(c2cc(Cl)c(Cl)c(Cl)c2)C(F)(F)F)cc1C(F)(F)F] |
| F4 | 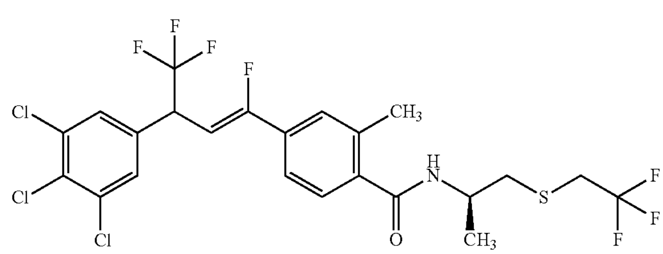 [SMILES: Cc1cc(/C(F)=C/C(c2cc(Cl)c(Cl)c(Cl)c2)C(F)(F)F)ccc1C(=O)N[C@H](C)CSCC(F)(F)F] |

| No. | Structure |
|---|---|
| F5 | 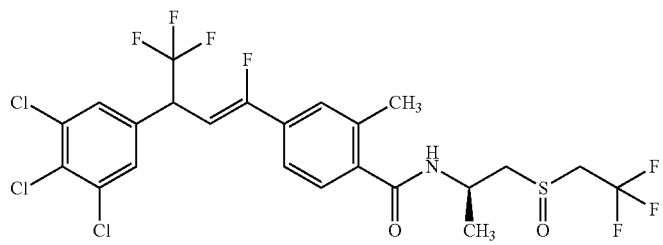 [SMILES: Cc1cc(/C(F)=C/C(c2cc(Cl)c(Cl)c(Cl)c2)C(F)(F)F)ccc1C(=O)N[C@H](C)CS(=O)CC(F)(F)F] |
| F6 | 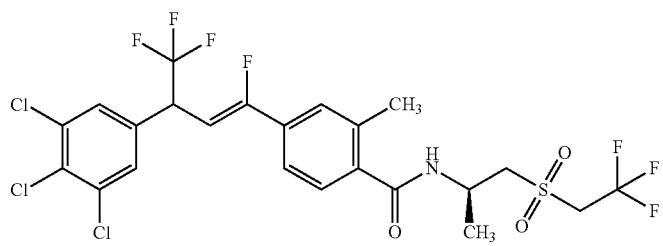 [SMILES: Cc1cc(/C(F)=C/C(c2cc(Cl)c(Cl)c(Cl)c2)C(F)(F)F)ccc1C(=O)N[C@H](C)CS(=O)(=O)CC(F)(F)F] |
| F7 | 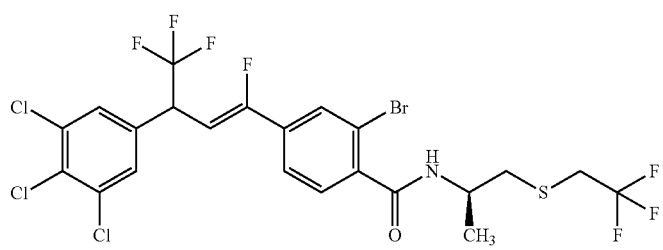 |
| F8 | 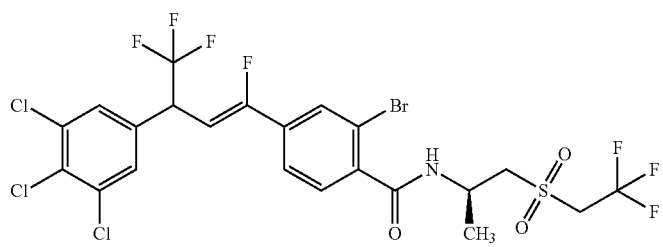 [SMILES: C[C@H](CS(=O)(=O)CC(F)(F)F)NC(=O)c1ccc(/C(F)=C/C(c2cc(Cl)c(Cl)c(Cl)c2)C(F)(F)F)cc1Br] |
| F9 | 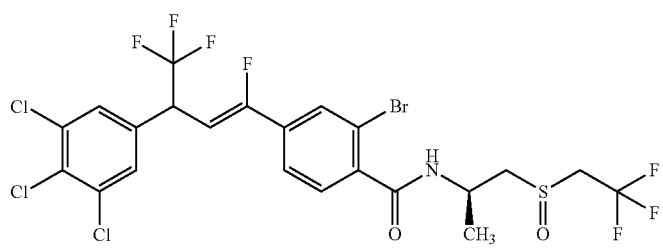 |
| F10 | 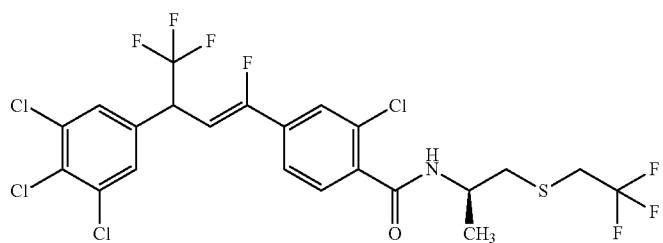 [SMILES: C[C@H](CSCC(F)(F)F)NC(=O)c1ccc(/C(F)=C/C(c2cc(Cl)c(Cl)c(Cl)c2)C(F)(F)F)cc1Cl] |

-continued
| No. | Structure |
|---|---|
| F11 | 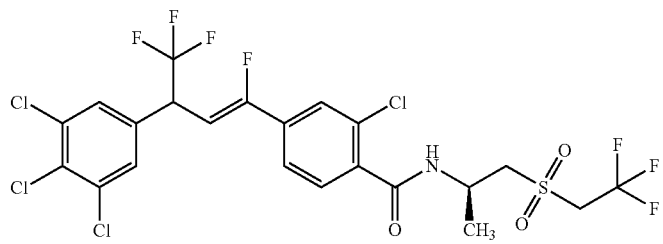 |
| F12 | 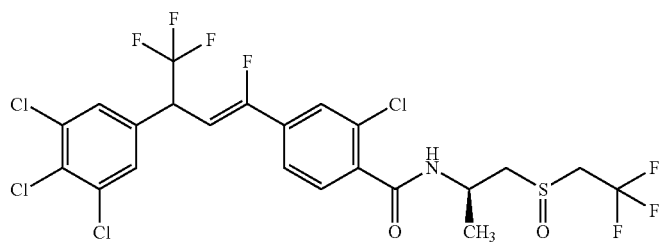 [SMILES: C[C@H](CS(=O)CC(F)(F)F)NC(=O)c1ccc(/C(F)=C/C(c2cc(Cl)c(Cl)c(Cl)c2)C(F)(F)F)cc1Cl] |
| F13 | 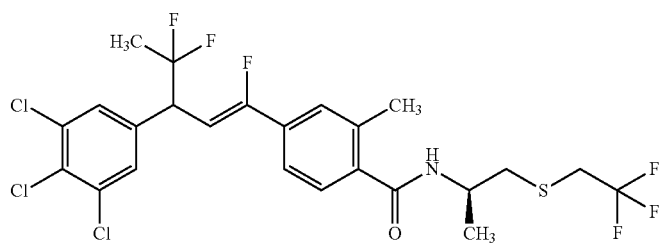 [SMILES: Cc1cc(/C(F)=C/C(c2cc(Cl)c(Cl)c(Cl)c2)C(C)(F)F)ccc1C(=O)N[C@H](C)CSCC(F)(F)F] |
| F14 | 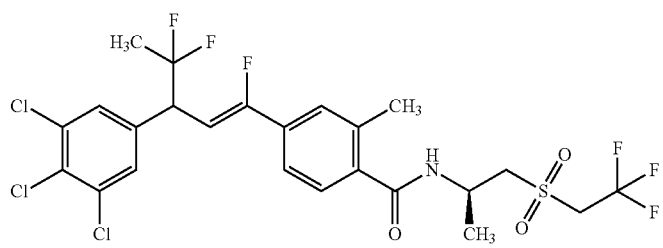 |
| F15 | 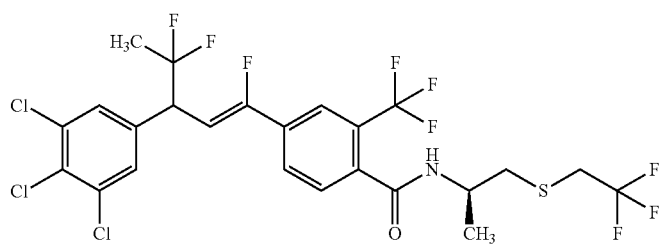 [SMILES: C[C@H](CSCC(F)(F)F)NC(=O)c1ccc(/C(F)=C/C(c2cc(Cl)c(Cl)c(Cl)c2)C(C)(F)F)cc1C(F)(F)F] |
| F16 | 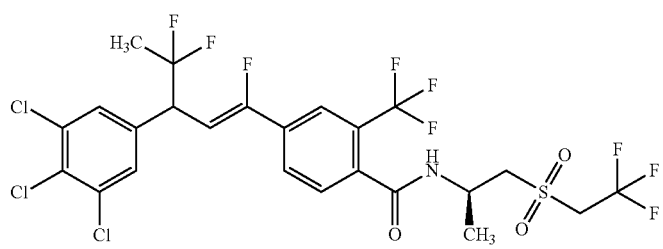 [SMILES: C[C@H](CS(=O)(=O)CC(F)(F)F)NC(=O)c1ccc(/C(F)=C/C(c2cc(Cl)c(Cl)c(Cl)c2)C(C)(F)F)cc1C(F)(F)F] |

-continued
| No. | Structure |
|---|---|
| F17 | 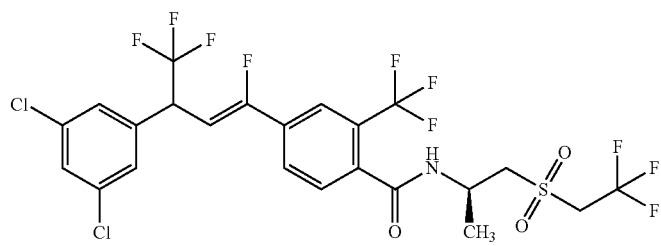 [SMILES: C[C@H](CS(=O)(=O)CC(F)(F)F)NC(=O)c1ccc(/C(F)=C/C(c2cc(Cl)cc(Cl)c2)C(F)(F)F)cc1C(F)(F)F] |
| F18 | 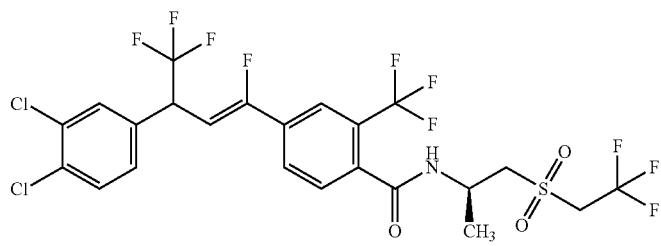 |
| F19 | 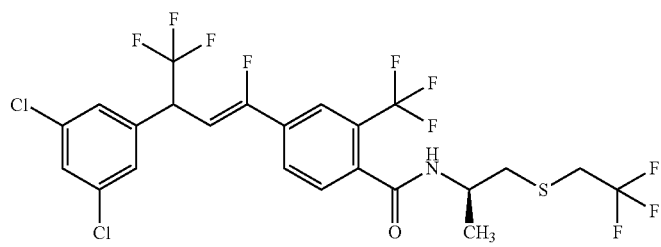 [SMILES: C[C@H](CSCC(F)(F)F)NC(=O)c1ccc(/C(F)=C/C(c2cc(Cl)cc(Cl)c2)C(F)(F)F)cc1C(F)(F)F] |
| F20 | 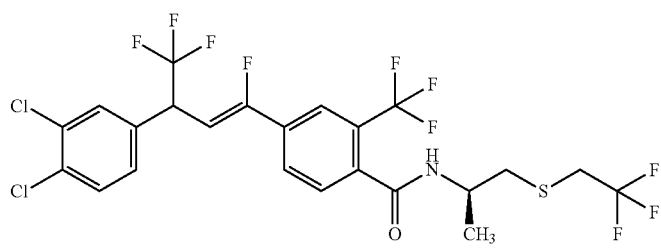 [SMILES: C[C@H](CSCC(F)(F)F)NC(=O)c1ccc(/C(F)=C/C(c2ccc(Cl)c(Cl)c2)C(F)(F)F)cc1C(F)(F)F] |
| F21 | 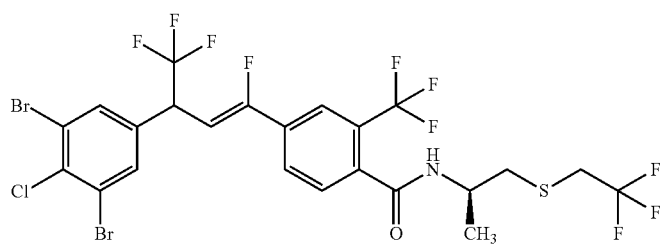 |
| F22 | 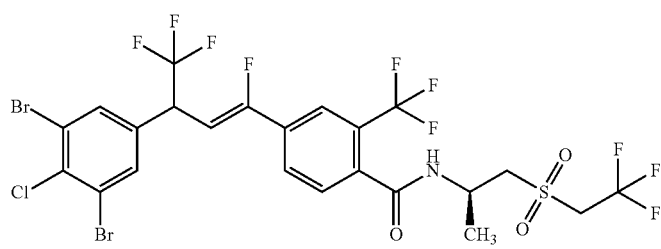 |

| No. | Structure |
|---|---|
| F23 | 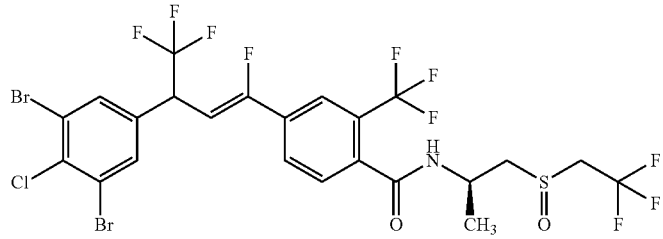 |
| F24 | 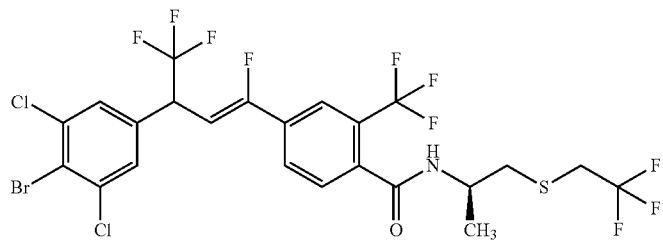 |
| F25 | 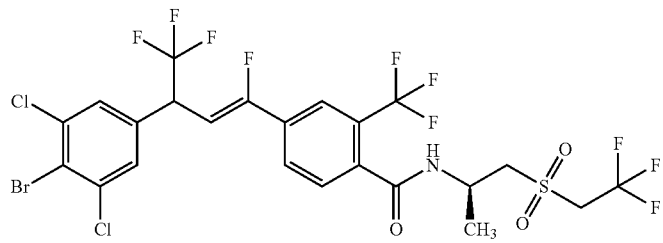 |
| F26 | 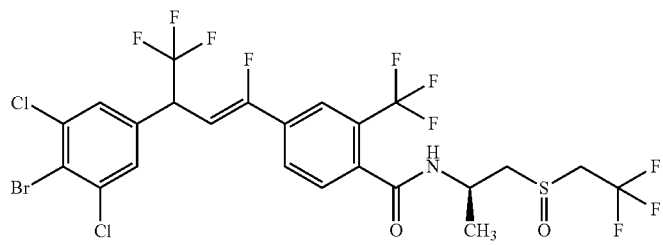 |
| F27 | 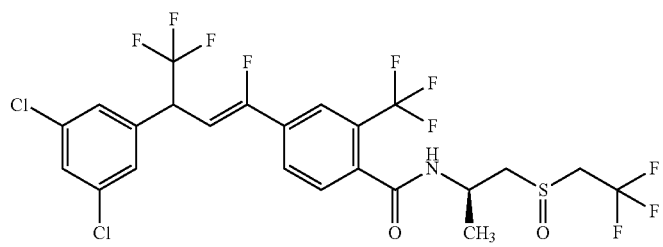 |
| F28 | 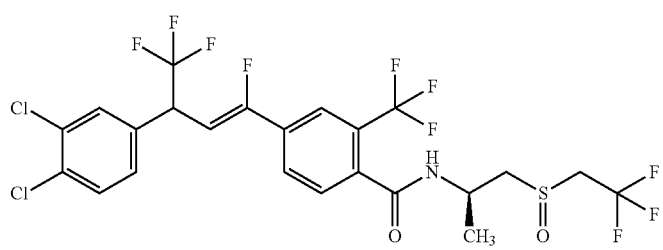 [SMILES: C[C@H](CS(=O)CC(F)(F)F)NC(=O)c1ccc(/C(F)=C/C(c2ccc(Cl)c(Cl)c2)C(F)(F)F)cc1C(F)(F)F] |

-continued
| No. | Structure |
|---|---|
| F29 | 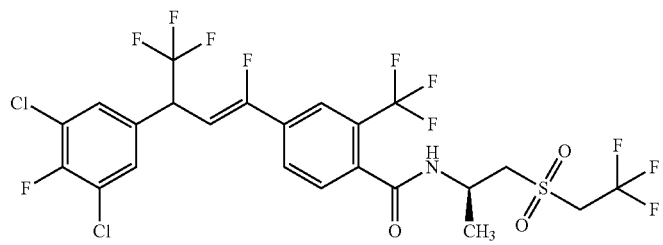 [SMILES: C[C@H](CS(=O)(=O)CC(F)(F)F)NC(=O)c1ccc(/C(F)=C/C(c2cc(Cl)c(F)c(Cl)c2)C(F)(F)F)cc1C(F)(F)F] |
| F30 | 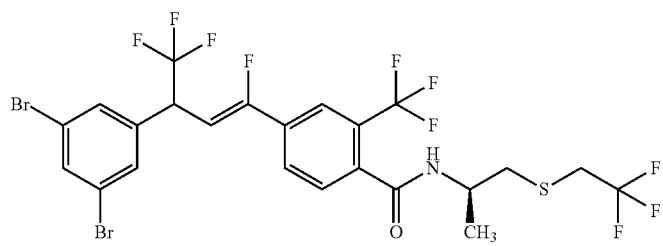 |
| F31 | 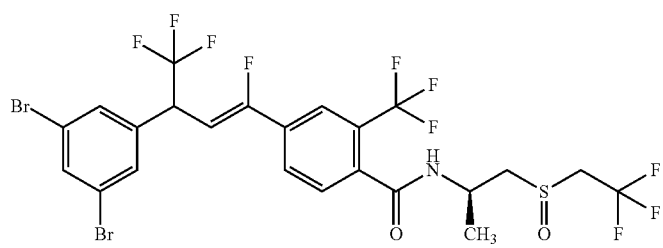 |
| F32 | 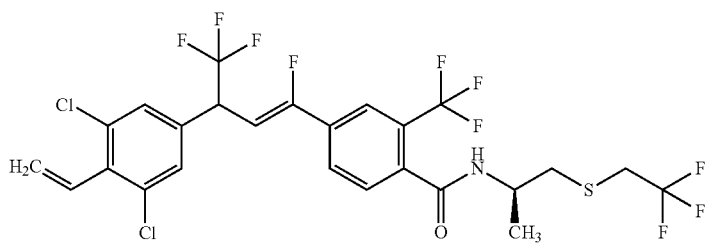 [SMILES: C=Cc1c(Cl)cc(C(/C=C(\F)c2ccc(C(=O)N[C@H](C)CSCC(F)(F)F)c(C(F)(F)F)c2)C(F)(F)F)cc1Cl] |
| F33 | 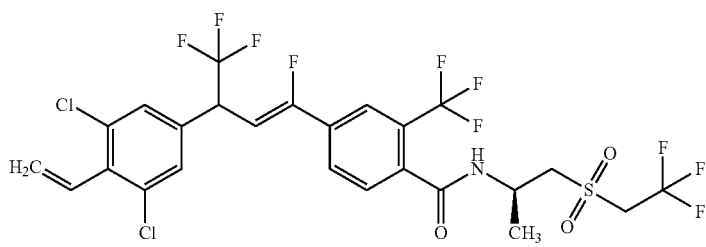 [SMILES: C=Cc1c(Cl)cc(C(/C=C(\F)c2ccc(C(=O)N[C@H](C)CS(=O)(=O)CC(F)(F)F)c(C(F)(F)F)c2)C(F)(F)F)cc1Cl] |
| F34 | 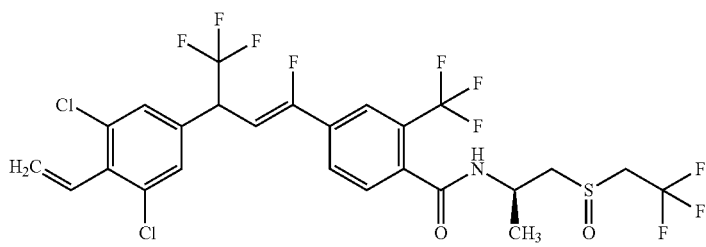 |

| No. | Structure |
|---|---|
| F35 | 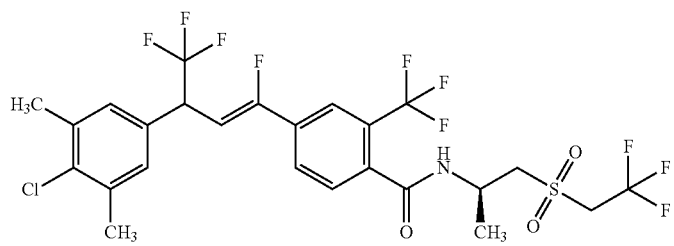 [SMILES: Cc1cc(C(/C=C(\F)c2ccc(C(=O)N[C@H](C)CS(=O)(=O)CC(F)(F)F)c(C(F)(F)F)c2)C(F)(F)F)cc(C)c1Cl] |
| F36 | 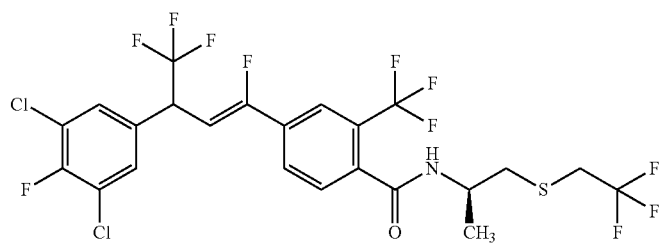 |
| F37 | 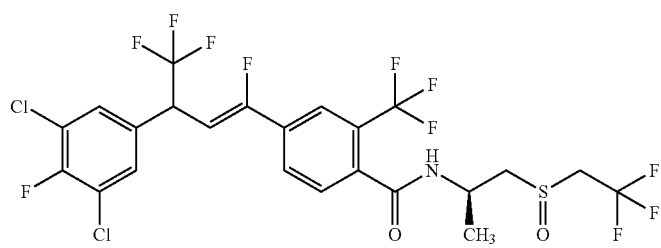 [SMILES: C[C@H](CS(=O)CC(F)(F)F)NC(=O)c1ccc(/C(F)=C/C(c2cc(Cl)c(F)c(Cl)c2)C(F)(F)F)cc1C(F)(F)F] |
| F38 | 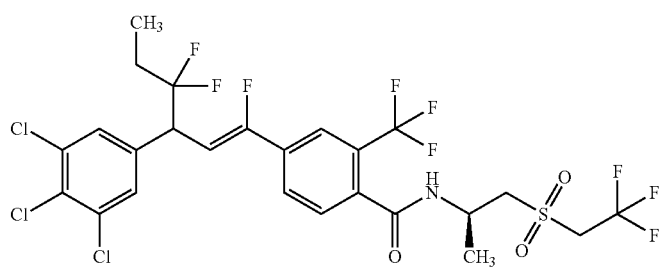 [SMILES: CCC(F)(F)C(/C=C(\F)c1ccc(C(=O)N[C@H](C)CS(=O)(=O)CC(F)(F)F)c(C(F)(F)F)c1)c1cc(Cl)c(Cl)c(Cl)c1] |
| F39 | 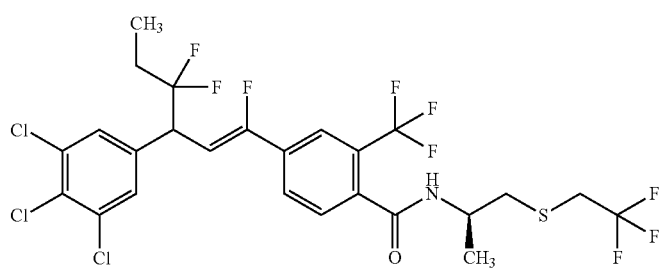 [SMILES: CCC(F)(F)C(/C=C(\F)c1ccc(C(=O)N[C@H](C)CSCC(F)(F)F)c(C(F)(F)F)c1)c1cc(Cl)c(Cl)c(Cl)c1] |
| F40 | 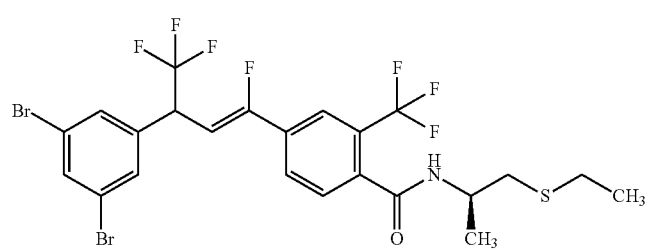 |

-continued

| No. | Structure |
|---|---|
| F41 | 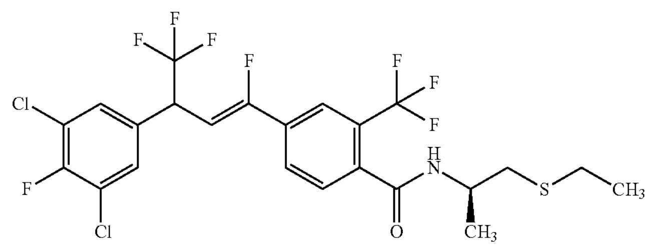 [SMILES: CCSC[C@@H](C)NC(=O)c1ccc(/C(F)=C/C(c2cc(Cl)c(F)c(Cl)c2)C(F)(F)F)cc1C(F)(F)F] |
| F42 | 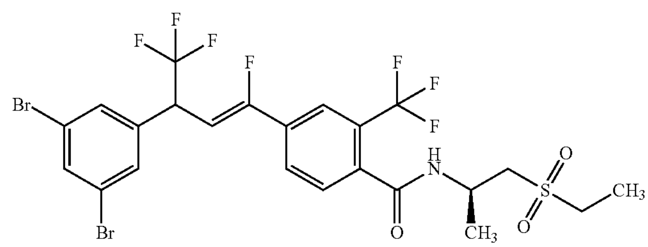 |
| F43 | 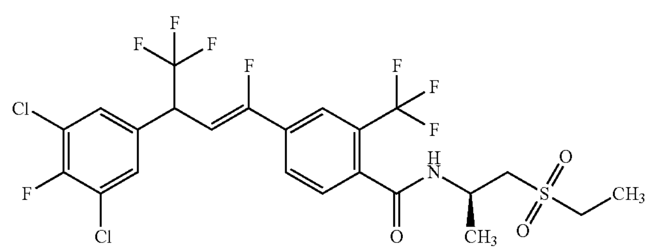 [SMILES: CCS(=O)(=O)C[C@@H](C)NC(=O)c1ccc(/C(F)=C/C(c2cc(Cl)c(F)c(Cl)c2)C(F)(F)F)cc1C(F)(F)F] |
| F44 | 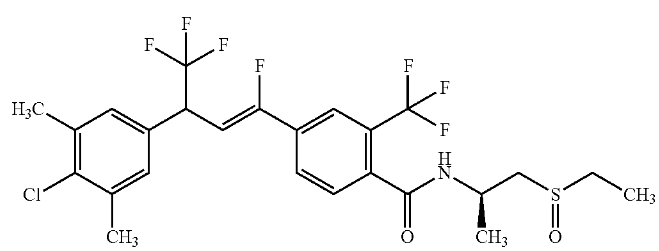 [SMILES: CCS(=O)C[C@@H](C)NC(=O)c1ccc(/C(F)=C/C(c2cc(C)c(Cl)c(C)c2)C(F)(F)F)cc1C(F)(F)F] |
| F45 | 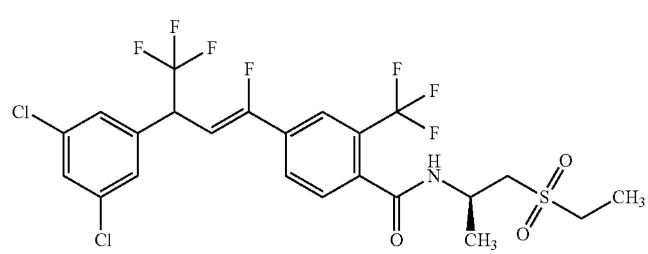 [SMILES: CCS(=O)(=O)C[C@@H](C)NC(=O)c1ccc(/C(F)=C/C(c2cc(Cl)cc(Cl)c2)C(F)(F)F)cc1C(F)(F)F] |
| F46 | 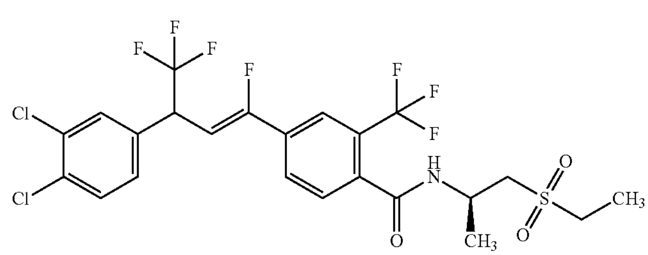 [SMILES: CCS(=O)(=O)C[C@@H](C)NC(=O)c1ccc(/C(F)=C/C(c2ccc(Cl)c(Cl)c2)C(F)(F)F)cc1C(F)(F)F] |

| No. | Structure |
|---|---|
| F47 | 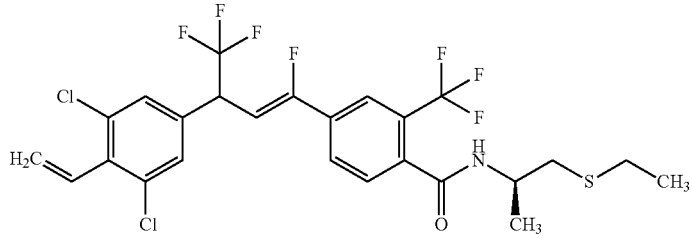 [SMILES: C=Cc1c(Cl)cc(C(/C=C(\F)c2ccc(C(=O)N[C@H](C)CSCC)c(C(F)(F)F)c2)C(F)(F)F)cc1Cl] |
| F48 | 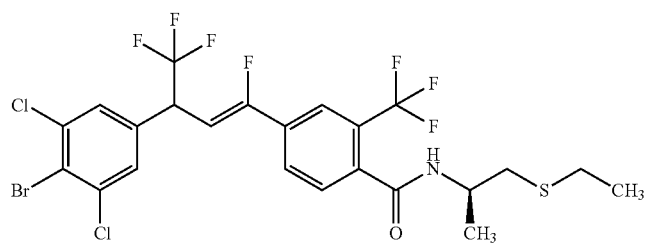 |
| F49 | 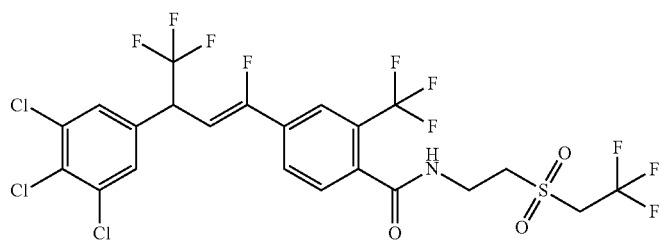 [SMILES: O=C(NCCS(=O)(=O)CC(F)(F)F)c1ccc(/C(F)=C/C(c2cc(Cl)c(Cl)c(Cl)c2)C(F)(F)F)cc1C(F)(F)F] |
| F50 | 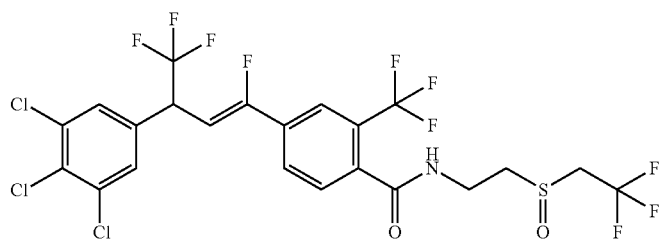 [SMILES: O=C(NCCS(=O)CC(F)(F)F)c1ccc(/C(F)=C/C(c2cc(Cl)c(Cl)c(Cl)c2)C(F)(F)F)cc1C(F)(F)F] |
| F51 | 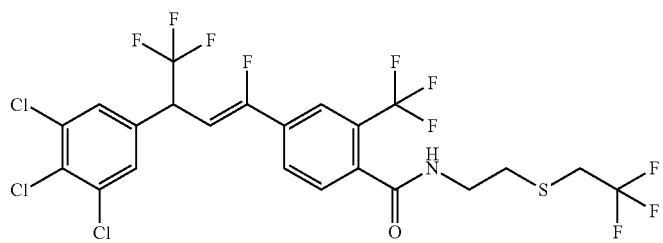 [SMILES: O=C(NCCSCC(F)(F)F)c1ccc(/C(F)=C/C(c2cc(Cl)c(Cl)c(Cl)c2)C(F)(F)F)cc1C(F)(F)F] |
| F52 | 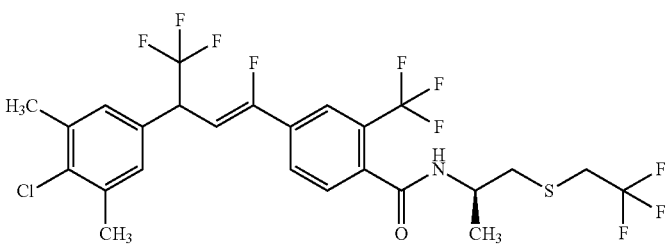 [SMILES: Cc1cc(C(/C=C(\F)c2ccc(C(=O)N[C@H](C)CSCC(F)(F)F)c(C(F)(F)F)c2)C(F)(F)F)cc(C)c1Cl] |

-continued
| No. | Structure |
|---|---|
| F53 | 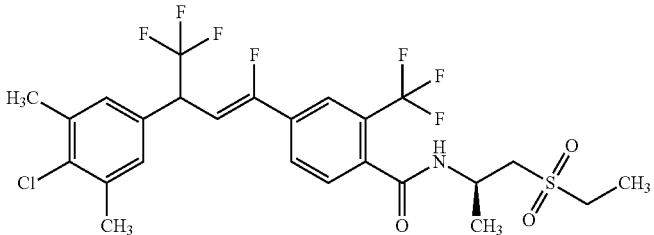 |
| F54 | 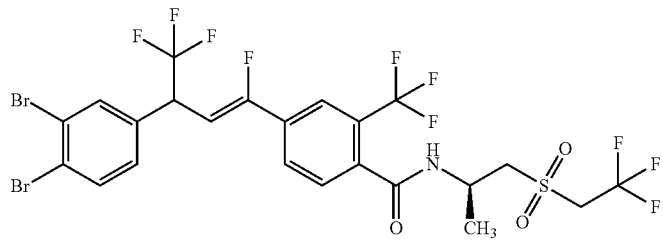 [SMILES: C[C@H](CS(=O)(=O)CC(F)(F)F)NC(=O)c1ccc(/C(F)=C/C(c2ccc(Br)c(Br)c2)C(F)(F)F)cc1C(F)(F)F] |
| F55 | 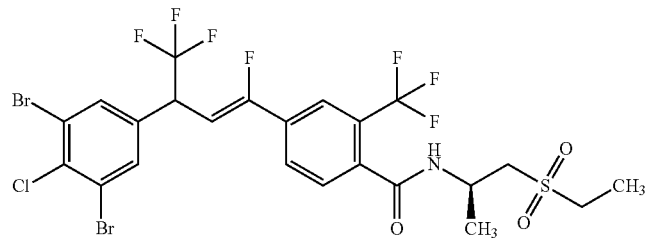 |
| F56 | 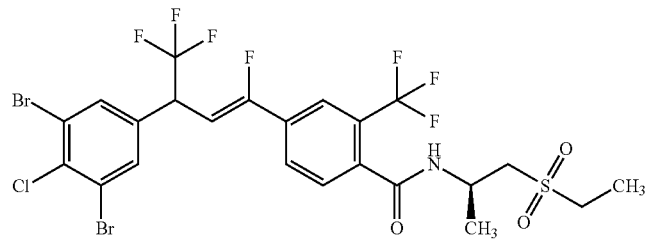 |
| F57 | 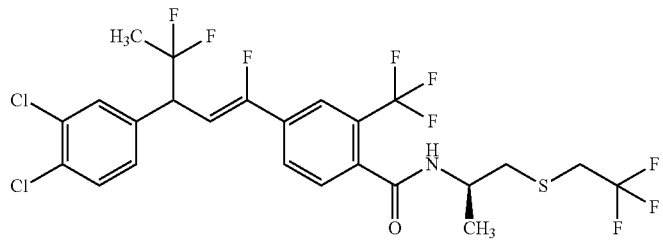 [SMILES: C[C@H](CSCC(F)(F)F)NC(=O)c1ccc(/C(F)=C/C(c2ccc(Cl)c(Cl)c2)C(C)(F)F)cc1C(F)(F)F] |
| F58 | 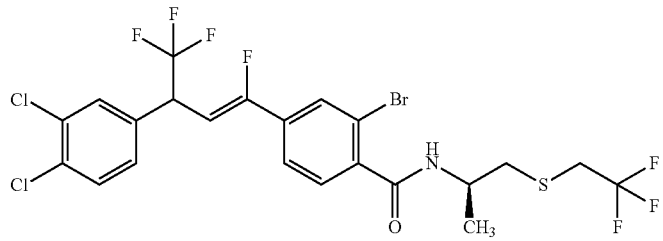 [SMILES: C[C@H](CSCC(F)(F)F)NC(=O)c1ccc(/C(F)=C/C(c2ccc(Cl)c(Cl)c2)C(F)(F)F)cc1Br] |

| No. | Structure |
|---|---|
| F59 | 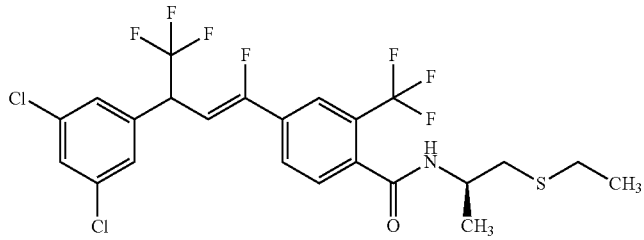 [SMILES: CCSC[C@@H](C)NC(=O)c1ccc(/C(F)=C/C(c2cc(Cl)cc(Cl)c2)C(F)(F)F)cc1C(F)(F)F] |
| F60 | 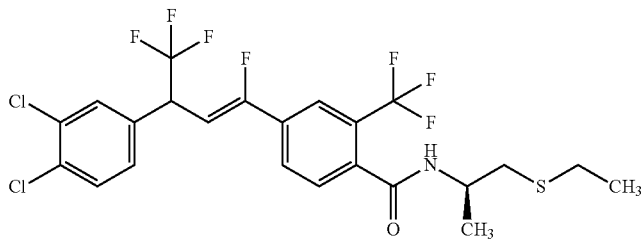 [SMILES: CCSC[C@@H](C)NC(=O)c1ccc(/C(F)=C/C(c2ccc(Cl)c(Cl)c2)C(F)(F)F)cc1C(F)(F)F] |
| F61 | 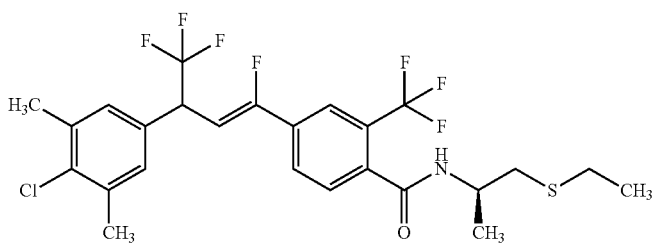 [SMILES: CCSC[C@@H](C)NC(=O)c1ccc(/C(F)=C/C(c2cc(C)c(Cl)c(C)c2)C(F)(F)F)cc1C(F)(F)F] |
| F62 | 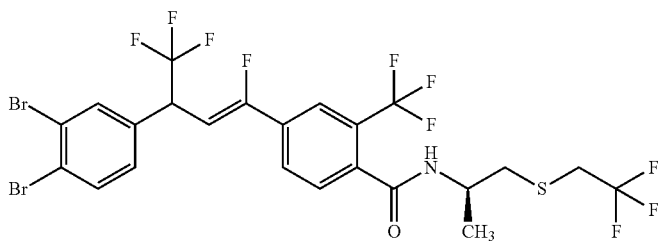 [SMILES: C[C@H](CSCC(F)(F)F)NC(=O)c1ccc(/C(F)=C/C(c2ccc(Br)c(Br)c2)C(F)(F)F)cc1C(F)(F)F] |
| F63 | 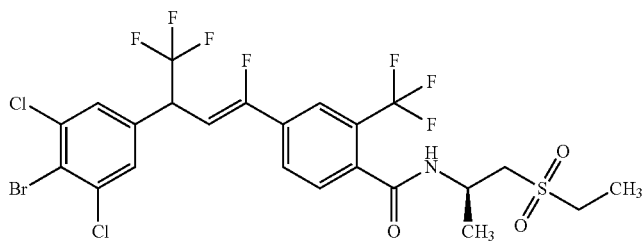 [SMILES: CCS(=O)(=O)C[C@@H](C)NC(=O)c1ccc(/C(F)=C/C(c2cc(Cl)c(Br)c(Cl)c2)C(F)(F)F)cc1C(F)(F)F] |
| F64 | 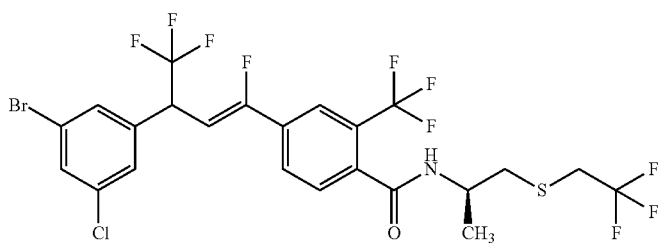 [SMILES: C[C@H](CSCC(F)(F)F)NC(=O)c1ccc(/C(F)=C/C(c2cc(Cl)cc(Br)c2)C(F)(F)F)cc1C(F)(F)F] |

| No. | Structure |
|---|---|
| F65 | 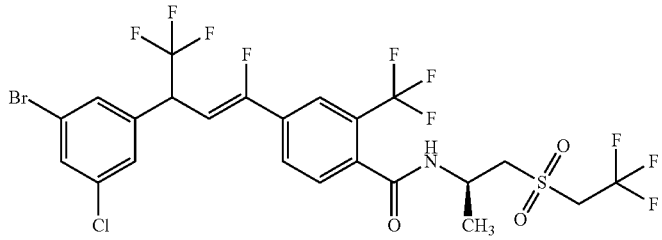 [SMILES: C[C@H](CS(=O)(=O)CC(F)(F)F)NC(=O)c1ccc(/C(F)=C/C(c2cc(Cl)cc(Br)c2)C(F)(F)F)cc1C(F)(F)F] |
| F66 | 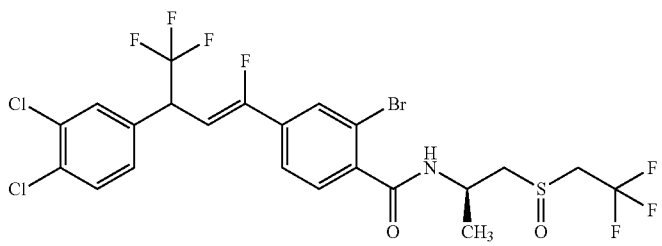 |
| F67 | 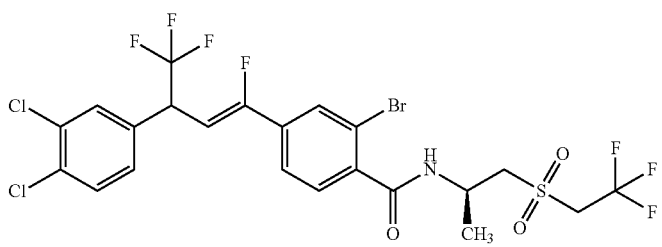 [SMILES: C[C@H](CS(=O)(=O)CC(F)(F)F)NC(=O)c1ccc(/C(F)=C/C(c2ccc(Cl)c(Cl)c2)C(F)(F)F)cc1Br] |
| F68 | 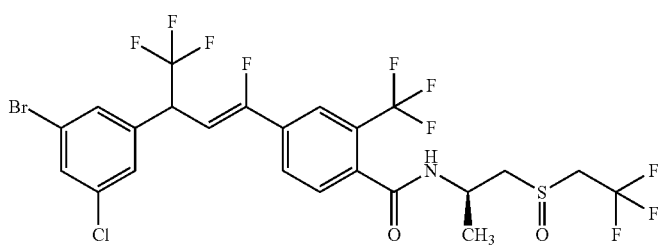 [SMILES: C[C@H](CS(=O)CC(F)(F)F)NC(=O)c1ccc(/C(F)=C/C(c2cc(Cl)cc(Br)c2)C(F)(F)F)cc1C(F)(F)F] |
| F69 | 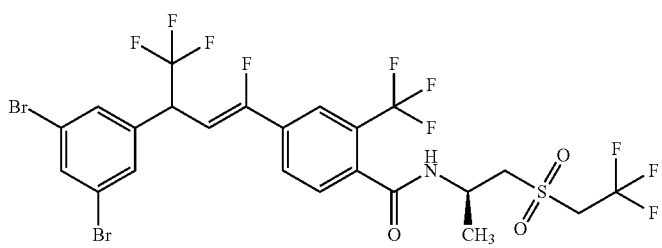 |
| F70 | 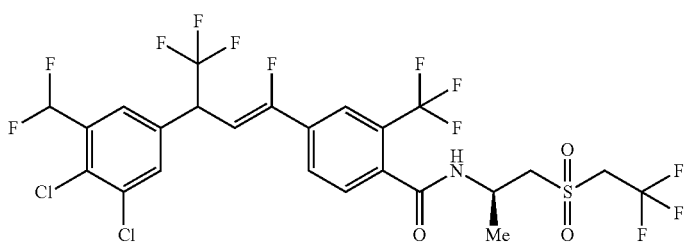 [SMILES: C[C@H](CS(=O)(=O)CC(F)(F)F)NC(=O)c1ccc(/C(F)=C/C(c2cc(Cl)c(Cl)c(C(F)F)c2)C(F)(F)F)cc1C(F)(F)F] |

| No. | Structure |
|---|---|
| F71 | 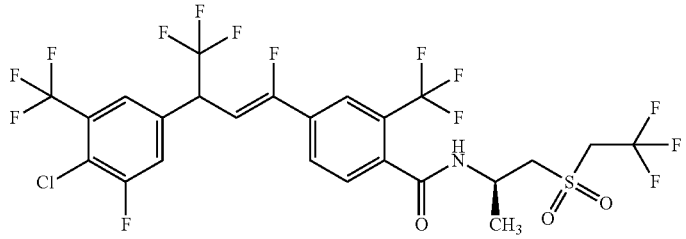 [SMILES: C[C@H](CS(=O)(=O)CC(F)(F)F)NC(=O)c1ccc(/C(F)=C/C(c2cc(F)c(Cl)c(C(F)(F)F)c2)C(F)(F)F)cc1C(F)(F)F] |
| F72 | 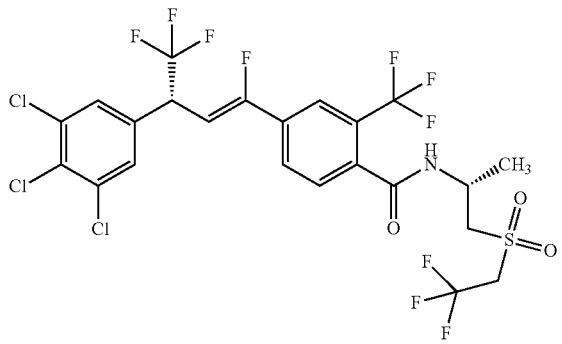 enantiomerically pure |
| F73 | 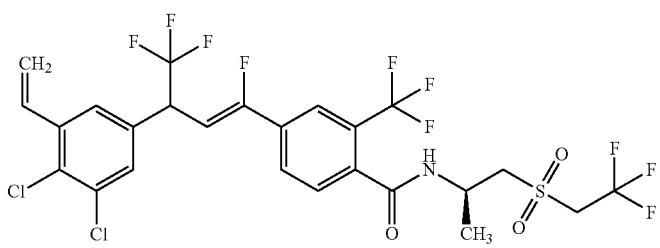 [SMILES: C=Cc1cc(C(/C=C(\F)c2ccc(C(=O)N[C@H](C)CS(=O)(=O)CC(F)(F)F)c(C(F)(F)F)c2)C(F)(F)F)cc(Cl)c1Cl] |
| F75 | 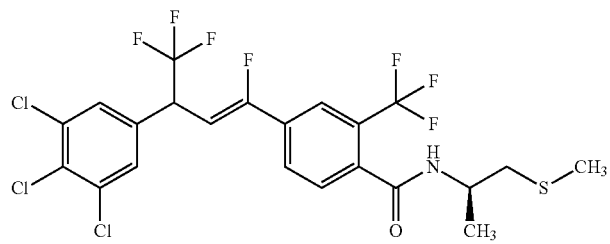 |
| F77 | 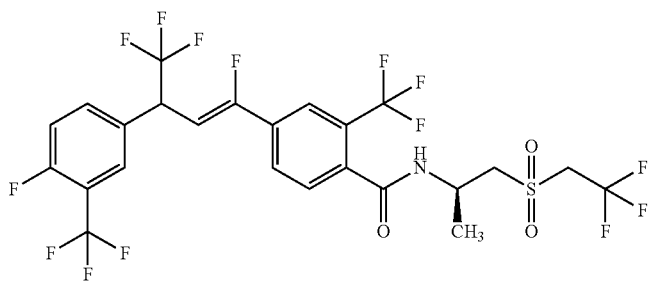 [SMILES: C[C@H](CS(=O)(=O)CC(F)(F)F)NC(=O)c1ccc(/C(F)=C/C(c2ccc(F)c(C(F)(F)F)c2)C(F)(F)F)cc1C(F)(F)F] |

| No. | Structure |
|---|---|
| F78 | 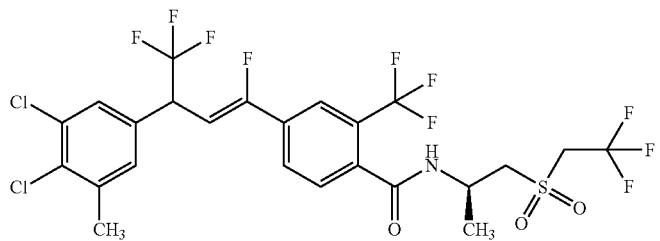 [SMILES: Cc1cc(C(/C=C(\F)c2ccc(C(=O)N[C@H](C)CS(=O)(=O)CC(F)(F)F)c(C(F)(F)F)c2)C(F)(F)F)cc(Cl)c1Cl] |
| F79 | 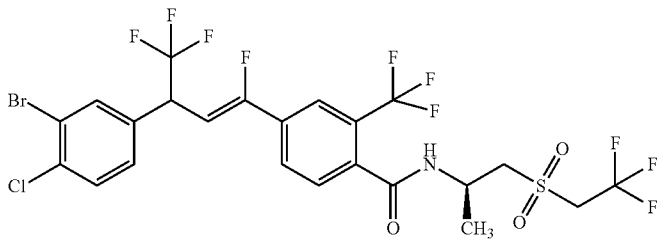 [SMILES: C[C@H](CS(=O)(=O)CC(F)(F)F)NC(=O)c1ccc(/C(F)=C/C(c2ccc(Cl)c(Br)c2)C(F)(F)F)cc1C(F)(F)F] |
| F80 | 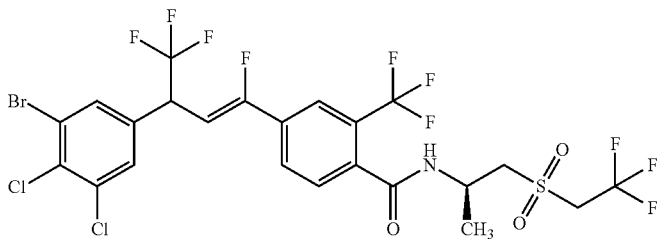 |
| F81 | 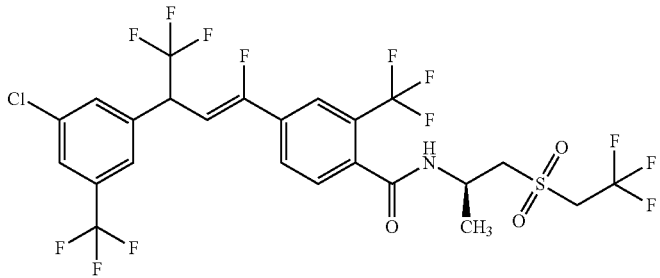 [SMILES: C[C@H](CS(=O)(=O)CC(F)(F)F)NC(=O)c1ccc(/C(F)=C/C(c2cc(Cl)cc(C(F)(F)F)c2)C(F)(F)F)cc1C(F)(F)F] |
| F82 | 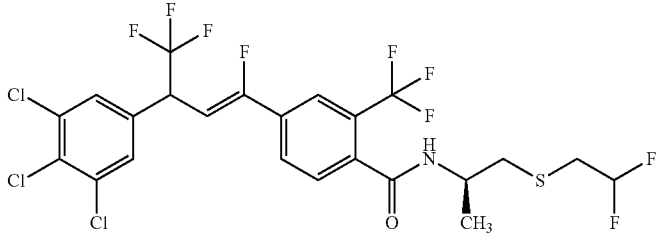 [SMILES: C[C@H](CSCC(F)F)NC(=O)c1ccc(/C(F)=C/C(c2cc(Cl)c(Cl)c(Cl)c2)C(F)(F)F)cc1C(F)(F)F] |
| F83 | 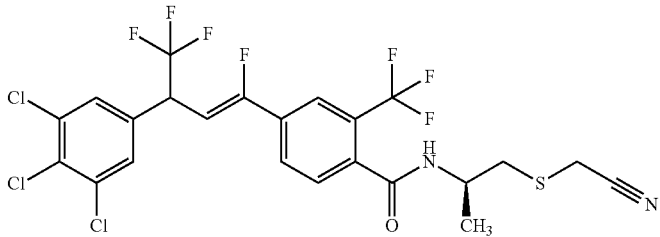 [SMILES: C[C@H](CSCC#N)NC(=O)c1ccc(/C(F)=C/C(c2cc(Cl)c(Cl)c(Cl)c2)C(F)(F)F)cc1C(F)(F)F] |

-continued
| No. | Structure |
|---|---|
| F84 | 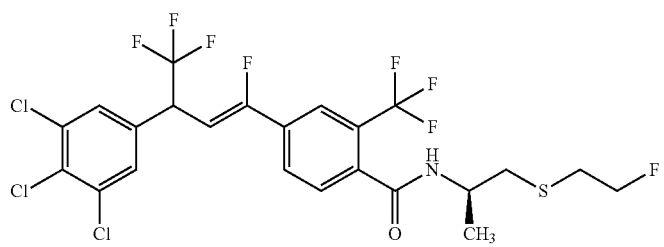 |
| F85 | 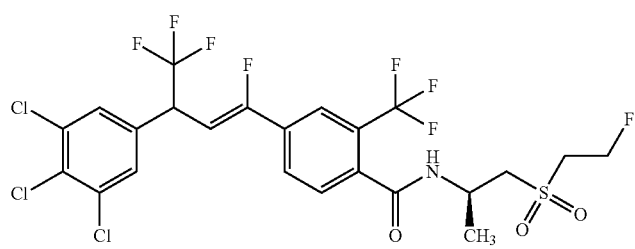 |
| F86 | 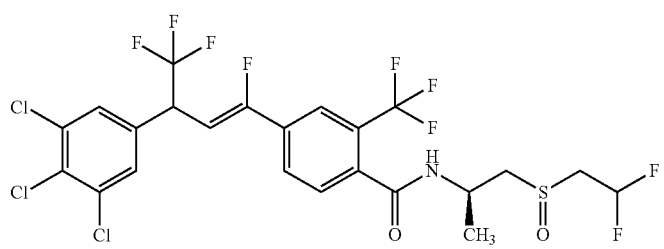 [SMILES: C[C@H](CS(=O)CC(F)F)NC(=O)c1ccc(/C(F)=C/C(c2cc(Cl)c(Cl)c(Cl)c2)C(F)(F)F)cc1C(F)(F)F] |
| F87 | 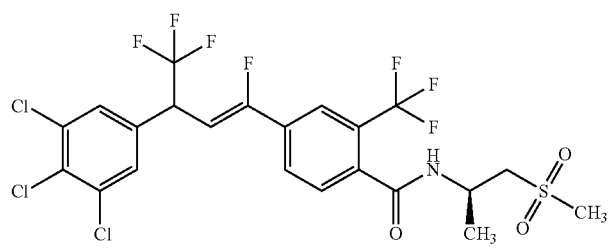 [SMILES: C[C@H](CS(C)(=O)=O)NC(=O)c1ccc(/C(F)=C/C(c2cc(Cl)c(Cl)c(Cl)c2)C(F)(F)F)cc1C(F)(F)F] |
| F88 | 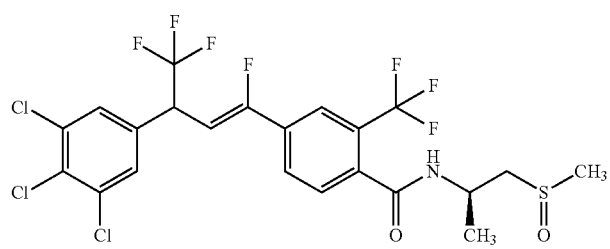 [SMILES: C[C@H](CS(C)=O)NC(=O)c1ccc(/C(F)=C/C(c2cc(Cl)c(Cl)c(Cl)c2)C(F)(F)F)cc1C(F)(F)F] |
| F89 | 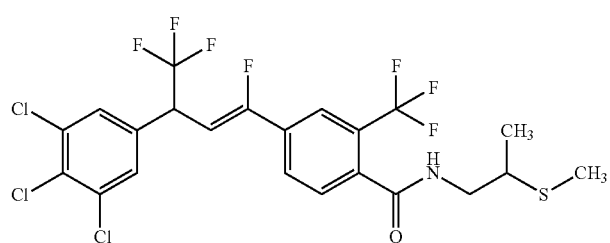 [SMILES: CSC(C)CNC(=O)c1ccc(/C(F)=C/C(c2cc(Cl)c(Cl)c(Cl)c2)C(F)(F)F)cc1C(F)(F)F] |

| No. | Structure |
|---|---|
| F90 | 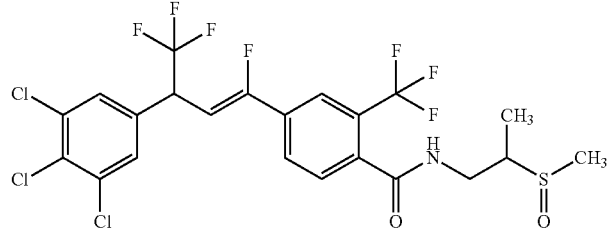 [SMILES: CC(CNC(=O)c1ccc(/C(F)=C/C(c2cc(Cl)c(Cl)c(Cl)c2)C(F)(F)F)cc1C(F)(F)F)S(C)=O] |
| F91 | 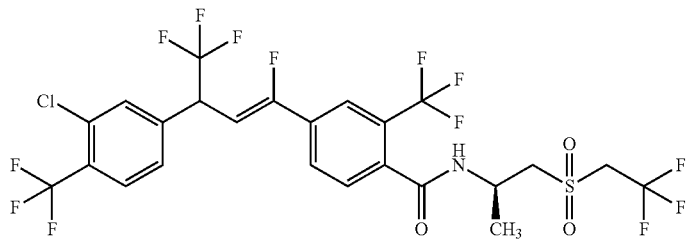 [SMILES: C[C@H](CS(=O)(=O)CC(F)(F)F)NC(=O)c1ccc(/C(F)=C/C(c2ccc(C(F)(F)F)c(Cl)c2)C(F)(F)F)cc1C(F)(F)F] |
| F92 | 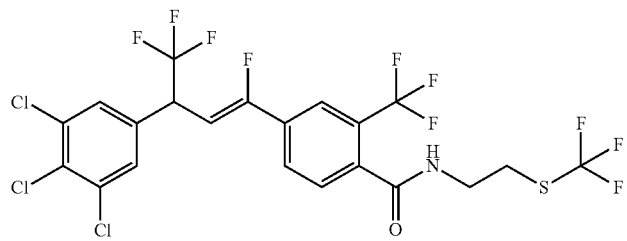 [SMILES: O=C(NCCSC(F)(F)F)c1ccc(/C(F)=C/C(c2cc(Cl)c(Cl)c(Cl)c2)C(F)(F)F)cc1C(F)(F)F] |
| F93 | 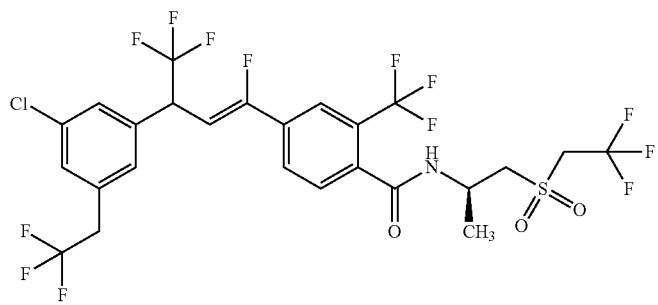 [SMILES: C[C@H](CS(=O)(=O)CC(F)(F)F)NC(=O)c1ccc(/C(F)=C/C(c2cc(Cl)cc(CC(F)(F)F)c2)C(F)(F)F)cc1C(F)(F)F] |
| F94 | 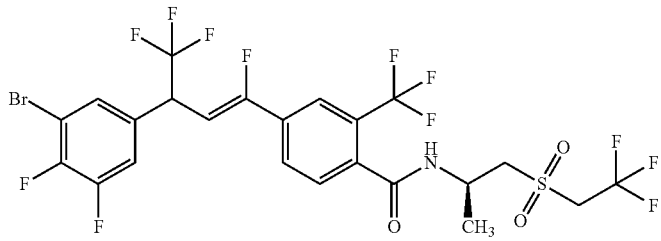 |
| F95 | 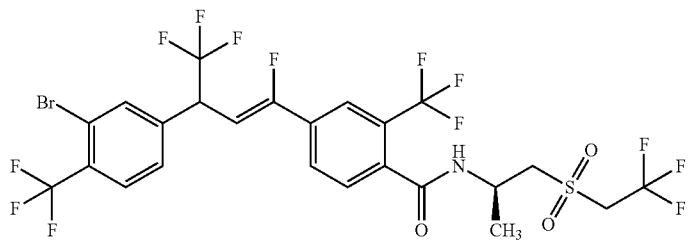 [SMILES: C[C@H](CS(=O)(=O)CC(F)(F)F)NC(=O)c1ccc(/C(F)=C/C(c2ccc(C(F)(F)F)c(Br)c2)C(F)(F)F)cc1C(F)(F)F] |

| No. | Structure |
|---|---|
| F96 | 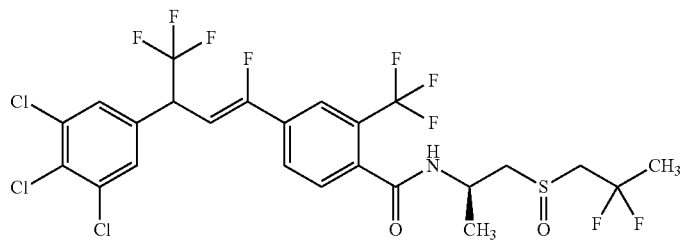 [SMILES: C[C@H](CS(=O)CC(C)(F)F)NC(=O)c1ccc(/C(F)=C/C(c2cc(Cl)c(Cl)c(Cl)c2)C(F)(F)F)cc1C(F)(F)F] |
| F97 | 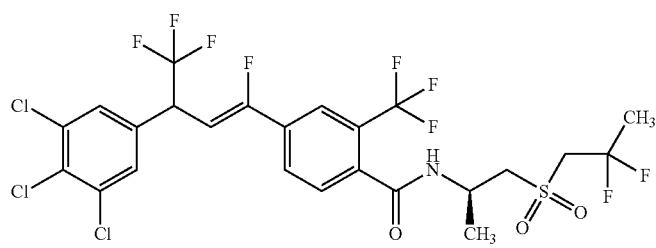 [SMILES: C[C@H](CS(=O)(=O)CC(C)(F)F)NC(=O)c1ccc(/C(F)=C/C(c2cc(Cl)c(Cl)c(Cl)c2)C(F)(F)F)cc1C(F)(F)F] |
| F98 | 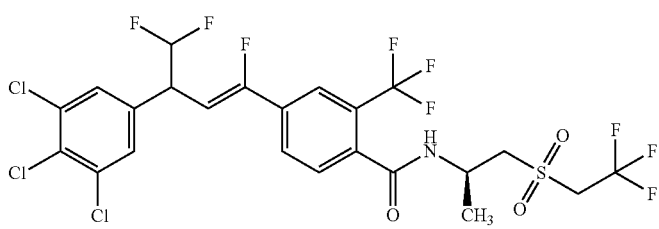 [SMILES: C[C@H](CS(=O)(=O)CC(F)(F)F)NC(=O)c1ccc(/C(F)=C/C(c2cc(Cl)c(Cl)c(Cl)c2)C(F)F)cc1C(F)(F)F] |
| F99 | 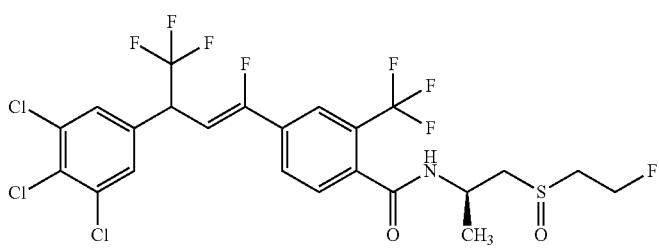 [SMILES: C[C@H](CS(=O)CCF)NC(=O)c1ccc(/C(F)=C/C(c2cc(Cl)c(Cl)c(Cl)c2)C(F)(F)F)cc1C(F)(F)F] |
| F100 | 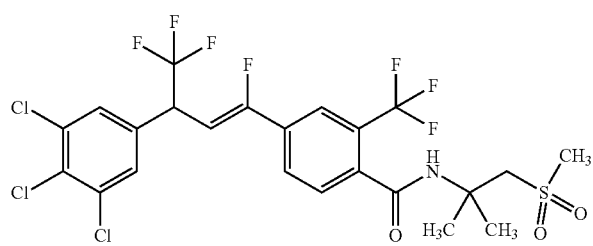 [SMILES: CC(C)(CS(C)(=O)=O)NC(=O)c1ccc(/C(F)=C/C(c2cc(Cl)c(Cl)c(Cl)c2)C(F)(F)F)cc1C(F)(F)F] |
| F101 | 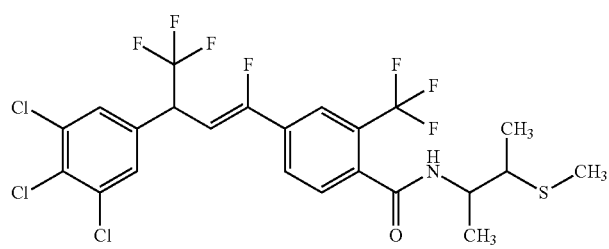 [SMILES: CSC(C)C(C)NC(=O)c1ccc(/C(F)=C/C(c2cc(Cl)c(Cl)c(Cl)c2)C(F)(F)F)cc1C(F)(F)F] |

| No. | Structure |
|---|---|
| F102 | 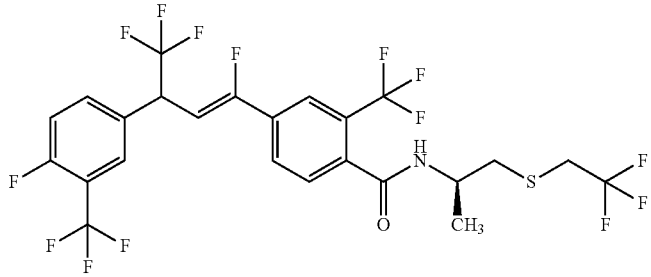 [SMILES: C[C@H](CSCC(F)(F)F)NC(=O)c1ccc(/C(F)=C/C(c2ccc(F)c(C(F)(F)F)c2)C(F)(F)F)cc1C(F)(F)F] |
| F103 | 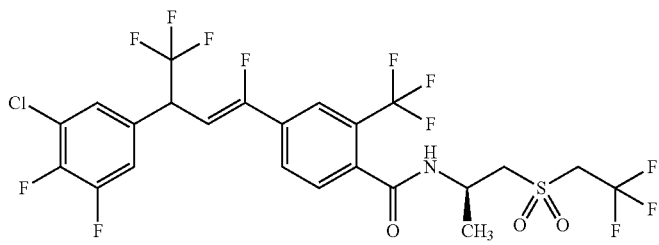 |
| F104 | 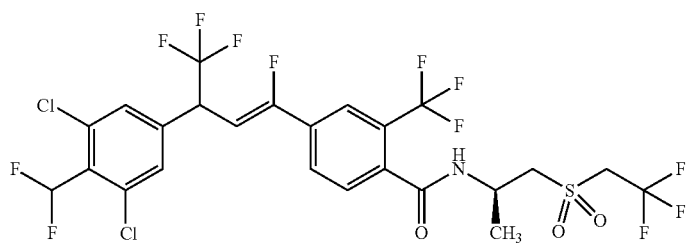 [SMILES: C[C@H](CS(=O)(=O)CC(F)(F)F)NC(=O)c1ccc(/C(F)=C/C(c2cc(Cl)c(C(F)F)c(Cl)c2)C(F)(F)F)cc1C(F)(F)F] |
| F109 | 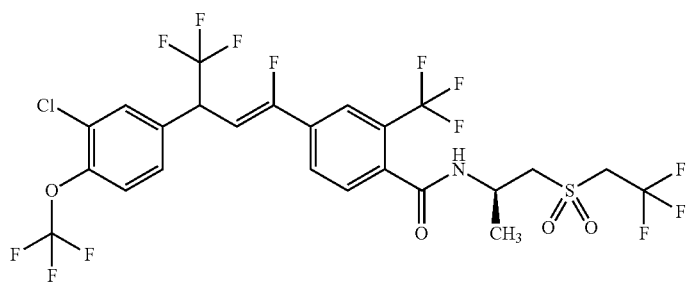 [SMILES: C[C@H](CS(=O)(=O)CC(F)(F)F)NC(=O)c1ccc(/C(F)=C/C(c2ccc(OC(F)(F)F)c(Cl)c2)C(F)(F)F)cc1C(F)(F)F] |
| F110 | 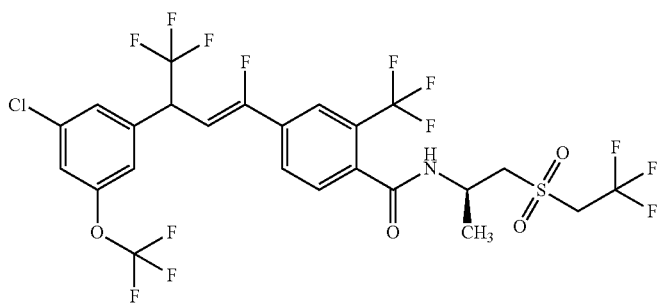 [SMILES: C[C@H](CS(=O)(=O)CC(F)(F)F)NC(=O)c1ccc(/C(F)=C/C(c2cc(Cl)cc(OC(F)(F)F)c2)C(F)(F)F)cc1C(F)(F)F] |

| No. | Structure |
| --- | --- |
| F112 | 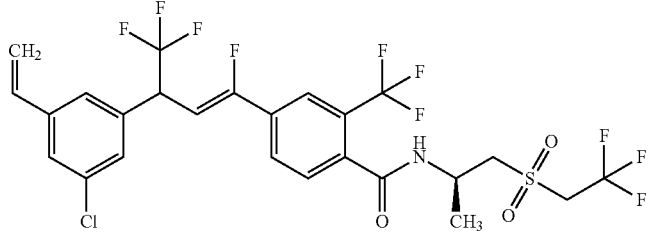 [SMILES: C=Cc1cc(Cl)cc(C(/C=C(\F)c2ccc(C(=O)N[C@H](C)CS(=O)(=O)CC(F)(F)F)c(C(F)(F)F)c2)C(F)(F)F)c1] |
| F113 | 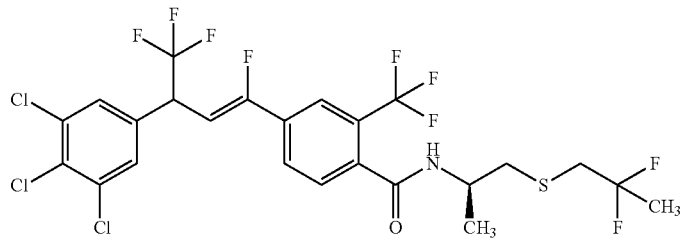 [SMILES: C[C@H](CSCC(C)(F)F)NC(=O)c1ccc(/C(F)=C/C(c2cc(Cl)c(Cl)c(Cl)c2)C(F)(F)F)cc1C(F)(F)F] |
| F114 | 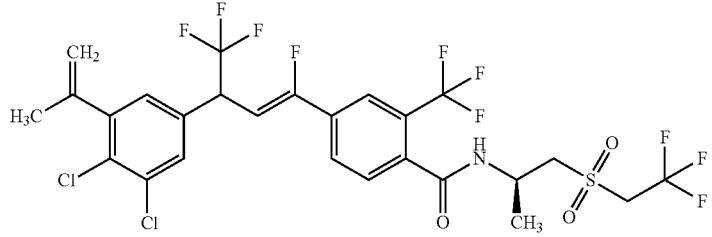 [SMILES: C=C(C)c1cc(C(/C=C(\F)c2ccc(C(=O)N[C@H](C)CS(=O)(=O)CC(F)(F)F)c(C(F)(F)F)c2)C(F)(F)F)cc(Cl)c1Cl] |
| F116 | 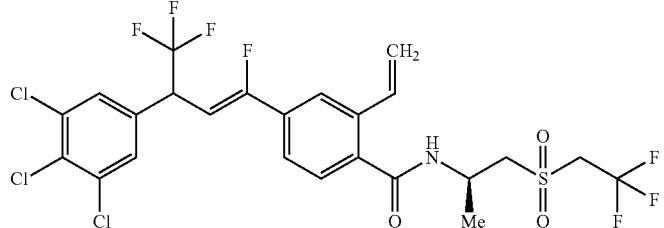 [SMILES: C=Cc1cc(/C(F)=C/C(c2cc(Cl)c(Cl)c(Cl)c2)C(F)(F)F)ccc1C(=O)N[C@H](C)CS(=O)(=O)CC(F)(F)F] |
| F117 | 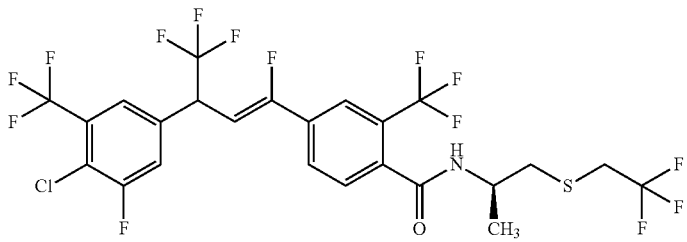 [SMILES: C[C@H](CSCC(F)(F)F)NC(=O)c1ccc(/C(F)=C/C(c2cc(F)c(Cl)c(C(F)(F)F)c2)C(F)(F)F)cc1C(F)(F)F] |
| F119 | 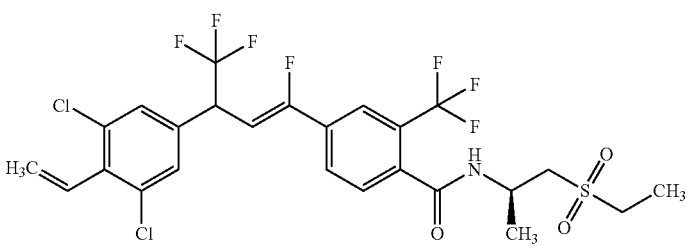 [SMILES: C=Cc1c(Cl)cc(C(/C=C(\F)c2ccc(C(=O)N[C@H](C)CS(=O)(=O)CC)c(C(F)(F)F)c2)C(F)(F)F)cc1Cl] |

-continued
| No. | Structure |
|---|---|
| F120 | 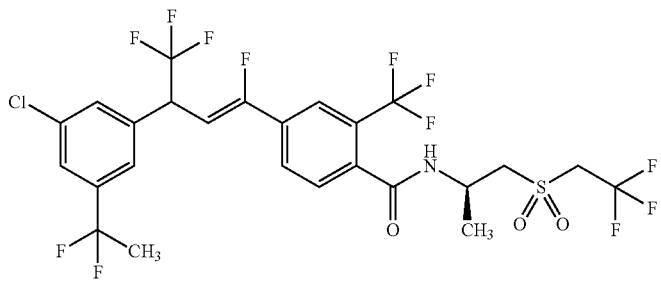 [SMILES: C[C@H](CS(=O)(=O)CC(F)(F)F)NC(=O)c1ccc(/C(F)=C/C(c2cc(Cl)cc(C(C)(F)F)c2)C(F)(F)F)cc1C(F)(F)F] |
| F121 | 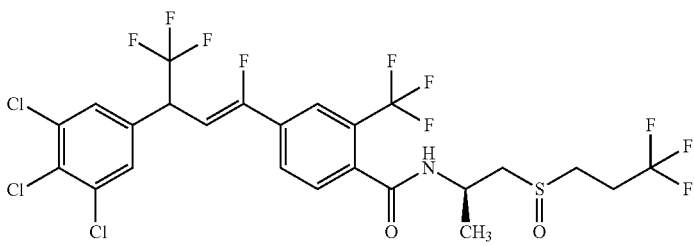 |
| F122 | 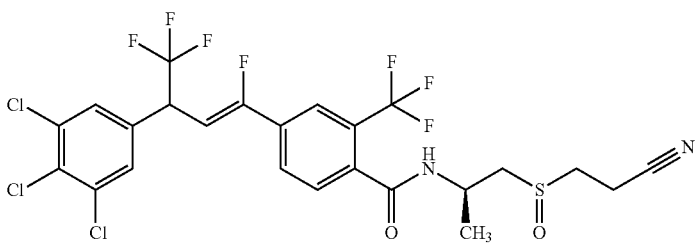 [SMILES: C[C@H](CS(=O)CCC#N)NC(=O)c1ccc(/C(F)=C/C(c2cc(Cl)c(Cl)c(Cl)c2)C(F)(F)F)cc1C(F)(F)F] |
| F123 | 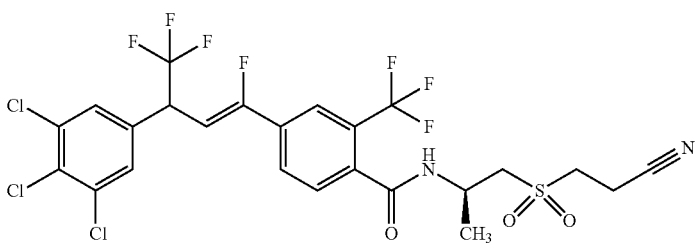 [SMILES: C[C@H](CS(=O)(=O)CCC#N)NC(=O)c1ccc(/C(F)=C/C(c2cc(Cl)c(Cl)c(Cl)c2)C(F)(F)F)cc1C(F)(F)F] |
| F124 | 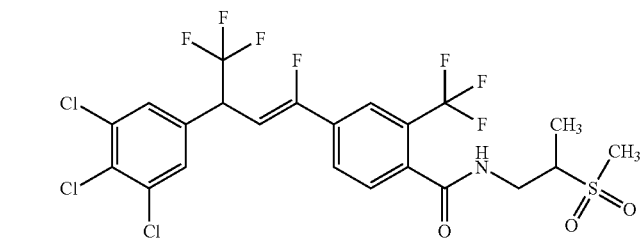 [SMILES: CC(CNC(=O)c1ccc(/C(F)=C/C(c2cc(Cl)c(Cl)c(Cl)c2)C(F)(F)F)cc1C(F)(F)F)S(C)(=O)=O] |
| F125 | 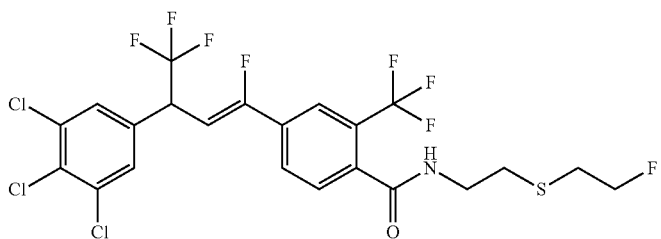 [SMILES: O=C(NCCSCCF)c1ccc(/C(F)=C/C(c2cc(Cl)c(Cl)c(Cl)c2)C(F)(F)F)cc1C(F)(F)F] |

-continued
| No. | Structure |
|---|---|
| F126 | 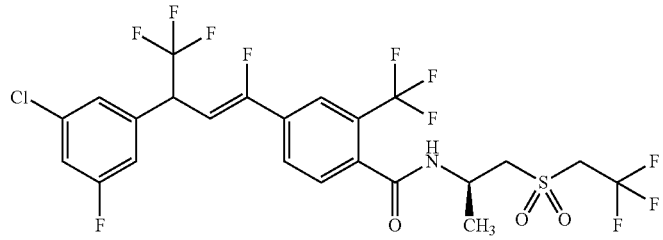 [SMILES: C[C@H](CS(=O)(=O)CC(F)(F)F)NC(=O)c1ccc(/C(F)=C/C(c2cc(F)cc(Cl)c2)C(F)(F)F)cc1C(F)(F)F] |
| F127 | 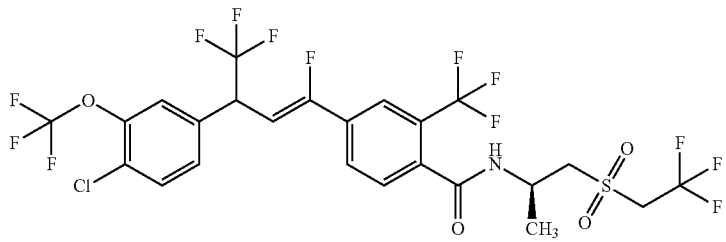 |
| F128 | 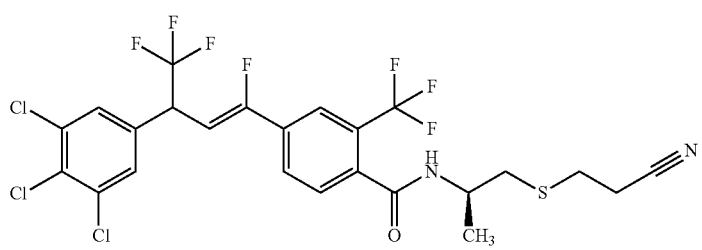 [SMILES: C[C@H](CSCCC#N)NC(=O)c1ccc(/C(F)=C/C(c2cc(Cl)c(Cl)c(Cl)c2)C(F)(F)F)cc1C(F)(F)F] |
| F129 | 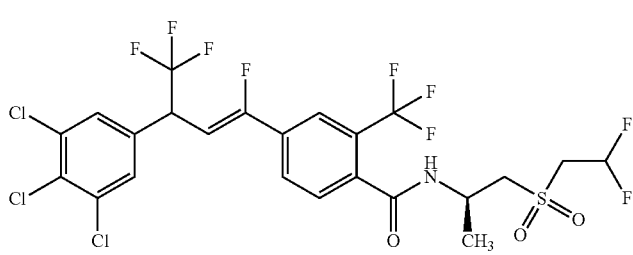 [SMILES: C[C@H](CS(=O)(=O)CC(F)F)NC(=O)c1ccc(/C(F)=C/C(c2cc(Cl)c(Cl)c(Cl)c2)C(F)(F)F)cc1C(F)(F)F] |
| F130 | 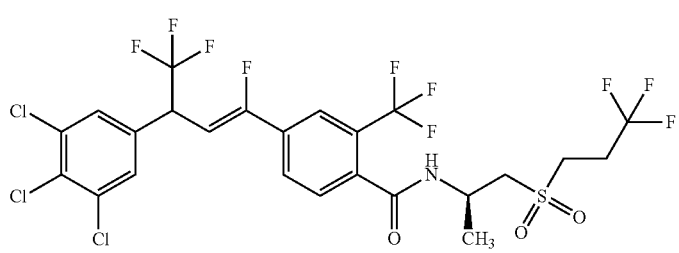 [SMILES: C[C@H](CS(=O)(=O)CCC(F)(F)F)NC(=O)c1ccc(/C(F)=C/C(c2cc(Cl)c(Cl)c(Cl)c2)C(F)(F)F)cc1C(F)(F)F] |
| F131 | 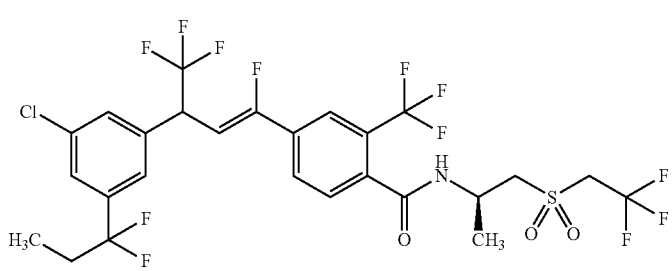 [SMILES: CCC(F)(F)c1cc(Cl)cc(C(/C=C(\F)c2ccc(C(=O)N[C@H](C)CS(=O)(=O)CC(F)(F)F)c(C(F)(F)F)c2)C(F)(F)F)c1] |

| No. | Structure |
|---|---|
| F132 | 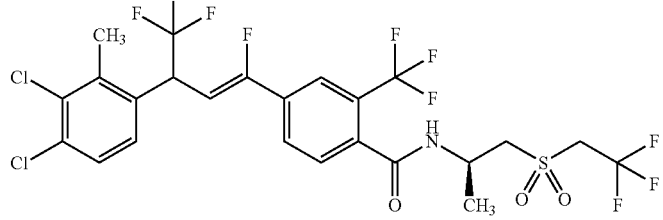 |
| F133 | 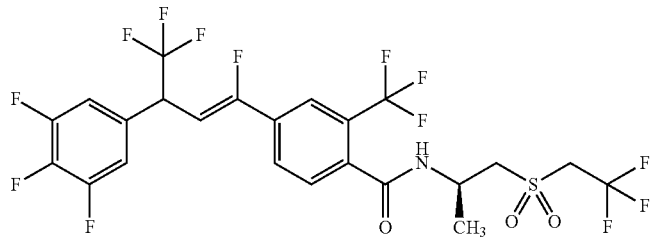 [SMILES: C[C@H](CS(=O)(=O)CC(F)(F)F)NC(=O)c1ccc(/C(F)=C/C(c2cc(F)c(F)c(F)c2)C(F)(F)F)cc1C(F)(F)F] |
| F136 | 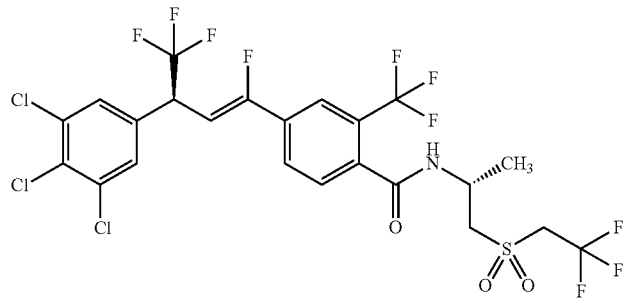<br>enantiomerically pure |
| F137 | 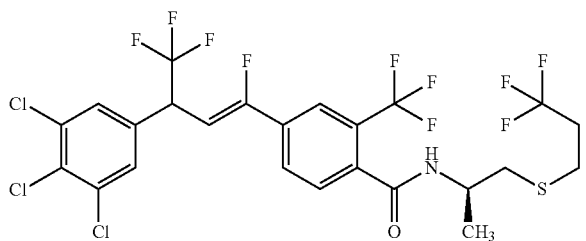 |
| F138 | 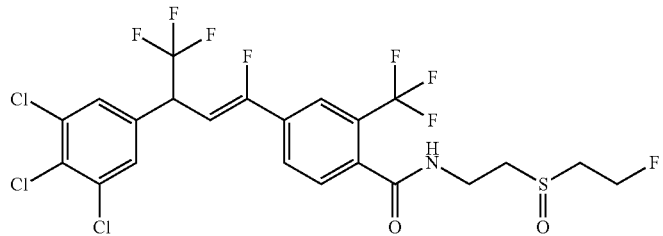 [SMILES: O=C(NCCS(=O)CCF)c1ccc(/C(F)=C/C(c2cc(Cl)c(Cl)c(Cl)c2)C(F)(F)F)cc1C(F)(F)F] |
| F141 | 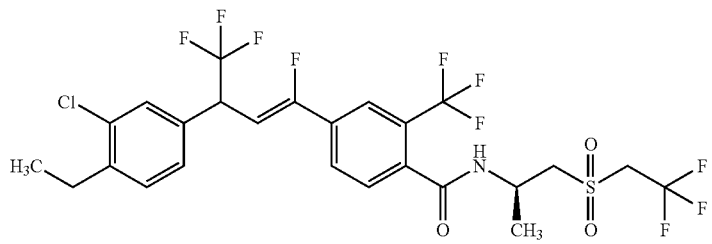 [SMILES: CCc1ccc(C(/C=C(\F)c2ccc(C(=O)N[C@H](C)CS(=O)(=O)CC(F)(F)F)c(C(F)(F)F)c2)C(F)(F)F)cc1Cl] |

| No. | Structure |
|---|---|
| F142 | 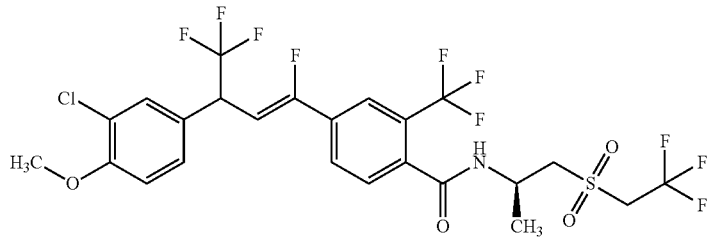 |
| F143 | 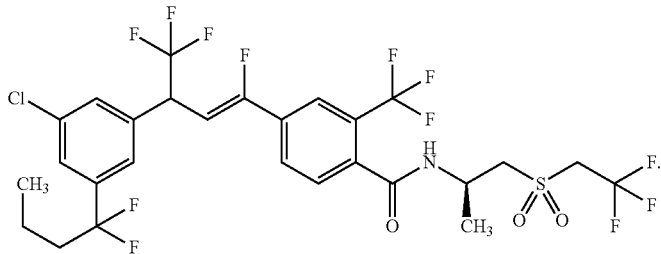 [SMILES: CCCC(F)(F)c1cc(Cl)cc(C(/C=C(\F)c2ccc(C(=O)N[C@H](C)CS(=O)(=O)CC(F)(F)F)c(C(F)(F)F)c2)C(F)(F)F)c1] |
19. A molecule according to claim 2 wherein said molecule is selected from one of the following molecules
| No. | Structure |
|---|---|
| P1 | 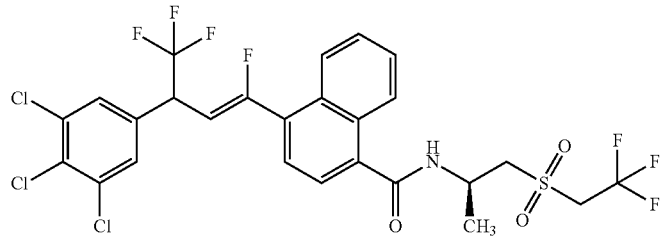 [SMILES: C[C@H](CS(=O)(=O)CC(F)(F)F)NC(=O)c1ccc(/C(F)=C/C(c2cc(Cl)c(Cl)c(Cl)c2)C(F)(F)F)c2ccccc12] |
| P2 | 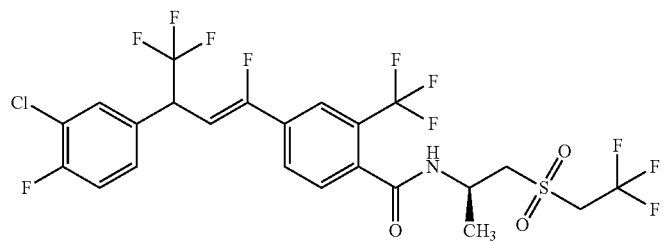 [SMILES: C[C@H](CS(=O)(=O)CC(F)(F)F)NC(=O)c1ccc(/C(F)=C/C(c2ccc(F)c(Cl)c2)C(F)(F)F)cc1C(F)(F)F] |
| P3 | 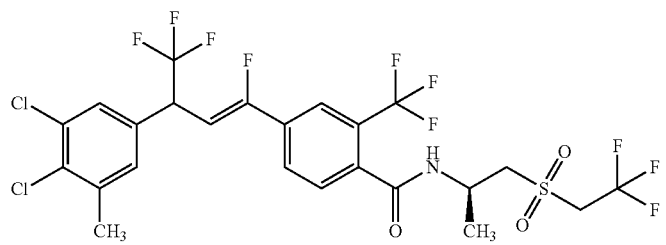 [SMILES: Cc1cc(C(/C=C(\F)c2ccc(C(=O)N[C@H](C)CS(=O)(=O)CC(F)(F)F)c(C(F)(F)F)c2)C(F)(F)F)cc(Cl)c1Cl] |

-continued
| No. | Structure |
|---|---|
| P4 | 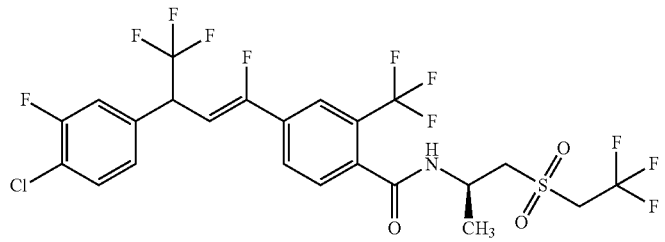 [SMILES: C[C@H](CS(=O)(=O)CC(F)(F)F)NC(=O)c1ccc(/C(F)=C/C(c2ccc(Cl)c(F)c2)C(F)(F)F)cc1C(F)(F)F] |
| P5 | 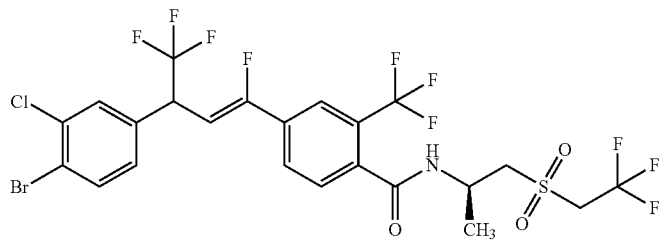 |
| P6 | 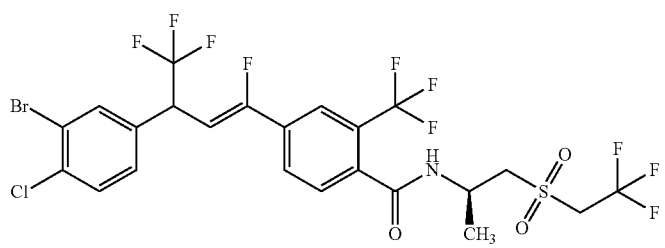 |
| P7 | 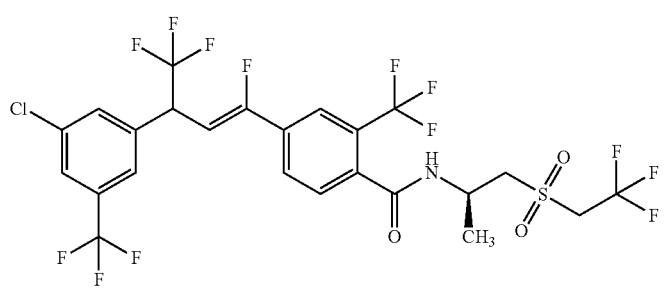 [SMILES: C[C@H](CS(=O)(=O)CC(F)(F)F)NC(=O)c1ccc(/C(F)=C/C(c2cc(Cl)cc(C(F)(F)F)c2)C(F)(F)F)cc1C(F)(F)F] |
| P8 | 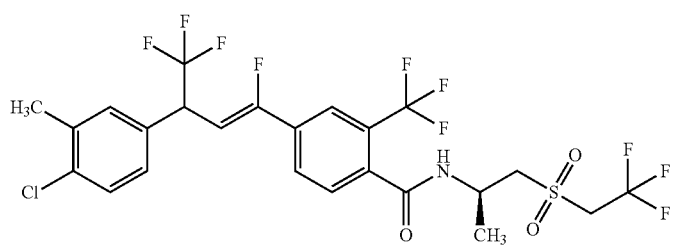 [SMILES: Cc1cc(C(/C=C(\F)c2ccc(C(=O)N[C@H](C)CS(=O)(=O)CC(F)(F)F)c(C(F)(F)F)c2)C(F)(F)F)ccc1Cl] |
| P9 | 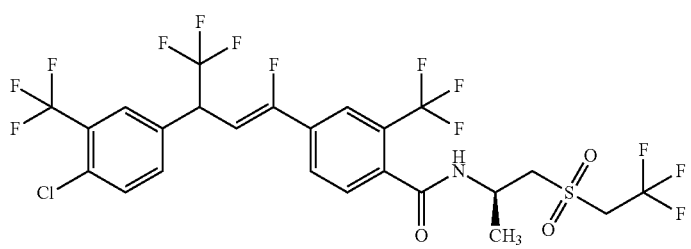 [SMILES: C[C@H](CS(=O)(=O)CC(F)(F)F)NC(=O)c1ccc(/C(F)=C/C(c2ccc(Cl)c(C(F)(F)F)c2)C(F)(F)F)cc1C(F)(F)F] |

| No. | Structure |
|---|---|
| P10 | 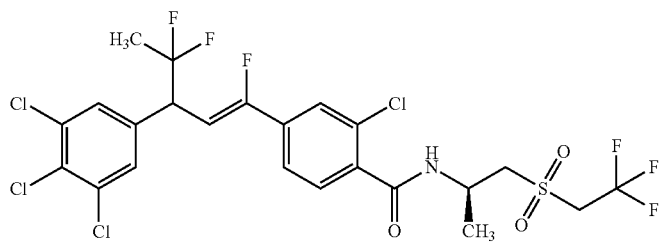 [SMILES: C[C@H](CS(=O)(=O)CC(F)(F)F)NC(=O)c1ccc(/C(F)=C/C(c2cc(Cl)c(Cl)c(Cl)c2)C(C)(F)F)cc1Cl] |
| P11 | 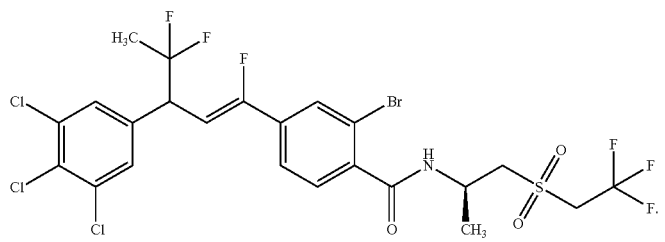 [SMILES: C[C@H](CS(=O)(=O)CC(F)(F)F)NC(=O)c1ccc(/C(F)=C/C(c2cc(Cl)c(Cl)c(Cl)c2)C(C)(F)F)cc1Br] |

20. A pesticidal composition comprising a pesticidally effective amount of a molecule according to claim 1, and further comprising a seed.

21. A pesticidal composition comprising a pesticidally effective amount of a molecule according to claim 18, and further comprising a seed.

22. A process to control a pest said process comprising applying to a locus, wherein the locus is a habitat, breeding ground, plant, seed, soil, material, or environment, in which a pest is growing, may grow, or may traverse, a pesticidally effective amount of a pesticidal composition wherein said pesticidal composition comprises a molecule according to claim 1.

23. A process to control a pest said process comprising applying to a locus, wherein the locus is a habitat, breeding ground, plant, seed, soil, material, or environment, in which a pest is growing, may grow, or may traverse, a pesticidally effective amount of a pesticidal composition wherein said pesticidal composition comprises a molecule according to claim 18.

* * * * *